US012577226B2

(12) United States Patent
Sydorenko et al.

(10) Patent No.: US 12,577,226 B2
(45) Date of Patent: Mar. 17, 2026

(54) COMPOUNDS FOR TREATING HUNTINGTON'S DISEASE

(71) Applicant: PTC THERAPEUTICS, INC., Warren, NJ (US)

(72) Inventors: Nadiya Sydorenko, Princeton, NJ (US); Rauful Alam, Middlesex, NJ (US); Lukiana Amedzo, Somerset, NJ (US); Michael A. Arnold, Flemington, NJ (US); Suresh Babu, Pennington, NJ (US); Anuradha Bhattacharyya, Edison, NJ (US); Gary Mitchell Karp, Princeton Junction, NJ (US); Nathaniel T. Kenton, Arlington, MA (US); Tom Tuan Luong, Piscataway, NJ (US); Anthony R. Mazzotti, Rahway, NJ (US); Young-Choon Moon, Belle Mead, NJ (US); Christie Morrill, Green Brook, NJ (US); Nicholas Walter Mszar, New Brunswick, NJ (US); Jana Narasimhan, Scotch Plains, NJ (US); Jigar S. Patel, Westfield, NJ (US); Hongyu Ren, Florence, NJ (US); Anthony Turpoff, Hillsborough, NJ (US); Gang Wang, Jersey City, NJ (US); Matthew G. Woll, Dunellen, NJ (US); Nanjing Zhang, Princeton, NJ (US); Xiaoyan Zhang, Belle Mead, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 913 days.

(21) Appl. No.: 17/610,617

(22) PCT Filed: May 12, 2020

(86) PCT No.: PCT/US2020/032446

§ 371 (c)(1),
(2) Date: Nov. 11, 2021

(87) PCT Pub. No.: WO2020/231977

PCT Pub. Date: Nov. 19, 2020

(65) Prior Publication Data

US 2022/0204478 A1 Jun. 30, 2022

Related U.S. Application Data

(60) Provisional application No. 62/846,896, filed on May 13, 2019.

(51) Int. Cl.

| | |
|---|---|
| ***C07D 401/14*** | (2006.01) |
| ***C07D 413/14*** | (2006.01) |

(Continued)

(52) U.S. Cl.

CPC ......... *C07D 401/14* (2013.01); *C07D 413/14* (2013.01); *C07D 417/14* (2013.01); (Continued)

(58) Field of Classification Search

None

See application file for complete search history.

(56) References Cited

U.S. PATENT DOCUMENTS

| | | | |
|---|---|---|---|
| 3,558,618 | A | 1/1971 | Trepanier |
| 4,122,274 | A | 10/1978 | Juby |

(Continued)

FOREIGN PATENT DOCUMENTS

| | | | |
|---|---|---|---|
| CN | 101360738 | A | 2/2009 |
| CN | 102971311 | A | 3/2013 |

(Continued)

OTHER PUBLICATIONS

Brunhilde Wirth et al., "Moving towards treatments for spinal muscular atrophy: hopes and limits", Expert Opinion on Emerging drugs, 20(3):353-356, Apr. 28, 2015.

(Continued)

*Primary Examiner* — Jeffrey S Lundgren
*Assistant Examiner* — Anthony Joseph Seitz
(74) *Attorney, Agent, or Firm* — McCarter & English, LLP; Michael J. DeGrazia

(57) ABSTRACT

The present description relates to compounds, forms, and pharmaceutical compositions thereof and methods of using such compounds, forms, or compositions thereof for treating or ameliorating Huntington's disease.

(I)

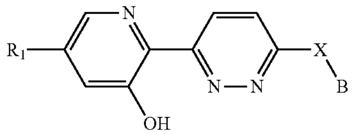

(II)

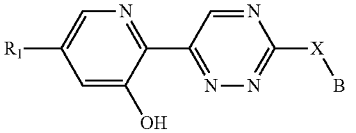

(III)

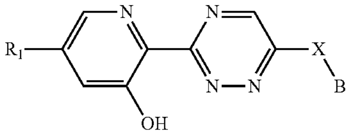

In particular, the present description relates to substituted monocyclic heteroaryl compounds of Formula (I), Formula (II), or Formula (III), forms and pharmaceutical composi- (Continued)

tions thereof and methods of using such compounds, forms, or compositions thereof for treating or ameliorating Huntington's disease.

16 Claims, No Drawings

(51) Int. Cl.

| | |
|---|---|
| ***C07D 417/14*** | (2006.01) |
| ***C07D 487/04*** | (2006.01) |
| ***C07D 487/08*** | (2006.01) |
| ***C07D 487/10*** | (2006.01) |
| ***C07D 491/107*** | (2006.01) |

(52) U.S. Cl.
CPC ......... *C07D 487/04* (2013.01); *C07D 487/08* (2013.01); *C07D 487/10* (2013.01); *C07D 491/107* (2013.01)

(56) References Cited

U.S. PATENT DOCUMENTS

| | | | |
|---|---|---|---|
| 4,342,870 | A | 8/1982 | Kennis et al. |
| 4,613,603 | A | 9/1986 | Biziere et al. |
| 4,902,695 | A | 2/1990 | Ornstein |
| 5,089,633 | A | 2/1992 | Powers et al. |
| 5,599,816 | A | 2/1997 | Chu et al. |
| 5,627,274 | A | 5/1997 | Kole et al. |
| 5,665,593 | A | 9/1997 | Kole et al. |
| 5,916,808 | A | 6/1999 | Kole et al. |
| 5,916,916 | A | 6/1999 | Hauser et al. |
| 5,976,879 | A | 11/1999 | Kole et al. |
| 6,172,216 | B1 | 1/2001 | Bennett et al. |
| 6,210,892 | B1 | 4/2001 | Bennett et al. |
| 6,214,986 | B1 | 4/2001 | Bennett et al. |
| 6,468,607 | B1 | 10/2002 | Takehara et al. |
| 6,630,488 | B1 | 10/2003 | Lamothe et al. |
| 6,977,255 | B2 | 12/2005 | Robertson et al. |
| 7,326,711 | B2 | 2/2008 | Wang et al. |
| 7,399,767 | B2 | 7/2008 | Zhang et al. |
| 7,473,784 | B2 | 1/2009 | Liu et al. |
| 7,569,337 | B2 | 8/2009 | Auberson |
| 7,576,110 | B2 | 8/2009 | Cowart et al. |
| 7,655,657 | B2 | 2/2010 | Stoner et al. |
| 7,897,792 | B2 | 3/2011 | Iikuea et al. |
| 7,910,578 | B2 | 3/2011 | Peters et al. |
| 8,143,274 | B2 | 3/2012 | Hattori et al. |
| 8,314,119 | B2 | 11/2012 | Schrimpf et al. |
| 8,337,941 | B2 | 12/2012 | Gubernator et al. |
| 8,563,550 | B2 | 10/2013 | Pevarello et al. |
| 8,633,019 | B2 | 1/2014 | Paushkin et al. |
| 8,765,747 | B2 | 7/2014 | Choi et al. |
| 8,846,661 | B2 | 9/2014 | Schrimpf et al. |
| 8,921,361 | B2 | 12/2014 | Cmiljanovic et al. |
| 8,940,716 | B2 | 1/2015 | Ye et al. |
| 9,340,537 | B2 | 5/2016 | Furet et al. |
| 9,371,336 | B2 | 6/2016 | Lee et al. |
| 9,399,649 | B2 | 7/2016 | Chen et al. |
| 9,617,268 | B2 | 4/2017 | Woll et al. |
| 9,969,754 | B2 | 5/2018 | Ratni et al. |
| 2002/0099208 | A1 | 7/2002 | Yu et al. |
| 2003/0004164 | A1 | 1/2003 | Bebbington et al. |
| 2003/0199526 | A1 | 10/2003 | Choquette et al. |
| 2004/0224952 | A1 | 11/2004 | Cowart et al. |
| 2005/0054836 | A1 | 3/2005 | Krainer et al. |
| 2005/0074801 | A1 | 4/2005 | Monia et al. |
| 2005/0159597 | A1 | 7/2005 | Ji et al. |
| 2006/0172962 | A1 | 8/2006 | Vickers et al. |
| 2006/0205741 | A1 | 9/2006 | Zhang et al. |
| 2007/0078144 | A1 | 4/2007 | Stockwell et al. |
| 2007/0105807 | A1 | 5/2007 | Sazani et al. |
| 2007/0191374 | A1 | 8/2007 | Hodgetts |
| 2008/0171792 | A1 | 7/2008 | Jobdevairakkam et al. |
| 2008/0255162 | A1 | 10/2008 | Bruendl et al. |
| 2009/0163464 | A1 | 6/2009 | Black et al. |
| 2009/0163515 | A1 | 6/2009 | Birault et al. |
| 2009/0170793 | A1 | 7/2009 | Gaur |
| 2009/0264433 | A1 | 10/2009 | Russell et al. |
| 2010/0004233 | A1 | 1/2010 | Iikura et al. |
| 2010/0035279 | A1 | 2/2010 | Gubernator et al. |
| 2010/0267721 | A1 | 10/2010 | Hohlweg et al. |
| 2011/0086833 | A1 | 4/2011 | Paushkin et al. |
| 2011/0118289 | A1 | 5/2011 | Giordani et al. |
| 2012/0083495 | A1 | 4/2012 | Heemskerk et al. |
| 2013/0046093 | A1 | 2/2013 | Lee et al. |
| 2014/0051672 | A1 | 2/2014 | Cheung et al. |
| 2014/0121197 | A1 | 5/2014 | Burli et al. |
| 2014/0206661 | A1 | 7/2014 | Axford et al. |
| 2014/0329825 | A1 | 11/2014 | Heback et al. |
| 2015/0005289 | A1 | 1/2015 | Qi et al. |
| 2015/0018301 | A1 | 1/2015 | Lee et al. |
| 2015/0057218 | A1 | 2/2015 | Zhong et al. |
| 2015/0080383 | A1 | 3/2015 | Yang et al. |
| 2015/0119380 | A1 | 4/2015 | Woll et al. |
| 2016/0244762 | A1 | 8/2016 | Vorechovsky et al. |
| 2017/0000794 | A1 | 1/2017 | Naryshkin |
| 2017/0001995 | A1 | 1/2017 | Metzger et al. |
| 2017/0002016 | A1 | 1/2017 | Shishido et al. |
| 2017/0096411 | A1 | 4/2017 | Vechorkin et al. |
| 2017/0151225 | A1 | 6/2017 | Dahl |
| 2017/0355989 | A1 | 12/2017 | Konstantinova et al. |
| 2018/0118748 | A1 | 5/2018 | Slaugenhaupt et al. |
| 2018/0161456 | A1 | 6/2018 | Naryshkin et al. |
| 2018/0282347 | A1 | 10/2018 | Arlt et al. |
| 2019/0264267 | A1 | 8/2019 | Yang et al. |
| 2020/0056173 | A1 | 2/2020 | Vargeese et al. |
| 2020/0080083 | A1 | 3/2020 | Vargeese et al. |
| 2023/0234942 | A1 * | 7/2023 | Sydorenko ........... C07D 417/14 514/210.2 |

FOREIGN PATENT DOCUMENTS

| | | | |
|---|---|---|---|
| CN | 103533835 | A | 1/2014 |
| CN | 101426772 | A | 5/2014 |
| CN | 104768960 | B | 3/2017 |
| DE | 2345064 | A1 | 4/1974 |
| EP | 1227084 | A1 | 7/2002 |
| EP | 2560008 | A2 | 2/2013 |
| EP | 2841428 | B1 | 8/2018 |
| FR | 2914188 | A1 | 10/2008 |
| GB | 1047935 | A | 11/1966 |
| GB | 1383409 | | 2/1975 |
| JP | S58-52307 | A | 3/1983 |
| JP | S61-36282 | | 2/1986 |
| JP | 2006 219453 | A | 8/2006 |
| JP | 2009/508957 | A | 3/2009 |
| JP | 2009/545540 | | 12/2009 |
| JP | 2012-530071 | A | 11/2012 |
| JP | 2013/40945 | | 2/2013 |
| JP | 2017-512834 | | 5/2017 |
| JP | 2017-533237 | A | 11/2017 |
| WO | 1993/023398 | A1 | 11/1993 |
| WO | 1994/026887 | A1 | 11/1994 |
| WO | 1996/039407 | A1 | 12/1996 |
| WO | 1998/025930 | A1 | 6/1998 |
| WO | 2001/053266 | A1 | 7/2001 |
| WO | 2002/062290 | A2 | 8/2002 |
| WO | 2002/087589 | A1 | 11/2002 |
| WO | 2004/009558 | A1 | 1/2004 |
| WO | 2004/019002 | A2 | 3/2004 |
| WO | 2004/029053 | A1 | 4/2004 |
| WO | 2004/043458 | A1 | 5/2004 |
| WO | 2004/113335 | A2 | 12/2004 |
| WO | 2005/012288 | A1 | 2/2005 |
| WO | 2005/019215 | A1 | 3/2005 |
| WO | 2005/061513 | A1 | 7/2005 |
| WO | 2005/066166 | A2 | 7/2005 |
| WO | 2005/072720 | A1 | 8/2005 |
| WO | 2005/105801 | A1 | 11/2005 |
| WO | 2006/131835 | A2 | 12/2006 |
| WO | 2006/138418 | A2 | 12/2006 |
| WO | 2007/003604 | A2 | 1/2007 |
| WO | 2007/016392 | A2 | 2/2007 |

(56) References Cited

FOREIGN PATENT DOCUMENTS

| | | | |
|---|---|---|---|
| WO | 2007/018738 A1 | 2/2007 | |
| WO | 2007/047913 A2 | 4/2007 | |
| WO | 2007/056580 A2 | 5/2007 | |
| WO | 2007/065892 A1 | 6/2007 | |
| WO | 2007/071055 A1 | 6/2007 | |
| WO | 2007/089584 A2 | 8/2007 | |
| WO | 2007/089611 A2 | 8/2007 | |
| WO | 2007/090073 A2 | 8/2007 | |
| WO | 2007/109211 A2 | 9/2007 | |
| WO | 2007/110364 A1 | 10/2007 | |
| WO | 2007/130383 A2 | 11/2007 | |
| WO | 2007/133561 A2 | 11/2007 | |
| WO | 2007/133756 A2 | 11/2007 | |
| WO | 2007/135121 A1 | 11/2007 | |
| WO | 2008/011109 A2 | 1/2008 | |
| WO | 2008/014822 A1 | 2/2008 | |
| WO | 2008/020302 A2 | 2/2008 | |
| WO | 2008/049864 A1 | 5/2008 | |
| WO | 2008/077188 A1 | 7/2008 | |
| WO | 2009/042907 A1 | 4/2009 | |
| WO | 2009/085945 A1 | 7/2009 | |
| WO | 2009/114874 A2 | 9/2009 | |
| WO | 2009/126635 A1 | 10/2009 | |
| WO | 2009/151546 A2 | 12/2009 | |
| WO | 2009/156861 A2 | 12/2009 | |
| WO | 2010/000032 A1 | 1/2010 | |
| WO | 2010/019236 A1 | 2/2010 | |
| WO | 2010/024903 A1 | 3/2010 | |
| WO | 2010/045303 A2 | 4/2010 | |
| WO | 2010/071819 A1 | 6/2010 | |
| WO | 2010/093425 A1 | 8/2010 | |
| WO | 2010/130934 A2 | 11/2010 | |
| WO | 2010/145208 A1 | 12/2010 | |
| WO | 2011/032045 A1 | 3/2011 | |
| WO | 2011/050245 A1 | 4/2011 | |
| WO | 2011/057204 A2 | 5/2011 | |
| WO | 2011/062853 A1 | 5/2011 | |
| WO | 2011/085990 A1 | 7/2011 | |
| WO | 2011/097641 A1 | 8/2011 | |
| WO | 2011/097643 A1 | 8/2011 | |
| WO | 2011/097644 A2 | 8/2011 | |
| WO | 2012/012467 A2 | 1/2012 | |
| WO | 2012/019106 A2 | 2/2012 | |
| WO | 2012/075393 A2 | 6/2012 | |
| WO | 2012/103806 A1 | 8/2012 | |
| WO | 2012/104823 A2 | 8/2012 | |
| WO | 2012/109395 A1 | 8/2012 | |
| WO | 2012/116965 A1 | 9/2012 | |
| WO | 2013/019938 A1 | 2/2013 | |
| WO | 2013/020993 A1 | 2/2013 | |
| WO | 2013/022990 A1 | 2/2013 | |
| WO | 2013/033223 A1 | 3/2013 | |
| WO | 2013/059606 A1 | 4/2013 | |
| WO | 2013/068769 A1 | 5/2013 | |
| WO | 2013/101974 A1 | 7/2013 | |
| WO | 2013/112788 A1 | 8/2013 | |
| WO | 2013/119916 A1 | 8/2013 | |
| WO | 2013/130689 A1 | 9/2013 | |
| WO | 2013/142236 A1 | 9/2013 | |
| WO | 2013/151877 A1 | 10/2013 | |
| WO | 2013/163190 A1 | 10/2013 | |
| WO | 2014/012050 A2 | 1/2014 | |
| WO | 2014/028459 A1 | 2/2014 | |
| WO | 2014/059341 A2 | 4/2014 | |
| WO | 2014/059356 A2 | 4/2014 | |
| WO | 2014/066836 A1 | 5/2014 | |
| WO | 2014/069675 A1 | 5/2014 | |
| WO | 2014/116845 A1 | 7/2014 | |
| WO | 2014/121287 A2 | 8/2014 | |
| WO | 2014/135244 A1 | 9/2014 | |
| WO | 2014/184163 A1 | 11/2014 | |
| WO | 2014/209841 A2 | 12/2014 | |
| WO | 2015/024876 A2 | 12/2014 | |
| WO | 2015/017589 A1 | 2/2015 | |
| WO | 2015/095446 A1 | 6/2015 | |
| WO | 2015/095449 A1 | 6/2015 | |
| WO | 2015/105657 A1 | 7/2015 | |
| WO | 2015/107425 A2 | 7/2015 | |
| WO | 2015/107494 A1 | 7/2015 | |
| WO | 2015/110446 A1 | 7/2015 | |
| WO | 2017/080967 A1 | 7/2015 | |
| WO | 2015/143185 A1 | 9/2015 | |
| WO | 2015/173181 A1 | 11/2015 | |
| WO | 2015/197503 A1 | 12/2015 | |
| WO | 2016/071283 A1 | 5/2016 | |
| WO | 2016/087417 A1 | 6/2016 | |
| WO | 2016/128343 A1 | 8/2016 | |
| WO | 2016/131776 A1 | 8/2016 | |
| WO | 2016/144351 A1 | 9/2016 | |
| WO | 2016/170163 A1 | 10/2016 | |
| WO | 2016/184832 A1 | 11/2016 | |
| WO | 2017/023987 A1 | 2/2017 | |
| WO | 2017/081111 A1 | 5/2017 | |
| WO | 2017/097728 A1 | 6/2017 | |
| WO | WO-2017100726 A1 * | 6/2017 | ........... A61K 31/415 |
| WO | 2017/153601 A1 | 9/2017 | |
| WO | 2017/175068 A1 | 10/2017 | |
| WO | 2017/189829 A1 | 11/2017 | |
| WO | 2017/210134 A1 | 12/2017 | |
| WO | 2018/013770 A1 | 1/2018 | |
| WO | 2018/081091 A1 | 5/2018 | |
| WO | 2018/187209 A1 | 10/2018 | |
| WO | 2018/218133 A1 | 11/2018 | |
| WO | 2018/226622 A1 | 12/2018 | |
| WO | 2019/005980 A1 | 1/2019 | |
| WO | 2019/005993 A1 | 1/2019 | |
| WO | 2019/028440 A1 | 2/2019 | |
| WO | 2019/165073 A1 | 8/2019 | |
| WO | 2019/183364 A1 | 9/2019 | |
| WO | 2019/183367 A1 | 9/2019 | |
| WO | 2019/191092 A1 | 10/2019 | |
| WO | 2019/191229 A1 | 10/2019 | |
| WO | 2020/005873 A1 | 1/2020 | |
| WO | 2020/005877 A1 | 1/2020 | |
| WO | 2020/005882 A1 | 1/2020 | |
| WO | 2020/190793 A1 | 9/2020 | |
| WO | 2020/231977 A1 | 11/2020 | |
| WO | 2021/007378 A1 | 1/2021 | |
| WO | 2021/084495 A1 | 5/2021 | |
| WO | 2021/174163 A1 | 9/2021 | |
| WO | 2021/207453 A1 | 10/2021 | |
| WO | 2022/103980 A1 | 5/2022 | |
| WO | 2023/009816 A1 | 2/2023 | |
| WO | 2023/244996 A2 | 12/2023 | |

OTHER PUBLICATIONS

Cheung et al., "Discovery of Small Molecule Splicing Modulators of Survival Motor Neuron-2 (SMN2) for the Treatment of Spinal Muscular Atrophy (Sma)", J. Med. Chem. vol. 61(24):11021-11036, Aug. 15, 2018 (received), Nov. 8, 2018 (published), pp. A-P.

Chiara Zanetta et al., "Molecular Therapeutic Strategies for Spinal Muscular Atrophies: Current and Future Clinical Trials", Clinical Therapeutics, 36(1):128-140, Dec. 17, 2013.

Coady et al., 2010, "Trans-splicing-mediated improvement in a severe mouse model of spinal muscular atrophy", J. Neurosci., vol. 30(1), pp. 126-130, 2010.

Combrink et al., "Respiratory syncytial virus fusion inhibitors. Part 6: An examination of the effect of structural variation for the benzimidazol-2-one heterocycle moiety", Bioorganic & Medicinal Chemistry Letters, 17(17):4784-4790, Aug. 4, 2007.

European Patent Office, Communication pursuant to Article 94(3) EPC, European Application No. 14877918.4, date of mailing Mar. 23, 2018.

Greene, Protective Groups in Organic Syntehsis, 1991, Wiley, New York, pp. v-xxi and 1-17.

H. Kubinyi, "3D QSAR in Drug Design—Theory Methods and Applications", pp. vii-ix and pp. 243-244, 1998.

Higuchi and V. Stella, "Pro-drugs as novel delivery systems", vol. 14 of the A.C.S., Symposium Series and in Bioreversible Carriers in Drug Design, ed., Edward B. Roche, American Pharmaceutical Association and Pergamon Press (1975).

(56) References Cited

OTHER PUBLICATIONS

Hua et al., "Peripheral SMN restoration is essential for long-term rescue of a severe SMA mouse model", Nature, vol. 478(7367), pp. 123-126, 2012.
Jarecki et al., "Diverse small-molecule modulators of SMN expression found by high-throughput compound screening: early leads towards a therapeutic for spinal muscular atrophy", Human molecular genetics, 14(14):2003-2018, 2005.
Knight et al., "Isoform-specific phosphoinositide 3-kinase inhibitors from an arylmorpholine scaffold", *Bioorganic & Medicinal Chemistry*, vol. 12(17):4749-4759, 2004.
Kocar, Transformations of 3-aminopyridazines. Synthesis of 4-oxo-4H-pyrimido [1,2-b]pyridazine and 1-(substituted pyridazin-3-yl)-1H-1,2,3-triazole derivatives, Arkivoc, vol. 8, 2002, 143-156.
Lazarev et al., "Factors Affecting Aggregate Formation in Cell Models of Huntington's Disease and Amyotrophic Lateral Sclerosis", *Acta Naturae*, vol. 5(2):81-89, Apr. 2013.
Le et al., "SMND7, the major product of the centromeric survival motor neuron (SMN2) gene, extends survival in mice with spinal muscular atrophy and associates with full-length SMN", Human Molecular Genetics, vol. 14(5), pp. 845-857, 2005.
Liu et al., "A novel nuclear structure containing the survival of motor neurons protein", EMBO J. vol. 15(14), pp. 3555-3565 (1996).
MacDonald et al., "Quantification Assays for Total and Polyglutamine-Expanded Huntington Proteins", PLOS One, 2014, vol. 9(5), published May 9, 2014, pp. 1-17.
Makhortova et al., "A screen for regulators of survival of motor neuron proteins levels", Nature chemical biology, vol. 7(8):544-552, 2011.
Markus Riessland et al., "The benzamide M344, a novel histone deacetylase inhibitor, significantly increases SMN2 RNA/protein levels in spinal muscular atrophy cells", Hum Genet 120:101-110, May 26, 2006.
Naryshkin et al., "SMN2 splicing modifiers improve motor function and longevity in mice with spinal muscular atrophy", Science, vol. 345(6197):688-693, 2014 (including supplementary materials).
Palacino et al., "SMN2 splice modulators enhance U1-pre-mRNA association and rescue SMA mice", Nature: Chemical Biology, pp. 511-517 and 5 Supplemental Pages +S1-S20, vol. 11, Jun. 1, 2015.
Passini et al., "Antisense Oligonucleotides delivered to the mouse CNS ameliorate symptoms of severe spinal muscular atrophy", Sci Transl. Med., vol. 3(72), 2001.
Peng, Lijie et al., "Identification of pyrido[1,2-alpha]pyrimidine-4-ones as new molecules improving the transcriptional functions of estrogen- related receptor alpha", Journal of medicinal chemistry, vol. 54(21):7729-7733, 2011.
Potkin et al., "New directions in therapeutics for Huntington disease", Future Neurology, vol. 13(2):101-121, May 2018.
Pryor et al., "Huntingtin promotes mTORC1 signaling in the pathogenesis of Huntington's disease", Sci. Signal, dated Oct. 28, 2014, 2014, vol. 7, Issue 349, ra103, pp. 1-12.
PubChem/NCBI Database accession No. CID 377422 [online], 2005, retrieved on Jul. 4, 2016, URL http://pubchem.nci.nlm.nih.gov/compound/377422.
Seisuke Mimori et al., "Protective Effects of 4-phenylbutyrate derivatives on the neuronal cell death and endoplasmic reticulum stress," Biological & Pharmaceutical Bulletin of Japan, 35(1):84-90, Jan. 1, 2012.
Shao, Ning et al., "Synthesis and structure-activity relationship (SAR) study of 4-azabenzoxazole analogues as H3 antagonists", Bioorganic & Medicinal chemistry letters, vol. 22(5):2075-2078, 2012.
Sin et al., "Respiratory syncytial virus fusion inhibitors. Part 7: Structure-activity relationships associated with a series of isatin oximes that demonstrate antiviral activity in vivo", Bioorganic & Medicinal Chemistry Letters, 19(16):4857-4862, Aug. 15, 2009.
Yuo et al., 2008, "5-(N-ethyl-N-isopropyl)-amiloride enhances SMN2 exon 7 inclusion and protein expression in spinal muscular atrophy cells", Annals of neurology, vol. 63(1):26-34, 2008.
Wermuth, "The Practice of Medicinal Chemistry", 2nd ed., 2003, Chapters 9-10.
Pubchem, Substance Record for SID 249779947, Mar. 31, 2015, "4H-Quinolizin-4one1; Hydrobromide".
International Search Report for PCT/EP2012/065499, mailed Sep. 28, 2012.
Written Opinion of the International Searching Authority in PCT/EP2012/065499, mailed Sep. 28, 2012.
International Search Report for PCT/EP2014/059699, mailed Aug. 25, 2014.
Written Opinion of the International Searching Authority in PCT/EP2014/059699, mailed Aug. 25, 2014.
International Search Report for PCT/EP2015/051066, mailed Feb. 19, 2015.
Written Opinion of the International Searching Authority in PCT/EP2015/051066, mailed Feb. 19, 2015.
International Search Report for PCT/EP2015/060343, mailed Jul. 13, 2015.
Written Opinion of the International Searching Authority in PCT/EP2015/060343, mailed Jul. 13, 2015.
International Search Report for PCT/EP2016/060952, mailed Jun. 29, 2016.
Written Opinion of the International Searching Authority in PCT/EP2016/060952, mailed Jun. 29, 2016.
International Search Report for PCT/EP2016/076905, mailed Feb. 9, 2017.
Written Opinion of the International Searching Authority in PCT/EP2016/076905, Feb. 9, 2017.
Written Opinion of the International Searching Authority in PCT/EP2016/077190, mailed Mar. 1, 2017.
International Search Report for PCT/EP2016/077190, mailed Mar. 1, 2017.
International Search Report for PCT/EP2016/079816, mailed Jan. 19, 2017.
Written Opinion of the International Searching Authority in PCT/EP2016/079816, mailed Jan. 19, 2017.
International Search Report for PCT/US2013/025292, mailed Aug. 30, 2013.
Written Opinion of the International Searching Authority in PCT/US2013/025292, mailed Aug. 30, 2013.
International Search Report for PCT/US2016/066042, mailed Mar. 16, 2017.
Written Opinion of the International Searching Authority in PCT/US2016/066042, mailed Mar. 16, 2017.
International Search Report for PCT/US2018/035954, mailed Oct. 1, 2018.
Written Opinion of the International Searching Authority in PCT/US2018/035954, mailed Oct. 1, 2018.
International Search Report for PCT/US2018/039775, mailed Oct. 29, 2018.
Written Opinion of the International Searching Authority in PCT/US2018/039775, mailed Oct. 29, 2018.
International Search Report for PCT/US2018/039794, mailed Oct. 25, 2018.
Written Opinion of the International Searching Authority in PCT/US2018/039794, mailed Oct. 25, 2018.
International Search Report for PCT/US2019/024068, mailed Jul. 10, 2019.
Written Opinion of the International Searching Authority in PCT/US2019/024068, mailed Jul. 10, 2019.
International Search Report for PCT/US2019/024278, mailed May 28, 2019.
Written Opinion of the International Searching Authority in PCT/US2019/024278, mailed May 28, 2019.
Andreassi, C. et al. 2001. Human Molecular Genetics 10, 2841-2849. "Aclarubicin treatment restores SMN levels to cells derived from type I spinal muscular atrophy patients."
Artursson P., et al. 1991. Biochem Biophys Res Comm 175, 880-5. "Correlation between oral drug absorption in humans and apparent drug permeability coefficients in human intestinal epithelial (Caco-2) cells."

(56) References Cited

OTHER PUBLICATIONS

Baldo, B. et al. 2012. J. Biol. Chem. 287, 1406-1414. "A screen for enhancers of clearance identifies huntingtin as a heat shock protein 90 (Hsp90) client protein."
Barbaro, B.A. et al. 2015. Human Molecular Genetics 24, 913-925 (published online Oct. 9, 2014). "Comparative study of naturally occurring huntingtin fragments in *Drosophila* points to exon 1 as the most pathogenic species in Huntington's disease."
Bates, G.P. et al. 2015. Nature Reviews, Disease Primers 1, 15005 (published online Apr. 23, 2015). "Huntington disease."
Bengart, P. et al. 2004. Nucleic Acids Res. 32, W154-W159. "Riboswitch finder—a tool for indentification of riboswitch RNAs."
Bhattacharyya, A. et al. 2007 Drug Discovery Today 12, 553-560. "Mining the GEMS—a novel platform technology targeting post-transcriptional control mechanisms."
Bibillo, A and Eickbush, T.H. 2002. J. Biol. Chem. 277, 34836-34845. "High Processivity of the Reverse Transcriptase from a Non-long Terminal Repeat Retrotransposon."
Carroll, J.B. et al. 2015. Lancet Neurol 14, 1135-1142 (No. 11—Nov. 2015). "Treating the whole body in Huntington's disease."
Cartegni, L. et al. 2003. Nucleic Acids Res. 31, 3568-3571. "ESEfinder: a web resource to identify exonic splicing enhancers."
Crooks, G. E., et al. 2004. Genome Research 14, 1188-1190. "WebLogo: a sequence logo generator."
Daguenet et al. 2015. EMBO reports 16, 1640-1655 (published online Nov. 13, 2015). "The pathogenicity of splicing defects: mechanistic insights into pre-mRNA processing inform novel therapeutic approaches."
DiFiglia, et al 1997. Science 277, 1990-1993. "Aggregation of Huntingtin in Neuronal Intranuclear Inclusions and Dystrophic Neurites in Brain".
Dobin, A. et al. 2013. Bioinformatics 29, 15-21. "STAR: ultrafast universal RNA-seq aligner."
Evers, M.M. et al. 2015. Molecular Neurodegeneration 10, Article No. 21 (published online Apr. 28, 2015). "Making (anti-) sense out of huntingtin levels in Huntington disease."
Fardaei, M. et al. 2002. Human Molecular Genetics 11, 805-814. "Three proteins, MBNL, MBLL and MBXL, co-localize in vivo with nuclear foci of expanded-repeat transcripts in DM1 and DM2 cells."
Fernandez-Nogales, M. et al. 2014. Nature Medicine 20, 881-885. "Huntington's disease is a four-repeat tauopathy with tau nuclear rods."
Gipson, T. A. et al. 2013. RNA Biology 10, 1647-1652. "Aberrantly spliced HTT, a new player in Huntington's disease pathogenesis."
Gray, M. et al. 2008. J. Neurosci. 28, 6182-6195. "Full-length human mutant huntingtin with a stable polyglutamine repeat can elicit progressive and selective neuropathogenesis in BACHD mice."
Griffiths-Jones, S. et al. 2005. Nucleic Acids Res. 33, D121-D124. "Rfam: annotating non-coding RNAs in complete genomes."
Griffiths-Jones, S. et al. 2006. Nucleic Acids Res. 34, D140-D144. "miRBase: microRNA sequences, targets and gene nomenclature."
Grillo, G. et al. 2003. Nucleic Acids Res. 31, 3608-3612. "PatSearch: a program for the detection of patterns and structural motifs in nucleotide sequences."
Grimson, A. et al. 2007. Molecular Cell 27, 91-105. "MicroRNA Targeting Specificity in Mammals: Determinants beyond Seed Pairing."
Heemskerk, J. et al. 2002. Nature Neuroscience Supplement 5, 1027-1029. "From chemical to drug: neurodegeneration drug screening and the ethics of clinical trials."
Heemskerk, J, et al. 2002. Trends Neurosci. 25, 494-496. "Teaching old drugs new tricks."
Heemskerk, J. et al. 2005. Chapter 16—"Therapeutics Development for Hereditary Disorders" in ed. Waxman, S. From Neuroscience to Neurology: Neuroscience, Molecular Medicine, and the Therapeutic Transformation of Neurology, pp. 285-291.
Hernandez-Imas, E. et al. 2015. PLoS One 10, e141735 (published online Oct. 28, 2015). "Functional Analysis of Mutations in Exon 9 of NF1 Revales the Presence of Several Elements Regulating Splicing."
Hodges, A. et al. 2006. Human Molecular Genetics 15, 965-977. "Regional and cellular gene expression changes in human Huntington's disease brain."
Hua et al. 2007. PLoS Biol 5, e73. Enhancement of SMN2 Exon 7 "Inclusion by Antisense Oligonucleotides Targeting the Exon."
Hua et al. 2008. American J. of Human Genetics 82, 834-848. "Antisense Masking of an hnRNP A1/A2 Intronic Splicing Silencer Corrects SMN2 Splicing in Transgenic Mice."
Hughes, A.C. et al. 2014. J. Mol. Biol. 426, 1428-1438. "Identification of Novel Alternative Splicing Events in the Huntingtin Gene and Assessment of the Functional Consequences Using Structural Protein Homology Modelling."
The Huntington's Disease Collaborative Research Group, 1993, Cell, 72, pp. 971-983 (1993). "A novel gene containing a trinucleotide repeat that is expanded and unstable on Huntington's Disease chromosomes."
Janas, A. M. 2015. "A Stem Cell Model of the Motor Circuit Reveals Distinct Requirements for SMN in Motor Neuron Survival and Function."
Jacobs, G.H. et al. 2006. Nucleic Acids Res. 34, suppl_1, D37-D40. "Transterm-extended search facilities and improved integration with other databases."
Kanadia, R.N. et al. 2003. Science 302, 1978-1980. "A Muscleblind Knockout Model for Myotonic Dystrophy."
Kaplan, A. et al. 2012. Prog. Neurobiol. 99(3), 262-280. "Therapeutic approaches to preventing cell death in Huntington disease."
Kim, D. et al. 2013. Genome Biology 14, Article No. R36. "TopHat2: accurate alignment of transcriptomes in the presence of insertions, deletions and gene fusions."
Kordasiewicz, H.B. et al. 2012. Neuron, 74, 1031-1044. "Sustained Therapeutic Reversal of Huntington's Disease by Transient Repression of Huntingtin Synthesis".
Kuhn, A. et al. 2007. Human Molecular Genetics 16, 1845-1861. "Mutant huntingtin's effects on striatal gene expression in mice recapitulate changes observed in human Huntington's disease brain and do not differ with mutant huntingtin length or wild-type huntingtin dosage."
Labadorf, A.T. et al. 2015. Plos One 10(10): e0141298 (published online Oct. 23, 2015). "Evidence of Extensive Alternative Splicing in Post Mortem Human Brain HTT Transcription by mRNA Sequencing." (including supplemental information).
Labadorf, A. et al. 2015. PLoS One 10(12): e0143563 (published online Dec. 4, 2015). "RNA Sequence Analysis of Human Huntington Disease Brain Reveals an Extensive Increase in Inflammatory and Developmental Gene Expression."
Labbadia, J. et al. 2013. Trends Biochem. Sci. 38, 378-385. "Huntington's disease: underlying molecular mechanisms and emerging concepts."
Landles, C. et al. 2010. J. Bio. Chem. 285, 8808-8823. "Protoelysis of Mutant Huntington Produces an Exon 1 Fragment That Accumulates as an Aggregated Protein in Neuronal Nuclei in Huntington Disease."
Lei, et al. 2005. Nucleic Acids Res 33, 3897-3909. "Exonization of AluYa5 in the human ACE gene requires mutations in both 3' and 5' splice sites and is facilitated by a conserved splicing enhancer."
Liang, Y. et al. 2009. Brain Res. 2009 1286, 221-229. "ATF3 plays a protective role against toxicity by N-terminal fragment of mutant huntingtin in stable PC12 cell line."
Love, M. I. et al. 2014. Genome Biology 15, 550. "Moderated estimation of fold change and dispersion for RNA-seq data with DESeq2."
Lunkes, A. et al. 2002. Molecular Cell 10, 259-269. "Proteases Acting on Mutant Huntingtin Generate Cleaved Products that Differentially Build Up Cytoplasmic and Nuclear Inclusions."
Macke, T.J. 2001. Nucleic Acids Res. 29, 4724-4735. "RNAMotif, an RNA secondary structure definition and search algorithm."
Mahmood, I. et al. 1996. Xenobiotica 26, 887-895. "Interspecies scaling: predicting clearance of drugs in humans. Three different approaches."

(56) References Cited

OTHER PUBLICATIONS

Mahmood, I. 2006. Pharm. Sci. 95, 1810-1821. "Prediction of human drug clearance from animal data: Application of the rule of exponents and 'fu corrected intercept method' (FCIM)."
Mahmoudi, S et al. 2010. PLoS Biology 8(11), e10000521. "WRAP53 is Essential for Cajal Body and for Targeting the Survival of Motor Neuron Complex to Cajal Bodies."
Mangiarini, L. 1996. Cell 87, 493-506. "Exon 1 of the HD Gene with an Expanded CAG Repeat Is Sufficient to Cause a Progressive Neurological Phenotype in Transgenic Mice."
Mantione, K.J. et al. 2014. Med. Sci. Monit. Basic Res. 20, 138-141. "Comparing Bioinformation Gene Expression Profiling Methods: Microarray and RNA-Seq."
Mendoza, L.G. et al. 1999. BioTechniques 27, 778-788. "Hight-Throughput Microarray-Based Enzyme-Linked Immunosorbent Assay (ELISA)."
Mielcarek, M. et al. 2014. PLOS Genetics 10: 8 e1004550. "Dysfunction of the CNS-Heart Axis in Mouse Models of Huntington's Disease."
Mignone, F. et al. 2005. Nucleic Acids Res. 33, D141-D146. "UTRdb and UTRsite: a collection of sequences and regulatory motifs of the untranslated regions of eukaryotic mRNAs."
Mort, M. et al. 2015. J. of Huntington's Disease 4(2 of 4), 161-171. "Huntingtin Exists as Multiple Splice Forms in Human Brain."
Neuder, A. et al. 2014. BMC Medical Genomics 7:60. "A common gene expression signature in Huntington's disease patient brain regions."
Paganetti, P. et al. 2009. ChemBioChem 10, 1678-1688. "Development of Method for the High-Throughput Quantification of Cellular Proteins."
Pouladi, M. et al. 2013. Nature Review Neuroscience 14, 709-721. "Choosing an animal model for the study of Huntington's disease."
Ratovitski, T. et al. 2012. Cell Cycle 11, 2006-2021. "Huntingtin protein interactions altered by polyglutamine expansion as determined by quantitative proteomic analysis."
Reiner, A. et al. 2011. International Review of Neurobiology 98, 325-372. "Genetics and neuropathology of Huntington's disease."
Ruzo, A. et al. 2015. PLoS One 10, e0127678 (published online May 26, 2015). "Discovery of Novel Isoforms of Huntingtin Reveals a New Hominid-Specific Exon."
Sadeghian, H. et al. 2011. Arch. Neurol. 68, 650-652. "Huntington Chorea Presenting with Motor Neuron Disease."
Sathasivam, K. et al. 2013. Proc. Natl. Acad. Sci. 110, 2366-2370. "Aberrant splicing of HTT generates the pathogenic exon 1 protein in Huntington disease."
Schilling, G. et al. 2007. J Neuropathol. Exp. Neurol. 66, 313-320. "Characterization of Huntingtin Pathologic Fragments in Human Huntington Disease, Transgenic Mice, and Cell Models."
Schwab, C. et al. 2008. J. Neuropathol Exp Neurol 67, 1159-1165. "Colocalization of Transactivation-Responsive DNA-Binding Protein 43 and Huntingtin in Inclusions of Huntington Disease."
Shlyakhtenko, L.S. et al. 2007. Nanomedicine: Nanotech., Bio., and Med. 3, 192-197. "Single-molecule selection and recovery of structure-specific antibodies using atomic force microscopy."
Southwell, A.L. et al. 2013. Hum. Mol. Genet. 22, 18-34. "A fully humanized transgenic mouse model of Huntington disease."
Stanek, L.M. et al. 2014. Human Gene Therapy 25, 461-474. "Silencing Mutant Huntingtin by Adeno-Associated Virus-Mediated RNA Interference Ameliorates Disease Manifestations in the YAC128 Mouse Model of Huntington's Disease."
Stoilov, P. et al. 2008. Proc. Natl. Acad. Sci. 105, 11218-11223. "A high-throughput screening strategy identifies cardiotonic steroids as alternative splicing modulators."
Taylor et al. 1999. Nat. Biotechnol. 17, 1097-1100 "Induction of endogenous Bcl-xS through the control of Bcl-x pre-mRNA splicing by antisense oligonucleotides."
Van der Burg, J.M.M. et al. 2009. The Lancet (Neurology) 8, 765-774. "Beyond the brain: widespread pathology in Huntington's disease."
Varma, H. et al. 2008. Comb Chem High Throughput Screen 11, 238-248. "High Throughput Screening for Neurodegeneration and Complex Disease Phenotypes."
Vickers et al., 2006. J. Immunol. 176, 3652-3661 "Modification of MyD88 mRNA splicing and inhibition of IL-1beta signaling in cell culture and in mice with a 2'-O-methoxyethyl-modified oligonucleotide."
Wachter, A. 2014. Trends in Genetics 30, 172-181. "Gene regulation by structured mRNA elements."
Weiland, M. et al. 2012. Methods 56, 351-357. "Engineering of ribozyme-based riboswitches for mammalian cells."
Wild, E.J. et al. 2014. Movement Disorders 29, 1434-1445. "Targets for Future Clinical Trials in Huntington's Disease: What's in the Pipeline?"
Wilton et al. 1999. Neuromuscul. Disord. 9, 330-338. "Specific removal of the nonsense mutation from the mdx dystrophin mRNA using antisense oligonucleotides."
Xiong, H.Y. et al. 2015. Science 347, 1254806 (published online Dec. 18, 2014.) "The human splicing code reveals new insights into the genetic determinants of disease."
Yen, L. et al. 2004. Nature 431, 471-6. "Exogenous control of mammalian gene expression through modulation of RNA self-cleavage."
Yeo, G. et al. 2004. J. Comput. Biol. 11, 377-394. "Maximum entropy modeling of short sequence motifs with applications to RNA splicing signals."
Younis et al. 2010. Molecular and Cellular Biology 30, 1718-1728. "Rapid-Response Splicing Reporter Screens Identify Differential Regulators of Constitutive and Alternative Splicing."
Yu, S. et al. 2014. Trends in Pharmacological Sci. 35, 53-62. "Drugging unconventional targets: insights from Huntington's disease."
Zona, S. et al. 2014. Biochimica et Biophysica Acta 1839, 1316-1322. "FOXM1: An emerging master regulator of DNA damage response and genotoxic agent resistance."
Nair, A.B. et al. 2016. J. Basic and Clinical Pharmacy 7, 27-31. "A simple and practical guide for dose conversion between animals and human."
Neuder, A. et al. 2017. Scientific Reports 7, 1307 (published online May 2, 2017). "The pathogenic exon 1 HTT protein is produced by incomplete splicing in Huntington's disease patients."
Nopoulos, P. C. 2016. Dialogues Clin Neurosci 18, 91-98. "Huntington disease: a single-gene degenerative disorder of the striatum."
Ratni, H. et al. 2016. J. Med. Chem. 59, 6086-6100. "Specific Correction of Alternative Survival Motor Neuron 2 Splicing by Small Molecules: Discovery of a Potential Novel Medicine To Treat Spinal Muscular Atrophy."
Rüb, U. et al. 2016. Brain Pathol. 26, 726-740. "Huntington's disease (HD): the neuropathology of a multisystem neurodegenerative disorder of the human brain."
Saudou, F. et al. 2016. Neuron 89, 910-926. "The Biology of Huntingtin."
Wang, G. et al. 2016. Proc. Natl. Acad. Sci. 113, 3359-3364. "Ablation of huntingtin in adult neurons is nondeleterious but its depletion in young mice causes acute pancreatitis."
Woll, M.G. et al. 2016. J. Med. Chem. 59, 6070-6085. "Discovery and Optimization of Small Molecule Splicing Modifiers of Survival Motor Neuron 2 as a Treatment for Spinal Muscular Atrophy."
International Search Report for PCT/EP2015/063894, mailed Aug. 6, 2015.
Written Opinion of the International Searching Authority in PCT/EP2015/063894, mailed Aug. 6, 2015.
Nair et al., "Synthesis and fluorescence properties of 3-benzoxa- and thiazol-2-ylquinoline-5 or 7-maleimides," Indian Journal of Chemistry, Sep. 2004, vol. 43B, pp. 1944-1949.
Naik et al., "Studies in the Vilsmeier-Haack Reaction: Part XVI-Synthesis of 7-Amino-3-hetrarylquinoline Fluorophore & Derivatives," Indian Journal of Chemistry, Jun. 1977, pp. 506-508.
International Search Report for PCT/US19/38889, mailed Aug. 8, 2019.
Written Opinion of the International Searching Authority in PCT/US19/38889, mailed Aug. 8, 2019.

(56) References Cited

OTHER PUBLICATIONS

International Search Report for PCT/US19/38895, mailed Aug. 14, 2019.
Written Opinion of the International Searching Authority in PCT/US19/38895, mailed Aug. 14, 2019.
International Search Report for PCT/US19/38900, mailed Aug. 20, 2019.
Written Opinion of the International Searching Authority in PCT/US19/38900, mailed Aug. 20, 2019.
International Search Report for PCT/US20/32446, mailed Jul. 7, 2020.
Written Opinion of the International Searching Authority in PCT/US20/32446, mailed Jul. 7, 2020.
International Search Report for PCT/US20/41300, mailed Oct. 16, 2020.
Written Opinion of the International Searching Authority in PCT/US20/41300, mailed Oct. 16, 2020.
Abdul Khader K K et al., "Regioselective synthesis of C-2 substituted imidazo[4,5-b]pyridines utilizing palladium catalysed C—N bond forming reactions with enolizable heterocycles", Tetrahedron Letters, Elsevier, Amsterdam, NL, vol. 55, No. 10, Feb. 1, 2014, p. 1778-1783.
Mariusz Mojzych et al., "Synthesis of pyrazolo[4,3-e][1,2,4]triazine sulfonamides, novel Sildenafil analogs with tyrosinase inhibitory activity", Bioorganic & Medicinal Chemistry, vol. 22, No. 23, Oct. 18, 2014, p. 6616-6624.
Ingo Knepper et al., "3-Acylindoles as versatile starting materials for pyridine ring annulation: synthesis of 1-deazapurine isosteres", Tetrahedron, vol. 67, No. 29, May 14, 2011, p. 5293-5303.
Chloé Copin et al, "S N Ar versus Buchwald-Hartwig Amination/Amidation in the Imidazo[2,1-b][1,3,4]thiadiazole Series : S N Ar versus Buchwald-Hartwig Amination/Amidation", European Journal of Organic Chemistry, vol. 2015, No. 31, Sep. 29, 2015, p. 6932-6942.
Patel Harun M et al, "2,5,6-Trisubstituted imidazo[2,1-b][1,3,4]thiadiazoles: Search for antihyperlipidemic agents", European Journal of Medicinal Chemistry, Editions Scientifique Elsevier, Paris, FR, vol. 65, Apr. 18, 2013, p. 119-133.
Mazzone G et al., "Sintesi e valutazione biologica preliminare di imidazo[2,1-b]-1,3-4-tiadiazoli-2,6-diarilsostituti", Farmaco, Edizione Scientifica, Societa Chimica Italiana, Pavia, IT, vol. 39, No. 7, Jan. 1, 1984, p. 585-598. English abstract only.
Fascio Mirta L et al, "Synthesis and antiviral activity of some imidazo[1,2-b][1,3,4]thiadiazole carbohydrate derivatives", Carbohydrate Research, vol. 480, May 21, 2019, p. 61-66.
Database Registry [Online], Chemical Abstracts Service, Columbus, Ohio, US; Feb. 22, 2018, Database accession No. 2178867-25-7.
Database Registry [Online], Chemical Abstracts Service, Columbus, Ohio, US; Sep. 25, 2017, Database accession No. 2130694-60-7.
Database Registry [Online], Chemical Abstracts Service, Columbus, Ohio, US; Sep. 24, 2017, Database accession No. 2130300-22-8.
Database Registry [Online], Chemical Abstracts Service, Columbus, Ohio, US; Sep. 18, 2017, Database accession No. 2128311-64-6.
Chemical Abstracts Registry No. 2107242-04-04, indexed in the Registry file on STN CAS Online Aug. 2, 2017. (Year: 2017).
USPTO, Office Action dated Feb. 4, 2021 in U.S. Appl. No. 16/617,450; see whole document in general and compounds on pp. 10-14 and 15-18 in particular.
Daldin et al., "Polyglutamine expansion affects huntingtin conformation in multiple Huntington's disease models", Scientific Reports, vol. 7, 15 pages, 2017.
Gleave et al., "Synthesis and evaluation of 3-amino-6-aryl- pyridazines as selective CB2 agonists for the treatment of inflammatory pain", Bioorganic & Medicinal Chemistry Letters, vol. 20, pp. 465-468, 2010.
Kaida et al., "U1 snRNP protects pre-mRNAs from premature cleavage and polyadenylation"; Nature, vol. 468, pp. 664-669; Dec. 2, 2010.
Ross & Tabrizi, "Huntington's disease: from molecular pathogenesis to clinical treatment"; The Lancet Neurology, vol. 10, pp. 83-98, Jan. 2011.
Wang et al., "Mechanism of alternative splicing and its regulation (Review)", Biomedical Reports, vol. 3, pp. 152-158, 2015.
Berg, J.M., Tymoczko, J.L., & Stryer, L., *Biochemistry* ($5^{th}$ ed.), p. 798, 2002.
Opposition in European Patent No. 3,386,511, Feb. 25, 2022, 29 pages.
Bhattacharyya et al., Small molecule splicing modifiers with systemic HTT-lowering activity Nature Communications 12(7299), 2021.
Boudreau et al., 2009. "Nonallele-Specific Silencing of Mutant and Wild-Type Huntingtin Demonstrates Therapeutic Efficacy in Huntington''s Disease Mice." Molecular Therapy: The Journal of the American Society of Gene Therapy 17 (6): 1053-63.
Campagne et al., 2019. "Structural Basis of a Small Molecule Targeting RNA for a Specific Splicing Correction." Nature Chemical Biology 15 (12): 1191-98, 2019.
Connelly et al., 2016. "The Emerging Role of RNA as a Therapeutic Target for Small Molecules." Cell Chemical Biology 23 (9): 1077-90.
Effenberger et al., 2016. "Modulating Splicing with Small Molecular Inhibitors of the Spliceosome." Wiley Interdisciplinary Reviews. RNA 8 (2).
Holste et al., 2008. "Strategies for Identifying RNA Splicing Regulatory Motifs and Predicting Alternative Splicing Events." PLoS Computational Biology 4 (1): e21.
Marxreiter et al., 2020. "Huntington Lowering Strategies." International Journal of Molecular Sciences 21 (6).
Mount et al., A catalogue of splice junction sequences Nucleic Acids Research 10(2):459-472 (Jan. 22, 1982).
Nishigaki et al., Syntheses of 9-Deazatheophyllines and 6-Deoxy-9-deazatheophyllines Chemical and Pharmaceutical Bulletin 28(5):1636-1641 (1980).
Ratni et al., Discovery of Risdiplam, a Selective Survival of Motor Neuron-2 (SMN2) Gene Splicing Modifier . . . , Journal of Medicinal Chemistry, 61 (15), 6501-6517 (2018).
Ritz et al., Dose-Response Analysis Using R PLos One 10(12) (Dec. 30, 2015).
Romo et al., 2018. "A Fresh Look at Huntington mRNA Processing in Huntington''s Disease." Journal of Huntington''s Disease 7 (2): 101-8.
Schilling Judith, Meike Broemer, Ilian Atanassov, Yvonne Duernberger, Ina Vorberg, Christoph Dieterich, Alina Dagane, et al. 2019. "Deregulated Splicing Is a Major Mechanism of RNA-Induced Toxicity in Huntington''s Disease." Journal of Molecular Biology 431 (9): 1869-77.
Sibley et al., 2016. "Lessons from Non-Canonical Splicing." Nature Reviews. Genetics 17 (7): 407-21.
Sivaramakrishnan et al., Binding to SMN2 pre-mRNA-protein complex elicits specificity for small molecule splicing modifiers Nature Communications 8(1) (Nov. 2017).
Southwell et al. 2018. "Huntingtin Suppression Restores Cognitive Function in a Mouse Model of Huntington''s Disease." Science Translational Medicine (10) 1-12.
Southwell et al. 2017. "A Novel Humanized Mouse Model of Huntington Disease for Preclinical Development of Therapeutics Targeting Mutant Huntingtin Alleles." Human Molecular Genetics 26 (6): 1115-32.
Tabrizi et al., Huntington Lowering Strategies for Disease Modification in Huntington's Disease J. Neuron 101(5):801-819 (Mar. 6, 2019).
Wild et al., 2017. "Therapies Targeting DNA and RNA in Huntington''s Disease." Lancet Neurology 16 (10): 837-47.
International Search Report in PCT/US2021/059010, dated Apr. 26, 2022.
Written Opinion of the International Searching Authority in PCT/US2021/059010, dated Apr. 26, 2022.

(56) References Cited

OTHER PUBLICATIONS

Reply to Opposition in European Patent No. 3,386,511, Jul. 7, 2022, 427 pages.
EPO Board Communication in Opposition in European Patent No. 3,386,511, Oct. 18, 2022, 12 pages.
International Search Report in PCT/US2021/026316, dated Aug. 5, 2021.
Written Opinion of the International Searching Authority in PCT/US2021/026316, dated Aug. 5, 2021.
Burli et al., "Design, Synthesis, and Biological Evaluation of Potent and Selective Class IIa Histone Deacetylase (HDAC) Inhibitors as a Potential Therapy for Huntington's Disease", Journal of Medicinal Chemistry, vol. 56, pp. 9934-9954, 2013.
Chemical Abstracts Registry No. 1381103-87-2, indexed in the Registry file on STN CAS Online Jul. 4, 2012. (Year: 2012).
Chemical Abstracts Registry No. 1381109-95-0, indexed in the Registry file on STN CAS Online Jul. 4, 2012. (Year: 2012).
Chemical Abstracts Registry No. 1381103-06-5, indexed in the Registry file on STN CAS Online Jul. 4, 2012. (Year: 2012).
Chemical Abstracts Registry No. 1381085-12-6, indexed in the Registry file on STN CAS Online Jul. 4, 2012. (Year: 2012).
Chemical Abstracts Registry No. 1381084-38-3, indexed in the Registry file on STN CAS Online Jul. 4, 2012. (Year: 2012).
Chemical Abstracts Registry No. 1381084-19-0, indexed in the Registry file on STN CAS Online Jul. 4, 2012. (Year: 2012).
Chemical Abstracts Registry No. 1381069-02-8, indexed in the Registry file on STN CAS Online Jul. 4, 2012. (Year: 2012).
Chemical Abstracts Registry No. 1381060-23-6, indexed in the Registry file on STN CAS Online Jul. 4, 2012. (Year: 2012).
Chemical Abstracts Registry No. 1381036-73-2, indexed in the Registry file on STN CAS Online Jul. 4, 2012. (Year: 2012).
Chemical Abstracts Registry No. 1381033-11-9, indexed in the Registry file on STN CAS Online Jul. 4, 2012. (Year: 2012).
Chemical Abstracts Registry No. 1381016-89-2, indexed in the Registry file on STN CAS Online Jul. 4, 2012. (Year: 2012).
Chemical Abstracts Registry No. 1381016-41-6, indexed in the Registry file on STN CAS Online Jul. 4, 2012. (Year: 2012).
Chemical Abstracts Registry No. 1381013-97-3, indexed in the Registry file on STN CAS Online Jul. 4, 2012. (Year: 2012).
Chemical Abstracts Registry No. 1380991-96-7, indexed in the Registry file on STN CAS Online Jul. 4, 2012. (Year: 2012).
Chemical Abstracts Registry No. 1380991-09-2, indexed in the Registry file on STN CAS Online Jul. 4, 2012. (Year: 2012).
Chemical Abstracts Registry No. 1380955-66-7, indexed in the Registry file on STN CAS Online Jul. 4, 2012. (Year: 2012).
Chemical Abstracts Registry No. 1380889-28-0, indexed in the Registry file on STN CAS Online Jul. 3, 2012. (Year: 2012).
Chemical Abstracts Registry No. 1380857-75-9, indexed in the Registry file on STN CAS Online Jul. 3, 2012. (Year: 2012).
Chemical Abstracts Registry No. 1350420-68-6, indexed in the Registry file on STN CAS Online Dec. 7, 2011. (Year: 2011).
Chemical Abstracts Registry No. 1350191-80-8, indexed in the Registry file on STN CAS Online Dec. 7, 2011. (Year: 2011).
Chemical Abstracts Registry No. 919610-78-9, indexed in the Registry file on STN CAS Online Feb. 6, 2007. (Year: 2007).
Chemical Abstracts Registry No. 919610-77-8, indexed in the Registry file on STN CAS Online Feb. 6, 2007. (Year: 2007).
Chemical Abstracts Registry No. 919610-71-2, indexed in the Registry file on STN CAS Online Feb. 6, 2007. (Year: 2007).
Chemical Abstracts Registry No. 919610-70-1, indexed in the Registry file on STN CAS Online Feb. 6, 2007. (Year: 2007).
Chemical Abstracts Registry No. 919610-69-8, indexed in the Registry file on STN CAS Online Feb. 6, 2007. (Year: 2007).
Chemical Abstracts Registry No. 919494-40-9, indexed in the Registry file on STN CAS Online Feb. 6, 2007. (Year: 2007).
Chemical Abstracts Registry No. 919494-38-5, indexed in the Registry file on STN CAS Online Feb. 6, 2007. (Year: 2007).
Chemical Abstracts Registry No. 919494-22-7, indexed in the Registry file on STN CAS Online Feb. 6, 2007. (Year: 2007).
Chemical Abstracts Registry No. 1348577-48-9, indexed in the Registry file on STN CAS Online Dec. 4, 2011. (Year: 2011).
Chemical Abstracts Registry No. 1380990-95-3, indexed in the Registry file on STN CAS Online Jul. 4, 2012. (Year: 2012).
Chemical Abstracts Registry No. 1380944-26-2, indexed in the Registry file on STN CAS Online Jul. 4, 2012. (Year: 2012).
Chemical Abstracts Registry No. 1380879-49-1, indexed in the Registry file on STN CAS Online Jul. 3, 2012. (Year: 2012).
Chemical Abstracts Registry No. 1380858-18-3, indexed in the Registry file on STN CAS Online Jul. 3, 2012. (Year: 2012).
Chemical Abstracts Registry No. 1381109-36-9, indexed in the Registry file on STN CAS Online Jul. 4, 2012. (Year: 2012).
Chemical Abstracts Registry No. 1381106-70-2, indexed in the Registry file on STN CAS Online Jul. 4, 2012. (Year: 2012).
Chemical Abstracts Registry No. 1380864-49-2, indexed in the Registry file on STN CAS Online Jul. 3, 2012. (Year: 2012).
Chemical Abstracts Registry No. 1380859-62-0, indexed in the Registry file on STN CAS Online Jul. 3, 2012. (Year: 2012).
Chemical Abstracts Registry No. 1381035-24-0, indexed in the Registry file on STN CAS Online Jul. 4, 2012. (Year: 2012).
Chemical Abstracts Registry No. 2059673-20-8, indexed in the Registry file on STN CAS Online Jan. 26, 2017. (Year: 2017).
Chemical Abstracts Registry No. 2224380-48-5, indexed in the Registry file on STN CAS Online May 20, 2018.
Chemical Abstracts Registry No. 2055492-51-6, indexed in the Registry file on STN CAS Online Jan. 5, 2017.
Chemical Abstracts Registry No. 1608159-30-3, indexed in the Registry file on STN CAS Online May 22, 2014.
Chemical Abstracts Registry No. 1349790-59-5, indexed in the Registry file on STN CAS Online Dec. 6, 2011.
Chemical Abstracts Registry No. 1349075-20-2, indexed in the Registry file on STN CAS Online Dec. 5, 2011.
Chemical Abstracts Registry No. 1348522-09-7, indexed in the Registry file on STN CAS Online Dec. 4, 2011.
Chemical Abstracts Registry No. 1348048-78-1, indexed in the Registry file on STN CAS Online Dec. 4, 2011.
Chemical Abstracts Registry No. 1347905-79-6, indexed in the Registry file on STN CAS Online Dec. 4, 2011.
Chemical Abstracts Registry No. 1347641-28-4, indexed in the Registry file on STN CAS Online Dec. 2, 2011.
Chemical Abstracts Registry No. 1347614-67-8, indexed in the Registry file on STN CAS Online Dec. 2, 2011.
Chemical Abstracts Registry No. 1347467-65-5, indexed in the Registry file on STN CAS Online Dec. 2, 2011.
Chemical Abstracts Registry No. 2213453-82-6, indexed in the Registry file on STN CAS Online Apr. 16, 2018.
Chemical Abstracts Registry No. 2170880-44-9, indexed in the Registry file on STN CAS Online Jan. 24, 2018.
Chemical Abstracts Registry No. 2170880-30-3, indexed in the Registry file on STN CAS Online Jan. 24, 2018.
Chemical Abstracts Registry No. 2170880-29-0, indexed in the Registry file on STN CAS Online Jan. 24, 2018.
Chemical Abstracts Registry No. 2170876-00-1, indexed in the Registry file on STN CAS Online Jan. 24, 2018.
Chemical Abstracts Registry No. 2170875-99-5, indexed in the Registry file on STN CAS Online Jan. 24, 2018.
Chemical Abstracts Registry No. 2138484-61-2, indexed in the Registry file on STN CAS Online Nov. 3, 2017.
Chemical Abstracts Registry No. 2117679-02-2, indexed in the Registry file on STN CAS Online Aug. 21, 2017.
Chemical Abstracts Registry No. 2098833-57-7, indexed in the Registry file on STN CAS Online Jun. 21, 2017.
Chemical Abstracts Registry No. 2096985-34-9, indexed in the Registry file on STN CAS Online May 23, 2017.
Chemical Abstracts Registry No. 1957192-78-7, indexed in the Registry file on STN CAS Online Jul. 21, 2016.
Chemical Abstracts Registry No. 1579964-39-8, indexed in the Registry file on STN CAS Online Apr. 3, 2014.
Chemical Abstracts Registry No. 1381102-22-2, indexed in the Registry file on STN CAS Online Jul. 4, 2012.
Chemical Abstracts Registry No. 1381055-52-2, indexed in the Registry file on STN CAS Online Jul. 4, 2012.

(56) References Cited

OTHER PUBLICATIONS

Chemical Abstracts Registry No. 1380859-69-7, indexed in the Registry file on STN CAS Online Jul. 4, 2012.
Chemical Abstracts Registry No. 1283718-58-0, indexed in the Registry file on STN CAS Online Apr. 21, 2011.
Chemical Abstracts Registry No. 919610-72-3, indexed in the Registry file on STN CAS Online Feb. 6, 2007.
Chemical Abstracts Registry No. 919496-89-2, indexed in the Registry file on STN CAS Online Feb. 6, 2007.
Chemical Abstracts Registry No. 919494-45-4, indexed in the Registry file on STN CAS Online Feb. 6, 2007.
Chemical Abstracts Registry No. 919494-44-3, indexed in the Registry file on STN CAS Online Feb. 6, 2007.
Chemical Abstracts Registry No. 919494-39-6, indexed in the Registry file on STN CAS Online Feb. 6, 2007.
Chemical Abstracts Registry No. 919494-26-1, indexed in the Registry file on STN CAS Online Feb. 6, 2007.
Chemical Abstracts Registry No. 919494-23-8, indexed in the Registry file on STN CAS Online Feb. 6, 2007.
Chemical Abstracts Registry No. 919494-19-2, indexed in the Registry file on STN CAS Online Feb. 6, 2007.
Chemical Abstracts Registry No. 919493-72-4, indexed in the Registry file on STN CAS Online Feb. 6, 2007.
Chemical Abstracts Registry No. 919493-71-3, indexed in the Registry file on STN CAS Online Feb. 6, 2007.
Chemical Abstracts Registry No. 848953-00-4, indexed in the Registry file on STN CAS Online Apr. 21, 2005.
Chemical Abstracts Registry No. 848952-99-8, indexed in the Registry file on STN CAS Online Apr. 21, 2005.
Chemical Abstracts Registry No. 120821-79-6, indexed in the Registry file on STN CAS Online May 26, 1989.
Chemical Abstracts Registry No. 1369171-97-0, indexed in the Registry file on STN CAS Online Apr. 16, 2012.
Chemical Abstracts Registry No. 1330263-81-4, indexed in the Registry file on STN CAS Online Sep. 9, 2011.
Alessandro Stella et. al., A short and straightforward approach towards 6-amino and 6-aminoalkyl thiazolo[4,5-c]pyridazines, Tetrahedron Letters, 54(8) (2013) pp. 830-833.
Thuraya Al-Harthy et al., "Design, synthesis and antimicrobial evaluation of novel 2-arylbenzothiazole analogs bearing fluorine and piperazine moieties," Monatshefte fur Chemie (2018) 149(3) pp. 645-651.
Hye Ri Park et al., "Oxazolopyridines and thiazolopyridines as monoamine oxidase B inhibitors for the treatment of Parkinson's disease," Bioorganic & Medicinal Chemistry, 21(17) (2013) pp. 5480-5487.
Chemical Abstracts Registry No. 1368225-46-0, indexed in the Registry file on STN CAS Online Apr. 15, 2012.
Chemical Abstracts Registry No. 1330013-08-5, indexed in the Registry file on STN CAS Online Sep. 8, 2011.
Chemical Abstracts Registry No. 1329755-78-3, indexed in the Registry file on STN CAS Online Sep. 8, 2011.
Chemical Abstracts Registry No. 1329572-44-2, indexed in the Registry file on STN CAS Online Sep. 7, 2011.
Chemical Abstracts Registry No. 1329511-91-2, indexed in the Registry file on STN CAS Online Sep. 7, 2011.
Chemical Abstracts Registry No. 1327110-38-2, indexed in the Registry file on STN CAS Online Sep. 2, 2011.
Chemical Abstracts Registry No. 1310217-40-3, indexed in the Registry file on STN CAS Online Jun. 23, 2011.
Chemical Abstracts Registry No. 1310089-22-5, indexed in the Registry file on STN CAS Online Jun. 23, 2011.
Chemical Abstracts Registry No. 1267789-60-5, indexed in the Registry file on STN CAS Online Mar. 10, 2011.
Chemical Abstracts Registry No. 1267620-08-5, indexed in the Registry file on STN CAS Online Mar. 9, 2011.
Chemical Abstracts Registry No. 1267544-92-2, indexed in the Registry file on STN CAS Online Mar. 9, 2011.
Chemical Abstracts Registry No. 1267173-86-3, indexed in the Registry file on STN CAS Online Mar. 9, 2011.
Chemical Abstracts Registry No. 1267173-76-1, indexed in the Registry file on STN CAS Online Mar. 9, 2011.
Chemical Abstracts Registry No. 1266786-33-7, indexed in the Registry file on STN CAS Online Mar. 8, 2011.
"Chemical Encyclopedia", scientific publishing house "Great Russian Encyclopedia," Moskva, vol. 4, pp. 499-501, 1995.
V.V. Boltromeyuk, "General Chemistry", Minsk, Graduate School, Grodno State Medical University, Department of General and Bioorganic Chemistry, p. 65, 2012 (textbook).
Chemical Abstracts Registry No. 1202076-20-7, indexed in the Registry file on STN CAS Online Jan. 13, 2010.
Chemical Abstracts Registry No. 1202076-21-8, indexed in the Registry file on STN CAS Online Jan. 13, 2010.
Chemical Abstracts Registry No. 1202076-22-9, indexed in the Registry file on STN CAS Online Jan. 13, 2010.
Chemical Abstracts Registry No. 889062-91-3, indexed in the Registry file on STN CAS Online Jun. 23, 2006.
Chemical Abstracts Registry No. 667457-86-5, indexed in the Registry file on STN CAS Online Mar. 25, 2004.
Chemical Abstracts Registry No. 1691540-69-8, indexed in the Registry file on STN CAS Online Apr. 26, 2015.
Chemical Abstracts Registry No. 1691540-67-6, indexed in the Registry file on STN CAS Online Apr. 26, 2015.
Chemical Abstracts Registry No. 1691538-20-1, indexed in the Registry file on STN CAS Online Apr. 26, 2015.
Chemical Abstracts Registry No. 1691538-17-6, indexed in the Registry file on STN CAS Online Apr. 26, 2015.
International Search Report in PCT/US2022/038870, dated Nov. 9, 2022.
Written Opinion of the International Searching Authority in PCT/US2022/038870, dated Nov. 9, 2022.
Glenn Noronha, et al. Discovery of [7-(2,6-Dichlorophenyl)-5-methylbenzo[1,2,4]triazin-3-yl]-[4-(2-pyrrolidin-1-ylethoxy)phenyl]amine—A Potent, Orally Active Src Kinase Inhibitor with Antitumor Activity in Preclinical Assays. Bioorg. Med. Chem. Lett., vol. 17, No. 3, pp. 602-608, 2007.
Sara D. Reis et al., "Modulation of Molecular Chaperones in Huntington's Disease and Other Polyglutamine Disorders," Molecular Neurobiology, vol. 54, pp. 5829-5854, (2016) (Sep. 22, 2016).
Hideshi Nakamura et al., Synthesis and Chemiluminescence of 5-[(2-Pyridyl)-, (2-Pyrazinyl)-, and (Substituted 2-pyrazinyl)amino]-1,2,4-trioxanes, The Chemical Society of Japan, vol. 61, No. 10, (1988) pp. 3776-3778.
Written Opinion of the International Searching Authority in PCT/US2021/059139, mailed Mar. 14, 2022.
International Search Report for PCT/US2021/059139, mailed Mar. 14, 2022.
Stephen M. Berge, et al., "Pharmaceutical Salts," Journal of Pharmaceutical Sciences, vol. 66, No. 1, pp. 1-19 (1977).
Chemical Abstracts Registry No. 1207531-45-0, indexed in the Registry file on STN CAS Online Mar. 1, 2010.
"Drug Structure-Activity Relationship", edited by Li Renli, China Medical Science and Technology Press, 1st edition, Jan. 2004, 1st printing, pp. 182-183).
Written Opinion of the International Searching Authority in PCT/US23/68335, mailed Dec. 20, 2023.
International Search Report for PCT/US23/68335, mailed Dec. 20, 2023.

* cited by examiner

COMPOUNDS FOR TREATING HUNTINGTON'S DISEASE

CROSS-REFERENCE TO RELATED APPLICATIONS

This application is the U.S. National Stage filing under 35 U.S.C. § 371 of International Application No. PCT/US2020/032446, filed May 12, 2020, which in turn claims priority to U.S. Provisional Application No. 62/846,896, filed on May 13, 2019, the contents of which are incorporated by reference herein.

FIELD

An aspect of the present description relates to compounds, forms, and pharmaceutical compositions thereof and methods of using such compounds, forms, or compositions thereof useful for treating or ameliorating Huntington's disease. In particular, another aspect of the present description relates to substituted monocyclic heteroaryl compounds, forms and pharmaceutical compositions thereof and methods of using such compounds, forms, or compositions thereof for treating or ameliorating Huntington's disease.

BACKGROUND

Huntington's disease (HD) is a progressive, autosomal dominant neurodegenerative disorder of the brain, having symptoms characterized by involuntary movements, cognitive impairment, and mental deterioration. Death, typically caused by pneumonia or coronary artery disease, usually occurs 13 to 15 years after the onset of symptoms. The prevalence of HD is between three and seven individuals per 100.000 in populations of western European descent. In North America, an estimated 30,000 people have HD, while an additional 200.000 people are at risk of inheriting the disease from an affected parent. The disease is caused by an expansion of uninterrupted trinucleotide CAG repeats in the "mutant" huntingtin (Htt) gene, leading to production of HTT (Htt protein) with an expanded poly-glutamine (polyQ) stretch, also known as a "CAG repeat" sequence. There are no current small molecule therapies targeting the underlying cause of the disease, leaving a high unmet need for medications that can be used for treating or ameliorating HD. Consequently, there remains a need to identify and provide small molecule compounds for treating or ameliorating HD.

All other documents referred to herein are incorporated by reference into the present application as though fully set forth herein.

SUMMARY

An aspect of the present description includes compounds comprising, a compound of Formula (I), Formula (II), or Formula (III):

(I)

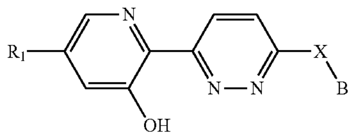

-continued (II)

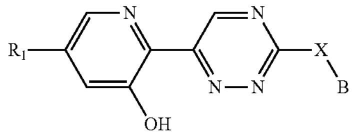

(III)

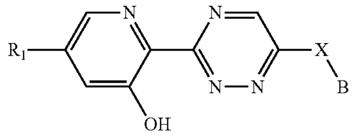

or a form thereof, wherein X, B, and $R_1$ are as defined herein.

An aspect of the present description includes a method for treating or ameliorating HD in a subject in need thereof comprising, administering to the subject an effective amount of a compound of Formula (I), Formula (II), or Formula (III), or a form thereof.

An aspect of the present description includes a method for use of a compound of Formula (I), Formula (II), or Formula (III), or a form or composition thereof for treating or ameliorating HD in a subject in need thereof comprising, administering to the subject an effective amount of the compound of Formula (I), Formula (II), or Formula (III), or a form or composition thereof.

An aspect of the present description includes a use for a compound of Formula (I), Formula (II), or Formula (III), or a form thereof for treating or ameliorating HD in a subject in need thereof comprising, administering to the subject an effective amount of the compound of Formula (I), Formula (II), or Formula (III), or a form thereof.

An aspect of the present description includes a use for a compound of Formula (I), Formula (II), or Formula (III), or a form thereof in the manufacture of a medicament for treating or ameliorating HD in a subject in need thereof comprising, administering to the subject an effective amount of the medicament.

An aspect of the present description includes a use for a compound of Formula (I), Formula (II), or Formula (III), or a form thereof in a combination product with one or more therapeutic agents for treating or ameliorating HD in a subject in need thereof comprising, administering to the subject an effective amount of the compound of Formula (I), Formula (II), or Formula (III), or a form thereof in combination with an effective amount of the one or more agents.

DETAILED DESCRIPTION

An aspect of the present description relates to compounds comprising, a compound of Formula (I), Formula (II), or Formula (III):

(I)

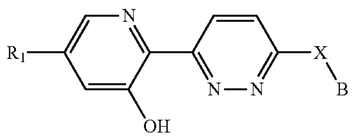

(II)

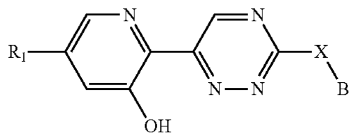

-continued (III)

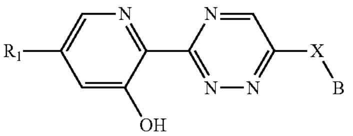

or a form thereof, wherein:

X is O, $NR_x$, or a bond;

$R_x$ is selected from hydrogen and $C_{1-4}$alkyl;

B is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, optionally substituted where allowed by available valences with 1, 2, 3, 4, or 5 $R_b$ substituents;

$R_b$ is independently selected from halogen, $C_{1-4}$alkyl, amino, $C_{1-4}$alkyl-amino, $(C_{1-4}alkyl)_2$-amino, and $C_{1-4}$cycloalkyl;

$R_1$ is selected from heteroaryl, heterocyclyl, phenyl, heteroaryl-$C_{1-4}$alkyl, heteroaryl-$C_{2-4}$alkenyl, heteroaryl-amino, and heteroaryl-$C_{1-4}$alkyl-amino, wherein heteroaryl is a 3-7 membered monocyclic or 6-10 membered bicyclic ring system having 1, 2, 3, or 4 heteroatom ring members independently selected from N, O, or S, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, and wherein each instance of phenyl, heteroaryl or heterocyclyl is optionally substituted where allowed by available valences with 1 or 2 $R_{1a}$ substituents; and $R_{1a}$ is independently selected from halogen, hydroxyl, cyano, $C_{1-4}$alkyl, deutero-$C_{1-4}$alkyl, halo-$C_{1-4}$alkyl, amino, $C_{1-4}$alkyl-amino, $(C_{1-4}alkyl)_2$-amino, $C_{1-4}$alkoxy, deutero-$C_{1-4}$alkoxy, and halo-$C_{1-4}$alkoxy;

wherein a form of the compound is selected from the group consisting of a salt, hydrate, solvate, racemate, enantiomer, diastereomer, tautomer, and mixtures thereof.

Aspects of the Description

An aspect of the present description relates to compounds comprising, a compound of Formula (I), Formula (II), or Formula (III):

(I)

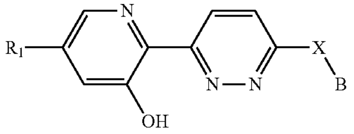

(II)

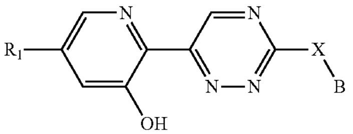

-continued (III)

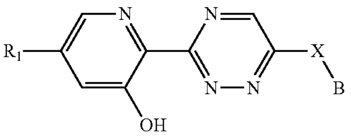

or a form thereof, wherein:

X is O, $NR_x$, or a bond;

$R_x$ is selected from hydrogen and $C_{1-4}$alkyl;

B is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, optionally substituted where allowed by available valences with 1, 2, 3, 4, or 5 $R_b$ substituents;

$R_b$ is independently selected from halogen, $C_{1-4}$alkyl, amino, $C_{1-4}$alkyl-amino, $(C_{1-4}alkyl)_2$-amino, and $C_{1-4}$cycloalkyl;

$R_1$ is selected from heteroaryl, heterocyclyl, phenyl, heteroaryl-$C_{1-4}$alkyl, heteroaryl-$C_{2-4}$alkenyl, heteroaryl-amino, and heteroaryl-$C_{1-4}$alkyl-amino, wherein heteroaryl is a 3-7 membered monocyclic or 6-10 membered bicyclic ring system having 1, 2, 3, or 4 heteroatom ring members independently selected from N, O, or S, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, and wherein each instance of phenyl, heteroaryl or heterocyclyl is optionally substituted where allowed by available valences with 1 or 2 $R_{1a}$ substituents; and $R_{1a}$ is independently selected from halogen, hydroxyl, cyano, $C_{1-4}$alkyl, deutero-$C_{1-4}$alkyl, halo-$C_{1-4}$alkyl, amino, $C_{1-4}$alkyl-amino, $(C_{1-4}alkyl)_2$-amino, $C_{1-4}$alkoxy, deutero-$C_{1-4}$alkoxy, and halo-$C_{1-4}$alkoxy.

One aspect includes a compound of Formula (I), Formula (II), or Formula (III), wherein X is selected from O, $NR_x$, and a bond.

Another aspect includes a compound of Formula (I), Formula (II), or Formula (III) wherein X is O.

Another aspect includes a compound of Formula (I), Formula (II), or Formula (III) wherein X is $NR_x$.

Another aspect includes a compound of Formula (I), Formula (II), or Formula (III) wherein X is a bond.

One aspect includes a compound of Formula (I), Formula (II), or Formula (III), wherein $R_x$ is selected from hydrogen and $C_{1-4}$alkyl.

Another aspect includes a compound of Formula (I), Formula (II), or Formula (III), wherein $R_x$ hydrogen.

Another aspect includes a compound of Formula (I), Formula (II), or Formula (III), wherein $R_x$ is $C_{1-4}$alkyl selected from methyl, ethyl, propyl, isopropyl, butyl, and tert-butyl.

Another aspect includes a compound of Formula (I), Formula (II), or Formula (III), wherein $R_x$ is methyl.

One aspect includes a compound of Formula (I), Formula (II), or Formula (III), wherein B is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, optionally substituted where allowed by available valences with 1, 2, 3, 4, or 5 $R_b$ substituents.

Another aspect includes a compound of Formula (I), Formula (II), or Formula (III), wherein B is unsubstituted heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S.

Another aspect includes a compound of Formula (I), Formula (II), or Formula (III), wherein B is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, substituted where allowed by available valences with one $R_b$ substituent.

Another aspect includes a compound of Formula (I), Formula (II), or Formula (III), wherein B is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, each substituted where allowed by available valences with two $R_b$ substituents.

Another aspect includes a compound of Formula (I), Formula (II), or Formula (III), wherein B is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, substituted where allowed by available valences with three $R_b$ substituents.

Another aspect includes a compound of Formula (I), Formula (II), or Formula (III), wherein B is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, substituted where allowed by available valences with four $R_b$ substituents.

Another aspect includes a compound of Formula (I), Formula (II), or Formula (III), wherein B is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, substituted where allowed by available valences with five $R_b$ substituents.

Another aspect includes a compound of Formula (I), Formula (II), or Formula (III), wherein B is heterocyclyl selected from azetidinyl, tetrahydrofuranyl, pyrrolidinyl, piperidinyl, piperidin-1-olate-yl, piperazinyl, 1,4-diazepanyl, 1,2-dihydropyridinyl, 1,2,5,6-tetrahydropyridinyl, 1,2,3,6-tetrahydropyridinyl, hexahydrocyclopentapyrrol-(1H)-yl, hexahydropyrrolo[3,2-b]pyrrol-(2H)-yl, hexahydropyrrolo[3,4-b]pyrrol-(2H)-yl, octahydro-2H-pyrrolo[3,4-c]pyridinyl, octahydro-5H-pyrrolo[3,2-c]pyridinyl, octahydro-6H-pyrrolo[3,4-b]pyridinyl, hexahydropyrrolo[1,2-a]pyrazin-(2H)-one, hexahydropyrrolo[1,2-a]pyrazin-(1H)-yl, hexahydro-1H-cyclobuta[1.2-c:1,4-c']dipyrrol-(3H)-yl, octahydropyrrolo[1,2-a]pyrazin-(1H)-yl, octahydro-2H-pyrido[1,2-a]pyrazinyl, hexahydropyrrolo[3,4-b][1,4]oxazin-(2H)-yl, 5-azaspiro[2.4]heptanyl, 1-azaspiro[3.3]heptanyl, 4-azaspiro[2.5]octanyl, 2-oxa-6-azaspiro[3.4]octanyl, 3-azabicyclo[3.1.0]hexanyl, 8-azabicyclo[3.2.1]octanyl, 8-azabicyclo[3.2.1]oct-2-en-yl, 9-azabicyclo[3.3.1]nonanyl, 2,5-diazabicyclo[2.2.1]heptanyl, 1,4-diazabicyclo[3.1.1]heptanyl, 3,6-diazabicyclo[3.2.0]heptanyl, 2,5-diazabicyclo[2.2.2]octanyl, 1,4-diazabicyclo[3.2.1]octanyl, 3,8-diazabicyclo[3.2.1]octanyl, 1,4-diazabicyclo[3.2.2]nonanyl, 4,7-diazaspiro[2.5]octanyl, 2,6-diazaspiro[3.3]heptanyl, 1,6-diazaspiro[3.4]octanyl, 2,6-diazaspiro[3.4]octanyl, 1,7,-diazaspiro[4.4]nonanyl, 1,7-diazaspiro[3.5]nonanyl, 2,6-diazaspiro[3.5]nonanyl, 2,7-diazaspiro[3.5]nonanyl, 5,8-diazaspiro[3.5]nonanyl, 2-oxa-5,8-diazaspiro[3.5]nonanyl, 2,7-diazaspiro[4.4]nonanyl, 2,7-diazaspiro[4.5]decanyl, 2,8-diazaspiro[4.5]decanyl, 6,9-diazaspiro[4.5]decyl, 6-oxa-2,9-diazaspiro[4.5]decanyl, 2,9-diazaspiro[5.5]undecanyl, 4-azadispiro[$2.1.2^5.3^3$]decanyl, and 7-azadispiro[$5.1.5^8.3^6$]hexadecanyl, optionally substituted where allowed by available valences with 1, 2, 3, 4, or 5 $R_b$ substituents.

Another aspect includes a compound of Formula (I), Formula (I), or Formula (III), wherein B is unsubstituted heterocyclyl selected from azetidinyl, tetrahydrofuranyl, pyrrolidinyl, piperidinyl, piperidin-1-olate-yl, piperazinyl, 1,4-diazepanyl, 1,2-dihydropyridinyl, 1,2,5,6-tetrahydropyridinyl, 1,2,3,6-tetrahydropyridinyl, hexahydrocyclopentapyrrol-(1H)-yl, hexahydropyrrolo[3,2-b]pyrrol-(2H)-yl, hexahydropyrrolo[3,4-b]pyrrol-(2H)-yl, octahydro-2H-pyrrolo[3,4-c]pyridinyl, octahydro-5H-pyrrolo[3,2-c]pyridinyl, octahydro-6H-pyrrolo[3,4-b]pyridinyl, hexahydropyrrolo[1,2-a]pyrazin-(2H)-one, hexahydropyrrolo[1,2-a]pyrazin-(1H)-yl, hexahydro-1H-cyclobuta[1.2-c:1,4-c']dipyrrol-(3H)-yl, octahydropyrrolo[1,2-a]pyrazin-(1H)-yl, octahydro-2H-pyrido[1,2-a]pyrazinyl, hexahydropyrrolo[3,4-b][1,4]oxazin-(2H)-yl, 5-azaspiro[2.4]heptanyl, I-azaspiro[3.3]heptanyl, 4-azaspiro[2.5]octanyl, 2-oxa-6-azaspiro[3.4]octanyl, 3-azabicyclo[3.1.0]hexanyl, 8-azabicyclo[3.2.1]octanyl, 8-azabicyclo[3.2.1]oct-2-en-yl, 9-azabicyclo[3.3.1]nonanyl, 2,5-diazabicyclo[2.2.1]heptanyl, 1,4-diazabicyclo[3.1.1]heptanyl, 3,6-diazabicyclo[3.2.0]heptanyl, 2,5-diazabicyclo[2.2.2]octanyl, 1,4-diazabicyclo[3.2.1]octanyl, 3,8-diazabicyclo[3.2.1]octanyl, 1,4-diazabicyclo[3.2.2]nonanyl, 4,7-diazaspiro[2.5]octanyl, 2,6-diazaspiro[3.3]heptanyl, 1,6-diazaspiro[3.4]octanyl, 2,6-diazaspiro[3.4]octanyl, 1,7,-diazaspiro[4.4]nonanyl, 1,7-diazaspiro[3.5]nonanyl, 2,6-diazaspiro[3.5]nonanyl, 2,7-diazaspiro[3.5]nonanyl, 5,8-diazaspiro[3.5]nonanyl, 2-oxa-5,8-diazaspiro[3.5]nonanyl, 2,7-diazaspiro[4.4]nonanyl, 2,7-diazaspiro[4.5]decanyl, 2,8-diazaspiro[4.5]decanyl, 6,9-diazaspiro[4.5]decyl, 6-oxa-2,9-diazaspiro[4.5]decanyl, 2,9-diazaspiro[5.5]undecanyl, 4-azadispiro[$2.1.2^5.3^3$]decanyl, and 7-azadispiro[$5.1.5^8.3^6$]hexadecanyl.

Another aspect includes a compound of Formula (I), Formula (II), or Formula (III), wherein B is heterocyclyl selected from azetidinyl, tetrahydrofuranyl, pyrrolidinyl, piperidinyl, piperidin-1-olate-yl, piperazinyl, 1,4-diazepanyl, 1,2-dihydropyridinyl, 1,2,5,6-tetrahydropyridinyl, 1,2,3,6-tetrahydropyridinyl, hexahydrocyclopentapyrrol-(1H)-yl, hexahydropyrrolo[3,2-b]pyrrol-(2H)-yl, hexahydropyrrolo[3,4-b]pyrrol-(2H)-yl, octahydro-2H-pyrrolo[3,4-c]pyridinyl, octahydro-5H-pyrrolo[3,2-c]pyridinyl, octahydro-6H-pyrrolo[3,4-b]pyridinyl, hexahydropyrrolo[1,2-a]pyrazin-(2H)-one, hexahydropyrrolo[1,2-a]pyrazin-(1H)-yl, hexahydro-1H-cyclobuta[1.2-c:1,4-c']dipyrrol-(3H)-yl, octahydropyrrolo[1,2-a]pyrazin-(1H)-yl, octahydro-2H-pyrido[1,2-a]pyrazinyl, hexahydropyrrolo[3,4-b][1,4]oxazin-(2H)-yl, 5-azaspiro[2.4]heptanyl, 1-azaspiro[3.3]heptanyl, 4-azaspiro[2.5]octanyl, 2-oxa-6-azaspiro[3.4]octanyl, 3-azabicyclo[3.1.0]hexanyl, 8-azabicyclo[3.2.1]octanyl, 8-azabicyclo[3.2.1]oct-2-en-yl, 9-azabicyclo[3.3.1]nonanyl, 2,5-diazabicyclo[2.2.1]heptanyl, 1,4-diazabicyclo[3.1.1]heptanyl, 3,6-diazabicyclo[3.2.0]heptanyl, 2,5-diazabicyclo[2.2.2]octanyl, 1,4-diazabicyclo[3.2.1]octanyl, 3,8-diazabicyclo[3.2.1]octanyl, 1,4-diazabicyclo[3.2.2]nonanyl, 4,7-diazaspiro[2.5]octanyl, 2,6-diazaspiro[3.3]heptanyl, 1,6-diazaspiro[3.4]octanyl, 2,6-diazaspiro[3.4]octanyl, 1,7,-diazaspiro[4.4]nonanyl, 1,7-diazaspiro[3.5]nonanyl, 2,6-diazaspiro[3.5]nonanyl, 2,7-diazaspiro[3.5]nonanyl, 5,8-diazaspiro[3.5]nonanyl, 2-oxa-5,8-diazaspiro[3.5]nonanyl, 2,7-diazaspiro[4.4]nonanyl, 2,7-diazaspiro[4.5]decanyl, 2,8-diazaspiro[4.5]decanyl, 6,9-diazaspiro[4.5]decyl, 6-oxa-2,9-diazaspiro[4.5]decanyl, 2,9-diazaspiro[5.5]undecanyl, 4-azadispiro[$2.1.2^5.3^3$]decanyl, and 7-azadispiro[$5.1.5^8.3^6$]hexadecanyl, substituted where allowed by available valences with one $R_b$ substituent.

Another aspect includes a compound of Formula (I), Formula (II), or Formula (III), wherein B is heterocyclyl selected from azetidinyl, tetrahydrofuranyl, pyrrolidinyl, piperidinyl, piperidin-1-olate-yl, piperazinyl, 1,4-diazepanyl, 1,2-dihydropyridinyl, 1,2,5,6-tetrahydropyridinyl, 1,2,3,6-tetrahydropyridinyl, hexahydrocyclopentapyrrol-(1H)-yl, hexahydropyrrolo[3,2-b]pyrrol-(2H)-yl, hexahydropyrrolo[3,4-b]pyrrol-(2H)-yl, octahydro-2H-pyrrolo[3,4-c]pyridinyl, octahydro-5H-pyrrolo[3,2-c]pyridinyl, octahydro-6H-pyrrolo[3,4-b]pyridinyl, hexahydropyrrolo[1,2-a]pyrazin-(2H)-one, hexahydropyrrolo[1,2-a]pyrazin-(1H)-yl, hexahydro-1H-cyclobuta[1.2-c:1,4-c']dipyrrol-(3H)-yl, octahydropyrrolo[1,2-a]pyrazin-(1H)-yl, octahydro-2H-pyrido[1,2-a]pyrazinyl, hexahydropyrrolo[3,4-b][1,4]oxazin-(2H)-yl, 5-azaspiro[2.4]heptanyl, 1-azaspiro[3.3]heptanyl, 4-azaspiro[2.5]octanyl, 2-oxa-6-azaspiro[3.4]octanyl, 3-azabicyclo[3.1.0]hexanyl, 8-azabicyclo[3.2.1]octanyl, 8-azabicyclo[3.2.1]oct-2-en-yl, 9-azabicyclo[3.3.1]nonanyl, 2,5-diazabicyclo[2.2.1]heptanyl, 1.4-diazabicyclo[3.1.1]heptanyl, 3,6-diazabicyclo[3.2.0]heptanyl, 2,5-diazabicyclo[2.2.2]octanyl, 1,4-diazabicyclo[3.2.1]octanyl, 3,8-diazabicyclo[3.2.1]octanyl, 1,4-diazabicyclo[3.2.2]nonanyl, 4,7-diazaspiro[2.5]octanyl, 2,6-diazaspiro[3.3]heptanyl, 1,6-diazaspiro[3.4]octanyl, 2,6-diazaspiro[3.4]octanyl, 1.7,-diazaspiro[4.4]nonanyl, 1,7-diazaspiro[3.5]nonanyl, 2,6-diazaspiro[3.5]nonanyl, 2,7-diazaspiro[3.5]nonanyl, 5,8-diazaspiro[3.5]nonanyl, 2-oxa-5,8-diazaspiro[3.5]nonanyl, 2,7-diazaspiro[4.4]nonanyl, 2,7-diazaspiro[4.5]decanyl, 2,8-diazaspiro[4.5]decanyl, 6,9-diazaspiro[4.5]decyl, 6-oxa-2,9-diazaspiro[4.5]decanyl, 2,9-diazaspiro[5.5]undecanyl, 4-azadispiro[$2.1.2^5.3^3$]decanyl, and 7-azadispiro[$5.1.5^8.3^6$]hexadecanyl, substituted where allowed by available valences with two $R_b$ substituents.

Another aspect includes a compound of Formula (I), Formula (II), or Formula (III), wherein B is heterocyclyl selected from azetidinyl, tetrahydrofuranyl, pyrrolidinyl, piperidinyl, piperidin-1-olate-yl, piperazinyl, 1,4-diazepanyl, 1,2-dihydropyridinyl, 1,2,5,6-tetrahydropyridinyl, 1,2,3,6-tetrahydropyridinyl, hexahydrocyclopentapyrrol-(1H)-yl, hexahydropyrrolo[3,2-b]pyrrol-(2H)-yl, hexahydropyrrolo[3,4-b]pyrrol-(2H)-yl, octahydro-2H-pyrrolo[3,4-c]pyridinyl, octahydro-5H-pyrrolo[3,2-c]pyridinyl, octahydro-6H-pyrrolo[3,4-b]pyridinyl, hexahydropyrrolo[1,2-a]pyrazin-(2H)-one, hexahydropyrrolo[1,2-a]pyrazin-(1H)-yl, hexahydro-1H-cyclobuta[1.2-c:1,4-c']dipyrrol-(3H)-yl, octahydropyrrolo[1,2-a]pyrazin-(1H)-yl, octahydro-2H-pyrido[1,2-a]pyrazinyl, hexahydropyrrolo[3,4-b][1,4]oxazin-(2H)-yl, 5-azaspiro[2.4]heptanyl, I-azaspiro[3.3]heptanyl, 4-azaspiro[2.5]octanyl, 2-oxa-6-azaspiro[3.4]octanyl, 3-azabicyclo[3.1.0]hexanyl, 8-azabicyclo[3.2.1]octanyl, 8-azabicyclo[3.2.1]oct-2-en-yl, 9-azabicyclo[3.3.1]nonanyl, 2,5-diazabicyclo[2.2.1]heptanyl, 1,4-diazabicyclo

[3.1.1]heptanyl, 3,6-diazabicyclo[3.2.0]heptanyl, 2,5-diazabicyclo[2.2.2]octanyl, 1,4-diazabicyclo[3.2.1]octanyl, 3,8-diazabicyclo[3.2.1]octanyl, 1,4-diazabicyclo[3.2.2]nonanyl, 4,7-diazaspiro[2.5]octanyl, 2,6-diazaspiro[3.3]heptanyl, 1,6-diazaspiro[3.4]octanyl, 2,6-diazaspiro[3.4]octanyl, 1,7,-diazaspiro[4.4]nonanyl, 1,7-diazaspiro[3.5]nonanyl, 2,6-diazaspiro[3.5]nonanyl, 2,7-diazaspiro[3.5]nonanyl, 5,8-diazaspiro[3.5]nonanyl, 2-oxa-5,8-diazaspiro[3.5]nonanyl, 2,7-diazaspiro[4.4]nonanyl, 2,7-diazaspiro[4.5]decanyl, 2,8-diazaspiro[4.5]decanyl, 6,9-diazaspiro[4.5]decyl, 6-oxa-2,9-diazaspiro[4.5]decanyl, 2,9-diazaspiro[5.5]undecanyl, 4-azadispiro[$2.1.2^5.3^3$]decanyl, and 7-azadispiro[$5.1.5^8.3^6$]hexadecanyl, substituted where allowed by available valences with three $R_b$ substituents.

Another aspect includes a compound of Formula (I), Formula (II), or Formula (III), wherein B is heterocyclyl selected from azetidinyl, tetrahydrofuranyl, pyrrolidinyl, piperidinyl, piperidin-1-olate-yl, piperazinyl, 1,4-diazepanyl, 1,2-dihydropyridinyl, 1,2,5,6-tetrahydropyridinyl, 1,2,3,6-tetrahydropyridinyl, hexahydrocyclopentapyrrol-(1H)-yl, hexahydropyrrolo[3,2-b]pyrrol-(2H)-yl, hexahydropyrrolo[3,4-b]pyrrol-(2H)-yl, octahydro-2H-pyrrolo[3,4-c]pyridinyl, octahydro-5H-pyrrolo[3,2-c]pyridinyl, octahydro-6H-pyrrolo[3,4-b]pyridinyl, hexahydropyrrolo[1,2-a]pyrazin-(2H)-one, hexahydropyrrolo[1,2-a]pyrazin-(1H)-yl, hexahydro-1H-cyclobuta[1.2-c:1,4-c']dipyrrol-(3H)-yl, octahydropyrrolo[1,2-a]pyrazin-(1H)-yl, octahydro-2H-pyrido[1,2-a]pyrazinyl, hexahydropyrrolo[3,4-b][1,4]oxazin-(2H)-yl, 5-azaspiro[2.4]heptanyl, 1-azaspiro[3.3]heptanyl, 4-azaspiro[2.5]octanyl, 2-oxa-6-azaspiro[3.4]octanyl, 3-azabicyclo[3.1.0]hexanyl, 8-azabicyclo[3.2.1]octanyl, 8-azabicyclo[3.2.1]oct-2-en-yl, 9-azabicyclo[3.3.1]nonanyl, 2,5-diazabicyclo[2.2.1]heptanyl, 1.4-diazabicyclo[3.1.1]heptanyl, 3,6-diazabicyclo[3.2.0]heptanyl, 2,5-diazabicyclo[2.2.2]octanyl, 1,4-diazabicyclo[3.2.1]octanyl, 3,8-diazabicyclo[3.2.1]octanyl, 1,4-diazabicyclo[3.2.2]nonanyl, 4,7-diazaspiro[2.5]octanyl, 2,6-diazaspiro[3.3]heptanyl, 1,6-diazaspiro[3.4]octanyl, 2,6-diazaspiro[3.4]octanyl, 1,7,-diazaspiro[4.4]nonanyl, 1,7-diazaspiro[3.5]nonanyl, 2,6-diazaspiro[3.5]nonanyl, 2,7-diazaspiro[3.5]nonanyl, 5,8-diazaspiro[3.5]nonanyl, 2-oxa-5,8-diazaspiro[3.5]nonanyl, 2,7-diazaspiro[4.4]nonanyl, 2,7-diazaspiro[4.5]decanyl, 2,8-diazaspiro[4.5]decanyl, 6,9-diazaspiro[4.5]decyl, 6-oxa-2,9-diazaspiro[4.5]decanyl, 2,9-diazaspiro[5.5]undecanyl, 4-azadispiro[$2.1.2^5.3^3$]decanyl, and 7-azadispiro[$5.1.5^8.3^6$]hexadecanyl, substituted where allowed by available valences with four $R_b$ substituents.

Another aspect includes a compound of Formula (I), Formula (II), or Formula (III), wherein B is heterocyclyl selected from azetidinyl, tetrahydrofuranyl, pyrrolidinyl, piperidinyl, piperidin-1-olate-yl, piperazinyl, 1,4-diazepanyl, 1,2-dihydropyridinyl, 1,2,5,6-tetrahydropyridinyl, 1,2,3,6-tetrahydropyridinyl, hexahydrocyclopentapyrrol-(1H)-yl, hexahydropyrrolo[3,2-b]pyrrol-(2H)-yl, hexahydropyrrolo[3,4-b]pyrrol-(2H)-yl, octahydro-2H-pyrrolo[3,4-c]pyridinyl, octahydro-5H-pyrrolo[3,2-c]pyridinyl, octahydro-6H-pyrrolo[3,4-b]pyridinyl, hexahydropyrrolo[1,2-a]pyrazin-(2H)-one, hexahydropyrrolo[1,2-a]pyrazin-(1H)-yl, hexahydro-1H-cyclobuta[1.2-c:1,4-c']dipyrrol-(3H)-yl, octahydropyrrolo[1,2-a]pyrazin-(1H)-yl, octahydro-2H-pyrido[1,2-a]pyrazinyl, hexahydropyrrolo[3,4-b][1,4]oxazin-(2H)-yl, 5-azaspiro[2.4]heptanyl, 1-azaspiro[3.3]heptanyl, 4-azaspiro[2.5]octanyl, 2-oxa-6-azaspiro[3.4]octanyl, 3-azabicyclo[3.1.0]hexanyl, 8-azabicyclo[3.2.1]octanyl, 8-azabicyclo[3.2.1]oct-2-en-yl, 9-azabicyclo[3.3.1]nonanyl, 2,5-diazabicyclo[2.2.1]heptanyl, 1,4-diazabicyclo[3.1.1]heptanyl, 3,6-diazabicyclo

[3.2.0]heptanyl, 2,5-diazabicyclo[2.2.2]octanyl, 1,4-diazabicyclo[3.2.1]octanyl, 3,8-diazabicyclo[3.2.1]octanyl, 1,4-diazabicyclo[3.2.2]nonanyl, 4,7-diazaspiro[2.5]octanyl, 2,6-diazaspiro[3.3]heptanyl, 1,6-diazaspiro[3.4]octanyl, 2,6-diazaspiro[3.4]octanyl, 1,7,-diazaspiro[4.4]nonanyl, 1,7-diazaspiro[3.5]nonanyl, 2,6-diazaspiro[3.5]nonanyl, 2,7-diazaspiro[3.5]nonanyl, 5,8-diazaspiro[3.5]nonanyl, 2-oxa-5,8-diazaspiro[3.5]nonanyl, 2,7-diazaspiro[4.4]nonanyl, 2,7-diazaspiro[4.5]decanyl, 2,8-diazaspiro[4.5]decanyl, 6,9-diazaspiro[4.5]decyl, 6-oxa-2,9-diazaspiro[4.5]decanyl, 2,9-diazaspiro[5.5]undecanyl, 4-azadispiro[$2.1.2^5.3^3$]decanyl, and 7-azadispiro[$5.1.5^8.3^6$]hexadecanyl, substituted where allowed by available valences with five $R_b$ substituents.

Another aspect includes a compound of Formula (I), Formula (II), or Formula (III), wherein B is heterocyclyl selected from pyrrolidinyl, piperidinyl, piperidin-1-olate-yl, piperazinyl, 4-azaspiro[2.5]octanyl, 8-azabicyclo[3.2.1]octanyl, 2,5-diazabicyclo[2.2.1]heptanyl, 1,6-diazaspiro[3.4]octanyl, 2-oxa-5,8-diazaspiro[3.5]nonanyl, and 4-azadispiro[$2.1.2^5.3^3$]decanyl, optionally substituted where allowed by available valences with 1, 2, 3, 4, or 5 $R_b$ substituents.

Another aspect includes a compound of Formula (I), Formula (II), or Formula (III), wherein B is unsubstituted heterocyclyl selected from pyrrolidinyl, piperidinyl, piperidin-1-olate-yl, piperazinyl, 4-azaspiro[2.5]octanyl, 8-azabicyclo[3.2.1]octanyl, 2,5-diazabicyclo[2.2.1]heptanyl, 1,6-diazaspiro[3.4]octanyl, 2-oxa-5,8-diazaspiro[3.5]nonanyl, and 4-azadispiro[$2.1.2^5.3^3$]decanyl.

Another aspect includes a compound of Formula (I), Formula (II), or Formula (III), wherein B is heterocyclyl selected from pyrrolidinyl, piperidinyl, piperidin-1-olate-yl, piperazinyl, 4-azaspiro[2.5]octanyl, 8-azabicyclo[3.2.1]octanyl, 2,5-diazabicyclo[2.2.1]heptanyl, 1,6-diazaspiro[3.4]octanyl, 2-oxa-5,8-diazaspiro[3.5]nonanyl, and 4-azadispiro[$2.1.2^5.3^3$]decanyl, substituted where allowed by available valences with one $R_b$ substituent.

Another aspect includes a compound of Formula (I), Formula (II), or Formula (III), wherein B is heterocyclyl selected from pyrrolidinyl, piperidinyl, piperidin-1-olate-yl, piperazinyl, 4-azaspiro[2.5]octanyl, 8-azabicyclo[3.2.1]octanyl, 2,5-diazabicyclo[2.2.1]heptanyl, 1,6-diazaspiro[3.4]octanyl, 2-oxa-5,8-diazaspiro[3.5]nonanyl, and 4-azadispiro[$2.1.2^5.3^3$]decanyl, substituted where allowed by available valences with two $R_b$ substituents.

Another aspect includes a compound of Formula (I), Formula (II), or Formula (III), wherein B is heterocyclyl selected from pyrrolidinyl, piperidinyl, piperidin-1-olate-yl, piperazinyl, 4-azaspiro[2.5]octanyl, 8-azabicyclo[3.2.1]octanyl, 2,5-diazabicyclo[2.2.1]heptanyl, 1.6-diazaspiro[3.4]octanyl, 2-oxa-5,8-diazaspiro[3.5]nonanyl, and 4-azadispiro[$2.1.2^5.3^3$]decanyl, substituted where allowed by available valences with three $R_b$ substituents.

Another aspect includes a compound of Formula (I), Formula (II), or Formula (III), wherein B is heterocyclyl selected from pyrrolidinyl, piperidinyl, piperazinyl, and 4-azaspiro[2.5]octanyl, optionally substituted where allowed by available valences with 1, 2, 3, 4, or 5 $R_b$ substituents.

Another aspect includes a compound of Formula (I), Formula (II), or Formula (III), wherein B is unsubstituted heterocyclyl selected from pyrrolidinyl, piperidinyl, piperazinyl, and 4-azaspiro[2.5]octanyl.

Another aspect includes a compound of Formula (I), Formula (II), or Formula (III), wherein B is heterocyclyl selected from pyrrolidinyl, piperidinyl, piperazinyl, and 4-azaspiro[2.5]octanyl, substituted where allowed by available valences with one $R_b$ substituent.

Another aspect includes a compound of Formula (I), Formula (II), or Formula (III), wherein B is heterocyclyl selected from pyrrolidinyl, piperidinyl, piperazinyl, and 4-azaspiro[2.5]octanyl, substituted where allowed by available valences with two $R_b$ substituents.

Another aspect includes a compound of Formula (I), Formula (II), or Formula (III), wherein B is heterocyclyl selected from pyrrolidinyl, piperidinyl, piperazinyl, and 4-azaspiro[2.5]octanyl, substituted where allowed by available valences with three $R_b$ substituents.

Another aspect includes a compound of Formula (I), Formula (II), or Formula (III), wherein B is heterocyclyl selected from pyrrolidinyl, piperidinyl, piperazinyl, and 4-azaspiro[2.5]octanyl, substituted where allowed by available valences with four $R_b$ substituents.

Another aspect includes a compound of Formula (I), Formula (II), or Formula (III), wherein B is heterocyclyl selected from pyrrolidinyl, piperidinyl, piperazinyl, and 4-azaspiro[2.5]octanyl, substituted where allowed by available valences with five $R_b$ substituents.

Another aspect includes a compound of Formula (I), Formula (II), or Formula (III), wherein B is pyrrolidinyl, substituted where allowed by available valences with one $R_b$ substituent.

Another aspect includes a compound of Formula (I), Formula (II), or Formula (III), wherein B is piperidinyl, substituted where allowed by available valences with four $R_b$ substituents.

Another aspect includes a compound of Formula (I), Formula (II), or Formula (III), wherein B is piperidinyl, substituted where allowed by available valences with five $R_b$ substituents.

Another aspect includes a compound of Formula (I), Formula (II), or Formula (III), wherein B is unsubstituted piperazinyl.

Another aspect includes a compound of Formula (I), Formula (II), or Formula (III), wherein B is piperazinyl, substituted where allowed by available valences with one $R_b$ substituent.

Another aspect includes a compound of Formula (I), Formula (II), or Formula (III), wherein B is piperazinyl, substituted where allowed by available valences with two $R_b$ substituents.

Another aspect includes a compound of Formula (I), Formula (II), or Formula (III), wherein B is piperazinyl, substituted where allowed by available valences with three $R_b$ substituents.

Another aspect includes a compound of Formula (I), Formula (II), or Formula (III), wherein B is piperazinyl, substituted where allowed by available valences with four $R_b$ substituents.

Another aspect includes a compound of Formula (I), Formula (II), or Formula (III), wherein B is unsubstituted 4-azaspiro[2.5]octanyl.

Another aspect includes a compound of Formula (I), Formula (II), or Formula (III), wherein B is 4-azaspiro[2.5]octanyl, substituted where allowed by available valences with one $R_b$ substituent.

Another aspect includes a compound of Formula (I), Formula (II), or Formula (III), wherein B is 4-azaspiro[2.5]octanyl, substituted where allowed by available valences with two $R_b$ substituents.

Another aspect includes a compound of Formula (I), Formula (II), or Formula (III), wherein B is heterocyclyl selected from azetidin-1-yl, tetrahydrofuran-3-yl, pyrrolidin-1-yl, pyrrolidin-3-yl, piperidin-1-yl, piperidin-3-yl, piperidin-4-yl, piperidin-1-olate-4-yl, piperazin-1-yl, 1,4-diazepan-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,2,5,6-tetrahydropyridin-5-yl, 1,2,3,6-tetrahydropyridin-4-yl, hexahydrocyclopentapyrrol-2(1H)-yl, hexahydropyrrolo[3,2-b]pyrrol-1(2H)-yl, hexahydropyrrolo[3,4-b]pyrrol-1(2H)-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, octahydro-5H-pyrrolo[3,2-c]pyridin-5-yl, octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, hexahydro-1H-cyclobuta[1.2-c:1,4-c']dipyrrol-2(3H)-yl, octahydropyrrolo[1,2-a]pyrazin-2(1H)-yl, octahydro-2H-pyrido[1,2-a]pyrazin-2-yl, hexahydropyrrolo[3,4-b][1,4]oxazin-6(2H)-yl, 5-azaspiro[2.4]heptan-5-yl, 1-azaspiro[3.3]heptan-2-yl, 4-azaspiro[2.5]octan-7-yl, 2-oxa-6-azaspiro[3.4]octan-6-yl, 3-azabicyclo[3.1.0]hexan-3-yl, 8-azabicyclo[3.2.1]octan-3-yl, 8-azabicyclo[3.2.1]oct-2-en-3-yl, 9-azabicyclo[3.3.1]nonan-3-yl, 2,5-diazabicyclo[2.2.1]heptan-2-yl, 1,4-diazabicyclo[3.1.1]heptan-4-yl, 3,6-diazabicyclo[3.2.0]heptan-3-yl, 3,6-diazabicyclo[3.2.0]heptan-6-yl, 2,5-diazabicyclo[2.2.2]octan-2-yl, 1,4-diazabicyclo[3.2.1]octan-4-yl, 3,8-diazabicyclo[3.2.1]octan-3-yl, 1,4-diazabicyclo[3.2.2]nonan-4-yl, 4,7-diazaspiro[2.5]octan-4-yl, 4,7-diazaspiro[2.5]octan-7-yl, 2,6-diazaspiro[3.3]heptan-2-yl, 1,6-diazaspiro[3.4]octan-6-yl, 2,6-diazaspiro[3.4]octan-2-yl, 2,6-diazaspiro[3.4]octan-6-yl, 1,7,-diazaspiro[4.4]nonan-1-yl, 1,7,-diazaspiro[4.4]nonan-7-yl, 1,7-diazaspiro[3.5]nonan-7-yl, 2,6-diazaspiro[3.5]nonan-2-yl, 2,6-diazaspiro[3.5]nonan-6-yl, 1,7-diazaspiro[3.5]nonan-7-yl, 2,7-diazaspiro[3.5]nonan-2-yl, 2,7-diazaspiro[3.5]nonan-7-yl, 5,8-diazaspiro[3.5]nonan-8-yl, 2-oxa-5,8-diazaspiro[3.5]nonan-8-yl, 2,7-diazaspiro[4.4]nonan-2-yl, 2,7-diazaspiro[4.5]decan-2-yl, 2,7-diazaspiro[4.5]decan-7-yl, 2,8-diazaspiro[4.5]decan-8-yl, 6,9-diazaspiro[4.5]dec-9-yl, 6-oxa-2,9-diazaspiro[4.5]decan-2-yl, 2,9-diazaspiro[5.5]undecan-9-yl, 4-azadispiro[$2.1.2^5.3^3$]decan-9-yl, and 7-azadispiro[$5.1.5^8.3^6$]hexadecan-15-yl, optionally substituted where allowed by available valences with 1, 2, 3, 4, or 5 $R_b$ substituents.

Another aspect includes a compound of Formula (I), Formula (II), or Formula (II), wherein B is unsubstituted heterocyclyl selected from azetidin-1-yl, tetrahydrofuran-3-yl, pyrrolidin-1-yl, pyrrolidin-3-yl, piperidin-1-yl, piperidin-3-yl, piperidin-4-yl, piperidin-1-olate-4-yl, piperazin-1-yl, 1,4-diazepan-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,2,5,6-tetrahydropyridin-5-yl, 1,2,3,6-tetrahydropyridin-4-yl, hexahydrocyclopentapyrrol-2(1H)-yl, hexahydropyrrolo[3,2-b]pyrrol-1(2H)-yl, hexahydropyrrolo[3,4-b]pyrrol-1(2H)-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, octahydro-5H-pyrrolo[3,2-c]pyridin-5-yl, octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, hexahydro-1H-cyclobuta[1.2-c:1,4-c']dipyrrol-2(3H)-yl, octahydropyrrolo[1,2-a]pyrazin-2(1H)-yl, octahydro-2H-pyrido[1,2-a]pyrazin-2-yl, hexahydropyrrolo[3,4-b][1,4]oxazin-6(2H)-yl, 5-azaspiro[2.4]heptan-5-yl, 1-azaspiro[3.3]heptan-2-yl, 4-azaspiro[2.5]octan-7-yl, 2-oxa-6-azaspiro[3.4]octan-6-yl, 3-azabicyclo[3.1.0]hexan-3-yl, 8-azabicyclo[3.2.1]octan-3-yl, 8-azabicyclo[3.2.1]oct-2-en-3-yl, 9-azabicyclo[3.3.1]nonan-3-yl, 2,5-diazabicyclo[2.2.1]heptan-2-yl, 1,4-diazabicyclo[3.1.1]heptan-4-yl, 3,6-diazabicyclo[3.2.0]heptan-3-yl, 3,6-diazabicyclo[3.2.0]heptan-6-yl, 2,5-diazabicyclo[2.2.2]octan-2-yl, 1,4-diazabicyclo[3.2.1]octan-4-yl, 3,8-diazabicyclo[3.2.1]octan-3-yl, 1,4-diazabicyclo[3.2.2]nonan-4-yl, 4,7-diazaspiro[2.5]octan-4-yl, 4,7-diazaspiro[2.5]octan-7-yl, 2,6-diazaspiro[3.3]heptan-2-yl, 1,6-diazaspiro[3.4]octan-6-yl, 2,6-diazaspiro[3.4]octan-2-yl, 2,6-diazaspiro[3.4]octan-6-yl, 1,7,-diazaspiro[4.4]nonan-1-yl, 1,7,-diazaspiro[4.4]nonan-7-yl, 1,7-diazaspiro[3.5]nonan-7-yl, 2,6-diazaspiro[3.5]nonan-2-yl, 2,6-diazaspiro[3.5]nonan-6-yl, 1,7-diazaspiro[3.5]nonan-7-yl, 2,7-diazaspiro[3.5]nonan-2-yl, 2.7-diazaspiro[3.5]nonan-7-yl, 5,8-diazaspiro[3.5]nonan-8-yl, 2-oxa-5.8-diazaspiro[3.5]nonan-8-yl, 2,7-diazaspiro[4.4]nonan-2-yl, 2,7-diazaspiro[4.5]decan-2-yl, 2,7-diazaspiro[4.5]decan-7-yl, 2,8-diazaspiro[4.5]decan-8-yl, 6,9-diazaspiro[4.5]dec-9-yl, 6-oxa-2,9-diazaspiro[4.5]decan-2-yl, 2,9-diazaspiro[5.5]undecan-9-yl, 4-azadispiro[$2.1.2^5.3$]decan-9-yl, and 7-azadispiro[$5.1.5^8.3^6$]hexadecan-15-yl.

Another aspect includes a compound of Formula (I), Formula (II), or Formula (III), wherein B is heterocyclyl selected from azetidin-1-yl, tetrahydrofuran-3-yl, pyrrolidin-1-yl, pyrrolidin-3-yl, piperidin-1-yl, piperidin-3-yl, piperidin-4-yl, piperidin-1-olate-4-yl, piperazin-1-yl, 1,4-diazepan-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,2,5,6-tetrahydropyridin-5-yl, 1,2,3,6-tetrahydropyridin-4-yl, hexahydrocyclopentapyrrol-2(1H)-yl, hexahydropyrrolo[3,2-b]pyrrol-1(2H)-yl, hexahydropyrrolo[3,4-b]pyrrol-1(2H)-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, octahydro-5H-pyrrolo[3,2-c]pyridin-5-yl, octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, hexahydro-1H-cyclobuta[1.2-c:1,4-c']dipyrrol-2(3H)-yl, octahydropyrrolo[1,2-a]pyrazin-2(1H)-yl, octahydro-2H-pyrido[1,2-a]pyrazin-2-yl, hexahydropyrrolo[3,4-b][1,4]oxazin-6(2H)-yl, 5-azaspiro[2.4]heptan-5-yl, 1-azaspiro[3.3]heptan-2-yl, 4-azaspiro[2.5]octan-7-yl, 2-oxa-6-azaspiro[3.4]octan-6-yl, 3-azabicyclo[3.1.0]hexan-3-yl, 8-azabicyclo[3.2.1]octan-3-yl, 8-azabicyclo[3.2.1]oct-2-en-3-yl, 9-azabicyclo[3.3.1]nonan-3-yl, 2,5-diazabicyclo[2.2.1]heptan-2-yl, 1,4-diazabicyclo[3.1.1]heptan-4-yl, 3,6-diazabicyclo[3.2.0]heptan-3-yl, 3,6-diazabicyclo[3.2.0]heptan-6-yl, 2,5-diazabicyclo[2.2.2]octan-2-yl, 1,4-diazabicyclo[3.2.1]octan-4-yl, 3,8-diazabicyclo[3.2.1]octan-3-yl, 1,4-diazabicyclo[3.2.2]nonan-4-yl, 4,7-diazaspiro[2.5]octan-4-yl, 4,7-diazaspiro[2.5]octan-7-yl, 2,6-diazaspiro[3.3]heptan-2-yl, 1,6-diazaspiro[3.4]octan-6-yl, 2,6-diazaspiro[3.4]octan-2-yl, 2,6-diazaspiro[3.4]octan-6-yl, 1,7,-diazaspiro[4.4]nonan-1-yl, 1,7,-diazaspiro[4.4]nonan-7-yl, 1,7-diazaspiro[3.5]nonan-7-yl, 2,6-diazaspiro[3.5]nonan-2-yl, 2,6-diazaspiro[3.5]nonan-6-yl, 1,7-diazaspiro[3.5]nonan-7-yl, 2,7-diazaspiro[3.5]nonan-2-yl, 2,7-diazaspiro[3.5]nonan-7-yl, 5,8-diazaspiro[3.5]nonan-8-yl, 2-oxa-5,8-diazaspiro[3.5]nonan-8-yl, 2,7-diazaspiro[4.4]nonan-2-yl, 2,7-diazaspiro[4.5]decan-2-yl, 2,7-diazaspiro[4.5]decan-7-yl, 2,8-diazaspiro[4.5]decan-8-yl, 6,9-diazaspiro[4.5]dec-9-yl, 6-oxa-2,9-diazaspiro[4.5]decan-2-yl, 2,9-diazaspiro[5.5]undecan-9-yl, 4-azadispiro[$2.1.2^5.3^3$]decan-9-yl, and 7-azadispiro[$5.1.5^8.3^6$]hexadecan-15-yl, substituted where allowed by available valences with one $R_b$ substituent.

Another aspect includes a compound of Formula (I), Formula (II), or Formula (III), wherein B is heterocyclyl selected from azetidin-1-yl, tetrahydrofuran-3-yl, pyrrolidin-1-yl, pyrrolidin-3-yl, piperidin-1-yl, piperidin-3-yl, piperidin-4-yl, piperidin-1-olate-4-yl, piperazin-1-yl, 1,4-diazepan-1-yl, 1,2-dihydropyridin-2-yl, 1,2-dihydropyridin-3- yl, 1,2-dihydropyridin-4-yl, 1,2-dihydropyridin-5-yl, 1,2-dihydropyridin-6-yl, 1,2,5,6-tetrahydropyridin-5-yl, 1,2,3,6-tetrahydropyridin-4-yl, hexahydrocyclopentapyrrol-2(1H)-yl, hexahydropyrrolo[3,2-b]pyrrol-1(2H)-yl, hexahydropyrrolo[3,4-b]pyrrol-1(2H)-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, octahydro-5H-pyrrolo[3,2-c]pyridin-5-yl, octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, hexahydro-1H-cyclobuta[1.2-c:1,4-c']dipyrrol-2(3H)-yl, octahydropyrrolo[1,2-a]pyrazin-2(1H)-yl, octahydro-2H-pyrido[1,2-a]pyrazin-2-yl, hexahydropyrrolo[3,4-b][1,4]oxazin-6(2H)-yl, 5-azaspiro[2.4]heptan-5-yl, 1-azaspiro[3.3]heptan-2-yl, 4-azaspiro[2.5]octan-7-yl, 2-oxa-6-azaspiro[3.4]octan-6-yl, 3-azabicyclo[3.1.0]hexan-3-yl, 8-azabicyclo[3.2.1]octan-3-yl, 8-azabicyclo[3.2.1]oct-2-en-3-yl, 9-azabicyclo[3.3.1]nonan-3-yl, 2,5-diazabicyclo[2.2.1]heptan-2-yl, 1,4-diazabicyclo[3.1.1]heptan-4-yl, 3,6-diazabicyclo[3.2.0]heptan-3-yl, 3,6-diazabicyclo[3.2.0]heptan-6-yl, 2,5-diazabicyclo[2.2.2]octan-2-yl, 1,4-diazabicyclo[3.2.1]octan-4-yl, 3,8-diazabicyclo[3.2.1]octan-3-yl, 1,4-diazabicyclo[3.2.2]nonan-4-yl, 4,7-diazaspiro[2.5]octan-4-yl, 4,7-diazaspiro[2.5]octan-7-yl, 2,6-diazaspiro[3.3]heptan-2-yl, 1,6-diazaspiro[3.4]octan-6-yl, 2,6-diazaspiro[3.4]octan-2-yl, 2,6-diazaspiro[3.4]octan-6-yl, 1,7,-diazaspiro[4.4]nonan-1-yl, 1.7,-diazaspiro[4.4]nonan-7-yl, 1.7-diazaspiro[3.5]nonan-7-yl, 2,6-diazaspiro[3.5]nonan-2-yl, 2,6-diazaspiro[3.5]nonan-6-yl, 1,7-diazaspiro[3.5]nonan-7-yl, 2,7-diazaspiro[3.5]nonan-2-yl, 2,7-diazaspiro[3.5]nonan-7-yl, 5,8-diazaspiro[3.5]nonan-8-yl, 2-oxa-5,8-diazaspiro[3.5]nonan-8-yl, 2,7-diazaspiro[4.4]nonan-2-yl, 2,7-diazaspiro[4.5]decan-2-yl, 2.7-diazaspiro[4.5]decan-7-yl, 2,8-diazaspiro[4.5]decan-8-yl, 6,9-diazaspiro[4.5]dec-9-yl, 6-oxa-2,9-diazaspiro[4.5]decan-2-yl, 2,9-diazaspiro[5.5]undecan-9-yl, 4-azadispiro[2.1.2$^{5}$.3$^{3}$]decan-9-yl, and 7-azadispiro[5.1.5$^{8}$.3$^{6}$]hexadecan-15-yl, substituted where allowed by available valences with two $R_b$ substituents.

Another aspect includes a compound of Formula (I), Formula (II), or Formula (III), wherein B is heterocyclyl selected from azetidin-1-yl, tetrahydrofuran-3-yl, pyrrolidin-1-yl, pyrrolidin-3-yl, piperidin-1-yl, piperidin-3-yl, piperidin-4-yl, piperidin-1-olate-4-yl, piperazin-1-yl, 1,4-diazepan-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,2,5,6-tetrahydropyridin-5-yl, 1,2,3,6-tetrahydropyridin-4-yl, hexahydrocyclopentapyrrol-2(1H)-yl, hexahydropyrrolo[3,2-b]pyrrol-1(2H)-yl, hexahydropyrrolo[3,4-b]pyrrol-1(2H)-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, octahydro-5H-pyrrolo[3,2-c]pyridin-5-yl, octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, hexahydro-1H-cyclobuta[1.2-c:1,4-c']dipyrrol-2(3H)-yl, octahydropyrrolo[1,2-a]pyrazin-2(1H)-yl, octahydro-2H-pyrido[1,2-a]pyrazin-2-yl, hexahydropyrrolo[3,4-b][1,4]oxazin-6(2H)-yl, 5-azaspiro[2.4]heptan-5-yl, I-azaspiro[3.3]heptan-2-yl, 4-azaspiro[2.5]octan-7-yl, 2-oxa-6-azaspiro[3.4]octan-6-yl, 3-azabicyclo[3.1.0]hexan-3-yl, 8-azabicyclo[3.2.1]octan-3-yl, 8-azabicyclo[3.2.1]oct-2-en-3-yl, 9-azabicyclo[3.3.1]nonan-3-yl, 2,5-diazabicyclo[2.2.1]heptan-2-yl, 1,4-diazabicyclo[3.1.1]heptan-4-yl, 3,6-diazabicyclo[3.2.0]heptan-3-yl, 3,6-diazabicyclo[3.2.0]heptan-6-yl, 2,5-diazabicyclo[2.2.2]octan-2-yl, 1,4-diazabicyclo[3.2.1]octan-4-yl, 3,8-diazabicyclo[3.2.1]octan-3-yl, 1,4-diazabicyclo[3.2.2]nonan-4-yl, 4,7-diazaspiro[2.5]octan-4-yl, 4,7-diazaspiro[2.5]octan-7-yl, 2,6-diazaspiro[3.3]heptan-2-yl, 1,6-diazaspiro[3.4]octan-6-yl, 2,6-diazaspiro[3.4]octan-2-yl, 2,6-diazaspiro[3.4]octan-6-yl, 1,7,-diazaspiro[4.4]nonan-1-yl, 1.7,-diazaspiro[4.4]nonan-7-yl, 1.7-diazaspiro[3.5]nonan-7-yl, 2,6-diazaspiro[3.5]nonan-2-yl, 2,6-diazaspiro[3.5]nonan-6-yl, 1,7-diazaspiro[3.5]nonan-7-yl, 2,7-diazaspiro[3.5]nonan-2-yl, 2,7-diazaspiro[3.5]nonan-7-yl, 5,8-diazaspiro[3.5]nonan-8-yl, 2-oxa-5,8-diazaspiro[3.5]nonan-8-yl, 2,7-diazaspiro[4.4]nonan-2-yl, 2,7-diazaspiro[4.5]decan-2-yl, 2,7-diazaspiro[4.5]decan-7-yl, 2,8-diazaspiro[4.5]decan-8-yl, 6,9-diazaspiro[4.5]dec-9-yl, 6-oxa-2,9-diazaspiro[4.5]decan-2-yl, 2,9-diazaspiro[5.5]undecan-9-yl, 4-azadispiro[2.1.2$^{5}$.3$^{3}$]decan-9-yl, and 7-azadispiro[5.1.5$^{8}$.3$^{6}$]hexadecan-15-yl, substituted where allowed by available valences with three $R_b$ substituents.

Another aspect includes a compound of Formula (I), Formula (II), or Formula (III), wherein B is heterocyclyl selected from azetidin-1-yl, tetrahydrofuran-3-yl, pyrrolidin-1-yl, pyrrolidin-3-yl, piperidin-1-yl, piperidin-3-yl, piperidin-4-yl, piperidin-1-olate-4-yl, piperazin-1-yl, 1,4-diazepan-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,2,5,6-tetrahydropyridin-5-yl, 1,2,3,6-tetrahydropyridin-4-yl, hexahydrocyclopentapyrrol-2(1H)-yl, hexahydropyrrolo[3,2-b]pyrrol-1(2H)-yl, hexahydropyrrolo[3,4-b]pyrrol-1(2H)-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, octahydro-5H-pyrrolo[3,2-c]pyridin-5-yl, octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, hexahydro-1H-cyclobuta[1.2-c:1,4-c']dipyrrol-2(3H)-yl, octahydropyrrolo[1,2-a]pyrazin-2(1H)-yl, octahydro-2H-pyrido[1,2-a]pyrazin-2-yl, hexahydropyrrolo[3,4-b][1,4]oxazin-6(2H)-yl, 5-azaspiro[2.4]heptan-5-yl, 1-azaspiro[3.3]heptan-2-yl, 4-azaspiro[2.5]octan-7-yl, 2-oxa-6-azaspiro[3.4]octan-6-yl, 3-azabicyclo[3.1.0]hexan-3-yl, 8-azabicyclo[3.2.1]octan-3-yl, 8-azabicyclo[3.2.1]oct-2-en-3-yl, 9-azabicyclo[3.3.1]nonan-3-yl, 2,5-diazabicyclo[2.2.1]heptan-2-yl, 1,4-diazabicyclo[3.1.1]heptan-4-yl, 3,6-diazabicyclo[3.2.0]heptan-3-yl, 3,6-diazabicyclo[3.2.0]heptan-6-yl, 2,5-diazabicyclo[2.2.2]octan-2-yl, 1,4-diazabicyclo[3.2.1]octan-4-yl, 3,8-diazabicyclo[3.2.1]octan-3-yl, 1,4-diazabicyclo[3.2.2]nonan-4-yl, 4,7-diazaspiro[2.5]octan-4-yl, 4,7-diazaspiro[2.5]octan-7-yl, 2,6-diazaspiro[3.3]heptan-2-yl, 1,6-diazaspiro[3.4]octan-6-yl, 2,6-diazaspiro[3.4]octan-2-yl, 2,6-diazaspiro[3.4]octan-6-yl, 1,7,-diazaspiro[4.4]nonan-1-yl, 1,7,-diazaspiro[4.4]nonan-7-yl, 1,7-diazaspiro[3.5]nonan-7-yl, 2,6-diazaspiro[3.5]nonan-2-yl, 2,6-diazaspiro[3.5]nonan-6-yl, 1,7-diazaspiro[3.5]nonan-7-yl, 2,7-diazaspiro[3.5]nonan-2-yl, 2,7-diazaspiro[3.5]nonan-7-yl, 5,8-diazaspiro[3.5]nonan-8-yl, 2-oxa-5,8-diazaspiro[3.5]nonan-8-yl, 2,7-diazaspiro[4.4]nonan-2-yl, 2,7-diazaspiro[4.5]decan-2-yl, 2,7-diazaspiro[4.5]decan-7-yl, 2,8-diazaspiro[4.5]decan-8-yl, 6,9-diazaspiro[4.5]dec-9-yl, 6-oxa-2,9-diazaspiro[4.5]decan-2-yl, 2,9-diazaspiro[5.5]undecan-9-yl, 4-azadispiro[2.1.2$^{5}$.3$^{3}$]decan-9-yl, and 7-azadispiro[5.1.5$^{8}$.3$^{6}$]hexadecan-15-yl, substituted where allowed by available valences with four $R_b$ substituents.

Another aspect includes a compound of Formula (I), Formula (II), or Formula (III), wherein B is heterocyclyl selected from azetidin-1-yl, tetrahydrofuran-3-yl, pyrrolidin-1-yl, pyrrolidin-3-yl, piperidin-1-yl, piperidin-3-yl, piperidin-4-yl, piperidin-1-olate-4-yl, piperazin-1-yl, 1,4-diazepan-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,2,5,6-tetrahydropyridin-5-yl, 1,2,3,6- tetrahydropyridin-4-yl, hexahydrocyclopentapyrrol-2(1H)-yl, hexahydropyrrolo[3,2-b]pyrrol-1(2H)-yl, hexahydropyrrolo[3,4-b]pyrrol-1(2H)-yl, hexahydropyrrolo [3,4-c]pyrrol-1(1H)-yl, hexahydropyrrolo[3,4-c]pyrrol-2 (1H)-yl, hexahydropyrrolo[3,4-c]pyrrol-5(1H)-yl, octahydro-5H-pyrrolo[3,2-c]pyridin-5-yl, octahydro-6H-pyrrolo [3,4-b]pyridin-6-yl, hexahydropyrrolo[1,2-a]pyrazin-6(2H)-one, hexahydropyrrolo[1,2-a]pyrazin-2(1H)-yl, hexahydro-1H-cyclobuta[1.2-c:1,4-c']dipyrrol-2(3H)-yl, octahydropyrrolo[1,2-a]pyrazin-2(1H)-yl, octahydro-2H-pyrido[1,2-a]pyrazin-2-yl, hexahydropyrrolo[3,4-b][1,4] oxazin-6(2H)-yl, 5-azaspiro[2.4]heptan-5-yl, I-azaspiro[3.3] heptan-2-yl, 4-azaspiro[2.5]octan-7-yl, 2-oxa-6-azaspiro [3.4]octan-6-yl, 3-azabicyclo[3.1.0]hexan-3-yl, 8-azabicyclo[3.2.1]octan-3-yl, 8-azabicyclo[3.2.1]oct-2-en-3-yl, 9-azabicyclo[3.3.1]nonan-3-yl, 2,5-diazabicyclo[2.2.1] heptan-2-yl, 1,4-diazabicyclo[3.1.1]heptan-4-yl, 3,6-diazabicyclo[3.2.0]heptan-3-yl, 3,6-diazabicyclo[3.2.0]heptan-6-yl, 2,5-diazabicyclo[2.2.2]octan-2-yl, 1,4-diazabicyclo [3.2.1]octan-4-yl, 3,8-diazabicyclo[3.2.1]octan-3-yl, 1,4-diazabicyclo[3.2.2]nonan-4-yl, 4,7-diazaspiro[2.5]octan-4-yl, 4,7-diazaspiro[2.5]octan-7-yl, 2,6-diazaspiro[3.3]heptan-2-yl, 1,6-diazaspiro[3.4]octan-6-yl, 2,6-diazaspiro[3.4] octan-2-yl, 2,6-diazaspiro[3.4]octan-6-yl, 1,7,-diazaspiro [4.4]nonan-1-yl, 1.7,-diazaspiro[4.4]nonan-7-yl, 1,7-diazaspiro[3.5]nonan-7-yl, 2,6-diazaspiro[3.5]nonan-2-yl, 2,6-diazaspiro[3.5]nonan-6-yl, 1,7-diazaspiro[3.5]nonan-7-yl, 2,7-diazaspiro[3.5]nonan-2-yl, 2,7-diazaspiro[3.5] nonan-7-yl, 5,8-diazaspiro[3.5]nonan-8-yl, 2-oxa-5,8-diazaspiro[3.5]nonan-8-yl, 2,7-diazaspiro[4.4]nonan-2-yl, 2,7-diazaspiro[4.5]decan-2-yl, 2.7-diazaspiro[4.5]decan-7-yl, 2,8-diazaspiro[4.5]decan-8-yl, 6,9-diazaspiro[4.5]dec-9-yl, 6-oxa-2,9-diazaspiro[4.5]decan-2-yl, 2,9-diazaspiro[5.5]undecan-9-yl, 4-azadispiro[$2.1.2^5.3^3$]decan-9-yl, and 7-azadispiro[$5.1.5^8.3^6$]hexadecan-15-yl, substituted where allowed by available valences with five $R_b$ substituents.

Another aspect includes a compound of Formula (I), Formula (II), or Formula (III), wherein B is heterocyclyl selected from pyrrolidin-1-yl, piperidin-4-yl, piperidin-1-olate-4-yl, piperazin-1-yl, 4-azaspiro[2.5]octan-7-yl, 8-azabicyclo[3.2.1]octan-3-yl, 2,5-diazabicyclo[2.2.1]heptan-2-yl, 1,6-diazaspiro[3.4]octan-6-yl, 2-oxa-5,8-diazaspiro[3.5]nonan-8-yl, and 4-azadispiro[$2.1.2^5.3^3$]decan-9-yl, optionally substituted where allowed by available valences with 1, 2, 3, 4, or 5 $R_b$ substituents.

Another aspect includes a compound of Formula (I), Formula (II), or Formula (III), wherein B is unsubstituted heterocyclyl selected from pyrrolidin-1-yl, piperidin-4-yl, piperidin-1-olate-4-yl, piperazin-1-yl, 4-azaspiro[2.5]octan-7-yl, 8-azabicyclo[3.2.1]octan-3-yl, 2,5-diazabicyclo[2.2.1] heptan-2-yl, 1,6-diazaspiro[3.4]octan-6-yl, 2-oxa-5,8-diazaspiro[3.5]nonan-8-yl, and 4-azadispiro[$2.1.2^5.3^3$]decan-9-yl.

Another aspect includes a compound of Formula (I), Formula (II), or Formula (III), wherein B is heterocyclyl selected from pyrrolidin-1-yl, piperidin-4-yl, piperidin-1-olate-4-yl, piperazin-1-yl, 4-azaspiro[2.5]octan-7-yl, 8-azabicyclo[3.2.1]octan-3-yl, 2,5-diazabicyclo[2.2.1]heptan-2-yl, 1,6-diazaspiro[3.4]octan-6-yl, 2-oxa-5,8-diazaspiro[3.5]nonan-8-yl, and 4-azadispiro[$2.1.2^5.3^3$]decan-9-yl, substituted where allowed by available valences with one $R_b$ substituent.

Another aspect includes a compound of Formula (I), Formula (II), or Formula (III), wherein B is heterocyclyl selected from pyrrolidin-1-yl, piperidin-4-yl, piperidin-1-olate-4-yl, piperazin-1-yl, 4-azaspiro[2.5]octan-7-yl, 8-azabicyclo[3.2.1]octan-3-yl, 2,5-diazabicyclo[2.2.1]heptan-2-yl, 1,6-diazaspiro[3.4]octan-6-yl, 2-oxa-5,8-diazaspiro[3.5]nonan-8-yl, and 4-azadispiro[$2.1.2^5.3^3$]decan-9-yl, substituted where allowed by available valences with two $R_b$ substituents.

Another aspect includes a compound of Formula (I), Formula (II), or Formula (III), wherein B is heterocyclyl selected from pyrrolidin-1-yl, piperidin-4-yl, piperidin-1-olate-4-yl, piperazin-1-yl, 4-azaspiro[2.5]octan-7-yl, 8-azabicyclo[3.2.1]octan-3-yl, 2,5-diazabicyclo[2.2.1]heptan-2-yl, 1,6-diazaspiro[3.4]octan-6-yl, 2-oxa-5.8-diazaspiro[3.5]nonan-8-yl, and 4-azadispiro[$2.1.2^5.3^3$]decan-9-yl, substituted where allowed by available valences with three $R_b$ substituents.

Another aspect includes a compound of Formula (I), Formula (II), or Formula (III), wherein B is heterocyclyl selected from pyrrolidin-1-yl, piperidin-4-yl, piperidin-1-olate-4-yl, piperazin-1-yl, 4-azaspiro[2.5]octan-7-yl, 8-azabicyclo[3.2.1]octan-3-yl, 2,5-diazabicyclo[2.2.1]heptan-2-yl, 1,6-diazaspiro[3.4]octan-6-yl, 2-oxa-5,8-diazaspiro[3.5]nonan-8-yl, and 4-azadispiro[$2.1.2^5.3^3$]decan-9-yl, substituted where allowed by available valences with four $R_b$ substituents.

Another aspect includes a compound of Formula (I), Formula (II), or Formula (III), wherein B is heterocyclyl selected from pyrrolidin-1-yl, piperidin-4-yl, piperidin-1-olate-4-yl, piperazin-1-yl, 4-azaspiro[2.5]octan-7-yl, 8-azabicyclo[3.2.1]octan-3-yl, 2,5-diazabicyclo[2.2.1]heptan-2-yl, 1,6-diazaspiro[3.4]octan-6-yl, 2-oxa-5.8-diazaspiro[3.5]nonan-8-yl, and 4-azadispiro[$2.1.2^5.3^3$]decan-9-yl, substituted where allowed by available valences with five $R_b$ substituents.

Another aspect includes a compound of Formula (I), Formula (II), or Formula (III), wherein B is heterocyclyl selected from pyrrolidin-1-yl, piperidin-4-yl, piperazin-1-yl, and 4-azaspiro[2.5]octan-7-yl, optionally substituted where allowed by available valences with 1, 2, 3, 4, or 5 $R_b$ substituents.

Another aspect includes a compound of Formula (I), Formula (II), or Formula (III), wherein B is unsubstituted heterocyclyl selected from pyrrolidin-1-yl, piperidin-4-yl, piperazin-1-yl, and 4-azaspiro[2.5]octan-7-yl.

Another aspect includes a compound of Formula (I), Formula (II), or Formula (III), wherein B is heterocyclyl selected from pyrrolidin-1-yl, piperidin-4-yl, piperazin-1-yl, and 4-azaspiro[2.5]octan-7-yl, substituted where allowed by available valences with one $R_b$ substituent.

Another aspect includes a compound of Formula (I), Formula (II), or Formula (III), wherein B is heterocyclyl selected from pyrrolidin-1-yl, piperidin-4-yl, piperazin-1-yl, and 4-azaspiro[2.5]octan-7-yl, substituted where allowed by available valences with two $R_b$ substituents.

Another aspect includes a compound of Formula (I), Formula (II), or Formula (III), wherein B is heterocyclyl selected from pyrrolidin-1-yl, piperidin-4-yl, piperazin-1-yl, and 4-azaspiro[2.5]octan-7-yl, substituted where allowed by available valences with three $R_b$ substituents.

Another aspect includes a compound of Formula (I), Formula (II), or Formula (III), wherein B is heterocyclyl selected from pyrrolidin-1-yl, piperidin-4-yl, piperazin-1-yl, and 4-azaspiro[2.5]octan-7-yl, substituted where allowed by available valences with four $R_b$ substituents.

Another aspect includes a compound of Formula (I), Formula (II), or Formula (III), wherein B is heterocyclyl selected from pyrrolidin-1-yl, piperidin-4-yl, piperazin-1-yl, and 4-azaspiro[2.5]octan-7-yl, substituted where allowed by available valences with five $R_b$ substituents.

Another aspect includes a compound of Formula (I), Formula (II), or Formula (III), wherein B is pyrrolidin-1-yl, substituted where allowed by available valences with one $R_b$ substituent.

Another aspect includes a compound of Formula (I), Formula (II), or Formula (III), wherein B is piperidin-4-yl, substituted where allowed by available valences with 4 or 5 $R_b$ substituents.

Another aspect includes a compound of Formula (I), Formula (II), or Formula (III), wherein B is piperidin-4-yl, substituted where allowed by available valences with four $R_b$ substituents.

Another aspect includes a compound of Formula (I), Formula (II), or Formula (III), wherein B is piperidin-4-yl, substituted where allowed by available valences with five $R_b$ substituents.

Another aspect includes a compound of Formula (I), Formula (II), or Formula (III), wherein B is unsubstituted piperazin-1-yl.

Another aspect includes a compound of Formula (I), Formula (II), or Formula (III), wherein B is m piperazin-1-yl, substituted where allowed by available valences with one $R_b$ substituent.

Another aspect includes a compound of Formula (I), Formula (II), or Formula (III), wherein B is piperazin-1-yl, substituted where allowed by available valences with two $R_b$ substituents.

Another aspect includes a compound of Formula (I), Formula (II), or Formula (III), wherein B is piperazin-1-yl, substituted where allowed by available valences with three $R_b$ substituents.

Another aspect includes a compound of Formula (I), Formula (II), or Formula (III), wherein B is piperazin-1-yl, substituted where allowed by available valences with four $R_b$ substituents.

Another aspect includes a compound of Formula (I), Formula (II), or Formula (III), wherein B is unsubstituted 4-azaspiro[2.5]octan-7-yl.

Another aspect includes a compound of Formula (I), Formula (II), or Formula (III), wherein B is 4-azaspiro[2.5]octan-7-yl, substituted where allowed by available valences with one $R_b$ substituent.

Another aspect includes a compound of Formula (I), Formula (II), or Formula (III), wherein B is 4-azaspiro[2.5]octan-7-yl, substituted where allowed by available valences with two $R_b$ substituents.

Another aspect includes a compound of Formula (I), Formula (II), or Formula (III), wherein B is heterocyclyl containing at least one chiral carbon atom having an (R) configuration.

Another aspect includes a compound of Formula (I), Formula (II), or Formula (III), wherein B is heterocyclyl containing at least one chiral carbon atom having an (S) configuration.

One aspect includes a compound of Formula (I), Formula (II), or Formula (III), wherein $R_b$ is selected from halogen, $C_{1-4}$alkyl, amino, $C_{1-4}$alkyl-amino, $(C_{1-4}alkyl)_2$-amino, and $C_{3-6}$cycloalkyl.

Another aspect includes a compound of Formula (I), Formula (II), or Formula (III), wherein $R_b$ is selected from halogen, $C_{1-4}$alkyl, $C_{1-4}$alkyl-amino, and $C_{3-6}$cycloalkyl.

Another aspect includes a compound of Formula (I), Formula (II), or Formula (III), wherein $R_b$ is halogen selected from bromo, chloro, fluoro, and iodo.

Another aspect includes a compound of Formula (I), Formula (II), or Formula (III), wherein $R_b$ is fluoro.

Another aspect includes a compound of Formula (I), Formula (II), or Formula (III), wherein $R_b$ is $C_{1-4}$alkyl selected from methyl, ethyl, propyl, isopropyl, butyl, and tert-butyl.

Another aspect includes a compound of Formula (I), Formula (II), or Formula (III), wherein $R_b$ is $C_{1-4}$alkyl selected from methyl, ethyl, and isopropyl.

Another aspect includes a compound of Formula (I), Formula (II), or Formula (III), wherein $R_b$ is methyl.

Another aspect includes a compound of Formula (I), Formula (II), or Formula (III), wherein $R_b$ is ethyl.

Another aspect includes a compound of Formula (I), Formula (II), or Formula (III), wherein $R_b$ is isopropyl.

Another aspect includes a compound of Formula (I), Formula (II), or Formula (III), wherein $R_b$ is $C_{1-4}$alkyl-amino.

Another aspect includes a compound of Formula (I), Formula (II), or Formula (III), wherein $R_b$ is $C_{1-4}$alkyl-amino, wherein $C_{1-4}$alkyl is selected from methyl, ethyl, propyl, isopropyl, butyl, and tert-butyl.

Another aspect includes a compound of Formula (I), Formula (II), or Formula (III), wherein $R_b$ is selected from methylamino and tert-butylamino.

Another aspect includes a compound of Formula (I), Formula (II), or Formula (III), wherein $R_b$ is methylamino.

Another aspect includes a compound of Formula (I), Formula (II), or Formula (III), wherein $R_b$ is tert-butylamino.

Another aspect includes a compound of Formula (I), Formula (II), or Formula (III), wherein $R_b$ is $C_{3-6}$cycloalkyl selected from cyclopropyl, cyclobutyl, cyclopentyl, and cyclohexyl.

Another aspect includes a compound of Formula (I), Formula (II), or Formula (III), wherein $R_b$ is cyclopropyl.

One aspect includes a compound of Formula (I), Formula (II), or Formula (III), wherein $R_1$ is selected from heteroaryl, heterocyclyl, phenyl, heteroaryl-$C_{1-4}$alkyl, heteroaryl-$C_{2-4}$alkenyl, heteroaryl-amino, and heteroaryl-$C_{1-4}$alkyl-amino, wherein heteroaryl is a 3-7 membered monocyclic or 6-10 membered bicyclic ring system having 1, 2, 3, or 4 heteroatom ring members independently selected from N, O, or S, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S; and wherein each instance of phenyl, heteroaryl or heterocyclyl is optionally substituted where allowed by available valences with 1 or 2 $R_{1a}$ substituents.

Another aspect includes a compound of Formula (I), Formula (II), or Formula (III), wherein $R_1$ is selected from heteroaryl, heterocyclyl, phenyl, heteroaryl-$C_{1-4}$alkyl, heteroaryl-$C_{2-4}$alkenyl, heteroaryl-amino, and heteroaryl-$C_{1-4}$alkyl-amino, wherein heteroaryl is a 3-7 membered monocyclic or 6-10 membered bicyclic ring system having 1, 2, 3, or 4 heteroatom ring members independently selected from N, O, or S, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S; and wherein each instance of phenyl, heteroaryl or heterocyclyl is unsubstituted.

Another aspect includes a compound of Formula (I), Formula (II), or Formula (III), wherein $R_1$ is selected from heteroaryl, heterocyclyl, phenyl, heteroaryl-$C_{1-4}$alkyl, heteroaryl-$C_{2-4}$alkenyl, heteroaryl-amino, and heteroaryl-$C_{1-4}$alkyl-amino, wherein heteroaryl is a 3-7 membered monocyclic or 6-10 membered bicyclic ring system having 1, 2, 3, or 4 heteroatom ring members independently selected from N, O, or S, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S; and wherein each instance of phenyl, heteroaryl or heterocyclyl is substituted where allowed by available valences with one $R_{1a}$ substituent.

Another aspect includes a compound of Formula (I), Formula (II), or Formula (III), wherein $R_1$ is selected from heteroaryl, heterocyclyl, phenyl, heteroaryl-$C_{1-4}$alkyl, heteroaryl-$C_{2-4}$alkenyl, heteroaryl-amino, and heteroaryl-$C_{1-4}$alkyl-amino, wherein heteroaryl is a 3-7 membered monocyclic or 6-10 membered bicyclic ring system having 1, 2, 3, or 4 heteroatom ring members independently selected from N, O, or S, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S; and wherein each instance of phenyl, heteroaryl or heterocyclyl is substituted where allowed by available valences with two $R_{1a}$ substituents.

Another aspect includes a compound of Formula (I), Formula (II), or Formula (III), wherein $R_1$ is selected from heteroaryl, heteroaryl-$C_{2-4}$alkenyl, heteroaryl-amino, and heteroaryl-$C_{1-4}$alkyl-amino, wherein heteroaryl is a 3-7 membered monocyclic or 6-10 membered bicyclic ring system having 1, 2, 3, or 4 heteroatom ring members independently selected from N, O, or S; and wherein heteroaryl is optionally substituted where allowed by available valences with 1 or 2 $R_{1a}$ substituents.

Another aspect includes a compound of Formula (I), Formula (II), or Formula (III), wherein $R_1$ is selected from heteroaryl, heteroaryl-$C_{2-4}$alkenyl, heteroaryl-amino, and heteroaryl-$C_{1-4}$alkyl-amino, wherein heteroaryl is a 3-7 membered monocyclic or 6-10 membered bicyclic ring system having 1, 2, 3, or 4 heteroatom ring members independently selected from N, O, or S; and wherein heteroaryl is unsubstituted.

Another aspect includes a compound of Formula (I), Formula (II), or Formula (III), wherein $R_1$ is selected from heteroaryl, heteroaryl-$C_{2-4}$alkenyl, heteroaryl-amino, and heteroaryl-$C_{1-4}$alkyl-amino, wherein heteroaryl is a 3-7 membered monocyclic or 6-10 membered bicyclic ring system having 1, 2, 3, or 4 heteroatom ring members independently selected from N, O, or S; and wherein heteroaryl is substituted where allowed by available valences with one $R_{1a}$ substituent.

Another aspect includes a compound of Formula (I), Formula (II), or Formula (III), wherein $R_1$ is selected from heteroaryl, heteroaryl-$C_{2-4}$alkenyl, heteroaryl-amino, and heteroaryl-$C_{1-4}$alkyl-amino, wherein heteroaryl is a 3-7 membered monocyclic or 6-10 membered bicyclic ring system having 1, 2, 3, or 4 heteroatom ring members independently selected from N, O, or S; and wherein heteroaryl is substituted where allowed by available valences with two $R_{1a}$ substituents.

Another aspect includes a compound of Formula (I), Formula (II), or Formula (III), wherein $R_1$ is heteroaryl selected from thienyl, 1H-pyrazolyl, 1H-imidazolyl, 1,3-thiazolyl, oxazolyl, 1,2,4-oxadiazolyl, 1,3,4-oxadiazolyl, 1,2,4-thiadiazolyl, 1H-1,2,3-triazolyl, 2H-1,2,3-triazolyl, 1H-1,2,4-triazolyl, 1H-tetrazolyl, 2H-tetrazolyl, pyridinyl, pyridin-2(1H)-on-yl, pyrazinyl, pyrimidinyl, pyrimidin-4(3H)-on-yl, pyridazinyl, pyridazin-3(2H)-on-yl, 1,2,4-triazinyl, 1,3,5-triazinyl, 1H-indolyl, 1H-indazolyl, 2H-indazolyl, indolizinyl, benzofuranyl, benzothienyl, 1H-benzimidazolyl, 1,3-benzoxazolyl, 1,3-benzothiazolyl, 1,3-benzodioxolyl, 1,2,3-benzotriazolyl, 9H-purinyl, furo[3,2-b]pyridinyl, furo[3,2-c]pyridinyl, furo[2,3-c]pyridinyl, 1,3-oxazolo[5,4-b]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, pyrazolo[1,5-a]pyrimidinyl, pyrazolo[1,5-a]pyrazinyl, 1H-pyrazolo[3,4-b]pyridinyl, 1H-pyrazolo[3,4-b]pyrazinyl, 1H-pyrazolo[3,4-c]pyridinyl, 1H-pyrazolo[4,3-b]pyridinyl, 1H-pyrazolo[4,3-d]pyrimidinyl, 2H-pyrazolo[4,3-b]pyridinyl, 2H-pyrazolo[4,3-c]pyridin-yl, 5H-pyrrolo[2,3-b]pyrazinyl, imidazo[1,2-a]pyridinyl, imidazo[1,2-a]pyrazinyl, imidazo[1,2-a]pyrimidinyl, imidazo[1,2-b]pyridazinyl, imidazo[1,2-c]pyrimidinyl, 1H-imidazo[4,5-b]pyridinyl, 3H-imidazo[4,5-b]pyridinyl, imidazo[2,1-b][1,3]thiazolyl, imidazo[2,1-b][1,3,4]thiadiazolyl, [1,3]oxazolo[4,5-b]pyridinyl, [1,2,3]triazolo[1,5-a]pyridinyl, 1H-[1,2,3]triazolo[4,5-b]pyridinyl, 3H-[1,2,3]triazolo[4,5-b]pyridinyl, [1,2,4]triazolo[15-a]pyridinyl, [1,2,4]triazolo[1,5-a]pyrazinyl, [1,2,4]triazolo[4,3-a]pyridinyl, tetrazolo[1,5-a]pyridinyl, tetrazolo[1,5-b]pyridazinyl, quinolinyl, isoquinolinyl, and quinoxalinyl, optionally substituted where allowed by available valences with 1 or 2 $R_{1a}$ substituents.

Another aspect includes a compound of Formula (I), Formula (II), or Formula (III), wherein $R_1$ is unsubstituted heteroaryl selected from thienyl, 1H-pyrazolyl, 1H-imidazolyl, 1,3-thiazolyl, oxazolyl, 1,2,4-oxadiazolyl, 1,3,4-oxadiazolyl, 1,2,4-thiadiazolyl, 1H-1,2,3-triazolyl, 2H-1,2,3-triazolyl, 1H-1,2,4-triazolyl, 1H-tetrazolyl, 2H-tetrazolyl, pyridinyl, pyridin-2(1H)-on-yl, pyrazinyl, pyrimidinyl, pyrimidin-4(3H)-on-yl, pyridazinyl, pyridazin-3(2H)-on-yl, 1,2,4-triazinyl, 1,3,5-triazinyl, 1H-indolyl, 1H-indazolyl, 2H-indazolyl, indolizinyl, benzofuranyl, benzothienyl, 1H-benzimidazolyl, 1,3-benzoxazolyl, 1,3-benzothiazolyl, 1,3-benzodioxolyl, 1,2,3-benzotriazolyl, 9H-purinyl, furo[3,2-b]pyridinyl, furo[3,2-c]pyridinyl, furo[2,3-c]pyridinyl, 1,3-oxazolo[5,4-b]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, pyrazolo[1,5-a]pyrimidinyl, pyrazolo[1,5-a]pyrazinyl, 1H-pyrazolo[3,4-b]pyridinyl, 1H-pyrazolo[3,4-b]pyrazinyl, 1H-pyrazolo[3,4-c]pyridinyl, 1H-pyrazolo[4,3-b]pyridinyl, 1H-pyrazolo[4,3-d]pyrimidinyl, 2H-pyrazolo[4,3-b]pyridinyl, 2H-pyrazolo[4,3-c]pyridin-yl, 5H-pyrrolo[2,3-b]pyrazinyl, imidazo[1,2-a]pyridinyl, imidazo[1,2-a]pyrazinyl, imidazo[1,2-a]pyrimidinyl, imidazo[1,2-b]pyridazinyl, imidazo[1,2-c]pyrimidinyl, 1H-imidazo[4,5-b]pyridinyl, 3H-imidazo[4,5-b]pyridinyl, imidazo[2,1-b][1,3]thiazolyl, imidazo[2,1-b][1,3,4]thiadiazolyl, [1,3]oxazolo[4,5-b]pyridinyl, [1,2,3]triazolo[1,5-a]pyridinyl, 1H-[1,2,3]triazolo[4,5-b]pyridinyl, 2H-[1,2,3]triazolo[4,5-b]pyridinyl, 3H-[1,2,3]triazolo[4,5-b]pyridinyl, [1,2,4]triazolo[1,5-a]pyridinyl, [1,2,4]triazolo[1,5-a]pyrazinyl, [1,2,4]triazolo[4,3-a]pyridinyl, tetrazolo[1,5-a]pyridinyl, tetrazolo[1,5-b]pyridazinyl, quinolinyl, isoquinolinyl, and quinoxalinyl.

Another aspect includes a compound of Formula (I), Formula (II), or Formula (III), wherein $R_1$ is heteroaryl selected from thienyl, 1H-pyrazolyl, 1H-imidazolyl, 1,3-thiazolyl, oxazolyl, 1,2,4-oxadiazolyl, 1,3,4-oxadiazolyl, 1,2,4-thiadiazolyl, 1H-1,2,3-triazolyl, 2H-1,2,3-triazolyl, 1H-1,2,4-triazolyl, 1H-tetrazolyl, 2H-tetrazolyl, pyridinyl, pyridin-2(1H)-on-yl, pyrazinyl, pyrimidinyl, pyrimidin-4(3H)-on-yl, pyridazinyl, pyridazin-3(2H)-on-yl, 1,2,4-triazinyl, 1,3,5-triazinyl, 1H-indolyl, 1H-indazolyl, 2H-indazolyl, indolizinyl, benzofuranyl, benzothienyl, 1H-benzimidazolyl, 1,3-benzoxazolyl, 1,3-benzothiazolyl, 1,3-benzodioxolyl, 1,2,3-benzotriazolyl, 9H-purinyl, furo[3.2-b]pyridinyl, furo[3,2-c]pyridinyl, furo[2.3-c]pyridinyl, 1,3-oxazolo[5,4-b]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, pyrazolo[1,5-a]pyrimidinyl, pyrazolo[1,5-a]pyrazinyl, 1H-pyrazolo[3,4-b]pyridinyl, 1H-pyrazolo[3,4-b]pyrazinyl, 1H-pyrazolo[3,4-c]pyridinyl, 1H-pyrazolo[4,3-b]pyridinyl, 1H-pyrazolo[4,3-d]pyrimidinyl, 2H-pyrazolo[4,3-b]pyridinyl, 2H-pyrazolo[4,3-c]pyridin-yl, 5H-pyrrolo[2,3-b]pyrazinyl, imidazo[1,2-a]pyridinyl, imidazo[1,2-a]pyrazinyl, imidazo[1,2-a]pyrimidinyl, imidazo[1,2-b]pyridazinyl, imidazo[1,2-c]pyrimidinyl, 1H-imidazo[4,5-b]pyridinyl, 3H-imidazo[4,5-b]pyridinyl, imidazo[2,1-b][1,3]thiazolyl, imidazo[2,1-b][1,3,4]thiadiazolyl, [1,3]oxazolo[4,5-b]pyridinyl, [1,2,3]triazolo[1,5-a]pyridinyl, 1H-[1,2,3]triazolo[4,5-b]pyridinyl, 2H-[1,2,3]triazolo[4,5-b]pyridinyl, 3H-[1,2,3]triazolo[4,5-b]pyridinyl, [1,2,4]triazolo[1,5-a]pyridinyl, [1,2,4]triazolo[1,5-a]pyrazinyl, [1,2,4]triazolo[4,3-a]pyridinyl, tetrazolo[1,5-a]pyridinyl, tetrazolo[1,5-b]pyridazinyl, quinolinyl, isoquinolinyl, and quinoxalinyl, substituted where allowed by available valences with one $R_{1a}$ substituent.

Another aspect includes a compound of Formula (I), Formula (II), or Formula (III), wherein $R_1$ is heteroaryl selected from thienyl, 1H-pyrazolyl, 1H-imidazolyl, 1,3-thiazolyl, oxazolyl, 1,2,4-oxadiazolyl, 1,3,4-oxadiazolyl, 1,2,4-thiadiazolyl, 1H-1,2,3-triazolyl, 2H-1,2,3-triazolyl, 1H-1,2,4-triazolyl, 1H-tetrazolyl, 2H-tetrazolyl, pyridinyl, pyridin-2(1H)-on-yl, pyrazinyl, pyrimidinyl, pyrimidin-4(3H)-on-yl, pyridazinyl, pyridazin-3(2H)-on-yl, 1,2,4-triazinyl, 1,3,5-triazinyl, 1H-indolyl, 1H-indazolyl, 2H-indazolyl, indolizinyl, benzofuranyl, benzothienyl, 1H-benzimidazolyl, 1,3-benzoxazolyl, 1,3-benzothiazolyl, 1,3-benzodioxolyl, 1,2,3-benzotriazolyl, 9H-purinyl, furo[3,2-b]pyridinyl, furo[3,2-c]pyridinyl, furo[2,3-c]pyridinyl, 1,3-oxazolo[5,4-b]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, pyrazolo[1,5-a]pyrimidinyl, pyrazolo[1,5-a]pyrazinyl, 1H-pyrazolo[3,4-b]pyridinyl, 1H-pyrazolo[3,4-b]pyrazinyl, 1H-pyrazolo[3,4-c]pyridinyl, 1H-pyrazolo[4,3-b]pyridinyl, 1H-pyrazolo[4,3-d]pyrimidinyl, 2H-pyrazolo[4,3-b]pyridinyl, 2H-pyrazolo[4,3-c]pyridin-yl, 5H-pyrrolo[2,3-b]pyrazinyl, imidazo[1,2-a]pyridinyl, imidazo[1,2-a]pyrazinyl, imidazo[1,2-a]pyrimidinyl, imidazo[1,2-b]pyridazinyl, imidazo[1,2-c]pyrimidinyl, 1H-imidazo[4,5-b]pyridinyl, 3H-imidazo[4,5-b]pyridinyl, imidazo[2,1-b][1,3]thiazolyl, imidazo[2,1-b][1,3,4]thiadiazol, [1,3]oxazolo[4,5-b]pyridinyl, [1,2,3]triazolo[1,5-a]pyridinyl, 1H-[1,2,3]triazolo[4,5-b]pyridinyl, 2H-[1,2,3]triazolo[4,5-b]pyridinyl, 3H-[1,2,3]triazolo[4,5-b]pyridinyl, [1,2,4]triazolo[1,5-a]pyridinyl, [1,2,4]triazolo[1,5-a]pyrazinyl, [1,2,4]triazolo[4,3-a]pyridinyl, tetrazolo[1,5-a]pyridinyl, tetrazolo[1,5-b]pyridazinyl, quinolinyl, isoquinolinyl, and quinoxalinyl, substituted where allowed by available valences with two $R_{1a}$ substituents.

Another aspect includes a compound of Formula (I), Formula (II), or Formula (III), wherein $R_1$ is heteroaryl selected from 1H-pyrazolyl, 1H-imidazolyl, 1,3-thiazolyl, oxazolyl, 1H-1,2,3-triazolyl, 2H-1,2,3-triazolyl, 1H-1,2,4-triazolyl, pyridinyl, pyridin-2(1H)-on-yl, pyrimidin-4(3H)-on-yl, pyridazinyl, 1H-indazolyl, 2H-indazolyl, 1,3-benzoxazolyl, pyrrolo[1,2-a]pyrazinyl, imidazo[1,2-a]pyridinyl, imidazo[1,2-a]pyrazinyl, imidazo[1,2-a]pyrimidinyl, imidazo[1,2-b]pyridazinyl, 2H-[1,2,3]triazolo[4,5-b]pyridinyl, [1,2,4]triazolo[1,5-a]pyridinyl, and [1,2,4]triazolo[1,5-a]pyrazinyl, optionally substituted where allowed by available valences with 1 or 2 $R_{1a}$ substituents.

Another aspect includes a compound of Formula (I), Formula (II), or Formula (III), wherein $R_1$ is unsubstituted heteroaryl selected from 1H-pyrazolyl, 1H-imidazolyl, 1,3-thiazolyl, oxazolyl, 1H-1,2,3-triazolyl, 2H-1,2,3-triazolyl, 1H-1,2,4-triazolyl, pyridinyl, pyridin-2(0H)-on-yl, pyrimidin-4(3H)-on-yl, pyridazinyl, 1H-indazolyl, 2H-indazolyl, 1,3-benzoxazolyl, pyrrolo[1,2-a]pyrazinyl, imidazo[1,2-a]pyridinyl, imidazo[1,2-a]pyrazinyl, imidazo[1,2-a]pyrimidinyl, imidazo[1,2-b]pyridazinyl, 2H-[1,2,3]triazolo[4,5-b]pyridinyl, [1,2,4]triazolo[1,5-a]pyridinyl, and [1,2,4]triazolo[1,5-a]pyrazinyl.

Another aspect includes a compound of Formula (I), Formula (II), or Formula (III), wherein $R_1$ is heteroaryl selected from 1H-pyrazolyl, 1H-imidazolyl, 1,3-thiazolyl, oxazolyl, 1H-1,2,3-triazolyl, 2H-1,2,3-triazolyl, 1H-1,2,4-triazolyl, pyridinyl, pyridin-2(1H)-on-yl, pyrimidin-4(3H)-on-yl, pyridazinyl, 1H-indazolyl, 2H-indazolyl, 1,3-benzoxazolyl, pyrrolo[1,2-a]pyrazinyl, imidazo[1,2-a]pyridinyl, imidazo[1,2-a]pyrazinyl, imidazo[1,2-a]pyrimidinyl, imidazo[1,2-b]pyridazinyl, 2H-[1,2,3]triazolo[4,5-b]pyridinyl, [1,2,4]triazolo[1,5-a]pyridinyl, and [1,2,4]triazolo[1,5-a]pyrazinyl, substituted where allowed by available valences with one $R_{1a}$ substituent.

Another aspect includes a compound of Formula (I), Formula (II), or Formula (III), wherein $R_1$ is heteroaryl selected from 1H-pyrazolyl, 1H-imidazolyl, 1,3-thiazolyl, oxazolyl, 1H-1,2,3-triazolyl, 2H-1,2,3-triazolyl, 1H-1,2,4-triazolyl, pyridinyl, pyridin-2(1H)-on-yl, pyrimidin-4(3H)-on-yl, pyridazinyl, 1H-indazolyl, 2H-indazolyl, 1,3-benzoxazolyl, pyrrolo[1,2-a]pyrazinyl, imidazo[1,2-a]pyridinyl, imidazo[1,2-a]pyrazinyl, imidazo[1,2-a]pyrimidinyl, imidazo[1,2-b]pyridazinyl, 2H-[1,2,3]triazolo[4.5-b]pyridinyl, [1,2,4]triazolo[1,5-a]pyridinyl, and [1,2,4]triazolo[1,5-a]pyrazinyl, substituted where allowed by available valences with two $R_{1a}$ substituents.

Another aspect includes a compound of Formula (I), Formula (II), or Formula (III), wherein $R_1$ is heteroaryl selected from thien-2-yl, thien-3-yl, 1H-pyrazol-1-yl, 1H-pyrazol-3-yl, 1H-pyrazol-4-yl, 1H-pyrazol-5-yl, 1H-imidazol-1-yl, 1H-imidazol-4-yl, 1,3-thiazol-2-yl, 1,3-thiazol-5-yl, 1,3-oxazol-2-yl, 1,3-oxazol-4-yl, 1,3-oxazol-5-yl, 1,2,4-oxadiazol-3-yl, 1,3,4-oxadiazol-2-yl, 1,2,4-thiadiazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-3-yl, 1H-1,2,4-triazol-5-yl, 1H-tetrazol-1-yl, 1H-tetrazol-5-yl, 2H-tetrazol-2-yl, 2H-tetrazol-5-yl, pyridin-2-yl, pyridin-3-yl, pyridin-4-yl, pyridin-2(1H)-on-4-yl, pyridin-2(1H)-on-5- yl, pyridin-2(1H)-on-6-yl, pyrazin-2-yl, pyrazin-3-yl, pyrimidin-2-yl, pyrimidin-4-yl, pyrimidin-5-yl, pyrimidin-4(3H)-on-6-yl, pyridazin-3-yl, pyridazin-4-yl, pyridazin-3(2H)-on-5-yl, 1,2,4-triazin-3-yl, 1,3,5-triazin-2-yl, 1H-indol-3-yl, 1H-indol-4-yl, 1H-indol-5-yl, 1H-indol-6-yl, 1H-indazol-5-yl, 1H-indazol-6-yl, 2H-indazol-4-yl, 2H-indazol-5-yl, 2H-indazol-6-yl, indolizin-2-yl, benzofuran-2-yl, benzofuran-5-yl, benzothien-2-yl, benzothien-3-yl, 1H-benzimidazol-2-yl, 1H-benzimidazol-5-yl, 1H-benzimidazol-6-yl, 1,3-benzoxazol-2-yl, 1,3-benzoxazol-5-yl, 1,3-benzoxazol-6-yl, 1,3-benzothiazol-2-yl, 1,3-benzothiazol-5-yl, 1,3-benzothiazol-6-yl, 1,3-benzodioxol-5-yl, 1,2,3-benzotriazol-5-yl, 9H-purin-8-yl, furo[3,2-b]pyridin-2-yl, furo[3,2-c]pyridin-2-yl, furo[2,3-c]pyridin-2-yl, 1,3-oxazolo[5.4-b]pyridine-5-yl, thieno[3,2-c]pyridin-2-yl, thieno[2,3-d]pyrimidin-6-yl, 1H-pyrrolo[2,3-b]pyridin-5-yl, 1H-pyrrolo[2,3-c]pyridin-4-yl, pyrrolo[1,2-a]pyrimidin-7-yl, pyrrolo[1,2-a]pyrazin-7-yl, pyrrolo[1,2-b]pyridazin-2-yl, pyrazolo[15-a]pyridin-2-yl, pyrazolo[1,5-a]pyridin-5-yl, pyrazolo[1,5-a]pyrazin-2-yl, pyrazolo[1,5-a]pyrimidin-2-yl, pyrazolo[1,5-a]pyrimidin-5-yl, 1H-pyrazolo[3,4-b]pyrazin-5-yl, 1H-pyrazolo[3,4-b]pyridin-5-yl, 1H-pyrazolo[3,4-b]pyridin-6-yl, 1H-pyrazolo[3,4-c]pyridin-1-yl, 1H-pyrazolo[3,4-c]pyridin-5-yl, 1H-pyrazolo[4,3-b]pyridin-5-yl, 1H-pyrazolo[4,3-b]pyridin-6-yl, 1H-pyrazolo[4,3-d]pyrimidin-5-yl, 2H-pyrazolo[4,3-b]pyridin-5-yl, 2H-pyrazolo[4,3-c]pyridin-5-yl, 5H-pyrrolo[2,3-b]pyrazin-2-yl, imidazo[1,2-a]pyridin-2-yl, imidazo[1,2-a]pyridin-6-yl, imidazo[1,2-a]pyrazin-2-yl, imidazo[1,2-a]pyrazin-6-yl, imidazo[1,2-a]pyrimidin-2-yl, imidazo[1,2-a]pyrimidin-6-yl, imidazo[1,2-b]pyridazin-2-yl, imidazo[1,2-b]pyridazin-6-yl, imidazo[1,2-c]pyrimidin-2-yl, 1H-imidazo[4,5-b]pyridin-5-yl, 3H-imidazo[4,5-b]pyridin-5-yl, imidazo[2,1-b][1,3]thiazol-6-yl, imidazo[2,1-b][1,3,4]thiadiazol-6-yl, [1,3]oxazolo[4,5-b]pyridin-2-yl, [1,2,3]triazolo[1.5-a]pyridin-5-yl, [1,2,3]triazolo[1,5-a]pyridin-6-yl, 1H-[1,2,3]triazolo[4,5-b]pyridin-5-yl, 2H-[1,2,3]triazolo[4.5-b]pyridin-6-yl, 3H-[1,2,3]triazolo[4,5-b]pyridin-5-yl, [1,2,4]triazolo[1,5-a]pyridin-2-yl, [1,2,4]triazolo[1,5-a]pyridin-6-yl, [1,2,4]triazolo[1,5-a]pyridin-7-yl, [1,2,4]triazolo[1,5-a]pyrazin-2-yl, [1,2,4]triazolo[1,5-a]pyrazin-5-yl, [1,2,4]triazolo[1,5-a]pyrazin-6-yl, [1,2,4]triazolo[4,3-a]pyridn-6-yl, [1,2,4]triazolo[4,3-a]pyridn-7-yl, tetrazolo[1,5-a]pyridin-7-yl, tetrazolo[1,5-b]pyridazin-7-yl, quinolin-6-yl, isoquinolin-6-yl, and quinoxalin-2-yl, optionally substituted where allowed by available valences with 1 or 2 $R_{1a}$ substituents.

Another aspect includes a compound of Formula (I), Formula (II), or Formula (III), wherein $R_1$ is unsubstituted heteroaryl selected from thien-2-yl, thien-3-yl, 1H-pyrazol-1-yl, 1H-pyrazol-3-yl, 1H-pyrazol-4-yl, 1H-pyrazol-5-yl, 1H-imidazol-1-yl, 1H-imidazol-4-yl, 1,3-thiazol-2-yl, 1,3-thiazol-5-yl, 1,3-oxazol-2-yl, 1,3-oxazol-4-yl, 1,3-oxazol-5-yl, 1,2,4-oxadiazol-3-yl, 1,3,4-oxadiazol-2-yl, 1,2,4-thiadiazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-3-yl, 1H-1,2,4-triazol-5-yl, 1H-tetrazol-1-yl, 1H-tetrazol-5-yl, 2H-tetrazol-2-yl, 2H-tetrazol-5-yl, pyridin-2-yl, pyridin-3-yl, pyridin-4-yl, pyridin-2(1H)-on-4-yl, pyridin-2(1H)-on-5-yl, pyridin-2(1H)-on-6-yl, pyrazin-2-yl, pyrazin-3-yl, pyrimidin-2-yl, pyrimidin-4-yl, pyrimidin-5-yl, pyrimidin-4(3H)-on-6-yl, pyridazin-3-yl, pyridazin-4-yl, pyridazin-3(2H)-on-5-yl, 1,2,4-triazin-3-yl, 1,3,5-triazin-2-yl, 1H-indol-3-yl, 1H-indol-4-yl, 1H-indol-5-yl, 1H-indol-6-yl, 1H-indazol-5-yl, 1H-indazol-6-yl, 2H-indazol-4-yl, 2H-indazol-5-yl, 2H-indazol-6-yl, indolizin-2-yl, benzofuran-2-yl, benzofuran-5-yl, benzothien-2-yl, benzothien-3-yl, 1H-benzimidazol-2-yl, 1H-benzimidazol-5-yl, 1H-benzimidazol-6-yl, 1,3-benzoxazol-2-yl, 1,3-benzoxazol-5-yl, 1,3-benzoxazol-6-yl, 1,3-benzothiazol-2-yl, 1,3-benzothiazol-5-yl, 1.3-benzothiazol-6-yl, 1,3-benzodioxol-5-yl, 1,2,3-benzotriazol-5-yl, 9H-purin-8-yl, furo[3,2-b]pyridin-2-yl, furo[3,2-c]pyridin-2-yl, furo[2,3-c]pyridin-2-yl, 1,3-oxazolo[5,4-b]pyridine-5-yl, thieno[3,2-c]pyridin-2-yl, thieno[2,3-d]pyrimidin-6-yl, 1H-pyrrolo[2,3-b]pyridin-5-yl, 1H-pyrrolo[2,3-c]pyridin-4-yl, pyrrolo[1,2-a]pyrimidin-7-yl, pyrrolo[1,2-a]pyrazin-7-yl, pyrrolo[1,2-b]pyridazin-2-yl, pyrazolo[1,5-a]pyridin-2-yl, pyrazolo[1,5-a]pyridin-5-yl, pyrazolo[1,5-a]pyrazin-2-yl, pyrazolo[1,5-a]pyrimidin-2-yl, pyrazolo[1,5-a]pyrimidin-5-yl, 1H-pyrazolo[3,4-b]pyrazin-5-yl, 1H-pyrazolo[3,4-b]pyridin-5-yl, 1H-pyrazolo[3,4-b]pyridin-6-yl, 1H-pyrazolo[3,4-c]pyridin-1-yl, 1H-pyrazolo[3,4-c]pyridin-5-yl, 1H-pyrazolo[4,3-b]pyridin-5-yl, 1H-pyrazolo[4,3-b]pyridin-6-yl, 1H-pyrazolo[4,3-d]pyrimidin-5-yl, 2H-pyrazolo[4,3-b]pyridin-5-yl, 2H-pyrazolo[4,3-c]pyridin-5-yl, 5H-pyrrolo[2,3-b]pyrazin-2-yl, imidazo[1,2-a]pyridin-2-yl, imidazo[1,2-a]pyridin-6-yl, imidazo[1,2-a]pyrazin-2-yl, imidazo[1,2-a]pyrazin-6-yl, imidazo[1,2-a]pyrimidin-2-yl, imidazo[1,2-a]pyrimidin-6-yl, imidazo[1,2-b]pyridazin-2-yl, imidazo[1,2-b]pyridazin-6-yl, imidazo[1,2-c]pyrimidin-2-yl, 1H-imidazo[4,5-b]pyridin-5-yl, 3H-imidazo[4,5-b]pyridin-5-yl, imidazo[2,1-b][1,3]thiazol-6-yl, imidazo[2,1-b][1,3,4]thiadiazol-6-yl, [1,3]oxazolo[4,5-b]pyridin-2-yl, [1,2,3]triazolo[1,5-a]pyridin-5-yl, [1,2,3]triazolo[1,5-a]pyridin-6-yl, 1H-[1,2,3]triazolo[4,5-b]pyridin-5-yl, 2H-[1,2,3]triazolo[4,5-b]pyridin-6-yl, 3H-[1,2,3]triazolo[4,5-b]pyridin-5-yl, [1,2,4]triazolo[1,5-a]pyridin-2-yl, [1,2,4]triazolo[1,5-a]pyridin-6-yl, [1,2,4]triazolo[1,5-a]pyridin-7-yl, [1,2,4]triazolo[1,5-a]pyrazin-2-yl, [1,2,4]triazolo[1,5-a]pyrazin-5-yl, [1,2,4]triazolo[1,5-a]pyrazin-6-yl, [1,2,4]triazolo[4,3-a]pyridn-6-yl, [1,2,4]triazolo[4,3-a]pyridn-7-yl, tetrazolo[1,5-a]pyridin-7-yl, tetrazolo[1,5-b]pyridazin-7-yl, quinolin-6-yl, isoquinolin-6-yl, and quinoxalin-2-yl.

Another aspect includes a compound of Formula (I), Formula (II), or Formula (III), wherein $R_1$ is heteroaryl selected from thien-2-yl, thien-3-yl, 1H-pyrazol-1-yl, 1H-pyrazol-3-yl, 1H-pyrazol-4-yl, 1H-pyrazol-5-yl, 1H-imidazol-1-yl, 1H-imidazol-4-yl, 1,3-thiazol-2-yl, 1,3-thiazol-5-yl, 1,3-oxazol-2-yl, 1,3-oxazol-4-yl, 1,3-oxazol-5-yl, 1,2,4-oxadiazol-3-yl, 1,3,4-oxadiazol-2-yl, 1,2,4-thiadiazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-3-yl, 1H-1,2,4-triazol-5-yl, 1H-tetrazol-1-yl, 1H-tetrazol-5-yl, 2H-tetrazol-2-yl, 2H-tetrazol-5-yl, pyridin-2-yl, pyridin-3-yl, pyridin-4-yl, pyridin-2(1H)-on-4-yl, pyridin-2(1H)-on-5-yl, pyridin-2(1H)-on-6-yl, pyrazin-2-yl, pyrazin-3-yl, pyrimidin-2-yl, pyrimidin-4-yl, pyrimidin-5-yl, pyrimidin-4(3H)-on-6-yl, pyridazin-3-yl, pyridazin-4-yl, pyridazin-3(2H)-on-5-yl, 1,2,4-triazin-3-yl, 1,3,5-triazin-2-yl, 1H-indol-3-yl, 1H-indol-4-yl, 1H-indol-5-yl, 1H-indol-6-yl, 1H-indazol-5-yl, 1H-indazol-6-yl, 2H-indazol-4-yl, 2H-indazol-5-yl, 2H-indazol-6-yl, indolizin-2-yl, benzofuran-2-yl, benzofuran-5-yl, benzothien-2-yl, benzothien-3-yl, 1H-benzimidazol-2-yl, 1H-benzimidazol-5-yl, 1H-benzimidazol-6-yl, 1,3-benzoxazol-2-yl, 1,3-benzoxazol-5-yl, 1,3-benzoxazol-6-yl, 1,3-benzothiazol-2-yl, 1,3-benzothiazol-5-yl, 1,3-benzothiazol-6-yl, 1,3-benzodioxol-5-yl, 1,2,3-benzotriazol-5-yl, 9H-purin-8-yl, furo[3,2-b]pyridin-2-yl, furo[3,2-c]pyridin-2-v, furo[2,3-c]pyridin-2-yl, 1,3-oxazolo[5,4-b]pyridine-5-yl, thieno[3,2-c]pyridin-2-yl, thieno[2,3-d]pyrimidin-6-yl, 1H-pyrrolo[2,3-b]pyridin-5-yl, 1H-pyrrolo[2,3-c]pyridin-4-yl, pyrrolo[1,2-a]pyrimidin-7-yl, pyrrolo[1,2-a]pyrazin-7-yl, pyrrolo[1,2-b]pyridazin-2-yl, pyrazolo[1,5-a]pyridin-2-yl, pyrazolo[1,5-a]pyridin-5-yl, pyrazolo[1,5-a]pyrazin-2-yl, pyrazolo[1,5-a]pyrimidin-2-yl, pyrazolo[1,5-a]pyrimidin-5-yl, 1H-pyrazolo[3,4-b]pyrazin-5-yl, 1H-pyrazolo[3,4-b]pyridin-5-yl, 1H-pyrazolo[3,4-b]pyridin-6-yl, 1H-pyrazolo[3,4-c]pyridin-1-yl, 1H-pyrazolo[3,4-c]pyridin-5-yl, 1H-pyrazolo[4,3-b]pyridin-5-yl, 1H-pyrazolo[4,3-b]pyridin-6-yl, 1H-pyrazolo[4,3-d]pyrimidin-5-yl, 2H-pyrazolo[4,3-b]pyridin-5-yl, 2H-pyrazolo[4,3-c]pyridin-5-yl, 5H-pyrrolo[2,3-b]pyrazin-2-yl, imidazo[1,2-a]pyridin-2-yl, imidazo[1,2-a]pyridin-6-yl, imidazo[1,2-a]pyrazin-2-yl, imidazo[1,2-a]pyrazin-6-yl, imidazo[1,2-a]pyrimidin-2-yl, imidazo[1,2-a]pyrimidin-6-yl, imidazo[1,2-b]pyridazin-2-yl, imidazo[1,2-b]pyridazin-6-yl, imidazo[1,2-c]pyrimidin-2-yl, 1H-imidazo[4,5-b]pyridin-5-yl, 3H-imidazo[4,5-b]pyridin-5-yl, imidazo[2,1-b][1,3]thiazol-6-yl, imidazo[2,1-b][1,3,4]thiadiazol-6-yl, [1,3]oxazolo[4,5-b]pyridin-2-yl, [1,2,3]triazolo[1,5-a]pyridin-5-yl, [1,2,3]triazolo[1,5-a]pyridin-6-yl, 1H-[1,2,3]triazolo[4,5-b]pyridin-5-yl, 2H-[1,2,3]triazolo[4,5-b]pyridin-6-yl, 3H-[1,2,3]triazolo[4,5-b]pyridin-5-yl, [1,2,4]triazolo[1,5-a]pyridin-2-yl, [1,2,4]triazolo[1,5-a]pyridin-6-yl, [1,2,4]triazolo[1,5-a]pyridin-7-yl, [1,2,4]triazolo[1,5-a]pyrazin-2-yl, [1,2,4]triazolo[1,5-a]pyrazin-5-yl, [1,2,4]triazolo[1,5-a]pyrazin-6-yl, [1,2,4]triazolo[4,3-a]pyridn-6-yl, [1,2,4]triazolo[4,3-a]pyridn-7-yl, tetrazolo[1,5-a]pyridin-7-yl, tetrazolo[1,5-b]pyridazin-7-yl, quinolin-6-yl, isoquinolin-6-yl, and quinoxalin-2-yl, substituted where allowed by available valences with one $R_{1a}$ substituent.

Another aspect includes a compound of Formula (I), Formula (II), or Formula (III), wherein $R_1$ is heteroaryl selected from thien-2-yl, thien-3-yl, 1H-pyrazol-1-yl, 1H-pyrazol-3-yl, 1H-pyrazol-4-yl, 1H-pyrazol-5-yl, 1H-imidazol-1-yl, 1H-imidazol-4-yl, 1,3-thiazol-2-yl, 1,3-thiazol-5-yl, 1,3-oxazol-2-yl, 1,3-oxazol-4-yl, 1,3-oxazol-5-yl, 1,2,4-oxadiazol-3-yl, 1,3,4-oxadiazol-2-yl, 1,2,4-thiadiazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-3-yl, 1H-1,2,4-triazol-5-yl, 1H-tetrazol-1-yl, 1H-tetrazol-5-yl, 2H-tetrazol-2-yl, 2H-tetrazol-5-yl, pyridin-2-yl, pyridin-3-yl, pyridin-4-yl, pyridin-2(1H)-on-4-yl, pyridin-2(1H)-on-5-yl, pyridin-2(1H)-on-6-yl, pyrazin-2-yl, pyrazin-3-yl, pyrimidin-2-yl, pyrimidin-4-yl, pyrimidin-5-yl, pyrimidin-4(3H)-on-6-yl, pyridazin-3-yl, pyridazin-4-yl, pyridazin-3(2H)-on-5-yl, 1,2,4-triazin-3-yl, 1,3,5-triazin-2-yl, 1H-indol-3-yl, 1H-indol-4-yl, 1H-indol-5-yl, 1H-indol-6-yl, 1H-indazol-5-yl, 1H-indazol-6-yl, 2H-indazol-4-yl, 2H-indazol-5-yl, 2H-indazol-6-yl, indolizin-2-yl, benzofuran-2-yl, benzofuran-5-yl, benzothien-2-yl, benzothien-3-yl, 1H-benzimidazol-2-yl, 1H-benzimidazol-5-yl, 1H-benzimidazol-6-yl, 1,3-benzoxazol-2-yl, 1,3-benzoxazol-5-yl, 1,3-benzoxazol-6-yl, 1,3-benzothiazol-2-yl, 1,3-benzothiazol-5-yl, 1,3-benzothiazol-6-yl, 1,3-benzodioxol-5-yl, 1,2,3-benzotriazol-5-yl, 9H-purin-8-yl, furo[3,2-b]pyridin-2-yl, furo[3,2-c]pyridin-2-yl, furo[2,3-c]pyridin-2-yl, 1,3-oxazolo[5,4-b]pyridine-5-yl, thieno[3,2-c]pyridin-2-yl, thieno[2,3-d]pyrimidin-6-yl, 1H-pyrrolo[2,3-b]pyridin-5-yl, 1H-pyrrolo[2,3-c]pyridin-4-yl, pyrrolo[1,2-a]pyrimidin-7-yl, pyrrolo[1,2-a]pyrazin-7-yl, pyrrolo[1,2-b]pyridazin-2-yl, pyrazolo[1,5-a]pyridin-2-yl, pyrazolo[1,5-a]pyridin-5-yl, pyrazolo[1,5-a]pyrazin-2-yl, pyrazolo[1,5-a]pyrimidin-2-yl, pyrazolo[15-a]pyrimidin-5-yl, 1H-pyrazolo[3,4-b]pyrazin-5-yl, 1H-pyrazolo[3,4-b]pyridin-5-yl, 1H-pyrazolo[3,4-b]pyridin-6-yl, 1H-pyrazolo[3,4-c]pyridin-1-yl, 1H-pyrazolo[3,4-c]pyridin-5-yl, 1H-pyrazolo[4,3-b]pyridin-5-yl, 1H-pyrazolo[4,3-b]pyridin-6-yl, 1H-pyrazolo[4,3-d]pyrimidin-5-yl, 2H-pyrazolo[4,3-b]pyridin-5-yl, 2H-pyrazolo[4,3-c]pyridin-5-yl, 5H-pyrrolo[2,3-b]pyrazin-2-yl, imidazo[1,2-a]pyridin-2-yl, imidazo[1,2-a]pyridin-6-yl, imidazo[1,2-a]pyrazin-2-yl, imidazo[1,2-a]pyrazin-6-yl, imidazo[1,2-a]pyrimidin-2-yl, imidazo[1,2-a]pyrimidin-6-yl, imidazo[1,2-b]pyridazin-2-yl, imidazo[1,2-b]pyridazin-6-yl, imidazo[1,2-c]pyrimidin-2-yl, 1H-imidazo[4,5-b]pyridin-5-yl, 3H-imidazo[4,5-b]pyridin-5-yl, imidazo[2,1-b][1,3]thiazol-6-yl, imidazo[2,1-b][1,3,4]thiadiazol-6-yl, [1,3]oxazolo[4,5-b]pyridin-2-yl, [1,2,3]triazolo[1,5-a]pyridin-5-yl, [1,2,3]triazolo[1,5-a]pyridin-6-yl, 1H-[1,2,3]triazolo[4,5-b]pyridin-5-yl, 2H-[1,2,3]triazolo[4,5-b]pyridin-6-yl, 3H-[1,2,3]triazolo[4,5-b]pyridin-5-yl, [1,2,4]triazolo[1,5-a]pyridin-2-yl, [1,2,4]triazolo[1,5-a]pyridin-6-yl, [1,2,4]triazolo[1,5-a]pyridin-7-yl, [1,2,4]triazolo[1,5-a]pyrazin-2-yl, [1,2,4]triazolo[1,5-a]pyrazin-5-yl, [1,2,4]triazolo[1,5-a]pyrazin-6-yl, [1,2,4]triazolo[4,3-a]pyridn-6-yl, [1,2,4]triazolo[4,3-a]pyridn-7-yl, tetrazolo[1,5-a]pyridin-7-yl, tetrazolo[1,5-b]pyridazin-7-yl, quinolin-6-yl, isoquinolin-6-yl, and quinoxalin-2-yl, substituted where allowed by available valences with two $R_{1a}$ substituents.

Another aspect includes a compound of Formula (I), Formula (II), or Formula (III), wherein $R_1$ is heteroaryl selected from 1H-pyrazol-3-yl, 1H-pyrazol-4-yl, 1H-imidazol-1-yl, 1,3-thiazol-2-yl, 1,3-oxazol-2-yl, 1,3-oxazol-5-yl, 1H-1,2,3-triazol-1-yl, 2H-1,2,3-triazol-2-yl, 1H-1,2,4-triazol-1-yl, pyridin-4-yl, pyridin-2(1H)-on-4-yl, pyrimidin-4(3H)-on-6-yl, pyridazin-3-yl, 1H-indazol-5-yl, 2H-indazol-4-yl, 2H-indazol-5-yl, 1,3-benzoxazol-6-yl, pyrrolo[1,2-a]pyrazin-7-yl, imidazo[1,2-a]pyridin-6-yl, imidazo[1,2-a]pyrazin-6-yl, imidazo[1,2-a]pyrimidin-6-yl, imidazo[1,2-b]pyridazin-6-yl, 2H-[1,2,3]triazolo[4,5-b]pyridin-6-yl, [1,2,4]triazolo[1,5-a]pyridin-6-yl, and [1,2,4]triazolo[1,5-a]pyrazin-2-yl, optionally substituted where allowed by available valences with 1 or 2 $R_{1a}$ substituents.

Another aspect includes a compound of Formula (I), Formula (II), or Formula (III), wherein $R_1$ is unsubstituted heteroaryl selected from 1H-pyrazol-3-yl, 1H-pyrazol-4-yl, 1H-imidazol-1-yl, 1,3-thiazol-2-yl, 1,3-oxazol-2-yl, 1,3-oxazol-5-yl, 1H-1,2,3-triazol-1-yl, 2H-1,2,3-triazol-2-yl, 1H-1,2,4-triazol-1-yl, pyridin-4-yl, pyridin-2(1H)-on-4-yl, pyrimidin-4(3H)-on-6-yl, pyridazin-3-yl, 1H-indazol-5-yl, 2H-indazol-4-yl, 2H-indazol-5-yl, 1,3-benzoxazol-6-yl, pyrrolo[1,2-a]pyrazin-7-yl, imidazo[1,2-a]pyridin-6-yl, imidazo[1,2-a]pyrazin-6-yl, imidazo[1,2-a]pyrimidin-6-yl, imidazo[1,2-b]pyridazin-6-yl, 2H-[1,2,3]triazolo[4,5-b]pyridin-6-yl, [1,2,4]triazolo[1,5-a]pyridin-6-yl, and [1,2,4]triazolo[1,5-a]pyrazin-2-yl.

Another aspect includes a compound of Formula (I), Formula (II), or Formula (III), wherein $R_1$ is heteroaryl selected from 1H-pyrazol-3-yl, 1H-pyrazol-4-yl, 1H-imidazol-1-yl, 1,3-thiazol-2-yl, 1,3-oxazol-2-yl, 1,3-oxazol-5-yl, 1H-1,2,3-triazol-1-yl, 2H-1,2,3-triazol-2-yl, 1H-1,2,4-triazol-1-yl, pyridin-4-yl, pyridin-2(0H)-on-4-yl, pyrimidin-4(3H)-on-6-yl, pyridazin-3-yl, 1H-indazol-5-yl, 2H-indazol-4-yl, 2H-indazol-5-yl, 1,3-benzoxazol-6-yl, pyrrolo[1,2-a]pyrazin-7-yl, imidazo[1,2-a]pyridin-6-yl, imidazo[1,2-a]pyrazin-6-yl, imidazo[1,2-a]pyrimidin-6-yl, imidazo[1,2-b]pyridazin-6-yl, 2H-[1,2,3]triazolo[4,5-b]pyridin-6-yl, [1,2,4]triazolo[1,5-a]pyridin-6-yl, and [1,2,4]triazolo[1,5-a]pyrazin-2-yl, substituted where allowed by available valences with one $R_{1a}$ substituent.

Another aspect includes a compound of Formula (I), Formula (II), or Formula (III), wherein $R_1$ is heteroaryl selected from 1H-pyrazol-3-yl, 1H-pyrazol-4-yl, 1H-imidazol-1-yl, 1,3-thiazol-2-yl, 1,3-oxazol-2-yl, 1,3-oxazol-5-yl, 1H-1,2,3-triazol-1-yl, 2H-1,2,3-triazol-2-yl, 1H-1,2,4-triazol-1-yl, pyridin-4-yl, pyridin-2(1H)-on-4-yl, pyrimidin-4(3H)-on-6-yl, pyridazin-3-yl, 1H-indazol-5-yl, 2H-indazol-4-yl, 2H-indazol-5-yl, 1,3-benzoxazol-6-yl, pyrrolo[1,2-a]pyrazin-7-yl, imidazo[1,2-a]pyridin-6-yl, imidazo[1,2-a]pyrazin-6-yl, imidazo[1,2-a]pyrimidin-6-yl, imidazo[1,2-b]pyridazin-6-yl, 2H-[1,2,3]triazolo[4,5-b]pyridin-6-yl, [1,2,4]triazolo[1,5-a]pyridin-6-yl, and [1,2,4]triazolo[1,5-a]pyrazin-2-yl, substituted where allowed by available valences with two $R_{1a}$ substituents.

Another aspect includes a compound of Formula (I), Formula (II), or Formula (III), wherein $R_1$ is heteroaryl-$C_{2-4}$alkenyl, wherein heteroaryl is a 3-7 membered monocyclic or 6-10 membered bicyclic ring system having 1, 2, 3, or 4 heteroatom ring members independently selected from N, O, or S; and wherein heteroaryl is optionally substituted where allowed by available valences with 1 or 2 $R_{1a}$ substituents.

Another aspect includes a compound of Formula (I), Formula (II), or Formula (III), wherein $R_1$ is heteroaryl-$C_{2-4}$alkenyl, wherein heteroaryl is selected from thienyl, 1H-pyrazolyl, 1H-imidazolyl, 1,3-thiazolyl, oxazolyl, 1,2,4-oxadiazolyl, 1,3,4-oxadiazolyl, 1,2,4-thiadiazolyl, 1H-tetrazolyl, 2H-tetrazolyl, pyridinyl, pyridinyl, pyrazinyl, pyrimidinyl, 1,2,4-triazinyl, 1,3,5-triazinyl, 1H-indolyl, 1H-indazolyl, 2H-indazolyl, indolizinyl, benzofuranyl, benzothienyl, 1H-benzimidazolyl, 1,3-benzoxazolyl, 1,3-benzothiazolyl, 1,3-benzodioxolyl, 1,2,3-benzotriazolyl, 9H-purinyl, quinolinyl, isoquinolinyl, and quinoxalinyl;

wherein $C_{2-4}$alkenyl is selected from ethenyl, propenyl, and butenyl; and wherein heteroaryl is optionally substituted where allowed by available valences with 1 or 2 $R_{1a}$ substituents.

Another aspect includes a compound of Formula (I), Formula (II), or Formula (III), wherein $R_1$ is 2-(1H-pyrazol-4-yl)ethenyl, optionally substituted where allowed by available valences with 1 or 2 $R_{1a}$ substituents.

Another aspect includes a compound of Formula (I), Formula (I), or Formula (III), wherein $R_1$ is heteroaryl-amino, wherein heteroaryl is selected from thienyl, 1H-pyrazolyl, 1H-imidazolyl, 1,3-thiazolyl, oxazolyl, 1,2,4-oxadiazolyl, 1,3,4-oxadiazolyl, 1,2,4-thiadiazolyl, 1H-tetrazolyl, 2H-tetrazolyl, pyridinyl, pyrazinyl, pyrimidinyl, pyridazinyl, 1,2,4-triazinyl, 1,3,5-triazinyl, 1H-indolyl, 1H-indazolyl, 2H-indazolyl, indolizinyl, benzofuranyl, benzothienyl, 1H-benzimidazolyl, 1,3-benzoxazolyl, 1,3-benzothiazolyl, 1,3-benzodioxolyl, 1,2,3-benzotriazolyl, 9H-purinyl, quinolinyl, isoquinolinyl, and quinoxalinyl; and wherein heteroaryl is optionally substituted where allowed by available valences with 1 or 2 $R_{1a}$ substituents.

Another aspect includes a compound of Formula (I), Formula (II), or Formula (III), wherein $R_1$ is (pyridin-3-yl)amino, (pyrazin-2-yl)amino, and (pyrimidin-5-yl)amino, optionally substituted where allowed by available valences with 1 or 2 $R_{1a}$ substituents.

Another aspect includes a compound of Formula (I), Formula (II), or Formula (III), wherein $R_1$ is heteroaryl-$C_{1-4}$alkyl-amino, wherein heteroaryl is selected from thienyl, 1H-pyrazolyl, 1H-imidazolyl, 1,3-thiazolyl, oxazolyl, 1,2,4-oxadiazolyl, 1,3,4-oxadiazolyl, 1,2,4-thiadiazolyl, 1H-tetrazolyl, 2H-tetrazolyl, pyridinyl, pyrazinyl, pyrimidinyl, pyridazinyl, 1,2,4-triazinyl, 1,3,5-triazinyl, 1H-indolyl, 1H-indazolyl, 2H-indazolyl, indolizinyl, benzofuranyl, benzothienyl, 1H-benzimidazolyl, 1,3-benzoxazolyl, 1,3-benzothiazolyl, 1,3-benzodioxolyl, 1,2,3-benzotriazolyl, 9H-purinyl, quinolinyl, isoquinolinyl, and quinoxalinyl;

wherein $C_{1-4}$alkyl is selected from methyl, ethyl, propyl, and butyl; and wherein heteroaryl is optionally substituted where allowed by available valences with 1 or 2 $R_{1a}$ substituents.

Another aspect includes a compound of Formula (I), Formula (II), or Formula (III), wherein $R_1$ is (1H-pyrazol-4-yl)methylamino, (pyridin-3-yl)methylamino, (pyridin-4-yl)methylamino, (quinolin-3-yl)methylamino, and (quinolin-8-yl)methylamino, optionally substituted where allowed by available valences with 1 or 2 $R_{1a}$ substituents.

One aspect includes a compound of Formula (I), Formula (II), or Formula (III), wherein $R_{1a}$ is independently selected from halogen, hydroxyl, cyano, $C_{1-4}$alkyl, deutero-$C_{1-4}$alkyl, halo-$C_{1-4}$alkyl, amino, $C_{1-4}$alkyl-amino, $(C_{1-4}alkyl)_2$-amino, $C_{1-4}$alkoxy, deutero-$C_{1-4}$alkoxy, and halo-$C_{1-4}$alkoxy.

Another aspect includes a compound of Formula (I), Formula (II), or Formula (III), wherein $R_{1a}$ is independently selected from halogen, cyano, $C_{1-4}$alkyl, deutero-$C_{1-4}$alkyl, halo-$C_{1-4}$alkyl, $C_{1-4}$alkoxy, and deutero-$C_{1-4}$alkoxy.

Another aspect includes a compound of Formula (I), Formula (II), or Formula (III), wherein $R_{1a}$ is $C_{1-4}$alkyl selected from methyl, ethyl, propyl, isopropyl, butyl, and tert-butyl.

Another aspect includes a compound of Formula (I), Formula (II), or Formula (III), wherein $R_{1a}$ is selected from methyl and ethyl.

Another aspect includes a compound of Formula (I), Formula (II), or Formula (III), wherein $R_{1a}$ is methyl.

Another aspect includes a compound of Formula (I), Formula (II), or Formula (III), wherein $R_{1a}$ is ethyl.

Another aspect includes a compound of Formula (I), Formula (II), or Formula (III), wherein $R_{1a}$ is halogen selected from bromo, chloro, fluoro, and iodo.

Another aspect includes a compound of Formula (I), Formula (II), or Formula (III), wherein $R_{1a}$ is fluoro.

Another aspect includes a compound of Formula (I), Formula (II), or Formula (III), wherein $R_{1a}$ is cyano.

Another aspect includes a compound of Formula (I), Formula (II), or Formula (III), wherein $R_{1a}$ is deutero-$C_{1-4}$alkyl wherein $C_{1-4}$alkyl is selected from methyl, ethyl, propyl, isopropyl, butyl, and tert-butyl, partially or completely substituted with one or more deuterium atoms where allowed by available valences.

Another aspect includes a compound of Formula (I), Formula (II), or Formula (III), wherein $R_{1a}$ is $(^2H_3)$methyl.

Another aspect includes a compound of Formula (I), Formula (II), or Formula (III), wherein $R_{1a}$ is halo-$C_{1-4}$alkyl wherein $C_{1-4}$alkyl is selected from methyl, ethyl, propyl, isopropyl, butyl, and tert-butyl partially or completely substituted with one or more halogen atoms where allowed by available valences.

Another aspect includes a compound of Formula (I), Formula (II), or Formula (III), wherein $R_{1a}$ is trifluromethyl.

Another aspect includes a compound of Formula (I), Formula (II), or Formula (III), wherein $R_{1a}$ is $C_{1-4}$alkoxy selected from methoxy, ethoxy, propoxy, isopropoxy, butoxy and tert-butoxy.

Another aspect includes a compound of Formula (I), Formula (II), or Formula (III), wherein $R_{1a}$ is methoxy.

Another aspect includes a compound of Formula (I), Formula (II), or Formula (III), wherein $R_{1a}$ is deutero-$C_{1-4}$alkoxy wherein $C_{1-4}$alkoxy is selected from methoxy, ethoxy, propoxy, isopropoxy, butoxy and tert-butoxy, partially or completely substituted with one or more deuterium atoms where allowed by available valences.

Another aspect includes a compound of Formula (I), Formula (II), or Formula (III), wherein $R_{1a}$ is $(^2H_3)$methoxy.

Another aspect of the present description includes a compound of Formula (I):

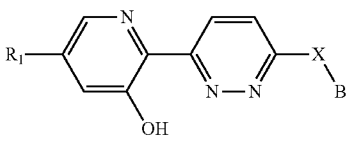

(I)

or a form thereof, wherein:

X is O, $NR_x$, or a bond;

$R_x$ is selected from hydrogen and $C_{1-4}$alkyl;

B is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, each optionally substituted where allowed by available valences with 1, 2, 3, 4, or 5 substituents $R_b$;

$R_b$ is independently selected from halogen, $C_{1-4}$alkyl, amino, $C_{1-4}$alkyl-amino, $(C_{1-4}alkyl)_2$-amino, and $C_{3-6}$cycloalkyl;

$R_1$ is selected from heteroaryl, heterocyclyl, phenyl, heteroaryl-$C_{1-4}$alkyl, heteroaryl-$C_{2-4}$alkenyl, heteroaryl-amino, heteroaryl-$C_{1-4}$alkyl-amino, wherein heteroaryl is a 3-7 membered monocyclic or 6-10 membered bicyclic ring system having 1, 2, 3, or 4 heteroatom ring members independently selected from N, O, or S, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, and wherein each instance of phenyl, heteroaryl or heterocyclyl is optionally substituted where allowed by available valences with 1 or 2 $R_{1a}$ substituents; and $R_{1a}$ is independently selected from halogen, hydroxyl, cyano, $C_{1-4}$alkyl, deutero-$C_{1-4}$alkyl, halo-$C_{1-4}$alkyl, amino, $C_{1-4}$alkyl-amino, $(C_{1-4}alkyl)_2$-amino, $C_{1-4}$alkoxy, deutero-$C_{1-4}$alkoxy, and halo-$C_{1-4}$alkoxy.

One aspect includes a compound of Formula (I), wherein X is selected from O, $NR_x$, and a bond.

Another aspect includes a compound of Formula (I) wherein X is O.

Another aspect includes a compound of Formula (I) wherein X is $NR_x$.

Another aspect includes a compound of Formula (I) wherein X is a bond.

One aspect includes a compound of Formula (I), wherein $R_x$ is selected from hydrogen and $C_{1-4}$alkyl.

Another aspect includes a compound of Formula (I), wherein $R_x$ hydrogen.

Another aspect includes a compound of Formula (I), wherein $R_x$ is $C_{1-4}$alkyl selected from methyl, ethyl, propyl, isopropyl, butyl, and tert-butyl.

Another aspect includes a compound of Formula (I), wherein $R_x$ is methyl.

One aspect includes a compound of Formula (I), wherein B is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, optionally substituted where allowed by available valences with 1, 2, 3, 4, or 5 $R_b$ substituents.

Another aspect includes a compound of Formula (I), wherein B is unsubstituted heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S.

Another aspect includes a compound of Formula (I), wherein B is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, substituted where allowed by available valences with one $R_b$ substituent.

Another aspect includes a compound of Formula (I), wherein B is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, each substituted where allowed by available valences with two $R_b$ substituents.

Another aspect includes a compound of Formula (I), wherein B is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, substituted where allowed by available valences with three $R_b$ substituents.

Another aspect includes a compound of Formula (I), wherein B is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, substituted where allowed by available valences with four $R_b$ substituents.

Another aspect includes a compound of Formula (I), wherein B is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, substituted where allowed by available valences with five $R_b$ substituents.

Another aspect includes a compound of Formula (I), wherein B is heterocyclyl selected from azetidinyl, tetrahydrofuranyl, pyrrolidinyl, piperidinyl, piperidin-1-olate-yl, piperazinyl, 1,4-diazepanyl, 1,2-dihydropyridinyl, 1,2,5,6-tetrahydropyridinyl, 1,2,3,6-tetrahydropyridinyl, hexahydrocyclopentapyrrol-(1H)-yl, hexahydropyrrolo[3,2-b]pyrrol-(2H)-yl, hexahydropyrrolo[3,4-b]pyrrol-(2H)-yl, octahydro-2H-pyrrolo[3,4-c]pyridinyl, octahydro-5H-pyrrolo[3,2-c]pyridinyl, octahydro-6H-pyrrolo[3,4-b]pyridinyl, hexahydropyrrolo[1,2-a]pyrazin-(2H)-one, hexahydropyrrolo[1,2-a]pyrazin-(1H)-yl, hexahydro-1H-cyclobuta[1.2-c:1,4-c']dipyrrol-(3H)-yl, octahydropyrrolo[1,2-a]pyrazin-(1H)-yl, octahydro-2H-pyrido[1,2-a]pyrazinyl, hexahydropyrrolo[3,4-b][1,4]oxazin-(2H)-yl, 5-azaspiro[2.4]heptanyl, 1-azaspiro[3.3]heptanyl, 4-azaspiro[2.5]octanyl, 2-oxa-6-azaspiro[3.4]octanyl, 3-azabicyclo[3.1.0]hexanyl, 8-azabicyclo[3.2.1]octanyl, 8-azabicyclo[3.2.1]oct-2-en-yl, 9-azabicyclo[3.3.1]nonanyl, 2,5-diazabicyclo[2.2.1]heptanyl, 1.4-diazabicyclo[3.1.1]heptanyl, 3,6-diazabicyclo[3.2.0]heptanyl, 2,5-diazabicyclo[2.2.2]octanyl, 1,4-diazabicyclo[3.2.1]octanyl, 3,8-diazabicyclo[3.2.1]octanyl, 1,4-diazabicyclo[3.2.2]nonanyl, 4,7-diazaspiro[2.5]octanyl, 2,6-diazaspiro[3.3]heptanyl, 1,6-diazaspiro[3.4]octanyl, 2,6-diazaspiro[3.4]octanyl, 1.7,-diazaspiro[4.4]nonanyl, 1,7-diazaspiro[3.5]nonanyl, 2,6-diazaspiro[3.5]nonanyl, 2,7-diazaspiro[3.5]nonanyl, 5,8-diazaspiro[3.5]nonanyl, 2-oxa-5,8-diazaspiro[3.5]nonanyl, 2,7-diazaspiro[4.4]nonanyl, 2,7-diazaspiro[4.5]decanyl, 2,8-diazaspiro[4.5]decanyl, 6,9-diazaspiro[4.5]decyl, 6-oxa-2,9-diazaspiro[4.5]decanyl, 2,9-diazaspiro[5.5]undecanyl, 4-azadispiro[2.1.2$^5$.3$^3$]decanyl, and 7-azadispiro[5.1.5$^8$.3$^6$]hexadecanyl, optionally substituted where allowed by available valences with 1, 2, 3, 4, or 5 $R_b$ substituents.

Another aspect includes a compound of Formula (I), wherein B is unsubstituted heterocyclyl selected from azetidinyl, tetrahydrofuranyl, pyrrolidinyl, piperidinyl, piperidin-1-olate-yl, piperazinyl, 1,4-diazepanyl, 1,2-dihydropyridinyl, 1,2,5,6-tetrahydropyridinyl, 1,2,3,6-tetrahydropyridinyl, hexahydrocyclopentapyrrol-(1H)-yl, hexahydropyrrolo[3,2-b]pyrrol-(2H)-yl, hexahydropyrrolo[3,4-b]pyrrol-(2H)-yl, octahydro-2H-pyrrolo[3,4-c]pyridinyl, octahydro-5H-pyrrolo[3,2-c]pyridinyl, octahydro-6H-pyrrolo[3,4-b]pyridinyl, hexahydropyrrolo[1,2-a]pyrazin-(2H)-one, hexahydropyrrolo[1,2-a]pyrazin-(1H)-yl, hexahydro-1H-cyclobuta[1.2-c:1,4-c']dipyrrol-(3H)-yl, octahydropyrrolo[1,2-a]pyrazin-(1H)-yl, octahydro-2H-pyrido[1,2-a]pyrazinyl, hexahydropyrrolo[3,4-b][1,4]oxazin-(2H)-yl, 5-azaspiro[2.4]heptanyl, I-azaspiro[3.3]heptanyl, 4-azaspiro[2.5]octanyl, 2-oxa-6-azaspiro[3.4]octanyl, 3-azabicyclo[3.1.0]hexanyl, 8-azabicyclo[3.2.1]octanyl, 8-azabicyclo[3.2.1]oct-2-en-yl, 9-azabicyclo[3.3.1]nonanyl, 2,5-diazabicyclo[2.2.1]heptanyl, 1,4-diazabicyclo[3.1.1]heptanyl, 3,6-diazabicyclo[3.2.0]heptanyl, 2,5-diazabicyclo[2.2.2]octanyl, 1,4-diazabicyclo[3.2.1]octanyl, 3,8-diazabicyclo[3.2.1]octanyl, 1,4-diazabicyclo[3.2.2]nonanyl, 4,7-diazaspiro[2.5]octanyl, 2,6-diazaspiro[3.3]heptanyl, 1,6-diazaspiro[3.4]octanyl, 2,6-diazaspiro[3.4]octanyl, 1,7,-diazaspiro[4.4]nonanyl, 1,7-diazaspiro[3.5]nonanyl, 2,6-diazaspiro[3.5]nonanyl, 2,7-diazaspiro[3.5]nonanyl, 5,8-diazaspiro[3.5]nonanyl, 2-oxa-5,8-diazaspiro[3.5]nonanyl, 2,7-diazaspiro[4.4]nonanyl, 2,7-diazaspiro[4.5]decanyl, 2,8-diazaspiro[4.5]decanyl, 6,9-diazaspiro[4.5]decyl, 6-oxa-2,9-diazaspiro[4.5]decanyl, 2,9-diazaspiro[5.5]undecanyl, 4-azadispiro[2.1.2$^5$.3$^3$]decanyl, and 7-azadispiro[5.1.5$^8$.3$^6$]hexadecanyl.

Another aspect includes a compound of Formula (I), Wherein B is heterocyclyl selected from azetidinyl, tetrahydrofuranyl, pyrrolidinyl, piperidinyl, piperidin-1-olate-yl, piperazinyl, 1,4-diazepanyl, 1,2-dihydropyridinyl, 1,2,5,6-tetrahydropyridinyl, 1,2,3,6-tetrahydropyridinyl, hexahydrocyclopentapyrrol-(1H)-yl, hexahydropyrrolo[3,2-b]pyrrol-(2H)-yl, hexahydropyrrolo[3,4-b]pyrrol-(2H)-yl, octahydro-2H-pyrrolo[3,4-c]pyridinyl, octahydro-5H-pyrrolo[3,2-c]pyridinyl, octahydro-6H-pyrrolo[3,4-b]pyridinyl, hexahydropyrrolo[1,2-a]pyrazin-(2H)-one, hexahydropyrrolo[1,2-a]pyrazin-(0H)-yl, hexahydro-1H-cyclobuta[1.2-c:1,4-c']dipyrrol-(3H)-yl, octahydropyrrolo[1,2-a]pyrazin-(1H)-yl, octahydro-2H-pyrido[1,2-a]pyrazinyl, hexahydropyrrolo[3,4-b][1,4]oxazin-(2H)-yl, 5-azaspiro[2.4]heptanyl, 1-azaspiro[3.3]heptanyl, 4-azaspiro[2.5]octanyl, 2-oxa-6-azaspiro[3.4]octanyl, 3-azabicyclo[3.1.0]hexanyl, 8-azabicyclo[3.2.1]octanyl, 8-azabicyclo[3.2.1]oct-2-en-yl, 9-azabicyclo[3.3.1]nonanyl, 2,5-diazabicyclo[2.2.1]heptanyl, 1,4-diazabicyclo[3.1.1]heptanyl, 3,6-diazabicyclo[3.2.0]heptanyl, 2,5-diazabicyclo[2.2.2]octanyl, 1,4-diazabicyclo[3.2.1]octanyl, 3,8-diazabicyclo[3.2.1]octanyl, 1,4-diazabicyclo[3.2.2]nonanyl, 4,7-diazaspiro[2.5]octanyl, 2,6-diazaspiro[3.3]heptanyl, 1,6-diazaspiro[3.4]octanyl, 2,6-diazaspiro[3.4]octanyl, 1.7,-diazaspiro[4.4]nonanyl, 1,7-diazaspiro[3.5]nonanyl, 2,6-diazaspiro[3.5]nonanyl, 2,7-diazaspiro[3.5]nonanyl, 5,8-diazaspiro[3.5]nonanyl, 2-oxa-5,8-diazaspiro[3.5]nonanyl, 2,7-diazaspiro[4.4]nonanyl, 2,7-diazaspiro[4.5]decanyl, 2,8-diazaspiro[4.5]decanyl, 6,9-diazaspiro[4.5]decyl, 6-oxa-2,9-diazaspiro[4.5]decanyl, 2,9-diazaspiro[5.5]undecanyl, 4-azadispiro[2.1.2$^5$.3$^3$]decanyl, and 7-azadispiro[5.1.5$^8$.3$^6$]hexadecanyl, substituted where allowed by available valences with one $R_b$ substituent.

Another aspect includes a compound of Formula (I), wherein B is heterocyclyl selected from azetidinyl, tetrahydrofuranyl, pyrrolidinyl, piperidinyl, piperidin-1-olate-yl, piperazinyl, 1,4-diazepanyl, 1,2-dihydropyridinyl, 1,2,5,6-tetrahydropyridinyl, 1,2,3,6-tetrahydropyridinyl, hexahydrocyclopentapyrrol-(1H)-yl, hexahydropyrrolo[3,2-b]pyrrol-(2H)-yl, hexahydropyrrolo[3,4-b]pyrrol-(2H)-yl, octahydro-2H-pyrrolo[3,4-c]pyridinyl, octahydro-5H-pyrrolo[3,2-c]pyridinyl, octahydro-6H-pyrrolo[3,4-b]pyridinyl, hexahydropyrrolo[1,2-a]pyrazin-(2H)-one, hexahydropyrrolo[1,2-a]pyrazin-(1H)-yl, hexahydro-1H-cyclobuta[1.2-c:1,4-c']dipyrrol-(3H)-yl, octahydropyrrolo[1,2-a]pyrazin-(1H)-yl, octahydro-2H-pyrido[1,2-a]pyrazinyl, hexahydropyrrolo[3,4-b][1,4]oxazin-(2H)-yl, 5-azaspiro[2.4]heptanyl, 1-azaspiro[3.3]heptanyl, 4-azaspiro[2.5]octanyl, 2-oxa-6-azaspiro[3.4]octanyl, 3-azabicyclo[3.1.0]hexanyl, 8-azabicyclo[3.2.1]octanyl, 8-azabicyclo[3.2.1]oct-2-en-yl, 9-azabicyclo[3.3.1]nonanyl, 2,5-diazabicyclo[2.2.1]heptanyl, 1.4-diazabicyclo[3.1.1]heptanyl, 3,6-diazabicyclo[3.2.0]heptanyl, 2,5-diazabicyclo[2.2.2]octanyl, 1,4-diazabicyclo[3.2.1]octanyl, 3,8-diazabicyclo[3.2.1]octanyl, 1,4-diazabicyclo[3.2.2]nonanyl, 4,7-diazaspiro[2.5]octanyl, 2,6-diazaspiro[3.3]heptanyl, 1,6-diazaspiro[3.4]octanyl, 2,6-diazaspiro[3.4]octanyl, 1.7,-diazaspiro[4.4]nonanyl, 1,7-diazaspiro[3.5]nonanyl, 2,6-diazaspiro[3.5]nonanyl, 2,7-diazaspiro[3.5]nonanyl, 5,8-diazaspiro[3.5]nonanyl, 2-oxa-5,8-diazaspiro[3.5]nonanyl, 2,7-diazaspiro[4.4]nonanyl, 2,7-diazaspiro[4.5]decanyl, 2,8-diazaspiro[4.5]decanyl, 6,9-diazaspiro[4.5]decyl, 6-oxa-2,9-diazaspiro[4.5]decanyl, 2,9-diazaspiro[5.5]undecanyl, 4-azadispiro[2.1.2$^5$.3$^3$]decanyl, and 7-azadispiro[5.1.5$^8$.3$^6$]hexadecanyl, substituted where allowed by available valences with two $R_b$ substituents.

Another aspect includes a compound of Formula (I), wherein B is heterocyclyl selected from azetidinyl, tetrahydrofuranyl, pyrrolidinyl, piperidinyl, piperidin-1-olate-yl, piperazinyl, 1,4-diazepanyl, 1,2-dihydropyridinyl, 1,2,5,6-tetrahydropyridinyl, 1,2,3,6-tetrahydropyridinyl, hexahydrocyclopentapyrrol-(1H)-yl, hexahydropyrrolo[3,2-b]pyrrol-(2H)-yl, hexahydropyrrolo[3,4-b]pyrrol-(2H)-yl, octahydro-2H-pyrrolo[3,4-c]pyridinyl, octahydro-5H-pyrrolo[3,2-c]pyridinyl, octahydro-6H-pyrrolo[3,4-b]pyridinyl, hexahydropyrrolo[1,2-a]pyrazin-(2H)-one, hexahydropyrrolo[1,2-a]pyrazin-(1H)-yl, hexahydro-1H-cyclobuta[1.2-c:1,4-c']dipyrrol-(3H)-yl, octahydropyrrolo[1,2-a]pyrazin-(1H)-yl, octahydro-2H-pyrido[1,2-a]pyrazinyl, hexahydropyrrolo[3,4-b][1,4]oxazin-(2H)-yl, 5-azaspiro[2.4]heptanyl, I-azaspiro[3.3]heptanyl, 4-azaspiro[2.5]octanyl, 2-oxa-6-azaspiro[3.4]octanyl, 3-azabicyclo[3.1.0]hexanyl, 8-azabicyclo[3.2.1]octanyl, 8-azabicyclo[3.2.1]oct-2-en-yl, 9-azabicyclo[3.3.1]nonanyl, 2,5-diazabicyclo[2.2.1]heptanyl, 1,4-diazabicyclo[3.1.1]heptanyl, 3,6-diazabicyclo[3.2.0]heptanyl, 2,5-diazabicyclo[2.2.2]octanyl, 1,4-diazabicyclo[3.2.1]octanyl, 3,8-diazabicyclo[3.2.1]octanyl, 1,4-diazabicyclo[3.2.2]nonanyl, 4,7-diazaspiro[2.5]octanyl, 2,6-diazaspiro[3.3]heptanyl, 1,6-diazaspiro[3.4]octanyl, 2,6-diazaspiro[3.4]octanyl, 1,7,-diazaspiro[4.4]nonanyl, 1,7-diazaspiro[3.5]nonanyl, 2,6-diazaspiro[3.5]nonanyl, 2,7-diazaspiro[3.5]nonanyl, 5,8-diazaspiro[3.5]nonanyl, 2-oxa-5,8-diazaspiro[3.5]nonanyl, 2,7-diazaspiro[4.4]nonanyl, 2,7-diazaspiro[4.5]decanyl, 2,8-diazaspiro[4.5]decanyl, 6,9-diazaspiro[4.5]decyl, 6-oxa-2,9-diazaspiro[4.5]decanyl, 2,9-diazaspiro[5.5]undecanyl, 4-azadispiro[2.1.$2^5$.$3^3$]decanyl, and 7-azadispiro[5.1.$5^8$.$3^6$]hexadecanyl, substituted where allowed by available valences with three $R_b$ substituents.

Another aspect includes a compound of Formula (I), wherein B is heterocyclyl selected from azetidinyl, tetrahydrofuranyl, pyrrolidinyl, piperidinyl, piperidin-1-olate-yl, piperazinyl, 1,4-diazepanyl, 1,2-dihydropyridinyl, 1,2,5,6-tetrahydropyridinyl, 1,2,3,6-tetrahydropyridinyl, hexahydrocyclopentapyrrol-(1H)-yl, hexahydropyrrolo[3,2-b]pyrrol-(2H)-yl, hexahydropyrrolo[3,4-b]pyrrol-(2H)-yl, octahydro-2H-pyrrolo[3,4-c]pyridinyl, octahydro-5H-pyrrolo[3,2-c]pyridinyl, octahydro-6H-pyrrolo[3,4-b]pyridinyl, hexahydropyrrolo[1,2-a]pyrazin-(2H)-one, hexahydropyrrolo[1,2-a]pyrazin-(1H)-yl, hexahydro-1H-cyclobuta[1.2-c:1,4-c']dipyrrol-(3H)-yl, octahydropyrrolo[1,2-a]pyrazin-(1H)-yl, octahydro-2H-pyrido[1,2-a]pyrazinyl, hexahydropyrrolo[3,4-b][1,4]oxazin-(2H)-yl, 5-azaspiro[2.4]heptanyl, 1-azaspiro[3.3]heptanyl, 4-azaspiro[2.5]octanyl, 2-oxa-6-azaspiro[3.4]octanyl, 3-azabicyclo[3.1.0]hexanyl, 8-azabicyclo[3.2.1]octanyl, 8-azabicyclo[3.2.1]oct-2-en-yl, 9-azabicyclo[3.3.1]nonanyl, 2,5-diazabicyclo[2.2.1]heptanyl, 1,4-diazabicyclo[3.1.1]heptanyl, 3,6-diazabicyclo[3.2.0]heptanyl, 2,5-diazabicyclo[2.2.2]octanyl, 1,4-diazabicyclo[3.2.1]octanyl, 3,8-diazabicyclo[3.2.1]octanyl, 1,4-diazabicyclo[3.2.2]nonanyl, 4,7-diazaspiro[2.5]octanyl, 2,6-diazaspiro[3.3]heptanyl, 1,6-diazaspiro[3.4]octanyl, 2,6-diazaspiro[3.4]octanyl, 1,7,-diazaspiro[4.4]nonanyl, 1,7-diazaspiro[3.5]nonanyl, 2,6-diazaspiro[3.5]nonanyl, 2,7-diazaspiro[3.5]nonanyl, 5,8-diazaspiro[3.5]nonanyl, 2-oxa-5,8-diazaspiro[3.5]nonanyl, 2,7-diazaspiro[4.4]nonanyl, 2,7-diazaspiro[4.5]decanyl, 2,8-diazaspiro[4.5]decanyl, 6,9-diazaspiro[4.5]decyl, 6-oxa-2,9-diazaspiro[4.5]decanyl, 2,9-diazaspiro[5.5]undecanyl, 4-azadispiro[2.1.$2^5$.$3^3$]decanyl, and 7-azadispiro[5.1.$5^8$.$3^6$]hexadecanyl, substituted where allowed by available valences with four $R_b$ substituents.

Another aspect includes a compound of Formula (I), wherein B is heterocyclyl selected from azetidinyl, tetrahydrofuranyl, pyrrolidinyl, piperidinyl, piperidin-1-olate-yl, piperazinyl, 1,4-diazepanyl, 1,2-dihydropyridinyl, 1,2,5,6-tetrahydropyridinyl, 1,2,3,6-tetrahydropyridinyl, hexahydrocyclopentapyrrol-(1H)-yl, hexahydropyrrolo[3,2-b]pyrrol-(2H)-yl, hexahydropyrrolo[3,4-b]pyrrol-(2H)-yl, octahydro-2H-pyrrolo[3,4-c]pyridinyl, octahydro-5H-pyrrolo[3,2-c]pyridinyl, octahydro-6H-pyrrolo[3,4-b]pyridinyl, hexahydropyrrolo[1,2-a]pyrazin-(2H)-one, hexahydropyrrolo[1,2-a]pyrazin-(1H)-yl, hexahydro-1H-cyclobuta[1.2-c:1,4-c']dipyrrol-(3H)-yl, octahydropyrrolo[1,2-a]pyrazin-(1H)-yl, octahydro-2H-pyrido[1,2-a]pyrazinyl, hexahydropyrrolo[3,4-b][1,4]oxazin-(2H)-yl, 5-azaspiro[2.4]heptanyl, 1-azaspiro[3.3]heptanyl, 4-azaspiro[2.5]octanyl, 2-oxa-6-azaspiro[3.4]octanyl, 3-azabicyclo[3.1.0]hexanyl, 8-azabicyclo[3.2.1]octanyl, 8-azabicyclo[3.2.1]oct-2-en-yl, 9-azabicyclo[3.3.1]nonanyl, 2,5-diazabicyclo[2.2.1]heptanyl, 1,4-diazabicyclo[3.1.1]heptanyl, 3,6-diazabicyclo[3.2.0]heptanyl, 2,5-diazabicyclo[2.2.2]octanyl, 1,4-diazabicyclo[3.2.1]octanyl, 3.8-diazabicyclo[3.2.1]octanyl, 1,4-diazabicyclo[3.2.2]nonanyl, 4,7-diazaspiro[2.5]octanyl, 2,6-diazaspiro[3.3]heptanyl, 1,6-diazaspiro[3.4]octanyl, 2,6-diazaspiro[3.4]octanyl, 1,7,-diazaspiro[4.4]nonanyl, 1,7-diazaspiro[3.5]nonanyl, 2,6-diazaspiro[3.5]nonanyl, 2,7-diazaspiro[3.5]nonanyl, 5,8-diazaspiro[3.5]nonanyl, 2-oxa-5,8-diazaspiro[3.5]nonanyl, 2.7-diazaspiro[4.4]nonanyl, 2,7-diazaspiro[4.5]decanyl, 2,8-diazaspiro[4.5]decanyl, 6,9-diazaspiro[4.5]decyl, 6-oxa-2,9-diazaspiro[4.5]decanyl, 2,9-diazaspiro[5.5]undecanyl, 4-azadispiro[2.1.$2^5$.$3^3$]decanyl, and 7-azadispiro[5.1.$5^8$.$3^6$]hexadecanyl, substituted where allowed by available valences with five $R_b$ substituents.

Another aspect includes a compound of Formula (I), wherein B is heterocyclyl selected from pyrrolidinyl, piperidinyl, piperidin-1-olate-yl, piperazinyl, 4-azaspiro[2.5]octanyl, 8-azabicyclo[3.2.1]octanyl, 2,5-diazabicyclo[2.2.1]heptanyl, 1,6-diazaspiro[3.4]octanyl, 2-oxa-5,8-diazaspiro[3.5]nonanyl, and 4-azadispiro[2.1.$2^5$.$3^3$]decanyl, optionally substituted where allowed by available valences with 1, 2, 3, 4, or 5 $R_b$ substituents.

Another aspect includes a compound of Formula (I), wherein B is unsubstituted heterocyclyl selected from pyrrolidinyl, piperidinyl, piperidin-1-olate-yl, piperazinyl, 4-azaspiro[2.5]octanyl, 8-azabicyclo[3.2.1]octanyl, 2,5-diazabicyclo[2.2.1]heptanyl, 1,6-diazaspiro[3.4]octanyl, 2-oxa-5.8-diazaspiro[3.5]nonanyl, and 4-azadispiro[2.1.$2^5$.$3^3$]decanyl.

Another aspect includes a compound of Formula (I), Formula (II), or Formula (III), wherein B is heterocyclyl selected from pyrrolidinyl, piperidinyl, piperidin-1-olate-yl, piperazinyl, 4-azaspiro[2.5]octanyl, 8-azabicyclo[3.2.1]octanyl, 2,5-diazabicyclo[2.2.1]heptanyl, 1,6-diazaspiro[3.4]octanyl, 2-oxa-5,8-diazaspiro[3.5]nonanyl, and 4-azadispiro[2.1.$2^5$.$3^3$]decanyl, substituted where allowed by available valences with one $R_b$ substituent.

Another aspect includes a compound of Formula (I), wherein B is heterocyclyl selected from pyrrolidinyl, piperidinyl, piperidin-1-olate-yl, piperazinyl, 4-azaspiro[2.5]octanyl, 8-azabicyclo[3.2.1]octanyl, 2,5-diazabicyclo[2.2.1]heptanyl, 1,6-diazaspiro[3.4]octanyl, 2-oxa-5,8-diazaspiro[3.5]nonanyl, and 4-azadispiro[2.1.$2^5$.$3^3$]decanyl, substituted where allowed by available valences with two $R_b$ substituents.

Another aspect includes a compound of Formula (I), wherein B is heterocyclyl selected from pyrrolidinyl, piperidinyl, piperidin-1-olate-yl, piperazinyl, 4-azaspiro[2.5]octanyl, 8-azabicyclo[3.2.1]octanyl, 2,5-diazabicyclo[2.2.1]heptanyl, 1,6-diazaspiro[3.4]octanyl, 2-oxa-5,8-diazaspiro[3.5]nonanyl, and 4-azadispiro[2.1.$2^5$.$3^3$]decanyl, substituted where allowed by available valences with three $R_b$ substituents.

Another aspect includes a compound of Formula (I), wherein B is heterocyclyl selected from pyrrolidinyl, piperidinyl, piperidin-1-olate-yl, piperazinyl, 4-azaspiro[2.5]octanyl, 8-azabicyclo[3.2.1]octanyl, 2,5-diazabicyclo[2.2.1]heptanyl, 1,6-diazaspiro[3.4]octanyl, 2-oxa-5,8-diazaspiro[3.5]nonanyl, and 4-azadispiro[2.1.$2^5$.$3^3$]decanyl, substituted where allowed by available valences with four $R_b$ substituents.

Another aspect includes a compound of Formula (I), wherein B is heterocyclyl selected from pyrrolidinyl, piperidinyl, piperidin-1-olate-yl, piperazinyl, 4-azaspiro[2.5]octanyl, 8-azabicyclo[3.2.1]octanyl, 2,5-diazabicyclo[2.2.1]heptanyl, 1,6-diazaspiro[3.4]octanyl, 2-oxa-5,8-diazaspiro[3.5]nonanyl, and 4-azadispiro[2.1.$2^5$.$3^3$]decanyl, substituted where allowed by available valences with five $R_b$ substituents.

Another aspect includes a compound of Formula (I), wherein B is heterocyclyl selected from pyrrolidinyl, piperidinyl, piperazinyl, and 4-azaspiro[2.5]octanyl, optionally substituted where allowed by available valences with 1, 2, 3, 4, or 5 $R_b$ substituents.

Another aspect includes a compound of Formula (I), wherein B is unsubstituted heterocyclyl selected from pyrrolidinyl, piperidinyl, piperazinyl, and 4-azaspiro[2.5]octanyl.

Another aspect includes a compound of Formula (I), wherein B is heterocyclyl selected from pyrrolidinyl, piperidinyl, piperazinyl, and 4-azaspiro[2.5]octanyl, substituted where allowed by available valences with one $R_b$ substituent.

Another aspect includes a compound of Formula (I), wherein B is heterocyclyl selected from pyrrolidinyl, piperidinyl, piperazinyl, and 4-azaspiro[2.5]octanyl, substituted where allowed by available valences with two $R_b$ substituents.

Another aspect includes a compound of Formula (I), wherein B is heterocyclyl selected from pyrrolidinyl, piperidinyl, piperazinyl, and 4-azaspiro[2.5]octanyl, substituted where allowed by available valences with three $R_b$ substituents.

Another aspect includes a compound of Formula (I), wherein B is heterocyclyl selected from pyrrolidinyl, piperidinyl, piperazinyl, and 4-azaspiro[2.5]octanyl, substituted where allowed by available valences with four $R_b$ substituents.

Another aspect includes a compound of Formula (I), wherein B is heterocyclyl selected from pyrrolidinyl, piperidinyl, piperazinyl, and 4-azaspiro[2.5]octanyl, substituted where allowed by available valences with five $R_b$ substituents.

Another aspect includes a compound of Formula (I), wherein B is pyrrolidinyl, substituted where allowed by available valences with one $R_b$ substituent.

Another aspect includes a compound of Formula (I), wherein B is piperidinyl, substituted where allowed by available valences with 4 or 5 $R_b$ substituents.

Another aspect includes a compound of Formula (I), wherein B is piperidinyl, substituted where allowed by available valences with four $R_b$ substituents.

Another aspect includes a compound of Formula (I), wherein B is piperidinyl, substituted where allowed by available valences with five $R_b$ substituents.

Another aspect includes a compound of Formula (I), wherein B is unsubstituted piperazinyl.

Another aspect includes a compound of Formula (I), wherein B is piperazinyl, substituted where allowed by available valences with one $R_b$ substituent.

Another aspect includes a compound of Formula (I), wherein B is piperazinyl, substituted where allowed by available valences with two $R_b$ substituents.

Another aspect includes a compound of Formula (I), wherein B is piperazinyl, substituted where allowed by available valences with three $R_b$ substituents.

Another aspect includes a compound of Formula (I), wherein B is piperazinyl, substituted where allowed by available valences with four $R_b$ substituents.

Another aspect includes a compound of Formula (I), wherein B is unsubstituted 4-azaspiro[2.5]octanyl.

Another aspect includes a compound of Formula (I), wherein B is 4-azaspiro[2.5]octanyl, substituted where allowed by available valences with one $R_b$ substituent.

Another aspect includes a compound of Formula (I), wherein B is 4-azaspiro[2.5]octanyl, substituted where allowed by available valences with two $R_b$ substituents.

Another aspect includes a compound of Formula (I), wherein B is heterocyclyl selected from azetidin-1-yl, tetrahydrofuran-3-yl, pyrrolidin-1-yl, pyrrolidin-3-yl, piperidin-1-yl, piperidin-3-yl, piperidin-4-yl, piperidin-1-olate-4-yl, piperazin-1-yl, 1,4-diazepan-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,2,5,6-tetrahydropyridin-5-yl, 1,2,3,6-tetrahydropyridin-4-yl, hexahydrocyclopentapyrrol-2(1H)-yl, hexahydropyrrolo[3,2-b]pyrrol-1(2H)-yl, hexahydropyrrolo[3,4-b]pyrrol-1(2H)-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, octahydro-5H-pyrrolo[3,2-c]pyridin-5-yl, octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, hexahydro-1H-cyclobuta[1.2-c:1,4-c']dipyrrol-2(3H)-yl, octahydropyrrolo[1,2-a]pyrazin-2(1H)-yl, octahydro-2H-pyrido[1,2-a]pyrazin-2-yl, hexahydropyrrolo[3,4-b][1,4]oxazin-6(2H)-yl, 5-azaspiro[2.4]heptan-5-yl, 1-azaspiro[3.3]heptan-2-yl, 4-azaspiro[2.5]octan-7-yl, 2-oxa-6-azaspiro[3.4]octan-6-yl, 3-azabicyclo[3.1.0]hexan-3-yl, 8-azabicyclo[3.2.1]octan-3-yl, 8-azabicyclo[3.2.1]oct-2-en-3-yl, 9-azabicyclo[3.3.1]nonan-3-yl, 2,5-diazabicyclo[2.2.1]heptan-2-yl, 1,4-diazabicyclo[3.1.1]heptan-4-yl, 3,6-diazabicyclo[3.2.0]heptan-3-yl, 3,6-diazabicyclo[3.2.0]heptan-6-yl, 2,5-diazabicyclo[2.2.2]octan-2-yl, 1,4-diazabicyclo[3.2.1]octan-4-yl, 3,8-diazabicyclo[3.2.1]octan-3-yl, 1,4-diazabicyclo[3.2.2]nonan-4-yl, 4,7-diazaspiro[2.5]octan-4-yl, 4,7-diazaspiro[2.5]octan-7-yl, 2,6-diazaspiro[3.3]heptan-2-yl, 1,6-diazaspiro[3.4]octan-6-yl, 2,6-diazaspiro[3.4]octan-2-yl, 2,6-diazaspiro[3.4]octan-6-yl, 1,7,-diazaspiro[4.4]nonan-1-yl, 1.7,-diazaspiro[4.4]nonan-7-yl, 1.7-diazaspiro[3.5]nonan-7-yl, 2,6-diazaspiro[3.5]nonan-2-yl, 2,6-diazaspiro[3.5]nonan-6-yl, 1,7-diazaspiro[3.5]nonan-7-yl, 2,7-diazaspiro[3.5]nonan-2-yl, 2,7-diazaspiro[3.5]nonan-7-yl, 5,8-diazaspiro[3.5]nonan-8-yl, 2-oxa-5,8-diazaspiro[3.5]nonan-8-yl, 2,7-diazaspiro[4.4]nonan-2-yl, 2,7-diazaspiro[4.5]decan-2-yl, 2.7-diazaspiro[4.5]decan-7-yl, 2,8-diazaspiro[4.5]decan-8-yl, 6,9-diazaspiro[4.5]dec-9-yl, 6-oxa-2,9-diazaspiro[4.5]decan-2-yl, 2,9-diazaspiro[5.5]undecan-9-yl, 4-azadispiro[$2.1.2^5.3^3$]decan-9-yl, and 7-azadispiro[$5.1.5^8.3^6$]hexadecan-15-yl, optionally substituted where allowed by available valences with 1, 2, 3, 4, or 5 $R_b$ substituents.

Another aspect includes a compound of Formula (I), wherein B is unsubstituted heterocyclyl selected from azetidin-1-yl, tetrahydrofuran-3-yl, pyrrolidin-1-yl, pyrrolidin-3-yl, piperidin-1-yl, piperidin-3-yl, piperidin-4-yl, piperidin-1-olate-4-yl, piperazin-1-yl, 1,4-diazepan-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,2,5,6-tetrahydropyridin-5-yl, 1,2,3,6-tetrahydropyridin-4-yl, hexahydrocyclopentapyrrol-2(1H)-yl, hexahydropyrrolo[3,2-b]pyrrol-1(2H)-yl, hexahydropyrrolo[3,4-b]pyrrol-1(2H)-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, octahydro-5H-pyrrolo[3,2-c]pyridin-5-yl, octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, hexahydro-1H-cyclobuta[1.2-c:1,4-c']dipyrrol-2(3H)-yl, octahydropyrrolo[1,2-a]pyrazin-2(1H)-yl, octahydro-2H-pyrido[1,2-a]pyrazin-2-yl, hexahydropyrrolo[3,4-b][1,4]oxazin-6(2H)-yl, 5-azaspiro[2.4]heptan-5-yl, I-azaspiro[3.3]heptan-2-yl, 4-azaspiro[2.5]octan-7-yl, 2-oxa-6-azaspiro[3.4]octan-6-yl, 3-azabicyclo[3.1.0]hexan-3-yl, 8-azabicyclo[3.2.1]octan-3-yl, 8-azabicyclo[3.2.1]oct-2-en-3-yl, 9-azabicyclo[3.3.1]nonan-3-yl, 2,5-diazabicyclo[2.2.1]heptan-2-yl, 1,4-diazabicyclo[3.1.1]heptan-4-yl, 3,6-diazabicyclo[3.2.0]heptan-3-yl, 3,6-diazabicyclo[3.2.0]heptan- 6-yl, 2,5-diazabicyclo[2.2.2]octan-2-yl, 1,4-diazabicyclo[3.2.1]octan-4-yl, 3,8-diazabicyclo[3.2.1]octan-3-yl, 1,4-diazabicyclo[3.2.2]nonan-4-yl, 4,7-diazaspiro[2.5]octan-4-yl, 4,7-diazaspiro[2.5]octan-7-yl, 2,6-diazaspiro[3.3]heptan-2-yl, 1,6-diazaspiro[3.4]octan-6-yl, 2,6-diazaspiro[3.4]octan-2-yl, 2,6-diazaspiro[3.4]octan-6-yl, 1,7,-diazaspiro[4.4]nonan-1-yl, 1.7,-diazaspiro[4.4]nonan-7-yl, 1.7-diazaspiro[3.5]nonan-7-yl, 2,6-diazaspiro[3.5]nonan-2-yl, 2,6-diazaspiro[3.5]nonan-6-yl, 1,7-diazaspiro[3.5]nonan-7-yl, 2,7-diazaspiro[3.5]nonan-2-yl, 2,7-diazaspiro[3.5]nonan-7-yl, 5,8-diazaspiro[3.5]nonan-8-yl, 2-oxa-5,8-diazaspiro[3.5]nonan-8-yl, 2,7-diazaspiro[4.4]nonan-2-yl, 2,7-diazaspiro[4.5]decan-2-yl, 2,7-diazaspiro[4.5]decan-7-yl, 2,8-diazaspiro[4.5]decan-8-yl, 6,9-diazaspiro[4.5]dec-9-yl, 6-oxa-2,9-diazaspiro[4.5]decan-2-yl, 2,9-diazaspiro[5.5]undecan-9-yl, 4-azadispiro[2.1.2$^5$.3$^3$]decan-9-yl, and 7-azadispiro[5.1.5$^8$.3$^6$]hexadecan-15-yl.

Another aspect includes a compound of Formula (I), wherein B is heterocyclyl selected from azetidin-1-yl, tetrahydrofuran-3-yl, pyrrolidin-1-yl, pyrrolidin-3-yl, piperidin-1-yl, piperidin-3-yl, piperidin-4-yl, piperidin-1-olate-4-yl, piperazin-1-yl, 1,4-diazepan-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,2,5,6-tetrahydropyridin-5-yl, 1,2,3,6-tetrahydropyridin-4-yl, hexahydrocyclopentapyrrol-2(1H)-yl, hexahydropyrrolo[3,2-b]pyrrol-1(2H)-yl, hexahydropyrrolo[3,4-b]pyrrol-1(2H)-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, octahydro-5H-pyrrolo[3,2-c]pyridin-5-yl, octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, hexahydro-1H-cyclobuta[1.2-c:1,4-c']dipyrrol-2(3H)-yl, octahydropyrrolo[1,2-a]pyrazin-2(1H)-yl, octahydro-2H-pyrido[1,2-a]pyrazin-2-yl, hexahydropyrrolo[3,4-b][1,4]oxazin-6(2H)-yl, 5-azaspiro[2.4]heptan-5-yl, 1-azaspiro[3.3]heptan-2-yl, 4-azaspiro[2.5]octan-7-yl, 2-oxa-6-azaspiro[3.4]octan-6-yl, 3-azabicyclo[3.1.0]hexan-3-yl, 8-azabicyclo[3.2.1]octan-3-yl, 8-azabicyclo[3.2.1]oct-2-en-3-yl, 9-azabicyclo[3.3.1]nonan-3-yl, 2,5-diazabicyclo[2.2.1]heptan-2-yl, 1,4-diazabicyclo[3.1.1]heptan-4-yl, 3,6-diazabicyclo[3.2.0]heptan-3-yl, 3,6-diazabicyclo[3.2.0]heptan-6-yl, 2,5-diazabicyclo[2.2.2]octan-2-yl, 1,4-diazabicyclo[3.2.1]octan-4-yl, 3,8-diazabicyclo[3.2.1]octan-3-yl, 1,4-diazabicyclo[3.2.2]nonan-4-yl, 4,7-diazaspiro[2.5]octan-4-yl, 4.7-diazaspiro[2.5]octan-7-yl, 2,6-diazaspiro[3.3]heptan-2-yl, 1,6-diazaspiro[3.4]octan-6-yl, 2,6-diazaspiro[3.4]octan-2-yl, 2,6-diazaspiro[3.4]octan-6-yl, 1,7,-diazaspiro[4.4]nonan-1-yl, 1,7,-diazaspiro[4.4]nonan-7-yl, 1,7-diazaspiro[3.5]nonan-7-yl, 2,6-diazaspiro[3.5]nonan-2-yl, 2.6-diazaspiro[3.5]nonan-6-yl, 1,7-diazaspiro[3.5]nonan-7-yl, 2,7-diazaspiro[3.5]nonan-2-yl, 2,7-diazaspiro[3.5]nonan-7-yl, 5,8-diazaspiro[3.5]nonan-8-yl, 2-oxa-5,8-diazaspiro[3.5]nonan-8-yl, 2,7-diazaspiro[4.4]nonan-2-yl, 2,7-diazaspiro[4.5]decan-2-yl, 2,7-diazaspiro[4.5]decan-7-yl, 2,8-diazaspiro[4.5]decan-8-yl, 6,9-diazaspiro[4.5]dec-9-yl, 6-oxa-2,9-diazaspiro[4.5]decan-2-yl, 2,9-diazaspiro[5.5]undecan-9-yl, 4-azadispiro[2.1.2$^5$.3$^3$]decan-9-yl, and 7-azadispiro[5.1.5$^8$.3$^6$]hexadecan-15-yl, substituted where allowed by available valences with one $R_b$ substituent.

Another aspect includes a compound of Formula (I), wherein B is heterocyclyl selected from azetidin-1-yl, tetrahydrofuran-3-yl, pyrrolidin-1-yl, pyrrolidin-3-yl, piperidin-1-yl, piperidin-3-yl, piperidin-4-yl, piperidin-1-olate-4-yl, piperazin-1-yl, 1,4-diazepan-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,2,5,6-tetrahydropyridin-5-yl, 1,2,3,6-tetrahydropyridin-4-yl, hexahydrocyclopentapyrrol-2(1H)-yl, hexahydropyrrolo[3,2-b]pyrrol-1(2H)-yl, hexahydropyrrolo[3,4-b]pyrrol-1(2H)-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, octahydro-5H-pyrrolo[3,2-c]pyridin-5-yl, octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, hexahydro-1H-cyclobuta[1.2-c:1,4-c']dipyrrol-2(3H)-yl, octahydropyrrolo[1,2-a]pyrazin-2(1H)-yl, octahydro-2H-pyrido[1,2-a]pyrazin-2-yl, hexahydropyrrolo[3,4-b][1,4]oxazin-6(2H)-yl, 5-azaspiro[2.4]heptan-5-yl, I-azaspiro[3.3]heptan-2-yl, 4-azaspiro[2.5]octan-7-yl, 2-oxa-6-azaspiro[3.4]octan-6-yl, 3-azabicyclo[3.1.0]hexan-3-yl, 8-azabicyclo[3.2.1]octan-3-yl, 8-azabicyclo[3.2.1]oct-2-en-3-yl, 9-azabicyclo[3.3.1]nonan-3-yl, 2,5-diazabicyclo[2.2.1]heptan-2-yl, 1,4-diazabicyclo[3.1.1]heptan-4-yl, 3,6-diazabicyclo[3.2.0]heptan-3-yl, 3,6-diazabicyclo[3.2.0]heptan-6-yl, 2,5-diazabicyclo[2.2.2]octan-2-yl, 1,4-diazabicyclo[3.2.1]octan-4-yl, 3,8-diazabicyclo[3.2.1]octan-3-yl, 1,4-diazabicyclo[3.2.2]nonan-4-yl, 4,7-diazaspiro[2.5]octan-4-yl, 4,7-diazaspiro[2.5]octan-7-yl, 2,6-diazaspiro[3.3]heptan-2-yl, 1,6-diazaspiro[3.4]octan-6-yl, 2,6-diazaspiro[3.4]octan-2-yl, 2,6-diazaspiro[3.4]octan-6-yl, 1,7,-diazaspiro[4.4]nonan-1-yl, 1.7,-diazaspiro[4.4]nonan-7-yl, 1,7-diazaspiro[3.5]nonan-7-yl, 2,6-diazaspiro[3.5]nonan-2-yl, 2,6-diazaspiro[3.5]nonan-6-yl, 1,7-diazaspiro[3.5]nonan-7-yl, 2,7-diazaspiro[3.5]nonan-2-yl, 2,7-diazaspiro[3.5]nonan-7-yl, 5,8-diazaspiro[3.5]nonan-8-yl, 2-oxa-5,8-diazaspiro[3.5]nonan-8-yl, 2,7-diazaspiro[4.4]nonan-2-yl, 2,7-diazaspiro[4.5]decan-2-yl, 2.7-diazaspiro[4.5]decan-7-yl, 2,8-diazaspiro[4.5]decan-8-yl, 6,9-diazaspiro[4.5]dec-9-yl, 6-oxa-2,9-diazaspiro[4.5]decan-2-yl, 2,9-diazaspiro[5.5]undecan-9-yl, 4-azadispiro[2.1.2$^5$.3$^3$]decan-9-yl, and 7-azadispiro[5.1.5$^8$.3$^6$]hexadecan-15-yl, substituted where allowed by available valences with two $R_b$ substituents.

Another aspect includes a compound of Formula (I), wherein B is heterocyclyl selected from azetidin-1-yl, tetrahydrofuran-3-yl, pyrrolidin-1-yl, pyrrolidin-3-yl, piperidin-1-yl, piperidin-3-yl, piperidin-4-yl, piperidin-1-olate-4-yl, piperazin-1-yl, 1,4-diazepan-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,2,5,6-tetrahydropyridin-5-yl, 1,2,3,6-tetrahydropyridin-4-yl, hexahydrocyclopentapyrrol-2(1H)-yl, hexahydropyrrolo[3,2-b]pyrrol-1(2H)-yl, hexahydropyrrolo[3,4-b]pyrrol-1(2H)-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, octahydro-5H-pyrrolo[3,2-c]pyridin-5-yl, octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, hexahydro-1H-cyclobuta[1.2-c:1,4-c']dipyrrol-2(3H)-yl, octahydropyrrolo[1,2-a]pyrazin-2(1H)-yl, octahydro-2H-pyrido[1,2-a]pyrazin-2-yl, hexahydropyrrolo[3,4-b][1,4]oxazin-6(2H)-yl, 5-azaspiro[2.4]heptan-5-yl, 1-azaspiro[3.3]heptan-2-yl, 4-azaspiro[2.5]octan-7-yl, 2-oxa-6-azaspiro[3.4]octan-6-yl, 3-azabicyclo[3.1.0]hexan-3-yl, 8-azabicyclo[3.2.1]octan-3-yl, 8-azabicyclo[3.2.1]oct-2-en-3-yl, 9-azabicyclo[3.3.1]nonan-3-yl, 2,5-diazabicyclo[2.2.1]heptan-2-yl, 1,4-diazabicyclo[3.1.1]heptan-4-yl, 3,6-diazabicyclo[3.2.0]heptan-3-yl, 3,6-diazabicyclo[3.2.0]heptan-6-yl, 2,5-diazabicyclo[2.2.2]octan-2-yl, 1,4-diazabicyclo[3.2.1]octan-4-yl, 3,8-diazabicyclo[3.2.1]octan-3-yl, 1,4-diazabicyclo[3.2.2]nonan-4-yl, 4,7-diazaspiro[2.5]octan-4-yl, 4,7-diazaspiro

[2.5]octan-7-yl, 2,6-diazaspiro[3.3]heptan-2-yl, 1,6-diazaspiro[3.4]octan-6-yl, 2,6-diazaspiro[3.4]octan-2-yl, 2,6-diazaspiro[3.4]octan-6-yl, 1,7,-diazaspiro[4.4]nonan-1-yl, 1,7,-diazaspiro[4.4]nonan-7-yl, 1,7-diazaspiro[3.5]nonan-7-yl, 2,6-diazaspiro[3.5]nonan-2-yl, 2,6-diazaspiro[3.5]nonan-6-yl, 1,7-diazaspiro[3.5]nonan-7-yl, 2,7-diazaspiro[3.5]nonan-2-yl, 2,7-diazaspiro[3.5]nonan-7-yl, 5,8-diazaspiro[3.5]nonan-8-yl, 2-oxa-5,8-diazaspiro[3.5]nonan-8-yl, 2,7-diazaspiro[4.4]nonan-2-yl, 2,7-diazaspiro[4.5]decan-2-yl, 2,7-diazaspiro[4.5]decan-7-yl, 2,8-diazaspiro[4.5]decan-8-yl, 6,9-diazaspiro[4.5]dec-9-yl, 6-oxa-2,9-diazaspiro[4.5]decan-2-yl, 2,9-diazaspiro[5.5]undecan-9-yl, 4-azadispiro[2.1.2$^5$.3$^3$]decan-9-yl, and 7-azadispiro[5.1.5$^8$.3$^6$]hexadecan-15-yl, substituted where allowed by available valences with three $R_b$ substituents.

Another aspect includes a compound of Formula (I), wherein B is heterocyclyl selected from azetidin-1-yl, tetrahydrofuran-3-yl, pyrrolidin-1-yl, pyrrolidin-3-yl, piperidin-1-yl, piperidin-3-yl, piperidin-4-yl, piperidin-1-olate-4-yl, piperazin-1-yl, 1,4-diazepan-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,2,5,6-tetrahydropyridin-5-yl, 1,2,3,6-tetrahydropyridin-4-yl, hexahydrocyclopentapyrrol-2(1H)-yl, hexahydropyrrolo[3,2-b]pyrrol-1(2H)-yl, hexahydropyrrolo[3,4-b]pyrrol-1(2H)-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, octahydro-5H-pyrrolo[3,2-c]pyridin-5-yl, octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, hexahydro-1H-cyclobuta[1.2-c:1,4-c']dipyrrol-2(3H)-yl, octahydropyrrolo[1,2-a]pyrazin-2(1H)-yl, octahydro-2H-pyrido[1,2-a]pyrazin-2-yl, hexahydropyrrolo[3,4-b][1,4]oxazin-6(2H)-yl, 5-azaspiro[2.4]heptan-5-yl, 1-azaspiro[3.3]heptan-2-yl, 4-azaspiro[2.5]octan-7-yl, 2-oxa-6-azaspiro[3.4]octan-6-yl, 3-azabicyclo[3.1.0]hexan-3-yl, 8-azabicyclo[3.2.1]octan-3-yl, 8-azabicyclo[3.2.1]oct-2-en-3-yl, 9-azabicyclo[3.3.1]nonan-3-yl, 2,5-diazabicyclo[2.2.1]heptan-2-yl, 1,4-diazabicyclo[3.1.1]heptan-4-yl, 3,6-diazabicyclo[3.2.0]heptan-3-yl, 3,6-diazabicyclo[3.2.0]heptan-6-yl, 2,5-diazabicyclo[2.2.2]octan-2-yl, 1,4-diazabicyclo[3.2.1]octan-4-yl, 3,8-diazabicyclo[3.2.1]octan-3-yl, 1,4-diazabicyclo[3.2.2]nonan-4-yl, 4,7-diazaspiro[2.5]octan-4-yl, 4,7-diazaspiro[2.5]octan-7-yl, 2,6-diazaspiro[3.3]heptan-2-yl, 1,6-diazaspiro[3.4]octan-6-yl, 2,6-diazaspiro[3.4]octan-2-yl, 2,6-diazaspiro[3.4]octan-6-yl, 1,7,-diazaspiro[4.4]nonan-1-yl, 1,7,-diazaspiro[4.4]nonan-7-yl, 1,7-diazaspiro[3.5]nonan-7-yl, 2,6-diazaspiro[3.5]nonan-2-yl, 2,6-diazaspiro[3.5]nonan-6-yl, 1,7-diazaspiro[3.5]nonan-7-yl, 2,7-diazaspiro[3.5]nonan-2-yl, 2,7-diazaspiro[3.5]nonan-7-yl, 5,8-diazaspiro[3.5]nonan-8-yl, 2-oxa-5,8-diazaspiro[3.5]nonan-8-yl, 2,7-diazaspiro[4.4]nonan-2-yl, 2,7-diazaspiro[4.5]decan-2-yl, 2,7-diazaspiro[4.5]decan-7-yl, 2,8-diazaspiro[4.5]decan-8-yl, 6,9-diazaspiro[4.5]dec-9-yl, 6-oxa-2,9-diazaspiro[4.5]decan-2-yl, 2,9-diazaspiro[5.5]undecan-9-yl, 4-azadispiro[2.1.2$^5$.3$^1$]decan-9-yl, and 7-azadispiro[5.1.5$^8$.3$^6$]hexadecan-15-yl, substituted where allowed by available valences with four $R_b$ substituents.

Another aspect includes a compound of Formula (I), wherein B is heterocyclyl selected from azetidin-1-yl, tetrahydrofuran-3-yl, pyrrolidin-1-yl, pyrrolidin-3-yl, piperidin-1-yl, piperidin-3-yl, piperidin-4-yl, piperidin-1-olate-4-yl, piperazin-1-yl, 1,4-diazepan-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,2,5,6-tetrahydropyridin-5-yl, 1,2,3,6-tetrahydropyridin-4-yl, hexahydrocyclopentapyrrol-2(1H)-yl, hexahydropyrrolo[3,2-b]pyrrol-1(2H)-yl, hexahydropyrrolo[3,4-b]pyrrol-1(2H)-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, octahydro-5H-pyrrolo[3,2-c]pyridin-5-yl, octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, hexahydro-1H-cyclobuta[1.2-c:1,4-c']dipyrrol-2(3H)-yl, octahydropyrrolo[1,2-a]pyrazin-2(1H)-yl, octahydro-2H-pyrido[1,2-a]pyrazin-2-yl, hexahydropyrrolo[3,4-b][1,4]oxazin-6(2H)-yl, 5-azaspiro[2.4]heptan-5-yl, 1-azaspiro[3.3]heptan-2-yl, 4-azaspiro[2.5]octan-7-yl, 2-oxa-6-azaspiro[3.4]octan-6-yl, 3-azabicyclo[3.1.0]hexan-3-yl, 8-azabicyclo[3.2.1]octan-3-yl, 8-azabicyclo[3.2.1]oct-2-en-3-yl, 9-azabicyclo[3.3.1]nonan-3-yl, 2,5-diazabicyclo[2.2.1]heptan-2-yl, 1,4-diazabicyclo[3.1.1]heptan-4-yl, 3,6-diazabicyclo[3.2.0]heptan-3-yl, 3,6-diazabicyclo[3.2.0]heptan-6-yl, 2,5-diazabicyclo[2.2.2]octan-2-yl, 1,4-diazabicyclo[3.2.1]octan-4-yl, 3,8-diazabicyclo[3.2.1]octan-3-yl, 1,4-diazabicyclo[3.2.2]nonan-4-yl, 4,7-diazaspiro[2.5]octan-4-yl, 4,7-diazaspiro[2.5]octan-7-yl, 2,6-diazaspiro[3.3]heptan-2-yl, 1,6-diazaspiro[3.4]octan-6-yl, 2,6-diazaspiro[3.4]octan-2-yl, 2,6-diazaspiro[3.4]octan-6-yl, 1,7,-diazaspiro[4.4]nonan-1-yl, 1,7,-diazaspiro[4.4]nonan-7-yl, 1,7-diazaspiro[3.5]nonan-7-yl, 2,6-diazaspiro[3.5]nonan-2-yl, 2.6-diazaspiro[3.5]nonan-6-yl, 1,7-diazaspiro[3.5]nonan-7-yl, 2,7-diazaspiro[3.5]nonan-2-yl, 2,7-diazaspiro[3.5]nonan-7-yl, 5,8-diazaspiro[3.5]nonan-8-yl, 2-oxa-5,8-diazaspiro[3.5]nonan-8-yl, 2,7-diazaspiro[4.4]nonan-2-yl, 2,7-diazaspiro[4.5]decan-2-yl, 2,7-diazaspiro[4.5]decan-7-yl, 2,8-diazaspiro[4.5]decan-8-yl, 6,9-diazaspiro[4.5]dec-9-yl, 6-oxa-2,9-diazaspiro[4.5]decan-2-yl, 2,9-diazaspiro[5.5]undecan-9-yl, 4-azadispiro[2.1.2$^5$.3$^3$]decan-9-yl, and 7-azadispiro[5.1.5$^8$.3$^6$]hexadecan-15-yl, substituted where allowed by available valences with five $R_b$ substituents.

Another aspect includes a compound of Formula (I), wherein B is heterocyclyl selected from pyrrolidin-1-yl, piperidin-4-yl, piperidin-1-olate-4-yl, piperazin-1-yl, 4-azaspiro[2.5]octan-7-yl, 8-azabicyclo[3.2.1]octan-3-yl, 2,5-diazabicyclo[2.2.1]heptan-2-yl, 1,6-diazaspiro[3.4]octan-6-yl, 2-oxa-5,8-diazaspiro[3.5]nonan-8-yl, and 4-azadispiro[2.1.2$^5$.3$^3$]decan-9-yl, optionally substituted where allowed by available valences with 1, 2, 3, 4, or 5 $R_b$ substituents.

Another aspect includes a compound of Formula (I), wherein B is unsubstituted heterocyclyl selected from pyrrolidin-1-yl, piperidin-4-yl, piperidin-1-olate-4-yl, piperazin-1-yl, 4-azaspiro[2.5]octan-7-yl, 8-azabicyclo[3.2.1]octan-3-yl, 2,5-diazabicyclo[2.2.1]heptan-2-yl, 1,6-diazaspiro[3.4]octan-6-yl, 2-oxa-5,8-diazaspiro[3.5]nonan-8-yl, and 4-azadispiro[2.1.2$^5$.3$^3$]decan-9-yl.

Another aspect includes a compound of Formula (I), wherein B is heterocyclyl selected from pyrrolidin-1-yl, piperidin-4-yl, piperidin-1-olate-4-yl, piperazin-1-yl, 4-azaspiro[2.5]octan-7-yl, 8-azabicyclo[3.2.1]octan-3-yl, 2,5-diazabicyclo[2.2.1]heptan-2-yl, 1,6-diazaspiro[3.4]octan-6-yl, 2-oxa-5,8-diazaspiro[3.5]nonan-8-yl, and 4-azadispiro[2.1.2$^5$.3$^3$]decan-9-yl, substituted where allowed by available valences with one $R_b$ substituent.

Another aspect includes a compound of Formula (I), wherein B is heterocyclyl selected from pyrrolidin-1-yl, piperidin-4-yl, piperidin-1-olate-4-yl, piperazin-1-yl, 4-azaspiro[2.5]octan-7-yl, 8-azabicyclo[3.2.1]octan-3-yl, 2,5-diazabicyclo[2.2.1]heptan-2-yl, 1,6-diazaspiro[3.4]octan-6-yl, 2-oxa-5,8-diazaspiro[3.5]nonan-8-yl, and 4-azadispiro[$2.1.2^5.3^3$]decan-9-yl, substituted where allowed by available valences with two $R_b$ substituents.

Another aspect includes a compound of Formula (I), wherein B is heterocyclyl selected from pyrrolidin-1-yl, piperidin-4-yl, piperidin-1-olate-4-yl, piperazin-1-yl, 4-azaspiro[2.5]octan-7-yl, 8-azabicyclo[3.2.1]octan-3-yl, 2,5-diazabicyclo[2.2.1]heptan-2-yl, 1,6-diazaspiro[3.4]octan-6-yl, 2-oxa-5,8-diazaspiro[3.5]nonan-8-yl, and 4-azadispiro[$2.1.2^5.3^3$]decan-9-yl, substituted where allowed by available valences with three $R_b$ substituents.

Another aspect includes a compound of Formula (I), wherein B is heterocyclyl selected from pyrrolidin-1-yl, piperidin-4-yl, piperidin-1-olate-4-yl, piperazin-1-yl, 4-azaspiro[2.5]octan-7-yl, 8-azabicyclo[3.2.1]octan-3-yl, 2,5-diazabicyclo[2.2.1]heptan-2-yl, 1,6-diazaspiro[3.4]octan-6-yl, 2-oxa-5,8-diazaspiro[3.5]nonan-8-yl, and 4-azadispiro[$2.1.2^5.3^3$]decan-9-yl, substituted where allowed by available valences with four $R_b$ substituents.

Another aspect includes a compound of Formula (I), wherein B is heterocyclyl selected from pyrrolidin-1-yl, piperidin-4-yl, piperidin-1-olate-4-yl, piperazin-1-yl, 4-azaspiro[2.5]octan-7-yl, 8-azabicyclo[3.2.1]octan-3-yl, 2,5-diazabicyclo[2.2.1]heptan-2-yl, 1,6-diazaspiro[3.4]octan-6-yl, 2-oxa-5,8-diazaspiro[3.5]nonan-8-yl, and 4-azadispiro[$2.1.2^5.3^3$]decan-9-yl, substituted where allowed by available valences with five $R_b$ substituents.

Another aspect includes a compound of Formula (I), wherein B is heterocyclyl selected from pyrrolidin-1-yl, piperidin-4-yl, piperazin-1-yl, and 4-azaspiro[2.5]octan-7-yl, optionally substituted where allowed by available valences with 1, 2, 3, 4, or 5 $R_b$ substituents.

Another aspect includes a compound of Formula (I), wherein B is unsubstituted heterocyclyl selected from pyrrolidin-1-yl, piperidin-4-yl, piperazin-1-yl, and 4-azaspiro [2.5]octan-7-yl.

Another aspect includes a compound of Formula (I), wherein B is heterocyclyl selected from pyrrolidin-1-yl, piperidin-4-yl, piperazin-1-yl, and 4-azaspiro[2.5]octan-7-yl, substituted where allowed by available valences with one $R_b$ substituent.

Another aspect includes a compound of Formula (I), wherein B is heterocyclyl selected from pyrrolidin-1-yl, piperidin-4-yl, piperazin-1-yl, and 4-azaspiro[2.5]octan-7-yl, substituted where allowed by available valences with two $R_b$ substituents.

Another aspect includes a compound of Formula (I), wherein B is heterocyclyl selected from pyrrolidin-1-yl, piperidin-4-yl, piperazin-1-yl, and 4-azaspiro[2.5]octan-7-yl, substituted where allowed by available valences with three $R_b$ substituents.

Another aspect includes a compound of Formula (I), wherein B is heterocyclyl selected from pyrrolidin-1-yl, piperidin-4-yl, piperazin-1-yl, and 4-azaspiro[2.5]octan-7-yl, substituted where allowed by available valences with four $R_b$ substituents.

Another aspect includes a compound of Formula (I), wherein B is heterocyclyl selected from pyrrolidin-1-yl, piperidin-4-yl, piperazin-1-yl, and 4-azaspiro[2.5]octan-7-yl, substituted is where allowed by available valences with five $R_b$ substituents.

Another aspect includes a compound of Formula (I), wherein B is pyrrolidin-1-yl, substituted where allowed by available valences with one $R_b$ substituent.

Another aspect includes a compound of Formula (I), wherein B is piperidin-4-yl, substituted where allowed by available valences with 4 or 5 $R_b$ substituents.

Another aspect includes a compound of Formula (I), wherein B is piperidin-4-yl, substituted where allowed by available valences with four $R_b$ substituents.

Another aspect includes a compound of Formula (I), wherein B is piperidin-4-yl, substituted where allowed by available valences with five $R_b$ substituents.

Another aspect includes a compound of Formula (I), wherein B is unsubstituted piperazin-1-yl.

Another aspect includes a compound of Formula (I), wherein B is piperazin-1-yl, substituted where allowed by available valences with one $R_b$ substituent.

Another aspect includes a compound of Formula (I), wherein B is piperazin-1-yl, substituted where allowed by available valences with two $R_b$ substituents.

Another aspect includes a compound of Formula (I), wherein B is piperazin-1-yl, substituted where allowed by available valences with three $R_b$ substituents.

Another aspect includes a compound of Formula (I), wherein B is piperazin-1-yl, substituted where allowed by available valences with four $R_b$ substituents.

Another aspect includes a compound of Formula (I), wherein B is unsubstituted 4-azaspiro[2.5]octan-7-yl.

Another aspect includes a compound of Formula (I), wherein B is 4-azaspiro[2.5]octan-7-yl, substituted where allowed by available valences with one $R_b$ substituent.

Another aspect includes a compound of Formula (I), wherein B is 4-azaspiro[2.5]octan-7-yl, substituted where allowed by available valences with two $R_b$ substituents.

Another aspect includes a compound of Formula (I), wherein B is heterocyclyl containing at least one chiral carbon atom having an (R) configuration.

Another aspect includes a compound of Formula (I), wherein B is heterocyclyl containing at least one chiral carbon atom having an (S) configuration.

One aspect includes a compound of Formula (I), wherein $R_b$ is selected from halogen. $C_{1-4}$alkyl, amino, $C_{1-4}$alkyl-amino, $(C_{1-4}alkyl)_2$-amino, and $C_{1-4}$cycloalkyl.

Another aspect includes a compound of Formula (I), wherein $R_b$ is selected from halogen, $C_{1-4}$alkyl, $C_{1-4}$alkyl-amino, and $C_{3-6}$cycloalkyl.

Another aspect includes a compound of Formula (I), wherein $R_b$ is halogen selected from bromo, chloro, fluoro, and iodo.

Another aspect includes a compound of Formula (I), wherein $R_b$ is fluoro.

Another aspect includes a compound of Formula (I), wherein $R_b$ is $C_{1-4}$alkyl selected from methyl, ethyl, propyl, isopropyl, butyl, and tert-butyl.

Another aspect includes a compound of Formula (I), wherein $R_b$ is $C_{1-4}$alkyl selected from methyl, ethyl, and isopropyl.

Another aspect includes a compound of Formula (I), wherein $R_b$ is methyl.

Another aspect includes a compound of Formula (I), wherein $R_b$ is ethyl.

Another aspect includes a compound of Formula (I), wherein $R_b$ is isopropyl.

Another aspect includes a compound of Formula (I), wherein $R_b$ is $C_{1-4}$alkyl-amino.

Another aspect includes a compound of Formula (I), wherein $R_b$ is $C_{1-4}$alkyl-amino, wherein $C_{1-4}$alkyl is selected from methyl, ethyl, propyl, isopropyl, butyl, and tert-butyl.

Another aspect includes a compound of Formula (I), wherein $R_b$ is selected from methylamino and tert-butylamino.

Another aspect includes a compound of Formula (I), wherein $R_b$ is methylamino.

Another aspect includes a compound of Formula (I), wherein $R_b$ is tert-butylamino.

Another aspect includes a compound of Formula (I), wherein $R_b$ is $C_{3-6}$cycloalkyl selected from cyclopropyl, cyclobutyl, cyclopentyl, and cyclohexyl.

Another aspect includes a compound of Formula (I), wherein $R_b$ is cyclopropyl.

One aspect includes a compound of Formula (I), wherein $R_1$ is selected from heteroaryl, heterocyclyl, phenyl, heteroaryl-$C_{1-4}$alkyl, heteroaryl-$C_{2-4}$alkenyl, heteroaryl-amino, and heteroaryl-$C_{1-4}$alkyl-amino,

- wherein heteroaryl is a 3-7 membered monocyclic or 6-10 membered bicyclic ring system having 1, 2, 3, or 4 heteroatom ring members independently selected from N, O, or S,
- wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S; and
- wherein each instance of phenyl, heteroaryl or heterocyclyl is optionally substituted where allowed by available valences with 1 or 2 $R_{1a}$ substituents.

Another aspect includes a compound of Formula (I), wherein $R_1$ is selected from heteroaryl, heterocyclyl, phenyl, heteroaryl-$C_{1-4}$alkyl, heteroaryl-$C_{2-4}$alkenyl, heteroaryl-amino, and heteroaryl-$C_{1-4}$alkyl-amino,

- wherein heteroaryl is a 3-7 membered monocyclic or 6-10 membered bicyclic ring system having 1, 2, 3, or 4 heteroatom ring members independently selected from N, O, or S,
- wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S; and
- wherein each instance of phenyl, heteroaryl or heterocyclyl is unsubstituted.

Another aspect includes a compound of Formula (I), wherein $R_1$ is selected from heteroaryl, heterocyclyl, phenyl, heteroaryl-$C_{1-4}$alkyl, heteroaryl-$C_{2-4}$alkenyl, heteroaryl-amino, and heteroaryl-$C_{1-4}$alkyl-amino,

- wherein heteroaryl is a 3-7 membered monocyclic or 6-10 membered bicyclic ring system having 1, 2, 3, or 4 heteroatom ring members independently selected from N, O, or S,
- wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S; and
- wherein each instance of phenyl, heteroaryl or heterocyclyl is substituted where allowed by available valences with one $R_{1a}$ substituent.

Another aspect includes a compound of Formula (I), wherein $R_1$ is selected from heteroaryl, heterocyclyl, phenyl, heteroaryl-$C_{1-4}$alkyl, heteroaryl-$C_{2-4}$alkenyl, heteroaryl-amino, and heteroaryl-$C_{1-4}$alkyl-amino,

- wherein heteroaryl is a 3-7 membered monocyclic or 6-10 membered bicyclic ring system having 1, 2, 3, or 4 heteroatom ring members independently selected from N, O, or S,
- wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S; and
- wherein each instance of phenyl, heteroaryl or heterocyclyl is substituted where allowed by available valences with two $R_{1a}$ substituents.

Another aspect includes a compound of Formula (I), wherein $R_1$ is selected from heteroaryl, heteroaryl-$C_{2-4}$alkenyl, heteroaryl-amino, and heteroaryl-$C_{1-4}$alkyl-amino, wherein heteroaryl is a 3-7 membered monocyclic or 6-10 membered bicyclic ring system having 1, 2, 3, or 4 heteroatom ring members independently selected from N, O, or S; and wherein heteroaryl is optionally substituted where allowed by available valences with 1 or 2 $R_{1a}$ substituents.

Another aspect includes a compound of Formula (I), wherein $R_1$ is independently selected from heteroaryl, heteroaryl-$C_{2-4}$alkenyl, heteroaryl-amino, and heteroaryl-$C_{1-4}$alkyl-amino,

- wherein heteroaryl is a 3-7 membered monocyclic or 6-10 membered bicyclic ring system having 1, 2, 3, or 4 heteroatom ring members independently selected from N, O, or S; and wherein heteroaryl is unsubstituted.

Another aspect includes a compound of Formula (I), wherein $R_1$ is selected from heteroaryl, heteroaryl-$C_{2-4}$alkenyl, heteroaryl-amino, and heteroaryl-$C_{1-4}$alkyl-amino,

- wherein heteroaryl is a 3-7 membered monocyclic or 6-10 membered bicyclic ring system having 1, 2, 3, or 4 heteroatom ring members independently selected from N, O, or S; and wherein heteroaryl is substituted where allowed by available valences with one $R_{1a}$ substituent.

Another aspect includes a compound of Formula (I), wherein $R_1$ is selected from heteroaryl, heteroaryl-$C_{2-4}$alkenyl, heteroaryl-amino, and heteroaryl-$C_{2-4}$alkyl-amino,

- wherein heteroaryl is a 3-7 membered monocyclic or 6-10 membered bicyclic ring system having 1, 2, 3, or 4 heteroatom ring members independently selected from N, O, or S; and wherein heteroaryl is substituted where allowed by available valences with two $R_1$, substituents.

Another aspect includes a compound of Formula (I), wherein $R_1$ is heteroaryl selected from thienyl, 1H-pyrazolyl, 1H-imidazolyl, 1,3-thiazolyl, oxazolyl, 1,2,4-oxadiazolyl, 1,3,4-oxadiazolyl, 1,2,4-thiadiazolyl, 1H-1,2,3-triazolyl, 2H-1,2,3-triazolyl, 1H-1,2,4-triazolyl, 1H-tetrazolyl, 2H-tetrazolyl, pyridinyl, pyridin-2(1H)-on-yl, pyrazinyl, pyrimidinyl, pyrimidin-4(3H)-on-yl, pyridazinyl, pyridazin-3(2H)-on-yl, 1,2,4-triazinyl, 1,3,5-triazinyl, 1H-indolyl, 1H-indazolyl, 2H-indazolyl, indolizinyl, benzofuranyl, benzothienyl, 1H-benzimidazolyl, 1,3-benzoxazolyl, 1,3-benzothiazolyl, 1,3-benzodioxolyl, 1,2,3-benzotriazolyl, 9H-purinyl, furo[3,2-b]pyridinyl, furo[3,2-c]pyridinyl, furo[2,3-c]pyridinyl, 1,3-oxazolo[5,4-b]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, pyrazolo[1,5-a]pyrimidinyl, pyrazolo[1,5-a]pyrazinyl, 1H-pyrazolo[3,4-b]pyridinyl, 1H-pyrazolo[3,4-b]pyrazinyl, 1H-pyrazolo[3,4-c]pyridinyl, 1H-pyrazolo[4,3-b]pyridinyl, 1H-pyrazolo[4,3-d]pyrimidinyl, 2H-pyrazolo[4,3-b]pyridinyl, 2H-pyrazolo[4,3-c]pyridin-yl, 5H-pyrrolo[2,3-b]pyrazinyl, imidazo[1,2-a]pyridinyl, imidazo[1,2-a]pyrazinyl, imidazo[1,2-a]pyrimidinyl, imidazo[1,2-b]pyridazinyl, imidazo[1,2-c]pyrimidinyl, 1H-imidazo[4,5-b]pyridinyl, 3H-imidazo[4,5-b]pyridinyl, imidazo[2,1-b][1,3]thiazolyl, imidazo[2,1-b][1,3,4]thiadiazolyl, [1,3]oxazolo[4,5-b]pyridinyl, [1,2,3]triazolo[1,5-a]pyridinyl, 1H-[1,2,3]triazolo[4,5-b]pyridinyl, 2H-[1,2,3]triazolo[4,5-b]pyridinyl, 3H-[1,2,3]triazolo[4,5-b]pyridinyl, [1,2,4]triazolo[1,5-a]pyridinyl, [1,2,4]triazolo[1,5-a]pyrazinyl, [1,2,4]triazolo[4,3-a]pyridinyl, tetrazolo

[1,5-a]pyridinyl, tetrazolo[1,5-b]pyridazinyl, quinolinyl, isoquinolinyl, and quinoxalinyl, optionally substituted where allowed by available valences with 1 or 2 $R_{1a}$ substituents.

Another aspect includes a compound of Formula (I), wherein $R_1$ is unsubstituted heteroaryl selected from thienyl, 1H-pyrazolyl, 1H-imidazolyl, 1,3-thiazolyl, oxazolyl, 1,2,4-oxadiazolyl, 1,3,4-oxadiazolyl, 1,2,4-thiadiazolyl, 1H-1,2,3-triazolyl, 2H-1,2,3-triazolyl, 1H-1,2,4-triazolyl, 1H-tetrazolyl, 2H-tetrazolyl, pyridinyl, pyridin-2(1H)-on-yl, pyrazinyl, pyrimidinyl, pyrimidin-4(3H)-on-yl, pyridazinyl, pyridazin-3(2H)-on-yl, 1,2,4-triazinyl, 1,3,5-triazinyl, 1H-indolyl, 1H-indazolyl, 2H-indazolyl, indolizinyl, benzofuranyl, benzothienyl, 1H-benzimidazolyl, 1,3-benzoxazolyl, 1,3-benzothiazolyl, 1,3-benzodioxolyl, 1,2,3-benzotriazolyl, 9H-purinyl, furo[3,2-b]pyridinyl, furo[3,2-c]pyridinyl, furo[2,3-c]pyridinyl, 1,3-oxazolo[5,4-b]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, pyrazolo[1,5-a]pyrimidinyl, pyrazolo[1,5-a]pyrazinyl, 1H-pyrazolo[3,4-b]pyridinyl, 1H-pyrazolo[3,4-b]pyrazinyl, 1H-pyrazolo[3,4-c]pyridinyl, 1H-pyrazolo[4,3-b]pyridinyl, 1H-pyrazolo[4,3-d]pyrimidinyl, 2H-pyrazolo[4,3-b]pyridinyl, 2H-pyrazolo[4,3-c]pyridin-yl, 5H-pyrrolo[2,3-b]pyrazinyl, imidazo[1,2-a]pyridinyl, imidazo[1,2-a]pyrazinyl, imidazo[1,2-a]pyrimidinyl, imidazo[1,2-b]pyridazinyl, imidazo[1,2-c]pyrimidinyl, 1H-imidazo[4,5-b]pyridinyl, 3H-imidazo[4,5-b]pyridinyl, imidazo[2,1-b][1,3]thiazolyl, imidazo[2,1-b][1,3,4]thiadiazolyl, [1,3]oxazolo[4,5-b]pyridinyl, [1,2,3]triazolo[1,5-a]pyridinyl, 1H-[1,2,3]triazolo[4,5-b]pyridinyl, 2H-[1,2,3]triazolo[4,5-b]pyridinyl, 3H-[1,2,3]triazolo[4,5-b]pyridinyl, [1,2,4]triazolo[1,5-a]pyridinyl, [1,2,4]triazolo[1,5-a]pyrazinyl, [1,2,4]triazolo[4,3-a]pyridinyl, tetrazolo[1,5-a]pyridinyl, tetrazolo[1,5-b]pyridazinyl, quinolinyl, isoquinolinyl, and quinoxalinyl.

Another aspect includes a compound of Formula (I), wherein $R_1$ is heteroaryl selected from thienyl, 1H-pyrazolyl, 1H-imidazolyl, 1,3-thiazolyl, oxazolyl, 1,2,4-oxadiazolyl, 1,3,4-oxadiazolyl, 1,2,4-thiadiazolyl, 1H-1,2,3-triazolyl, 2H-1,2,3-triazolyl, 1H-1,2,4-triazolyl, 1H-tetrazolyl, 2H-tetrazolyl, pyridinyl, pyridin-2(1H)-on-yl, pyrazinyl, pyrimidinyl, pyrimidin-4(3H)-on-yl, pyridazinyl, pyridazin-3(2H)-on-yl, 1,2,4-triazinyl, 1,3,5-triazinyl, 1H-indolyl, 1H-indazolyl, 2H-indazolyl, indolizinyl, benzofuranyl, benzothienyl, 1H-benzimidazolyl, 1,3-benzoxazolyl, 1,3-benzothiazolyl, 1,3-benzodioxolyl, 1,2,3-benzotriazolyl, 9H-purinyl, furo[3,2-b]pyridinyl, furo[3,2-c]pyridinyl, furo[2,3-c]pyridinyl, 1,3-oxazolo[5,4-b]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, pyrazolo[1,5-a]pyrimidinyl, pyrazolo[1,5-a]pyrazinyl, 1H-pyrazolo[3,4-b]pyridinyl, 1H-pyrazolo[3,4-b]pyrazinyl, 1H-pyrazolo[3,4-c]pyridinyl, 1H-pyrazolo[4,3-b]pyridinyl, 1H-pyrazolo[4,3-d]pyrimidinyl, 2H-pyrazolo[4,3-b]pyridinyl, 2H-pyrazolo[4,3-c]pyridin-yl, 5H-pyrrolo[2,3-b]pyrazinyl, imidazo[1,2-a]pyridinyl, imidazo[1,2-a]pyrazinyl, imidazo[1,2-a]pyrimidinyl, imidazo[1,2-b]pyridazinyl, imidazo[1,2-c]pyrimidinyl, 1H-imidazo[4,5-b]pyridinyl, 3H-imidazo[4,5-b]pyridinyl, imidazo[2,1-b][1,3]thiazolyl, imidazo[2,1-b][1,3,4]thiadiazolyl, [1,3]oxazolo[4,5-b]pyridinyl, [1,2,3]triazolo[1,5-a]pyridinyl, 1H-[1,2,3]triazolo[4,5-b]pyridinyl, 2H-[1,2,3]triazolo[4,5-b]pyridinyl, 3H-[1,2,3]triazolo[4,5-b]pyridinyl, [1,2,4]triazolo[1,5-a]pyridinyl, [1,2,4]triazolo[1,5-a]pyrazinyl, [1,2,4]triazolo[4,3-a]pyridinyl, tetrazolo[1,5-a]pyridinyl, tetrazolo[1,5-b]pyridazinyl, quinolinyl, isoquinolinyl, and quinoxalinyl, substituted where allowed by available valences with one $R_{1a}$ substituent.

Another aspect includes a compound of Formula (I), wherein $R_1$ is heteroaryl selected from thienyl, 1H-pyrazolyl, 1H-imidazolyl, 1,3-thiazolyl, oxazolyl, 1,2,4-oxadiazolyl, 1,3,4-oxadiazolyl, 1,2,4-thiadiazolyl, 1H-1,2,3-triazolyl, 2H-1,2,3-triazolyl, 1H-1,2,4-triazolyl, 1H-tetrazolyl, 2H-tetrazolyl, pyridinyl, pyridin-2(1H)-on-yl, pyrazinyl, pyrimidinyl, pyrimidin-4(3H)-on-yl, pyridazinyl, pyridazin-3(2H)-on-yl, 1,2,4-triazinyl, 1,3,5-triazinyl, 1H-indolyl, 1H-indazolyl, 2H-indazolyl, indolizinyl, benzofuranyl, benzothienyl, 1H-benzimidazolyl, 1,3-benzoxazolyl, 1,3-benzothiazolyl, 1,3-benzodioxolyl, 1,2,3-benzotriazolyl, 9H-purinyl, furo[3,2-b]pyridinyl, furo[3,2-c]pyridinyl, furo[2,3-c]pyridinyl, 1,3-oxazolo[5,4-b]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, pyrazolo[1,5-a]pyrimidinyl, pyrazolo[1,5-a]pyrazinyl, 1H-pyrazolo[3,4-b]pyridinyl, 1H-pyrazolo[3,4-b]pyrazinyl, 1H-pyrazolo[3,4-c]pyridinyl, 1H-pyrazolo[4,3-b]pyridinyl, 1H-pyrazolo[4,3-d]pyrimidinyl, 2H-pyrazolo[4,3-b]pyridinyl, 2H-pyrazolo[4,3-c]pyridin-yl, 5H-pyrrolo[2,3-b]pyrazinyl, imidazo[1,2-a]pyridinyl, imidazo[1,2-a]pyrazinyl, imidazo[1,2-a]pyrimidinyl, imidazo[1,2-b]pyridazinyl, imidazo[1,2-c]pyrimidinyl, 1H-imidazo[4,5-b]pyridinyl, 3H-imidazo[4,5-b]pyridinyl, imidazo[2,1-b][1,3]thiazolyl, imidazo[2,1-b][1,3,4]thiadiazolyl, [1,3]oxazolo[4,5-b]pyridinyl, [1,2,3]triazolo[1,5-a]pyridinyl, 1H-[1,2,3]triazolo[4,5-b]pyridinyl, 2H-[1,2,3]triazolo[4,5-b]pyridinyl, 3H-[1,2,3]triazolo[4,5-b]pyridinyl, [1,2,4]triazolo[1,5-a]pyridinyl, [1,2,4]triazolo[1,5-a]pyrazinyl, [1,2,4]triazolo[4,3-a]pyridinyl, tetrazolo[1,5-a]pyridinyl, tetrazolo[1,5-b]pyridazinyl, quinolinyl, isoquinolinyl, and quinoxalinyl, substituted where allowed by available valences with two $R_{1a}$ substituents.

Another aspect includes a compound of Formula (I), wherein $R_1$ is heteroaryl selected from 1H-pyrazolyl, 1H-imidazolyl, 1,3-thiazolyl, oxazolyl, 1H-1,2,3-triazolyl, 2H-1,2,3-triazolyl, 1H-1,2,4-triazolyl, pyridinyl, pyridin-2(1H)-on-yl, pyrimidin-4(3H)-on-yl, pyridazinyl, 1H-indazolyl, 2H-indazolyl, 1,3-benzoxazolyl, pyrrolo[1,2-a]pyrazinyl, imidazo[1,2-a]pyridinyl, imidazo[1,2-a]pyrazinyl, imidazo[1,2-a]pyrimidinyl, imidazo[1,2-b]pyridazinyl, [1,2,4]triazolo[1,5-a]pyridinyl, and [1,2,4]triazolo[1,5-a]pyrazinyl, optionally substituted where allowed by available valences with 1 or 2 $R_{1a}$ substituents.

Another aspect includes a compound of Formula (I), wherein $R_1$ is unsubstituted heteroaryl selected from 1H-pyrazolyl, 1H-imidazolyl, 1,3-thiazolyl, oxazolyl, 1H-1,2,3-triazolyl, 2H-1,2,3-triazolyl, 1H-1,2,4-triazolyl, pyridinyl, pyridin-2(1H)-on-yl, pyrimidin-4(3H)-on-yl, pyridazinyl, 1H-indazolyl, 2H-indazolyl, 1,3-benzoxazolyl, pyrrolo[1,2-a]pyrazinyl, imidazo[1,2-a]pyridinyl, imidazo[1,2-a]pyrazinyl, imidazo[1,2-a]pyrimidinyl, imidazo[1,2-b]pyridazinyl, [1,2,4]triazolo[1,5-a]pyridinyl, and [1,2,4]triazolo[1,5-a]pyrazinyl.

Another aspect includes a compound of Formula (I), wherein $R_1$ is heteroaryl selected from 1H-pyrazolyl, 1H-imidazolyl, 1,3-thiazolyl, oxazolyl, 1H-1,2,3-triazolyl, 2H-1,2,3-triazolyl, 1H-1,2,4-triazolyl, pyridinyl, pyridin-2(1H)-on-yl, pyrimidin-4(3H)-on-yl, pyridazinyl, 1H-indazolyl, 2H-indazolyl, 1,3-benzoxazolyl, pyrrolo[1,2-a]pyrazinyl, imidazo[1,2-a]pyridinyl, imidazo[1,2-a]pyrazinyl, imidazo[1,2-a]pyrimidinyl, imidazo[1,2-b]

pyridazinyl, [1,2,4]triazolo[1,5-a]pyridinyl, and [1,2,4] triazolo[1,5-a]pyrazinyl, substituted where allowed by available valences with one $R_{1a}$ substituent.

Another aspect includes a compound of Formula (I), wherein $R_1$ is heteroaryl selected from 1H-pyrazolyl, 1H-imidazolyl, 1,3-thiazolyl, oxazolyl, 1H-1,2,3-triazolyl, 2H-1,2,3-triazolyl, 1H-1,2,4-triazolyl, pyridinyl, pyridin-2 (1H)-on-yl, pyrimidin-4(3H)-on-yl, pyridazinyl, 1H-indazolyl, 2H-indazolyl, 1,3-benzoxazolyl, pyrrolo[1,2-a] pyrazinyl, imidazo[1,2-a]pyridinyl, imidazo[1,2-a] pyrazinyl, imidazo[1,2-a]pyrimidinyl, imidazo[1,2-b] pyridazinyl, [1,2,4]triazolo[1,5-a]pyridinyl, and [1,2,4] triazolo[1,5-a]pyrazinyl, substituted where allowed by available valences with two $R_{1a}$ substituents.

Another aspect includes a compound of Formula (I), wherein $R_1$ is heteroaryl selected from thien-2-yl, thien-3-yl, 1H-pyrazol-1-yl, 1H-pyrazol-3-yl, 1H-pyrazol-4-yl, 1H-pyrazol-5-yl, 1H-imidazol-1-yl, 1H-imidazol-4-yl, 1,3-thiazol-2-yl, 1,3-thiazol-5-yl, 1,3-oxazol-2-yl, 1,3-oxazol-4-yl, 1,3-oxazol-5-yl, 1,2,4-oxadiazol-3-yl, 1,3,4-oxadiazol-2-yl, 1,2,4-thiadiazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-3-yl, 1H-1,2,4-triazol-5-yl, 1H-tetrazol-1-yl, 1H-tetrazol-5-yl, 2H-tetrazol-2-yl, 2H-tetrazol-5-yl, pyridin-2-yl, pyridin-3-yl, pyridin-4-yl, pyridin-2(1H)-on-4-yl, pyridin-2 (1H)-on-5-yl, pyridin-2(1H)-on-6-yl, pyrazin-2-yl, pyrazin-3-yl, pyrimidin-2-yl, pyrimidin-4-yl, pyrimidin-5-yl, pyrimidin-4(3H)-on-6-yl, pyridazin-3-yl, pyridazin-4-yl, pyridazin-3(2H)-on-5-yl, 1,2,4-triazin-3-yl, 1,3,5-triazin-2-yl, 1H-indol-3-yl, 1H-indol-4-yl, 1H-indol-5-yl, 1H-indol-6-yl, 1H-indazol-5-yl, 1H-indazol-6-yl, 2H-indazol-4-yl, 2H-indazol-5-yl, 2H-indazol-6-yl, indolizin-2-yl, benzofuran-2-yl, benzofuran-5-yl, benzothien-2-yl, benzothien-3-yl, 1H-benzimidazol-2-yl, 1H-benzimidazol-5-yl, 1H-benzimidazol-6-yl, 1,3-benzoxazol-2-yl, 1,3-benzoxazol-5-yl, 1,3-benzoxazol-6-yl, 1,3-benzothiazol-2-yl, 1,3-benzothiazol-5-yl, 1,3-benzothiazol-6-yl, 1,3-benzodioxol-5-yl, 1,2,3-benzotriazol-5-yl, 9H-purin-8-yl, furo[3,2-b]pyridin-2-yl, furo[3,2-c]pyridin-2-yl, furo[2,3-c]pyridin-2-yl, 1,3-oxazolo[5,4-b]pyridine-5-yl, thieno[3,2-c]pyridin-2-yl, thieno [2,3-d]pyrimidin-6-yl, 1H-pyrrolo[2,3-b]pyridin-5-yl, 1H-pyrrolo[2,3-c]pyridin-4-yl, pyrrolo[1,2-a]pyrimidin-7-yl, pyrrolo[1,2-a]pyrazin-7-yl, pyrrolo[1,2-b]pyridazin-2-yl, pyrazolo[1,5-a]pyridin-2-yl, pyrazolo[1,5-a]pyridin-5-yl, pyrazolo[1,5-a]pyrazin-2-yl, pyrazolo[1,5-a]pyrimidin-2-yl, pyrazolo[1,5-a]pyrimidin-5-yl, 1H-pyrazolo[3,4-b]pyrazin-5-yl, 1H-pyrazolo[3,4-b]pyridin-5-yl, 1H-pyrazolo[3,4-b] pyridin-6-yl, 1H-pyrazolo[3,4-c]pyridin-1-yl, 1H-pyrazolo [3,4-c]pyridin-5-yl, 1H-pyrazolo[4,3-b]pyridin-5-yl, 1H-pyrazolo[4,3-b]pyridin-6-yl, 1H-pyrazolo[4,3-d]pyrimidin-5-yl, 2H-pyrazolo[4,3-b]pyridin-5-yl, 2H-pyrazolo[4,3-c]pyridin-5-yl, 5H-pyrrolo[2,3-b]pyrazin-2-yl, imidazo[1,2-a]pyridin-2-yl, imidazo[1,2-a]pyridin-6-yl, imidazo[1,2-a] pyrazin-2-yl, imidazo[1,2-a]pyrazin-6-yl, imidazo[1,2-a] pyrimidin-2-yl, imidazo[1,2-a]pyrimidin-6-yl, imidazo[1,2-b]pyridazin-2-yl, imidazo[1,2-b]pyridazin-6-yl, imidazo[1,2-c]pyrimidin-2-yl, 1H-imidazo[4,5-b]pyridin-5-yl, 3H-imidazo[4,5-b]pyridin-5-yl, imidazo[2,1-b][1,3]thiazol-6-yl, imidazo[2,1-b][1,3,4]thiadiazol-6-yl, [1,3]oxazolo[4,5-b]pyridin-2-yl, [1,2,3]triazolo[1,5-a]pyridin-5-yl, [1,2,3] triazolo[1,5-a]pyridin-6-yl, 1H-[1,2,3]triazolo[4,5-b] pyridin-5-yl, 2H-[1,2,3]triazolo[4,5-b]pyridin-6-yl, 3H-[1,2,3]triazolo[4,5-b]pyridin-5-yl, [1,2,4]triazolo[1.5-a]pyridin-2-yl, [1,2,4]triazolo[1,5-a]pyridin-6-yl, [1,2,4]triazolo[1,5-a]pyridin-7-yl, [1,2,4]triazolo[1,5-a]pyrazin-2-yl, [1,2,4] triazolo[1,5-a]pyrazin-5-yl, [1,2,4]triazolo[1,5-a]pyrazin-6-yl, [1,2,4]triazolo[4,3-a]pyridn-6-yl, [1,2,4]triazolo[4,3-a] pyridn-7-yl, tetrazolo[1,5-a]pyridin-7-yl, tetrazolo[1,5-b] pyridazin-7-yl, quinolin-6-yl, isoquinolin-6-yl, and quinoxalin-2-yl, optionally substituted where allowed by available valences with 1 or 2 $R_{1a}$ substituents.

Another aspect includes a compound of Formula (I), wherein $R_1$ is unsubstituted heteroaryl selected from thien-2-yl, thien-3-yl, 1H-pyrazol-1-yl, 1H-pyrazol-3-yl, 1H-pyrazol-4-yl, 1H-pyrazol-5-yl, 1H-imidazol-1-yl, 1H-imidazol-4-yl, 1,3-thiazol-2-yl, 1,3-thiazol-5-yl, 1,3-oxazol-2-yl, 1,3-oxazol-4-yl, 1,3-oxazol-5-yl, 1,2,4-oxadiazol-3-yl, 1,3,4-oxadiazol-2-yl, 1,2,4-thiadiazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-3-yl, 1H-1,2,4-triazol-5-yl, 1H-tetrazol-1-yl, 1H-tetrazol-5-yl, 2H-tetrazol-2-yl, 2H-tetrazol-5-yl, pyridin-2-yl, pyridin-3-yl, pyridin-4-yl, pyridin-2(1H)-on-4-yl, pyridin-2(1H)-on-5-yl, pyridin-2(1H)-on-6-yl, pyrazin-2-yl, pyrazin-3-yl, pyrimidin-2-yl, pyrimidin-4-yl, pyrimidin-5-yl, pyrimidin-4(3H)-on-6-yl, pyridazin-3-yl, pyridazin-4-yl, pyridazin-3(2H)-on-5-yl, 1,2,4-triazin-3-yl, 1,3,5-triazin-2-yl, 1H-indol-3-yl, 1H-indol-4-yl, 1H-indol-5-yl, 1H-indol-6-yl, 1H-indazol-5-yl, 1H-indazol-6-yl, 2H-indazol-4-yl, 2H-indazol-5-yl, 2H-indazol-6-yl, indolizin-2-yl, benzofuran-2-yl, benzofuran-5-yl, benzothien-2-yl, benzothien-3-yl, 1H-benzimidazol-2-yl, 1H-benzimidazol-5-yl, 1H-benzimidazol-6-yl, 1,3-benzoxazol-2-yl, 1,3-benzoxazol-5-yl, 1,3-benzoxazol-6-yl, 1,3-benzothiazol-2-yl, 1,3-benzothiazol-5-yl, 1,3-benzothiazol-6-yl, 1,3-benzodioxol-5-yl, 1,2,3-benzotriazol-5-yl, 9H-purin-8-yl, furo[3,2-b]pyridin-2-yl, furo[3,2-c]pyridin-2-yl, furo[2,3-c] pyridin-2-yl, 1,3-oxazolo[5,4-b]pyridine-5-yl, thieno[3,2-c] pyridin-2-yl, thieno[2,3-d]pyrimidin-6-yl, 1H-pyrrolo[2,3-b]pyridin-5-yl, 1H-pyrrolo[2,3-c]pyridin-4-yl, pyrrolo[1,2-a]pyrimidin-7-yl, pyrrolo[1,2-a]pyrazin-7-yl, pyrrolo[1,2-b] pyridazin-2-yl, pyrazolo[1,5-a]pyridin-2-yl, pyrazolo[1,5-a] pyridin-5-yl, pyrazolo[1,5-a]pyrazin-2-yl, pyrazolo[1,5-a] pyrimidin-2-yl, pyrazolo[1,5-a]pyrimidin-5-yl, 1H-pyrazolo [3,4-b]pyrazin-5-yl, 1H-pyrazolo[3,4-b]pyridin-5-yl, 1H-pyrazolo[3,4-b]pyridin-6-yl, 1H-pyrazolo[3,4-c]pyridin-1-yl, 1H-pyrazolo[3,4-c]pyridin-5-yl, 1H-pyrazolo[3,4-b]pyridin-5-yl, 1H-pyrazolo[4,3-b]pyridin-6-yl, 1H-pyrazolo[4,3-d]pyrimidin-5-yl, 2H-pyrazolo[4,3-b]pyridin-5-yl, 2H-pyrazolo[4,3-c]pyridin-5-yl, 5H-pyrrolo[2,3-b]pyrazin-2-yl, imidazo[1,2-a]pyridin-2-yl, imidazo[1,2-a]pyridin-6-yl, imidazo[1,2-a]pyrazin-2-yl, imidazo[1,2-a]pyrazin-6-yl, imidazo[1,2-a]pyrimidin-2-yl, imidazo[1,2-a]pyrimidin-6-yl, imidazo[1,2-b]pyridazin-2-yl, imidazo[1,2-b]pyridazin-6-yl, imidazo[1,2-c]pyrimidin-2-yl, 1H-imidazo[4,5-b]pyridin-5-yl, 3H-imidazo[4,5-b]pyridin-5-yl, imidazo[2,1-b][1,3]thiazol-6-yl, imidazo[2,1-b][1,3,4]thiadiazol-6-yl, [1,3] oxazolo[4,5-b]pyridin-2-yl, [1,2,3]triazolo[1,5-a]pyridin-5-yl, [1,2,3]triazolo[1,5-a]pyridin-6-yl, 1H-[1,2,3]triazolo[4,5-b]pyridin-5-yl, 2H-[1,2,3]triazolo[4,5-b]pyridin-6-yl, 3H-[1,2,3]triazolo[4,5-b]pyridin-5-yl, [1,2,4]triazolo[1,5-a] pyridin-2-yl, [1,2,4]triazolo[1,5-a]pyridin-6-yl, [1,2,4] triazolo[1,5-a]pyridin-7-yl, [1,2,4]triazolo[1,5-a]pyrazin-2-yl, [1,2,4]triazolo[1,5-a]pyrazin-5-yl, [1,2,4]triazolo[1,5-a] pyrazin-6-yl, [1,2,4]triazolo[4,3-a]pyridn-6-yl, [1,2,4] triazolo[4,3-a]pyridn-7-yl, tetrazolo[1,5-a]pyridin-7-yl, tetrazolo[1,5-b]pyridazin-7-yl, quinolin-6-yl, isoquinolin-6-yl, and quinoxalin-2-yl.

Another aspect includes a compound of Formula (I), wherein $R_1$ is heteroaryl selected from thien-2-yl, thien-3-yl, 1H-pyrazol-1-yl, 1H-pyrazol-3-yl, 1H-pyrazol-4-yl, 1H-pyrazol-5-yl, 1H-imidazol-1-yl, 1H-imidazol-4-yl, 1,3-thiazol-2-yl, 1,3-thiazol-5-yl, 1,3-oxazol-2-yl, 1,3-oxazol-4- yl, 1,3-oxazol-5-yl, 1,2,4-oxadiazol-3-yl, 1,3,4-oxadiazol-2-yl, 1,2,4-thiadiazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-3-yl, 1H-1,2,4-triazol-5-yl, 1H-tetrazol-1-yl, 1H-tetrazol-5-yl, 2H-tetrazol-2-yl, 2H-tetrazol-5-yl, pyridin-2-yl, pyridin-3-yl, pyridin-4-yl, pyridin-2(1H)-on-4-yl, pyridin-2(1H)-on-5-yl, pyridin-2(1H)-on-6-yl, pyrazin-2-yl, pyrazin-3-yl, pyrimidin-2-yl, pyrimidin-4-yl, pyrimidin-5-yl, pyrimidin-4(3H)-on-6-yl, pyridazin-3-yl, pyridazin-4-yl, pyridazin-3(2H)-on-5-yl, 1,2,4-triazin-3-yl, 1,3,5-triazin-2-yl, 1H-indol-3-yl, 1H-indol-4-yl, 1H-indol-5-yl, 1H-indol-6-yl, 1H-indazol-5-yl, 1H-indazol-6-yl, 2H-indazol-4-yl, 2H-indazol-5-yl, 2H-indazol-6-yl, indolizin-2-yl, benzofuran-2-yl, benzofuran-5-yl, benzothien-2-yl, benzothien-3-yl, 1H-benzimidazol-2-yl, 1H-benzimidazol-5-yl, 1H-benzimidazol-6-yl, 1,3-benzoxazol-2-yl, 1,3-benzoxazol-5-yl, 1,3-benzoxazol-6-yl, 1,3-benzothiazol-2-yl, 1,3-benzothiazol-5-yl, 1,3-benzothiazol-6-yl, 1,3-benzodioxol-5-yl, 1,2,3-benzotriazol-5-yl, 9H-purin-8-yl, furo[3,2-b]pyridin-2-yl, furo[3,2-c]pyridin-2-yl, furo[2,3-c]pyridin-2-yl, 1,3-oxazolo[5,4-b]pyridine-5-yl, thieno[3,2-c]pyridin-2-yl, thieno[2,3-d]pyrimidin-6-yl, 1H-pyrrolo[2,3-b]pyridin-5-yl, 1H-pyrrolo[2,3-c]pyridin-4-yl, pyrrolo[1,2-a]pyrimidin-7-yl, pyrrolo[1,2-a]pyrazin-7-yl, pyrrolo[1,2-b]pyridazin-2-yl, pyrazolo[1,5-a]pyridin-2-yl, pyrazolo[1,5-a]pyridin-5-yl, pyrazolo[1,5-a]pyrazin-2-yl, pyrazolo[1,5-a]pyrimidin-2-yl, pyrazolo[1,5-a]pyrimidin-5-yl, 1H-pyrazolo[3,4-b]pyrazin-5-yl, 1H-pyrazolo[3,4-b]pyridin-5-yl, 1H-pyrazolo[3,4-b]pyridin-6-yl, 1H-pyrazolo[3,4-c]pyridin-1-yl, 1H-pyrazolo[3,4-c]pyridin-5-yl, 1H-pyrazolo[4,3-b]pyridin-5-yl, 1H-pyrazolo[4,3-b]pyridin-6-yl, 1H-pyrazolo[4,3-d]pyrimidin-5-yl, 2H-pyrazolo[4,3-b]pyridin-5-yl, 2H-pyrazolo[4,3-c]pyridin-5-yl, 5H-pyrrolo[2,3-b]pyrazin-2-yl, imidazo[1,2-a]pyridin-2-yl, imidazo[1,2-a]pyridin-6-yl, imidazo[1,2-a]pyrazin-2-yl, imidazo[1,2-a]pyrazin-6-yl, imidazo[1,2-a]pyrimidin-2-yl, imidazo[1,2-a]pyrimidin-6-yl, imidazo[1,2-b]pyridazin-2-yl, imidazo[1,2-b]pyridazin-6-yl, imidazo[1,2-c]pyrimidin-2-yl, 1H-imidazo[4,5-b]pyridin-5-yl, 3H-imidazo[4,5-b]pyridin-5-yl, imidazo[2,1-b][1,3]thiazol-6-yl, imidazo[2,1-b][1,3,4]thiadiazol-6-yl, [1,3]oxazolo[4,5-b]pyridin-2-yl, [1,2,3]triazolo[1,5-a]pyridin-5-yl, [1,2,3]triazolo[1,5-a]pyridin-6-yl, 1H-[1,2,3]triazolo[4,5-b]pyridin-5-yl, 2H-[1,2,3]triazolo[4,5-b]pyridin-6-yl, 3H-[1,2,3]triazolo[4,5-b]pyridin-5-yl, [1,2,4]triazolo[1,5-a]pyridin-2-yl, [1,2,4]triazolo[1,5-a]pyridin-6-yl, [1,2,4]triazolo[1,5-a]pyridin-7-yl, [1,2,4]triazolo[1,5-a]pyrazin-2-yl, [1,2,4]triazolo[1,5-a]pyrazin-5-yl, [1,2,4]triazolo[1,5-a]pyrazin-6-yl, [1,2,4]triazolo[4,3-a]pyridn-6-yl, [1,2,4]triazolo[4,3-a]pyridn-7-yl, tetrazolo[1,5-a]pyridin-7-yl, tetrazolo[1,5-b]pyridazin-7-yl, quinolin-6-yl, isoquinolin-6-yl, and quinoxalin-2-yl, substituted where allowed by available valences with one $R_{1a}$ substituent.

Another aspect includes a compound of Formula (I), wherein $R_1$ is heteroaryl selected from thien-2-yl, thien-3-yl, 1H-pyrazol-1-yl, 1H-pyrazol-3-yl, 1H-pyrazol-4-yl, 1H-pyrazol-5-yl, 1H-imidazol-1-yl, 1H-imidazol-4-yl, 1,3-thiazol-2-yl, 1,3-thiazol-5-yl, 1,3-oxazol-2-yl, 1,3-oxazol-4-yl, 1,3-oxazol-5-yl, 1,2,4-oxadiazol-3-yl, 1,3,4-oxadiazol-2-yl, 1,2,4-thiadiazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-3-yl, 1H-1,2,4-triazol-5-yl, 1H-tetrazol-1-yl, 1H-tetrazol-5-yl, 2H-tetrazol-2-yl, 2H-tetrazol-5-yl, pyridin-2-yl, pyridin-3-yl, pyridin-4-yl, pyridin-2(1H)-on-4-yl, pyridin-2(1H)-on-5-yl, pyridin-2(H)-on-6-yl, pyrazin-2-yl, pyrazin-3-yl, pyrimidin-2-yl, pyrimidin-4-yl, pyrimidin-5-yl, pyrimidin-4(3H)-on-6-yl, pyridazin-3-yl, pyridazin-4-yl, pyridazin-3(2H)-on-5-yl, 1,2,4-triazin-3-yl, 1,3,5-triazin-2-yl, 1H-indol-3-yl, 1H-indol-4-yl, 1H-indol-5-yl, 1H-indol-6-yl, 1H-indazol-5-yl, 1H-indazol-6-yl, 2H-indazol-4-yl, 2H-indazol-5-yl, 2H-indazol-6-yl, indolizin-2-yl, benzofuran-2-yl, benzofuran-5-yl, benzothien-2-yl, benzothien-3-yl, 1H-benzimidazol-2-yl, 1H-benzimidazol-5-yl, 1H-benzimidazol-6-yl, 1,3-benzoxazol-2-yl, 1.3-benzoxazol-5-yl, 1,3-benzoxazol-6-yl, 1,3-benzothiazol-2-yl, 1,3-benzothiazol-5-yl, 1,3-benzothiazol-6-yl, 1,3-benzodioxol-5-yl, 1,2,3-benzotriazol-5-yl, 9H-purin-8-yl, furo[3,2-b]pyridin-2-yl, furo[3,2-c]pyridin-2-yl, furo[2,3-c]pyridin-2-yl, 1,3-oxazolo[5,4-b]pyridine-5-yl, thieno[3,2-c]pyridin-2-yl, thieno[2,3-d]pyrimidin-6-yl, 1H-pyrrolo[2,3-b]pyridin-5-yl, 1H-pyrrolo[2,3-c]pyridin-4-yl, pyrrolo[1,2-a]pyrimidin-7-yl, pyrrolo[1,2-a]pyrazin-7-yl, pyrrolo[1,2-b]pyridazin-2-yl, pyrazolo[1,5-a]pyridin-2-yl, pyrazolo[1,5-a]pyridin-5-yl, pyrazolo[1,5-a]pyrazin-2-yl, pyrazolo[1,5-a]pyrimidin-2-yl, pyrazolo[1,5-a]pyrimidin-5-yl, 1H-pyrazolo[3,4-b]pyrazin-5-yl, 1H-pyrazolo[3,4-b]pyridin-5-yl, 1H-pyrazolo[3,4-b]pyridin-6-yl, 1H-pyrazolo[3,4-c]pyridin-1-yl, 1H-pyrazolo[3,4-c]pyridin-5-yl, 1H-pyrazolo[4,3-b]pyridin-5-yl, 1H-pyrazolo[4,3-b]pyridin-6-yl, 1H-pyrazolo[4,3-d]pyrimidin-5-yl, 2H-pyrazolo[4,3-b]pyridin-5-yl, 2H-pyrazolo[4,3-c]pyridin-5-yl, 5H-pyrrolo[2,3-b]pyrazin-2-yl, imidazo[1,2-a]pyridin-2-yl, imidazo[1,2-a]pyridin-6-yl, imidazo[1,2-a]pyrazin-2-yl, imidazo[1,2-a]pyrazin-6-yl, imidazo[1,2-a]pyrimidin-2-yl, imidazo[1,2-a]pyrimidin-6-yl, imidazo[1,2-b]pyridazin-2-yl, imidazo[1,2-b]pyridazin-6-yl, imidazo[1,2-c]pyrimidin-2-yl, 1H-imidazo[4,5-b]pyridin-5-yl, 3H-imidazo[4,5-b]pyridin-5-yl, imidazo[2,1-b][1,3]thiazol-6-yl, imidazo[2,1-b][1,3,4]thiadiazol-6-yl, [1,3]oxazolo[4,5-b]pyridin-2-yl, [1,2,3]triazolo[1,5-a]pyridin-5-yl, [1,2,3]triazolo[1,5-a]pyridin-6-yl, 1H-[1,2,3]triazolo[4,5-b]pyridin-5-yl, 2H-[1,2,3]triazolo[4,5-b]pyridin-6-yl, 3H-[1,2,3]triazolo[4,5-b]pyridin-5-yl, [1,2,4]triazolo[1,5-a]pyridin-2-yl, [1,2,4]triazolo[1,5-a]pyridin-6-yl, [1,2,4]triazolo[1,5-a]pyridin-7-yl, [1,2,4]triazolo[1,5-a]pyrazin-2-yl, [1,2,4]triazolo[1,5-a]pyrazin-5-yl, [1,2,4]triazolo[1,5-a]pyrazin-6-yl, [1,2,4]triazolo[4,3-a]pyridn-6-yl, [1,2,4]triazolo[4,3-a]pyridn-7-yl, tetrazolo[1,5-a]pyridin-7-yl, tetrazolo[1,5-b]pyridazin-7-yl, quinolin-6-yl, isoquinolin-6-yl, and quinoxalin-2-yl, substituted where allowed by available valences with two $R_{1a}$ substituents.

Another aspect includes a compound of Formula (I), wherein $R_1$ is heteroaryl selected from 1H-pyrazol-3-yl, 1H-pyrazol-4-yl, 1H-imidazol-1-yl, 1,3-thiazol-2-yl, 1,3-oxazol-2-yl, 1,3-oxazol-5-yl, 1H-1,2,3-triazol-1-yl, 2H-1,2,3-triazol-2-yl, 1H-1,2,4-triazol-1-yl, pyridin-4-yl, pyridin-2(1H)-on-4-yl, pyrimidin-4(3H)-on-6-yl, pyridazin-3-yl, 1H-indazol-5-yl, 2H-indazol-4-yl, 2H-indazol-5-yl, 1,3-benzoxazol-6-yl, pyrrolo[1,2-a]pyrazin-7-yl, imidazo[1,2-a]pyridin-6-yl, imidazo[1,2-a]pyrazin-6-yl, imidazo[1,2-a]pyrimidin-6-yl, imidazo[1,2-b]pyridazin-6-yl, [1,2,4]triazolo[1,5-a]pyridin-6-yl, and [1,2,4]triazolo[1,5-a]pyrazin-2-yl, optionally substituted where allowed by available valences with 1 or 2 $R_{1a}$ substituents.

Another aspect includes a compound of Formula (I), wherein $R_1$ is unsubstituted heteroaryl selected from 1H-pyrazol-3-yl, 1H-pyrazol-4-yl, 1H-imidazol-1-yl, 1,3-thiazol-2-yl, 1,3-oxazol-2-yl, 1,3-oxazol-5-yl, 1H-1,2,3-triazol-1-yl, 2H-1,2,3-triazol-2-yl, 1H-1,2,4-triazol-1-yl, pyridin-4-yl, pyridin-2(1H)-on-4-yl, pyrimidin-4(3H)-on-6-yl, pyridazin-3-yl, 1H-indazol-5-yl, 2H-indazol-4-yl, 2H-indazol-5-yl, 1,3-benzoxazol-6-yl, pyrrolo[1,2-a]pyrazin-7-yl, imidazo[1,2-a]pyridin-6-yl, imidazo[1,2-a]pyrazin-6-yl, imidazo[1,2-a]pyrimidin-6-yl, imidazo[1,2-b]pyridazin-6-yl, [1,2,4]triazolo[1,5-a]pyridin-6-yl, and [1,2,4]triazolo[1,5-a]pyrazin-2-yl.

Another aspect includes a compound of Formula (I), wherein $R_1$ is heteroaryl selected from 1H-pyrazol-3-yl, 1H-pyrazol-4-yl, 1H-imidazol-1-yl, 1,3-thiazol-2-yl, 1,3-oxazol-2-yl, 1,3-oxazol-5-yl, 1H-1,2,3-triazol-1-yl, 2H-1,2,3-triazol-2-yl, 1H-1,2,4-triazol-1-yl, pyridin-4-yl, pyridin-2(1H)-on-4-yl, pyrimidin-4(3H)-on-6-yl, pyridazin-3-yl, 1H-indazol-5-yl, 2H-indazol-4-yl, 2H-indazol-5-yl, 1,3-benzoxazol-6-yl, pyrrolo[1,2-a]pyrazin-7-yl, imidazo[1,2-a]pyridin-6-yl, imidazo[1,2-a]pyrazin-6-yl, imidazo[1,2-a]pyrimidin-6-yl, imidazo[1,2-b]pyridazin-6-yl, [1,2,4]triazolo[1,5-a]pyridin-6-yl, and [1,2,4]triazolo[1,5-a]pyrazin-2-yl, substituted where allowed by available valences with one $R_{1a}$ substituent.

Another aspect includes a compound of Formula (I), wherein $R_1$ is heteroaryl selected from 1H-pyrazol-3-yl, 1H-pyrazol-4-yl, 1H-imidazol-1-yl, 1,3-thiazol-2-yl, 1,3-oxazol-2-yl, 1,3-oxazol-5-yl, 1H-1,2,3-triazol-1-yl, 2H-1,2,3-triazol-2-yl, 1H-1,2,4-triazol-1-yl, pyridin-4-yl, pyridin-2(1H)-on-4-yl, pyrimidin-4(3H)-on-6-yl, pyridazin-3-yl, 1H-indazol-5-yl, 2H-indazol-4-yl, 2H-indazol-5-yl, 1,3-benzoxazol-6-yl, pyrrolo[1,2-a]pyrazin-7-yl, imidazo[1,2-a]pyridin-6-yl, imidazo[1,2-a]pyrazin-6-yl, imidazo[1,2-a]pyrimidin-6-yl, imidazo[1,2-b]pyridazin-6-yl, [1,2,4]triazolo[1,5-a]pyridin-6-yl, and [1,2,4]triazolo[1,5-a]pyrazin-2-yl, substituted where allowed by available valences with two $R_{1a}$ substituents.

Another aspect includes a compound of Formula (I), wherein $R_1$ is heteroaryl-$C_{2-4}$alkenyl,

- wherein heteroaryl is a 3-7 membered monocyclic or 6-10 membered bicyclic ring system having 1, 2, 3, or 4 heteroatom ring members independently selected from N, O, or S; and wherein heteroaryl is optionally substituted where allowed by available valences with 1 or 2 $R_{1a}$ substituents.

Another aspect includes a compound of Formula (I), wherein $R_1$ is heteroaryl-$C_{2-4}$alkenyl,

- wherein heteroaryl is selected from thienyl, 1H-pyrazolyl, 1H-imidazolyl, 1,3-thiazolyl, oxazolyl, 1,2,4-oxadiazolyl, 1,3,4-oxadiazolyl, 1,2,4-thiadiazolyl, 1H-tetrazolyl, 2H-tetrazolyl, pyridinyl, pyridinyl, pyrazinyl, pyrimidinyl, 1,2,4-triazinyl, 1,3,5-triazinyl, 1H-indolyl, 1H-indazolyl, 2H-indazolyl, indolizinyl, benzofuranyl, benzothienyl, 1H-benzimidazolyl, 1,3-benzoxazolyl, 1.3-benzothiazolyl, 1,3-benzodioxolyl, 1,2,3-benzotriazolyl, 9H-purinyl, quinolinyl, isoquinolinyl, and quinoxalinyl;
- wherein $C_{2-4}$alkenyl is selected from ethenyl, propenyl, and butenyl; and
- wherein heteroaryl is optionally substituted where allowed by available valences with 1 or 2 $R_{1a}$ substituents.

Another aspect includes a compound of Formula (I), wherein $R_1$ is 2-(1H-pyrazol-4-yl)ethenyl, optionally substituted where allowed by available valences with 1 or 2 $R_{1a}$ substituents.

Another aspect includes a compound of Formula (I), wherein $R_1$ is heteroaryl-amino, wherein heteroaryl is selected from thienyl, 1H-pyrazolyl, 1H-imidazolyl, 1,3-thiazolyl, oxazolyl, 1,2,4-oxadiazolyl, 1,3,4-oxadiazolyl, 1,2,4-thiadiazolyl, 1H-tetrazolyl, 2H-tetrazolyl, pyridinyl, pyrazinyl, pyrimidinyl, pyridazinyl, 1,2,4-triazinyl, 1,3,5-triazinyl, 1H-indolyl, 1H-indazolyl, 2H-indazolyl, indolizinyl, benzofuranyl, benzothienyl, 1H-benzimidazolyl, 1,3-benzoxazolyl, 1,3-benzothiazolyl, 1,3-benzodioxolyl, 1,2,3-benzotriazolyl, 9H-purinyl, quinolinyl, isoquinolinyl, and quinoxalinyl; and wherein heteroaryl is optionally substituted where allowed by available valences with 1 or 2 $R_{1a}$ substituents.

Another aspect includes a compound of Formula (I), wherein $R_1$ is (pyridin-3-yl)amino, (pyrazin-2-yl)amino, and (pyrimidin-5-yl)amino, optionally substituted where allowed by available valences with 1 or 2 $R_{1a}$ substituents.

Another aspect includes a compound of Formula (I), wherein $R_1$ is heteroaryl-$C_{1-4}$alkyl-amino, wherein heteroaryl is selected from thienyl, 1H-pyrazolyl, 1H-imidazolyl, 1,3-thiazolyl, oxazolyl, 1,2,4-oxadiazolyl, 1,3,4-oxadiazolyl, 1,2,4-thiadiazolyl, 1H-tetrazolyl, 2H-tetrazolyl, pyridinyl, pyrazinyl, pyrimidinyl, pyridazinyl, 1,2,4-triazinyl, 1,3,5-triazinyl, 1H-indolyl, 1H-indazolyl, 2H-indazolyl, indolizinyl, benzofuranyl, benzothienyl, 1H-benzimidazolyl, 1,3-benzoxazolyl, 1,3-benzothiazolyl, 1,3-benzodioxolyl, 1,2,3-benzotriazolyl, 9H-purinyl, quinolinyl, isoquinolinyl, and quinoxalinyl;

- wherein $C_{1-4}$alkyl is selected from methyl, ethyl, propyl, and butyl; and
- wherein heteroaryl is optionally substituted where allowed by available valences with 1 or 2 $R_{1a}$ substituents.

Another aspect includes a compound of Formula (I), wherein $R_1$ is (1H-pyrazol-4-yl)methylamino, (pyridin-3-yl)methylamino, (pyridin-4-yl)methylamino, (quinolin-3-yl)methylamino, and (quinolin-8-yl)methylamino, optionally substituted where allowed by available valences with 1 or 2 $R_{1a}$ substituents.

One aspect includes a compound of Formula (I), wherein $R_{1a}$ is independently selected from halogen, hydroxyl, cyano, $C_{1-4}$alkyl, deutero-$C_{1-4}$alkyl, halo-$C_{1-4}$alkyl, amino, $C_{1-4}$alkyl-amino, $(C_{1-4}alkyl)_2$-amino, $C_{1-4}$alkoxy, deutero-$C_{1-4}$alkoxy, and halo-$C_{1-4}$alkoxy.

Another aspect includes a compound of Formula (I), wherein $R_{1a}$ is independently selected from halogen, cyano, $C_{1-4}$alkyl, deutero-$C_{1-4}$alkyl, halo-$C_{1-4}$alkyl, $C_{1-4}$alkoxy, and deutero-$C_{1-4}$alkoxy.

Another aspect includes a compound of Formula (I), wherein $R_{1a}$ is $C_{1-4}$alkyl selected from methyl, ethyl, propyl, isopropyl, butyl, and tert-butyl.

Another aspect includes a compound of Formula (I), wherein $R_{1a}$ is selected from methyl and ethyl.

Another aspect includes a compound of Formula (I), wherein $R_{1a}$ is methyl.

Another aspect includes a compound of Formula (I), wherein $R_{1a}$ is ethyl.

Another aspect includes a compound of Formula (I), wherein $R_{1a}$ is halogen selected from bromo, chloro, fluoro, and iodo.

Another aspect includes a compound of Formula (I), wherein $R_{1a}$ is fluoro.

Another aspect includes a compound of Formula (I), wherein $R_{1a}$ is cyano.

Another aspect includes a compound of Formula (I), wherein $R_{1a}$ is deutero-C-alkyl wherein $C_{1-4}$alkyl is selected from methyl, ethyl, propyl, isopropyl, butyl, and tert-butyl, partially or completely substituted with one or more deuterium atoms where allowed by available valences.

Another aspect includes a compound of Formula (I), wherein $R_{1a}$ is $(^2H_3)$methyl.

Another aspect includes a compound of Formula (I), wherein $R_{1a}$ is halo-$C_{1-4}$alkyl wherein $C_{1-4}$alkyl is selected from methyl, ethyl, propyl, isopropyl, butyl, and tert-butyl, partially or completely substituted with one or more halogen atoms where allowed by available valences.

Another aspect includes a compound of Formula (I), wherein $R_{1a}$ is trifluromethyl.

Another aspect includes a compound of Formula (I), wherein $R_{1a}$ is $C_{1-4}$alkoxy selected from methoxy, ethoxy, propoxy, isopropoxy, butoxy and tert-butoxy.

Another aspect includes a compound of Formula (I), wherein $R_{1a}$ is methoxy.

Another aspect includes a compound of Formula (I), wherein $R_{1a}$ is deutero-$C_{1-4}$alkoxy wherein $C_{1-4}$alkoxy is selected from methoxy, ethoxy, propoxy, isopropoxy, butoxy and tert-butoxy partially or completely substituted with one or more deuterium atoms where allowed by available valences.

Another aspect includes a compound of Formula (I), wherein $R_{1a}$ is ($^2H_3$)methoxy.

Another aspect of the present description includes a compound of Formula (II):

(II)

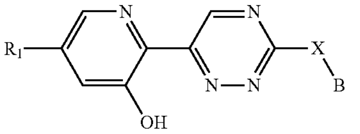

or a form thereof, wherein:

X is O, $NR_x$, or a bond;

$R_x$ is selected from hydrogen and $C_{1-4}$alkyl;

B is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, each optionally substituted where allowed by available valences with 1, 2, 3, 4, or 5 substituents $R_b$;

$R_b$ is independently selected from halogen, $C_{1-4}$alkyl, amino, $C_{1-4}$alkyl-amino, $(C_{1-4}alkyl)_2$-amino, and $C_{1-4}$cycloalkyl;

$R_1$ is selected from heteroaryl, heterocyclyl, phenyl, heteroaryl-$C_{1-4}$alkyl, heteroaryl-$C_{2-4}$alkenyl, heteroaryl-amino, heteroaryl-$C_{1-4}$alkyl-amino, wherein heteroaryl is a 3-7 membered monocyclic or 6-10 membered bicyclic ring system having 1, 2, 3, or 4 heteroatom ring members independently selected from N, O, or S, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, and wherein each instance of phenyl, heteroaryl or heterocyclyl is optionally substituted where allowed by available valences with 1 or 2 $R_{1a}$ substituents; and $R_{1a}$ is independently selected from halogen, hydroxyl, cyano, $C_{1-4}$alkyl, deutero-$C_{1-4}$alkyl, halo-$C_{1-4}$alkyl, amino, $C_{1-4}$ alkyl-amino, $(C_{1-4}alkyl)_2$-amino, $C_{1-4}$alkoxy, deutero-$C_{1-4}$alkoxy, and halo-$C_{1-4}$alkoxy.

One aspect includes a compound of Formula (II), wherein X is selected from O, $NR_x$, and a bond.

Another aspect includes a compound of Formula (II) wherein X is O.

Another aspect includes a compound of Formula (II) wherein X is $NR_x$.

Another aspect includes a compound of Formula (II) wherein X is a bond.

One aspect includes a compound of Formula (II), wherein $R_x$ is selected from hydrogen and $C_{1-4}$alkyl.

Another aspect includes a compound of Formula (II), wherein $R_x$ hydrogen.

Another aspect includes a compound of Formula (II), wherein $R_x$ is $C_{1-4}$alkyl selected from methyl, ethyl, propyl, isopropyl, butyl, and tert-butyl.

Another aspect includes a compound of Formula (II), wherein $R_x$ is methyl.

One aspect includes a compound of Formula (II), wherein B is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, optionally substituted where allowed by available valences with 1, 2, 3, 4, or 5 $R_b$ substituents.

Another aspect includes a compound of Formula (II), wherein B is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, substituted where allowed by available valences with one $R_b$ substituent.

Another aspect includes a compound of Formula (II), wherein B is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, substituted where allowed by available valences with four $R_b$ substituents.

Another aspect includes a compound of Formula (II), wherein B is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, substituted where allowed by available valences with five $R_b$ substituents.

Another aspect includes a compound of Formula (II), wherein B is heterocyclyl selected from azetidinyl, tetrahydrofuranyl, pyrrolidinyl, piperidinyl, piperidin-1-olate-yl, piperazinyl, 1,4-diazepanyl, 1,2-dihydropyridinyl, 1,2,5,6-tetrahydropyridinyl, 1,2,3,6-tetrahydropyridinyl, hexahydrocyclopentapyrrol-(1H)-yl, hexahydropyrrolo[3,2-b]pyrrol-(2H)-yl, hexahydropyrrolo[3,4-b]pyrrol-(2H)-yl, octahydro-2H-pyrrolo[3,4-c]pyridinyl, octahydro-5H-pyrrolo[3,2-c]pyridinyl, octahydro-6H-pyrrolo[3,4-b]pyridinyl, hexahydropyrrolo[1,2-a]pyrazin-(2H)-one, hexahydropyrrolo[1,2-a]pyrazin-(1H)-yl, hexahydro-1H-cyclobuta[1.2-c:1,4-c']dipyrrol-(3H)-yl, octahydropyrrolo[1,2-a]pyrazin-(1H)-yl, octahydro-2H-pyrido[1,2-a]pyrazinyl, hexahydropyrrolo[3,4-b][1,4]oxazin-(2H)-yl, 5-azaspiro[2.4]heptanyl, 1-azaspiro[3.3]heptanyl, 4-azaspiro[2.5]octanyl, 2-oxa-6-azaspiro[3.4]octanyl, 3-azabicyclo[3.1.0]hexanyl, 8-azabicyclo[3.2.1]octanyl, 8-azabicyclo[3.2.1]oct-2-en-yl, 9-azabicyclo[3.3.1]nonanyl, 2,5-diazabicyclo[2.2.1]heptanyl, 1.4-diazabicyclo[3.1.1]heptanyl, 3,6-diazabicyclo[3.2.0]heptanyl, 2,5-diazabicyclo[2.2.2]octanyl, 1,4-diazabicyclo[3.2.1]octanyl, 3,8-diazabicyclo[3.2.1]octanyl, 1,4-diazabicyclo[3.2.2]nonanyl, 4,7-diazaspiro[2.5]octanyl, 2,6-diazaspiro[3.3]heptanyl, 1,6-diazaspiro[3.4]octanyl, 2,6-diazaspiro[3.4]octanyl, 1.7,-diazaspiro[4.4]nonanyl, 1,7-diazaspiro[3.5]nonanyl, 2,6-diazaspiro[3.5]nonanyl, 2,7-diazaspiro[3.5]nonanyl, 5,8-diazaspiro[3.5]nonanyl, 2-oxa-5,8-diazaspiro[3.5]nonanyl, 2,7-diazaspiro[4.4]

nonanyl, 2,7-diazaspiro[4.5]decanyl, 2,8-diazaspiro[4.5]decanyl, 6,9-diazaspiro[4.5]decyl, 6-oxa-2,9-diazaspiro[4.5]decanyl, 2,9-diazaspiro[5.5]undecanyl, 4-azadispiro[2.1.2$^5$.3$^3$]decanyl, and 7-azadispiro[5.1.5$^8$.3$^6$]hexadecanyl, optionally substituted where allowed by available valences with 1, 2, 3, 4, or 5 $R_b$ substituents.

Another aspect includes a compound of Formula (II), wherein B is unsubstituted heterocyclyl selected from azetidinyl, tetrahydrofuranyl, pyrrolidinyl, piperidinyl, piperidin-1-olate-yl, piperazinyl, 1,4-diazepanyl, 1,2-dihydropyridinyl, 1,2,5,6-tetrahydropyridinyl, 1,2,3,6-tetrahydropyridinyl, hexahydrocyclopentapyrrol-(1H)-yl, hexahydropyrrolo[3,2-b]pyrrol-(2H)-yl, hexahydropyrrolo[3,4-b]pyrrol-(2H)-yl, octahydro-2H-pyrrolo[3,4-c]pyridinyl, octahydro-5H-pyrrolo[3,2-c]pyridinyl, octahydro-6H-pyrrolo[3,4-b]pyridinyl, hexahydropyrrolo[1,2-a]pyrazin-(2H)-one, hexahydropyrrolo[1,2-a]pyrazin-(1H)-yl, hexahydro-1H-cyclobuta[1.2-c:1,4-c']dipyrrol-(3H)-yl, octahydropyrrolo[1,2-a]pyrazin-(1H)-yl, octahydro-2H-pyrido[1,2-a]pyrazinyl, hexahydropyrrolo[3,4-b][1,4]oxazin-(2H)-yl, 5-azaspiro[2.4]heptanyl, 1-azaspiro[3.3]heptanyl, 4-azaspiro[2.5]octanyl, 2-oxa-6-azaspiro[3.4]octanyl, 3-azabicyclo[3.1.0]hexanyl, 8-azabicyclo[3.2.1]octanyl, 8-azabicyclo[3.2.1]oct-2-en-yl, 9-azabicyclo[3.3.1]nonanyl, 2,5-diazabicyclo[2.2.1]heptanyl, 1,4-diazabicyclo[3.1.1]heptanyl, 3,6-diazabicyclo[3.2.0]heptanyl, 2,5-diazabicyclo[2.2.2]octanyl, 1,4-diazabicyclo[3.2.1]octanyl, 3,8-diazabicyclo[3.2.1]octanyl, 1,4-diazabicyclo[3.2.2]nonanyl, 4,7-diazaspiro[2.5]octanyl, 2,6-diazaspiro[3.3]heptanyl, 1,6-diazaspiro[3.4]octanyl, 2,6-diazaspiro[3.4]octanyl, 1,7,-diazaspiro[4.4]nonanyl, 1,7-diazaspiro[3.5]nonanyl, 2,6-diazaspiro[3.5]nonanyl, 2,7-diazaspiro[3.5]nonanyl, 5,8-diazaspiro[3.5]nonanyl, 2-oxa-5,8-diazaspiro[3.5]nonanyl, 2,7-diazaspiro[4.4]nonanyl, 2,7-diazaspiro[4.5]decanyl, 2,8-diazaspiro[4.5]decanyl, 6,9-diazaspiro[4.5]decyl, 6-oxa-2,9-diazaspiro[4.5]decanyl, 2,9-diazaspiro[5.5]undecanyl, 4-azadispiro[2.1.2$^5$.3$^3$]decanyl, and 7-azadispiro[5.1.5$^8$.3$^6$]hexadecanyl.

Another aspect includes a compound of Formula (II), wherein B is heterocyclyl selected from azetidinyl, tetrahydrofuranyl, pyrrolidinyl, piperidinyl, piperidin-1-olate-yl, piperazinyl, 1,4-diazepanyl, 1,2-dihydropyridinyl, 1,2,5,6-tetrahydropyridinyl, 1,2,3,6-tetrahydropyridinyl, hexahydrocyclopentapyrrol-(1H)-yl, hexahydropyrrolo[3,2-b]pyrrol-(2H)-yl, hexahydropyrrolo[3,4-b]pyrrol-(2H)-yl, octahydro-2H-pyrrolo[3,4-c]pyridinyl, octahydro-5H-pyrrolo[3.2-c]pyridinyl, octahydro-6H-pyrrolo[3,4-b]pyridinyl, hexahydropyrrolo[1,2-a]pyrazin-(2H)-one, hexahydropyrrolo[1,2-a]pyrazin-(1H)-yl, hexahydro-1H-cyclobuta[1.2-c:1,4-c']dipyrrol-(3H)-yl, octahydropyrrolo[1,2-a]pyrazin-(1H)-yl, octahydro-2H-pyrido[1,2-a]pyrazinyl, hexahydropyrrolo[3,4-b][1,4]oxazin-(2H)-yl, 5-azaspiro[2.4]heptanyl, 1-azaspiro[3.3]heptanyl, 4-azaspiro[2.5]octanyl, 2-oxa-6-azaspiro[3.4]octanyl, 3-azabicyclo[3.1.0]hexanyl, 8-azabicyclo[3.2.1]octanyl, 8-azabicyclo[3.2.1]oct-2-en-yl, 9-azabicyclo[3.3.1]nonanyl, 2,5-diazabicyclo[2.2.1]heptanyl, 1,4-diazabicyclo[3.1.1]heptanyl, 3,6-diazabicyclo[3.2.0]heptanyl, 2,5-diazabicyclo[2.2.2]octanyl, 1,4-diazabicyclo[3.2.1]octanyl, 3,8-diazabicyclo[3.2.1]octanyl, 1,4-diazabicyclo[3.2.2]nonanyl, 4,7-diazaspiro[2.5]octanyl, 2,6-diazaspiro[3.3]heptanyl, 1,6-diazaspiro[3.4]octanyl, 2,6-diazaspiro[3.4]octanyl, 1.7,-diazaspiro[4.4]nonanyl, 1,7-diazaspiro[3.5]nonanyl, 2,6-diazaspiro[3.5]nonanyl, 2,7-diazaspiro[3.5]nonanyl, 5,8-diazaspiro[3.5]nonanyl, 2-oxa-5,8-diazaspiro[3.5]nonanyl, 2,7-diazaspiro[4.4]nonanyl, 2,7-diazaspiro[4.5]decanyl, 2,8-diazaspiro[4.5]decanyl, 6,9-diazaspiro[4.5]decyl, 6-oxa-2,9-diazaspiro[4.5]decanyl, 2,9-diazaspiro[5.5]undecanyl, 4-azadispiro[2.1.2$^5$.3$^3$]decanyl, and 7-azadispiro[5.1.5$^8$.3$^6$]hexadecanyl, substituted where allowed by available valences with one $R_b$ substituent.

Another aspect includes a compound of Formula (II), wherein B is heterocyclyl selected from azetidinyl, tetrahydrofuranyl, pyrrolidinyl, piperidinyl, piperidin-1-olate-yl, piperazinyl, 1,4-diazepanyl, 1,2-dihydropyridinyl, 1,2,5,6-tetrahydropyridinyl, 1,2,3,6-tetrahydropyridinyl, hexahydrocyclopentapyrrol-(1H)-yl, hexahydropyrrolo[3,2-b]pyrrol-(2H)-yl, hexahydropyrrolo[3,4-b]pyrrol-(2H)-yl, octahydro-2H-pyrrolo[3,4-c]pyridinyl, octahydro-5H-pyrrolo[3,2-c]pyridinyl, octahydro-6H-pyrrolo[3,4-b]pyridinyl, hexahydropyrrolo[1,2-a]pyrazin-(2H)-one, hexahydropyrrolo[1,2-a]pyrazin-(1H)-yl, hexahydro-1H-cyclobuta[1.2-c:1,4-c']dipyrrol-(3H)-yl, octahydropyrrolo[1,2-a]pyrazin-(1H)-yl, octahydro-2H-pyrido[1,2-a]pyrazinyl, hexahydropyrrolo[3,4-b][1,4]oxazin-(2H)-yl, 5-azaspiro[2.4]heptanyl, 1-azaspiro[3.3]heptanyl, 4-azaspiro[2.5]octanyl, 2-oxa-6-azaspiro[3.4]octanyl, 3-azabicyclo[3.1.0]hexanyl, 8-azabicyclo[3.2.1]octanyl, 8-azabicyclo[3.2.1]oct-2-en-yl, 9-azabicyclo[3.3.1]nonanyl, 2,5-diazabicyclo[2.2.1]heptanyl, 1.4-diazabicyclo[3.1.1]heptanyl, 3,6-diazabicyclo[3.2.0]heptanyl, 2,5-diazabicyclo[2.2.2]octanyl, 1,4-diazabicyclo[3.2.1]octanyl, 3,8-diazabicyclo[3.2.1]octanyl, 1,4-diazabicyclo[3.2.2]nonanyl, 4,7-diazaspiro[2.5]octanyl, 2,6-diazaspiro[3.3]heptanyl, 1,6-diazaspiro[3.4]octanyl, 2,6-diazaspiro[3.4]octanyl, 1.7,-diazaspiro[4.4]nonanyl, 1,7-diazaspiro[3.5]nonanyl, 2,6-diazaspiro[3.5]nonanyl, 2,7-diazaspiro[3.5]nonanyl, 5,8-diazaspiro[3.5]nonanyl, 2-oxa-5,8-diazaspiro[3.5]nonanyl, 2,7-diazaspiro[4.4]nonanyl, 2,7-diazaspiro[4.5]decanyl, 2,8-diazaspiro[4.5]decanyl, 6,9-diazaspiro[4.5]decyl, 6-oxa-2,9-diazaspiro[4.5]decanyl, 2,9-diazaspiro[5.5]undecanyl, 4-azadispiro[2.1.2$^5$.3$^3$]decanyl, and 7-azadispiro[5.1.5$^8$.3$^6$]hexadecanyl, substituted where allowed by available valences with two $R_b$ substituents.

Another aspect includes a compound of Formula (II), wherein B is heterocyclyl selected from azetidinyl, tetrahydrofuranyl, pyrrolidinyl, piperidinyl, piperidin-1-olate-yl, piperazinyl, 1,4-diazepanyl, 1,2-dihydropyridinyl, 1,2,5,6-tetrahydropyridinyl, 1,2,3,6-tetrahydropyridinyl, hexahydrocyclopentapyrrol-(1H)-yl, hexahydropyrrolo[3,2-b]pyrrol-(2H)-yl, hexahydropyrrolo[3,4-b]pyrrol-(2H)-yl, octahydro-2H-pyrrolo[3,4-c]pyridinyl, octahydro-5H-pyrrolo[3,2-c]pyridinyl, octahydro-6H-pyrrolo[3,4-b]pyridinyl, hexahydropyrrolo[1,2-a]pyrazin-(2H)-one, hexahydropyrrolo[1,2-a]pyrazin-(1H)-yl, hexahydro-1H-cyclobuta[1.2-c:1,4-c']dipyrrol-(3H)-yl, octahydropyrrolo[1,2-a]pyrazin-(1H)-yl, octahydro-2H-pyrido[1,2-a]pyrazinyl, hexahydropyrrolo[3,4-b][1,4]oxazin-(2H)-yl, 5-azaspiro[2.4]heptanyl, 1-azaspiro[3.3]heptanyl, 4-azaspiro[2.5]octanyl, 2-oxa-6-azaspiro[3.4]octanyl, 3-azabicyclo[3.1.0]hexanyl, 8-azabicyclo[3.2.1]octanyl, 8-azabicyclo[3.2.1]oct-2-en-yl, 9-azabicyclo[3.3.1]nonanyl, 2,5-diazabicyclo[2.2.1]heptanyl, 1,4-diazabicyclo[3.1.1]heptanyl, 3,6-diazabicyclo[3.2.0]heptanyl, 2,5-diazabicyclo[2.2.2]octanyl, 1,4-diazabicyclo[3.2.1]octanyl, 3,8-diazabicyclo[3.2.1]octanyl, 1,4-diazabicyclo[3.2.2]nonanyl, 4,7-diazaspiro[2.5]octanyl, 2,6-diazaspiro[3.3]heptanyl, 1,6-diazaspiro[3.4]octanyl, 2,6-diazaspiro[3.4]octanyl, 1,7,-diazaspiro[4.4]nonanyl, 1,7-diazaspiro[3.5]nonanyl, 2,6-diazaspiro[3.5]nonanyl, 2,7-diazaspiro[3.5]nonanyl, 5,8-diazaspiro[3.5]nonanyl, 2-oxa-5,8-diazaspiro[3.5]nonanyl, 2,7-diazaspiro[4.4]nonanyl, 2,7-diazaspiro[4.5]decanyl, 2,8-diazaspiro[4.5]decanyl, 6,9-diazaspiro[4.5]decyl, 6-oxa-2,9-diazaspiro[4.5]decanyl, 2,9-diazaspiro[5.5]undecanyl, 4-azadispiro $[2.1.2^5.3^3]$decanyl, and 7-azadispiro$[5.1.5^8.3^6]$hexadecanyl, substituted where allowed by available valences with three $R_b$ substituents.

Another aspect includes a compound of Formula (II), wherein B is heterocyclyl selected from azetidinyl, tetrahydrofuranyl, pyrrolidinyl, piperidinyl, piperidin-1-olate-yl, piperazinyl, 1,4-diazepanyl, 1,2-dihydropyridinyl, 1,2,5,6-tetrahydropyridinyl, 1,2,3,6-tetrahydropyridinyl, hexahydrocyclopentapyrrol-(1H)-yl, hexahydropyrrolo[3,2-b]pyrrol-(2H)-yl, hexahydropyrrolo[3,4-b]pyrrol-(2H)-yl, octahydro-2H-pyrrolo[3,4-c]pyridinyl, octahydro-5H-pyrrolo[3,2-c]pyridinyl, octahydro-6H-pyrrolo[3,4-b]pyridinyl, hexahydropyrrolo[1,2-a]pyrazin-(2H)-one, hexahydropyrrolo[1,2-a]pyrazin-(1H)-yl, hexahydro-1H-cyclobuta[1.2-c:1,4-c']dipyrrol-(3H)-yl, octahydropyrrolo[1,2-a]pyrazin-(1H)-yl, octahydro-2H-pyrido[1,2-a]pyrazinyl, hexahydropyrrolo[3,4-b][1,4]oxazin-(2H)-yl, 5-azaspiro[2.4]heptanyl, 1-azaspiro[3.3]heptanyl, 4-azaspiro[2.5]octanyl, 2-oxa-6-azaspiro[3.4]octanyl, 3-azabicyclo[3.1.0]hexanyl, 8-azabicyclo[3.2.1]octanyl, 8-azabicyclo[3.2.1]oct-2-en-yl, 9-azabicyclo[3.3.1]nonanyl, 2,5-diazabicyclo[2.2.1]heptanyl, 1,4-diazabicyclo[3.1.1]heptanyl, 3,6-diazabicyclo[3.2.0]heptanyl, 2,5-diazabicyclo[2.2.2]octanyl, 1,4-diazabicyclo[3.2.1]octanyl, 3,8-diazabicyclo[3.2.1]octanyl, 1,4-diazabicyclo[3.2.2]nonanyl, 4,7-diazaspiro[2.5]octanyl, 2,6-diazaspiro[3.3]heptanyl, 1,6-diazaspiro[3.4]octanyl, 2,6-diazaspiro[3.4]octanyl, 1,7,-diazaspiro[4.4]nonanyl, 1,7-diazaspiro[3.5]nonanyl, 2,6-diazaspiro[3.5]nonanyl, 2,7-diazaspiro[3.5]nonanyl, 5,8-diazaspiro[3.5]nonanyl, 2-oxa-5,8-diazaspiro[3.5]nonanyl, 2,7-diazaspiro[4.4]nonanyl, 2,7-diazaspiro[4.5]decanyl, 2,8-diazaspiro[4.5]decanyl, 6,9-diazaspiro[4.5]decyl, 6-oxa-2,9-diazaspiro[4.5]decanyl, 2,9-diazaspiro[5.5]undecanyl, 4-azadispiro$[2.1.2^5.3^3]$decanyl, and 7-azadispiro$[5.1.5^8.3^6]$hexadecanyl, substituted where allowed by available valences with four $R_b$ substituents.

Another aspect includes a compound of Formula (II), wherein B is heterocyclyl selected from azetidinyl, tetrahydrofuranyl, pyrrolidinyl, piperidinyl, piperidin-1-olate-yl, piperazinyl, 1,4-diazepanyl, 1,2-dihydropyridinyl, 1,2,5,6-tetrahydropyridinyl, 1,2,3,6-tetrahydropyridinyl, hexahydrocyclopentapyrrol-(1H)-yl, hexahydropyrrolo[3,2-b]pyrrol-(2H)-yl, hexahydropyrrolo[3,4-b]pyrrol-(2H)-yl, octahydro-2H-pyrrolo[3,4-c]pyridinyl, octahydro-5H-pyrrolo[3,2-c]pyridinyl, octahydro-6H-pyrrolo[3,4-b]pyridinyl, hexahydropyrrolo[1,2-a]pyrazin-(2H)-one, hexahydropyrrolo[1,2-a]pyrazin-(1H)-yl, hexahydro-1H-cyclobuta[1.2-c:1,4-c']dipyrrol-(3H)-yl, octahydropyrrolo[1,2-a]pyrazin-(1H)-yl, octahydro-2H-pyrido[1,2-a]pyrazinyl, hexahydropyrrolo[3,4-b][1,4]oxazin-(2H)-yl, 5-azaspiro[2.4]heptanyl, 1-azaspiro[3.3]heptanyl, 4-azaspiro[2.5]octanyl, 2-oxa-6-azaspiro[3.4]octanyl, 3-azabicyclo[3.1.0]hexanyl, 8-azabicyclo[3.2.1]octanyl, 8-azabicyclo[3.2.1]oct-2-en-yl, 9-azabicyclo[3.3.1]nonanyl, 2,5-diazabicyclo[2.2.1]heptanyl, 1,4-diazabicyclo[3.1.1]heptanyl, 3,6-diazabicyclo[3.2.0]heptanyl, 2,5-diazabicyclo[2.2.2]octanyl, 1,4-diazabicyclo[3.2.1]octanyl, 3.8-diazabicyclo[3.2.1]octanyl, 1,4-diazabicyclo[3.2.2]nonanyl, 4,7-diazaspiro[2.5]octanyl, 2,6-diazaspiro[3.3]heptanyl, 1,6-diazaspiro[3.4]octanyl, 2,6-diazaspiro[3.4]octanyl, 1,7,-diazaspiro[4.4]nonanyl, 1,7-diazaspiro[3.5]nonanyl, 2,6-diazaspiro[3.5]nonanyl, 2,7-diazaspiro[3.5]nonanyl, 5,8-diazaspiro[3.5]nonanyl, 2-oxa-5,8-diazaspiro[3.5]nonanyl, 2.7-diazaspiro[4.4]nonanyl, 2,7-diazaspiro[4.5]decanyl, 2,8-diazaspiro[4.5]decanyl, 6,9-diazaspiro[4.5]decyl, 6-oxa-2,9-diazaspiro[4.5]decanyl, 2,9-diazaspiro[5.5]undecanyl, 4-azadispiro$[2.1.2^5.3^3]$decanyl, and 7-azadispiro$[5.1.5^8.3^6]$hexadecanyl, substituted where allowed by available valences with five $R_b$ substituents.

Another aspect includes a compound of Formula (II), wherein B is unsubstituted heterocyclyl selected from pyrrolidinyl, piperidinyl, and piperazinyl.

Another aspect includes a compound of Formula (II), wherein B is heterocyclyl selected from pyrrolidinyl, piperidinyl, and piperazinyl, substituted where allowed by available valences with one $R_b$ substituent.

Another aspect includes a compound of Formula (II), wherein B is heterocyclyl selected from pyrrolidinyl, piperidinyl, and piperazinyl, substituted where allowed by available valences with two $R_b$ substituents.

Another aspect includes a compound of Formula (II), wherein B is heterocyclyl selected from pyrrolidinyl, piperidinyl, and piperazinyl, substituted where allowed by available valences with three $R_b$ substituents.

Another aspect includes a compound of Formula (II), wherein B is heterocyclyl selected from pyrrolidinyl, piperidinyl, and piperazinyl, substituted where allowed by available valences with four $R_b$ substituents.

Another aspect includes a compound of Formula (II), wherein B is heterocyclyl selected from pyrrolidinyl, piperidinyl, and piperazinyl, substituted where allowed by available valences with five $R_b$ substituents.

Another aspect includes a compound of Formula (II), wherein B is pyrrolidinyl, substituted where allowed by available valences with one $R_b$ substituent.

Another aspect includes a compound of Formula (II), wherein B is piperidinyl, substituted where allowed by available valences with 4 or 5 $R_b$ substituents.

Another aspect includes a compound of Formula (II), wherein B is piperidinyl, substituted where allowed by available valences with four $R_b$ substituents.

Another aspect includes a compound of Formula (II), wherein B is piperidinyl, substituted where allowed by available valences with five $R_b$ substituents.

Another aspect includes a compound of Formula (II), wherein B is heterocyclyl selected from piperazinyl, substituted where allowed by available valences with one $R_b$ substituent.

Another aspect includes a compound of Formula (II), wherein B is heterocyclyl selected from azetidin-1-yl, tetrahydrofuran-3-yl, pyrrolidin-1-yl, pyrrolidin-3-yl, piperidin-1-yl, piperidin-3-yl, piperidin-4-yl, piperidin-1-olate-4-yl, piperazin-1-yl, 1,4-diazepan-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,2,5,6-tetrahydropyridin-5-yl, 1,2,3,6-tetrahydropyridin-4-yl, hexahydrocyclopentapyrrol-2(1H)-yl, hexahydropyrrolo[3,2-b]pyrrol-1(2H)-yl, hexahydropyrrolo[3,4-b]pyrrol-1(2H)-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, octahydro-5H-pyrrolo[3,2-c]pyridin-5-yl, octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, hexahydro-1H-cyclobuta[1.2-c:1,4-c']dipyrrol-2(3H)-yl, octahydropyrrolo[1,2-a]pyrazin-2(1H)-yl, octahydro-2H-pyrido[1,2-a]pyrazin-2-yl, hexahydropyrrolo[3,4-b][1,4]oxazin-6(2H)-yl, 5-azaspiro[2.4]heptan-5-yl, 1-azaspiro[3.3]heptan-2-yl, 4-azaspiro[2.5]octan-7-yl, 2-oxa-6-azaspiro[3.4]octan-6-yl, 3-azabicyclo[3.1.0]hexan-3-yl, 8-azabicyclo[3.2.1]octan-3-yl, 8-azabicyclo[3.2.1]oct-2-en-3-yl, 9-azabicyclo[3.3.1]nonan-3-yl, 2,5-diazabicyclo[2.2.1]heptan-2-yl, 1,4-diazabicyclo[3.1.1]heptan-4-yl, 3,6-diazabicyclo[3.2.0]heptan-3- yl, 3,6-diazabicyclo[3.2.0]heptan-6-yl, 2,5-diazabicyclo[2.2.2]octan-2-yl, 1,4-diazabicyclo[3.2.1]octan-4-yl, 3,8-diazabicyclo[3.2.1]octan-3-yl, 1,4-diazabicyclo[3.2.2]nonan-4-yl, 4,7-diazaspiro[2.5]octan-4-yl, 4,7-diazaspiro[2.5]octan-7-yl, 2,6-diazaspiro[3.3]heptan-2-yl, 1,6-diazaspiro[3.4]octan-6-yl, 2,6-diazaspiro[3.4]octan-2-yl, 2,6-diazaspiro[3.4]octan-6-yl, 1,7,-diazaspiro[4.4]nonan-1-yl, 1,7,-diazaspiro[4.4]nonan-7-yl, 1,7-diazaspiro[3.5]nonan-7-yl, 2,6-diazaspiro[3.5]nonan-2-yl, 2,6-diazaspiro[3.5]nonan-6-yl, 1,7-diazaspiro[3.5]nonan-7-yl, 2,7-diazaspiro[3.5]nonan-2-yl, 2,7-diazaspiro[3.5]nonan-7-yl, 5,8-diazaspiro[3.5]nonan-8-yl, 2-oxa-5,8-diazaspiro[3.5]nonan-8-yl, 2,7-diazaspiro[4.4]nonan-2-yl, 2,7-diazaspiro[4.5]decan-2-yl, 2,7-diazaspiro[4.5]decan-7-yl, 2,8-diazaspiro[4.5]decan-8-yl, 6,9-diazaspiro[4.5]dec-9-yl, 6-oxa-2,9-diazaspiro[4.5]decan-2-yl, 2,9-diazaspiro[5.5]undecan-9-yl, 4-azadispiro[2.1.2$^5$.3$^1$]decan-9-yl, and 7-azadispiro[5.1.5$^8$.3$^6$]hexadecan-15-yl, optionally substituted where allowed by available valences with 1, 2, 3, 4, or 5 $R_b$ substituents.

Another aspect includes a compound of Formula (II), wherein B is unsubstituted heterocyclyl selected from azetidin-1-yl, tetrahydrofuran-3-yl, pyrrolidin-1-yl, pyrrolidin-3-yl, piperidin-1-yl, piperidin-3-yl, piperidin-4-yl, piperidin-1-olate-4-yl, piperazin-1-yl, 1,4-diazepan-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,2,5,6-tetrahydropyridin-5-yl, 1,2,3,6-tetrahydropyridin-4-yl, hexahydrocyclopentapyrrol-2(1H)-yl, hexahydropyrrolo[3,2-b]pyrrol-1(2H)-yl, hexahydropyrrolo[3,4-b]pyrrol-1(2H)-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, octahydro-5H-pyrrolo[3,2-c]pyridin-5-yl, octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, hexahydro-1H-cyclobuta[1.2-c:1,4-c']dipyrrol-2(3H)-yl, octahydropyrrolo[1,2-a]pyrazin-2(1H)-yl, octahydro-2H-pyrido[1,2-a]pyrazin-2-yl, hexahydropyrrolo[3,4-b][1,4]oxazin-6(2H)-yl, 5-azaspiro[2.4]heptan-5-yl, 1-azaspiro[3.3]heptan-2-yl, 4-azaspiro[2.5]octan-7-yl, 2-oxa-6-azaspiro[3.4]octan-6-yl, 3-azabicyclo[3.1.0]hexan-3-yl, 8-azabicyclo[3.2.1]octan-3-yl, 8-azabicyclo[3.2.1]oct-2-en-3-yl, 9-azabicyclo[3.3.1]nonan-3-yl, 2,5-diazabicyclo[2.2.1]heptan-2-yl, 1,4-diazabicyclo[3.1.1]heptan-4-yl, 3,6-diazabicyclo[3.2.0]heptan-3-yl, 3,6-diazabicyclo[3.2.0]heptan-6-yl, 2,5-diazabicyclo[2.2.2]octan-2-yl, 1,4-diazabicyclo[3.2.1]octan-4-yl, 3,8-diazabicyclo[3.2.1]octan-3-yl, 1,4-diazabicyclo[3.2.2]nonan-4-yl, 4,7-diazaspiro[2.5]octan-4-yl, 4,7-diazaspiro[2.5]octan-7-yl, 2,6-diazaspiro[3.3]heptan-2-yl, 1,6-diazaspiro[3.4]octan-6-yl, 2,6-diazaspiro[3.4]octan-2-yl, 2,6-diazaspiro[3.4]octan-6-yl, 1,7,-diazaspiro[4.4]nonan-1-yl, 1,7,-diazaspiro[4.4]nonan-7-yl, 1,7-diazaspiro[3.5]nonan-7-yl, 2,6-diazaspiro[3.5]nonan-2-yl, 2.6-diazaspiro[3.5]nonan-6-yl, 1,7-diazaspiro[3.5]nonan-7-yl, 2,7-diazaspiro[3.5]nonan-2-yl, 2,7-diazaspiro[3.5]nonan-7-yl, 5,8-diazaspiro[3.5]nonan-8-yl, 2-oxa-5,8-diazaspiro[3.5]nonan-8-yl, 2,7-diazaspiro[4.4]nonan-2-yl, 2,7-diazaspiro[4.5]decan-2-yl, 2,7-diazaspiro[4.5]decan-7-yl, 2,8-diazaspiro[4.5]decan-8-yl, 6,9-diazaspiro[4.5]dec-9-yl, 6-oxa-2,9-diazaspiro[4.5]decan-2-yl, 2,9-diazaspiro[5.5]undecan-9-yl, 4-azadispiro[2.1.2$^5$.3$^3$]decan-9-yl, and 7-azadispiro[5.1.5$^8$.3$^6$]hexadecan-15-yl.

Another aspect includes a compound of Formula (II), wherein B is heterocyclyl selected from azetidin-1-yl, tetrahydrofuran-3-yl, pyrrolidin-1-yl, pyrrolidin-3-yl, piperidin-1-yl, piperidin-3-yl, piperidin-4-yl, piperidin-1-olate-4- yl, piperazin-1-yl, 1,4-diazepan-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,2,5,6-tetrahydropyridin-5-yl, 1,2,3,6-tetrahydropyridin-4-yl, hexahydrocyclopentapyrrol-2(1H)-yl, hexahydropyrrolo[3,2-b]pyrrol-1(2H)-yl, hexahydropyrrolo[3,4-b]pyrrol-1(2H)-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, octahydro-5H-pyrrolo[3,2-c]pyridin-5-yl, octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, hexahydro-1H-cyclobuta[1.2-c:1,4-c']dipyrrol-2(3H)-yl, octahydropyrrolo[1,2-a]pyrazin-2(1H)-yl, octahydro-2H-pyrido[1,2-a]pyrazin-2-yl, hexahydropyrrolo[3,4-b][1,4]oxazin-6(2H)-yl, 5-azaspiro[2.4]heptan-5-yl, 1-azaspiro[3.3]heptan-2-yl, 4-azaspiro[2.5]octan-7-yl, 2-oxa-6-azaspiro[3.4]octan-6-yl, 3-azabicyclo[3.1.0]hexan-3-yl, 8-azabicyclo[3.2.1]octan-3-yl, 8-azabicyclo[3.2.1]oct-2-en-3-yl, 9-azabicyclo[3.3.1]nonan-3-yl, 2,5-diazabicyclo[2.2.1]heptan-2-yl, 1,4-diazabicyclo[3.1.1]heptan-4-yl, 3,6-diazabicyclo[3.2.0]heptan-3-yl, 3,6-diazabicyclo[3.2.0]heptan-6-yl, 2,5-diazabicyclo[2.2.2]octan-2-yl, 1,4-diazabicyclo[3.2.1]octan-4-yl, 3,8-diazabicyclo[3.2.1]octan-3-yl, 1,4-diazabicyclo[3.2.2]nonan-4-yl, 4,7-diazaspiro[2.5]octan-4-yl, 4,7-diazaspiro[2.5]octan-7-yl, 2,6-diazaspiro[3.3]heptan-2-yl, 1,6-diazaspiro[3.4]octan-6-yl, 2,6-diazaspiro[3.4]octan-2-yl, 2,6-diazaspiro[3.4]octan-6-yl, 1,7,-diazaspiro[4.4]nonan-1-yl, 1,7,-diazaspiro[4.4]nonan-7-yl, 1,7-diazaspiro[3.5]nonan-7-yl, 2,6-diazaspiro[3.5]nonan-2-yl, 2,6-diazaspiro[3.5]nonan-6-yl, 1,7-diazaspiro[3.5]nonan-7-yl, 2,7-diazaspiro[3.5]nonan-2-yl, 2,7-diazaspiro[3.5]nonan-7-yl, 5,8-diazaspiro[3.5]nonan-8-yl, 2-oxa-5,8-diazaspiro[3.5]nonan-8-yl, 2,7-diazaspiro[4.4]nonan-2-yl, 2,7-diazaspiro[4.5]decan-2-yl, 2,7-diazaspiro[4.5]decan-7-yl, 2,8-diazaspiro[4.5]decan-8-yl, 6,9-diazaspiro[4.5]dec-9-yl, 6-oxa-2,9-diazaspiro[4.5]decan-2-yl, 2,9-diazaspiro[5.5]undecan-9-yl, 4-azadispiro[2.1.2$^5$.3$^3$]decan-9-yl, and 7-azadispiro[5.1.5$^8$.3$^6$]hexadecan-15-yl, substituted where allowed by available valences with one $R_b$ substituent.

Another aspect includes a compound of Formula (II), wherein B is heterocyclyl selected from azetidin-1-yl, tetrahydrofuran-3-yl, pyrrolidin-1-yl, pyrrolidin-3-yl, piperidin-1-yl, piperidin-3-yl, piperidin-4-yl, piperidin-1-olate-4-yl, piperazin-1-yl, 1,4-diazepan-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,2,5,6-tetrahydropyridin-5-yl, 1,2,3,6-tetrahydropyridin-4-yl, hexahydrocyclopentapyrrol-2(1H)-yl, hexahydropyrrolo[3,2-b]pyrrol-1(2H)-yl, hexahydropyrrolo[3,4-b]pyrrol-1(2H)-v, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, octahydro-5H-pyrrolo[3,2-c]pyridin-5-yl, octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, hexahydro-1H-cyclobuta[1.2-c:1,4-c']dipyrrol-2(3H)-yl, octahydropyrrolo[1,2-a]pyrazin-2(1H)-yl, octahydro-2H-pyrido[1,2-a]pyrazin-2-yl, hexahydropyrrolo[3,4-b][1,4]oxazin-6(2H)-yl, 5-azaspiro[2.4]heptan-5-yl, 1-azaspiro[3.3]heptan-2-yl, 4-azaspiro[2.5]octan-7-yl, 2-oxa-6-azaspiro[3.4]octan-6-yl, 3-azabicyclo[3.1.0]hexan-3-yl, 8-azabicyclo[3.2.1]octan-3-yl, 8-azabicyclo[3.2.1]oct-2-en-3-yl, 9-azabicyclo[3.3.1]nonan-3-yl, 2,5-diazabicyclo[2.2.1]heptan-2-yl, 1,4-diazabicyclo[3.1.1]heptan-4-yl, 3,6-diazabicyclo[3.2.0]heptan-3-yl, 3,6-diazabicyclo[3.2.0]heptan-6-yl, 2,5-diazabicyclo[2.2.2]octan-2-yl, 1,4-diazabicyclo[3.2.1]octan-4-yl, 3,8- diazabicyclo[3.2.1]octan-3-yl, 1,4-diazabicyclo[3.2.2]nonan-4-yl, 4,7-diazaspiro[2.5]octan-4-yl, 4,7-diazaspiro[2.5]octan-7-yl, 2,6-diazaspiro[3.3]heptan-2-yl, 1,6-diazaspiro[3.4]octan-6-yl, 2.6-diazaspiro[3.4]octan-2-yl, 2,6-diazaspiro[3.4]octan-6-yl, 1,7,-diazaspiro[4.4]nonan-1-yl, 1,7,-diazaspiro[4.4]nonan-7-yl, 1,7-diazaspiro[3.5]nonan-7-yl, 2,6-diazaspiro[3.5]nonan-2-yl, 2,6-diazaspiro[3.5]nonan-6-yl, 1,7-diazaspiro[3.5]nonan-7-yl, 2,7-diazaspiro[3.5]nonan-2-yl, 2,7-diazaspiro[3.5]nonan-7-yl, 5,8-diazaspiro[3.5]nonan-8-yl, 2-oxa-5.8-diazaspiro[3.5]nonan-8-yl, 2,7-diazaspiro[4.4]nonan-2-yl, 2,7-diazaspiro[4.5]decan-2-yl, 2,7-diazaspiro[4.5]decan-7-yl, 2,8-diazaspiro[4.5]decan-8-yl, 6,9-diazaspiro[4.5]dec-9-yl, 6-oxa-2,9-diazaspiro[4.5]decan-2-yl, 2,9-diazaspiro[5.5]undecan-9-yl, 4-azadispiro[2.1.$2^5$.$3^3$]decan-9-yl, and 7-azadispiro[5.1.$5^8$.$3^6$]hexadecan-15-yl, substituted where allowed by available valences with two $R_b$ substituents.

Another aspect includes a compound of Formula (II), wherein B is heterocyclyl selected from azetidin-1-yl, tetrahydrofuran-3-yl, pyrrolidin-1-yl, pyrrolidin-3-yl, piperidin-1-yl, piperidin-3-yl, piperidin-4-yl, piperidin-1-olate-4-yl, piperazin-1-yl, 1,4-diazepan-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,2,5,6-tetrahydropyridin-5-yl, 1,2,3,6-tetrahydropyridin-4-yl, hexahydrocyclopentapyrrol-2(1H)-yl, hexahydropyrrolo[3,2-b]pyrrol-1(2H)-yl, hexahydropyrrolo[3,4-b]pyrrol-1(2H)-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, octahydro-5H-pyrrolo[3,2-c]pyridin-5-yl, octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, hexahydro-1H-cyclobuta[1.2-c:1,4-c']dipyrrol-2(3H)-yl, octahydropyrrolo[1,2-a]pyrazin-2(1H)-yl, octahydro-2H-pyrido[1,2-a]pyrazin-2-yl, hexahydropyrrolo[3,4-b][1,4]oxazin-6(2H)-yl, 5-azaspiro[2.4]heptan-5-yl, 1-azaspiro[3.3]heptan-2-yl, 4-azaspiro[2.5]octan-7-yl, 2-oxa-6-azaspiro[3.4]octan-6-yl, 3-azabicyclo[3.1.0]hexan-3-yl, 8-azabicyclo[3.2.1]octan-3-yl, 8-azabicyclo[3.2.1]oct-2-en-3-yl, 9-azabicyclo[3.3.1]nonan-3-yl, 2,5-diazabicyclo[2.2.1]heptan-2-yl, 1,4-diazabicyclo[3.1.1]heptan-4-yl, 3,6-diazabicyclo[3.2.0]heptan-3-yl, 3,6-diazabicyclo[3.2.0]heptan-6-yl, 2,5-diazabicyclo[2.2.2]octan-2-yl, 1,4-diazabicyclo[3.2.1]octan-4-yl, 3,8-diazabicyclo[3.2.1]octan-3-yl, 1,4-diazabicyclo[3.2.2]nonan-4-yl, 4,7-diazaspiro[2.5]octan-4-yl, 4,7-diazaspiro[2.5]octan-7-yl, 2,6-diazaspiro[3.3]heptan-2-yl, 1,6-diazaspiro[3.4]octan-6-yl, 2.6-diazaspiro[3.4]octan-2-yl, 2,6-diazaspiro[3.4]octan-6-yl, 1,7,-diazaspiro[4.4]nonan-1-yl, 1,7,-diazaspiro[4.4]nonan-7-yl, 1,7-diazaspiro[3.5]nonan-7-yl, 2,6-diazaspiro[3.5]nonan-2-yl, 2,6-diazaspiro[3.5]nonan-6-yl, 1,7-diazaspiro[3.5]nonan-7-yl, 2,7-diazaspiro[3.5]nonan-2-yl, 2,7-diazaspiro[3.5]nonan-7-yl, 5,8-diazaspiro[3.5]nonan-8-yl, 2-oxa-5,8-diazaspiro[3.5]nonan-8-yl, 2,7-diazaspiro[4.4]nonan-2-yl, 2,7-diazaspiro[4.5]decan-2-yl, 2,7-diazaspiro[4.5]decan-7-yl, 2,8-diazaspiro[4.5]decan-8-yl, 6,9-diazaspiro[4.5]dec-9-yl, 6-oxa-2,9-diazaspiro[4.5]decan-2-yl, 2,9-diazaspiro[5.5]undecan-9-yl, 4-azadispiro[2.1.$2^5$.$3^3$]decan-9-yl, and 7-azadispiro[5.1.$5^8$.$3^6$]hexadecan-15-yl, substituted where allowed by available valences with three $R_b$ substituents.

Another aspect includes a compound of Formula (II), wherein B is heterocyclyl selected from azetidin-1-yl, tetrahydrofuran-3-yl, pyrrolidin-1-yl, pyrrolidin-3-yl, piperidin-1-yl, piperidin-3-yl, piperidin-4-yl, piperidin-1-olate-4-yl, piperazin-1-yl, 1,4-diazepan-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,2,5,6-tetrahydropyridin-5-yl, 1,2,3,6-tetrahydropyridin-4-yl, hexahydrocyclopentapyrrol-2(1H)-yl, hexahydropyrrolo[3,2-b]pyrrol-1(2H)-yl, hexahydropyrrolo[3,4-b]pyrrol-1(2H)-v, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, octahydro-5H-pyrrolo[3,2-c]pyridin-5-yl, octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, hexahydro-1H-cyclobuta[1.2-c:1,4-c']dipyrrol-2(3H)-yl, octahydropyrrolo[1,2-a]pyrazin-2(1H)-yl, octahydro-2H-pyrido[1,2-a]pyrazin-2-yl, hexahydropyrrolo[3,4-b][1,4]oxazin-6(2H)-yl, 5-azaspiro[2.4]heptan-5-yl, 1-azaspiro[3.3]heptan-2-yl, 4-azaspiro[2.5]octan-7-yl, 2-oxa-6-azaspiro[3.4]octan-6-yl, 3-azabicyclo[3.1.0]hexan-3-yl, 8-azabicyclo[3.2.1]octan-3-yl, 8-azabicyclo[3.2.1]oct-2-en-3-yl, 9-azabicyclo[3.3.1]nonan-3-yl, 2,5-diazabicyclo[2.2.1]heptan-2-yl, 1,4-diazabicyclo[3.1.1]heptan-4-yl, 3,6-diazabicyclo[3.2.0]heptan-3-yl, 3,6-diazabicyclo[3.2.0]heptan-6-yl, 2,5-diazabicyclo[2.2.2]octan-2-yl, 1,4-diazabicyclo[3.2.1]octan-4-yl, 3,8-diazabicyclo[3.2.1]octan-3-yl, 1,4-diazabicyclo[3.2.2]nonan-4-yl, 4,7-diazaspiro[2.5]octan-4-yl, 4,7-diazaspiro[2.5]octan-7-yl, 2,6-diazaspiro[3.3]heptan-2-yl, 1,6-diazaspiro[3.4]octan-6-yl, 2,6-diazaspiro[3.4]octan-2-yl, 2,6-diazaspiro[3.4]octan-6-yl, 1,7,-diazaspiro[4.4]nonan-1-yl, 1,7,-diazaspiro[4.4]nonan-7-yl, 1,7-diazaspiro[3.5]nonan-7-yl, 2,6-diazaspiro[3.5]nonan-2-yl, 2,6-diazaspiro[3.5]nonan-6-yl, 1,7-diazaspiro[3.5]nonan-7-yl, 2,7-diazaspiro[3.5]nonan-2-yl, 2,7-diazaspiro[3.5]nonan-7-yl, 5,8-diazaspiro[3.5]nonan-8-yl, 2-oxa-5,8-diazaspiro[3.5]nonan-8-yl, 2,7-diazaspiro[4.4]nonan-2-yl, 2,7-diazaspiro[4.5]decan-2-yl, 2,7-diazaspiro[4.5]decan-7-yl, 2,8-diazaspiro[4.5]decan-8-yl, 6,9-diazaspiro[4.5]dec-9-yl, 6-oxa-2,9-diazaspiro[4.5]decan-2-yl, 2,9-diazaspiro[5.5]undecan-9-yl, 4-azadispiro[2.1.$2^5$.3]decan-9-yl, and 7-azadispiro[5.1.$5^8$.$3^6$]hexadecan-15-yl, substituted where allowed by available valences with four $R_b$ substituents.

Another aspect includes a compound of Formula (II), wherein B is heterocyclyl selected from azetidin-1-yl, tetrahydrofuran-3-yl, pyrrolidin-1-yl, pyrrolidin-3-yl, piperidin-1-yl, piperidin-3-yl, piperidin-4-yl, piperidin-1-olate-4-yl, piperazin-1-yl, 1,4-diazepan-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,2,5,6-tetrahydropyridin-5-yl, 1,2,3,6-tetrahydropyridin-4-yl, hexahydrocyclopentapyrrol-2(1H)-yl, hexahydropyrrolo[3,2-b]pyrrol-1(2H)-yl, hexahydropyrrolo[3,4-b]pyrrol-1(2H)-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, octahydro-5H-pyrrolo[3,2-c]pyridin-5-yl, octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, hexahydro-1H-cyclobuta[1.2-c:1,4-c']dipyrrol-2(3H)-yl, octahydropyrrolo[1,2-a]pyrazin-2(1H)-yl, octahydro-2H-pyrido[1,2-a]pyrazin-2-yl, hexahydropyrrolo[3,4-b][1,4]oxazin-6(2H)-yl, 5-azaspiro[2.4]heptan-5-yl, 1-azaspiro[3.3]heptan-2-yl, 4-azaspiro[2.5]octan-7-yl, 2-oxa-6-azaspiro[3.4]octan-6-yl, 3-azabicyclo[3.1.0]hexan-3-yl, 8-azabicyclo[3.2.1]octan-3-yl, 8-azabicyclo[3.2.1]oct-2-en-3-yl, 9-azabicyclo[3.3.1]nonan-3-yl, 2,5-diazabicyclo[2.2.1]heptan-2-yl, 1,4-diazabicyclo[3.1.1]heptan-4-yl, 3,6-diazabicyclo[3.2.0]heptan-3-yl, 3,6-diazabicyclo[3.2.0]heptan-6-yl, 2,5-diazabicyclo[2.2.2]octan-2-yl, 1,4-diazabicyclo[3.2.1]octan-4-yl, 3,8-diazabicyclo[3.2.1]octan-3-yl, 1,4-diazabicyclo[3.2.2]nonan-4-yl, 4,7-diazaspiro[2.5]octan-4-yl, 4.7-diazaspiro

[2.5]octan-7-yl, 2,6-diazaspiro[3.3]heptan-2-yl, 1,6-diazaspiro[3.4]octan-6-yl, 2.6-diazaspiro[3.4]octan-2-yl, 2,6-diazaspiro[3.4]octan-6-yl, 1,7,-diazaspiro[4.4]nonan-1-yl, 1,7,-diazaspiro[4.4]nonan-7-yl, 1,7-diazaspiro[3.5]nonan-7-yl, 2,6-diazaspiro[3.5]nonan-2-yl, 2,6-diazaspiro[3.5]nonan-6-yl, 1,7-diazaspiro[3.5]nonan-7-yl, 2,7-diazaspiro[3.5]nonan-2-yl, 2.7-diazaspiro[3.5]nonan-7-yl, 5,8-diazaspiro[3.5]nonan-8-yl, 2-oxa-5.8-diazaspiro[3.5]nonan-8-yl, 2,7-diazaspiro[4.4]nonan-2-yl, 2,7-diazaspiro[4.5]decan-2-yl, 2,7-diazaspiro[4.5]decan-7-yl, 2,8-diazaspiro[4.5]decan-8-yl, 6,9-diazaspiro[4.5]dec-9-yl, 6-oxa-2,9-diazaspiro[4.5]decan-2-yl, 2,9-diazaspiro[5.5]undecan-9-yl, 4-azadispiro[$2.1.2^5.3$]decan-9-yl, and 7-azadispiro[$5.1.5^8.3^6$]hexadecan-15-yl, substituted where allowed by available valences with five $R_b$ substituents.

Another aspect includes a compound of Formula (II), wherein B is heterocyclyl selected from pyrrolidin-1-yl, piperidin-4-yl, and piperazin-1-yl, optionally substituted where allowed by available valences with 1.2, 3, 4, or 5 $R_b$ substituents.

Another aspect includes a compound of Formula (II), wherein B is unsubstituted heterocyclyl selected from pyrrolidin-1-yl, piperidin-4-yl, and piperazin-1-yl.

Another aspect includes a compound of Formula (II), wherein B is heterocyclyl selected from pyrrolidin-1-yl, piperidin-4-yl, and piperazin-1-yl, substituted where allowed by available valences with one $R_b$ substituent.

Another aspect includes a compound of Formula (II), wherein B is heterocyclyl selected from pyrrolidin-1-yl, piperidin-4-yl, and piperazin-1-yl, substituted where allowed by available valences with two $R_b$ substituents.

Another aspect includes a compound of Formula (II), wherein B is heterocyclyl selected from pyrrolidin-1-yl, piperidin-4-yl, and piperazin-1-yl, substituted where allowed by available valences with three $R_b$ substituents.

Another aspect includes a compound of Formula (II), wherein B is heterocyclyl selected from pyrrolidin-1-yl, piperidin-4-yl, and piperazin-1-yl, substituted where allowed by available valences with four $R_b$ substituents.

Another aspect includes a compound of Formula (II), wherein B is heterocyclyl selected from pyrrolidin-1-yl, piperidin-4-yl, and piperazin-1-yl, substituted where allowed by available valences with five $R_b$ substituents.

Another aspect includes a compound of Formula (II), wherein B is pyrrolidin-1-yl, substituted where allowed by available valences with one $R_b$ substituent.

Another aspect includes a compound of Formula (II), wherein B is piperidin-4-yl, substituted where allowed by available valences with 4 or 5 $R_b$ substituents.

Another aspect includes a compound of Formula (II), wherein B is piperidin-4-yl, substituted where allowed by available valences with four $R_b$ substituents.

Another aspect includes a compound of Formula (II), wherein B is piperidin-4-yl, substituted where allowed by available valences with five $R_b$ substituents.

Another aspect includes a compound of Formula (II), wherein B is piperazin-1-yl, substituted where allowed by available valences with one $R_b$ substituent.

Another aspect includes a compound of Formula (II), wherein B is heterocyclyl containing at least one chiral carbon atom having an (R) configuration.

Another aspect includes a compound of Formula (II), wherein B is heterocyclyl containing at least one chiral carbon atom having an (S) configuration.

One aspect includes a compound of Formula (II), wherein $R_b$ is selected from halogen, $C_{1-4}$alkyl, amino, $C_{1-4}$alkyl-amino, $(C_{1-4}alkyl)_2$-amino, and $C_{3-6}$cycloalkyl.

Another aspect includes a compound of Formula (II), wherein $R_b$ is selected from halogen, $C_{1-4}$alkyl, $C_{1-4}$alkyl-amino, and $C_{3-6}$cycloalkyl.

Another aspect includes a compound of Formula (II), wherein $R_b$ is halogen selected from bromo, chloro, fluoro, and iodo.

Another aspect includes a compound of Formula (II), wherein $R_b$ is fluoro.

Another aspect includes a compound of Formula (II), wherein $R_b$ is $C_{1-4}$alkyl selected from methyl, ethyl, propyl, isopropyl, butyl, and tert-butyl.

Another aspect includes a compound of Formula (II), wherein $R_b$ is $C_{1-4}$alkyl selected from methyl and isopropyl.

Another aspect includes a compound of Formula (II), wherein $R_b$ is methyl.

Another aspect includes a compound of Formula (II), wherein $R_b$ is isopropyl.

Another aspect includes a compound of Formula (II), wherein $R_b$ is $C_{1-4}$alkyl-amino.

Another aspect includes a compound of Formula (II), wherein $R_b$ is $C_{1-4}$alkyl-amino, wherein $C_{1-4}$alkyl is selected from methyl, ethyl, propyl, isopropyl, butyl, and tert-butyl.

Another aspect includes a compound of Formula (II), wherein $R_b$ is tert-butylamino.

Another aspect includes a compound of Formula (II), wherein $R_b$ is $C_{3-6}$cycloalkyl selected from cyclopropyl, cyclobutyl, cyclopentyl, and cyclohexyl.

Another aspect includes a compound of Formula (II), wherein $R_b$ is cyclopropyl.

One aspect includes a compound of Formula (II), wherein $R_1$ is selected from heteroaryl, heterocyclyl, phenyl, heteroaryl-$C_{1-4}$alkyl, heteroaryl-$C_{2-4}$alkenyl, heteroaryl-amino, and heteroaryl-$C_{1-4}$alkyl-amino, wherein heteroaryl is a 3-7 membered monocyclic or 6-10 membered bicyclic ring system having 1, 2, 3, or 4 heteroatom ring members independently selected from N, O, or S, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S; and wherein each instance of phenyl, heteroaryl or heterocyclyl is optionally substituted where allowed by available valences with 1 or 2 $R_{1a}$ substituents.

Another aspect includes a compound of Formula (II), wherein $R_1$ is selected from heteroaryl, heterocyclyl, phenyl, heteroaryl-$C_{1-4}$alkyl, heteroaryl-$C_{2-4}$alkenyl, heteroaryl-amino, and heteroaryl-$C_{1-4}$alkyl-amino, wherein heteroaryl is a 3-7 membered monocyclic or 6-10 membered bicyclic ring system having 1, 2, 3, or 4 heteroatom ring members independently selected from N, O, or S, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S; and wherein each instance of phenyl, heteroaryl or heterocyclyl is unsubstituted.

Another aspect includes a compound of Formula (II), wherein $R_1$ is selected from heteroaryl, heterocyclyl, phenyl, heteroaryl-$C_{1-4}$alkyl, heteroaryl-$C_{2-4}$alkenyl, heteroaryl-amino, and heteroaryl-$C_{1-4}$alkyl-amino, wherein heteroaryl is a 3-7 membered monocyclic or 6-10 membered bicyclic ring system having 1, 2, 3, or 4 heteroatom ring members independently selected from N, O, or S, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S; and wherein each instance of phenyl, heteroaryl or heterocyclyl is substituted where allowed by available valences with one $R_{1a}$ substituent.

Another aspect includes a compound of Formula (II), wherein $R_1$ is selected from heteroaryl, heterocyclyl, phenyl, heteroaryl-$C_{1-4}$alkyl, heteroaryl-$C_{2-4}$alkenyl, heteroaryl-amino, and heteroaryl-$C_{1-4}$alkyl-amino, wherein heteroaryl is a 3-7 membered monocyclic or 6-10 membered bicyclic ring system having 1, 2, 3, or 4 heteroatom ring members independently selected from N, O, or S, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S; and wherein each instance of phenyl, heteroaryl or heterocyclyl is substituted where allowed by available valences with two $R_{1a}$ substituents.

Another aspect includes a compound of Formula (II), wherein $R_1$ is selected from heteroaryl, and heteroaryl-amino, wherein heteroaryl is a 3-7 membered monocyclic or 6-10 membered bicyclic ring system having 1, 2, 3, or 4 heteroatom ring members independently selected from N, O, or S; and wherein heteroaryl is optionally substituted where allowed by available valences with 1 or 2 $R_{1a}$ substituents.

Another aspect includes a compound of Formula (II), wherein $R_1$ is selected from heteroaryl, and heteroaryl-amino, wherein heteroaryl is a 3-7 membered monocyclic or 6-10 membered bicyclic ring system having 1, 2, 3, or 4 heteroatom ring members independently selected from N, O, or S; and wherein heteroaryl is unsubstituted.

Another aspect includes a compound of Formula (II), wherein $R_1$ is selected from heteroaryl, and heteroaryl-amino, wherein heteroaryl is a 3-7 membered monocyclic or 6-10 membered bicyclic ring system having 1, 2, 3, or 4 heteroatom ring members independently selected from N, O, or S; and wherein heteroaryl is substituted where allowed by available valences with one $R_{1a}$ substituent.

Another aspect includes a compound of Formula (II), wherein $R_1$ is selected from heteroaryl, and heteroaryl-amino, wherein heteroaryl is a 3-7 membered monocyclic or 6-10 membered bicyclic ring system having 1, 2, 3, or 4 heteroatom ring members independently selected from N, O, or S; and wherein heteroaryl is substituted where allowed by available valences with two $R_{1a}$ substituents.

Another aspect includes a compound of Formula (II), wherein $R_1$ is heteroaryl selected from thienyl, 1H-pyrazolyl, 1H-imidazolyl, 1,3-thiazolyl, oxazolyl, 1,2,4-oxadiazolyl, 1,3,4-oxadiazolyl, 1,2,4-thiadiazolyl, 1H-1,2,3-triazolyl, 2H-1,2,3-triazolyl, 1H-1,2,4-triazolyl, 1H-tetrazolyl, 2H-tetrazolyl, pyridinyl, pyridin-2(1H)-on-yl, pyrazinyl, pyrimidinyl, pyrimidin-4(3H)-on-yl, pyridazinyl, pyridazin-3(2H)-on-yl, 1,2,4-triazinyl, 1,3,5-triazinyl, 1H-indolyl, 1H-indazolyl, 2H-indazolyl, indolizinyl, benzofuranyl, benzothienyl, 1H-benzimidazolyl, 1,3-benzoxazolyl, 1,3-benzothiazolyl, 1,3-benzodioxolyl, 1,2,3-benzotriazolyl, 9H-purinyl, furo[3,2-b]pyridinyl, furo[3,2-c]pyridinyl, furo[2,3-c]pyridinyl, 1,3-oxazolo[5.4-b]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, pyrazolo[1.5-a]pyrimidinyl, pyrazolo[1,5-a]pyrazinyl, 1H-pyrazolo[3,4-b]pyridinyl, 1H-pyrazolo[3,4-b]pyrazinyl, 1H-pyrazolo[3,4-c]pyridinyl, 1H-pyrazolo[4,3-b]pyridinyl, 1H-pyrazolo[4,3-d]pyrimidinyl, 2H-pyrazolo[4,3-b]pyridinyl, 2H-pyrazolo[4,3-c]pyridin-yl, 5H-pyrrolo[2,3-b]pyrazinyl, imidazo[1,2-a]pyridinyl, imidazo[1,2-a]pyrazinyl, imidazo[1,2-a]pyrimidinyl, imidazo[1,2-b]pyridazinyl, imidazo[1,2-c]pyrimidinyl, 1H-imidazo[4,5-b]pyridinyl, 3H-imidazo[4,5-b]pyridinyl, imidazo[2,1-b][1,3]thiazolyl, imidazo[2,1-b][1,3,4]thiadiazolyl, [1,3]oxazolo[4,5-b]pyridinyl, [1,2,3]triazolo[1,5-a]pyridinyl, 1H-[1,2,3]triazolo[4,5-b]pyridinyl, 2H-[1,2,3]triazolo[4,5-b]pyridinyl, 3H-[1,2,3]triazolo[4,5-b]pyridinyl, [1,2,4]triazolo[1,5-a]pyridinyl, [1,2,4]triazolo[1,5-a]pyrazinyl, [1,2,4]triazolo[4,3-a]pyridinyl, tetrazolo[1,5-a]pyridinyl, tetrazolo[1,5-b]pyridazinyl, quinolinyl, isoquinolinyl, and quinoxalinyl, optionally substituted where allowed by available valences with 1 or 2 $R_{1a}$ substituents.

Another aspect includes a compound of Formula (II), wherein $R_1$ is unsubstituted heteroaryl selected from thienyl, 1H-pyrazolyl, 1H-imidazolyl, 1,3-thiazolyl, oxazolyl, 1,2,4-oxadiazolyl, 1,3,4-oxadiazolyl, 1,2,4-thiadiazolyl, 1H-1,2,3-triazolyl, 2H-1,2,3-triazolyl, 1H-1,2,4-triazolyl, 1H-tetrazolyl, 2H-tetrazolyl, pyridinyl, pyridin-2(1H)-on-yl, pyrazinyl, pyrimidinyl, pyrimidin-4(3H)-on-yl, pyridazinyl, pyridazin-3(2H)-on-yl, 1,2,4-triazinyl, 1,3,5-triazinyl, 1H-indolyl, 1H-indazolyl, 2H-indazolyl, indolizinyl, benzofuranyl, benzothienyl, 1H-benzimidazolyl, 1,3-benzoxazolyl, 1,3-benzothiazolyl, 1,3-benzodioxolyl, 1,2,3-benzotriazolyl, 9H-purinyl, furo[3,2-b]pyridinyl, furo[3,2-c]pyridinyl, furo[2,3-c]pyridinyl, 1,3-oxazolo[5,4-b]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, pyrazolo[1,5-a]pyrimidinyl, pyrazolo[1,5-a]pyrazinyl, 1H-pyrazolo[3,4-b]pyridinyl, 1H-pyrazolo[3,4-b]pyrazinyl, 1H-pyrazolo[3,4-c]pyridinyl, 1H-pyrazolo[4,3-b]pyridinyl, 1H-pyrazolo[4,3-d]pyrimidinyl, 2H-pyrazolo[4,3-b]pyridinyl, 2H-pyrazolo[4,3-c]pyridin-yl, 5H-pyrrolo[2,3-b]pyrazinyl, imidazo[1,2-a]pyridinyl, imidazo[1,2-a]pyrazinyl, imidazo[1,2-a]pyrimidinyl, imidazo[1,2-b]pyridazinyl, imidazo[1,2-c]pyrimidinyl, 1H-imidazo[4,5-b]pyridinyl, 3H-imidazo[4,5-b]pyridinyl, imidazo[2,1-b][1,3]thiazolyl, imidazo[2,1-b][1,3,4]thiadiazolyl, [1,3]oxazolo[4,5-b]pyridinyl, [1,2,3]triazolo[1,5-a]pyridinyl, 1H-[1,2,3]triazolo[4,5-b]pyridinyl, 2H-[1,2,3]triazolo[4.5-b]pyridinyl, 3H-[1,2,3]triazolo[4,5-b]pyridinyl, [1,2,4]triazolo[1,5-a]pyridinyl, [1,2,4]triazolo[1,5-a]pyrazinyl, [1,2,4]triazolo[4,3-a]pyridinyl, tetrazolo[1,5-a]pyridinyl, tetrazolo[1,5-b]pyridazinyl, quinolinyl, isoquinolinyl, and quinoxalinyl.

Another aspect includes a compound of Formula (II), wherein $R_1$ is heteroaryl selected from thienyl, 1H-pyrazolyl, 1H-imidazolyl, 1,3-thiazolyl, oxazolyl, 1,2,4-oxadiazolyl, 1,3,4-oxadiazolyl, 1,2,4-thiadiazolyl, 1H-1,2,3-triazolyl, 2H-1,2,3-triazolyl, 1H-1,2,4-triazolyl, 1H-tetrazolyl, 2H-tetrazolyl, pyridinyl, pyridin-2(1H)-on-yl, pyrazinyl, pyrimidinyl, pyrimidin-4(3H)-on-yl, pyridazinyl, pyridazin-3(2H)-on-yl, 1,2,4-triazinyl, 1,3,5-triazinyl, 1H-indolyl, 1H-indazolyl, 2H-indazolyl, indolizinyl, benzofuranyl, benzothienyl, 1H-benzimidazolyl, 1,3-benzoxazolyl, 1,3-benzothiazolyl, 1,3-benzodioxolyl, 1,2,3-benzotriazolyl, 9H-purinyl, furo[3,2-b]pyridinyl, furo[3,2-c]pyridinyl, furo[2,3-c]pyridinyl, 1,3-oxazolo[5.4-b]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, pyrazolo[1,5-a]pyrimidinyl, pyrazolo[1,5-a]pyrazinyl, 1H-pyrazolo[3,4-b]pyridinyl, 1H-pyrazolo[3,4-b]pyrazinyl, 1H-pyrazolo[3,4-c]pyridinyl, 1H-pyrazolo[4,3-b]pyridinyl, 1H-pyrazolo[4,3-d]pyrimidinyl, 2H-pyrazolo[4,3-b]pyridinyl, 2H-pyrazolo[4,3-c]pyridin-yl, 5H-pyrrolo[2,3-b]pyrazinyl, imidazo[1,2-a]pyridinyl, imidazo[1,2-a]pyrazinyl, imidazo[1,2-a]pyrimidinyl, imidazo[1,2-b]pyridazinyl, imidazo[1,2-c]pyrimidinyl, 1H-imidazo[4,5-b]pyridinyl, 3H-imidazo[4,5-b]pyridinyl, imidazo[2,1-b][1,3]thiazolyl, imidazo[2,1-b][1,3,4]thiadiazolyl, [1,3]oxazolo[4,5-b]pyridinyl, [1,2,3]triazolo[1,5-a]pyridinyl, 1H-[1,2,3]triazolo[4,5-b]pyridinyl, 2H-[1,2,3]triazolo[4,5-b]pyridinyl, 3H-[1,2,3]triazolo[4,5-b]pyridinyl, [1,2,4]triazolo[1,5-a]pyridinyl, [1,2,4]triazolo[1,5-a]pyrazinyl, [1,2,4]triazolo[4,3-a]pyridinyl, tetrazolo[1,5-a]pyridinyl, tetrazolo[1,5-b]pyridazinyl, quinolinyl, isoquinolinyl, and quinoxalinyl, substituted where allowed by available valences with one $R_{1a}$ substituent.

Another aspect includes a compound of Formula (II), wherein $R_1$ is heteroaryl selected from thienyl, 1H-pyrazolyl, 1H-imidazolyl, 1,3-thiazolyl, oxazolyl, 1,2,4-oxadiazolyl, 1,3,4-oxadiazolyl, 1,2,4-thiadiazolyl, 1H-1,2,3-triazolyl, 2H-1,2,3-triazolyl, 1H-1,2,4-triazolyl, 1H-tetrazolyl, 2H-tetrazolyl, pyridinyl, pyridin-2(1H)-on-yl, pyrazinyl, pyrimidinyl, pyrimidin-4(3H)-on-yl, pyridazinyl, pyridazin-3(2H)-on-yl, 1,2,4-triazinyl, 1,3,5-triazinyl, 1H-indolyl, 1H-indazolyl, 2H-indazolyl, indolizinyl, benzofuranyl, benzothienyl, 1H-benzimidazolyl, 1,3-benzoxazolyl, 1,3-benzothiazolyl, 1,3-benzodioxolyl, 1,2,3-benzotriazolyl, 9H-purinyl, furo[3,2-b]pyridinyl, furo[3,2-c]pyridinyl, furo[2,3-c]pyridinyl, 1,3-oxazolo[5.4-b]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, pyrazolo[1,5-a]pyrimidinyl, pyrazolo[1,5-a]pyrazinyl, 1H-pyrazolo[3,4-b]pyridinyl, 1H-pyrazolo[3,4-b]pyrazinyl, 1H-pyrazolo[3,4-c]pyridinyl, 1H-pyrazolo[4,3-b]pyridinyl, 1H-pyrazolo[4,3-d]pyrimidinyl, 2H-pyrazolo[4,3-b]pyridinyl, 2H-pyrazolo[4,3-c]pyridin-yl, 5H-pyrrolo[2,3-b]pyrazinyl, imidazo[1,2-a]pyridinyl, imidazo[1,2-a]pyrazinyl, imidazo[1,2-a]pyrimidinyl, imidazo[1,2-b]pyridazinyl, imidazo[1,2-c]pyrimidinyl, 1H-imidazo[4,5-b]pyridinyl, 3H-imidazo[4,5-b]pyridinyl, imidazo[2,1-b][1,3]thiazolyl, imidazo[2,1-b][1,3,4]thiadiazolyl, [1,3]oxazolo[4,5-b]pyridinyl, [1,2,3]triazolo[1,5-a]pyridinyl, 1H-[1,2,3]triazolo[4,5-b]pyridinyl, 2H-[1,2,3]triazolo[4,5-b]pyridinyl, 3H-[1,2,3]triazolo[4,5-b]pyridinyl, [1,2,4]triazolo[1,5-a]pyridinyl, [1,2,4]triazolo[1,5-a]pyrazinyl, [1,2,4]triazolo[4,3-a]pyridinyl, tetrazolo[1,5-a]pyridinyl, tetrazolo[1,5-b]pyridazinyl, quinolinyl, isoquinolinyl, and quinoxalinyl, substituted where allowed by available valences with two $R_{1a}$ substituents.

Another aspect includes a compound of Formula (II), wherein $R_1$ is heteroaryl selected from 1H-pyrazolyl, 2H-1,2,3-triazolyl, 2H-indazolyl, imidazo[1,2-a]pyridinyl, imidazo[1,2-b]pyridazinyl, and 2H-[1,2,3]triazolo[4,5-b]pyridinyl, optionally substituted where allowed by available valences with 1 or 2 $R_{1a}$ substituents.

Another aspect includes a compound of Formula (II), wherein $R_1$ is unsubstituted heteroaryl selected from 1H-pyrazolyl, 2H-1,2,3-triazolyl, 2H-indazolyl, imidazo[1,2-a]pyridinyl, imidazo[1,2-b]pyridazinyl, and 2H-[1,2,3]triazolo[4,5-b]pyridinyl.

Another aspect includes a compound of Formula (II), wherein $R_1$ is heteroaryl selected from 1H-pyrazolyl, 2H-1,2,3-triazolyl, 2H-indazolyl, imidazo[1,2-a]pyridinyl, imidazo[1,2-b]pyridazinyl, and 2H-[1,2,3]triazolo[4,5-b]pyridinyl, substituted where allowed by available valences with one $R_{1a}$ substituent.

Another aspect includes a compound of Formula (II), wherein $R_1$ is heteroaryl selected from 1H-pyrazolyl, 2H-1,2,3-triazolyl, 2H-indazolyl, imidazo[1,2-a]pyridinyl, imidazo[1,2-b]pyridazinyl, and 2H-[1,2,3]triazolo[4,5-b]pyridinyl, substituted where allowed by available valences with two $R_{1a}$ substituents.

Another aspect includes a compound of Formula (II), wherein $R_1$ is heteroaryl selected from thien-2-yl, thien-3-yl, 1H-pyrazol-1-yl, 1H-pyrazol-3-yl, 1H-pyrazol-4-yl, 1H-pyrazol-5-yl, 1H-imidazol-1-yl, 1H-imidazol-4-yl, 1,3-thiazol-2-yl, 1,3-thiazol-5-yl, 1,3-oxazol-2-yl, 1,3-oxazol-4-yl, 1,3-oxazol-5-yl, 1,2,4-oxadiazol-3-yl, 1,3,4-oxadiazol-2-yl, 1,2,4-thiadiazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-3-yl, 1H-1,2,4-triazol-5-yl, 1H-tetrazol-1-yl, 1H-tetrazol-5-yl, 2H-tetrazol-2-yl, 2H-tetrazol-5-yl, pyridin-2-yl, pyridin-3-yl, pyridin-4-yl, pyridin-2(1H)-on-4-yl, pyridin-2(1H)-on-5-yl, pyridin-2(H)-on-6-yl, pyrazin-2-yl, pyrazin-3-yl, pyrimidin-2-yl, pyrimidin-4-yl, pyrimidin-5-yl, pyrimidin-4(3H)-on-6-yl, pyridazin-3-yl, pyridazin-4-yl, pyridazin-3(2H)-on-5-yl, 1,2,4-triazin-3-yl, 1,3,5-triazin-2-yl, 1H-indol-3-yl, 1H-indol-4-yl, 1H-indol-5-yl, 1H-indol-6-yl, 1H-indazol-5-yl, 1H-indazol-6-yl, 2H-indazol-4-yl, 2H-indazol-5-yl, 2H-indazol-6-yl, indolizin-2-yl, benzofuran-2-yl, benzofuran-5-yl, benzothien-2-yl, benzothien-3-yl, 1H-benzimidazol-2-yl, 1H-benzimidazol-5-yl, 1H-benzimidazol-6-yl, 1,3-benzoxazol-2-yl, 1,3-benzoxazol-5-yl, 1,3-benzoxazol-6-yl, 1,3-benzothiazol-2-yl, 1,3-benzothiazol-5-yl, 1,3-benzothiazol-6-yl, 1,3-benzodioxol-5-yl, 1,2,3-benzotriazol-5-yl, 9H-purin-8-yl, furo[3,2-b]pyridin-2-yl, furo[3,2-c]pyridin-2-yl, furo[2,3-c]pyridin-2-yl, 1,3-oxazolo[5,4-b]pyridine-5-yl, thieno[3,2-c]pyridin-2-yl, thieno[2,3-d]pyrimidin-6-yl, 1H-pyrrolo[2,3-b]pyridin-5-yl, 1H-pyrrolo[2,3-c]pyridin-4-yl, pyrrolo[1,2-a]pyrimidin-7-yl, pyrrolo[1,2-a]pyrazin-7-yl, pyrrolo[1,2-b]pyridazin-2-yl, pyrazolo[1,5-a]pyridin-2-yl, pyrazolo[1,5-a]pyridin-5-yl, pyrazolo[1,5-a]pyrazin-2-yl, pyrazolo[1,5-a]pyrimidin-2-yl, pyrazolo[1,5-a]pyrimidin-5-yl, 1H-pyrazolo[3,4-b]pyrazin-5-yl, 1H-pyrazolo[3,4-b]pyridin-5-yl, 1H-pyrazolo[3,4-b]pyridin-6-yl, 1H-pyrazolo[3,4-c]pyridin-1-yl, 1H-pyrazolo[3,4-c]pyridin-5-yl, 1H-pyrazolo[4,3-b]pyridin-5-yl, 1H-pyrazolo[4,3-b]pyridin-6-yl, 1H-pyrazolo[4,3-d]pyrimidin-5-yl, 2H-pyrazolo[4,3-b]pyridin-5-yl, 2H-pyrazolo[4,3-c]pyridin-5-yl, 5H-pyrrolo[2,3-b]pyrazin-2-yl, imidazo[1,2-a]pyridin-2-yl, imidazo[1,2-a]pyridin-6-yl, imidazo[1,2-a]pyrazin-2-yl, imidazo[1,2-a]pyrazin-6-yl, imidazo[1,2-a]pyrimidin-2-yl, imidazo[1,2-a]pyrimidin-6-yl, imidazo[1,2-b]pyridazin-2-yl, imidazo[1,2-b]pyridazin-6-yl, imidazo[1,2-c]pyrimidin-2-yl, 1H-imidazo[4,5-b]pyridin-5-yl, 3H-imidazo[4,5-b]pyridin-5-yl, imidazo[2,1-b][1,3]thiazol-6-yl, imidazo[2,1-b][1,3,4]thiadiazol-6-yl, [1,3]oxazolo[4,5-b]pyridin-2-yl, [1,2,3]triazolo[1,5-a]pyridin-5-yl, [1,2,3]triazolo[1,5-a]pyridin-6-yl, 1H-[1,2,3]triazolo[4,5-b]

pyridin-5-yl, 2H-[1,2,3]triazolo[4,5-b]pyridin-6-yl, 3H-[1,2,3]triazolo[4,5-b]pyridin-5-yl, [1,2,4]triazolo[1,5-a]pyridin-2-yl, [1,2,4]triazolo[1,5-a]pyridin-6-yl, [1,2,4]triazolo[1,5-a]pyridin-7-yl, [1,2,4]triazolo[1,5-a]pyrazin-2-yl, [1,2,4]triazolo[1,5-a]pyrazin-5-yl, [1,2,4]triazolo[1,5-a]pyrazin-6-yl, [1,2,4]triazolo[4,3-a]pyridn-6-yl, [1,2,4]triazolo[4,3-a]pyridn-7-yl, tetrazolo[1,5-a]pyridin-7-yl, tetrazolo[1,5-b]pyridazin-7-yl, quinolin-6-yl, isoquinolin-6-yl, and quinoxalin-2-yl, optionally substituted where allowed by available valences with 1 or 2 $R_{1a}$ substituents.

Another aspect includes a compound of Formula (II), wherein $R_1$ is unsubstituted heteroaryl selected from thien-2-yl, thien-3-yl, 1H-pyrazol-1-yl, 1H-pyrazol-3-yl, 1H-pyrazol-4-yl, 1H-pyrazol-5-yl, 1H-imidazol-1-yl, 1H-imidazol-4-yl, 1,3-thiazol-2-yl, 1,3-thiazol-5-yl, 1,3-oxazol-2-yl, 1,3-oxazol-4-yl, 1,3-oxazol-5-yl, 1,2,4-oxadiazol-3-yl, 1,3,4-oxadiazol-2-yl, 1,2,4-thiadiazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-3-yl, 1H-1,2,4-triazol-5-yl, 1H-tetrazol-1-yl, 1H-tetrazol-5-yl, 2H-tetrazol-2-yl, 2H-tetrazol-5-yl, pyridin-2-yl, pyridin-3-yl, pyridin-4-yl, pyridin-2(1H)-on-4-yl, pyridin-2(1H)-on-5-yl, pyridin-2(I H)-on-6-yl, pyrazin-2-yl, pyrazin-3-yl, pyrimidin-2-yl, pyrimidin-4-yl, pyrimidin-5-yl, pyrimidin-4(3H)-on-6-yl, pyridazin-3-yl, pyridazin-4-yl, pyridazin-3(2H)-on-5-yl, 1,2,4-triazin-3-yl, 1,3,5-triazin-2-yl, 1H-indol-3-yl, 1H-indol-4-yl, 1H-indol-5-yl, 1H-indol-6-yl, 1H-indazol-5-yl, 1H-indazol-6-yl, 2H-indazol-4-yl, 2H-indazol-5-yl, 2H-indazol-6-yl, indolizin-2-yl, benzofuran-2-yl, benzofuran-5-yl, benzothien-2-yl, benzothien-3-yl, 1H-benzimidazol-2-yl, 1H-benzimidazol-5-yl, 1H-benzimidazol-6-yl, 1,3-benzoxazol-2-yl, 1,3-benzoxazol-5-yl, 1,3-benzoxazol-6-yl, 1,3-benzothiazol-2-yl, 1,3-benzothiazol-5-yl, 1,3-benzothiazol-6-yl, 1,3-benzodioxol-5-yl, 1,2,3-benzotriazol-5-yl, 9H-purin-8-yl, furo[3,2-b]pyridin-2-yl, furo[3,2-c]pyridin-2-yl, furo[2,3-c]pyridin-2-yl, 1,3-oxazolo[5,4-b]pyridine-5-yl, thieno[3,2-c]pyridin-2-yl, thieno[2,3-d]pyrimidin-6-yl, 1H-pyrrolo[2,3-b]pyridin-5-yl, 1H-pyrrolo[2,3-c]pyridin-4-yl, pyrrolo[1,2-a]pyrimidin-7-yl, pyrrolo[1,2-a]pyrazin-7-yl, pyrrolo[1,2-b]pyridazin-2-yl, pyrazolo[1,5-a]pyridin-2-yl, pyrazolo[1,5-a]pyridin-5-yl, pyrazolo[1,5-a]pyrazin-2-yl, pyrazolo[1,5-a]pyrimidin-2-yl, pyrazolo[15-a]pyrimidin-5-yl, 1H-pyrazolo[3,4-b]pyrazin-5-yl, 1H-pyrazolo[3,4-b]pyridin-5-yl, 1H-pyrazolo[3,4-b]pyridin-6-yl, 1H-pyrazolo[3,4-c]pyridin-1-yl, 1H-pyrazolo[3,4-c]pyridin-5-yl, 1H-pyrazolo[4,3-b]pyridin-5-yl, 1H-pyrazolo[4,3-b]pyridin-6-yl, 1H-pyrazolo[4,3-d]pyrimidin-5-yl, 2H-pyrazolo[4,3-b]pyridin-5-yl, 2H-pyrazolo[4,3-c]pyridin-5-yl, 5H-pyrrolo[2,3-b]pyrazin-2-yl, imidazo[1,2-a]pyridin-2-yl, imidazo[1,2-a]pyridin-6-yl, imidazo[1,2-a]pyrazin-2-yl, imidazo[1,2-a]pyrazin-6-yl, imidazo[1,2-a]pyrimidin-2-yl, imidazo[1,2-a]pyrimidin-6-yl, imidazo[1,2-b]pyridazin-2-yl, imidazo[1,2-b]pyridazin-6-yl, imidazo[1,2-c]pyrimidin-2-yl, 1H-imidazo[4,5-b]pyridin-5-yl, 3H-imidazo[4,5-b]pyridin-5-yl, imidazo[2,1-b][1,3]thiazol-6-yl, imidazo[2,1-b][1,3,4]thiadiazol-6-yl, [1,3]oxazolo[4,5-b]pyridin-2-yl, [1,2,3]triazolo[1,5-a]pyridin-5-yl, [1,2,3]triazolo[1,5-a]pyridin-6-yl, 1H-[1,2,3]triazolo[4,5-b]pyridin-5-yl, 2H-[1,2,3]triazolo[4.5-b]pyridin-6-yl, 3H-[1,2,3]triazolo[4,5-b]pyridin-5-yl, [1,2,4]triazolo[1.5-a]pyridin-2-yl, [1,2,4]triazolo[1,5-a]pyridin-6-yl, [1,2,4]triazolo[1,5-a]pyridin-7-yl, [1,2,4]triazolo[1,5-a]pyrazin-2-yl, [1,2,4]triazolo[1,5-a]pyrazin-5-yl, [1,2,4]triazolo[1,5-a]pyrazin-6-yl, [1,2,4]triazolo[4,3-a]pyridn-6-yl, [1,2,4]triazolo[4,3-a]pyridn-7-yl, tetrazolo[1,5-a]pyridin-7-yl, tetrazolo[1,5-b]pyridazin-7-yl, quinolin-6-yl, isoquinolin-6-yl, and quinoxalin-2-yl.

Another aspect includes a compound of Formula (II), wherein $R_1$ is heteroaryl selected from thien-2-yl, thien-3-yl, 1H-pyrazol-1-yl, 1H-pyrazol-3-yl, 1H-pyrazol-4-yl, 1H-pyrazol-5-yl, 1H-imidazol-1-yl, 1H-imidazol-4-yl, 1,3-thiazol-2-yl, 1,3-thiazol-5-yl, 1,3-oxazol-2-yl, 1,3-oxazol-4-yl, 1,3-oxazol-5-yl, 1,2,4-oxadiazol-3-yl, 1,3,4-oxadiazol-2-yl, 1,2,4-thiadiazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-3-yl, 1H-1,2,4-triazol-5-yl, 1H-tetrazol-1-yl, 1H-tetrazol-5-yl, 2H-tetrazol-2-yl, 2H-tetrazol-5-yl, pyridin-2-yl, pyridin-3-yl, pyridin-4-yl, pyridin-2(1H)-on-4-yl, pyridin-2(1H)-on-5-yl, pyridin-2(1H)-on-6-yl, pyrazin-2-yl, pyrazin-3-yl, pyrimidin-2-yl, pyrimidin-4-yl, pyrimidin-5-yl, pyrimidin-4(3H)-on-6-yl, pyridazin-3-yl, pyridazin-4-yl, pyridazin-3(2H)-on-5-yl, 1,2,4-triazin-3-yl, 1,3,5-triazin-2-yl, 1H-indol-3-yl, 1H-indol-4-yl, 1H-indol-5-yl, 1H-indol-6-yl, 1H-indazol-5-yl, 1H-indazol-6-yl, 2H-indazol-4-yl, 2H-indazol-5-yl, 2H-indazol-6-yl, indolizin-2-yl, benzofuran-2-yl, benzofuran-5-yl, benzothien-2-yl, benzothien-3-yl, 1H-benzimidazol-2-yl, 1H-benzimidazol-5-yl, 1H-benzimidazol-6-yl, 1,3-benzoxazol-2-yl, 1,3-benzoxazol-5-yl, 1,3-benzoxazol-6-yl, 1,3-benzothiazol-2-yl, 1,3-benzothiazol-5-yl, 1,3-benzothiazol-6-yl, 1,3-benzodioxol-5-yl, 1,2,3-benzotriazol-5-yl, 9H-purin-8-yl, furo[3,2-b]pyridin-2-yl, furo[3,2-c]pyridin-2-yl, furo[2,3-c]pyridin-2-yl, 1,3-oxazolo[5,4-b]pyridine-5-yl, thieno[3,2-c]pyridin-2-yl, thieno[2,3-d]pyrimidin-6-yl, 1H-pyrrolo[2,3-b]pyridin-5-yl, 1H-pyrrolo[2,3-c]pyridin-4-yl, pyrrolo[1,2-a]pyrimidin-7-yl, pyrrolo[1,2-a]pyrazin-7-yl, pyrrolo[1,2-b]pyridazin-2-yl, pyrazolo[1,5-a]pyridin-2-yl, pyrazolo[1,5-a]pyridin-5-yl, pyrazolo[1,5-a]pyrazin-2-yl, pyrazolo[1,5-a]pyrimidin-2-yl, pyrazolo[1,5-a]pyrimidin-5-yl, 1H-pyrazolo[3,4-b]pyrazin-5-yl, 1H-pyrazolo[3,4-b]pyridin-5-yl, 1H-pyrazolo[3,4-b]pyridin-6-yl, 1H-pyrazolo[3,4-c]pyridin-1-yl, 1H-pyrazolo[3,4-c]pyridin-5-yl, 1H-pyrazolo[4,3-b]pyridin-5-yl, 1H-pyrazolo[4,3-b]pyridin-6-yl, 1H-pyrazolo[4,3-d]pyrimidin-5-yl, 2H-pyrazolo[4,3-b]pyridin-5-yl, 2H-pyrazolo[4,3-c]pyridin-5-yl, 5H-pyrrolo[2,3-b]pyrazin-2-yl, imidazo[1,2-a]pyridin-2-yl, imidazo[1,2-a]pyridin-6-yl, imidazo[1,2-a]pyrazin-2-yl, imidazo[1,2-a]pyrazin-6-yl, imidazo[1,2-a]pyrimidin-2-yl, imidazo[1,2-a]pyrimidin-6-yl, imidazo[1,2-b]pyridazin-2-yl, imidazo[1,2-b]pyridazin-6-yl, imidazo[1,2-c]pyrimidin-2-yl, 1H-imidazo[4,5-b]pyridin-5-yl, 3H-imidazo[4,5-b]pyridin-5-yl, imidazo[2,1-b][1,3]thiazol-6-yl, imidazo[2,1-b][1,3,4]thiadiazol-6-yl, [1,3]oxazolo[4,5-b]pyridin-2-yl, [1,2,3]triazolo[1,5-a]pyridin-5-yl, [1,2,3]triazolo[1,5-a]pyridin-6-yl, 1H-[1,2,3]triazolo[4,5-b]pyridin-5-yl, 2H-[1,2,3]triazolo[4,5-b]pyridin-6-yl, 3H-[1,2,3]triazolo[4.5-b]pyridin-5-yl, [1,2,4]triazolo[1,5-a]pyridin-2-yl, [1,2,4]triazolo[1,5-a]pyridin-6-yl, [1,2,4]triazolo[1,5-a]pyridin-7-yl, [1,2,4]triazolo[1,5-a]pyrazin-2-yl, [1,2,4]triazolo[1,5-a]pyrazin-5-yl, [1,2,4]triazolo[1,5-a]pyrazin-6-yl, [1,2,4]triazolo[4,3-a]pyridn-6-yl, [1,2,4]triazolo[4,3-a]pyridn-7-yl, tetrazolo[1,5-a]pyridin-7-yl, tetrazolo[1,5-b]pyridazin-7-yl, quinolin-6-yl, isoquinolin-6-yl, and quinoxalin-2-yl, substituted where allowed by available valences with one $R_{1a}$ substituent.

Another aspect includes a compound of Formula (II), wherein $R_1$ is heteroaryl selected from thien-2-yl, thien-3-yl, 1H-pyrazol-1-yl, 1H-pyrazol-3-yl, 1H-pyrazol-4-yl, 1H-pyrazol-5-yl, 1H-imidazol-1-yl, 1H-imidazol-4-yl, 1,3-thiazol-2-yl, 1,3-thiazol-5-yl, 1,3-oxazol-2-yl, 1,3-oxazol-4-yl, 1,3-oxazol-5-yl, 1,2,4-oxadiazol-3-yl, 1,3,4-oxadiazol-2-yl, 1,2,4-thiadiazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-3-yl, 1H-1,2,4-triazol-5-yl, 1H-tetrazol-1-yl, 1H-tetrazol-5-yl, 2H-tetrazol-2-yl, 2H-tetrazol-5-yl, pyridin-2-yl, pyridin-3-yl, pyridin-4-yl, pyridin-2(1H)-on-4-yl, pyridin-2(1H)-on-5-yl, pyridin-2(1H)-on-6-yl, pyrazin-2-yl, pyrazin-3-yl, pyrimidin-2-yl, pyrimidin-4-yl, pyrimidin-5-yl, pyrimidin-4(3H)-on-6-yl, pyridazin-3-yl, pyridazin-4-yl, pyridazin-3(2H)-on-5-yl, 1,2,4-triazin-3-yl, 1,3,5-triazin-2-yl, 1H-indol-3-yl, 1H-indol-4-yl, 1H-indol-5-yl, 1H-indol-6-yl, 1H-indazol-5-yl, 1H-indazol-6-yl, 2H-indazol-4-yl, 2H-indazol-5-yl, 2H-indazol-6-yl, indolizin-2-yl, benzofuran-2-yl, benzofuran-5-yl, benzothien-2-yl, benzothien-3-yl, 1H-benzimidazol-2-yl, 1H-benzimidazol-5-yl, 1H-benzimidazol-6-yl, 1,3-benzoxazol-2-yl, 1,3-benzoxazol-5-yl, 1,3-benzoxazol-6-yl, 1,3-benzothiazol-2-yl, 1,3-benzothiazol-5-yl, 1,3-benzothiazol-6-yl, 1,3-benzodioxol-5-yl, 1,2,3-benzotriazol-5-yl, 9H-purin-8-yl, furo[3,2-b]pyridin-2-yl, furo[3,2-c]pyridin-2-yl, furo[2,3-c]pyridin-2-yl, 1,3-oxazolo[5,4-b]pyridine-5-yl, thieno[3,2-c]pyridin-2-yl, thieno[2,3-d]pyrimidin-6-yl, 1H-pyrrolo[2,3-b]pyridin-5-yl, 1H-pyrrolo[2,3-c]pyridin-4-yl, pyrrolo[1,2-a]pyrimidin-7-yl, pyrrolo[1,2-a]pyrazin-7-yl, pyrrolo[1,2-b]pyridazin-2-yl, pyrazolo[1,5-a]pyridin-2-yl, pyrazolo[1,5-a]pyridin-5-v, pyrazolo[1,5-a]pyrazin-2-yl, pyrazolo[1,5-a]pyrimidin-2-yl, pyrazolo[1,5-a]pyrimidin-5-yl, 1H-pyrazolo[3,4-b]pyrazin-5-yl, 1H-pyrazolo[3,4-b]pyridin-5-yl, 1H-pyrazolo[3,4-b]pyridin-6-yl, 1H-pyrazolo[3,4-c]pyridin-1-yl, 1H-pyrazolo[3,4-c]pyridin-5-yl, 1H-pyrazolo[4,3-b]pyridin-5-yl, 1H-pyrazolo[4,3-b]pyridin-6-yl, 1H-pyrazolo[4,3-d]pyrimidin-5-yl, 2H-pyrazolo[4,3-b]pyridin-5-yl, 2H-pyrazolo[4,3-c]pyridin-5-yl, 5H-pyrrolo[2,3-b]pyrazin-2-yl, imidazo[1,2-a]pyridin-2-yl, imidazo[1,2-a]pyridin-6-yl, imidazo[1,2-a]pyrazin-2-yl, imidazo[1,2-a]pyrazin-6-yl, imidazo[1,2-a]pyrimidin-2-yl, imidazo[1,2-a]pyrimidin-6-yl, imidazo[1,2-b]pyridazin-2-yl, imidazo[1,2-b]pyridazin-6-yl, imidazo[1,2-c]pyrimidin-2-yl, 1H-imidazo[4,5-b]pyridin-5-yl, 3H-imidazo[4,5-b]pyridin-5-yl, imidazo[2,1-b][1,3]thiazol-6-yl, imidazo[2,1-b][1,3,4]thiadiazol-6-yl, [1,3]oxazolo[4,5-b]pyridin-2-yl, [1,2,3]triazolo[1,5-a]pyridin-5-yl, [1,2,3]triazolo[1,5-a]pyridin-6-yl, 1H-[1,2,3]triazolo[4,5-b]pyridin-5-yl, 2H-[1,2,3]triazolo[4,5-b]pyridin-6-yl, 3H-[1,2,3]triazolo[4,5-b]pyridin-5-yl, [1,2,4]triazolo[1,5-a]pyridin-2-yl, [1,2,4]triazolo[1,5-a]pyridin-6-yl, [1,2,4]triazolo[1,5-a]pyridin-7-yl, [1,2,4]triazolo[1,5-a]pyrazin-2-yl, [1,2,4]triazolo[1,5-a]pyrazin-5-yl, [1,2,4]triazolo[1,5-a]pyrazin-6-yl, [1,2,4]triazolo[4,3-a]pyridn-6-yl, [1,2,4]triazolo[4,3-a]pyridn-7-yl, tetrazolo[1,5-a]pyridin-7-yl, tetrazolo[1,5-b]pyridazin-7-yl, quinolin-6-yl, isoquinolin-6-yl, and quinoxalin-2-yl, substituted where allowed by available valences with two $R_{1a}$ substituents.

Another aspect includes a compound of Formula (II), wherein $R_1$ is heteroaryl selected from 1H-pyrazol-4-yl, 2H-1,2,3-triazol-2-yl, 2H-indazol-5-yl, imidazo[1,2-a]pyridin-6-yl, imidazo[1,2-b]pyridazin-6-yl, and 2H-[1,2,3]triazolo[4,5-b]pyridin-6-yl, optionally substituted where allowed by available valences with 1 or 2 $R_{1a}$ substituents.

Another aspect includes a compound of Formula (II), wherein $R_1$ is unsubstituted heteroaryl selected from 1H-pyrazol-4-yl, 2H-1,2,3-triazol-2-yl, 2H-indazol-5-yl, imidazo[1,2-a]pyridin-6-yl, imidazo[1,2-b]pyridazin-6-yl, and 2H-[1,2,3]triazolo[4.5-b]pyridin-6-yl.

Another aspect includes a compound of Formula (II), wherein $R_1$ is heteroaryl selected from 1H-pyrazol-4-yl, 2H-1,2,3-triazol-2-yl, 2H-indazol-5-yl, imidazo[1,2-a]pyridin-6-yl, imidazo[1,2-b]pyridazin-6-yl, and 2H-[1,2,3]triazolo[4,5-b]pyridin-6-yl, substituted where allowed by available valences with 1 $R_{1a}$ substituent.

Another aspect includes a compound of Formula (II), wherein $R_1$ is heteroaryl selected from 1H-pyrazol-4-yl, 2H-1,2,3-triazol-2-yl, 2H-indazol-5-yl, imidazo[1,2-a]pyridin-6-yl, imidazo[1,2-b]pyridazin-6-yl, and 2H-[1,2,3]triazolo[4,5-b]pyridin-6-yl, substituted where allowed by available valences with 2 $R_{1a}$ substituents.

Another aspect includes a compound of Formula (II), wherein $R_1$ is heteroaryl-amino, wherein heteroaryl is selected from thienyl, 1H-pyrazolyl, 1H-imidazolyl, 1,3-thiazolyl, oxazolyl, 1,2,4-oxadiazolyl, 1,3,4-oxadiazolyl, 1,2,4-thiadiazolyl, 1H-tetrazolyl, 2H-tetrazolyl, pyridinyl, pyrazinyl, pyrimidinyl, pyridazinyl, 1,2,4-triazinyl, 1,3,5-triazinyl, 1H-indolyl, 1H-indazolyl, 2H-indazolyl, indolizinyl, benzofuranyl, benzothienyl, 1H-benzimidazolyl, 1,3-benzoxazolyl, 1,3-benzothiazolyl, 1,3-benzodioxolyl, 1,2,3-benzotriazolyl, 9H-purinyl, quinolinyl, isoquinolinyl, and quinoxalinyl; and wherein heteroaryl is optionally substituted where allowed by available valences with 1 or 2 $R_{1a}$ substituents.

Another aspect includes a compound of Formula (II), wherein $R_1$ is (pyrazin-2-yl)amino, optionally substituted where allowed by available valences with 1 or 2 $R_{1a}$ substituents.

One aspect includes a compound of Formula (II), wherein $R_{1a}$ is independently selected from halogen, hydroxyl, cyano, $C_{1-4}$alkyl, deutero-$C_{1-4}$alkyl, halo-$C_{1-4}$alkyl, amino, $C_{1-4}$alkyl-amino, $(C_{1-4}alkyl)_2$-amino, $C_{1-4}$alkoxy, deutero-$C_{1-4}$alkoxy, and halo-$C_{1-4}$alkoxy.

Another aspect includes a compound of Formula (II), wherein $R_{1a}$ is independently selected from halogen, cyano, $C_{1-4}$alkyl, deutero-$C_{1-4}$alkyl, and $C_{1-4}$alkoxy.

Another aspect includes a compound of Formula (II), wherein $R_{1a}$ is $C_{1-4}$alkyl selected from methyl, ethyl, propyl, isopropyl, butyl, and tert-butyl.

Another aspect includes a compound of Formula (II), wherein $R_{1a}$ is methyl.

Another aspect includes a compound of Formula (II), wherein $R_{1a}$ is halogen selected from bromo, chloro, fluoro, and iodo.

Another aspect includes a compound of Formula (II), wherein $R_{1a}$ is fluoro.

Another aspect includes a compound of Formula (II), wherein $R_{1a}$ is cyano.

Another aspect includes a compound of Formula (II), wherein $R_{1a}$ is deutero-$C_{1-4}$alkyl wherein $C_{1-4}$alkyl is selected from methyl, ethyl, propyl, isopropyl, butyl, and tert-butyl, partially or completely substituted with one or more deuterium atoms where allowed by available valences.

Another aspect includes a compound of Formula (II), wherein $R_{1a}$ is $(^2H_3)$methyl.

Another aspect includes a compound of Formula (II), wherein $R_{1a}$ is $C_{1-4}$alkoxy selected from methoxy, ethoxy, propoxy, isopropoxy, butoxy and tert-butoxy.

Another aspect includes a compound of Formula (II), wherein $R_{1a}$ is methoxy.

Another aspect of the present description includes a compound of Formula (III):

(III)

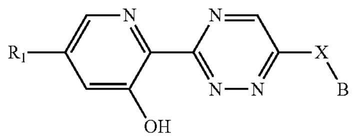

or a form thereof, wherein:

X is O, $NR_x$, or a bond;

$R_x$ is selected from hydrogen and $C_{1-4}$alkyl;

B is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, each optionally substituted where allowed by available valences with 1, 2, 3, 4, or 5 substituents $R_b$;

$R_b$ is independently selected from halogen, $C_{1-4}$alkyl, amino, $C_{1-4}$alkyl-amino, $(C_{1-4}alkyl)_2$-amino, and $C_{3-6}$cycloalkyl;

$R_1$ is selected from heteroaryl, heterocyclyl, phenyl, heteroaryl-$C_{1-4}$alkyl, heteroaryl-$C_{2-4}$alkenyl, heteroaryl-amino, heteroaryl-$C_{1-4}$alkyl-amino, wherein heteroaryl is a 3-7 membered monocyclic or 6-10 membered bicyclic ring system having 1, 2, 3, or 4 heteroatom ring members independently selected from N, O, or S, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, and wherein each instance of phenyl, heteroaryl or heterocyclyl is optionally substituted where allowed by available valences with 1 or 2 $R_{1a}$ substituents; and $R_{1a}$ is independently selected from halogen, hydroxyl, cyano, $C_{1-4}$alkyl, deutero-$C_{1-4}$alkyl, halo-$C_{1-4}$alkyl, amino, $C_{1-4}$alkyl-amino, $(C_{1-4}alkyl)_2$-amino, $C_{1-4}$alkoxy, deutero-$C_{1-4}$ alkoxy, and halo-$C_{1-4}$alkoxy.

One aspect includes a compound of Formula (III), wherein X is selected from O, $NR_x$, and a bond.

Another aspect includes a compound of Formula (III) wherein X is $NR_x$.

Another aspect includes a compound of Formula (III) wherein X is a bond.

One aspect includes a compound of Formula (III), wherein $R_x$ is selected from hydrogen and $C_{1-4}$alkyl.

Another aspect includes a compound of Formula (III), wherein $R_x$ hydrogen.

Another aspect includes a compound of Formula (III), wherein $R_x$ is $C_{1-4}$alkyl selected from methyl, ethyl, propyl, isopropyl, butyl, and tert-butyl.

Another aspect includes a compound of Formula (III), wherein $R_x$ is methyl.

One aspect includes a compound of Formula (III), wherein B is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, optionally substituted where allowed by available valences with 1, 2, 3, 4, or 5 $R_b$ substituents.

Another aspect includes a compound of Formula (III), wherein B is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, substituted where allowed by available valences with two $R_b$ substituents.

Another aspect includes a compound of Formula (III), wherein B is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, substituted where allowed by available valences with four $R_b$ substituents.

Another aspect includes a compound of Formula (III), wherein B is heterocyclyl selected from azetidinyl, tetrahydrofuranyl, pyrrolidinyl, piperidinyl, piperidin-1-olate-yl, piperazinyl, 1,4-diazepanyl, 1,2-dihydropyridinyl, 1,2,5,6-tetrahydropyridinyl, 1,2,3,6-tetrahydropyridinyl, hexahydrocyclopentapyrrol-(1H)-yl, hexahydropyrrolo[3,2-b]pyrrol-(2H)-yl, hexahydropyrrolo[3,4-b]pyrrol-(2H)-yl, octahydro-2H-pyrrolo[3,4-c]pyridinyl, octahydro-5H-pyrrolo[3,2-c]pyridinyl, octahydro-6H-pyrrolo[3,4-b]pyridinyl, hexahydropyrrolo[1,2-a]pyrazin-(2H)-one, hexahydropyrrolo[1,2-a]pyrazin-(1H)-yl, hexahydro-1H-cyclobuta[1.2-c:1,4-c']dipyrrol-(3H)-yl, octahydropyrrolo[1,2-a]pyrazin-(1H)-yl, octahydro-2H-pyrido[1,2-a]pyrazinyl, hexahydropyrrolo[3,4-b][1,4]oxazin-(2H)-yl, 5-azaspiro[2.4]heptanyl, 1-azaspiro[3.3]heptanyl, 4-azaspiro[2.5]octanyl, 2-oxa-6-azaspiro[3.4]octanyl, 3-azabicyclo[3.1.0]hexanyl, 8-azabicyclo[3.2.1]octanyl, 8-azabicyclo[3.2.1]oct-2-en-yl, 9-azabicyclo[3.3.1]nonanyl, 2,5-diazabicyclo[2.2.1]heptanyl, 1,4-diazabicyclo[3.1.1]heptanyl, 3,6-diazabicyclo[3.2.0]heptanyl, 2,5-diazabicyclo[2.2.2]octanyl, 1,4-diazabicyclo[3.2.1]octanyl, 3,8-diazabicyclo[3.2.1]octanyl, 1,4-diazabicyclo[3.2.2]nonanyl, 4,7-diazaspiro[2.5]octanyl, 2,6-diazaspiro[3.3]heptanyl, 1,6-diazaspiro[3.4]octanyl, 2,6-diazaspiro[3.4]octanyl, 1,7,-diazaspiro[4.4]nonanyl, 1,7-diazaspiro[3.5]nonanyl, 2,6-diazaspiro[3.5]nonanyl, 2,7-diazaspiro[3.5]nonanyl, 5,8-diazaspiro[3.5]nonanyl, 2-oxa-5.8-diazaspiro[3.5]nonanyl, 2,7-diazaspiro[4.4]nonanyl, 2,7-diazaspiro[4.5]decanyl, 2,8-diazaspiro[4.5]decanyl, 6,9-diazaspiro[4.5]decyl, 6-oxa-2,9-diazaspiro[4.5]decanyl, 2,9-diazaspiro[5.5]undecanyl, 4-azadispiro[$2.1.2^5.3^3$]decanyl, and 7-azadispiro[$5.1.5^8.3^6$]hexadecanyl, optionally substituted where allowed by available valences with 1, 2, 3, 4, or 5 $R_b$ substituents.

Another aspect includes a compound of Formula (III), wherein B is unsubstituted heterocyclyl selected from azetidinyl, tetrahydrofuranyl, pyrrolidinyl, piperidinyl, piperidin-1-olate-yl, piperazinyl, 1,4-diazepanyl, 1,2-dihydropyridinyl, 1,2,5,6-tetrahydropyridinyl, 1,2,3,6-tetrahydropyridinyl, hexahydrocyclopentapyrrol-(1H)-yl, hexahydropyrrolo[3,2-b]pyrrol-(2H)-yl, hexahydropyrrolo[3,4-b]pyrrol-(2H)-yl, octahydro-2H-pyrrolo[3,4-c]pyridinyl, octahydro-5H-pyrrolo[3,2-c]pyridinyl, octahydro-6H-pyrrolo[3,4-b]pyridinyl, hexahydropyrrolo[1,2-a]pyrazin-(2H)-one, hexahydropyrrolo[1,2-a]pyrazin-(1H)-yl, hexahydro-1H-cyclobuta[1.2-c:1,4-c']dipyrrol-(3H)-yl, octahydropyrrolo[1,2-a]pyrazin-(1H)-yl, octahydro-2H-pyrido[1,2-a]pyrazinyl, hexahydropyrrolo[3,4-b][1,4]oxazin-(2H)-yl, 5-azaspiro[2.4]heptanyl, 1-azaspiro[3.3]heptanyl, 4-azaspiro[2.5]octanyl, 2-oxa-6-azaspiro[3.4]octanyl, 3-azabicyclo[3.1.0]hexanyl, 8-azabicyclo[3.2.1]octanyl, 8-azabicyclo[3.2.1]oct-2-en-yl, 9-azabicyclo[3.3.1]nonanyl, 2,5-diazabicyclo[2.2.1]heptanyl, 1,4-diazabicyclo[3.1.1]heptanyl, 3,6-diazabicyclo[3.2.0]heptanyl, 2,5-diazabicyclo[2.2.2]octanyl, 1,4-diazabicyclo[3.2.1]octanyl, 3,8-diazabicyclo[3.2.1]octanyl, 1,4-diazabicyclo[3.2.2]nonanyl, 4,7-diazaspiro[2.5]octanyl, 2,6-diazaspiro[3.3]heptanyl, 1,6-diazaspiro[3.4]octanyl, 2,6-diazaspiro[3.4]octanyl, 1,7,-diazaspiro[4.4]nonanyl, 1,7-diazaspiro[3.5]nonanyl, 2,6-diazaspiro[3.5]nonanyl, 2,7-diazaspiro[3.5]nonanyl, 5,8-diazaspiro[3.5]nonanyl, 2-oxa-5,8-diazaspiro[3.5]nonanyl, 2,7-diazaspiro[4.4]nonanyl, 2,7-diazaspiro[4.5]decanyl, 2,8-diazaspiro[4.5]decanyl, 6,9-diazaspiro[4.5]decyl, 6-oxa-2,9-diazaspiro[4.5]decanyl, 2,9-diazaspiro

[5.5]undecanyl, 4-azadispiro[2.1.2$^5$.3$^3$]decanyl, and 7-azadispiro[5.1.5$^8$.3$^6$]hexadecanyl.

Another aspect includes a compound of Formula (III), wherein B is heterocyclyl selected from azetidinyl, tetrahydrofuranyl, pyrrolidinyl, piperidinyl, piperidin-1-olate-yl, piperazinyl, 1,4-diazepanyl, 1,2-dihydropyridinyl, 1,2,5,6-tetrahydropyridinyl, 1,2,3,6-tetrahydropyridinyl, hexahydrocyclopentapyrrol-(1H)-yl, hexahydropyrrolo[3,2-b]pyrrol-(2H)-yl, hexahydropyrrolo[3,4-b]pyrrol-(2H)-yl, octahydro-2H-pyrrolo[3,4-c]pyridinyl, octahydro-5H-pyrrolo[3,2-c]pyridinyl, octahydro-6H-pyrrolo[3,4-b]pyridinyl, hexahydropyrrolo[1,2-a]pyrazin-(2H)-one, hexahydropyrrolo[1,2-a]pyrazin-(1H)-yl, hexahydro-1H-cyclobuta[1.2-c:1,4-c']dipyrrol-(3H)-yl, octahydropyrrolo[1,2-a]pyrazin-(1H)-yl, octahydro-2H-pyrido[1,2-a]pyrazinyl, hexahydropyrrolo[3,4-b][1,4]oxazin-(2H)-yl, 5-azaspiro[2.4]heptanyl, 1-azaspiro[3.3]heptanyl, 4-azaspiro[2.5]octanyl, 2-oxa-6-azaspiro[3.4]octanyl, 3-azabicyclo[3.1.0]hexanyl, 8-azabicyclo[3.2.1]octanyl, 8-azabicyclo[3.2.1]oct-2-en-yl, 9-azabicyclo[3.3.1]nonanyl, 2,5-diazabicyclo[2.2.1]heptanyl, 1,4-diazabicyclo[3.1.1]heptanyl, 3,6-diazabicyclo[3.2.0]heptanyl, 2,5-diazabicyclo[2.2.2]octanyl, 1,4-diazabicyclo[3.2.1]octanyl, 3.8-diazabicyclo[3.2.1]octanyl, 1,4-diazabicyclo[3.2.2]nonanyl, 4,7-diazaspiro[2.5]octanyl, 2,6-diazaspiro[3.3]heptanyl, 1,6-diazaspiro[3.4]octanyl, 2,6-diazaspiro[3.4]octanyl, 1,7,-diazaspiro[4.4]nonanyl, 1,7-diazaspiro[3.5]nonanyl, 2,6-diazaspiro[3.5]nonanyl, 2,7-diazaspiro[3.5]nonanyl, 5,8-diazaspiro[3.5]nonanyl, 2-oxa-5.8-diazaspiro[3.5]nonanyl, 2,7-diazaspiro[4.4]nonanyl, 2,7-diazaspiro[4.5]decanyl, 2,8-diazaspiro[4.5]decanyl, 6,9-diazaspiro[4.5]decyl, 6-oxa-2,9-diazaspiro[4.5]decanyl, 2,9-diazaspiro[5.5]undecanyl, 4-azadispiro[2.1.2$^5$.3$^3$]decanyl, and 7-azadispiro[5.1.5$^8$.3$^6$]hexadecanyl, substituted where allowed by available valences with one $R_b$ substituent.

Another aspect includes a compound of Formula (III), wherein B is heterocyclyl selected from azetidinyl, tetrahydrofuranyl, pyrrolidinyl, piperidinyl, piperidin-1-olate-yl, piperazinyl, 1,4-diazepanyl, 1,2-dihydropyridinyl, 1,2,5,6-tetrahydropyridinyl, 1,2,3,6-tetrahydropyridinyl, hexahydrocyclopentapyrrol-(1H)-yl, hexahydropyrrolo[3,2-b]pyrrol-(2H)-yl, hexahydropyrrolo[3,4-b]pyrrol-(2H)-yl, octahydro-2H-pyrrolo[3,4-c]pyridinyl, octahydro-5H-pyrrolo[3,2-c]pyridinyl, octahydro-6H-pyrrolo[3,4-b]pyridinyl, hexahydropyrrolo[1,2-a]pyrazin-(2H)-one, hexahydropyrrolo[1,2-a]pyrazin-(1H)-yl, hexahydro-1H-cyclobuta[1.2-c:1,4-c']dipyrrol-(3H)-yl, octahydropyrrolo[1,2-a]pyrazin-(1H)-yl, octahydro-2H-pyrido[1,2-a]pyrazinyl, hexahydropyrrolo[3,4-b][1,4]oxazin-(2H)-yl, 5-azaspiro[2.4]heptanyl, 1-azaspiro[3.3]heptanyl, 4-azaspiro[2.5]octanyl, 2-oxa-6-azaspiro[3.4]octanyl, 3-azabicyclo[3.1.0]hexanyl, 8-azabicyclo[3.2.1]octanyl, 8-azabicyclo[3.2.1]oct-2-en-yl, 9-azabicyclo[3.3.1]nonanyl, 2,5-diazabicyclo[2.2.1]heptanyl, 1,4-diazabicyclo[3.1.1]heptanyl, 3,6-diazabicyclo[3.2.0]heptanyl, 2,5-diazabicyclo[2.2.2]octanyl, 1,4-diazabicyclo[3.2.1]octanyl, 3,8-diazabicyclo[3.2.1]octanyl, 1,4-diazabicyclo[3.2.2]nonanyl, 4,7-diazaspiro[2.5]octanyl, 2,6-diazaspiro[3.3]heptanyl, 1,6-diazaspiro[3.4]octanyl, 2,6-diazaspiro[3.4]octanyl, 1,7,-diazaspiro[4.4]nonanyl, 1,7-diazaspiro[3.5]nonanyl, 2,6-diazaspiro[3.5]nonanyl, 2,7-diazaspiro[3.5]nonanyl, 5,8-diazaspiro[3.5]nonanyl, 2-oxa-5.8-diazaspiro[3.5]nonanyl, 2,7-diazaspiro[4.4]nonanyl, 2,7-diazaspiro[4.5]decanyl, 2,8-diazaspiro[4.5]decanyl, 6,9-diazaspiro[4.5]decyl, 6-oxa-2,9-diazaspiro[4.5]decanyl, 2,9-diazaspiro[5.5]undecanyl, 4-azadispiro[2.1.2$^5$.3$^3$]decanyl, and 7-azadispiro[5.1.5$^8$.3$^6$]hexadecanyl, substituted where allowed by available valences with two $R_b$ substituents.

Another aspect includes a compound of Formula (III), wherein B is heterocyclyl selected from azetidinyl, tetrahydrofuranyl, pyrrolidinyl, piperidinyl, piperidin-1-olate-yl, piperazinyl, 1,4-diazepanyl, 1,2-dihydropyridinyl, 1,2,5,6-tetrahydropyridinyl, 1,2,3,6-tetrahydropyridinyl, hexahydrocyclopentapyrrol-(1H)-yl, hexahydropyrrolo[3,2-b]pyrrol-(2H)-yl, hexahydropyrrolo[3,4-b]pyrrol-(2H)-yl, octahydro-2H-pyrrolo[3,4-c]pyridinyl, octahydro-5H-pyrrolo[3,2-c]pyridinyl, octahydro-6H-pyrrolo[3,4-b]pyridinyl, hexahydropyrrolo[1,2-a]pyrazin-(2H)-one, hexahydropyrrolo[1,2-a]pyrazin-(1H)-yl, hexahydro-1H-cyclobuta[1.2-c:1,4-c']dipyrrol-(3H)-yl, octahydropyrrolo[1,2-a]pyrazin-(1H)-yl, octahydro-2H-pyrido[1,2-a]pyrazinyl, hexahydropyrrolo[3,4-b][1,4]oxazin-(2H)-yl, 5-azaspiro[2.4]heptanyl, 1-azaspiro[3.3]heptanyl, 4-azaspiro[2.5]octanyl, 2-oxa-6-azaspiro[3.4]octanyl, 3-azabicyclo[3.1.0]hexanyl, 8-azabicyclo[3.2.1]octanyl, 8-azabicyclo[3.2.1]oct-2-en-yl, 9-azabicyclo[3.3.1]nonanyl, 2,5-diazabicyclo[2.2.1]heptanyl, 1,4-diazabicyclo[3.1.1]heptanyl, 3,6-diazabicyclo[3.2.0]heptanyl, 2,5-diazabicyclo[2.2.2]octanyl, 1,4-diazabicyclo[3.2.1]octanyl, 3,8-diazabicyclo[3.2.1]octanyl, 1,4-diazabicyclo[3.2.2]nonanyl, 4,7-diazaspiro[2.5]octanyl, 2,6-diazaspiro[3.3]heptanyl, 1,6-diazaspiro[3.4]octanyl, 2,6-diazaspiro[3.4]octanyl, 1,7,-diazaspiro[4.4]nonanyl, 1,7-diazaspiro[3.5]nonanyl, 2,6-diazaspiro[3.5]nonanyl, 2,7-diazaspiro[3.5]nonanyl, 5,8-diazaspiro[3.5]nonanyl, 2-oxa-5,8-diazaspiro[3.5]nonanyl, 2,7-diazaspiro[4.4]nonanyl, 2,7-diazaspiro[4.5]decanyl, 2,8-diazaspiro[4.5]decanyl, 6,9-diazaspiro[4.5]decyl, 6-oxa-2,9-diazaspiro[4.5]decanyl, 2,9-diazaspiro[5.5]undecanyl, 4-azadispiro[2.1.2$^5$.3$^3$]decanyl, and 7-azadispiro[5.1.5$^8$.3$^6$]hexadecanyl, substituted where allowed by available valences with three $R_b$ substituents.

Another aspect includes a compound of Formula (III), wherein B is heterocyclyl selected from azetidinyl, tetrahydrofuranyl, pyrrolidinyl, piperidinyl, piperidin-1-olate-yl, piperazinyl, 1.4-diazepanyl, 1,2-dihydropyridinyl, 1,2,5,6-tetrahydropyridinyl, 1,2,3,6-tetrahydropyridinyl, hexahydrocyclopentapyrrol-(1H)-yl, hexahydropyrrolo[3,2-b]pyrrol-(2H)-yl, hexahydropyrrolo[3,4-b]pyrrol-(2H)-yl, octahydro-2H-pyrrolo[3,4-c]pyridinyl, octahydro-5H-pyrrolo[3.2-c]pyridinyl, octahydro-6H-pyrrolo[3,4-b]pyridinyl, hexahydropyrrolo[1,2-a]pyrazin-(2H)-one, hexahydropyrrolo[1,2-a]pyrazin-(1H)-yl, hexahydro-1H-cyclobuta[1.2-c:1,4-c']dipyrrol-(3H)-yl, octahydropyrrolo[1,2-a]pyrazin-(1H)-yl, octahydro-2H-pyrido[1,2-a]pyrazinyl, hexahydropyrrolo[3,4-b][1,4]oxazin-(2H)-yl, 5-azaspiro[2.4]heptanyl, 1-azaspiro[3.3]heptanyl, 4-azaspiro[2.5]octanyl, 2-oxa-6-azaspiro[3.4]octanyl, 3-azabicyclo[3.1.0]hexanyl, 8-azabicyclo[3.2.1]octanyl, 8-azabicyclo[3.2.1]oct-2-en-yl, 9-azabicyclo[3.3.1]nonanyl, 2,5-diazabicyclo[2.2.1]heptanyl, 1,4-diazabicyclo[3.1.1]heptanyl, 3,6-diazabicyclo[3.2.0]heptanyl, 2.5-diazabicyclo[2.2.2]octanyl, 1,4-diazabicyclo[3.2.1]octanyl, 3,8-diazabicyclo[3.2.1]octanyl, 1,4-diazabicyclo[3.2.2]nonanyl, 4,7-diazaspiro[2.5]octanyl, 2,6-diazaspiro[3.3]heptanyl, 1,6-diazaspiro[3.4]octanyl, 2,6-diazaspiro[3.4]octanyl, 1,7,-diazaspiro[4.4]nonanyl, 1,7-diazaspiro[3.5]nonanyl, 2,6-diazaspiro[3.5]nonanyl, 2,7-diazaspiro[3.5]nonanyl, 5,8-diazaspiro[3.5]nonanyl, 2-oxa-5,8-diazaspiro[3.5]nonanyl, 2,7-diazaspiro[4.4]nonanyl, 2,7-diazaspiro[4.5]decanyl, 2,8-diazaspiro[4.5]decanyl, 6,9-diazaspiro[4.5]decyl, 6-oxa-2,9-diazaspiro[4.5]decanyl, 2,9-diazaspiro[5.5]undecanyl, 4-azadispiro

[2.1.2$^5$.3$^3$]decanyl, and 7-azadispiro[5.1.5$^8$.3$^6$]hexadecanyl, substituted where allowed by available valences with four $R_b$ substituents.

Another aspect includes a compound of Formula (II), wherein B is heterocyclyl selected from azetidinyl, tetrahydrofuranyl, pyrrolidinyl, piperidinyl, piperidin-1-olate-yl, piperazinyl, 1,4-diazepanyl, 1,2-dihydropyridinyl, 1,2,5,6-tetrahydropyridinyl, 1,2,3,6-tetrahydropyridinyl, hexahydrocyclopentapyrrol-(1H)-yl, hexahydropyrrolo[3,2-b]pyrrol-(2H)-yl, hexahydropyrrolo[3,4-b]pyrrol-(2H)-yl, octahydro-2H-pyrrolo[3,4-c]pyridinyl, octahydro-5H-pyrrolo[3,2-c]pyridinyl, octahydro-6H-pyrrolo[3,4-b]pyridinyl, hexahydropyrrolo[1,2-a]pyrazin-(2H)-one, hexahydropyrrolo[1,2-a]pyrazin-(1H)-yl, hexahydro-1H-cyclobuta[1.2-c:1.4-c']dipyrrol-(3H)-yl, octahydropyrrolo[1,2-a]pyrazin-(1H)-yl, octahydro-2H-pyrido[1,2-a]pyrazinyl, hexahydropyrrolo[3,4-b][1,4]oxazin-(2H)-yl, 5-azaspiro[2.4]heptanyl, 1-azaspiro[3.3]heptanyl, 4-azaspiro[2.5]octanyl, 2-oxa-6-azaspiro[3.4]octanyl, 3-azabicyclo[3.1.0]hexanyl, 8-azabicyclo[3.2.1]octanyl, 8-azabicyclo[3.2.1]oct-2-en-yl, 9-azabicyclo[3.3.1]nonanyl, 2,5-diazabicyclo[2.2.1]heptanyl, 1,4-diazabicyclo[3.1.1]heptanyl, 3,6-diazabicyclo[3.2.0]heptanyl, 2,5-diazabicyclo[2.2.2]octanyl, 1,4-diazabicyclo[3.2.1]octanyl, 3,8-diazabicyclo[3.2.1]octanyl, 1,4-diazabicyclo[3.2.2]nonanyl, 4,7-diazaspiro[2.5]octanyl, 2,6-diazaspiro[3.3]heptanyl, 1,6-diazaspiro[3.4]octanyl, 2,6-diazaspiro[3.4]octanyl, 1.7,-diazaspiro[4.4]nonanyl, 1,7-diazaspiro[3.5]nonanyl, 2,6-diazaspiro[3.5]nonanyl, 2,7-diazaspiro[3.5]nonanyl, 5,8-diazaspiro[3.5]nonanyl, 2-oxa-5,8-diazaspiro[3.5]nonanyl, 2,7-diazaspiro[4.4]nonanyl, 2,7-diazaspiro[4.5]decanyl, 2,8-diazaspiro[4.5]decanyl, 6,9-diazaspiro[4.5]decyl, 6-oxa-2,9-diazaspiro[4.5]decanyl, 2,9-diazaspiro[5.5]undecanyl, 4-azadispiro[2.1.2$^5$.3$^3$]decanyl, and 7-azadispiro[5.1.5$^8$.3$^6$]hexadecanyl, substituted where allowed by available valences with five $R_b$ substituents.

Another aspect includes a compound of Formula (III), wherein B is heterocyclyl selected from piperidinyl and piperazinyl, optionally substituted where allowed by available valences with 1, 2, 3, 4, or 5 $R_b$ substituents.

Another aspect includes a compound of Formula (III), wherein B is unsubstituted heterocyclyl selected from piperidinyl and piperazinyl.

Another aspect includes a compound of Formula (III), wherein B is heterocyclyl selected from piperidinyl and piperazinyl, substituted where allowed by available valences with one $R_b$ substituent.

Another aspect includes a compound of Formula (III), wherein B is heterocyclyl selected from piperidinyl and piperazinyl, substituted where allowed by available valences with two $R_b$ substituents.

Another aspect includes a compound of Formula (III), wherein B is heterocyclyl selected from piperidinyl and piperazinyl, substituted where allowed by available valences with three $R_b$ substituents.

Another aspect includes a compound of Formula (III), wherein B is heterocyclyl selected from piperidinyl and piperazinyl, substituted where allowed by available valences with four $R_b$ substituents.

Another aspect includes a compound of Formula (III), wherein B is heterocyclyl selected from piperidinyl and piperazinyl, substituted where allowed by available valences with five $R_b$ substituents.

Another aspect includes a compound of Formula (III), wherein B is piperidinyl, substituted where allowed by available valences with four $R_b$ substituents.

Another aspect includes a compound of Formula (III), wherein B is piperazinyl, substituted where allowed by available valences with two $R_b$ substituents.

Another aspect includes a compound of Formula (III), wherein B is heterocyclyl selected from azetidin-1-yl, tetrahydrofuran-3-yl, pyrrolidin-1-yl, pyrrolidin-3-yl, piperidin-1-yl, piperidin-3-yl, piperidin-4-yl, piperidin-1-olate-4-yl, piperazin-1-yl, 1,4-diazepan-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,2,5,6-tetrahydropyridin-5-yl, 1,2,3,6-tetrahydropyridin-4-yl, hexahydrocyclopentapyrrol-2(1H)-yl, hexahydropyrrolo[3,2-b]pyrrol-1(2H)-yl, hexahydropyrrolo[3,4-b]pyrrol-1(2H)-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, octahydro-5H-pyrrolo[3,2-c]pyridin-5-yl, octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, hexahydro-1H-cyclobuta[1.2-c:1,4-c']dipyrrol-2(3H)-yl, octahydropyrrolo[1,2-a]pyrazin-2(1H)-yl, octahydro-2H-pyrido[1,2-a]pyrazin-2-yl, hexahydropyrrolo[3,4-b][1,4]oxazin-6(2H)-yl, 5-azaspiro[2.4]heptan-5-yl, 1-azaspiro[3.3]heptan-2-yl, 4-azaspiro[2.5]octan-7-yl, 2-oxa-6-azaspiro[3.4]octan-6-yl, 3-azabicyclo[3.1.0]hexan-3-yl, 8-azabicyclo[3.2.1]octan-3-yl, 8-azabicyclo[3.2.1]oct-2-en-3-yl, 9-azabicyclo[3.3.1]nonan-3-yl, 2,5-diazabicyclo[2.2.1]heptan-2-yl, 1,4-diazabicyclo[3.1.1]heptan-4-yl, 3,6-diazabicyclo[3.2.0]heptan-3-yl, 3,6-diazabicyclo[3.2.0]heptan-6-yl, 2,5-diazabicyclo[2.2.2]octan-2-yl, 1,4-diazabicyclo[3.2.1]octan-4-yl, 3,8-diazabicyclo[3.2.1]octan-3-yl, 1,4-diazabicyclo[3.2.2]nonan-4-yl, 4,7-diazaspiro[2.5]octan-4-yl, 4,7-diazaspiro[2.5]octan-7-yl, 2,6-diazaspiro[3.3]heptan-2-yl, 1,6-diazaspiro[3.4]octan-6-yl, 2,6-diazaspiro[3.4]octan-2-yl, 2,6-diazaspiro[3.4]octan-6-yl, 1,7,-diazaspiro[4.4]nonan-1-yl, 1,7,-diazaspiro[4.4]nonan-7-yl, 1,7-diazaspiro[3.5]nonan-7-yl, 2,6-diazaspiro[3.5]nonan-2-yl, 2,6-diazaspiro[3.5]nonan-6-yl, 1,7-diazaspiro[3.5]nonan-7-yl, 2,7-diazaspiro[3.5]nonan-2-yl, 2,7-diazaspiro[3.5]nonan-7-yl, 5,8-diazaspiro[3.5]nonan-8-yl, 2-oxa-5,8-diazaspiro[3.5]nonan-8-yl, 2,7-diazaspiro[4.4]nonan-2-yl, 2,7-diazaspiro[4.5]decan-2-yl, 2.7-diazaspiro[4.5]decan-7-yl, 2,8-diazaspiro[4.5]decan-8-yl, 6,9-diazaspiro[4.5]dec-9-yl, 6-oxa-2,9-diazaspiro[4.5]decan-2-yl, 2,9-diazaspiro[5.5]undecan-9-yl, 4-azadispiro[2.1.2$^5$.3$^3$]decan-9-yl, and 7-azadispiro[5.1.5$^8$.3$^6$]hexadecan-15-yl, optionally substituted where allowed by available valences with 1, 2, 3, 4, or 5 $R_b$ substituents.

Another aspect includes a compound of Formula (III), wherein B is unsubstituted heterocyclyl selected from azetidin-1-yl, tetrahydrofuran-3-yl, pyrrolidin-1-yl, pyrrolidin-3-yl, piperidin-1-yl, piperidin-3-yl, piperidin-4-yl, piperidin-1-olate-4-yl, piperazin-1-v, 1,4-diazepan-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,2,5,6-tetrahydropyridin-5-yl, 1,2,3,6-tetrahydropyridin-4-yl, hexahydrocyclopentapyrrol-2(1H)-yl, hexahydropyrrolo[3,2-b]pyrrol-1(2H)-yl, hexahydropyrrolo[3,4-b]pyrrol-1(2H)-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, octahydro-5H-pyrrolo[3,2-c]pyridin-5-yl, octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, hexahydro-1H-cyclobuta[1.2-c:1,4-c']dipyrrol-2(3H)-yl, octahydropyrrolo[1,2-a]pyrazin-2(1H)-yl, octahydro-2H-pyrido[1,2-a]pyrazin-2-yl, hexahydropyrrolo[3,4-b][1,4]

oxazin-6(2H)-yl, 5-azaspiro[2.4]heptan-5-yl, I-azaspiro[3.3]heptan-2-yl, 4-azaspiro[2.5]octan-7-yl, 2-oxa-6-azaspiro[3.4]octan-6-yl, 3-azabicyclo[3.1.0]hexan-3-yl, 8-azabicyclo[3.2.1]octan-3-yl, 8-azabicyclo[3.2.1]oct-2-en-3-yl, 9-azabicyclo[3.3.1]nonan-3-yl, 2,5-diazabicyclo[2.2.1]heptan-2-yl, 1,4-diazabicyclo[3.1.1]heptan-4-yl, 3,6-diazabicyclo[3.2.0]heptan-3-yl, 3,6-diazabicyclo[3.2.0]heptan-6-yl, 2,5-diazabicyclo[2.2.2]octan-2-yl, 1,4-diazabicyclo[3.2.1]octan-4-yl, 3,8-diazabicyclo[3.2.1]octan-3-yl, 1,4-diazabicyclo[3.2.2]nonan-4-yl, 4,7-diazaspiro[2.5]octan-4-yl, 4,7-diazaspiro[2.5]octan-7-yl, 2,6-diazaspiro[3.3]heptan-2-yl, 1,6-diazaspiro[3.4]octan-6-yl, 2,6-diazaspiro[3.4]octan-2-yl, 2,6-diazaspiro[3.4]octan-6-yl, 1,7,-diazaspiro[4.4]nonan-1-yl, 1,7,-diazaspiro[4.4]nonan-7-yl, 1,7-diazaspiro[3.5]nonan-7-yl, 2,6-diazaspiro[3.5]nonan-2-yl, 2.6-diazaspiro[3.5]nonan-6-yl, 1,7-diazaspiro[3.5]nonan-7-yl, 2,7-diazaspiro[3.5]nonan-2-yl, 2,7-diazaspiro[3.5]nonan-7-yl, 5,8-diazaspiro[3.5]nonan-8-yl, 2-oxa-5,8-diazaspiro[3.5]nonan-8-yl, 2,7-diazaspiro[4.4]nonan-2-yl, 2,7-diazaspiro[4.5]decan-2-yl, 2,7-diazaspiro[4.5]decan-7-yl, 2,8-diazaspiro[4.5]decan-8-yl, 6,9-diazaspiro[4.5]dec-9-yl, 6-oxa-2,9-diazaspiro[4.5]decan-2-yl, 2,9-diazaspiro[5.5]undecan-9-yl, 4-azadispiro$[2.1.2^5.3^3]$decan-9-yl, and 7-azadispiro$[5.1.5^8.3^6]$hexadecan-15-yl.

Another aspect includes a compound of Formula (III), wherein B is heterocyclyl selected from azetidin-1-yl, tetrahydrofuran-3-yl, pyrrolidin-1-yl, pyrrolidin-3-yl, piperidin-1-yl, piperidin-3-yl, piperidin-4-yl, piperidin-1-olate-4-yl, piperazin-1-yl, 1,4-diazepan-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,2,5,6-tetrahydropyridin-5-yl, 1,2,3,6-tetrahydropyridin-4-yl, hexahydrocyclopentapyrrol-2(1H)-yl, hexahydropyrrolo[3,2-b]pyrrol-1(2H)-yl, hexahydropyrrolo[3,4-b]pyrrol-1(2H)-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, octahydro-5H-pyrrolo[3,2-c]pyridin-5-yl, octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, hexahydro-1H-cyclobuta[1.2-c:1,4-c']dipyrrol-2(3H)-yl, octahydropyrrolo[1,2-a]pyrazin-2(1H)-yl, octahydro-2H-pyrido[1,2-a]pyrazin-2-yl, hexahydropyrrolo[3,4-b][1,4]oxazin-6(2H)-yl, 5-azaspiro[2.4]heptan-5-yl, 1-azaspiro[3.3]heptan-2-yl, 4-azaspiro[2.5]octan-7-yl, 2-oxa-6-azaspiro[3.4]octan-6-yl, 3-azabicyclo[3.1.0]hexan-3-yl, 8-azabicyclo[3.2.1]octan-3-yl, 8-azabicyclo[3.2.1]oct-2-en-3-yl, 9-azabicyclo[3.3.1]nonan-3-yl, 2,5-diazabicyclo[2.2.1]heptan-2-yl, 1,4-diazabicyclo[3.1.1]heptan-4-yl, 3,6-diazabicyclo[3.2.0]heptan-3-yl, 3,6-diazabicyclo[3.2.0]heptan-6-yl, 2,5-diazabicyclo[2.2.2]octan-2-yl, 1,4-diazabicyclo[3.2.1]octan-4-yl, 3,8-diazabicyclo[3.2.1]octan-3-yl, 1,4-diazabicyclo[3.2.2]nonan-4-yl, 4,7-diazaspiro[2.5]octan-4-yl, 4.7-diazaspiro[2.5]octan-7-yl, 2,6-diazaspiro[3.3]heptan-2-yl, 1,6-diazaspiro[3.4]octan-6-yl, 2,6-diazaspiro[3.4]octan-2-yl, 2,6-diazaspiro[3.4]octan-6-yl, 1,7,-diazaspiro[4.4]nonan-1-yl, 1,7,-diazaspiro[4.4]nonan-7-yl, 1,7-diazaspiro[3.5]nonan-7-yl, 2,6-diazaspiro[3.5]nonan-2-yl, 2,6-diazaspiro[3.5]nonan-6-yl, 1,7-diazaspiro[3.5]nonan-7-yl, 2,7-diazaspiro[3.5]nonan-2-yl, 2,7-diazaspiro[3.5]nonan-7-yl, 5,8-diazaspiro[3.5]nonan-8-yl, 2-oxa-5,8-diazaspiro[3.5]nonan-8-yl, 2,7-diazaspiro[4.4]nonan-2-yl, 2,7-diazaspiro[4.5]decan-2-yl, 2,7-diazaspiro[4.5]decan-7-yl, 2,8-diazaspiro[4.5]decan-8-yl, 6,9-diazaspiro[4.5]dec-9-yl, 6-oxa-2,9-diazaspiro[4.5]decan-2-yl, 2,9-diazaspiro[5.5]undecan-9-yl, 4-azadispiro$[2.1.2^5.3^3]$decan-9-yl, and 7-azadispiro$[5.1.5^8.3^6]$hexadecan-15-yl, substituted where allowed by available valences with one $R_b$ substituent.

Another aspect includes a compound of Formula (III), wherein B is heterocyclyl selected from azetidin-1-yl, tetrahydrofuran-3-yl, pyrrolidin-1-yl, pyrrolidin-3-yl, piperidin-1-yl, piperidin-3-yl, piperidin-4-yl, piperidin-1-olate-4-yl, piperazin-1-yl, 1,4-diazepan-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,2,5,6-tetrahydropyridin-5-yl, 1,2,3,6-tetrahydropyridin-4-yl, hexahydrocyclopentapyrrol-2(1H)-yl, hexahydropyrrolo[3,2-b]pyrrol-1(2H)-yl, hexahydropyrrolo[3,4-b]pyrrol-1(2H)-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, octahydro-5H-pyrrolo[3,2-c]pyridin-5-yl, octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, hexahydro-1H-cyclobuta[1.2-c:1,4-c']dipyrrol-2(3H)-yl, octahydropyrrolo[1,2-a]pyrazin-2(1H)-yl, octahydro-2H-pyrido[1,2-a]pyrazin-2-yl, hexahydropyrrolo[3,4-b][1,4]oxazin-6(2H)-yl, 5-azaspiro[2.4]heptan-5-yl, 1-azaspiro[3.3]heptan-2-yl, 4-azaspiro[2.5]octan-7-yl, 2-oxa-6-azaspiro[3.4]octan-6-yl, 3-azabicyclo[3.1.0]hexan-3-yl, 8-azabicyclo[3.2.1]octan-3-yl, 8-azabicyclo[3.2.1]oct-2-en-3-yl, 9-azabicyclo[3.3.1]nonan-3-yl, 2,5-diazabicyclo[2.2.1]heptan-2-yl, 1,4-diazabicyclo[3.1.1]heptan-4-yl, 3,6-diazabicyclo[3.2.0]heptan-3-yl, 3,6-diazabicyclo[3.2.0]heptan-6-yl, 2,5-diazabicyclo[2.2.2]octan-2-yl, 1,4-diazabicyclo[3.2.1]octan-4-yl, 3,8-diazabicyclo[3.2.1]octan-3-yl, 1,4-diazabicyclo[3.2.2]nonan-4-yl, 4,7-diazaspiro[2.5]octan-4-yl, 4,7-diazaspiro[2.5]octan-7-yl, 2,6-diazaspiro[3.3]heptan-2-yl, 1,6-diazaspiro[3.4]octan-6-yl, 2,6-diazaspiro[3.4]octan-2-yl, 2,6-diazaspiro[3.4]octan-6-yl, 1,7,-diazaspiro[4.4]nonan-1-yl, 1,7,-diazaspiro[4.4]nonan-7-yl, 1,7-diazaspiro[3.5]nonan-7-yl, 2,6-diazaspiro[3.5]nonan-2-yl, 2,6-diazaspiro[3.5]nonan-6-yl, 1,7-diazaspiro[3.5]nonan-7-yl, 2,7-diazaspiro[3.5]nonan-2-yl, 2,7-diazaspiro[3.5]nonan-7-yl, 5,8-diazaspiro[3.5]nonan-8-yl, 2-oxa-5,8-diazaspiro[3.5]nonan-8-yl, 2,7-diazaspiro[4.4]nonan-2-yl, 2,7-diazaspiro[4.5]decan-2-yl, 2,7-diazaspiro[4.5]decan-7-yl, 2,8-diazaspiro[4.5]decan-8-yl, 6,9-diazaspiro[4.5]dec-9-yl, 6-oxa-2,9-diazaspiro[4.5]decan-2-yl, 2,9-diazaspiro[5.5]undecan-9-yl, 4-azadispiro$[2.1.2^5.3]$decan-9-yl, and 7-azadispiro$[5.1.5^8.3^6]$hexadecan-15-yl, substituted where allowed by available valences with two $R_b$ substituents.

Another aspect includes a compound of Formula (II), wherein B is heterocyclyl selected from azetidin-1-yl, tetrahydrofuran-3-yl, pyrrolidin-1-yl, pyrrolidin-3-yl, piperidin-1-yl, piperidin-3-yl, piperidin-4-yl, piperidin-1-olate-4-yl, piperazin-1-yl, 1,4-diazepan-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,2,5,6-tetrahydropyridin-5-yl, 1,2,3,6-tetrahydropyridin-4-yl, hexahydrocyclopentapyrrol-2(1H)-yl, hexahydropyrrolo[3,2-b]pyrrol-1(2H)-yl, hexahydropyrrolo[3,4-b]pyrrol-1(2H)-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, octahydro-5H-pyrrolo[3,2-c]pyridin-5-yl, octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, hexahydro-1H-cyclobuta[1.2-c:1,4-c']dipyrrol-2(3H)-yl, octahydropyrrolo[1,2-a]pyrazin-2(1H)-yl, octahydro-2H-pyrido[1,2-a]pyrazin-2-yl, hexahydropyrrolo[3,4-b][1,4]oxazin-6(2H)-yl, 5-azaspiro[2.4]heptan-5-yl, 1-azaspiro[3.3]heptan-2-yl, 4-azaspiro[2.5]octan-7-yl, 2-oxa-6-azaspiro[3.4]octan-6-yl, 3-azabicyclo[3.1.0]hexan-3-yl, 8-azabicyclo[3.2.1]octan-3-yl, 8-azabicyclo[3.2.1]oct-2-en-3-yl, 9-azabicyclo[3.3.1]nonan-3-yl, 2,5-diazabicyclo[2.2.1]heptan-2-yl, 1,4-diazabicyclo[3.1.1]heptan-4-yl, 3,6-diazabicyclo[3.2.0]heptan-3-yl, 3,6-diazabicyclo[3.2.0]heptan-6-yl, 2,5-diazabicyclo[2.2.2]octan-2-yl, 1,4-diazabicyclo[3.2.1]octan-4-yl, 3,8-diazabicyclo[3.2.1]octan-3-yl, 1,4-diazabicyclo[3.2.2]nonan-4-yl, 4,7-diazaspiro[2.5]octan-4-yl, 4.7-diazaspiro[2.5]octan-7-yl, 2,6-diazaspiro[3.3]heptan-2-yl, 1,6-diazaspiro[3.4]octan-6-yl, 2.6-diazaspiro[3.4]octan-2-yl, 2,6-diazaspiro[3.4]octan-6-yl, 1,7,-diazaspiro[4.4]nonan-1-yl, 1,7,-diazaspiro[4.4]nonan-7-yl, 1,7-diazaspiro[3.5]nonan-7-yl, 2,6-diazaspiro[3.5]nonan-2-yl, 2,6-diazaspiro[3.5]nonan-6-yl, 1,7-diazaspiro[3.5]nonan-7-yl, 2,7-diazaspiro[3.5]nonan-2-yl, 2.7-diazaspiro[3.5]nonan-7-yl, 5,8-diazaspiro[3.5]nonan-8-yl, 2-oxa-5.8-diazaspiro[3.5]nonan-8-yl, 2,7-diazaspiro[4.4]nonan-2-yl, 2,7-diazaspiro[4.5]decan-2-yl, 2,7-diazaspiro[4.5]decan-7-yl, 2,8-diazaspiro[4.5]decan-8-yl, 6,9-diazaspiro[4.5]dec-9-yl, 6-oxa-2,9-diazaspiro[4.5]decan-2-yl, 2,9-diazaspiro[5.5]undecan-9-yl, 4-azadispiro[2.1.$2^5$.3]decan-9-yl, and 7-azadispiro[5.1.$5^8$.$3^6$]hexadecan-15-yl, substituted where allowed by available valences with three $R_b$ substituents.

Another aspect includes a compound of Formula (III), wherein B is heterocyclyl selected from azetidin-1-yl, tetrahydrofuran-3-yl, pyrrolidin-1-yl, pyrrolidin-3-yl, piperidin-1-yl, piperidin-3-yl, piperidin-4-yl, piperidin-1-olate-4-yl, piperazin-1-yl, 1,4-diazepan-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,2,5,6-tetrahydropyridin-5-yl, 1,2,3,6-tetrahydropyridin-4-yl, hexahydrocyclopentapyrrol-2(1H)-yl, hexahydropyrrolo[3,2-b]pyrrol-1(2H)-yl, hexahydropyrrolo[3,4-b]pyrrol-1(2H)-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, octahydro-5H-pyrrolo[3,2-c]pyridin-5-yl, octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, hexahydro-1H-cyclobuta[1.2-c:1,4-c']dipyrrol-2(3H)-yl, octahydropyrrolo[1,2-a]pyrazin-2(1H)-yl, octahydro-2H-pyrido[1,2-a]pyrazin-2-yl, hexahydropyrrolo[3,4-b][1,4]oxazin-6(2H)-yl, 5-azaspiro[2.4]heptan-5-yl, 1-azaspiro[3.3]heptan-2-yl, 4-azaspiro[2.5]octan-7-yl, 2-oxa-6-azaspiro[3.4]octan-6-yl, 3-azabicyclo[3.1.0]hexan-3-yl, 8-azabicyclo[3.2.1]octan-3-yl, 8-azabicyclo[3.2.1]oct-2-en-3-yl, 9-azabicyclo[3.3.1]nonan-3-yl, 2,5-diazabicyclo[2.2.1]heptan-2-yl, 1,4-diazabicyclo[3.1.1]heptan-4-yl, 3,6-diazabicyclo[3.2.0]heptan-3-yl, 3,6-diazabicyclo[3.2.0]heptan-6-yl, 2,5-diazabicyclo[2.2.2]octan-2-yl, 1,4-diazabicyclo[3.2.1]octan-4-yl, 3,8-diazabicyclo[3.2.1]octan-3-yl, 1,4-diazabicyclo[3.2.2]nonan-4-yl, 4,7-diazaspiro[2.5]octan-4-yl, 4,7-diazaspiro[2.5]octan-7-yl, 2,6-diazaspiro[3.3]heptan-2-yl, 1,6-diazaspiro[3.4]octan-6-yl, 2,6-diazaspiro[3.4]octan-2-yl, 2,6-diazaspiro[3.4]octan-6-yl, 1,7,-diazaspiro[4.4]nonan-1-yl, 1,7,-diazaspiro[4.4]nonan-7-yl, 1,7-diazaspiro[3.5]nonan-7-yl, 2,6-diazaspiro[3.5]nonan-2-yl, 2,6-diazaspiro[3.5]nonan-6-yl, 1,7-diazaspiro[3.5]nonan-7-yl, 2,7-diazaspiro[3.5]nonan-2-yl, 2,7-diazaspiro[3.5]nonan-7-yl, 5,8-diazaspiro[3.5]nonan-8-yl, 2-oxa-5,8-diazaspiro[3.5]nonan-8-yl, 2,7-diazaspiro[4.4]nonan-2-yl, 2,7-diazaspiro[4.5]decan-2-yl, 2,7-diazaspiro[4.5]decan-7-yl, 2,8-diazaspiro[4.5]decan-8-yl, 6,9-diazaspiro[4.5]dec-9-yl, 6-oxa-2,9-diazaspiro[4.5]decan-2-yl, 2,9-diazaspiro[5.5]undecan-9-yl, 4-azadispiro[2.1.$2^5$.$3^3$]decan-9-yl, and 7-azadispiro[5.1.$5^8$.$3^6$]hexadecan-15-yl, substituted where allowed by available valences with four $R_b$ substituents.

Another aspect includes a compound of Formula (III), wherein B is heterocyclyl selected from azetidin-1-yl, tetrahydrofuran-3-yl, pyrrolidin-1-yl, pyrrolidin-3-yl, piperidin-1-yl, piperidin-3-yl, piperidin-4-yl, piperidin-1-olate-4-yl, piperazin-1-yl, 1,4-diazepan-1-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 1,2,5,6-tetrahydropyridin-5-yl, 1,2,3,6-tetrahydropyridin-4-yl, hexahydrocyclopentapyrrol-2(1H)-yl, hexahydropyrrolo[3,2-b]pyrrol-1(2H)-yl, hexahydropyrrolo[3,4-b]pyrrol-1(2H)-yl, hexahydropyrrolo[3,4-c]pyrrol-1(1H)-yl, hexahydropyrrolo[3,4-c]pyrrol-2(1H)-yl, hexahydropyrrolo[3,4-c]pyrrol-5(1H)-yl, octahydro-5H-pyrrolo[3,2-c]pyridin-5-yl, octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, hexahydro-1H-cyclobuta[1.2-c:1,4-c']dipyrrol-2(3H)-yl, octahydropyrrolo[1,2-a]pyrazin-2(1H)-yl, octahydro-2H-pyrido[1,2-a]pyrazin-2-yl, hexahydropyrrolo[3,4-b][1,4]oxazin-6(2H)-yl, 5-azaspiro[2.4]heptan-5-yl, 1-azaspiro[3.3]heptan-2-yl, 4-azaspiro[2.5]octan-7-yl, 2-oxa-6-azaspiro[3.4]octan-6-yl, 3-azabicyclo[3.1.0]hexan-3-yl, 8-azabicyclo[3.2.1]octan-3-yl, 8-azabicyclo[3.2.1]oct-2-en-3-yl, 9-azabicyclo[3.3.1]nonan-3-yl, 2,5-diazabicyclo[2.2.1]heptan-2-yl, 1,4-diazabicyclo[3.1.1]heptan-4-yl, 3,6-diazabicyclo[3.2.0]heptan-3-yl, 3,6-diazabicyclo[3.2.0]heptan-6-yl, 2,5-diazabicyclo[2.2.2]octan-2-yl, 1,4-diazabicyclo[3.2.1]octan-4-yl, 3,8-diazabicyclo[3.2.1]octan-3-yl, 1,4-diazabicyclo[3.2.2]nonan-4-yl, 4,7-diazaspiro[2.5]octan-4-yl, 4,7-diazaspiro[2.5]octan-7-yl, 2,6-diazaspiro[3.3]heptan-2-yl, 1,6-diazaspiro[3.4]octan-6-yl, 2.6-diazaspiro[3.4]octan-2-yl, 2,6-diazaspiro[3.4]octan-6-yl, 1,7,-diazaspiro[4.4]nonan-1-yl, 1,7,-diazaspiro[4.4]nonan-7-yl, 1,7-diazaspiro[3.5]nonan-7-yl, 2,6-diazaspiro[3.5]nonan-2-yl, 2,6-diazaspiro[3.5]nonan-6-yl, 1,7-diazaspiro[3.5]nonan-7-yl, 2,7-diazaspiro[3.5]nonan-2-yl, 2,7-diazaspiro[3.5]nonan-7-yl, 5,8-diazaspiro[3.5]nonan-8-yl, 2-oxa-5,8-diazaspiro[3.5]nonan-8-yl, 2,7-diazaspiro[4.4]nonan-2-yl, 2,7-diazaspiro[4.5]decan-2-yl, 2,7-diazaspiro[4.5]decan-7-yl, 2,8-diazaspiro[4.5]decan-8-yl, 6,9-diazaspiro[4.5]dec-9-yl, 6-oxa-2,9-diazaspiro[4.5]decan-2-yl, 2,9-diazaspiro[5.5]undecan-9-yl, 4-azadispiro[2.1.$2^5$.3]decan-9-yl, and 7-azadispiro[5.1.$5^8$.$3^6$]hexadecan-15-yl, substituted where allowed by available valences with five $R_b$ substituents.

Another aspect includes a compound of Formula (III), wherein B is heterocyclyl selected from piperidin-4-yl and piperazin-1-yl, optionally substituted where allowed by available valences with 1, 2, 3, 4, or 5 $R_b$ substituents.

Another aspect includes a compound of Formula (III), wherein B is unsubstituted heterocyclyl selected from piperidin-4-yl and piperazin-1-yl.

Another aspect includes a compound of Formula (III), wherein B is heterocyclyl selected from piperidin-4-yl and piperazin-1-yl, substituted where allowed by available valences with one $R_b$ substituent.

Another aspect includes a compound of Formula (MII), wherein B is heterocyclyl selected from piperidin-4-yl and piperazin-1-yl, substituted where allowed by available valences with two $R_b$ substituents.

Another aspect includes a compound of Formula (III), wherein B is heterocyclyl selected from piperidin-4-yl and piperazin-1-yl, substituted where allowed by available valences with three $R_b$ substituents.

Another aspect includes a compound of Formula (III), wherein B is heterocyclyl selected from piperidin-4-yl and piperazin-1-yl, substituted where allowed by available valences with four $R_b$ substituents.

Another aspect includes a compound of Formula (III), wherein B is heterocyclyl selected from piperidin-4-yl and piperazin-1-yl, substituted where allowed by available valences with five $R_b$ substituents.

Another aspect includes a compound of Formula (III), wherein B is piperidin-4-yl, substituted where allowed by available valences with four $R_b$ substituents.

Another aspect includes a compound of Formula (III), wherein B is heterocyclyl selected from piperazin-4-yl, substituted where allowed by available valences with two $R_b$ substituents.

Another aspect includes a compound of Formula (III), wherein B is heterocyclyl containing at least one chiral carbon atom having an (R) configuration.

Another aspect includes a compound of Formula (III), wherein B is heterocyclyl containing at least one chiral carbon atom having an (S) configuration.

One aspect includes a compound of Formula (III), wherein $R_b$ is selected from halogen, $C_{1-4}$alkyl, amino, $C_{1-4}$alkyl-amino, $(C_{1-4}alkyl)_2$-amino, and C-cycloalkyl.

Another aspect includes a compound of Formula (III), wherein $R_b$ is $C_{1-4}$alkyl selected from methyl, ethyl, propyl, isopropyl, butyl, and tert-butyl.

Another aspect includes a compound of Formula (III), wherein $R_b$ is methyl.

One aspect includes a compound of Formula (III), wherein $R_1$ is selected from heteroaryl, heterocyclyl, phenyl, heteroaryl-$C_{1-4}$alkyl, heteroaryl-$C_{2-4}$alkenyl, heteroaryl-amino, and heteroaryl-$C_{1-4}$alkyl-amino, wherein heteroaryl is a 3-7 membered monocyclic or 6-10 membered bicyclic ring system having 1, 2, 3, or 4 heteroatom ring members independently selected from N, O, or S, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S; and wherein each instance of phenyl, heteroaryl or heterocyclyl is optionally substituted where allowed by available valences with 1 or 2 $R_{1a}$ substituents.

Another aspect includes a compound of Formula (III), wherein $R_1$ is selected from heteroaryl, heterocyclyl, phenyl, heteroaryl-$C_{1-4}$alkyl, heteroaryl-$C_{2-4}$alkenyl, heteroaryl-amino, and heteroaryl-$C_{1-4}$alkyl-amino, wherein heteroaryl is a 3-7 membered monocyclic or 6-10 membered bicyclic ring system having 1, 2, 3, or 4 heteroatom ring members independently selected from N, O, or S, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S; and wherein each instance of phenyl, heteroaryl or heterocyclyl is unsubstituted.

Another aspect includes a compound of Formula (III), wherein $R_1$ is selected from heteroaryl, heterocyclyl, phenyl, heteroaryl-$C_{1-4}$ alkyl, heteroaryl-$C_{2-4}$alkenyl, heteroaryl-amino, and heteroaryl-$C_{1-4}$alkyl-amino, wherein heteroaryl is a 3-7 membered monocyclic or 6-10 membered bicyclic ring system having 1, 2, 3, or 4 heteroatom ring members independently selected from N, O, or S, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S; and wherein each instance of phenyl, heteroaryl or heterocyclyl is substituted where allowed by available valences with one $R_{1a}$ substituent.

Another aspect includes a compound of Formula (III), wherein $R_1$ is heteroaryl, wherein heteroaryl is a 3-7 membered monocyclic or 6-10 membered bicyclic ring system having 1, 2, 3, or 4 heteroatom ring members independently selected from N, O, or S; and wherein heteroaryl is optionally substituted where allowed by available valences with 1 or 2 $R_{1a}$ substituents.

Another aspect includes a compound of Formula (III), wherein $R_1$ is heteroaryl, wherein heteroaryl is a 3-7 membered monocyclic or 6-10 membered bicyclic ring system having 1, 2, 3, or 4 heteroatom ring members independently selected from N, O, or S; and wherein heteroaryl is unsubstituted.

Another aspect includes a compound of Formula (III), wherein $R_1$ is heteroaryl, wherein heteroaryl is a 3-7 membered monocyclic or 6-10 membered bicyclic ring system having 1, 2, 3, or 4 heteroatom ring members independently selected from N, O, or S; and wherein heteroaryl is substituted where allowed by available valences with one $R_{1a}$ substituent.

Another aspect includes a compound of Formula (III), wherein $R_1$ is heteroaryl selected from thienyl, 1H-pyrazolyl, 1H-imidazolyl, 1,3-thiazolyl, oxazolyl, 1,2,4-oxadiazolyl, 1,3,4-oxadiazolyl, 1,2,4-thiadiazolyl, 1H-1,2,3-triazolyl, 2H-1,2,3-triazolyl, 1H-1,2,4-triazolyl, 1H-tetrazolyl, 2H-tetrazolyl, pyridinyl, pyridin-2(1H)-on-yl, pyrazinyl, pyrimidinyl, pyrimidin-4(3H)-on-yl, pyridazinyl, pyridazin-3(2H)-on-yl, 1,2,4-triazinyl, 1,3,5-triazinyl, 1H-indolyl, 1H-indazolyl, 2H-indazolyl, indolizinyl, benzofuranyl, benzothienyl, 1H-benzimidazolyl, 1,3-benzoxazolyl, 1,3-benzothiazolyl, 1,3-benzodioxolyl, 1,2,3-benzotriazolyl, 9H-purinyl, furo[3,2-b]pyridinyl, furo[3,2-c]pyridinyl, furo[2,3-c]pyridinyl, 1,3-oxazolo[5,4-b]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, pyrazolo[1,5-a]pyrimidinyl, pyrazolo[1,5-a]pyrazinyl, 1H-pyrazolo[3,4-b]pyridinyl, 1H-pyrazolo[3,4-b]pyrazinyl, 1H-pyrazolo[3,4-c]pyridinyl, 1H-pyrazolo[4,3-b]pyridinyl, 1H-pyrazolo[4,3-d]pyrimidinyl, 2H-pyrazolo[4,3-b]pyridinyl, 2H-pyrazolo[4,3-c]pyridin-yl, 5H-pyrrolo[2,3-b]pyrazinyl, imidazo[1,2-a]pyridinyl, imidazo[1,2-a]pyrazinyl, imidazo[1,2-a]pyrimidinyl, imidazo[1,2-b]pyridazinyl, imidazo[1,2-c]pyrimidinyl, 1H-imidazo[4,5-b]pyridinyl, 3H-imidazo[4,5-b]pyridinyl, imidazo[2,1-b][1,3]thiazolyl, imidazo[2,1-b][1,3,4]thiadiazolyl, [1,3]oxazolo[4,5-b]pyridinyl, [1,2,3]triazolo[1,5-a]pyridinyl, 1H-[1,2,3]triazolo[4,5-b]pyridinyl, 2H-[1,2,3]triazolo[4,5-b]pyridinyl, 3H-[1,2,3]triazolo[4,5-b]pyridinyl, [1,2,4]triazolo[1,5-a]pyridinyl, [1,2,4]triazolo[1,5-a]pyrazinyl, [1,2,4]triazolo[4,3-a]pyridinyl, tetrazolo[1,5-a]pyridinyl, tetrazolo[1,5-b]pyridazinyl, quinolinyl, isoquinolinyl, and quinoxalinyl, optionally substituted where allowed by available valences with 1 or 2 $R_{1a}$ substituents.

Another aspect includes a compound of Formula (III), wherein $R_1$ is unsubstituted heteroaryl selected from thienyl, 1H-pyrazolyl, 1H-imidazolyl, 1,3-thiazolyl, oxazolyl, 1,2,4-oxadiazolyl, 1,3,4-oxadiazolyl, 1,2,4-thiadiazolyl, 1H-1,2,3-triazolyl, 2H-1,2,3-triazolyl, 1H-1,2,4-triazolyl, 1H-tetrazolyl, 2H-tetrazolyl, pyridinyl, pyridin-2(1H)-on-yl, pyrazinyl, pyrimidinyl, pyrimidin-4(3H)-on-yl, pyridazinyl, pyridazin-3(2H)-on-yl, 1,2,4-triazinyl, 1,3,5-triazinyl, 1H-indolyl, 1H-indazolyl, 2H-indazolyl, indolizinyl, benzofuranyl, benzothienyl, 1H-benzimidazolyl, 1,3-benzoxazolyl, 1,3-benzothiazolyl, 1,3-benzodioxolyl, 1,2,3-benzotriazolyl, 9H-purinyl, furo[3,2-b]pyridinyl, furo[3,2-c]pyridinyl, furo[2,3-c]pyridinyl, 1,3-oxazolo[5,4-b]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, pyrazolo[1,5-a]pyrimidinyl, pyrazolo[1,5-a]pyrazinyl, 1H-pyrazolo[3,4-b]pyridinyl, 1H-pyrazolo[3,4-b]pyrazinyl, 1H-pyrazolo[3,4-c]pyridinyl, 1H-pyrazolo[4,3-b]pyridinyl, 1H-pyrazolo[4,3-d]pyrimidinyl, 2H-pyrazolo[4,3-b]pyridinyl, 2H-pyrazolo[4,3-c]pyridin-yl, 5H-pyrrolo[2,3-b]pyrazinyl, imidazo[1,2-a]pyridinyl, imidazo[1,2-a]pyrazinyl, imidazo[1,2-a]pyrimidinyl, imidazo[1,2-b]pyridazinyl, imidazo[1,2-c]pyrimidinyl, 1H-imidazo[4,5-b]pyridinyl, 3H-imidazo[4,5-b]pyridinyl, imidazo[2,1-b][1,3]thiazolyl, imidazo[2,1-b][1,3,4]thiadiazolyl, [1,3]oxazolo[4,5-b]pyridinyl, [1,2,3]triazolo[1,5-a]pyridinyl, 1H-[1,2,3]triazolo[4,5-b]pyridinyl, 2H-[1,2,3]triazolo[4,5-b]pyridinyl, 3H-[1,2,3]triazolo[4,5-b]pyridinyl, [1,2,4]triazolo[1,5-a]pyridinyl, [1,2,4]triazolo[1,5-a]pyrazinyl, [1,2,4]triazolo[4,3-a]pyridinyl, tetrazolo[1,5-a]pyridinyl, tetrazolo[1,5-b]pyridazinyl, quinolinyl, isoquinolinyl, and quinoxalinyl.

Another aspect includes a compound of Formula (III), wherein $R_1$ is heteroaryl selected from thienyl, 1H-pyrazolyl, 1H-imidazolyl, 1,3-thiazolyl, oxazolyl, 1,2,4-oxadiazolyl, 1,3,4-oxadiazolyl, 1,2,4-thiadiazolyl, 1H-1,2,3-triazolyl, 2H-1,2,3-triazolyl, 1H-1,2,4-triazolyl, 1H-tetrazolyl, 2H-tetrazolyl, pyridinyl, pyridin-2(1H)-on-yl, pyrazinyl, pyrimidinyl, pyrimidin-4(3H)-on-yl, pyridazinyl, pyridazin-3(2H)-on-yl, 1,2,4-triazinyl, 1,3,5-triazinyl, 1H-indolyl, 1H-indazolyl, 2H-indazolyl, indolizinyl, benzofuranyl, benzothienyl, 1H-benzimidazolyl, 1,3-benzoxazolyl, 1,3-benzothiazolyl, 1,3-benzodioxolyl, 1,2,3-benzotriazolyl, 9H-purinyl, furo[3,2-b]pyridinyl, furo[3,2-c]pyridinyl, furo[2,3-c]pyridinyl, 1,3-oxazolo[5,4-b]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, pyrazolo[1,5-a]pyrimidinyl, pyrazolo[1,5-a]pyrazinyl, 1H-pyrazolo[3,4-b]pyridinyl, 1H-pyrazolo[3,4-b]pyrazinyl, 1H-pyrazolo[3,4-c]pyridinyl, 1H-pyrazolo[4,3-b]pyridinyl, 1H-pyrazolo[4,3-d]pyrimidinyl, 2H-pyrazolo[4,3-b]pyridinyl, 2H-pyrazolo[4,3-c]pyridin-yl, 5H-pyrrolo[2,3-b]pyrazinyl, imidazo[1,2-a]pyridinyl, imidazo[1,2-a]pyrazinyl, imidazo[1,2-a]pyrimidinyl, imidazo[1,2-b]pyridazinyl, imidazo[1,2-c]pyrimidinyl, 1H-imidazo[4,5-b]pyridinyl, 3H-imidazo[4,5-b]pyridinyl, imidazo[2,1-b][1,3]thiazolyl, imidazo[2,1-b][1,3,4]thiadiazolyl, [1,3]oxazolo[4,5-b]pyridinyl, [1,2,3]triazolo[1,5-a]pyridinyl, 1H-[1,2,3]triazolo[4,5-b]pyridinyl, 2H-[1,2,3]triazolo[4,5-b]pyridinyl, 3H-[1,2,3]triazolo[4,5-b]pyridinyl, [1,2,4]triazolo[1,5-a]pyridinyl, [1,2,4]triazolo[1,5-a]pyrazinyl, [1,2,4]triazolo[4,3-a]pyridinyl, tetrazolo[1,5-a]pyridinyl, tetrazolo[1,5-b]pyridazinyl, quinolinyl, isoquinolinyl, and quinoxalinyl, substituted where allowed by available valences with one $R_{1a}$ substituent.

Another aspect includes a compound of Formula (III), wherein $R_1$ is heteroaryl selected from 1H-pyrazolyl, 2H-1,2,3-triazolyl, and 2H-indazolyl, optionally substituted where allowed by available valences with 1 or 2 $R_{1a}$ substituents.

Another aspect includes a compound of Formula (III), wherein $R_1$ is unsubstituted heteroaryl selected from 1H-pyrazolyl, 2H-1,2,3-triazolyl, and 2H-indazolyl.

Another aspect includes a compound of Formula (III), wherein $R_1$ is heteroaryl selected from 1H-pyrazolyl, 2H-1,2,3-triazolyl, and 2H-indazolyl, substituted where allowed by available valences with one $R_{1a}$ substituent.

Another aspect includes a compound of Formula (III), wherein $R_1$ is heteroaryl selected from thien-2-yl, thien-3-yl, 1H-pyrazol-1-yl, 1H-pyrazol-3-yl, 1H-pyrazol-4-yl, 1H-pyrazol-5-yl, 1H-imidazol-1-yl, 1H-imidazol-4-yl, 1,3-thiazol-2-yl, 1,3-thiazol-5-yl, 1,3-oxazol-2-yl, 1,3-oxazol-4-yl, 1,3-oxazol-5-yl, 1,2,4-oxadiazol-3-yl, 1,3,4-oxadiazol-2-yl, 1,2,4-thiadiazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-3-yl, 1H-1,2,4-triazol-5-yl, 1H-tetrazol-1-yl, 1H-tetrazol-5-yl, 2H-tetrazol-2-yl, 2H-tetrazol-5-yl, pyridin-2-yl, pyridin-3-yl, pyridin-4-yl, pyridin-2(1H)-on-4-yl, pyridin-2(1H)-on-5-yl, pyridin-2(1H)-on-6-yl, pyrazin-2-yl, pyrazin-3-yl, pyrimidin-2-yl, pyrimidin-4-yl, pyrimidin-5-yl, pyrimidin-4(3H)-on-6-yl, pyridazin-3-yl, pyridazin-4-yl, pyridazin-3(2H)-on-5-yl, 1,2,4-triazin-3-yl, 1,3,5-triazin-2-yl, 1H-indol-3-yl, 1H-indol-4-yl, 1H-indol-5-yl, 1H-indol-6-yl, 1H-indazol-5-yl, 1H-indazol-6-yl, 2H-indazol-4-yl, 2H-indazol-5-yl, 2H-indazol-6-yl, indolizin-2-yl, benzofuran-2-yl, benzofuran-5-yl, benzothien-2-yl, benzothien-3-yl, 1H-benzimidazol-2-yl, 1H-benzimidazol-5-yl, 1H-benzimidazol-6-yl, 1,3-benzoxazol-2-yl, 1,3-benzoxazol-5-yl, 1,3-benzoxazol-6-yl, 1,3-benzothiazol-2-yl, 1,3-benzothiazol-5-yl, 1,3-benzothiazol-6-yl, 1,3-benzodioxol-5-yl, 1,2,3-benzotriazol-5-yl, 9H-purin-8-yl, furo[3,2-b]pyridin-2-yl, furo[3,2-c]pyridin-2-yl, furo[2,3-c]pyridin-2-yl, 1,3-oxazolo[5,4-b]pyridine-5-yl, thieno[3,2-c]pyridin-2-yl, thieno[2,3-d]pyrimidin-6-yl, 1H-pyrrolo[2,3-b]pyridin-5-yl, 1H-pyrrolo[2,3-c]pyridin-4-yl, pyrrolo[1,2-a]pyrimidin-7-yl, pyrrolo[1,2-a]pyrazin-7-yl, pyrrolo[1,2-b]pyridazin-2-yl, pyrazolo[1,5-a]pyridin-2-yl, pyrazolo[1,5-a]pyridin-5-yl, pyrazolo[1,5-a]pyrazin-2-yl, pyrazolo[1,5-a]pyrimidin-2-yl, pyrazolo[1,5-a]pyrimidin-5-yl, 1H-pyrazolo[3,4-b]pyrazin-5-yl, 1H-pyrazolo[3,4-b]pyridin-5-yl, 1H-pyrazolo[3,4-b]pyridin-6-yl, 1H-pyrazolo[3,4-c]pyridin-1-yl, 1H-pyrazolo[3,4-c]pyridin-5-yl, 1H-pyrazolo[4,3-b]pyridin-5-yl, 1H-pyrazolo[4,3-b]pyridin-6-yl, 1H-pyrazolo[4,3-d]pyrimidin-5-yl, 2H-pyrazolo[4,3-b]pyridin-5-yl, 2H-pyrazolo[4,3-c]pyridin-5-yl, 5H-pyrrolo[2,3-b]pyrazin-2-yl, imidazo[1,2-a]pyridin-2-yl, imidazo[1,2-a]pyridin-6-yl, imidazo[1,2-a]pyrazin-2-yl, imidazo[1,2-a]pyrazin-6-yl, imidazo[1,2-a]pyrimidin-2-yl, imidazo[1,2-a]pyrimidin-6-yl, imidazo[1,2-b]pyridazin-2-yl, imidazo[1,2-b]pyridazin-6-yl, imidazo[1,2-c]pyrimidin-2-yl, 1H-imidazo[4,5-b]pyridin-5-yl, 3H-imidazo[4,5-b]pyridin-5-yl, imidazo[2,1-b][1,3]thiazol-6-yl, imidazo[2,1-b][1,3,4]thiadiazol-6-yl, [1,3]oxazolo[4,5-b]pyridin-2-yl, [1,2,3]triazolo[1,5-a]pyridin-5-yl, [1,2,3]triazolo[1,5-a]pyridin-6-yl, 1H-[1,2,3]triazolo[4,5-b]pyridin-5-yl, 2H-[1,2,3]triazolo[4,5-b]pyridin-6-yl, 3H-[1,2,3]triazolo[4,5-b]pyridin-5-yl, [1,2,4]triazolo[1,5-a]pyridin-2-yl, [1,2,4]triazolo[1,5-a]pyridin-6-yl, [1,2,4]triazolo[1,5-a]pyridin-7-yl, [1,2,4]triazolo[1,5-a]pyrazin-2-yl, [1,2,4]triazolo[1,5-a]pyrazin-5-yl, [1,2,4]triazolo[1,5-a]pyrazin-6-yl, [1,2,4]triazolo[4,3-a]pyridn-6-yl, [1,2,4]triazolo[4,3-a]pyridn-7-yl, tetrazolo[1,5-a]pyridin-7-yl, tetrazolo[1,5-b]pyridazin-7-yl, quinolin-6-yl, isoquinolin-6-yl, and quinoxalin-2-yl, optionally substituted where allowed by available valences with 1 or 2 $R_{1a}$ substituents.

Another aspect includes a compound of Formula (III), wherein $R_1$ is unsubstituted heteroaryl selected from thien- 2-yl, thien-3-yl, 1H-pyrazol-1-yl, 1H-pyrazol-3-yl, 1H-pyrazol-4-yl, 1H-pyrazol-5-yl, 1H-imidazol-1-yl, 1H-imidazol-4-yl, 1,3-thiazol-2-yl, 1,3-thiazol-5-yl, 1,3-oxazol-2-yl, 1,3-oxazol-4-yl, 1,3-oxazol-5-yl, 1,2,4-oxadiazol-3-yl, 1,3,4-oxadiazol-2-yl, 1,2,4-thiadiazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-3-yl, 1H-1,2,4-triazol-5-yl, 1H-tetrazol-1-yl, 1H-tetrazol-5-yl, 2H-tetrazol-2-yl, 2H-tetrazol-5-yl, pyridin-2-yl, pyridin-3-yl, pyridin-4-yl, pyridin-2(1H)-on-4-yl, pyridin-2(1H)-on-5-yl, pyridin-2(1H)-on-6-yl, pyrazin-2-yl, pyrazin-3-yl, pyrimidin-2-yl, pyrimidin-4-yl, pyrimidin-5-yl, pyrimidin-4(3H)-on-6-yl, pyridazin-3-yl, pyridazin-4-yl, pyridazin-3(2H)-on-5-yl, 1,2,4-triazin-3-yl, 1,3,5-triazin-2-yl, 1H-indol-3-yl, 1H-indol-4-yl, 1H-indol-5-yl, 1H-indol-6-yl, 1H-indazol-5-yl, 1H-indazol-6-yl, 2H-indazol-4-yl, 2H-indazol-5-yl, 2H-indazol-6-yl, indolizin-2-yl, benzofuran-2-yl, benzofuran-5-yl, benzothien-2-yl, benzothien-3-yl, 1H-benzimidazol-2-yl, 1H-benzimidazol-5-yl, 1H-benzimidazol-6-yl, 1,3-benzoxazol-2-yl, 1,3-benzoxazol-5-yl, 1,3-benzoxazol-6-yl, 1,3-benzothiazol-2-yl, 1,3-benzothiazol-5-yl, 1,3-benzothiazol-6-yl, 1,3-benzodioxol-5-yl, 1,2,3-benzotriazol-5-yl, 9H-purin-8-yl, furo[3,2-b]pyridin-2-yl, furo[3,2-c]pyridin-2-yl, furo[2,3-c]pyridin-2-yl, 1,3-oxazolo[5,4-b]pyridine-5-yl, thieno[3,2-c]pyridin-2-yl, thieno[2,3-d]pyrimidin-6-yl, 1H-pyrrolo[2,3-b]pyridin-5-yl, 1H-pyrrolo[2,3-c]pyridin-4-yl, pyrrolo[1,2-a]pyrimidin-7-yl, pyrrolo[1,2-a]pyrazin-7-yl, pyrrolo[1,2-b]pyridazin-2-yl, pyrazolo[1,5-a]pyridin-2-yl, pyrazolo[1,5-a]pyridin-5-yl, pyrazolo[1,5-a]pyrazin-2-yl, pyrazolo[1,5-a]pyrimidin-2-yl, pyrazolo[1,5-a]pyrimidin-5-yl, 1H-pyrazolo[3,4-b]pyrazin-5-yl, 1H-pyrazolo[3,4-b]pyridin-5-yl, 1H-pyrazolo[3,4-b]pyridin-6-yl, 1H-pyrazolo[3,4-c]pyridin-1-yl, 1H-pyrazolo[3,4-c]pyridin-5-yl, 1H-pyrazolo[4,3-b]pyridin-5-yl, 1H-pyrazolo[4,3-b]pyridin-6-yl, 1H-pyrazolo[4,3-d]pyrimidin-5-yl, 2H-pyrazolo[4,3-b]pyridin-5-yl, 2H-pyrazolo[4,3-c]pyridin-5-yl, 5H-pyrrolo[2,3-b]pyrazin-2-yl, imidazo[1,2-a]pyridin-2-yl, imidazo[1,2-a]pyridin-6-yl, imidazo[1,2-a]pyrazin-2-yl, imidazo[1,2-a]pyrazin-6-yl, imidazo[1,2-a]pyrimidin-2-yl, imidazo[1,2-a]pyrimidin-6-yl, imidazo[1,2-b]pyridazin-2-yl, imidazo[1,2-b]pyridazin-6-yl, imidazo[1,2-c]pyrimidin-2-yl, 1H-imidazo[4,5-b]pyridin-5-yl, 3H-imidazo[4,5-b]pyridin-5-yl, imidazo[2,1-b][1,3]thiazol-6-yl, imidazo[2,1-b][1,3,4]thiadiazol-6-yl, [1,3]oxazolo[4,5-b]pyridin-2-yl, [1,2,3]triazolo[1,5-a]pyridin-5-yl, [1,2,3]triazolo[1,5-a]pyridin-6-yl, 1H-[1,2,3]triazolo[4,5-b]pyridin-5-yl, 2H-[1,2,3]triazolo[4,5-b]pyridin-6-yl, 3H-[1,2,3]triazolo[4,5-b]pyridin-5-yl, [1,2,4]triazolo[1,5-a]pyridin-2-yl, [1,2,4]triazolo[1,5-a]pyridin-6-yl, [1,2,4]triazolo[1,5-a]pyridin-7-yl, [1,2,4]triazolo[1,5-a]pyrazin-2-yl, [1,2,4]triazolo[1,5-a]pyrazin-5-yl, [1,2,4]triazolo[1,5-a]pyrazin-6-yl, [1,2,4]triazolo[4,3-a]pyridn-6-yl, [1,2,4]triazolo[4,3-a]pyridn-7-yl, tetrazolo[1,5-a]pyridin-7-yl, tetrazolo[1,5-b]pyridazin-7-yl, quinolin-6-yl, isoquinolin-6-yl, and quinoxalin-2-yl.

Another aspect includes a compound of Formula (III), wherein $R_1$ is heteroaryl selected from thien-2-yl, thien-3-yl, 1H-pyrazol-1-yl, 1H-pyrazol-3-yl, 1H-pyrazol-4-yl, 1H-pyrazol-5-yl, 1H-imidazol-1-yl, 1H-imidazol-4-yl, 1,3-thiazol-2-yl, 1,3-thiazol-5-yl, 1,3-oxazol-2-yl, 1,3-oxazol-4-yl, 1,3-oxazol-5-yl, 1,2,4-oxadiazol-3-yl, 1,3,4-oxadiazol-2-yl, 1,2,4-thiadiazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-3-yl, 1H-1,2,4-triazol-5-yl, 1H-tetrazol-1-yl, 1H-tetrazol-5-yl, 2H-tetrazol-2-yl, 2H-tetrazol-5-yl, pyridin-2-yl, pyridin-3-yl, pyridin-4-yl, pyridin-2(1H)-on-4-yl, pyridin-2(1H)-on-5-yl, pyridin-2(1H)-on-6-yl, pyrazin-2-yl, pyrazin-3-yl, pyrimidin-2-yl, pyrimidin-4-yl, pyrimidin-5-yl, pyrimidin-4(3H)-on-6-yl, pyridazin-3-yl, pyridazin-4-yl, pyridazin-3(2H)-on-5-yl, 1,2,4-triazin-3-yl, 1,3,5-triazin-2-yl, 1H-indol-3-yl, 1H-indol-4-yl, 1H-indol-5-yl, 1H-indol-6-yl, 1H-indazol-5-yl, 1H-indazol-6-yl, 2H-indazol-4-yl, 2H-indazol-5-yl, 2H-indazol-6-yl, indolizin-2-yl, benzofuran-2-yl, benzofuran-5-yl, benzothien-2-yl, benzothien-3-yl, 1H-benzimidazol-2-yl, 1H-benzimidazol-5-yl, 1H-benzimidazol-6-yl, 1,3-benzoxazol-2-yl, 1,3-benzoxazol-5-yl, 1,3-benzoxazol-6-yl, 1,3-benzothiazol-2-yl, 1,3-benzothiazol-5-yl, 1,3-benzothiazol-6-yl, 1,3-benzodioxol-5-yl, 1,2,3-benzotriazol-5-yl, 9H-purin-8-yl, furo[3,2-b]pyridin-2-yl, furo[3,2-c]pyridin-2-yl, furo[2,3-c]pyridin-2-yl, 1,3-oxazolo[5,4-b]pyridine-5-yl, thieno[3,2-c]pyridin-2-yl, thieno[2,3-d]pyrimidin-6-yl, 1H-pyrrolo[2,3-b]pyridin-5-yl, 1H-pyrrolo[2,3-c]pyridin-4-yl, pyrrolo[1,2-a]pyrimidin-7-yl, pyrrolo[1,2-a]pyrazin-7-yl, pyrrolo[1,2-b]pyridazin-2-yl, pyrazolo[1,5-a]pyridin-2-yl, pyrazolo[1,5-a]pyridin-5-yl, pyrazolo[1,5-a]pyrazin-2-yl, pyrazolo[1,5-a]pyrimidin-2-yl, pyrazolo[1,5-a]pyrimidin-5-yl, 1H-pyrazolo[3,4-b]pyrazin-5-yl, 1H-pyrazolo[3,4-b]pyridin-5-yl, 1H-pyrazolo[3,4-b]pyridin-6-yl, 1H-pyrazolo[3,4-c]pyridin-1-yl, 1H-pyrazolo[3,4-c]pyridin-5-yl, 1H-pyrazolo[4,3-b]pyridin-5-yl, 1H-pyrazolo[4,3-b]pyridin-6-yl, 1H-pyrazolo[4,3-d]pyrimidin-5-yl, 2H-pyrazolo[4,3-b]pyridin-5-yl, 2H-pyrazolo[4,3-c]pyridin-5-yl, 5H-pyrrolo[2,3-b]pyrazin-2-yl, imidazo[1,2-a]pyridin-2-yl, imidazo[1,2-a]pyridin-6-yl, imidazo[1,2-a]pyrazin-2-yl, imidazo[1,2-a]pyrazin-6-yl, imidazo[1,2-a]pyrimidin-2-yl, imidazo[1,2-a]pyrimidin-6-yl, imidazo[1,2-b]pyridazin-2-yl, imidazo[1,2-b]pyridazin-6-yl, imidazo[1,2-c]pyrimidin-2-yl, 1H-imidazo[4,5-b]pyridin-5-yl, 3H-imidazo[4,5-b]pyridin-5-yl, imidazo[2,1-b][1,3]thiazol-6-yl, imidazo[2,1-b][1,3,4]thiadiazol-6-yl, [1,3]oxazolo[4,5-b]pyridin-2-yl, [1,2,3]triazolo[1,5-a]pyridin-5-yl, [1,2,3]triazolo[1,5-a]pyridin-6-yl, 1H-[1,2,3]triazolo[4,5-b]pyridin-5-yl, 2H-[1,2,3]triazolo[4,5-b]pyridin-6-yl, 3H-[1,2,3]triazolo[4,5-b]pyridin-5-yl, [1,2,4]triazolo[1,5-a]pyridin-2-yl, [1,2,4]triazolo[1,5-a]pyridin-6-yl, [1,2,4]triazolo[1,5-a]pyridin-7-yl, [1,2,4]triazolo[1,5-a]pyrazin-2-yl, [1,2,4]triazolo[1,5-a]pyrazin-5-yl, [1,2,4]triazolo[1,5-a]pyrazin-6-yl, [1,2,4]triazolo[4,3-a]pyridn-6-yl, [1,2,4]triazolo[4,3-a]pyridn-7-yl, tetrazolo[1,5-a]pyridin-7-yl, tetrazolo[1,5-b]pyridazin-7-yl, quinolin-6-yl, isoquinolin-6-yl, and quinoxalin-2-yl, substituted where allowed by available valences with one $R_{1a}$ substituent.

Another aspect includes a compound of Formula (III), wherein $R_1$ is heteroaryl selected from 1H-pyrazol-4-yl, 2H-1,2,3-triazol-2-yl, and 2H-indazol-5-yl, optionally substituted where allowed by available valences with 1 or 2 Rig substituents.

Another aspect includes a compound of Formula (III), wherein $R_1$ is unsubstituted heteroaryl selected from 1H-pyrazol-4-yl, 2H-1,2,3-triazol-2-yl, and 2H-indazol-5-yl.

Another aspect includes a compound of Formula (III), wherein $R_1$ is heteroaryl selected from 1H-pyrazol-4-yl, 2H-1,2,3-triazol-2-yl, and 2H-indazol-5-yl, substituted where allowed by available valences with one $R_{1a}$ substituent.

Another aspect includes a compound of Formula (III), wherein $R_{1a}$ is $C_{1-4}$alkyl selected from methyl, ethyl, propyl, isopropyl, butyl, and tert-butyl.

Another aspect includes a compound of Formula (III), wherein $R_{1a}$ is methyl.

An aspect of the compound of Formula (I), Formula (II), or Formula (III) or a form thereof includes a compound selected from the group consisting of the following; wherein "#" indicates that the compound is a racemic mixture of enantiomers; wherein "&" indicates that the compound is a meso-compound; and wherein "~" indicates that the compound is a single enantiomer, but the absolute stereochemistry is not known.

-continued
1
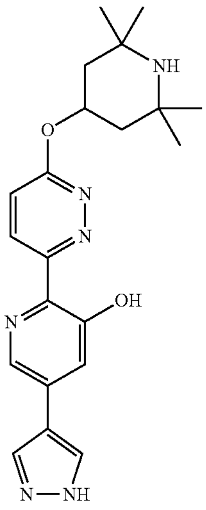
2
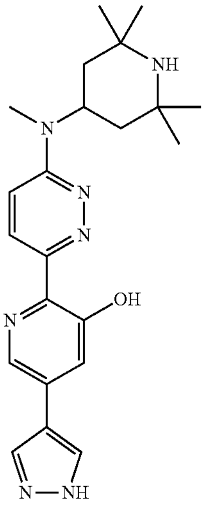
3
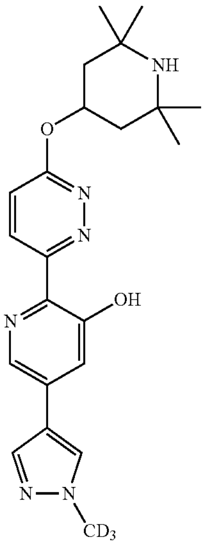
4
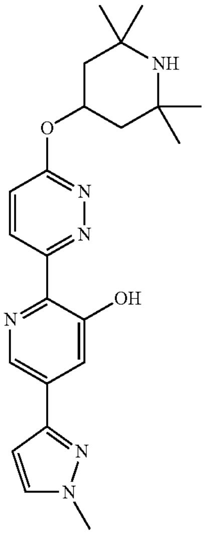
5
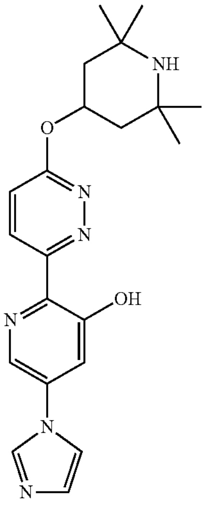
6#
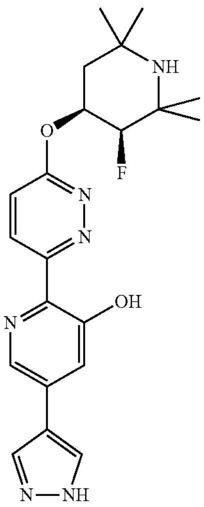

-continued
7~
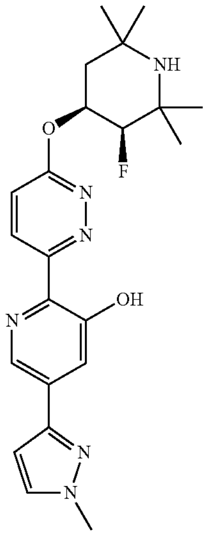
8
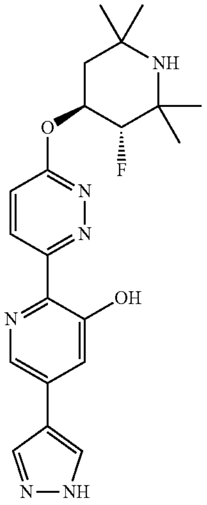
9~
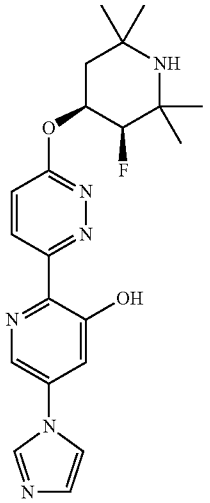
-continued
10
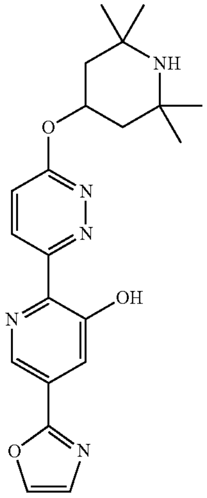
11~
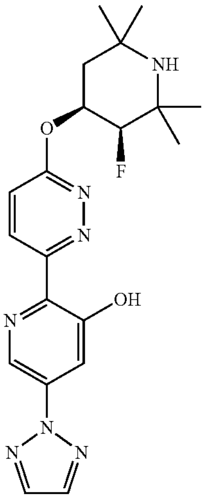
12~
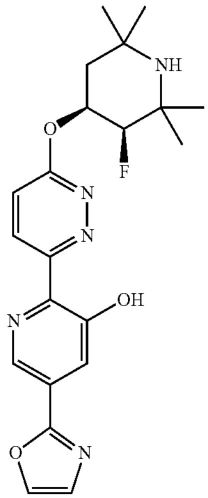

13
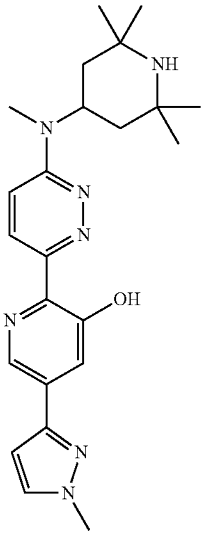
14
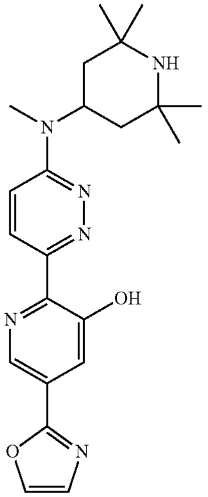
15
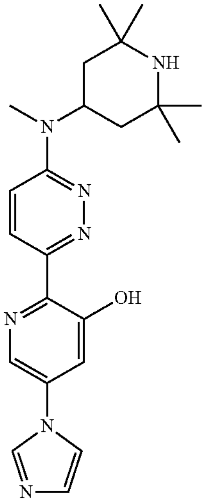
16#
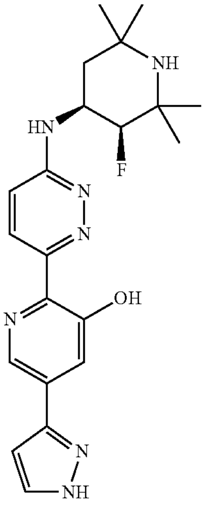
17#
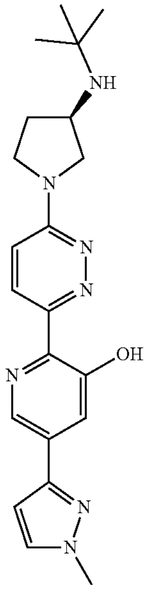
18#
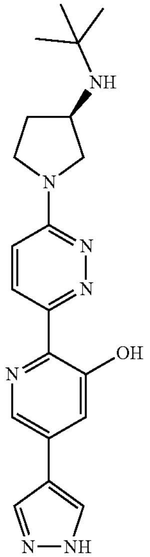

-continued
19
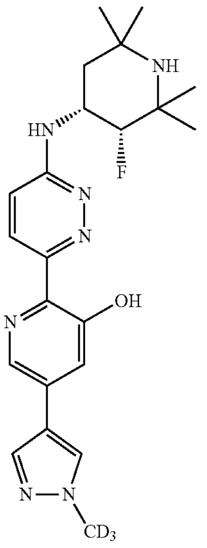
20
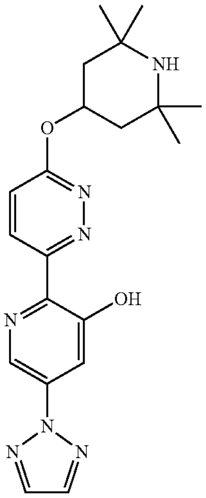
21
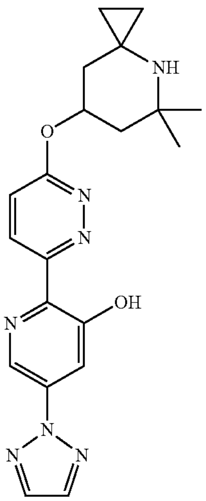
-continued
22
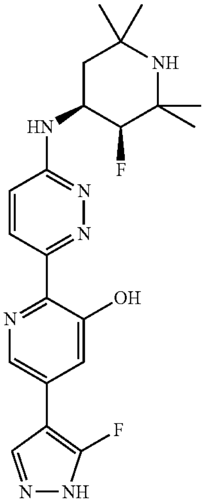
23
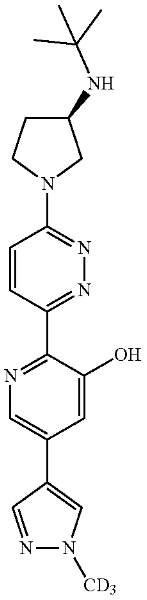
24
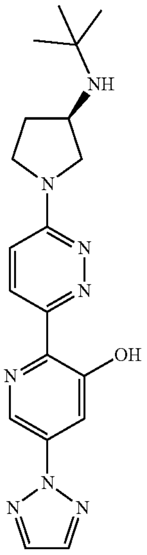

-continued
25
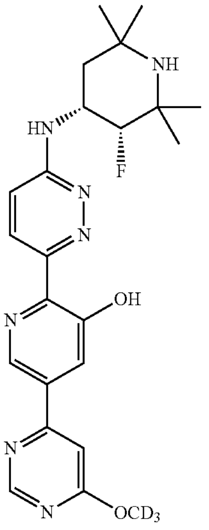
26
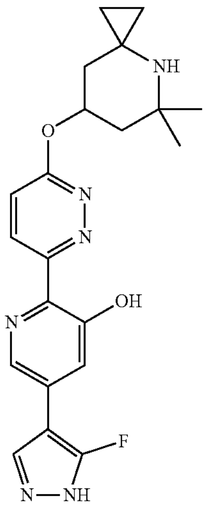
27
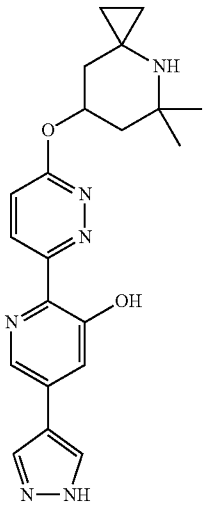
-continued
28
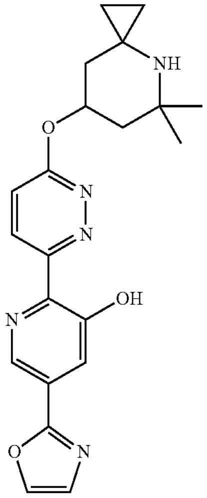
29
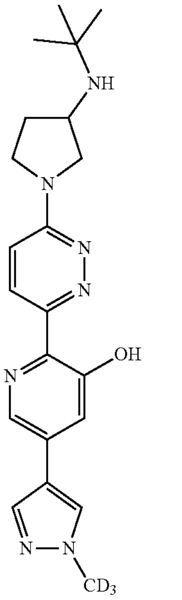

-continued
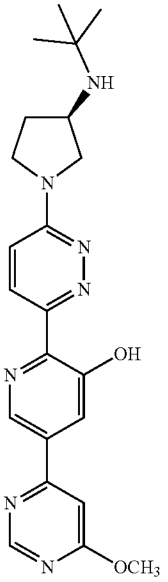
30
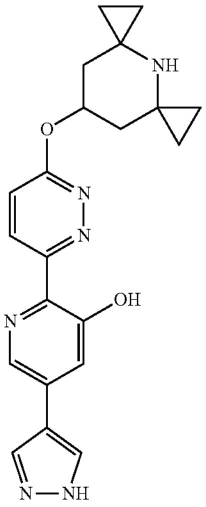
31
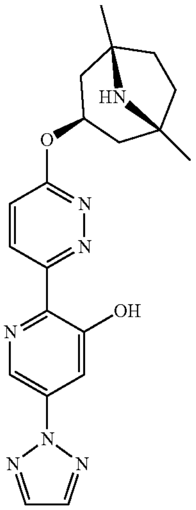
32&
-continued
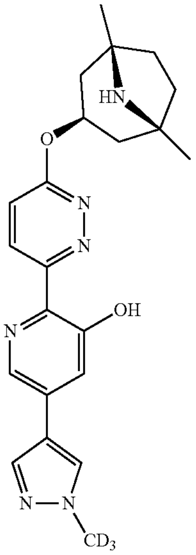
33&
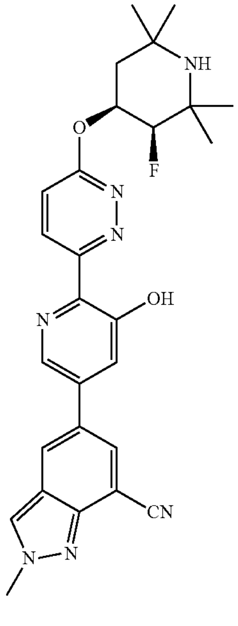
34~

-continued
35~
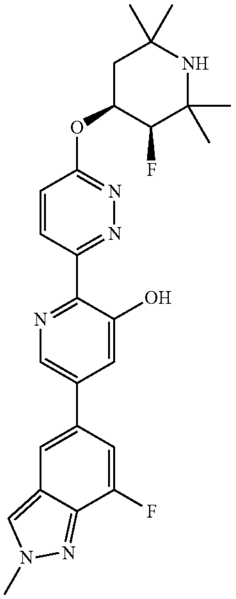
36&
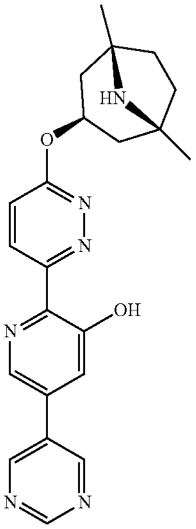
-continued
37~
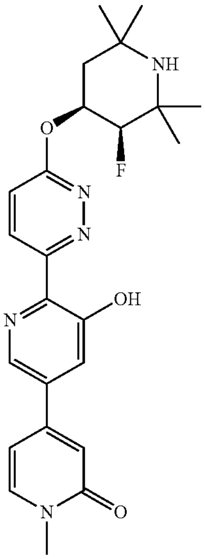
38~
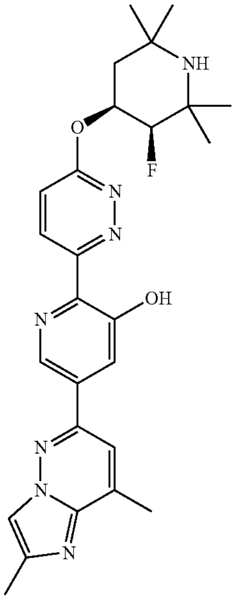

-continued
39~
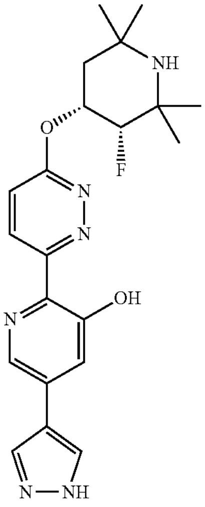
40
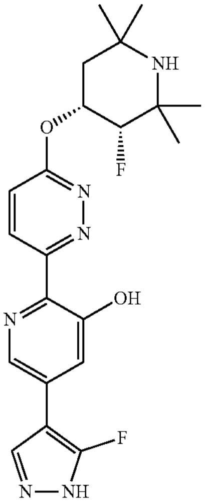
41#
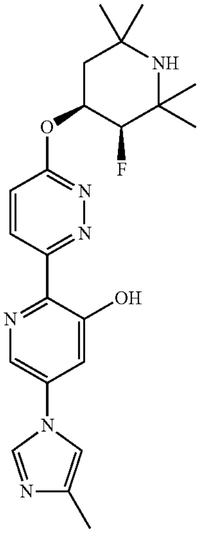
-continued
42#
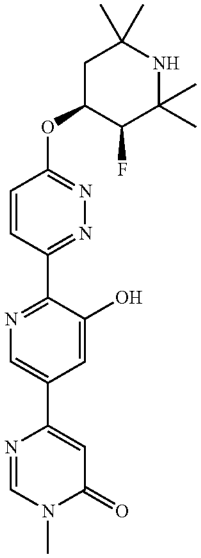
43#
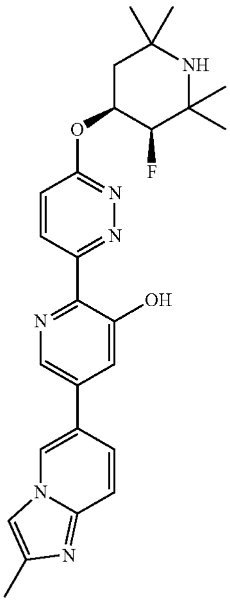

-continued
44#
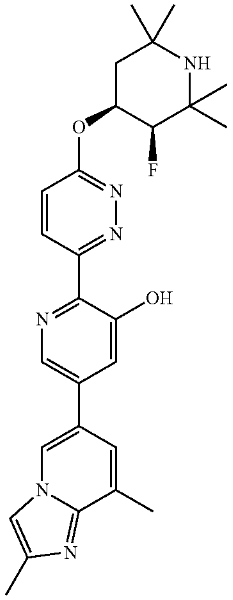
45#
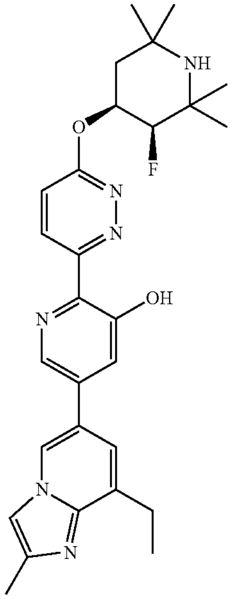
-continued
46#
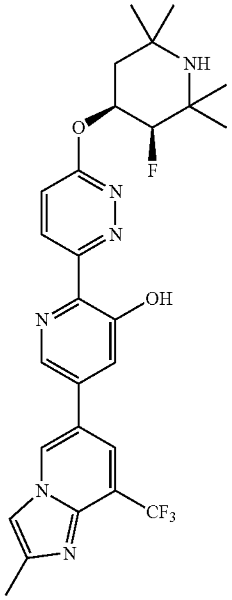
47#
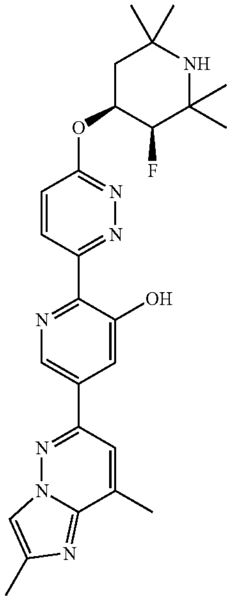

-continued
48#
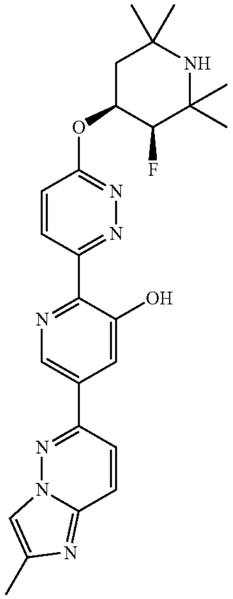
49#
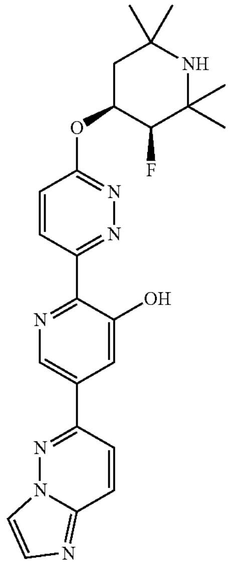
-continued
50
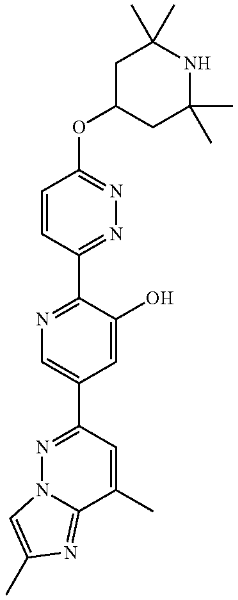
51~
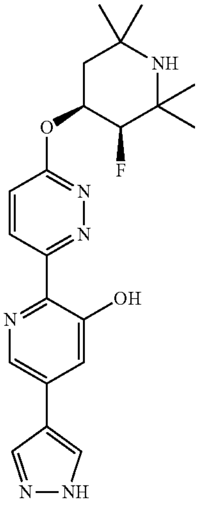

-continued
52
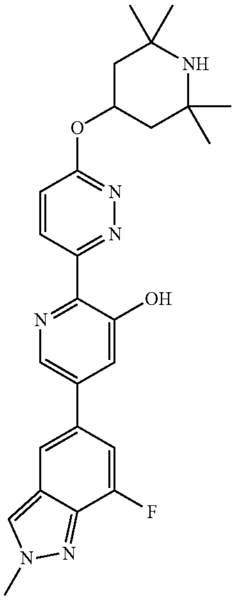
53
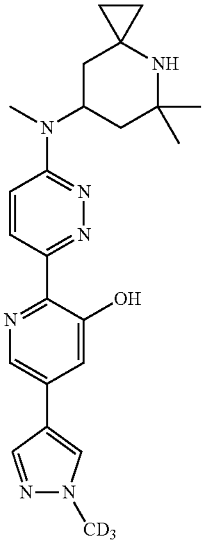
-continued
54#
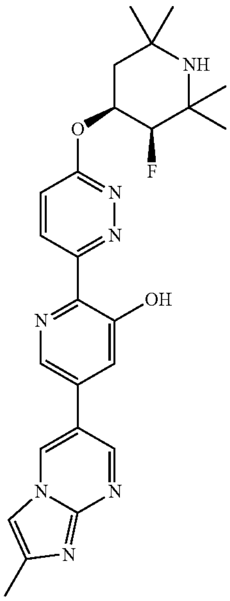
55#
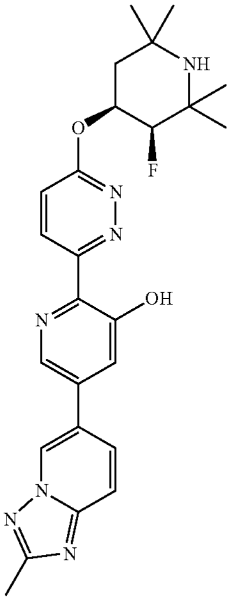

-continued
56#
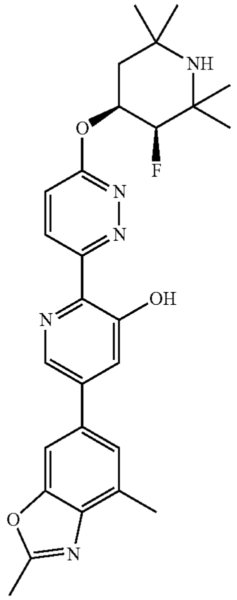
57#
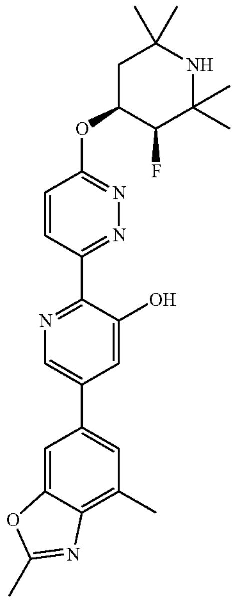
-continued
58#
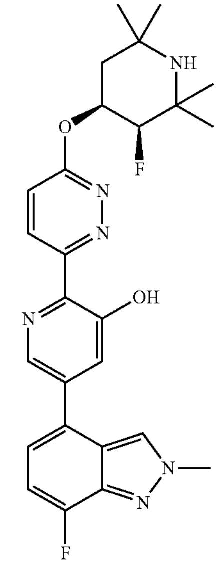
59#
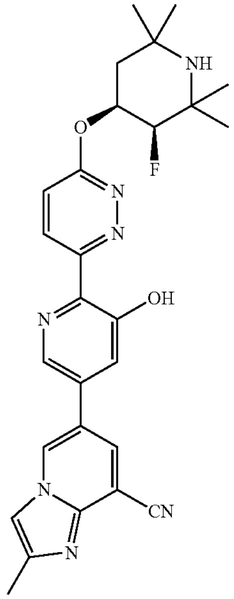

-continued
60#
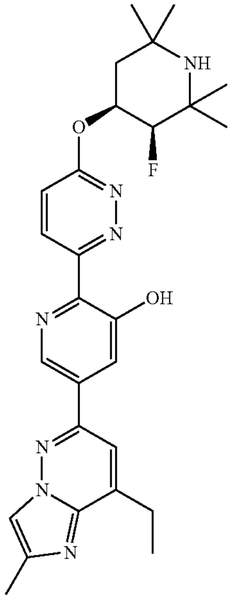
61
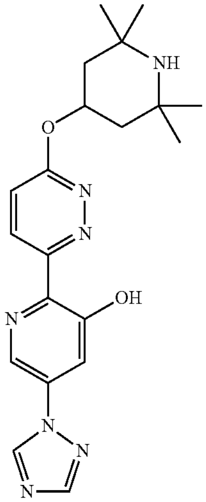
-continued
62
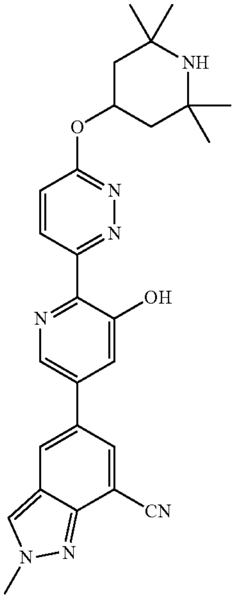
63
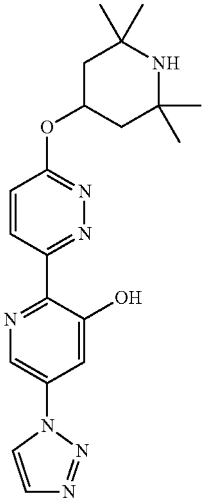

-continued
64
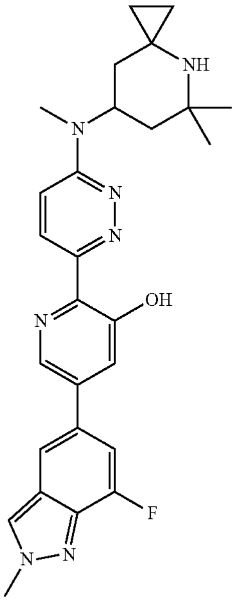
65
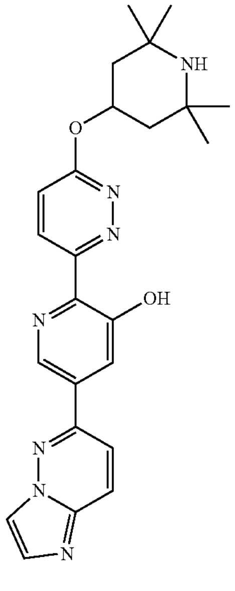
-continued
66#
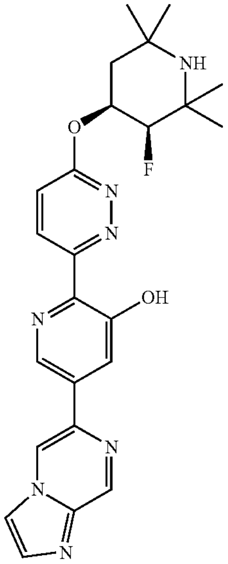
67#
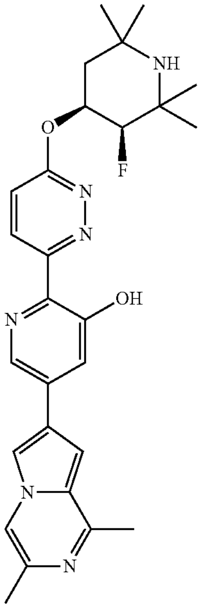

-continued
68#
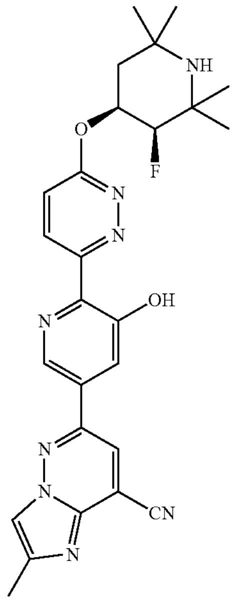
69&
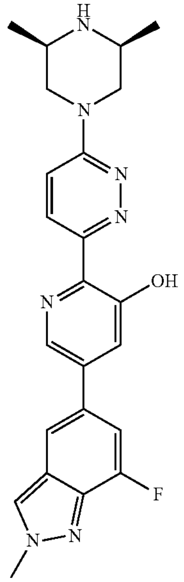
-continued
70
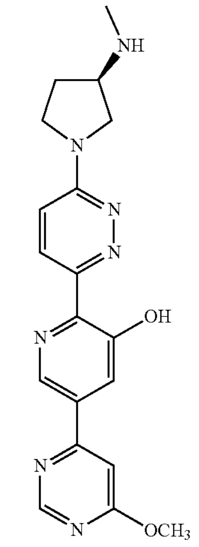
71#
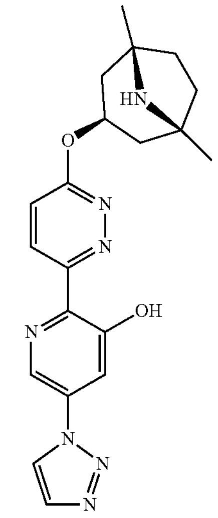
72#
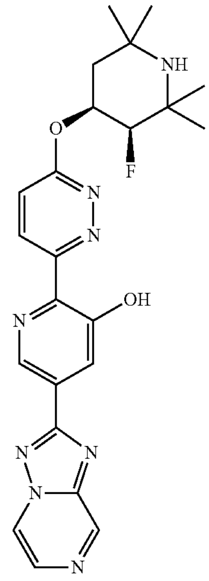

-continued
73
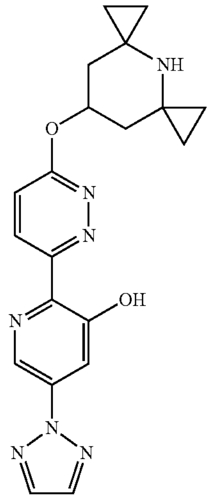
74
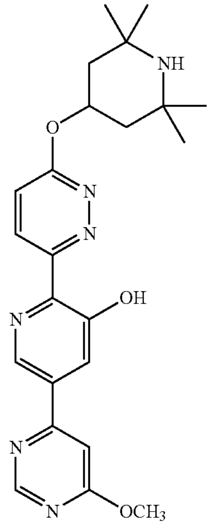
75
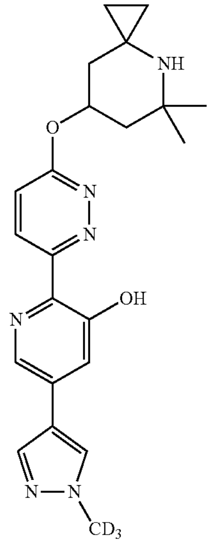
-continued
76
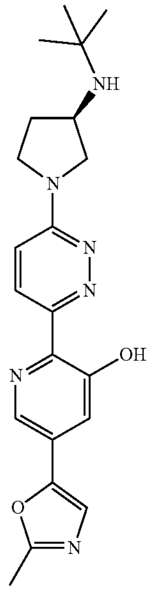
77
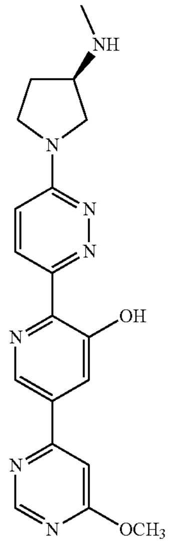

78#
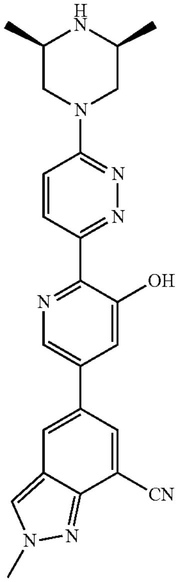
79
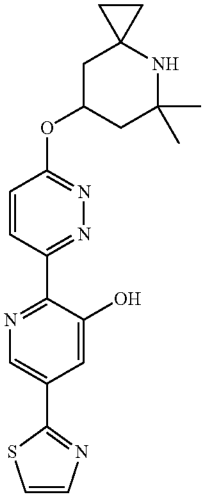
80
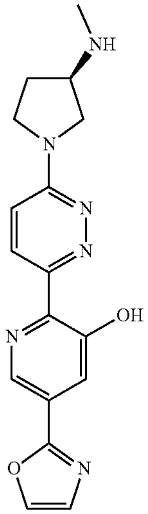
81
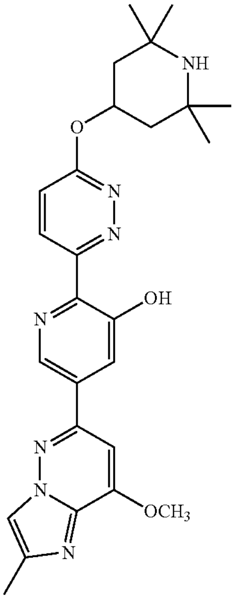
82
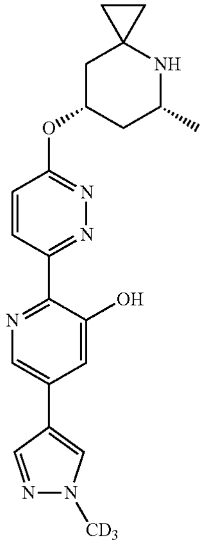

-continued
83
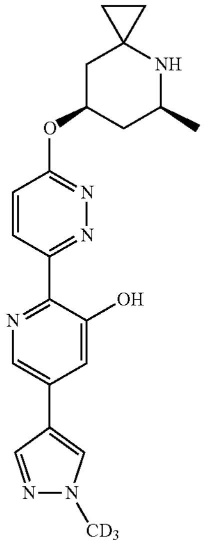
84
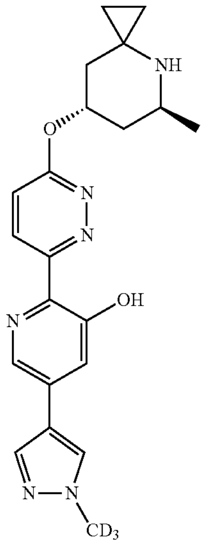
85
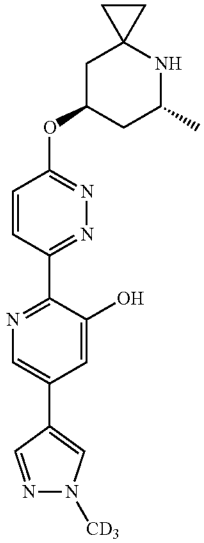
-continued
86&
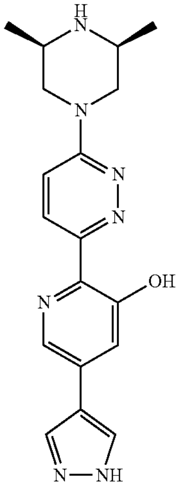
87&
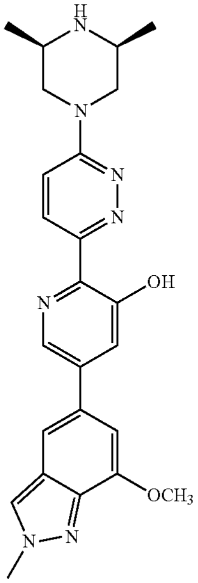
88
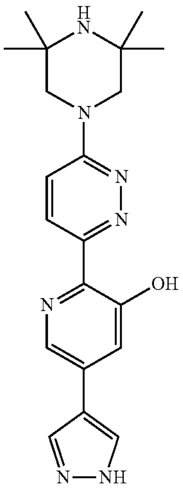

-continued
89
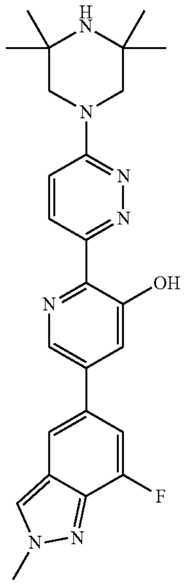
91[&]
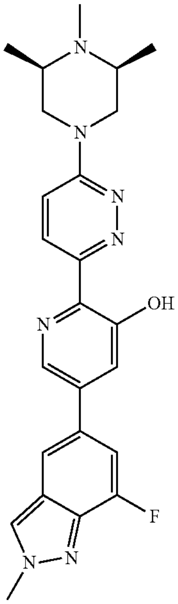
90[&]
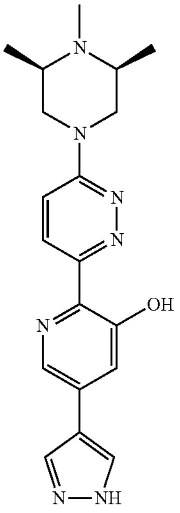
92[#]
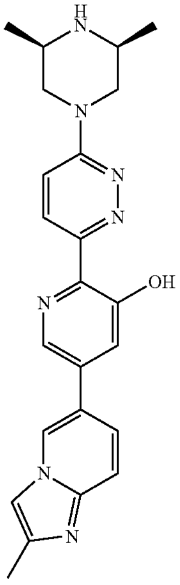

-continued
93
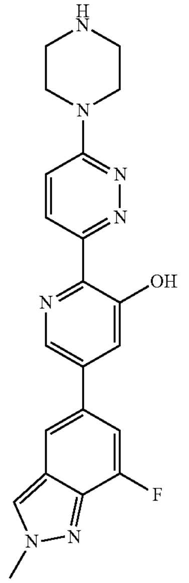
94&
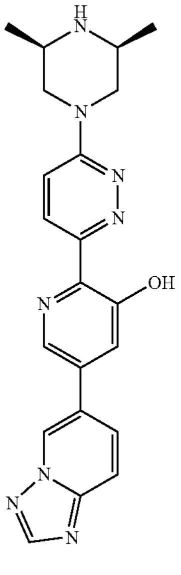
-continued
95
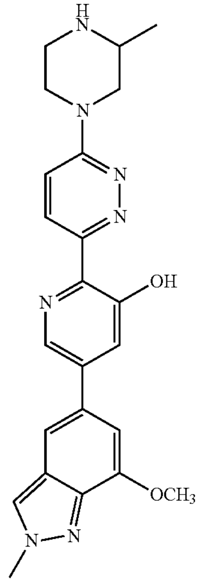
96&
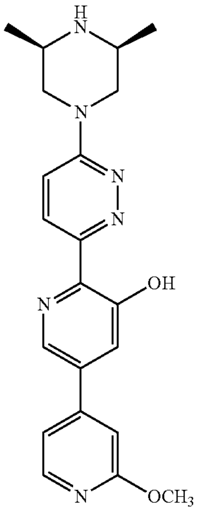

-continued
97
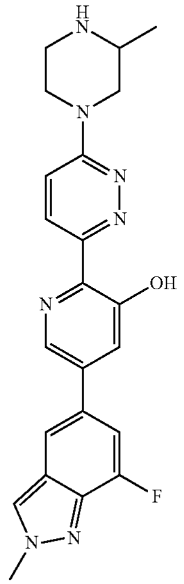
99&
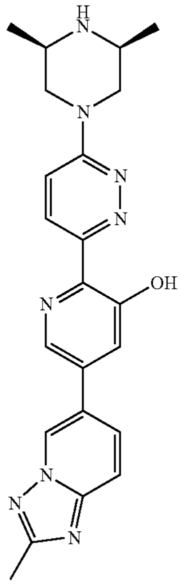
98
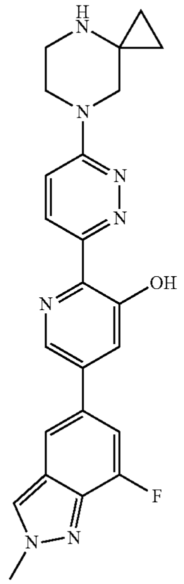
100
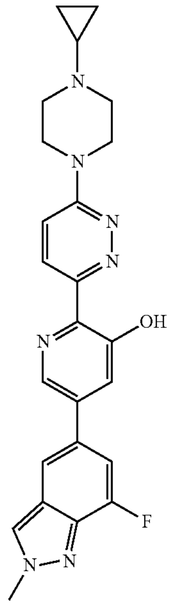

-continued
101
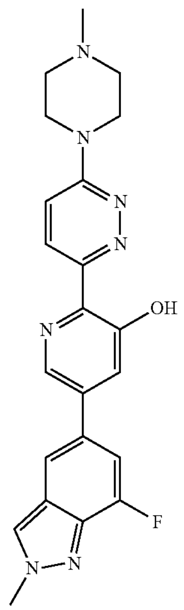
102
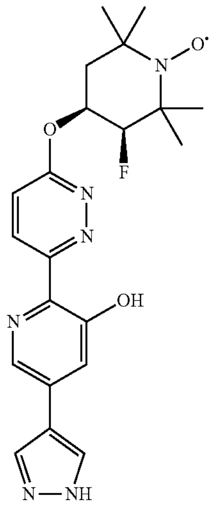
-continued
103
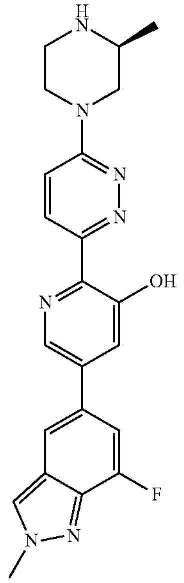
104
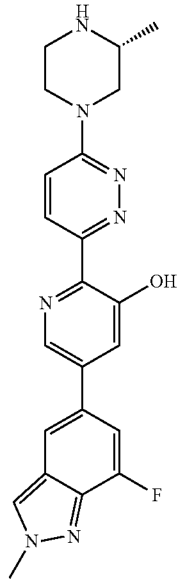

105
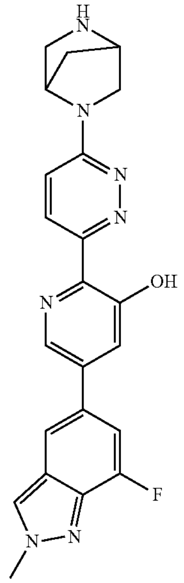
106#
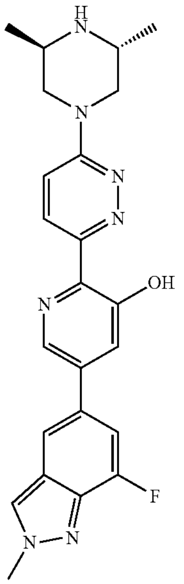
107
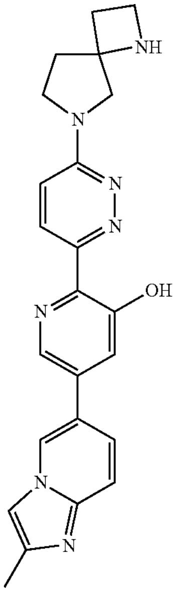
108
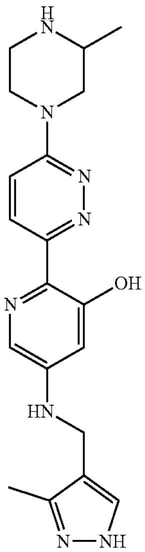

-continued
109
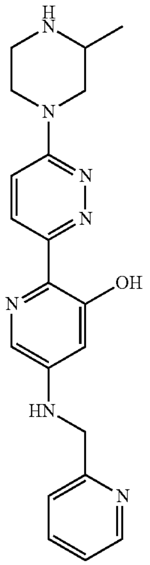
110
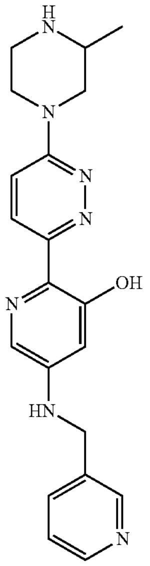
-continued
111
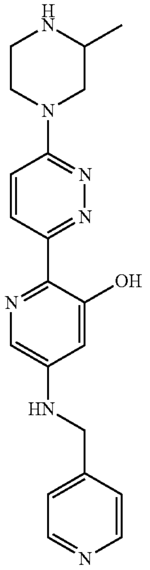
112
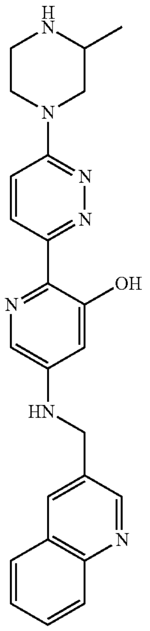

-continued
113
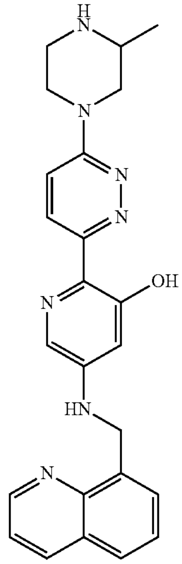
114
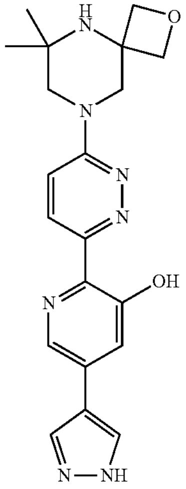
115#
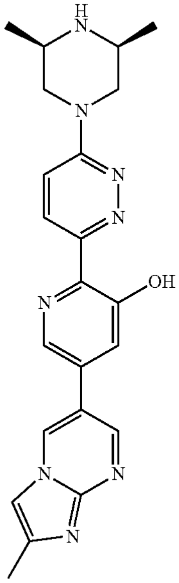
-continued
116
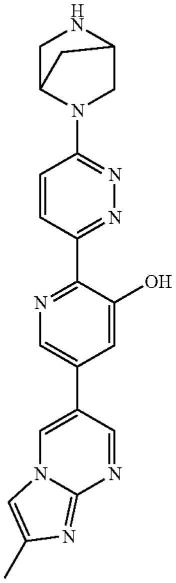
117
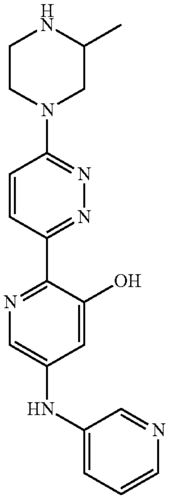

-continued
118#
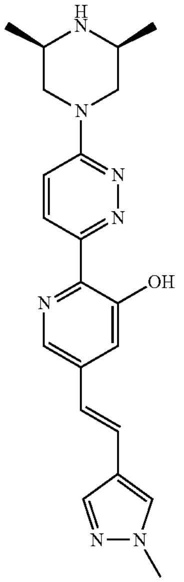
120
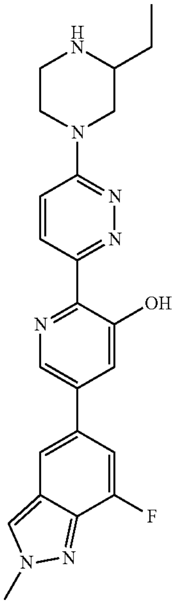
119
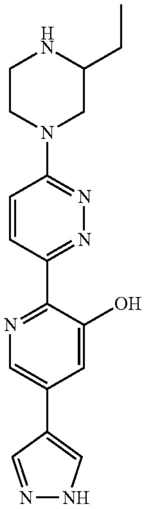
121#
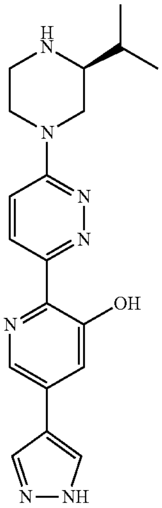

-continued
122
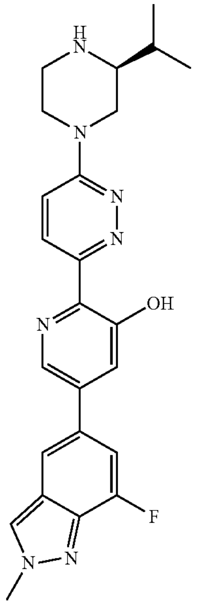
123
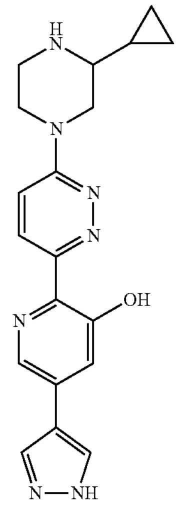
-continued
124&
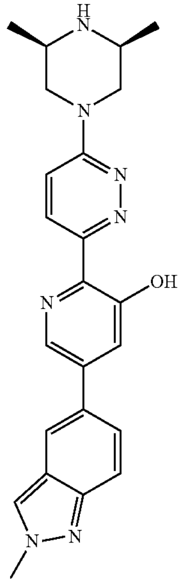
125
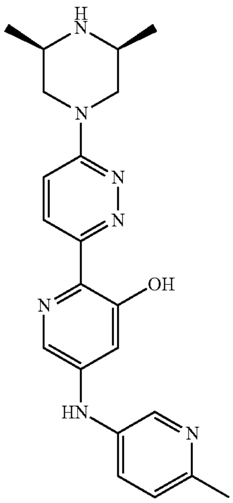
126&
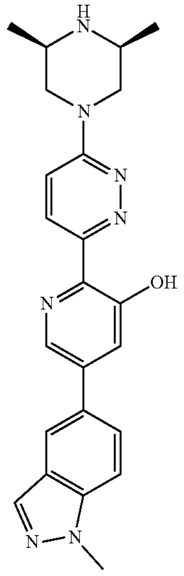

-continued
127#
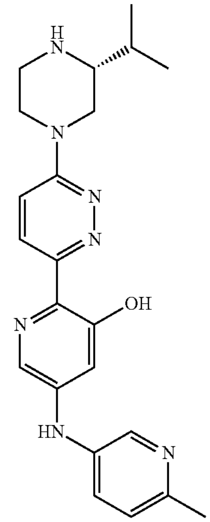
128
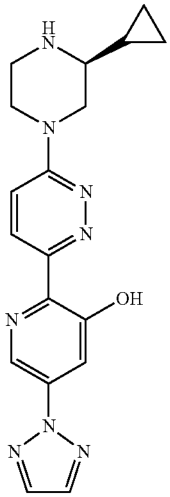
129
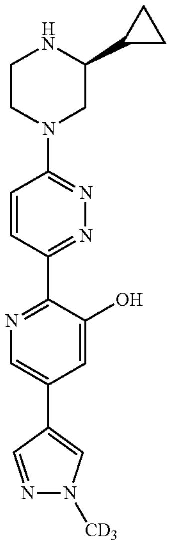
-continued
130
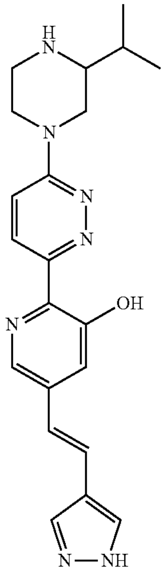
131&
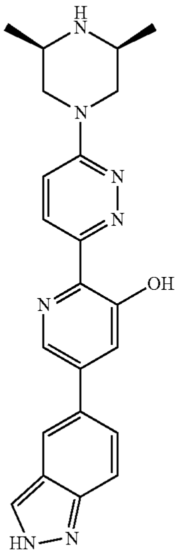
132
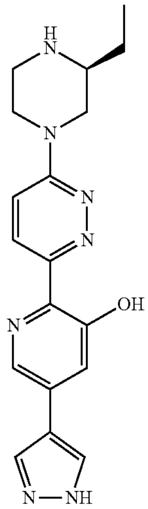

-continued
133#
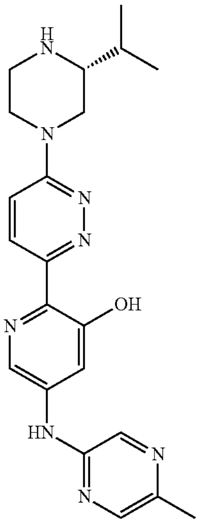
134#
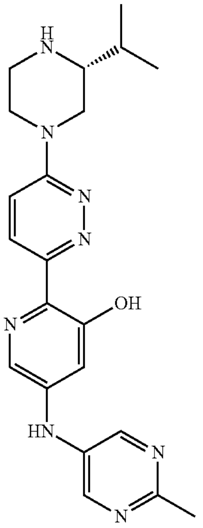
135
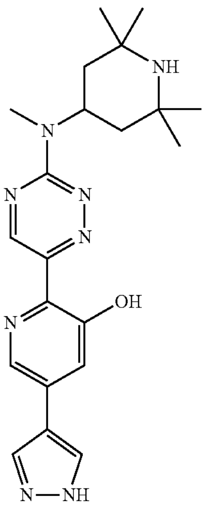
-continued
136
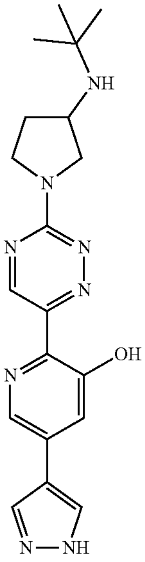
137
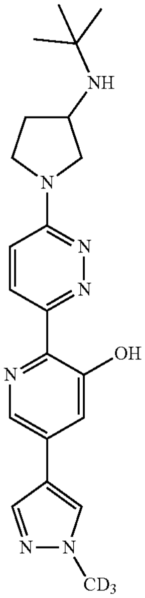

138
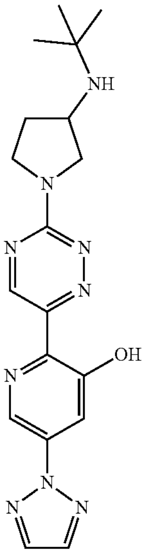
139#
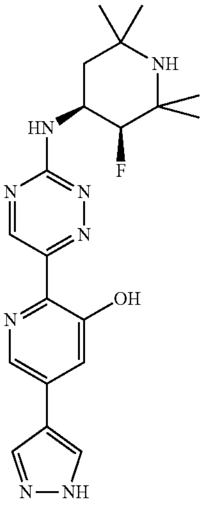
140#
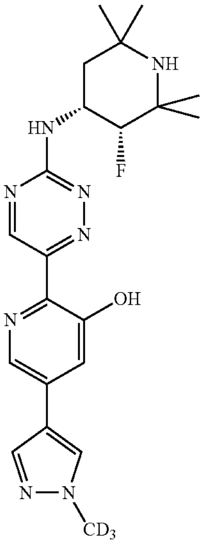
141
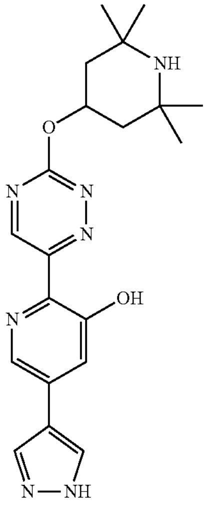
142
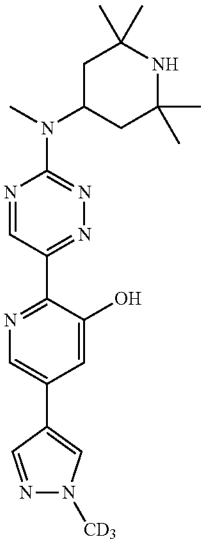
143
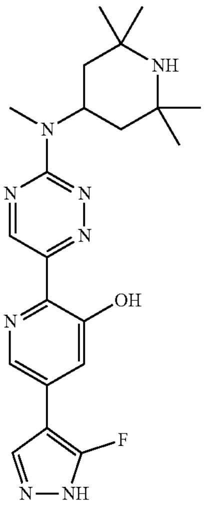

-continued
144
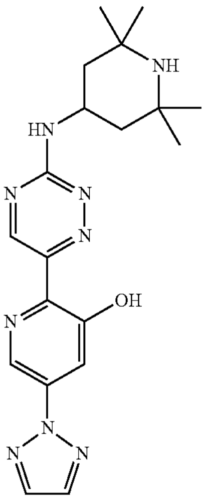
145
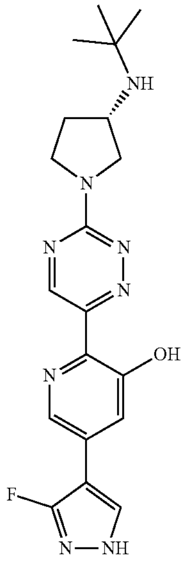
-continued
146
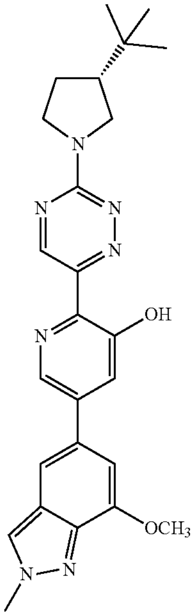
147
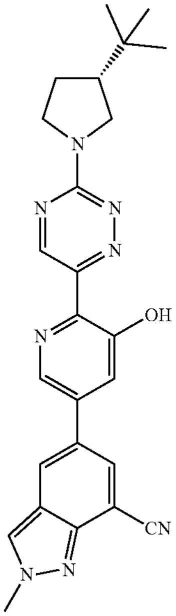

-continued
148
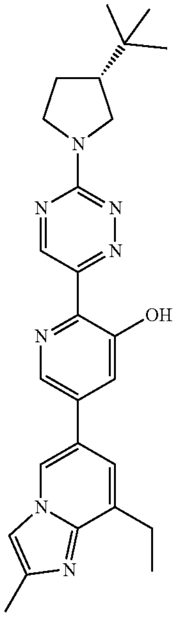
150
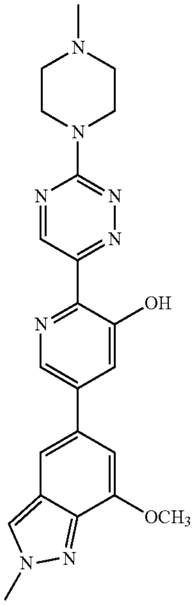
149
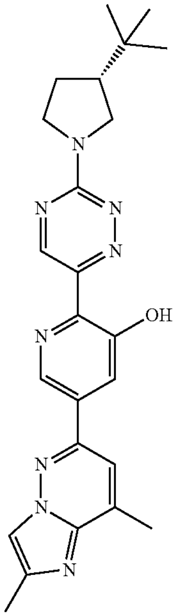
151
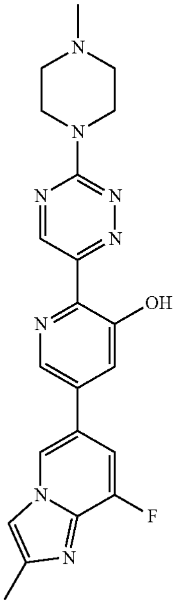

-continued
152
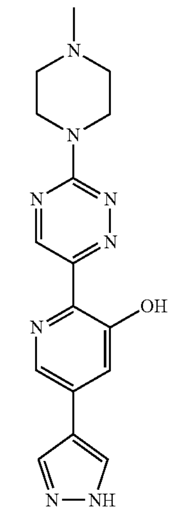
153
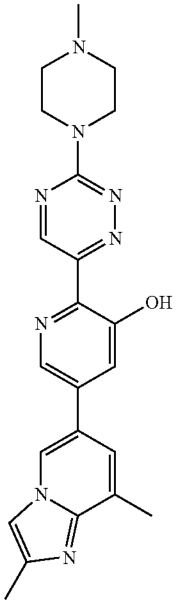
154
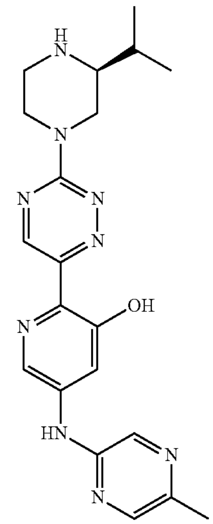
-continued
155
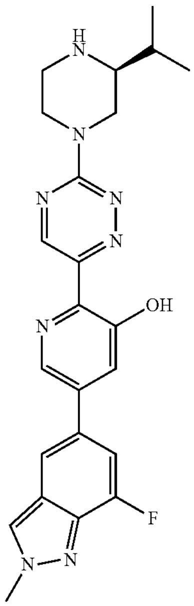
156
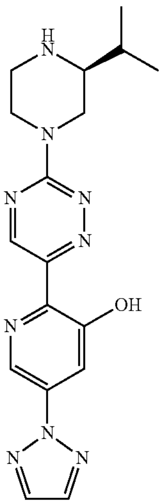

-continued
157
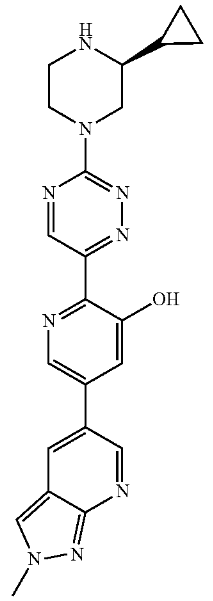
158
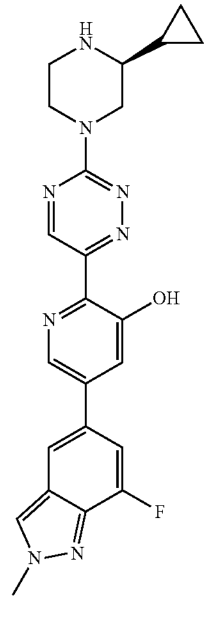
-continued
159
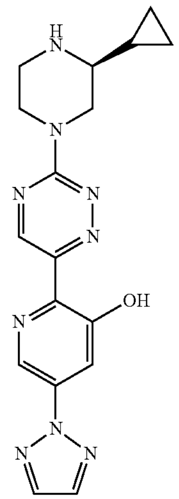
160
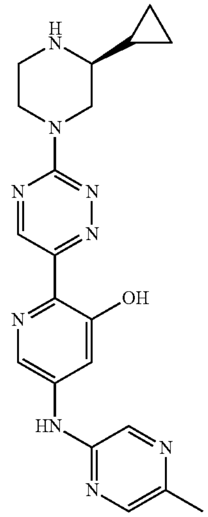
161
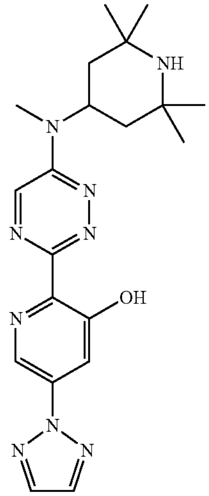

-continued

162

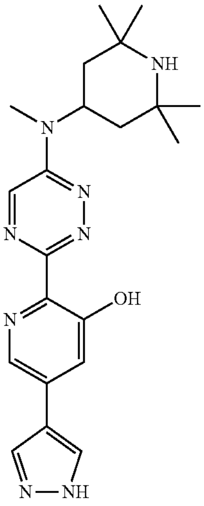

163

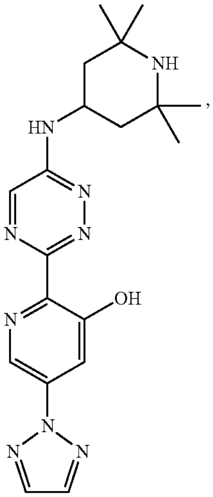

, and

-continued

164&

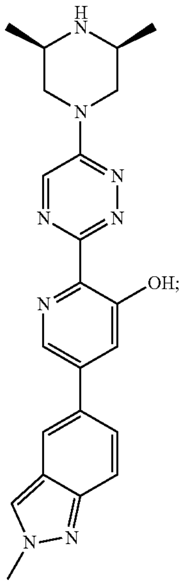

wherein a form of the compound is selected from the group consisting of a salt, hydrate, solvate, racemate, enantiomer, diastereomer, tautomer, and mixtures thereof.

An aspect the compound of Formula (I), Formula (II), or Formula (III) or a form thereof includes a compound selected from the group consisting of, wherein "^" indicates that the salt form was isolated:

| Cpd | Name |
|---|---|
| 1^ | 5-(1H-pyrazol-4-yl)-2-{6-[(2,2,6,6-tetramethylpiperidin-4-yl)oxy]pyridazin-3-yl}pyridin-3-ol |
| 2^ | 2-{6-[methyl(2,2,6,6-tetramethylpiperidin-4-yl)amino]pyridazin-3-yl}-5-(1H-pyrazol-4-yl)pyridin-3-ol |
| 3^ | 5-[1-($^{2}H_3$)methyl-1H-pyrazol-4-yl]-2-{6-[(2,2,6,6-tetramethylpiperidin-4-yl)oxy]pyridazin-3-yl}pyridin-3-ol |
| 4 | 5-(1-methyl-1H-pyrazol-3-yl)-2-{6-[(2,2,6,6-tetramethylpiperidin-4-yl)oxy]pyridazin-3-yl}pyridin-3-ol |
| 5 | 5-(1H-imidazol-1-yl)-2-{6-[(2,2,6,6-tetramethylpiperidin-4-yl)oxy]pyridazin-3-yl}pyridin-3-ol |
| 6 | 2-(6-{[(3R,4S)-3-fluoro-2,2,6,6-tetramethylpiperidin-4-yl]oxy}pyridazin-3-yl)-5-(1H-pyrazol-4-yl)pyridin-3-ol and 2-(6-{[(3S,4R)-3-fluoro-2,2,6,6-tetramethylpiperidin-4-yl]oxy}pyridazin-3-yl)-5-(1H-pyrazol-4-yl)pyridin-3-ol |
| 7 | 2-(6-{[(3R,4S)-3-fluoro-2,2,6,6-tetramethylpiperidin-4-yl]oxy}pyridazin-3-yl)-5-(1-methyl-1H-pyrazol-3-yl)pyridin-3-ol or 2-(6-{[(3S,4R)-3-fluoro-2,2,6,6-tetramethylpiperidin-4-yl]oxy}pyridazin-3-yl)-5-(1-methyl-1H-pyrazol-3-yl)pyridin-3-ol |
| 8 | 2-(6-{[(3R,4S)-3-fluoro-2,2,6,6-tetramethylpiperidin-4-yl]amino}pyridazin-3-yl)-5-(1H-pyrazol-4-yl)pyridin-3-ol |
| 9 | 2-(6-{[(3R,4S)-3-fluoro-2,2,6,6-tetramethylpiperidin-4-yl]oxy}pyridazin-3-yl)-5-(1H-imidazol-1-yl)pyridin-3-ol or 2-(6-{[(3S,4R)-3-fluoro-2,2,6,6-tetramethylpiperidin-4-yl]oxy}pyridazin-3-yl)-5-(1H-imidazol-1-yl)pyridin-3-ol |
| 10 | 5-(1,3-oxazol-2-yl)-2-{6-[(2,2,6,6-tetramethylpiperidin-4-yl)oxy]pyridazin-3-yl}pyridin-3-ol |

-continued

| Cpd | Name |
|---|---|
| 11 | 2-(6-{[(3R,4S)-3-fluoro-2,2,6,6-tetramethylpiperidin-4-yl]oxy}pyridazin-3-yl)-5-(2H-1,2,3-triazol-2-yl)pyridin-3-ol or 2-(6-{[(3S,4R)-3-fluoro-2,2,6,6-tetramethylpiperidin-4-yl]oxy}pyridazin-3-yl)-5-(2H-1,2,3-triazol-2-yl)pyridin-3-ol |
| 12 | 2-(6-{[(3R,4S)-3-fluoro-2,2,6,6-tetramethylpiperidin-4-yl]oxy}pyridazin-3-yl)-5-(1,3-oxazol-2-yl)pyridin-3-ol or 2-(6-{[(3S,4R)-3-fluoro-2,2,6,6-tetramethylpiperidin-4-yl]oxy}pyridazin-3-yl)-5-(1,3-oxazol-2-yl)pyridin-3-ol |
| 13 | 5-(1-methyl-1H-pyrazol-3-yl)-2-{6-[methyl(2,2,6,6-tetramethylpiperidin-4-yl)amino]pyridazin-3-yl}pyridin-3-ol |
| 14 | 2-{6-[methyl(2,2,6,6-tetramethylpiperidin-4-yl)amino]pyridazin-3-yl}-5-(1,3-oxazol-2-yl)pyridin-3-ol |
| 15 | 5-(1H-imidazol-1-yl)-2-{6-[methyl(2,2,6,6-tetramethylpiperidin-4-yl)amino]pyridazin-3-yl}pyridin-3-ol |
| 16 | 2-(6-{[(3S,4S)-3-fluoro-2,2,6,6-tetramethylpiperidin-4-yl]amino}pyridazin-3-yl)-5-(1H-pyrazol-3-yl)pyridin-3-ol and 2-(6-{[(3R,4R)-3-fluoro-2,2,6,6-tetramethylpiperidin-4-yl]amino}pyridazin-3-yl)-5-(1H-pyrazol-3-yl)pyridin-3-ol |
| 17 | 2-{6-[(3R)-(tert-butylamino)pyrrolidin-1-yl]pyridazin-3-yl}-5-(1-methyl-1H-pyrazol-3-yl)pyridin-3-ol and 2-{6-[(3S)-(tert-butylamino)pyrrolidin-1-yl]pyridazin-3-yl}-5-(1-methyl-1H-pyrazol-3-yl)pyridin-3-ol |
| 18 | 2-{6-[(3R)-(tert-butylamino)pyrrolidin-1-yl]pyridazin-3-yl}-5-(1H-pyrazol-4-yl)pyridin-3-ol and 2-{6-[(3S)-(tert-butylamino)pyrrolidin-1-yl]pyridazin-3-yl}-5-(1-methyl-1H-pyrazol-3-yl)pyridin-3-ol |
| 19^ | 2-(6-{[(3R,4R)-3-fluoro-2,2,6,6-tetramethylpiperidin-4-yl]amino}pyridazin-3-yl)-5-[1-($^{2}H_{3}$)methyl-1H-pyrazol-4-yl]pyridin-3-ol or 2-(6-{[(3S,4S)-3-fluoro-2,2,6,6-tetramethylpiperidin-4-yl]amino}pyridazin-3-yl)-5-[1-($^{2}H_{3}$)methyl-1H-pyrazol-4-yl]pyridin-3-ol |
| 20 | 2-{6-[(2,2,6,6-tetramethylpiperidin-4-yl)oxy]pyridazin-3-yl}-5-(2H-1,2,3-triazol-2-yl)pyridin-3-ol |
| 21^ | 2-{6-[(5,5-dimethyl-4-azaspiro[2.5]octan-7-yl)oxy]pyridazin-3-yl}-5-(2H-1,2,3-triazol-2-yl)pyridin-3-ol |
| 22^ | 5-(5-fluoro-1H-pyrazol-4-yl)-2-(6-{[(3R,4S)-3-fluoro-2,2,6,6-tetramethylpiperidin-4-yl]oxy}pyridazin-3-yl)pyridin-3-ol or 5-(5-fluoro-1H-pyrazol-4-yl)-2-(6-{[(3S,4R)-3-fluoro-2,2,6,6-tetramethylpiperidin-4-yl]oxy}pyridazin-3-yl)pyridin-3-ol |
| 23 | 2-{6-[(3R)-3-(tert-butylamino)pyrrolidin-1-yl]pyridazin-3-yl}-5-[1-($^{2}H_{3}$)methyl-1H-pyrazol-4-yl]pyridin-3-ol |
| 24 | 2-{6-[(3R)-3-(tert-butylamino)pyrrolidin-1-yl]pyridazin-3-yl}-5-(2H-1,2,3-triazol-2-yl)pyridin-3-ol |
| 25^ | 2-(6-{[(3R,4R)-3-fluoro-2,2,6,6-tetramethylpiperidin-4-yl]amino}pyridazin-3-yl)-5-{6-[($^{2}H_{3}$)methyloxy]pyrimidin-4-yl}pyridin-3-ol |
| 26^ | 2-{6-[(5,5-dimethyl-4-azaspiro[2.5]octan-7-yl)oxy]pyridazin-3-yl}-5-(5-fluoro-1H-pyrazol-4-yl)pyridin-3-ol |
| 27^ | 2-{6-[(5,5-dimethyl-4-azaspiro[2.5]octan-7-yl)oxy]pyridazin-3-yl}-5-(1H-pyrazol-4-yl)pyridin-3-ol |
| 28^ | 2-{6-[(5,5-dimethyl-4-azaspiro[2.5]octan-7-yl)oxy]pyridazin-3-yl}-5-(1,3-oxazol-2-yl)pyridin-3-ol |
| 29^ | 2-{6-[3-(tert-butylamino)pyrrolidin-1-yl]pyridazin-3-yl}-5-[1-($^{2}H_{3}$)methyl-1H-pyrazol-4-yl]pyridin-3-ol |
| 30 | 2-{6-[(3R)-3-(tert-butylamino)pyrrolidin-1-yl]pyridazin-3-yl}-5-(6-methoxypyrimidin-4-yl)pyridin-3-ol |
| 31^ | 2-{6-[(4-azadispiro[$2.1.2^{5}.3^{3}$]decan-9-yl)oxy]pyridazin-3-yl}-5-(1H-pyrazol-4-yl)pyridin-3-ol |
| 32^ | 2-(6-{[(1R,3s,5S)-1,5-dimethyl-8-azabicyclo[3.2.1]octan-3-yl]oxy}pyridazin-3-yl)-5-(2H-1,2,3-triazol-2-yl)pyridin-3-ol and 2-(6-{[(1S,3r,5R)-1,5-dimethyl-8-azabicyclo[3.2.1]octan-3-yl]oxy}pyridazin-3-yl)-5-(2H-1,2,3-triazol-2-yl)pyridin-3-ol |
| 33 | 2-(6-{[(1R,3s,5S)-1,5-dimethyl-8-azabicyclo[3.2.1]octan-3-yl]oxy}pyridazin-3-yl)-5-[1-($^{2}H_{3}$)methyl-1H-pyrazol-4-yl]pyridin-3-ol and 2-(6-{[(1S,3r,5R)-1,5-dimethyl-8-azabicyclo[3.2.1]octan-3-yl]oxy}pyridazin-3-yl)-5-[1-($^{2}H_{3}$)methyl-1H-pyrazol-4-yl]pyridin-3-ol |
| 34 | 5-[6-(6-{[(3R,4S)-3-fluoro-2,2,6,6-tetramethylpiperidin-4-yl]oxy}pyridazin-3-yl)-5-hydroxypyridin-3-yl]-2-methyl-2H-indazole-7-carbonitrile or 5-[6-(6-{[(3S,4R)-3-fluoro-2,2,6,6-tetramethylpiperidin-4-yl]oxy}pyridazin-3-yl)-5-hydroxypyridin-3-yl]-2-methyl-2H-indazole-7-carbonitrile |
| 35 | 5-(7-fluoro-2-methyl-2H-indazol-5-yl)-2-(6-{[(3R,4S)-3-fluoro-2,2,6,6-tetramethylpiperidin-4-yl]oxy}pyridazin-3-yl)pyridin-3-ol or 5-(7-fluoro-2-methyl-2H-indazol-5-yl)-2-(6-{[(3S,4R)-3-fluoro-2,2,6,6-tetramethylpiperidin-4-yl]oxy}pyridazin-3-yl)pyridin-3-ol |
| 36^ | 2-(6-{[(1R,3s,5S)-1,5-dimethyl-8-azabicyclo[3.2.1]octan-3-yl]oxy}pyridazin-3-yl)-5-(pyrimidin-5-yl)pyridin-3-ol and 2-(6-{[(1S,3r,5R)-1,5-dimethyl-8-azabicyclo[3.2.1]octan-3-yl]oxy}pyridazin-3-yl)-5-(pyrimidin-5-yl)pyridin-3-ol |

-continued

| Cpd | Name |
| --- | --- |
| 37 | 6-(6-{[(3R,4S)-3-fluoro-2,2,6,6-tetramethylpiperidin-4-yl]oxy}pyridazin-3-yl)-5-hydroxy-1'-methyl[3,4'-bipyridin]-2'(1'H)-one or 6-(6-{[(3S,4R)-3-fluoro-2,2,6,6-tetramethylpiperidin-4-yl]oxy}pyridazin-3-yl)-5-hydroxy-1'-methyl[3,4'-bipyridin]-2'(1'H)-one |
| 38 | 5-(2,8-dimethylimidazo[1,2-b]pyridazin-6-yl)-2-(6-{ [(3R,4S)-3-fluoro-2,2,6,6-tetramethylpiperidin-4-yl]oxy}pyridazin-3-yl)pyridin-3-ol or 5-(2,8-dimethylimidazo[1,2-b]pyridazin-6-yl)-2-(6-{ [(3S,4R)-3-fluoro-2,2,6,6-tetramethylpiperidin-4-yl]oxy}pyridazin-3-yl)pyridin-3-ol |
| 39^ | 2-(6-{[(3S,4R)-3-fluoro-2,2,6,6-tetramethylpiperidin-4-yl]oxy}pyridazin-3-yl)-5-(1H-pyrazol-4-yl)pyridin-3-ol or 2-(6-{[(3S,4R)-3-fluoro-2,2,6,6-tetramethylpiperidin-4-yl]oxy}pyridazin-3-yl)-5-(1H-pyrazol-4-yl)pyridin-3-ol |
| 40^ | 5-(5-fluoro-1H-pyrazol-4-yl)-2-(6-{[(3S,4R)-3-fluoro-2,2,6,6-tetramethylpiperidin-4-yl]oxy}pyridazin-3-yl)pyridin-3-ol |
| 41 | 2-(6-{[(3R,4S)-3-fluoro-2,2,6,6-tetramethylpiperidin-4-yl]oxy}pyridazin-3-yl)-5-(4-methyl-1H-imidazol-1-yl)pyridin-3-ol and 2-(6-{[(3S,4R)-3-fluoro-2,2,6,6-tetramethylpiperidin-4-yl]oxy}pyridazin-3-yl)-5-(4-methyl-1H-imidazol-1-yl)pyridin-3-ol |
| 42 | 6-[6-(6-{[(3R,4S)-3-fluoro-2,2,6,6-tetramethylpiperidin-4-yl]oxy}pyridazin-3-yl)-5-hydroxypyridin-3-yl]-3-methylpyrimidin-4(3H)-one and 6-[6-(6-{[(3S,4R)-3-fluoro-2,2,6,6-tetramethylpiperidin-4-yl]oxy}pyridazin-3-yl)-5-hydroxypyridin-3-yl]-3-methylpyrimidin-4(3H)-one |
| 43^ | 2-(6-{[(3R,4S)-3-fluoro-2,2,6,6-tetramethylpiperidin-4-yl]oxy}pyridazin-3-yl)-5-(2-methylimidazo[1,2-a]pyridin-6-yl)pyridin-3-ol and 2-(6-{[(3S,4R)-3-fluoro-2,2,6,6-tetramethylpiperidin-4-yl]oxy}pyridazin-3-yl)-5-(2-methylimidazo[1,2-a]pyridin-6-yl)pyridin-3-ol |
| 44^ | 5-(2,8-dimethylimidazo[1,2-a]pyridin-6-yl)-2-(6-{[(3R,4S)-3-fluoro-2,2,6,6-tetramethylpiperidin-4-yl]oxy}pyridazin-3-yl)pyridin-3-ol and 5-(2,8-dimethylimidazo[1,2-a]pyridin-6-yl)-2-(6-{[(3S,4R)-3-fluoro-2,2,6,6-tetramethylpiperidin-4-yl]oxy}pyridazin-3-yl)pyridin-3-ol |
| 45^ | 5-(8-ethyl-2-methylimidazo[1,2-a]pyridin-6-yl)-2-(6-{[(3R,4S)-3-fluoro-2,2,6,6-tetramethylpiperidin-4-yl]oxy}pyridazin-3-yl)pyridin-3-ol and 5-(8-ethyl-2-methylimidazo[1,2-a]pyridin-6-yl)-2-(6-{[(3S,4R)-3-fluoro-2,2,6,6-tetramethylpiperidin-4-yl]oxy}pyridazin-3-yl)pyridin-3-ol |
| 46^ | 2-(6-{[(3R,4S)-3-fluoro-2,2,6,6-tetramethylpiperidin-4-yl]oxy}pyridazin-3-yl)-5-[2-methyl-8-(trifluoromethyl)imidazo[1,2-a]pyridin-6-yl]pyridin-3-ol and 2-(6-{[(3S,4R)-3-fluoro-2,2,6,6-tetramethylpiperidin-4-yl]oxy}pyridazin-3-yl)-5-[2-methyl-8-(trifluoromethyl)imidazo[1,2-a]pyridin-6-yl]pyridin-3-ol |
| 47 | 5-(2,8-dimethylimidazo[1,2-b]pyridazin-6-yl)-2-(6-{[(3R,4S)-3-fluoro-2,2,6,6-tetramethylpiperidin-4-yl]oxy}pyridazin-3-yl)pyridin-3-ol and 5-(2,8-dimethylimidazo[1,2-b]pyridazin-6-yl)-2-(6-{[(3S,4R)-3-fluoro-2,2,6,6-tetramethylpiperidin-4-yl]oxy}pyridazin-3-yl)pyridin-3-ol |
| 48^ | 2-(6-{[(3R,4S)-3-fluoro-2,2,6,6-tetramethylpiperidin-4-yl]oxy}pyridazin-3-yl)-5-(2-methylimidazo[1,2-b]pyridazin-6-yl)pyridin-3-ol and 2-(6-{[(3S,4R)-3-fluoro-2,2,6,6-tetramethylpiperidin-4-yl]oxy}pyridazin-3-yl)-5-(2-methylimidazo[1,2-b]pyridazin-6-yl)pyridin-3-ol |
| 49^ | 2-(6-{[(3R,4S)-3-fluoro-2,2,6,6-tetramethylpiperidin-4-yl]oxy}pyridazin-3-yl)-5-(imidazo[1,2-b]pyridazin-6-yl)pyridin-3-ol and 2-(6-{[(3S,4R)-3-fluoro-2,2,6,6-tetramethylpiperidin-4-yl]oxy}pyridazin-3-yl)-5-(imidazo[1,2-b]pyridazin-6-yl)pyridin-3-ol |
| 50^ | 5-(2,8-dimethylimidazo[1,2-b]pyridazin-6-yl)-2-{6-[(2,2,6,6-tetramethylpiperidin-4-yl)oxy]pyridazin-3-yl}pyridin-3-ol |
| 51^ | 2-(6-{[(3R,4S)-3-fluoro-2,2,6,6-tetramethylpiperidin-4-yl]oxy}pyridazin-3-yl)-5-(1H-pyrazol-4-yl)pyridin-3-ol or 2-(6-{[(3S,4R)-3-fluoro-2,2,6,6-tetramethylpiperidin-4-yl]oxy}pyridazin-3-yl)-5-(1H-pyrazol-4-yl)pyridin-3-ol |
| 52^ | 5-(7-fluoro-2-methyl-2H-indazol-5-yl)-2-{6-[(2,2,6,6-tetramethylpiperidin-4-yl)oxy]pyridazin-3-yl}pyridin-3-ol |
| 53^ | 2-{6-[(5,5-dimethyl-4-azaspiro[2.5]octan-7-yl)(methyl)amino]pyridazin-3-yl}-5-[1-($^2H_3$)methyl-1H-pyrazol-4-yl]pyridin-3-ol |
| 54^ | 2-(6-{[(3R,4S)-3-fluoro-2,2,6,6-tetramethylpiperidin-4-yl]oxy}pyridazin-3-yl)-5-(2-methylimidazo[1,2-a]pyrimidin-6-yl)pyridin-3-ol and 2-(6-{[(3S,4R)-3-fluoro-2,2,6,6-tetramethylpiperidin-4-yl]oxy}pyridazin-3-yl)-5-(2-methylimidazo[1,2-a]pyrimidin-6-yl)pyridin-3-ol |
| 55^ | 2-(6-{[(3R,4S)-3-fluoro-2,2,6,6-tetramethylpiperidin-4-yl]oxy}pyridazin-3-yl)-5-(2-methyl[1,2,4]triazolo[1,5-a]pyridin-6-yl)pyridin-3-ol and 2-(6-{[(3S,4R)-3-fluoro-2,2,6,6-tetramethylpiperidin-4-yl]oxy}pyridazin-3-yl)-5-(2-methyl[1,2,4]triazolo[1,5-a]pyridin-6-yl)pyridin-3-ol |
| 56^ | 5-(2,4-dimethyl-1,3-benzoxazol-6-yl)-2-(6-{[(3R,4S)-3-fluoro-2,2,6,6-tetramethylpiperidin-4-yl]oxy}pyridazin-3-yl)pyridin-3-ol and 5-(2,4-dimethyl-1,3-benzoxazol-6-yl)-2-(6-{[(3S,4R)-3-fluoro-2,2,6,6-tetramethylpiperidin-4-yl]oxy}pyridazin-3-yl)pyridin-3-ol |
| 57^ | 2-(6-{[(3R,4S)-3-fluoro-2,2,6,6-tetramethylpiperidin-4-yl]oxy}pyridazin-3-yl)-5-(8-methoxy-2-methylimidazo[1,2-b]pyridazin-6-yl)pyridin-3-ol and 2-(6-{[(3S,4R)-3-fluoro-2,2,6,6-tetramethylpiperidin-4-yl]oxy}pyridazin-3-yl)-5-(8-methoxy-2-methylimidazo[1,2-b]pyridazin-6-yl)pyridin-3-ol |

-continued

| Cpd | Name |
|---|---|
| 58 | 5-(7-fluoro-2-methyl-2H-indazol-4-yl)-2-(6-{[(3R,4S)-3-fluoro-2,2,6,6-tetramethylpiperidin-4-yl]oxy}pyridazin-3-yl)pyridin-3-ol and 5-(7-fluoro-2-methyl-2H-indazol-4-yl)-2-(6-{[(3S,4R)-3-fluoro-2,2,6,6-tetramethylpiperidin-4-yl]oxy}pyridazin-3-yl)pyridin-3-ol |
| 59 | 6-[6-(6-{[(3R,4S)-3-fluoro-2,2,6,6-tetramethylpiperidin-4-yl]oxy}pyridazin-3-yl)-5-hydroxypyridin-3-yl]-2-methylimidazo[1,2-a]pyridine-8-carbonitrile and 6-[6-(6-{[(3S,4R)-3-fluoro-2,2,6,6-tetramethylpiperidin-4-yl]oxy}pyridazin-3-yl)-5-hydroxypyridin-3-yl]-2-methylimidazo[1,2-a]pyridine-8-carbonitrile |
| 60 | 5-(8-ethyl-2-methylimidazo[1,2-b]pyridazin-6-yl)-2-(6-{[(3R,4S)-3-fluoro-2,2,6,6-tetramethylpiperidin-4-yl]oxy}pyridazin-3-yl)pyridin-3-ol and 5-(8-ethyl-2-methylimidazo[1,2-b]pyridazin-6-yl)-2-(6-{[(3S,4R)-3-fluoro-2,2,6,6-tetramethylpiperidin-4-yl]oxy}pyridazin-3-yl)pyridin-3-ol |
| 61^ | 2-{6-[(2,2,6,6-tetramethylpiperidin-4-yl)oxy]pyridazin-3-yl}-5-(1H-1,2,4-triazol-1-yl)pyridin-3-ol |
| 62^ | 5-[6-(6-{[2,2,6,6-tetramethylpiperidin-4-yl]oxy}pyridazin-3-yl)-5-hydroxypyridin-3-yl]-2-methyl-2H-indazole-7-carbonitrile |
| 63 | 2-{6-[(2,2,6,6-tetramethylpiperidin-4-yl)oxy]pyridazin-3-yl}-5-(1H-1,2,3-triazol-1-yl)pyridin-3-ol |
| 64^ | 2-{6-[(5,5-dimethyl-4-azaspiro[2.5]octan-7-yl)(methyl)amino]pyridazin-3-yl}-5-(7-fluoro-2-methyl-2H-indazol-5-yl)pyridin-3-ol |
| 65^ | 5-(imidazo[1,2-b]pyridazin-6-yl)-2-{6-[(2,2,6,6-tetramethylpiperidin-4-yl)oxy]pyridazin-3-yl}pyridin-3-ol |
| 66 | 2-(6-{[(3R,4S)-3-fluoro-2,2,6,6-tetramethylpiperidin-4-yl]oxy}pyridazin-3-yl)-5-(imidazo[1,2-a]pyrazin-6-yl)pyridin-3-ol and 2-(6-{[(3S,4R)-3-fluoro-2,2,6,6-tetramethylpiperidin-4-yl]oxy}pyridazin-3-yl)-5-(imidazo[1,2-a]pyrazin-6-yl)pyridin-3-ol |
| 67 | 5-(1,3-dimethylpyrrolo[1,2-a]pyrazin-7-yl)-2-(6-{[(3R,4S)-3-fluoro-2,2,6,6-tetramethylpiperidin-4-yl]oxy}pyridazin-3-yl)pyridin-3-ol and 5-(1,3-dimethylpyrrolo[1,2-a]pyrazin-7-yl)-2-(6-{[(3S,4R)-3-fluoro-2,2,6,6-tetramethylpiperidin-4-yl]oxy}pyridazin-3-yl)pyridin-3-ol |
| 68 | 6-[6-(6-{[(3R,4S)-3-fluoro-2,2,6,6-tetramethylpiperidin-4-yl]oxy}pyridazin-3-yl)-5-hydroxypyridin-3-yl]-2-methylimidazo[1,2-b]pyridazine-8-carbonitrile and 6-[6-(6-{[(3S,4R)-3-fluoro-2,2,6,6-tetramethylpiperidin-4-yl]oxy}pyridazin-3-yl)-5-hydroxypyridin-3-yl]-2-methylimidazo[1,2-b]pyridazine-8-carbonitrile |
| 69^ | 2-{6-[(3R,5S)-3,5-dimethylpiperazin-1-yl]pyridazin-3-yl}-5-(7-fluoro-2-methyl-2H-indazol-5-yl)pyridin-3-ol and 2-{6-[(3S,5R)-3,5-dimethylpiperazin-1-yl]pyridazin-3-yl}-5-(7-fluoro-2-methyl-2H-indazol-5-yl)pyridin-3-ol |
| 70 | 5-(6-methoxypyrimidin-4-yl)-2-{6-[(3R)-3-(methylamino)pyrrolidin-1-yl]pyridazin-3-yl}pyridin-3-ol |
| 71^ | 2-(6-{[(1R,3s,5S)-1,5-dimethyl-8-azabicyclo[3.2.1]octan-3-yl]oxy}pyridazin-3-yl)-5-(1H-1,2,3-triazol-1-yl)pyridin-3-ol and 2-(6-{[(1S,3r,5R)-1,5-dimethyl-8-azabicyclo[3.2.1]octan-3-yl]oxy}pyridazin-3-yl)-5-(1H-1,2,3-triazol-1-yl)pyridin-3-ol |
| 72 | 2-(6-{[(3R,4S)-3-fluoro-2,2,6,6-tetramethylpiperidin-4-yl]oxy}pyridazin-3-yl)-5-([1,2,4]triazolo[1,5-a]pyrazin-2-yl)pyridin-3-ol and 2-(6-{[(3S,4R)-3-fluoro-2,2,6,6-tetramethylpiperidin-4-yl]oxy}pyridazin-3-yl)-5-([1,2,4]triazolo[1,5-a]pyrazin-2-yl)pyridin-3-ol |
| 73 | 2-{6-[(4-azadispiro[$2.1.2^{5}.3^{3}$]decan-9-yl)oxy]pyridazin-3-yl}-5-(2H-1,2,3-triazol-2-yl)pyridin-3-ol |
| 74^ | 5-(6-methoxypyrimidin-4-yl)-2-{6-[(2,2,6,6-tetramethylpiperidin-4-yl)oxy]pyridazin-3-yl}pyridin-3-ol |
| 75 | 2-{6-[(5,5-dimethyl-4-azaspiro[2.5]octan-7-yl)oxy]pyridazin-3-yl}-5-[1-($^{2}H_{3}$)methyl-1H-pyrazol-4-yl]pyridin-3-ol |
| 76^ | 2-{6-[(3R)-3-(tert-butylamino)pyrrolidin-1-yl]pyridazin-3-yl}-5-(2-methyl-1,3-oxazol-5-yl)pyridin-3-ol |
| 77 | 2-{6-[(3R)-3-(methylamino)pyrrolidin-1-yl]pyridazin-3-yl}-5-(2-methyl-1,3-oxazol-5-yl)pyridin-3-ol |
| 78 | 5-(6-{6-[(3R,5S)-3,5-dimethylpiperazin-1-yl]pyridazin-3-yl}-5-hydroxypyridin-3-yl)-2-methyl-2H-indazole-7-carbonitrile and 5-(6-{6-[(3S,5R)-3,5-dimethylpiperazin-1-yl]pyridazin-3-yl}-5-hydroxypyridin-3-yl)-2-methyl-2H-indazole-7-carbonitrile |
| 79 | 2-{6-[(5,5-dimethyl-4-azaspiro[2.5]octan-7-yl)oxy]pyridazin-3-yl}-5-(1,3-thiazol-2-yl)pyridin-3-ol |
| 80 | 2-{6-[(3R)-3-(methylamino)pyrrolidin-1-yl]pyridazin-3-yl}-5-(1,3-oxazol-2-yl)pyridin-3-ol |
| 81^ | 5-(8-methoxy-2-methylimidazo[1,2-b]pyridazin-6-yl)-2-{6-[(2,2,6,6-tetramethylpiperidin-4-yl)oxy]pyridazin-3-yl}pyridin-3-ol |
| 82^ | 2-(6-{[(5R,7S)-5-methyl-4-azaspiro[2.5]octan-7-yl]oxy}pyridazin-3-yl)-5-[1-($^{2}H_{3}$)methyl-1H-pyrazol-4-yl]pyridin-3-ol |
| 83 | 2-(6-{[(5S,7R)-5-methyl-4-azaspiro[2.5]octan-7-yl]oxy}pyridazin-3-yl)-5-[1-($^{2}H_{3}$)methyl-1H-pyrazol-4-yl]pyridin-3-ol |
| 84^ | 2-(6-{[(5S,7S)-5-methyl-4-azaspiro[2.5]octan-7-yl]oxy}pyridazin-3-yl)-5-[1-($^{2}H_{3}$)methyl-1H-pyrazol-4-yl]pyridin-3-ol |
| 85^ | 2-(6-{[(5R,7R)-5-methyl-4-azaspiro[2.5]octan-7-yl]oxy}pyridazin-3-yl)-5-[1-($^{2}H_{3}$)methyl-1H-pyrazol-4-yl]pyridin-3-ol |

-continued

| Cpd | Name |
|---|---|
| 86^ | 2-{6-[(3R,5S)-3,5-dimethylpiperazin-1-yl]pyridazin-3-yl}-5-(1H-pyrazol-4-yl)pyridin-3-ol and 2-{6-[(3S,5R)-3,5-dimethylpiperazin-1-yl]pyridazin-3-yl}-5-(1H-pyrazol-4-yl)pyridin-3-ol |
| 87^ | 2-{6-[(3R,5S)-3,5-dimethylpiperazin-1-yl]pyridazin-3-yl}-5-(7-methoxy-2-methyl-2H-indazol-5-yl)pyridin-3-ol and 2-{6-[(3S,5R)-3,5-dimethylpiperazin-1-yl]pyridazin-3-yl}-5-(7-methoxy-2-methyl-2H-indazol-5-yl)pyridin-3-ol |
| 88^ | 5-(1H-pyrazol-4-yl)-2-[6-(3,3,5,5-tetramethylpiperazin-1-yl)pyridazin-3-yl]pyridin-3-ol |
| 89^ | 5-(7-fluoro-2-methyl-2H-indazol-5-yl)-2-[6-(3,3,5,5-tetramethylpiperazin-1-yl)pyridazin-3-yl]pyridin-3-ol |
| 90^ | 5-(1H-pyrazol-4-yl)-2-{6-[(3R,5S)-3,4,5-trimethylpiperazin-1-yl]pyridazin-3-yl}pyridin-3-ol and 5-(1H-pyrazol-4-yl)-2-{6-[(3S,5R)-3,4,5-trimethylpiperazin-1-yl]pyridazin-3-yl}pyridin-3-ol |
| 91^ | 5-(7-fluoro-2-methyl-2H-indazol-5-yl)-2-{6-[(3R,5S)-3,4,5-trimethylpiperazin-1-yl]pyridazin-3-yl}pyridin-3-ol and 5-(7-fluoro-2-methyl-2H-indazol-5-yl)-2-{6-[(3S,5R)-3,4,5-trimethylpiperazin-1-yl]pyridazin-3-yl}pyridin-3-ol |
| 92^ | 2-{6-[(3R,5S)-3,5-dimethylpiperazin-1-yl]pyridazin-3-yl}-5-(2-methylimidazo[1,2-a]pyridin-6-yl)pyridin-3-ol and 2-{6-[(3S,5R)-3,5-dimethylpiperazin-1-yl]pyridazin-3-yl}-5-(2-methylimidazo[1,2-a]pyridin-6-yl)pyridin-3-ol |
| 93 | 5-(7-fluoro-2-methyl-2H-indazol-5-yl)-2-[6-(piperazin-1-yl)pyridazin-3-yl]pyridin-3-ol |
| 94^ | 2-{6-[(3R,5S)-3,5-dimethylpiperazin-1-yl]pyridazin-3-yl}-5-([1,2,4]triazolo[1,5-a]pyridin-6-yl)pyridin-3-ol and 2-{6-[(3S,5R)-3,5-dimethylpiperazin-1-yl]pyridazin-3-yl}-5-([1,2,4]triazolo[1,5-a]pyridin-6-yl)pyridin-3-ol |
| 95^ | 5-(7-methoxy-2-methyl-2H-indazol-5-yl)-2-[6-(3-methylpiperazin-1-yl)pyridazin-3-yl]pyridin-3-ol |
| 96 | 6-{6-[(3R,5S)-3,5-dimethylpiperazin-1-yl]pyridazin-3-yl}-2'-methoxy[3,4'-bipyridin]-5-ol and 6-{6-[(3S,5R)-3,5-dimethylpiperazin-1-yl]pyridazin-3-yl}-2'-methoxy[3,4'-bipyridin]-5-ol |
| 97 | 5-(7-fluoro-2-methyl-2H-indazol-5-yl)-2-[6-(3-methylpiperazin-1-yl)pyridazin-3-yl]pyridin-3-ol |
| 98 | 2-[6-(4,7-diazaspiro[2.5]octan-7-yl)pyridazin-3-yl]-5-(7-fluoro-2-methyl-2H-indazol-5-yl)pyridin-3-ol |
| 99 | 2-{6-[(3R,5S)-3,5-dimethylpiperazin-1-yl]pyridazin-3-yl}-5-(2-methyl[1,2,4]triazolo[1,5-a]pyridin-6-yl)pyridin-3-ol and 2-{6-[(3S,5R)-3,5-dimethylpiperazin-1-yl]pyridazin-3-yl}-5-(2-methyl[1,2,4]triazolo[1,5-a]pyridin-6-yl)pyridin-3-ol |
| 100 | 2-[6-(4-cyclopropylpiperazin-1-yl)pyridazin-3-yl]-5-(7-fluoro-2-methyl-2H-indazol-5-yl)pyridin-3-ol |
| 101^ | 5-(7-fluoro-2-methyl-2H-indazol-5-yl)-2-[6-(4-methylpiperazin-1-yl)pyridazin-3-yl]pyridin-3-ol |
| 102 | [(3R,4S)-3-fluoro-4-({6-[3-hydroxy-5-(1H-pyrazol-4-yl)pyridin-2-yl]pyridazin-3-yl}oxy)-2,2,6,6-tetramethylpiperidin-1-yl]oxidanyl |
| 103 | 5-(7-fluoro-2-methyl-2H-indazol-5-yl)-2-{6-[(3S)-3-methylpiperazin-1-yl]pyridazin-3-yl}pyridin-3-ol |
| 104 | 5-(7-fluoro-2-methyl-2H-indazol-5-yl)-2-{6-[(3R)-3-methylpiperazin-1-yl]pyridazin-3-yl}pyridin-3-ol |
| 105^ | 2-[6-(2,5-diazabicyclo[2.2.1]heptan-2-yl)pyridazin-3-yl]-5-(7-fluoro-2-methyl-2H-indazol-5-yl)pyridin-3-ol |
| 106 | 2-{6-[(3R,5R)-3,5-dimethylpiperazin-1-yl]pyridazin-3-yl}-5-(7-fluoro-2-methyl-2H-indazol-5-yl)pyridin-3-ol and 2-{6-[(3S,5R)-3,5-dimethylpiperazin-1-yl]pyridazin-3-yl}-5-(7-fluoro-2-methyl-2H-indazol-5-yl)pyridin-3-ol |
| 107^ | 2-[6-(1,6-diazaspiro[3.4]octan-6-yl)pyridazin-3-yl]-5-(2-methylimidazo[1,2-a]pyridin-6-yl)pyridin-3-ol |
| 108^ | 2-[6-(3-methylpiperazin-1-yl)pyridazin-3-yl]-5-{[(3-methyl-1H-pyrazol-4-yl)methyl]amino}pyridin-3-ol |
| 109^ | 2-[6-(3-methylpiperazin-1-yl)pyridazin-3-yl]-5-{[(pyridin-2-yl)methyl]amino}pyridin-3-ol |
| 110^ | 2-[6-(3-methylpiperazin-1-yl)pyridazin-3-yl]-5-{[(pyridin-3-yl)methyl]amino}pyridin-3-ol |
| 111^ | 2-[6-(3-methylpiperazin-1-yl)pyridazin-3-yl]-5-{[(pyridin-4-yl)methyl]amino}pyridin-3-ol |
| 112^ | 2-[6-(3-methylpiperazin-1-yl)pyridazin-3-yl]-5-{[(quinolin-3-yl)methyl]amino}pyridin-3-ol |
| 113^ | 2-[6-(3-methylpiperazin-1-yl)pyridazin-3-yl]-5-{[(quinolin-8-yl)methyl]amino}pyridin-3-ol |
| 114 | 2-{6-[(6,6-dimethyl-2-oxa-5-azaspiro[3.5]nonan-8-yl)oxy]pyridazin-3-yl}-5-(1H-pyrazol-4-yl)pyridin-3-ol |
| 115^ | 2-{6-[(3R,5S)-3,5-dimethylpiperazin-1-yl]pyridazin-3-yl}-5-(2-methylimidazo[1,2-a]pyrimidin-6-yl)pyridin-3-ol and |

-continued

| Cpd | Name |
|---|---|
| | 2-{6-[(3S,5R)-3,5-dimethylpiperazin-1-yl]pyridazin-3-yl}-5-(2-methylimidazo[1,2-a]pyrimidin-6-yl)pyridin-3-ol |
| 116^ | 2-[6-(2,5-diazabicyclo[2.2.1]heptan-2-yl)pyridazin-3-yl]-5-(2-methylimidazo[1,2-a]pyrimidin-6-yl)pyridin-3-ol |
| 117^ | 2-[6-(3-methylpiperazin-1-yl)pyridazin-3-yl]-5-[(pyridin-3-yl)amino]pyridin-3-ol |
| 118^ | 2-{6-[(3R,5S)-3,5-dimethylpiperazin-1-yl]pyridazin-3-yl}-5-[(E)-2-(1-methyl-1H-pyrazol-4-yl)ethenyl]pyridin-3-ol and 2-{6-[(3S,5R)-3,5-dimethylpiperazin-1-yl]pyridazin-3-yl}-5-[(E)-2-(1-methyl-1H-pyrazol-4-yl)ethenyl]pyridin-3-ol |
| 119^ | 2-[6-(3-ethylpiperazin-1-yl)pyridazin-3-yl]-5-(1H-pyrazol-4-yl)pyridin-3-ol |
| 120^ | 2-[6-(3-ethylpiperazin-1-yl)pyridazin-3-yl]-5-(7-fluoro-2-methyl-2H-indazol-5-yl)pyridin-3-ol |
| 121^ | 2-{6-[(3S)-3-(propan-2-yl)piperazin-1-yl]pyridazin-3-yl}-5-(1H-pyrazol-4-yl)pyridin-3-ol and 2-{6-[(3R)-3-(propan-2-yl)piperazin-1-yl]pyridazin-3-yl}-5-(1H-pyrazol-4-yl)pyridin-3-ol |
| 122^ | 5-(7-fluoro-2-methyl-2H-indazol-5-yl)-2-{6-[(3S)-3-(propan-2-yl)piperazin-1-yl]pyridazin-3-yl}pyridin-3-ol |
| 123^ | 2-[6-(3-cyclopropylpiperazin-1-yl)pyridazin-3-yl]-5-(1H-pyrazol-4-yl)pyridin-3-ol |
| 124 | 2-{6-[(3R,5S)-3,5-dimethylpiperazin-1-yl]pyridazin-3-yl}-5-(2-methyl-2H-indazol-5-yl)pyridin-3-ol and 2-{6-[(3S,5R)-3,5-dimethylpiperazin-1-yl]pyridazin-3-yl}-5-(2-methyl-2H-indazol-5-yl)pyridin-3-ol |
| 125^ | 2-{6-[(3R,5S)-3,5-dimethylpiperazin-1-yl]pyridazin-3-yl}-5-[(6-methylpyridin-3-yl)amino]pyridin-3-ol |
| 126^ | 2-{6-[(3R,5S)-3,5-dimethylpiperazin-1-yl]pyridazin-3-yl}-5-(1-methyl-1H-indazol-5-yl)pyridin-3-ol and 2-{6-[(3S,5R)-3,5-dimethylpiperazin-1-yl]pyridazin-3-yl}-5-(1-methyl-1H-indazol-5-yl)pyridin-3-ol |
| 127^ | 5-[(6-methylpyridin-3-yl)amino]-2-{6-[(3R)-3-(propan-2-yl)piperazin-1-yl]pyridazin-3-yl}pyridin-3-ol and 5-[(6-methylpyridin-3-yl)amino]-2-{6-[(3S)-3-(propan-2-yl)piperazin-1-yl]pyridazin-3-yl}pyridin-3-ol |
| 128^ | 2-{6-[(3S)-3-cyclopropylpiperazin-1-yl]pyridazin-3-yl}-5-(2H-1,2,3-triazol-2-yl)pyridin-3-ol |
| 129^ | 2-{6-[(3S)-3-cyclopropylpiperazin-1-yl]pyridazin-3-yl}-5-[ 1-($^2H_3$)methyl-1H-pyrazol-4-yl]pyridin-3-ol |
| 130^ | 2-{6-[3-(propan-2-yl)piperazin-1-yl]pyridazin-3-yl}-5-[(E)-2-(1H-pyrazol-4-yl)ethenyl]pyridin-3-ol |
| 131^ | 2-{6-[(3R,5S)-3,5-dimethylpiperazin-1-yl]pyridazin-3-yl}-5-(2H-indazol-5-yl)pyridin-3-ol and 2-{6-[(3S,5R)-3,5-dimethylpiperazin-1-yl]pyridazin-3-yl}-5-(2H-indazol-5-yl)pyridin-3-ol |
| 132^ | 2-{6-[(3S)-3-ethylpiperazin-1-yl]pyridazin-3-yl}-5-(1H-pyrazol-4-yl)pyridin-3-ol |
| 133^ | 5-[(5-methylpyrazin-2-yl)amino]-2-{6-[(3R)-3-(propan-2-yl)piperazin-1-yl]pyridazin-3-yl}pyridin-3-ol and 5-[(5-methylpyrazin-2-yl)amino]-2-{6-[(3S)-3-(propan-2-yl)piperazin-1-yl]pyridazin-3-yl}pyridin-3-ol |
| 134^ | 5-[(2-methylpyrimidin-5-yl)amino]-2-{6-[(3R)-3-(propan-2-yl)piperazin-1-yl]pyridazin-3-yl}pyridin-3-ol and 5-[(2-methylpyrimidin-5-yl)amino]-2-{6-[(3S)-3-(propan-2-yl)piperazin-1-yl]pyridazin-3-yl}pyridin-3-ol |
| 135^ | 2-{3-[methyl(2,2,6,6-tetramethylpiperidin-4-yl)amino]-1,2,4-triazin-6-yl}-5-(1H-pyrazol-4-yl)pyridin-3-ol |
| 136^ | 2-{3-[3-(tert-butylamino)pyrrolidin-1-yl]-1,2,4-triazin-6-yl}-5-(1H-pyrazol-4-yl)pyridin-3-ol |
| 137^ | 2-{3-[3-(tert-butylamino)pyrrolidin-1-yl]-1,2,4-triazin-6-yl}-5-[1-($^2H_3$)methyl-1H-pyrazol-4-yl]pyridin-3-ol |
| 138^ | 2-{3-[3-(tert-butylamino)pyrrolidin-1-yl]-1,2,4-triazin-6-yl}-5-(2H-1,2,3-triazol-2-yl)pyridin-3-ol |
| 139^ | 2-(3-{[(3S,4S)-3-fluoro-2,2,6,6-tetramethylpiperidin-4-yl]amino}-1,2,4-triazin-6-yl)-5-(1H-pyrazol-4-yl)pyridin-3-ol and 2-(3-{[(3R,4R)-3-fluoro-2,2,6,6-tetramethylpiperidin-4-yl]amino}-1,2,4-triazin-6-yl)-5-(1H-pyrazol-4-yl)pyridin-3-ol |
| 140 | 2-(3-{[(3R,4R)-3-fluoro-2,2,6,6-tetramethylpiperidin-4-yl]amino}-1,2,4-triazin-6-yl)-5-[1-($^2H_3$)methyl-1H-pyrazol-4-yl]pyridin-3-ol and 2-(3-{[(3S,4S)-3-fluoro-2,2,6,6-tetramethylpiperidin-4-yl]amino}-1,2,4-triazin-6-yl)-5-[1-($^2H_3$)methyl-1H-pyrazol-4-yl]pyridin-3-ol |
| 141^ | 5-(1H-pyrazol-4-yl)-2-{3-[(2,2,6,6-tetramethylpiperidin-4-yl)oxy]-1,2,4-triazin-6-yl}pyridin-3-ol |
| 142^ | 5-[1-($^2H_3$)methyl-1H-pyrazol-4-yl]-2-{3-[methyl(2,2,6,6-tetramethylpiperidin-4-yl)amino]-1,2,4-triazin-6-yl}pyridin-3-ol |
| 143^ | 5-(5-fluoro-1H-pyrazol-4-yl)-2-{3-[methyl(2,2,6,6-tetramethylpiperidin-4-yl)amino]-1,2,4-triazin-6-yl}pyridin-3-ol |
| 144^ | 2-{3-[methyl(2,2,6,6-tetramethylpiperidin-4-yl)amino]-1,2,4-triazin-6-yl}-5-(2H-1,2,3-triazol-2-yl)pyridin-3-ol |

-continued

| Cpd | Name |
|---|---|
| 145^ | 2-{3-[(3S)-3-(tert-butylamino)pyrrolidin-1-yl]-1,2,4-triazin-6-yl}-5-(3-fluoro-1H-pyrazol-4-yl)pyridin-3-ol |
| 146^ | 2-{3-[(3R)-3-(tert-butylamino)pyrrolidin-1-yl]-1,2,4-triazin-6-yl}-5-(7-methoxy-2-methyl-2H-indazol-5-yl)pyridin-3-ol |
| 147^ | 6-(6-{3-[(3R)-3-(tert-butylamino)pyrrolidin-1-yl]-1,2,4-triazin-6-yl}-5-hydroxypyridin-3-yl)-2-methylimidazo[1,2-a]pyridine-8-carbonitrile |
| 148^ | 2-{3-[(3R)-3-(tert-butylamino)pyrrolidin-1-yl]-1,2,4-triazin-6-yl}-5-(8-ethyl-2-methylimidazo[1,2-a]pyridin-6-yl)pyridin-3-ol |
| 149^ | 2-{3-[(3R)-3-(tert-butylamino)pyrrolidin-1-yl]-1,2,4-triazin-6-yl}-5-(2,8-dimethylimidazo[1,2-b]pyridazin-6-yl)pyridin-3-ol |
| 150^ | 5-(7-methoxy-2-methyl-2H-indazol-5-yl)-2-[3-(4-methylpiperazin-1-yl)-1,2,4-triazin-6-yl]pyridin-3-ol |
| 151^ | 5-(8-fluoro-2-methylimidazo[1,2-a]pyridin-6-yl)-2-[3-(4-methylpiperazin-1-yl)-1,2,4-triazin-6-yl]pyridin-3-ol |
| 152^ | 2-[3-(4-methylpiperazin-1-yl)-1,2,4-triazin-6-yl]-5-(1H-pyrazol-4-yl)pyridin-3-ol |
| 153^ | 5-(2,8-dimethylimidazo[1,2-a]pyridin-6-yl)-2-[3-(4-methylpiperazin-1-yl)-1,2,4-triazin-6-yl]pyridin-3-ol |
| 154^ | 5-[(5-methylpyrazin-2-yl)amino]-2-[3-[(3S)-3-(propan-2-yl)piperazin-1-yl]-1,2,4-triazin-6-yl}pyridin-3-ol |
| 155^ | 5-(7-fluoro-2-methyl-2H-indazol-5-yl)-2-{3-[(3S)-3-(propan-2-yl)piperazin-1-yl]-1,2,4-triazin-6-yl}pyridin-3-ol |
| 156^ | 2-{3-[(3S)-3-(propan-2-yl)piperazin-1-yl]-1,2,4-triazin-6-yl}-5-(2H-1,2,3-triazol-2-yl)pyridin-3-ol |
| 157^ | 2-{3-[(3S)-3-cyclopropylpiperazin-1-yl]-1,2,4-triazin-6-yl}-5-(2-methyl-2H-[1,2,3]triazolo[4,5-b]pyridin-6-yl)pyridin-3-ol |
| 158^ | 2-{3-[(3S)-3-cyclopropylpiperazin-1-yl]-1,2,4-triazin-6-yl}-5-(7-fluoro-2-methyl-2H-indazol-5-yl)pyridin-3-ol |
| 159^ | 2-{3-[(3S)-3-cyclopropylpiperazin-1-yl]-1,2,4-triazin-6-yl}-5-(2H-1,2,3-triazol-2-yl)pyridin-3-ol |
| 160^ | 2-{3-[(3S)-3-cyclopropylpiperazin-1-yl]-1,2,4-triazin-6-yl}-5-[(5-methylpyrazin-2-yl)amino]pyridin-3-ol |
| 161 | 2-{6-[methyl(2,2,6,6-tetramethylpiperidin-4-yl)amino]-1,2,4-triazin-3-yl}-5-(2H-1,2,3-triazol-2-yl)pyridin-3-ol |
| 162 | 2-{6-[methyl(2,2,6,6-tetramethylpiperidin-4-yl)amino]-1,2,4-triazin-3-yl}-5-(1H-pyrazol-4-yl)pyridin-3-ol |
| 163 | 2-{6-[(2,2,6,6-tetramethylpiperidin-4-yl)amino]-1,2,4-triazin-3-yl}-5-(2H-1,2,3-triazol-2-yl)pyridin-3-ol, and |
| 164 | 2-{6-[(3R,5S)-3,5-dimethylpiperazin-1-yl]-1,2,4-triazin-3-yl}-5-(7-fluoro-2-methyl-2H-indazol-5-yl)pyridin-3-ol and 2-{6-[(3S,5R)-3,5-dimethylpiperazin-1-yl]-1,2,4-triazin-3-yl}-5-(7-fluoro-2-methyl-2H-indazol-5-yl)pyridin-3-ol; |

wherein a form of the compound is selected from the group consisting of a salt, hydrate, solvate, racemate, enantiomer, diastereomer, tautomer, and mixtures thereof.

Another aspect includes a compound of Formula (I), Formula (II), or Formula (III), wherein the form of the compound is a compound salt selected from hydrochloride, dihydrochloride, trihydrochloride, hydrobromide, dihydrobromie, trihydrobromide, formate, diformate, triformate, trifluoroacetate, and ditrifluoroacetate.

Another aspect includes a compound of Formula (I), Formula (II), or Formula (III), wherein the form of the compound is a compound salt selected from hydrochloride, dihydrochloride, trihydrochloride, formate, diformate, and, trifluoroacetate.

Another aspect of the compound of Formula (I), Formula (II), or Formula (III) or a form thereof is a compound salt selected from the group consisting of:

| Cpd | Name |
|---|---|
| 1 | 5-(1H-pyrazol-4-yl)-2-{6-[(2,2,6,6-tetramethylpiperidin-4-yl)oxy]pyridazin-3-yl}pyridin-3-ol ditrifluroacetate |
| 2 | 2-{6-[methyl(2,2,6,6-tetramethylpiperidin-4-yl)amino]pyridazin-3-yl}-5-(1H-pyrazol-4-yl)pyridin-3-ol dihydrochloride |
| 3 | 5-[1-($^2H_3$)methyl-1H-pyrazol-4-yl]-2-{6-[(2,2,6,6-tetramethylpiperidin-4-yl)oxy]pyridazin-3-yl}pyridin-3-ol hydrochloride |
| 19 | 2-(6-{[(3R,4R)-3-fluoro-2,2,6,6-tetramethylpiperidin-4-yl]amino}pyridazin-3-yl)-5-[1-($^2H_3$)methyl-1H-pyrazol-4-yl]pyridin-3-ol formate and 2-(6-{[(3S,4S)-3-fluoro-2,2,6,6-tetramethylpiperidin-4-yl]amino}pyridazin-3-yl)-5-[1-($^2H_3$)methyl-1H-pyrazol-4-yl]pyridin-3-ol formate |
| 21 | 2-{6-[(5,5-dimethyl-4-azaspiro[2.5]octan-7-yl)oxy]pyridazin-3-yl}-5-(2H-1,2,3-triazol-2-yl)pyridin-3-ol dihydrochloride |
| 22 | 5-(5-fluoro-1H-pyrazol-4-yl)-2-(6-{[(3R,4S)-3-fluoro-2,2,6,6-tetramethylpiperidin-4-yl]oxy}pyridazin-3-yl)pyridin-3-ol ditrifluroacetate or 5-(5-fluoro-1H-pyrazol-4-yl)-2-(6-{[(3S,4R)-3-fluoro-2,2,6,6-tetramethylpiperidin-4-yl]oxy}pyridazin-3-yl)pyridin-3-ol ditrifluroacetate |

-continued

| Cpd | Name |
|---|---|
| 25 | 2-(6-{[(3R,4R)-3-fluoro-2,2,6,6-tetramethylpiperidin-4-yl]amino}pyridazin-3-yl)-5-{6-[($^2H_3$)methyloxy]pyrimidin-4-yl}pyridin-3-ol diformate |
| 26 | 2-{6-[(5,5-dimethyl-4-azaspiro[2.5]octan-7-yl)oxy]pyridazin-3-yl}-5-(5-fluoro-1H-pyrazol-4-yl)pyridin-3-ol ditrifluroacetate |
| 27 | 2-{6-[(5,5-dimethyl-4-azaspiro[2.5]octan-7-yl)oxy]pyridazin-3-yl}-5-(1H-pyrazol-4-yl)pyridin-3-ol dihydrochloride |
| 28 | 2-{6-[(5,5-dimethyl-4-azaspiro[2.5]octan-7-yl)oxy]pyridazin-3-yl}-5-(1,3-oxazol-2-yl)pyridin-3-ol dihydrochloride |
| 29 | 2-{6-[3-(tert-butylamino)pyrrolidin-1-yl]pyridazin-3-yl}-5-[1-($^2H_3$)methyl-1H-pyrazol-4-yl]pyridin-3-ol dihydrochloride |
| 31 | 2-{6-[(4-azadispiro[2.1.2$^5$.3$^3$]decan-9-yl)oxy]pyridazin-3-yl}-5-(1H-pyrazol-4-yl)pyridin-3-ol dihydrochloride |
| 32 | 2-(6-{[(1R,3s,5S)-1,5-dimethyl-8-azabicyclo[3.2.1]octan-3-yl]oxy}pyridazin-3-yl)-5-(2H-1,2,3-triazol-2-yl)pyridin-3-ol dihydrochloride and 2-(6-{[(1S,3r,5R)-1,5-dimethyl-8-azabicyclo[3.2.1]octan-3-yl]oxy}pyridazin-3-yl)-5-(2H-1,2,3-triazol-2-yl)pyridin-3-ol dihydrochloride |
| 36 | 2-(6-{[(1R,3s,5S)-1,5-dimethyl-8-azabicyclo[3.2.1]octan-3-yl]oxy}pyridazin-3-yl)-5-(pyrimidin-5-yl)pyridin-3-ol dihydrochloride and 2-(6-{[(1S,3r,5R)-1,5-dimethyl-8-azabicyclo[3.2.1]octan-3-yl]oxy}pyridazin-3-yl)-5-(pyrimidin-5-yl)pyridin-3-ol dihydrochloride |
| 39 | 2-(6-{[(3S,4R)-3-fluoro-2,2,6,6-tetramethylpiperidin-4-yl]oxy}pyridazin-3-yl)-5-(1H-pyrazol-4-yl)pyridin-3-ol hydrochloride or 2-(6-{[(3S,4R)-3-fluoro-2,2,6,6-tetramethylpiperidin-4-yl]oxy}pyridazin-3-yl)-5-(1H-pyrazol-4-yl)pyridin-3-ol hydrochloride |
| 40 | 5-(5-fluoro-1H-pyrazol-4-yl)-2-(6-{[(3S,4R)-3-fluoro-2,2,6,6-tetramethylpiperidin-4-yl]oxy}pyridazin-3-yl)pyridin-3-ol hydrochloride |
| 43 | 2-(6-{[(3R,4S)-3-fluoro-2,2,6,6-tetramethylpiperidin-4-yl]oxy}pyridazin-3-yl)-5-(2-methylimidazo[1,2-a]pyridin-6-yl)pyridin-3-ol trihydrochloride and 2-(6-{[(3S,4R)-3-fluoro-2,2,6,6-tetramethylpiperidin-4-yl]oxy}pyridazin-3-yl)-5-(2-methylimidazo[1,2-a]pyridin-6-yl)pyridin-3-ol trihydrochloride |
| 44 | 5-(2,8-dimethylimidazo[1,2-a]pyridin-6-yl)-2-(6-{[(3R,4S)-3-fluoro-2,2,6,6-tetramethylpiperidin-4-yl]oxy}pyridazin-3-yl)pyridin-3-ol trihydrochloride and 5-(2,8-dimethylimidazo[1,2-a]pyridin-6-yl)-2-(6-{[(3S,4R)-3-fluoro-2,2,6,6-tetramethylpiperidin-4-yl]oxy}pyridazin-3-yl)pyridin-3-ol trihydrochloride |
| 45 | 5-(8-ethyl-2-methylimidazo[1,2-a]pyridin-6-yl)-2-(6-{[(3R,4S)-3-fluoro-2,2,6,6-tetramethylpiperidin-4-yl]oxy}pyridazin-3-yl)pyridin-3-ol trihydrochloride and 5-(8-ethyl-2-methylimidazo[1,2-a]pyridin-6-yl)-2-(6-{[(3S,4R)-3-fluoro-2,2,6,6-tetramethylpiperidin-4-yl]oxy}pyridazin-3-yl)pyridin-3-ol trihydrochloride |
| 46 | 2-(6-{[(3R,4S)-3-fluoro-2,2,6,6-tetramethylpiperidin-4-yl]oxy}pyridazin-3-yl)-5-[2-methyl-8-(trifluoromethyl)imidazo[1,2-a]pyridin-6-yl]pyridin-3-ol trihydrochloride and 2-(6-{[(3S,4R)-3-fluoro-2,2,6,6-tetramethylpiperidin-4-yl]oxy}pyridazin-3-yl)-5-[2-methyl-8-(trifluoromethyl)imidazo[1,2-a]pyridin-6-yl]pyridin-3-ol trihydrochloride |
| 48 | 2-(6-{[(3R,4S)-3-fluoro-2,2,6,6-tetramethylpiperidin-4-yl]oxy}pyridazin-3-yl)-5-(2-methylimidazo[1,2-b]pyridazin-6-yl)pyridin-3-ol dihydrochloride and 2-(6-{[(3S,4R)-3-fluoro-2,2,6,6-tetramethylpiperidin-4-yl]oxy}pyridazin-3-yl)-5-(2-methylimidazo[1,2-b]pyridazin-6-yl)pyridin-3-ol dihydrochloride |
| 49 | 2-(6-{[(3R,4S)-3-fluoro-2,2,6,6-tetramethylpiperidin-4-yl]oxy}pyridazin-3-yl)-5-(imidazo[1,2-b]pyridazin-6-yl)pyridin-3-ol dihydrochloride and 2-(6-{[(3S,4R)-3-fluoro-2,2,6,6-tetramethylpiperidin-4-yl]oxy}pyridazin-3-yl)-5-(imidazo[1,2-b]pyridazin-6-yl)pyridin-3-ol dihydrochloride |
| 50 | 5-(2,8-dimethylimidazo[1,2-b]pyridazin-6-yl)-2-{6-[(2,2,6,6-tetramethylpiperidin-4-yl)oxy]pyridazin-3-yl}pyridin-3-ol dihydrochloride |
| 51 | 2-(6-{[(3R,4S)-3-fluoro-2,2,6,6-tetramethylpiperidin-4-yl]oxy}pyridazin-3-yl)-5-(1H-pyrazol-4-yl)pyridin-3-ol hydrochloride or 2-(6-{[(3S,4R)-3-fluoro-2,2,6,6-tetramethylpiperidin-4-yl]oxy}pyridazin-3-yl)-5-(1H-pyrazol-4-yl)pyridin-3-ol hydrochloride |
| 52 | 5-(7-fluoro-2-methyl-2H-indazol-5-yl)-2-{6-[(2,2,6,6-tetramethylpiperidin-4-yl)oxy]pyridazin-3-yl}pyridin-3-ol dihydrochloride |
| 53 | 2-{6-[(5,5-dimethyl-4-azaspiro[2.5]octan-7-yl)(methyl)amino]pyridazin-3-yl}-5-[1-($^2H_3$)methyl-1H-pyrazol-4-yl]pyridin-3-ol dihydrochloride |
| 54 | 2-(6-{[(3R,4S)-3-fluoro-2,2,6,6-tetramethylpiperidin-4-yl]oxy}pyridazin-3-yl)-5-(2-methylimidazo[1,2-a]pyrimidin-6-yl)pyridin-3-ol trihydrochloride and 2-(6-{[(3S,4R)-3-fluoro-2,2,6,6-tetramethylpiperidin-4-yl]oxy}pyridazin-3-yl)-5-(2-methylimidazo[1,2-a]pyrimidin-6-yl)pyridin-3-ol trihydrochloride |
| 55 | 2-(6-{[(3R,4S)-3-fluoro-2,2,6,6-tetramethylpiperidin-4-yl]oxy}pyridazin-3-yl)-5-(2-methyl[1,2,4]triazolo[1,5-a]pyridin-6-yl)pyridin-3-ol trihydrochloride and 2-(6-{[(3S,4R)-3-fluoro-2,2,6,6-tetramethylpiperidin-4-yl]oxy}pyridazin-3-yl)-5-(2-methyl[1,2,4]triazolo[1,5-a]pyridin-6-yl)pyridin-3-ol trihydrochloride |
| 56 | 5-(2,4-dimethyl-1,3-benzoxazol-6-yl)-2-(6-{[(3R,4S)-3-fluoro-2,2,6,6-tetramethylpiperidin-4-yl]oxy}pyridazin-3-yl)pyridin-3-ol dihydrochloride and 5-(2,4-dimethyl-1,3-benzoxazol-6-yl)-2-(6-{[(3S,4R)-3-fluoro-2,2,6,6-tetramethylpiperidin-4-yl]oxy}pyridazin-3-yl)pyridin-3-ol dihydrochloride |
| 57 | 2-(6-{[(3R,4S)-3-fluoro-2,2,6,6-tetramethylpiperidin-4-yl]oxy}pyridazin-3-yl)-5-(8-methoxy-2-methylimidazo[1,2-b]pyridazin-6-yl)pyridin-3-ol dihydrochloride and 2-(6-{[(3S,4R)-3-fluoro-2,2,6,6-tetramethylpiperidin-4-yl]oxy}pyridazin-3-yl)-5-(8-methoxy-2-methylimidazo[1,2-b]pyridazin-6-yl)pyridin-3-ol dihydrochloride |

-continued

| Cpd | Name |
|---|---|
| 61 | 2-{6-[(2,2,6,6-tetramethylpiperidin-4-yl)oxy]pyridazin-3-yl}-5-(1H-1,2,4-triazol-1-yl)pyridin-3-ol dihydrochloride |
| 62 | 5-[6-(6-{[2,2,6,6-tetramethylpiperidin-4-yl]oxy}pyridazin-3-yl)-5-hydroxypyridin-3-yl]-2-methyl-2H-indazole-7-carbonitrile dihydrochloride |
| 64 | 2-{6-[(5,5-dimethyl-4-azaspiro[2.5]octan-7-yl)(methyl)amino]pyridazin-3-yl}-5-(7-fluoro-2-methyl-2H-indazol-5-yl)pyridin-3-ol dihydrochloride |
| 65 | 5-(imidazo[1,2-b]pyridazin-6-yl)-2-{6-[(2,2,6,6-tetramethylpiperidin-4-yl)oxy]pyridazin-3-yl}pyridin-3-ol dihydrochloride |
| 69 | 2-{6-[(3R,5S)-3,5-dimethylpiperazin-1-yl]pyridazin-3-yl}-5-(7-fluoro-2-methyl-2H-indazol-5-yl)pyridin-3-ol dihydrochloride and 2-{6-[(3S,5R)-3,5-dimethylpiperazin-1-yl]pyridazin-3-yl}-5-(7-fluoro-2-methyl-2H-indazol-5-yl)pyridin-3-ol dihydrochloride |
| 71 | 2-(6-{[(1R,3s,5S)-1,5-dimethyl-8-azabicyclo[3.2.1]octan-3-yl]oxy}pyridazin-3-yl)-5-(1H-1,2,3-triazol-1-yl)pyridin-3-ol hydrochloride and 2-(6-{[(1S,3r,5R)-1,5-dimethyl-8-azabicyclo[3.2.1]octan-3-yl]oxy}pyridazin-3-yl)-5-(1H-1,2,3-triazol-1-yl)pyridin-3-ol hydrochloride |
| 74 | 5-(6-methoxypyrimidin-4-yl)-2-{6-[(2,2,6,6-tetramethylpiperidin-4-yl)oxy]pyridazin-3-yl}pyridin-3-ol dihydrochloride |
| 76 | 2-{6-[(3R)-3-(tert-butylamino)pyrrolidin-1-yl]pyridazin-3-yl}-5-(2-methyl-1,3-oxazol-5-yl)pyridin-3-ol dihydrochloride |
| 81 | 5-(8-methoxy-2-methylimidazo[1,2-b]pyridazin-6-yl)-2-{6-[(2,2,6,6-tetramethylpiperidin-4-yl)oxy]pyridazin-3-yl}pyridin-3-ol dihydrochloride |
| 82 | 2-(6-{[(5R,7S)-5-methyl-4-azaspiro[2.5]octan-7-yl]oxy}pyridazin-3-yl)-5-[1-($^2H_3$)methyl-1H-pyrazol-4-yl]pyridin-3-ol dihydrochloride |
| 84 | 2-(6-{[(5S,7S)-5-methyl-4-azaspiro[2.5]octan-7-yl]oxy}pyridazin-3-yl)-5-[1-($^2H_3$)methyl-1H-pyrazol-4-yl]pyridin-3-ol dihydrochloride |
| 85 | 2-(6-{[(5R,7R)-5-methyl-4-azaspiro[2.5]octan-7-yl]oxy}pyridazin-3-yl)-5-[1-($^2H_3$)methyl-1H-pyrazol-4-yl]pyridin-3-ol dihydrochloride |
| 86 | 2-{6-[(3R,5S)-3,5-dimethylpiperazin-1-yl]pyridazin-3-yl}-5-(1H-pyrazol-4-yl)pyridin-3-ol dihydrochloride and 2-{6-[(3S,5R)-3,5-dimethylpiperazin-1-yl]pyridazin-3-yl}-5-(1H-pyrazol-4-yl)pyridin-3-ol dihydrochloride |
| 87 | 2-{6-[(3R,5S)-3,5-dimethylpiperazin-1-yl]pyridazin-3-yl}-5-(7-methoxy-2-methyl-2H-indazol-5-yl)pyridin-3-ol dihydrochloride and 2-{6-[(3S,5R)-3,5-dimethylpiperazin-1-yl]pyridazin-3-yl}-5-(7-methoxy-2-methyl-2H-indazol-5-yl)pyridin-3-ol dihydrochloride |
| 88 | 5-(1H-pyrazol-4-yl)-2-[6-(3,3,5,5-tetramethylpiperazin-1-yl)pyridazin-3-yl]pyridin-3-ol hydrochloride |
| 89 | 5-(7-fluoro-2-methyl-2H-indazol-5-yl)-2-[6-(3,3,5,5-tetramethylpiperazin-1-yl)pyridazin-3-yl]pyridin-3-ol hydrochloride |
| 90 | 5-(1H-pyrazol-4-yl)-2-{6-[(3R,5S)-3,4,5-trimethylpiperazin-1-yl]pyridazin-3-yl}pyridin-3-ol dihydrochloride and 5-(1H-pyrazol-4-yl)-2-{6-[(3S,5R)-3,4,5-trimethylpiperazin-1-yl]pyridazin-3-yl}pyridin-3-ol dihydrochloride |
| 91 | 5-(7-fluoro-2-methyl-2H-indazol-5-yl)-2-{6-[(3R,5S)-3,4,5-trimethylpiperazin-1-yl]pyridazin-3-yl}pyridin-3-ol dihydrochloride and 5-(7-fluoro-2-methyl-2H-indazol-5-yl)-2-{6-[(3S,5R)-3,4,5-trimethylpiperazin-1-yl]pyridazin-3-yl}pyridin-3-ol dihydrochloride |
| 92 | 2-{6-[(3R,5S)-3,5-dimethylpiperazin-1-yl]pyridazin-3-yl}-5-(2-methylimidazo[1,2-a]pyridin-6-yl)pyridin-3-ol dihydrochloride and 2-{6-[(3S,5R)-3,5-dimethylpiperazin-1-yl]pyridazin-3-yl}-5-(2-methylimidazo[1,2-a]pyridin-6-yl)pyridin-3-ol dihydrochloride |
| 94 | 2-{6-[(3R,5S)-3,5-dimethylpiperazin-1-yl]pyridazin-3-yl}-5-([1,2,4]triazolo[1,5-a]pyridin-6-yl)pyridin-3-ol dihydrochloride and 2-{6-[(3S,5R)-3,5-dimethylpiperazin-1-yl]pyridazin-3-yl}-5-([1,2,4]triazolo[1,5-a]pyridin-6-yl)pyridin-3-ol dihydrochloride |
| 95 | 5-(7-methoxy-2-methyl-2H-indazol-5-yl)-2-[6-(3-methylpiperazin-1-yl)pyridazin-3-yl]pyridin-3-ol dihydrochloride |
| 101 | 5-(7-fluoro-2-methyl-2H-indazol-5-yl)-2-[6-(4-methylpiperazin-1-yl)pyridazin-3-yl]pyridin-3-ol dihydrochloride |
| 105 | 2-[6-(2,5-diazabicyclo[2.2.1]heptan-2-yl)pyridazin-3-yl]-5-(7-fluoro-2-methyl-2H-indazol-5-yl)pyridin-3-ol hydrochloride |
| 107 | 2-[6-(1,6-diazaspiro[3.4]octan-6-yl)pyridazin-3-yl]-5-(2-methylimidazo[1,2-a]pyridin-6-yl)pyridin-3-ol dihydrochloride |
| 108 | 2-[6-(3-methylpiperazin-1-yl)pyridazin-3-yl]-5-{[(3-methyl-1H-pyrazol-4-yl)methyl]amino}pyridin-3-ol dihydrochloride |
| 109 | 2-[6-(3-methylpiperazin-1-yl)pyridazin-3-yl]-5-{[(pyridin-2-yl)methyl]amino}pyridin-3-ol dihydrochloride |
| 110 | 2-[6-(3-methylpiperazin-1-yl)pyridazin-3-yl]-5-{[(pyridin-3-yl)methyl]amino}pyridin-3-ol dihydrochloride |
| 111 | 2-[6-(3-methylpiperazin-1-yl)pyridazin-3-yl]-5-{[(pyridin-4-yl)methyl]amino}pyridin-3-ol |
| 112 | 2-[6-(3-methylpiperazin-1-yl)pyridazin-3-yl]-5-{[(quinolin-3-yl)methyl]amino}pyridin-3-ol dihydrochloride |
| 113 | 2-[6-(3-methylpiperazin-1-yl)pyridazin-3-yl]-5-{[(quinolin-8-yl)methyl]amino}pyridin-3-ol dihydrochloride |

-continued

| Cpd | Name |
|---|---|
| 115 | 2-{6-[(3R,5S)-3,5-dimethylpiperazin-1-yl]pyridazin-3-yl}-5-(2-methylimidazo[1,2-a]pyrimidin-6-yl)pyridin-3-ol trifluoroacetate and 2-{6-[(3S,5R)-3,5-dimethylpiperazin-1-yl]pyridazin-3-yl}-5-(2-methylimidazo[1,2-a]pyrimidin-6-yl)pyridin-3-ol trifluoroacetate |
| 116 | 2-[6-(2,5-diazabicyclo[2.2.1]heptan-2-yl)pyridazin-3-yl]-5-(2-methylimidazo[1,2-a]pyrimidin-6-yl)pyridin-3-ol trifluoroacetate |
| 117 | 2-[6-(3-methylpiperazin-1-yl)pyridazin-3-yl]-5-[(pyridin-3-yl)amino]pyridin-3-ol dihydrochloride |
| 118 | 2-{6-[(3R,5S)-3,5-dimethylpiperazin-1-yl]pyridazin-3-yl}-5-[(E)-2-(1-methyl-1H-pyrazol-4-yl)ethenyl]pyridin-3-ol dihydrochloride and 2-{6-[(3S,5R)-3,5-dimethylpiperazin-1-yl]pyridazin-3-yl}-5-[(E)-2-(1-methyl-1H-pyrazol-4-yl)ethenyl]pyridin-3-ol dihydrochloride |
| 119 | 2-[6-(3-ethylpiperazin-1-yl)pyridazin-3-yl]-5-(1H-pyrazol-4-yl)pyridin-3-ol dihydrochloride |
| 120 | 2-[6-(3-ethylpiperazin-1-yl)pyridazin-3-yl]-5-(7-fluoro-2-methyl-2H-indazol-5-yl)pyridin-3-ol dihydrochloride |
| 121 | 2-{6-[(3S)-3-(propan-2-yl)piperazin-1-yl]pyridazin-3-yl}-5-(1H-pyrazol-4-yl)pyridin-3-ol dihydrochloride and 2-{6-[(3R)-3-(propan-2-yl)piperazin-1-yl]pyridazin-3-yl}-5-(1H-pyrazol-4-yl)pyridin-3-ol dihydrochloride |
| 122 | 5-(7-fluoro-2-methyl-2H-indazol-5-yl)-2-{6-[(3S)-3-(propan-2-yl)piperazin-1-yl]pyridazin-3-yl}pyridin-3-ol dihydrochloride |
| 123 | 2-[6-(3-cyclopropylpiperazin-1-yl)pyridazin-3-yl]-5-(1H-pyrazol-4-yl)pyridin-3-ol dihydrochloride |
| 125 | 2-{6-[(3R,5S)-3,5-dimethylpiperazin-1-yl]pyridazin-3-yl}-5-[(6-methylpyridin-3-yl)amino]pyridin-3-ol dihydrochloride |
| 126 | 2-{6-[(3R,5S)-3,5-dimethylpiperazin-1-yl]pyridazin-3-yl}-5-(1-methyl-1H-indazol-5-yl)pyridin-3-ol dihydrochloride and 2-{6-[(3S,5R)-3,5-dimethylpiperazin-1-yl]pyridazin-3-yl}-5-(1-methyl-1H-indazol-5-yl)pyridin-3-ol dihydrochloride |
| 127 | 5-[(6-methylpyridin-3-yl)amino]-2-{6-[(3R)-3-(propan-2-yl)piperazin-1-yl]pyridazin-3-yl}pyridin-3-ol dihydrochloride and 5-[(6-methylpyridin-3-yl)amino]-2-{6-[(3S)-3-(propan-2-yl)piperazin-1-yl]pyridazin-3-yl}pyridin-3-ol dihydrochloride |
| 128 | 2-{6-[(3S)-3-cyclopropylpiperazin-1-yl]pyridazin-3-yl}-5-(2H-1,2,3-triazol-2-yl)pyridin-3-ol dihydrochloride |
| 129 | 2-{6-[(3S)-3-cyclopropylpiperazin-1-yl]pyridazin-3-yl}-5-[1-($^2H_3$)methyl-1H-pyrazol-4-yl]pyridin-3-ol dihydrochloride |
| 130 | 2-{6-[3-(propan-2-yl)piperazin-1-yl]pyridazin-3-yl}-5-[(E)-2-(1H-pyrazol-4-yl)ethenyl]pyridin-3-ol dihydrochloride |
| 131 | 2-{6-[(3R,5S)-3,5-dimethylpiperazin-1-yl]pyridazin-3-yl}-5-(2H-indazol-5-yl)pyridin-3-ol dihydrochloride and 2-{6-[(3S,5R)-3,5-dimethylpiperazin-1-yl]pyridazin-3-yl}-5-(2H-indazol-5-yl)pyridin-3-ol dihydrochloride |
| 132 | 2-{6-[(3S)-3-ethylpiperazin-1-yl]pyridazin-3-yl}-5-(1H-pyrazol-4-yl)pyridin-3-ol dihydrochloride |
| 133 | 5-[(5-methylpyrazin-2-yl)amino]-2-{6-[(3R)-3-(propan-2-yl)piperazin-1-yl]pyridazin-3-yl}pyridin-3-ol dihydrochloride and 5-[(5-methylpyrazin-2-yl)amino]-2-{6-[(3S)-3-(propan-2-yl)piperazin-1-yl]pyridazin-3-yl}pyridin-3-ol dihydrochloride |
| 134 | 5-[(2-methylpyrimidin-5-yl)amino]-2-{6-[(3R)-3-(propan-2-yl)piperazin-1-yl]pyridazin-3-yl}pyridin-3-ol dihydrochloride and 5-[(2-methylpyrimidin-5-yl)amino]-2-{6-[(3S)-3-(propan-2-yl)piperazin-1-yl]pyridazin-3-yl}pyridin-3-ol dihydrochloride |
| 135 | 2-{3-[methyl(2,2,6,6-tetramethylpiperidin-4-yl)amino]-1,2,4-triazin-6-yl}-5-(1H-pyrazol-4-yl)pyridin-3-ol trifluoroacetate |
| 136 | 2-{3-[3-(tert-butylamino)pyrrolidin-1-yl]-1,2,4-triazin-6-yl}-5-(1H-pyrazol-4-yl)pyridin-3-ol diformate |
| 137 | 2-{3-[3-(tert-butylamino)pyrrolidin-1-yl]-1,2,4-triazin-6-yl}-5-[1-($^2H_3$)methyl-1H-pyrazol-4-yl]pyridin-3-ol diformate |
| 138 | 2-{3-[3-(tert-butylamino)pyrrolidin-1-yl]-1,2,4-triazin-6-yl}-5-(2H-1,2,3-triazol-2-yl)pyridin-3-ol ditrifluoroacetate |
| 139 | 2-(3-{[(3S,4S)-3-fluoro-2,2,6,6-tetramethylpiperidin-4-yl]amino}-1,2,4-triazin-6-yl)-5-(1H-pyrazol-4-yl)pyridin-3-ol trihydrochloride and 2-(3-{[(3R,4R)-3-fluoro-2,2,6,6-tetramethylpiperidin-4-yl]amino}-1,2,4-triazin-6-yl)-5-(1H-pyrazol-4-yl)pyridin-3-ol trihydrochloride |
| 141 | 5-(1H-pyrazol-4-yl)-2-{3-[(2,2,6,6-tetramethylpiperidin-4-yl)oxy]-1,2,4-triazin-6-yl}pyridin-3-ol trifluoroacetate |
| 142 | 5-[1-($^2H_3$)methyl-1H-pyrazol-4-yl]-2-{3-[methyl(2,2,6,6-tetramethylpiperidin-4-yl)amino]-1,2,4-triazin-6-yl}pyridin-3-ol ditrifluoroacetate |
| 143 | 5-(5-fluoro-1H-pyrazol-4-yl)-2-{3-[methyl(2,2,6,6-tetramethylpiperidin-4-yl)amino]-1,2,4-triazin-6-yl}pyridin-3-ol ditrifluoroacetate |
| 144 | 2-{3-[methyl(2,2,6,6-tetramethylpiperidin-4-yl)amino]-1,2,4-triazin-6-yl}-5-(2H-1,2,3-triazol-2-yl)pyridin-3-ol ditrifluoroacetate |
| 145 | 2-{3-[(3S)-3-(tert-butylamino)pyrrolidin-1-yl]-1,2,4-triazin-6-yl}-5-(3-fluoro-1H-pyrazol-4-yl)pyridin-3-ol hydrochloride |

-continued

| Cpd | Name |
|---|---|
| 146 | 2-{3-[(3R)-3-(tert-butylamino)pyrrolidin-1-yl]-1,2,4-triazin-6-yl}-5-(7-methoxy-2-methyl-2H-indazol-5-yl)pyridin-3-ol hydrochloride |
| 147 | 6-(6-{3-[(3R)-3-(tert-butylamino)pyrrolidin-1-yl]-1,2,4-triazin-6-yl}-5-hydroxypyridin-3-yl)-2-methylimidazo[1,2-a]pyridine-8-carbonitrile hydrochloride |
| 148 | 2-{3-[(3R)-3-(tert-butylamino)pyrrolidin-1-yl]-1,2,4-triazin-6-yl}-5-(8-ethyl-2-methylimidazo[1,2-a]pyridin-6-yl)pyridin-3-ol hydrochloride |
| 149 | 2-{3-[(3R)-3-(tert-butylamino)pyrrolidin-1-yl]-1,2,4-triazin-6-yl}-5-(2,8-dimethylimidazo[1,2-b]pyridazin-6-yl)pyridin-3-ol hydrochloride |
| 150 | 5-(7-methoxy-2-methyl-2H-indazol-5-yl)-2-[3-(4-methylpiperazin-1-yl)-1,2,4-triazin-6-yl]pyridin-3-ol hydrochloride |
| 151 | 5-(8-fluoro-2-methylimidazo[1,2-a]pyridin-6-yl)-2-[3-(4-methylpiperazin-1-yl)-1,2,4-triazin-6-yl]pyridin-3-ol hydrochloride |
| 152 | 2-[3-(4-methylpiperazin-1-yl)-1,2,4-triazin-6-yl]-5-(1H-pyrazol-4-yl)pyridin-3-ol hydrochloride |
| 153 | 5-(2,8-dimethylimidazo[1,2-a]pyridin-6-yl)-2-[3-(4-methylpiperazin-1-yl)-1,2,4-triazin-6-yl]pyridin-3-ol hydrochloride |
| 154 | 5-[(5-methylpyrazin-2-yl)amino]-2-{3-[(3S)-3-(propan-2-yl)piperazin-1-yl]-1,2,4-triazin-6-yl}pyridin-3-ol dihydrochloride |
| 155 | 5-(7-fluoro-2-methyl-2H-indazol-5-yl)-2-{3-[(3S)-3-(propan-2-yl)piperazin-1-yl]-1,2,4-triazin-6-yl}pyridin-3-ol hydrochloride |
| 156 | 2-{3-[(3S)-3-(propan-2-yl)piperazin-1-yl]-1,2,4-triazin-6-yl}-5-(2H-1,2,3-triazol-2-yl)pyridin-3-ol hydrochloride |
| 157 | 2-{3-[(3S)-3-cyclopropylpiperazin-1-yl]-1,2,4-triazin-6-yl}-5-(2-methyl-2H-[1,2,3]triazolo[4,5-b]pyridin-6-yl)pyridin-3-ol trifluoroacetate |
| 158 | 2-{3-[(3S)-3-cyclopropylpiperazin-1-yl]-1,2,4-triazin-6-yl}-5-(7-fluoro-2-methyl-2H-indazol-5-yl)pyridin-3-ol hydrochloride |
| 159 | 2-{3-[(3S)-3-cyclopropylpiperazin-1-yl]-1,2,4-triazin-6-yl}-5-(2H-1,2,3-triazol-2-yl)pyridin-3-ol trifluoroacetate, and |
| 160 | 2-{3-[(3S)-3-cyclopropylpiperazin-1-yl]-1,2,4-triazin-6-yl}-5-[(5-methylpyrazin-2-yl)amino]pyridin-3-ol hydrochloride; |

wherein a salt form of the compound is selected from the group consisting of a hydrate, solvate, racemate, enantiomer, diastereomer, tautomer, and mixtures thereof.

An aspect of the present description includes a method for preventing, treating or ameliorating HD in a subject in need thereof comprising, administering to the subject an effective amount of a compound of Formula (I), Formula (II), or Formula (III) or a form thereof.

An aspect of the present description includes a method for treating or ameliorating HD in a subject in need thereof comprising, administering to the subject an effective amount of a compound of Formula (I), Formula (II), or Formula (III) or a form thereof.

Another aspect of the present description includes a method for treating or ameliorating HD in a subject in need thereof comprising, administering to the subject an effective amount of a compound salt of Formula (I), Formula (II), or Formula (III) or a form thereof.

An aspect of the present description includes a method for use of a compound of Formula (I), Formula (II), or Formula (III) or a form or composition thereof for treating or ameliorating HD in a subject in need thereof comprising, administering to the subject an effective amount of the compound of Formula (I), Formula (II), or Formula (III) or a form or composition thereof.

Another aspect of the present description includes a method for use of a compound salt of Formula (I), Formula (II), or Formula (III) or a form or composition thereof for treating or ameliorating HD in a subject in need thereof comprising, administering to the subject an effective amount of the compound salt of Formula (I), Formula (II), or Formula (III) or a form thereof.

An aspect of the present description includes a use for a compound of Formula (I), Formula (II), or Formula (III) or a form thereof for treating or ameliorating HD in a subject in need thereof comprising, administering to the subject an effective amount of the compound of Formula (I), Formula (II), or Formula (III) or a form thereof.

Another aspect of the present description includes a use for a compound salt of Formula (I), Formula (II), or Formula (III) or a form thereof for treating or ameliorating HD in a subject in need thereof comprising, administering to the subject an effective amount of the compound salt of Formula (I), Formula (II), or Formula (III) or a form thereof.

An aspect of the present description includes a use for a compound of Formula (I), Formula (II), or Formula (III) or a form thereof in the manufacture of a medicament for treating or ameliorating HD in a subject in need thereof comprising, administering to the subject an effective amount of the medicament.

Another aspect of the present description includes a use for a compound salt of Formula (I), Formula (II), or Formula (III) or a form thereof in the manufacture of a medicament for treating or ameliorating HD in a subject in need thereof comprising, administering to the subject an effective amount of the medicament.

An aspect of the present description includes a use for a compound of Formula (I), Formula (II), or Formula (III) or a form thereof in a combination product with one or more therapeutic agents for treating or ameliorating HD in a subject in need thereof comprising, administering to the subject an effective amount of the compound of Formula (I), Formula (II), or Formula (III) or a form thereof in combination with an effective amount of the one or more agents.

Another aspect of the present description includes a use for a compound salt of Formula (I), Formula (II), or Formula (III) or a form thereof in a combination product with one or more therapeutic agents for treating or ameliorating HD in a subject in need thereof comprising, administering to the subject an effective amount of the compound salt of Formula (I), Formula (II), or Formula (III) or a form thereof in combination with an effective amount of the one or more agents.

Chemical Definitions

The chemical terms used above and throughout the description herein, unless specifically defined otherwise, shall be understood by one of ordinary skill in the art to have the following indicated meanings.

As used herein, the term "$C_{1-4}$alkyl" generally refers to saturated hydrocarbon radicals having from one to four carbon atoms in a straight or branched chain configuration, including, but not limited to, methyl, ethyl, n-propyl (also referred to as propyl or propanyl), isopropyl, n-butyl (also referred to as butyl or butanyl), isobutyl, sec-butyl, tert-butyl and the like. A $C_{1-4}$alkyl radical is optionally substituted with substituent species as described herein where allowed by available valences.

As used herein, the term "$C_{2-4}$alkenyl" generally refers to partially unsaturated hydrocarbon radicals having from two to four carbon atoms in a straight or branched chain configuration and one or more carbon-carbon double bonds therein, including, but not limited to, ethenyl (also referred to as vinyl), allyl, propenyl and the like. A $C_{2-4}$alkenyl radical is optionally substituted with substituent species as described herein where allowed by available valences.

As used herein, the term "$C_{2-4}$alkynyl" generally refers to partially unsaturated hydrocarbon radicals having from two to eight carbon atoms in a straight or branched chain configuration and one or more carbon-carbon triple bonds therein, including, but not limited to, ethynyl, propynyl, butynyl and the like. In certain aspects. $C_{2-4}$alkynyl includes, but is not limited to, $C_{2-4}$alkynyl, $C_2$alkynyl and the like. A $C_{2-4}$alkynyl radical is optionally substituted with substituent species as described herein where allowed by available valences.

As used herein, the term "$C_{1-4}$alkoxy" generally refers to saturated hydrocarbon radicals having from one to four carbon atoms in a straight or branched chain configuration of the formula: —O—$C_{1-4}$alkyl, including, but not limited to, methoxy, ethoxy, n-propoxy, isopropoxy, n-butoxy, isobutoxy, sec-butoxy, tert-butoxy and the like. A $C_{1-44}$alkoxy radical is optionally substituted with substituent species as described herein where allowed by available valences.

As used herein, the term "$C_{3-6}$cycloalkyl" generally refers to a saturated or partially unsaturated monocyclic, bicyclic or polycyclic hydrocarbon radical, including, but not limited to, cyclopropyl, cyclobutyl, cyclopentyl, cyclohexyl, and cyclohexenyl, and the like. A $C_{3-6}$cycloalkyl radical is optionally substituted with substituent species as described herein where allowed by available valences.

As used herein, the term "aryl" generally refers to a monocyclic, bicyclic or polycyclic aromatic carbon atom ring structure radical, including, but not limited to, phenyl, naphthyl, anthracenyl, fluorenyl, azulenyl, phenanthrenyl and the like. An aryl radical is optionally substituted with substituent species as described herein where allowed by available valences.

As used herein, the term "heteroaryl" generally refers to a monocyclic, bicyclic or polycyclic aromatic carbon atom ring structure radical in which one or more carbon atom ring members have been replaced, where allowed by structural stability, with one or more heteroatoms, such as an O, S or N atom, including, but not limited to, furanyl, thienyl, pyrrolyl, pyrazolyl, imidazolyl, isoxazolyl, isothiazolyl, oxazolyl, 1,3-thiazolyl, triazolyl, oxadiazolyl, thiadiazolyl, tetrazolyl, pyridinyl, pyrimidinyl, pyrazinyl, pyridazinyl, triazinyl, indolyl, indazolyl, indolizinyl, isoindolyl, benzofuranyl, benzothienyl, benzoimidazolyl, 1,3-benzothiazolyl, 1,3-benzoxazolyl, purinyl, quinolinyl, isoquinolinyl, quinazolinyl, quinoxalinyl, 1,3-diazinyl, 1,2-diazinyl, 1,2-diazolyl, 1,4-diazanaphthalenyl, acridinyl, furo[3,2-b]pyridinyl, furo[3,2-c]pyridinyl, furo[2,3-c]pyridinyl, 6H-thieno[2,3-b]pyrrolyl, thieno[3,2-c]pyridinyl, thieno[2,3-d]pyrimidinyl, 1H-pyrrolo[2,3-b]pyridinyl, 1H-pyrrolo[2,3-c]pyridinyl, 1H-pyrrolo[3,2-b]pyridinyl, pyrrolo[1,2-a]pyrazinyl, pyrrolo[1,2-b]pyridazinyl, pyrazolo[1,5-a]pyridinyl, pyrazolo[1,5-a]pyrazinyl, imidazo[1,2-a]pyridinyl, 3H-imidazo[4,5-b]pyridinyl, imidazo[1,2-a]pyrimidinyl, imidazo[1,2-c]pyrimidinyl, imidazo[1,2-b]pyridazinyl, imidazo[1,2-a]pyrazinyl, imidazo[2,1-b][1,3]thiazolyl, imidazo[2,1-b][1,3,4]thiadiazolyl. [1,2,4]triazolo[1,5-a]pyridinyl, [1,2,4]triazolo[4,3-a]pyridinyl and the like. A heteroaryl radical is optionally substituted on a carbon or nitrogen atom ring member with substituent species as described herein where allowed by available valences.

In certain aspects, the nomenclature for a heteroaryl radical may differ, such as in non-limiting examples where furanyl may also be referred to as furyl, thienyl may also be referred to as thiophenyl, pyridinyl may also be referred to as pyridyl, benzothienyl may also be referred to as benzothiophenyl and 1,3-benzoxazolyl may also be referred to as 1,3-benzooxazolyl.

In certain other aspects, the term for a heteroaryl radical may also include other regioisomers, such as in non-limiting examples where the term pyrrolyl may also include 2H-pyrrolyl, 3H-pyrrolyl and the like, the term pyrazolyl may also include 1H-pyrazolyl and the like, the term imidazolyl may also include 1H-imidazolyl and the like, the term triazolyl may also include 1H-1,2,3-triazolyl and the like, the term oxadiazolyl may also include 1,2,4-oxadiazolyl, 1,3,4-oxadiazolyl and the like, the term tetrazolyl may also include 1H-tetrazolyl, 2H-tetrazolyl and the like, the term indolyl may also include 1H-indolyl and the like, the term indazolyl may also include 1H-indazolyl, 2H-indazolyl and the like, the term benzoimidazolyl may also include 1H-benzoimidazolyl and the term purinyl may also include 9H-purinyl and the like.

As used herein, the term "heterocyclyl" generally refers to a saturated or partially unsaturated monocyclic, bicyclic or polycyclic carbon atom ring structure radical in which one or more carbon atom ring members have been replaced, where allowed by structural stability, with a heteroatom, such as an O, S or N atom, including, but not limited to, oxiranyl, oxetanyl, azetidinyl, tetrahydrofuranyl, pyrrolinyl, pyrrolidinyl, pyrazolinyl, pyrazolidinyl, imidazolinyl, imidazolidinyl, isoxazolinyl, isoxazolidinyl, isothiazolinyl, isothiazolidinyl, oxazolinyl, oxazolidinyl, thiazolinyl, thiazolidinyl, triazolinyl, triazolidinyl, oxadiazolinyl, oxadiazolidinyl, thiadiazolinyl, thiadiazolidinyl, tetrazolinyl, tetrazolidinyl, pyranyl, dihydro-2H-pyranyl, thiopyranyl, 1,3-dioxanyl, 1,2,5,6-tetrahydropyridinyl, 1,2,3,6-tetrahydropyridinyl, piperidinyl, piperazinyl, morpholinyl, thiomorpholinyl, 1,4-diazepanyl, 1,3-benzodioxolyl, 1,4-benzodioxanyl, 2,3-dihydro-1,4-benzodioxinyl, hexahydropyrrolo[3,4-b]pyrrol-(1H)-yl, (3aS,6aS)-hexahydropyrrolo[3,4-b]pyrrol-(1H)-yl, (3aR,6aR)-hexahydropyrrolo[3,4-b]pyrrol-(1H)-yl, hexahydropyrrolo[3,4-b]pyrrol-(2H)-yl, (3aS,6aS)-hexahydropyrrolo[3,4-b]pyrrol-(2H)-yl, (3aR,6aR)-hexahydropyrrolo[3,4-b]pyrrol-(2H)-yl, hexahydropyrrolo[3,4-c]pyrrol-(1H)-yl, (3aR,6aS)-hexahydropyrrolo[3,4-c]pyrrol-(1H)-yl, (3aR,6aR)-hexahydropyrrolo[3,4-c]pyrrol-(1H)-yl, octahydro-5H-pyrrolo[3,2-c]pyridinyl, octahydro-6H-pyrrolo[3,4-b]pyridinyl, (4aR,7aR)-octahydro-6H-pyrrolo[3,4-b]pyridinyl, (4aS,7aS)-octahydro-6H-pyrrolo[3,4-b]pyridinyl, hexahydropyrrolo[1,2-a]pyrazin-(1H)-yl, (7R,8aS)-hexahydropyrrolo[1,2-a]pyrazin- (1H)-yl, (8aS)-hexahydropyrrolo[1,2-a]pyrazin-(1H)-yl, (8aR)-hexahydropyrrolo[1,2-a]pyrazin-(1H)-yl, (8aS)-octahydropyrrolo[1,2-a]pyrazin-(1H)-yl, (8aR)-octahydropyrrolo[1,2-a]pyrazin-(1H)-yl, hexahydropyrrolo[1,2-a]pyrazin-(2H)-one, octahydro-2H-pyrido[1,2-a]pyrazinyl, 3-azabicyclo[3.1.0]hexyl, (1R,5S)-3-azabicyclo[3.1.0]hexyl, 8-azabicyclo[3.2.1]octyl, (1R,5S)-8-azabicyclo[3.2.1]octyl, 8-azabicyclo[3.2.1]oct-2-enyl, (1R,5S)-8-azabicyclo[3.2.1]oct-2-enyl, 9-azabicyclo[3.3.1]nonyl, (1R,5S)-9-azabicyclo[3.3.1]nonyl, 2,5-diazabicyclo[2.2.1]heptyl, (1S,4S)-2,5-diazabicyclo[2.2.1]heptyl, 2,5-diazabicyclo[2.2.2]octyl, 3,8-diazabicyclo[3.2.1]octyl, (1R,5S)-3,8-diazabicyclo[3.2.1]octyl, 1,4-diazabicyclo[3.2.2]nonyl, azaspiro[3.3]heptyl, 2,6-diazaspiro[3.3]heptyl, 2,6-diazaspiro[3.4]octyl, 2,7-diazaspiro[3.5]nonyl, 5,8-diazaspiro[3.5]nonyl, 2,7-diazaspiro[4.4]nonyl, 6,9-diazaspiro[4.5]decyl, 7-azadispiro[$5.1.5^8.3^6$]hexadecanyl and the like. A heterocyclyl radical is optionally substituted on a carbon or nitrogen atom ring member with substituent species as described herein where allowed by available valences.

In certain aspects, the nomenclature for a heterocyclyl radical may differ, such as in non-limiting examples where 1,3-benzodioxolyl may also be referred to as benzo[d][1,3]dioxolyl and 2,3-dihydro-1,4-benzodioxinyl may also be referred to as 2,3-dihydrobenzo[b][1,4]dioxinyl.

As used herein, the term "$C_{1-4}$alkoxy-$C_{1-4}$alkyl" refers to a radical of the formula: —$C_{1-4}$alkyl-O—$C_{1-4}$alkyl.

As used herein, the term "$C_{1-4}$alkoxy-carbonyl" refers to a radical of the formula: —C(O)—O—$C_{1-4}$alkyl.

As used herein, the term "$C_{1-4}$alkoxy-carbonyl-amino" refers to a radical of the formula: —NH—C(O)—O—$C_{1-4}$alkyl.

As used herein, the term "$C_{1-4}$alkyl-amino" refers to a radical of the formula: —NH—$C_{1-4}$ alkyl.

As used herein, the term "$(C_{1-4}alkyl)_2$-amino" refers to a radical of the formula: —$N(C_{1-4}alkyl)_2$.

As used herein, the term "$C_{1-4}$alkyl-carbonyl" refers to a radical of the formula: —C(O)—$C_{1-4}$alkyl.

As used herein, the term "$C_{1-4}$alkyl-carbonyl-amino" refers to a radical of the formula: —NH—C(O)—$C_{1-4}$alkyl.

As used herein, the term "$C_{1-4}$alkyl-thio" refers to a radical of the formula: —S—$C_{1-4}$alkyl.

As used herein, the term "amino" refers to a radical of the formula: —$NH_2$.

As used herein, the term "amino-$C_{1-4}$alkyl" refers to a radical of the formula: —$C_{1-4}$alkyl-$NH_2$.

As used herein, the term "deutero-$C_{1-4}$alkyl," refers to a radical of the formula: —$C_{1-4}$alkyl, wherein $C_{1-4}$alkyl is partially or completely substituted with one or more deuterium atoms where allowed by available valences.

As used herein, the term "deutero-$C_{1-4}$alkoxy," refers to a radical of the formula: —$C_{1-4}$alkoxy, wherein $C_{1-4}$alkoxy is partially or completely substituted with one or more deuterium atoms where allowed by available valences.

As used herein, the term "halo" or "halogen" generally refers to a halogen atom radical, including fluoro, chloro, bromo and iodo.

As used herein, the term "halo-$C_{1-4}$alkoxy" refers to a radical of the formula: —O—$C_{1-4}$alkyl-halo, wherein $C_{1-4}$alkyl is partially or completely substituted with one or more halogen atoms where allowed by available valences.

As used herein, the term "halo-$C_{1-4}$alkyl" refers to a radical of the formula: —$C_{1-4}$alkyl-halo, wherein $C_{1-4}$alkyl is partially or completely substituted with one or more halogen atoms where allowed by available valences.

As used herein, the term "halo-$C_{1-4}$alkyl-amino" refers to a radical of the formula: —NH—$C_{1-4}$alkyl-halo.

As used herein, the term "(halo-$C_{1-4}alkyl)_2$-amino" refers to a radical of the formula: —$N(C_{1-4}alkyl\text{-}halo)_2$.

As used herein, the term "heteroaryl-$C_{1-4}$alkyl" refers to a radical of the formula: —$C_{1-4}$alkyl-heteroaryl.

As used herein, the term "heteroaryl-$C_{2-4}$alkenyl" refers to a radical of the formula: —$C_{2-4}$alkenyl-heteroaryl.

As used herein, the term "heteroaryl-$C_{1-4}$alkyl-amino" refers to a radical of the formula: —NH—$C_{1-4}$alkyl-heteroaryl.

As used herein, the term "(heteroaryl-$C_{1-4}alkyl)_2$-amino" refers to a radical of the formula: —$N(C_{1-4}alkyl\text{-}heteroaryl)_2$.

As used herein, the term "heteroaryl-amino" refers to a radical of the formula: —NH-heteroaryl.

As used herein, the term "hydroxy" refers to a radical of the formula: —OH.

As used herein, the term "hydroxy-$C_{1-4}$alkyl" refers to a radical of the formula: —$C_{1-4}$alkyl-OH, wherein $C_{1-4}$alkyl is partially or completely substituted with one or more hydroxy radicals where allowed by available valences.

As used herein, the term "cyano" refers to a radical of the formula: —CN.

As used herein, the term "substituent" means positional variables on the atoms of a core molecule that are substituted at a designated atom position, replacing one or more hydrogens on the designated atom, provided that the designated atom's normal valency is not exceeded, and that the substitution results in a stable compound. Combinations of substituents and/or variables are permissible only if such combinations result in stable compounds. A person of ordinary skill in the art should note that any carbon as well as heteroatom with valences that appear to be unsatisfied as described or shown herein is assumed to have a sufficient number of hydrogen atom(s) to satisfy the valences described or shown. In certain instances one or more substituents having a double bond (e.g., "oxo" or "=O") as the point of attachment may be described, shown or listed herein within a substituent group, wherein the structure may only show a single bond as the point of attachment to the core structure of Formula (I), Formula (II), or Formula (III). A person of ordinary skill in the art would understand that, while only a single bond is shown, a double bond is intended for those substituents.

As used herein, the term "and the like," with reference to the definitions of chemical terms provided herein, means that variations in chemical structures that could be expected by one skilled in the art include, without limitation, isomers (including chain, branching or positional structural isomers), hydration of ring systems (including saturation or partial unsaturation of monocyclic, bicyclic or polycyclic ring structures) and all other variations where allowed by available valences which result in a stable compound.

For the purposes of this description, where one or more substituent variables for a compound of Formula (I), Formula (II), or Formula (III) or a form thereof encompass functionalities incorporated into a compound of Formula (I), Formula (II), or Formula (III), each functionality appearing at any location within the disclosed compound may be independently selected, and as appropriate, independently and/or optionally substituted.

As used herein, the terms "independently selected," or "each selected" refer to functional variables in a substituent list that may occur more than once on the structure of Formula (I), Formula (II), or Formula (III), the pattern of substitution at each occurrence is independent of the pattern at any other occurrence. Further, the use of a generic substituent variable on any formula or structure for a compound described herein is understood to include the replacement of the generic substituent with species substituents that are included within the particular genus, e.g., aryl may be replaced with phenyl or naphthalenyl and the like, and that the resulting compound is to be included within the scope of the compounds described herein.

As used herein, the terms “each instance of” or “in each instance, when present,” when used preceding a phrase such as “ . . . $C_{3-14}$cycloalkyl, $C_{3-14}$cycloalkyl-$C_{1-4}$alkyl, aryl, aryl-$C_{1-4}$alkyl, heteroaryl, heteroaryl-$C_{1-4}$alkyl, heterocyclyl and heterocyclyl-$C_{1-4}$alkyl,” are intended to refer to the $C_{3-14}$cycloalkyl, aryl, heteroaryl and heterocyclyl ring systems when each are present either alone or as a substituent.

As used herein, the term “optionally substituted” means optional substitution with the specified substituent variables, groups, radicals or moieties.

Compound Forms

As used herein, the term “form” means a compound of Formula (I), Formula (II), or Formula (III) having a form selected from the group consisting of a free acid, free base, salt, hydrate, solvate, clathrate, isotopologue, racemate, enantiomer, diastereomer, polymorph and tautomer form thereof.

In certain aspects described herein, the form of the compound of Formula (I), Formula (II), or Formula (III) is a free acid, free base or salt thereof.

In certain aspects described herein, the form of the compound of Formula (I), Formula (II), or Formula (III) is a salt thereof.

In certain aspects described herein, the form of the compound of Formula (I), Formula (II), or Formula (III) is a racemate, enantiomer, diastereomer, tautomer, or mixtures thereof.

In certain aspects described herein, the form of the compound of Formula (I), Formula (II), or Formula (III) is a racemate.

In certain aspects described herein, the form of the compound of Formula (I), Formula (II), or Formula (III) is a enantiomer or mixtures thereof.

In certain aspects described herein, the form of the compound of Formula (I), Formula (II), or Formula (III) is a diastereomer or mixtures thereof.

In certain aspects described herein, the form of the compound of Formula (I), Formula (II), or Formula (III) is a tautomer thereof.

In certain aspects described herein, the form of the compound of Formula (I), Formula (II), or Formula (III) is a pharmaceutically acceptable form.

In certain aspects described herein, the compound of Formula (I), Formula (II), or Formula (III) or a form thereof is isolated for use.

As used herein, the term “isolated” means the physical state of a compound of Formula (I), Formula (II), or Formula (III) or a form thereof after being isolated and/or purified from a synthetic process (e.g., from a reaction mixture) or natural source or combination thereof according to an isolation or purification process or processes described herein or which are well known to the skilled artisan (e.g., chromatography, recrystallization and the like) in sufficient purity to be characterized by standard analytical techniques described herein or well known to the skilled artisan.

As used herein, the term “protected” means that a functional group in a compound of Formula (I), Formula (II), or Formula (III) or a form thereof is in a form modified to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York. Such functional groups include hydroxy, phenol, amino and carboxylic acid. Suitable protecting groups for hydroxy or phenol include trialkylsilyl or diarylalkylsilyl (e.g., t-butyldimethylsilyl, t-butyldiphenylsilyl or trimethylsilyl), tetrahydropyranyl, benzyl, substituted benzyl, methyl, methoxymethanol, and the like. Suitable protecting groups for amino, amidino and guanidino include t-butoxycarbonyl, benzyloxycarbonyl, and the like. Suitable protecting groups for carboxylic acid include alkyl, aryl or arylalkyl esters. In certain instances, the protecting group may also be a polymer resin, such as a Wang resin or a 2-chlorotrityl-chloride resin. Protecting groups may be added or removed in accordance with standard techniques, which are well-known to those skilled in the art and as described herein. It will also be appreciated by those skilled in the art, although such protected derivatives of compounds described herein may not possess pharmacological activity as such, they may be administered to a subject and thereafter metabolized in the body to form compounds described herein which are pharmacologically active. Such derivatives may therefore be described as “prodrugs”. All prodrugs of compounds described herein are included within the scope of the use described herein.

In one example, when a compound of Formula (I), Formula (II), or Formula (III) or a form thereof contains a carboxylic acid functional group, a prodrug can comprise an ester formed by the replacement of the hydrogen atom of the acid group with a functional group such as alkyl and the like. In another example, when a compound of Formula (I), Formula (II), or Formula (III) or a form thereof contains a hydroxyl functional group, a prodrug form can be prepared by replacing the hydrogen atom of the hydroxyl with another functional group such as alkyl, alkylcarbonyl or a phosphonate ester and the like. In another example, when a compound of Formula (I), Formula (II), or Formula (III) or a form thereof contains an amine functional group, a prodrug form can be prepared by replacing one or more amine hydrogen atoms with a functional group such as alkyl or substituted carbonyl. Pharmaceutically acceptable prodrugs of compounds of Formula (I), Formula (II), or Formula (III) or a form thereof include those compounds substituted with one or more of the following groups: carboxylic acid esters, sulfonate esters, amino acid esters, phosphonate esters and mono-, di- or triphosphate esters or alkyl substituents, where appropriate. As described herein, it is understood by a person of ordinary skill in the art that one or more of such substituents may be used to provide a compound of Formula (I), Formula (II), or Formula (III) or a form thereof as a prodrug.

One or more compounds described herein may exist in unsolvated as well as solvated forms with pharmaceutically acceptable solvents such as water, ethanol, and the like, and the description herein is intended to embrace both solvated and unsolvated forms.

As used herein, the term “solvate” means a physical association of a compound described herein with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. As used herein, "solvate" encompasses both solution-phase and isolatable solvates. Non-limiting examples of suitable solvates include ethanolates, methanolates, and the like.

As used herein, the term "hydrate" means a solvate wherein the solvent molecule is water.

The compounds of Formula (I), Formula (II), or Formula (III) can form salts, which are intended to be included within the scope of this description. Reference to a compound of Formula (I), Formula (II), or Formula (III) or a form thereof herein is understood to include reference to salt forms thereof, unless otherwise indicated. The term "salt(s)", as employed herein, denotes acidic salts formed with inorganic and/or organic acids, as well as basic salts formed with inorganic and/or organic bases. In addition, when a compound of Formula (I), Formula (II), or Formula (III) or a form thereof contains both a basic moiety, such as, without limitation an amine moiety, and an acidic moiety, such as, but not limited to a carboxylic acid, zwitterions ("inner salts") may be formed and are included within the term "salt(s)" as used herein.

The term "pharmaceutically acceptable salt(s)", as used herein, means those salts of compounds described herein that are safe and effective (i.e., non-toxic, physiologically acceptable) for use in mammals and that possess biological activity, although other salts are also useful. Salts of the compounds of the Formula (I), Formula (II), or Formula (III) may be formed, for example, by reacting a compound of Formula (I), Formula (II), or Formula (III) or a form thereof with an amount of acid or base, such as an equivalent amount, in a medium such as one in which the salt precipitates or in an aqueous medium followed by lyophilization.

Pharmaceutically acceptable salts include one or more salts of acidic or basic groups present in compounds described herein. Particular aspects of acid addition salts include, and are not limited to, acetate, ascorbate, benzoate, benzenesulfonate, bisulfate, bitartrate, borate, bromide, hydrobromide, dihydrobromide, butyrate, chloride, hydrochloride, dihydrochloride, trihydrochloride, tetrahydrochloride, citrate, camphorate, camphorsulfonate, ethanesulfonate, formate, fumarate, gentisinate, gluconate, glucaronate, glutamate, iodide, isonicotinate, lactate, maleate, methanesulfonate, naphthalenesulfonate, nitrate, oxalate, pamoate, pantothenate, phosphate, propionate, saccharate, salicylate, succinate, sulfate, tartrate, thiocyanate, toluenesulfonate (also known as tosylate), trifluoroacetate, ditrifluoroacetate salts and the like.

One aspect includes acid addition salts selected from hydrochloride, hydrobromide, trifluoroacetate, formate, dihydrochloride, trihydrochloride, tetrahydrochloride, dihydrobromide, and ditrifluoroacetate.

Certain particular aspects of acid addition salts include trifluoroacetate, ditrifluoroacetate, hydrochloride or dihydrochloride and the like.

Additionally, acids which are generally considered suitable for the formation of pharmaceutically useful salts from basic pharmaceutical compounds are discussed, for example, by P. Stahl et al. Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33, 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Suitable basic salts include, but are not limited to, aluminum, ammonium, calcium, lithium, magnesium, potassium, sodium and zinc salts.

All such acid salts and base salts are intended to be included within the scope of pharmaceutically acceptable salts as described herein. In addition, all such acid and base salts are considered equivalent to the free forms of the corresponding compounds for purposes of this description.

Compounds of Formula (I), Formula (II), or Formula (III), may further exist in a tautomeric form. All such tautomeric forms are contemplated and intended to be included within the scope of the compounds of Formula (I), Formula (II), or Formula (III) or a form thereof as described herein.

Compounds of Formula (I), Formula (II), or Formula (III) may contain asymmetric or chiral centers, and, therefore, exist in different stereoisomeric forms. The present description is intended to include all stereoisomeric forms of the compounds of Formula (I), Formula (II), or Formula (III) as well as mixtures thereof, including racemic mixtures.

Compounds of Formula (I), Formula (II), or Formula (III) may include one or more chiral centers, and as such may exist as racemic mixtures (R,S) or as substantially pure enantiomers and diastereomers. The compounds may also exist as substantially pure (R) or (S) enantiomers (when one chiral center is present). In one particular aspect, the compounds described herein are (S) isomers and may exist as enantiomerically pure compositions substantially comprising only the (S) isomer. In another particular aspect, the compounds described herein are (R) isomers and may exist as enantiomerically pure compositions substantially comprising only the (R) isomer. As one of skill in the art will recognize, when more than one chiral center is present, the compounds described herein may also exist as a (R,R), (R,S), (S,R) or (S,S) isomer, as defined by IUPAC Nomenclature Recommendations.

As used herein, the term "chiral" refers to a carbon atom bonded to four nonidentical substituents. Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. In describing an optically active compound, the prefixes D and L, or R and S, are used to denote the absolute configuration of the molecule about its chiral center(s). The substituents attached to the chiral center under consideration are is ranked in accordance with the Sequence Rule of Cahn, Ingold and Prelog. (Cahn et al. Angew. Chem. Inter. Edit. 1966, 5, 385; errata 511).

Compounds of Formula (I), Formula (II), or Formula (III) may include enantiomers, diastereomers, or racemates. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. When a compound is a pure enantiomer the stereochemistry at each chiral carbon may be specified by either "R" or "S". A "meso-compound" is the achiral member(s) of a set of diasteromers which includes one or more chiral members. The pseudostereogenic center(s) in meso-compounds may be specified by either "r" or "s". Resolved compounds whose absolute configuration is unknown can be designated (+) or (−) depending on the direction (dextro- or levorotatory) which they rotate plane polarized light at the wavelength of the sodium D line. "Diastereomer" may also refer to the stereochemistry of double bonds which may be specified as cis or trans or, alternatively, E or Z.

Certain compounds described herein contain one or more asymmetric centers or axes and may thus give rise to enantiomers, diastereomers, and other stereoisomeric forms.

As used herein, the term "substantially pure" refers to compounds consisting substantially of a single isomer in an amount greater than or equal to 90%, in an amount greater than or equal to 92%, in an amount greater than or equal to 95%, in an amount greater than or equal to 98%, in an amount greater than or equal to 99%, or in an amount equal to 100% of the single isomer.

In one aspect of the description, a compound of Formula (I), Formula (II), or Formula (III) or a form thereof is a substantially pure (S) enantiomer form present in an amount greater than or equal to 90%, in an amount greater than or equal to 92%, in an amount greater than or equal to 95%, in an amount greater than or equal to 98%, in an amount greater than or equal to 99%, or in an amount equal to 100%.

In one aspect of the description, a compound of Formula (I), Formula (II), or Formula (III) or a form thereof is a substantially pure (R) enantiomer form present in an amount greater than or equal to 90%, in an amount greater than or equal to 92%, in an amount greater than or equal to 95%, in an amount greater than or equal to 98%, in an amount greater than or equal to 99%, or in an amount equal to 100%.

As used herein, a "racemate" is any mixture of isometric forms that are not "enantiomerically pure", including mixtures such as, without limitation, in a ratio of about 50/50, about 60/40, about 70/30, or about 80/20.

In addition, the present description embraces all geometric and positional isomers. For example, if a compound of Formula (I), Formula (II), or Formula (III) or a form thereof incorporates a double bond or a fused ring, both the cis- and trans-forms, as well as mixtures, are embraced within the scope of the description. Diastereomeric mixtures can be separated into their individual diastereomers on the basis of their physical chemical differences by methods well known to those skilled in the art, such as, for example, by chromatography and/or fractional crystallization. Enantiomers can be separated by use of chiral HPLC column or other chromatographic methods known to those skilled in the art. Enantiomers can also be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I), Formula (II), or Formula (III) may be atropisomers (e.g., substituted biaryls) and are considered as part of this description.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this description, as are positional isomers (such as, for example, 4-pyridyl and 3-pyridyl). Individual stereoisomers of the compounds described herein may, for example, be substantially free of other isomers, or may be present in a racemic mixture, as described supra.

The use of the terms "salt", "solvate", "ester", "prodrug" and the like, is intended to equally apply to the salt, solvate, ester and prodrug of enantiomers, stereoisomers, rotamers, tautomers, positional isomers, racemates or isotopologues of the instant compounds.

Certain isotopically-enriched compounds described herein (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances.

Compound Uses

In accordance with the intended scope of the present description, aspects of the present description include compounds that have been identified and have been demonstrated to be useful in selectively preventing, treating or ameliorating HD and have been provided for use for preventing, treating or ameliorating HD.

An aspect of the present description includes a method for preventing, treating or ameliorating HD in a subject in need thereof comprising, administering to the subject an effective amount of a compound of Formula (I), Formula (II), or Formula (III) or a form thereof.

An aspect of the present description includes a method for treating or ameliorating HD in a subject in need thereof comprising, administering to the subject an effective amount of a compound of Formula (I), Formula (II), or Formula (III) or a form thereof.

An aspect of the present description includes a method for preventing HD in a subject in need thereof comprising, administering to the subject an effective amount of a compound of Formula (I), Formula (II), or Formula (III) or a form thereof.

An aspect of the present description includes a method for treating HD in a subject in need thereof comprising, administering to the subject an effective amount of a compound of Formula (I), Formula (II), or Formula (III) or a form thereof.

An aspect of the present description includes a method for ameliorating HD in a subject in need thereof comprising, administering to the subject an effective amount of a compound of Formula (I), Formula (II), or Formula (III) or a form thereof.

Another aspect of the present description includes a method for treating or ameliorating HD in a subject in need thereof comprising, administering to the subject an effective amount of a compound salt of Formula (I), Formula (II), or Formula (III) or a form thereof.

An aspect of the present description includes a method for use of a compound of Formula (I), Formula (II), or Formula (III) or a form or composition thereof for treating or ameliorating HD in a subject in need thereof comprising, administering to the subject an effective amount of the compound of Formula (I), Formula (II), or Formula (III) or a form or composition thereof.

Another aspect of the present description includes a method for use of a compound salt of Formula (I), Formula (II), or Formula (III) or a form or composition thereof for treating or ameliorating HD in a subject in need thereof comprising, administering to the subject an effective amount of the compound salt of Formula (I), Formula (II), or Formula (III) or a form thereof.

An aspect of the present description includes a use for a compound of Formula (I), Formula (II), or Formula (III) or a form thereof for treating or ameliorating HD in a subject in need thereof comprising, administering to the subject an effective amount of the compound of Formula (I), Formula (II), or Formula (III) or a form thereof.

Another aspect of the present description includes a use for a compound salt of Formula (I), Formula (II), or Formula (III) or a form thereof for treating or ameliorating HD in a subject in need thereof comprising, administering to the subject an effective amount of the compound salt of Formula (I), Formula (II), or Formula (III) or a form thereof.

An aspect of the present description includes a use for a compound of Formula (I), Formula (II), or Formula (III) or a form thereof in the manufacture of a medicament for treating or ameliorating HD in a subject in need thereof comprising, administering to the subject an effective amount of the medicament.

Another aspect of the present description includes a use for a compound salt of Formula (I), Formula (II), or Formula (III) or a form thereof in the manufacture of a medicament for treating or ameliorating HD in a subject in need thereof comprising, administering to the subject an effective amount of the medicament.

An aspect of the present description includes in vitro or in vivo use of the compound of Formula (I), Formula (II), or Formula (III) or a form thereof having activity toward HD.

An aspect of the present description includes a use of the compound of Formula (I), Formula (II), or Formula (III) or a form thereof in a combination therapy to provide additive or synergistic activity, thus enabling the development of a combination product for treating or ameliorating HD.

Another aspect of the present description includes a combination therapy comprising compounds described herein in combination with one or more known drugs or one or more known therapies may be used to treat HD regardless of whether HD is responsive to the known drug.

An aspect of the present description includes a use for a compound of Formula (I), Formula (II), or Formula (III) or a form thereof in a combination product with one or more therapeutic agents for treating or ameliorating HD in a subject in need thereof comprising, administering to the subject an effective amount of the compound of Formula (I), Formula (II), or Formula (III) or a form thereof in combination with an effective amount of the one or more agents.

Another aspect of the present description includes a use for a compound salt of Formula (I), Formula (II), or Formula (III) or a form thereof in a combination product with one or more therapeutic agents for treating or ameliorating HD in a subject in need thereof comprising, administering to the subject an effective amount of the compound salt of Formula (I), Formula (II), or Formula (III) or a form thereof in combination with an effective amount of the one or more agents.

In an aspect of a use or method provided herein, compounds of Formula (I), Formula (II), or Formula (III) or a form thereof used in combination with one or more additional agents can be administered to a subject or contacted with a subject or patient cell(s) prior to, concurrently with, or subsequent to administering to the subject or patient or contacting the cell with an additional agent(s). A compound(s) of Formula (I), Formula (II), or Formula (III) or a form thereof and an additional agent(s) can be administered to a subject or contacted with a cell in single composition or different compositions. In a specific aspect, a compound(s) of Formula (I), Formula (II), or Formula (III) or a form thereof is used in combination with gene therapy to inhibit HTT expression (using, e.g., viral delivery vectors) or the administration of another small molecule HTT inhibitor. In another specific aspect, a compound(s) of Formula (I), Formula (II), or Formula (III) or a form thereof are used in combination with cell replacement using differentiated non-mutant HTT stem cells. In another specific aspect, a compound(s) of Formula (I), Formula (II), or Formula (III) or a form thereof are used in combination with cell replacement using differentiated HTT stem cells.

In one aspect, provided herein is the use of compounds of Formula (I), Formula (II), or Formula (III) or a form thereof in combination with supportive standard of care therapies, including palliative care.

An aspect of the present description includes a use for a compound of Formula (I), Formula (II), or Formula (III) or a form thereof in the preparation of a kit for treating or ameliorating HD in a subject in need thereof comprising, the compound of Formula (I), Formula (II), or Formula (III) or a form thereof and instructions for administering an effective amount of the compound of Formula (I), Formula (II), or Formula (III) or a form thereof.

An aspect of the present description includes a use for a compound of Formula (I), Formula (II), or Formula (III) or a form thereof in the preparation of a kit for treating or ameliorating HD in a subject in need thereof comprising, the compound of Formula (I), Formula (II), or Formula (III) or a form thereof and instructions for administering an effective amount of the compound of Formula (I), Formula (II), or Formula (III) or a form thereof; and optionally, for administering to the subject an effective amount of the compound of Formula (I), Formula (II), or Formula (III) or a form thereof in a combination product with an effective amount of one or more therapeutic agents.

An aspect of the present description includes a use for a compound of Formula (I), Formula (II), or Formula (III) or a form thereof in the preparation of a kit for treating or ameliorating HD in a subject in need thereof comprising, the compound of Formula (I), Formula (II), or Formula (III) or a form thereof and instructions for administering an effective amount of the compound of Formula (I), Formula (II), or Formula (III) or a form thereof; and optionally, for administering to the subject an effective amount of the compound of Formula (I), Formula (II), or Formula (III) or a form thereof in a combination product with an effective amount of the one or more therapeutic agents; and optionally, for administering to the subject an effective amount of the compound of Formula (I), Formula (II), or Formula (III) or a form thereof in a combination product with an effective amount of the one or more therapeutic agents in a combination therapy with a standard of care supportive therapy, wherein the standard of care supportive therapy is palliative care.

In one respect, for each of such aspects, the subject is treatment naive. In another respect, for each of such aspects, the subject is not treatment naive.

As used herein, the term “preventing” refers to keeping a disease, disorder or condition from occurring in a subject that may be predisposed to the disease, disorder and/or condition but has not yet been diagnosed as having the disease, disorder and/or condition.

As used herein, the term “treating” refers to inhibiting the progression of a disease, disorder or condition in a subject already exhibiting the symptoms of the disease, disorder and/or condition, i.e., arresting the development of a disease, disorder and/or condition that has already affected the subject.

As used herein, the term “ameliorating” refers to relieving the symptoms of a disease, disorder or condition in a subject already exhibiting the symptoms of the disease, disorder and/or condition, i.e., causing regression of the disease, disorder and/or condition that has already affected the subject.

As used herein, the term “subject” refers to an animal or any living organism having sensation and the power of voluntary movement, and which requires oxygen and organic food.

Nonlimiting examples include members of the human, primate, equine, porcine, bovine, murine, rattus, canine and feline specie. In certain aspects, the subject is a mammal or a warm-blooded vertebrate animal. In other aspects, the subject is a human. As used herein, the term “patient” may be used interchangeably with “subject” and “human”.

As used herein, the terms “effective amount” or “therapeutically effective amount” mean an amount of compound of Formula (I), Formula (II), or Formula (III) or a form, composition or medicament thereof that achieves a target plasma concentration that is effective in treating or ameliorating HD as described herein and thus producing the desired therapeutic, ameliorative, inhibitory or preventative effect in a subject in need thereof. In one aspect, the effective amount may be the amount required to treat HD in a subject or patient, more specifically, in a human.

In another aspect, the concentration-biological effect relationships observed with regard to a compound of Formula (I), Formula (II), or Formula (III) or a form thereof indicate a target plasma concentration ranging from approximately 0.001 μg/mL to approximately 50 μg/mL, from approximately 0.01 μg/mL to approximately 20 μg/mL, from approximately 0.05 μg/mL to approximately 10 μg/mL, or from approximately 0.1 μg/mL to approximately 5 μg/mL. To achieve such plasma concentrations, the compounds described herein may be administered at doses that vary, such as, for example, without limitation, from 1.0 ng to 10,000 mg.

In one aspect, the dose administered to achieve an effective target plasma concentration may be administered based upon subject or patient specific factors, wherein the doses administered on a weight basis may be in the range of from about 0.001 mg/kg/day to about 3500 mg/kg/day, or about 0.001 mg/kg/day to about 3000 mg/kg/day, or about 0.001 mg/kg/day to about 2500 mg/kg/day, or about 0.001 mg/kg/day to about 2000 mg/kg/day, or about 0.001 mg/kg/day to about 1500 mg/kg/day, or about 0.001 mg/kg/day to about 1000 mg/kg/day, or about 0.001 mg/kg/day to about 500 mg/kg/day, or about 0.001 mg/kg/day to about 250 mg/kg/day, or about 0.001 mg/kg/day to about 200 mg/kg/day, or about 0.001 mg/kg/day to about 150 mg/kg/day, or about 0.001 mg/kg/day to about 100 mg/kg/day, or about 0.001 mg/kg/day to about 75 mg/kg/day, or about 0.001 mg/kg/day to about 50 mg/kg/day, or about 0.001 mg/kg/day to about 25 mg/kg/day, or about 0.001 mg/kg/day to about 10 mg/kg/day, or about 0.001 mg/kg/day to about 5 mg/kg/day, or about 0.001 mg/kg/day to about 1 mg/kg/day, or about 0.001 mg/kg/day to about 0.5 mg/kg/day, or about 0.001 mg/kg/day to about 0.1 mg/kg/day, or from about 0.01 mg/kg/day to about 3500 mg/kg/day, or about 0.01 mg/kg/day to about 3000 mg/kg/day, or about 0.01 mg/kg/day to about 2500 mg/kg/day, or about 0.01 mg/kg/day to about 2000 mg/kg/day, or about 0.01 mg/kg/day to about 1500 mg/kg/day, or about 0.01 mg/kg/day to about 1000 mg/kg/day, or about 0.01 mg/kg/day to about 500 mg/kg/day, or about 0.01 mg/kg/day to about 250 mg/kg/day, or about 0.01 mg/kg/day to about 200 mg/kg/day, or about 0.01 mg/kg/day to about 150 mg/kg/day, or about 0.01 mg/kg/day to about 100 mg/kg/day, or about 0.01 mg/kg/day to about 75 mg/kg/day, or about 0.01 mg/kg/day to about 50 mg/kg/day, or about 0.01 mg/kg/day to about 25 mg/kg/day, or about 0.01 mg/kg/day to about 10 mg/kg/day, or about 0.01 mg/kg/day to about 5 mg/kg/day, or about 0.01 mg/kg/day to about 1 mg/kg/day, or about 0.01 mg/kg/day to about 0.5 mg/kg/day, or about 0.01 mg/kg/day to about 0.1 mg/kg/day, or from about 0.1 mg/kg/day to about 3500 mg/kg/day, or about 0.1 mg/kg/day to about 3000 mg/kg/day, or about 0.1 mg/kg/day to about 2500 mg/kg/day, or about 0.1 mg/kg/day to about 2000 mg/kg/day, or about 0.1 mg/kg/day to about 1500 mg/kg/day, or about 0.1 mg/kg/day to about 1000 mg/kg/day, or about 0.1 mg/kg/day to about 500 mg/kg/day, or about 0.1 mg/kg/day to about 250 mg/kg/day, or about 0.1 mg/kg/day to about 200 mg/kg/day, or about 0.1 mg/kg/day to about 150 mg/kg/day, or about 0.1 mg/kg/day to about 100 mg/kg/day, or about 0.1 mg/kg/day to about 75 mg/kg/day, or about 0.1 mg/kg/day to about 50 mg/kg/day, or about 0.1 mg/kg/day to about 25 mg/kg/day, or about 0.1 mg/kg/day to about 10 mg/kg/day, or about 0.1 mg/kg/day to about 5 mg/kg/day, or about 0.1 mg/kg/day to about 1 mg/kg/day, or about 0.1 mg/kg/day to about 0.5 mg/kg/day.

Effective amounts for a given subject may be determined by routine experimentation that is within the skill and judgment of a clinician or a practitioner skilled in the art in light of factors related to the subject. Dosage and administration may be adjusted to provide sufficient levels of the active agent(s) or to maintain the desired effect. Factors which may be taken into account include genetic screening, severity of the disease state, status of disease progression, general health of the subject, ethnicity, age, weight, gender, diet, time of day and frequency of administration, drug combination(s), reaction sensitivities, experience with other therapies, and tolerance/response to therapy.

The dose administered to achieve an effective target plasma concentration may be orally administered once (once in approximately a 24 hour period; i.e., “q.d.”), twice (once in approximately a 12 hour period; i.e., “b.i.d.” or “q.12 h”), thrice (once in approximately an 8 hour period; i.e., “t.i.d.” or “q.8 h”), or four times (once in approximately a 6 hour period; i.e., “q.d.s.”, “q.i.d.” or “q.6 h”) daily.

In certain aspects, the dose administered to achieve an effective target plasma concentration may also be administered in a single, divided, or continuous dose for a patient or subject having a weight in a range of between about 40 to about 200 kg (which dose may be adjusted for patients or subjects above or below this range, particularly children under 40 kg). The typical adult subject is expected to have a median weight in a range of about 70 kg. Long-acting pharmaceutical compositions may be administered every 2, 3 or 4 days, once every week, or once every two weeks depending on half-life and clearance rate of the particular formulation.

The compounds and compositions described herein may be administered to the subject via any drug delivery route known in the art. Nonlimiting examples include oral, ocular, rectal, buccal, topical, nasal, sublingual, transdermal, subcutaneous, intramuscular, intraveneous (bolus and infusion), intracerebral, and pulmonary routes of administration.

In another aspect, the dose administered may be adjusted based upon a dosage form described herein formulated for delivery at about 0.02, 0.025, 0.03, 0.05, 0.06, 0.075, 0.08, 0.09, 0.10, 0.20, 0.25, 0.30, 0.50, 0.60, 0.75, 0.80, 0.90, 1.0, 1.10, 1.20, 1.25, 1.50, 1.75, 2.0, 3.0, 5.0, 10, 20, 30, 40, 50, 100, 150, 200, 250, 300, 400, 500, 1000, 1500, 2000, 2500, 3000 or 4000 mg/day.

For any compound, the effective amount can be estimated initially either in cell culture assays or in relevant animal models, such as a mouse, guinea pig, chimpanzee, marmoset or tamarin animal model. Relevant animal models may also be used to determine the appropriate concentration range and route of administration. Such information can then be used to determine useful doses and routes for administration in humans. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is therapeutic index, and can be expressed as the ratio, $LD_{50}/ED_{50}$. In certain aspects, the effective amount is such that a large therapeutic index is achieved. In further particular aspects, the dosage is within a range of circulating concentrations that include an $ED_{50}$ with little or no toxicity. The dosage may vary within this range depending upon the dosage form employed, sensitivity of the patient, and the route of administration.

In one aspect, provided herein are methods for modulating the amount of HTT (huntingtin protein), comprising contacting a human cell with a compound of Formula (I), Formula (II), or Formula (II) or a form thereof. In a specific aspect, provided herein are methods for modulating the amount of HTT, comprising contacting a human cell with a compound of Formula (I), Formula (II), or Formula (III) or a form thereof that modulates the expression of HTT. The human cell can be contacted with a compound of Formula (I), Formula (I), or Formula (III) or a form thereof in vitro, or in vivo, e.g., in a non-human animal or in a human. In a specific aspect, the human cell is from or in a human. In another specific aspect, the human cell is from or in a human with HD. In another specific aspect, the human cell is from or in a human with HD, caused by a CAG repeat in the Htt gene, resulting in a loss of HTT expression and/or function. In another aspect, the human cell is from a human with HD. In another aspect, the human cell is in a human with HD. In one aspect, the compound is a form of the compound of Formula (I), Formula (II), or Formula (III).

In a specific aspect, provided herein is a method for enhancing the inhibition of mutant HTT transcribed from the Htt gene, comprising contacting a human cell with a compound of Formula (I), Formula (II), or Formula (III) or a form thereof. The human cell can be contacted with a compound of Formula (I), Formula (II), or Formula (III) or a form thereof n vitro, or in vivo, e.g., in a non-human animal or in a human. In a specific aspect, the human cell is from or in a human. In another specific aspect, the human cell is from or in a human with HD. In another specific aspect, the human cell is from or in a human with HD, caused by a CAG repeat in the Htt gene, resulting in a loss of wild-type "normal" HIT expression and/or function. In another aspect, the human cell is from a human with HD. In another aspect, the human cell is in a human with HD. In one aspect, the compound is a form of the compound of Formula (I), Formula (II), or Formula (III).

In another aspect, provided herein is a method for modulating the inhibition of mutant HTT transcribed from the Htt gene, comprising administering to a non-human animal model for HD a compound of Formula (I), Formula (II), or Formula (III) or a form thereof. In a specific aspect, provided herein is a method for modulating the inhibition of mutant HTT transcribed from the Htt gene, comprising administering to a non-human animal model for HD a compound of Formula (I), Formula (II), or Formula (III) or a form thereof. In a specific aspect, the compound is a form of the compound of Formula (I), Formula (II), or Formula (III).

In another aspect, provided herein is a method for decreasing the amount of mutant HTT, comprising contacting a human cell with a compound of Formula (I), Formula (II), or Formula (III) or a form thereof. In a specific aspect, provided herein is a method for decreasing the amount of mutant HTT, comprising contacting a human cell with a compound of Formula (I), Formula (II), or Formula (III) that inhibits the transcription of mutant HTT (huntingtin mRNA) from the Htt gene. In another specific aspect, provided herein is a method for decreasing the amount of HTT, comprising contacting a human cell with a compound of Formula (I), Formula (II), or Formula (II) that inhibits the expression of mutant HTT transcribed from the Htt gene. The human cell can be contacted with a compound of Formula (I), Formula (II), or Formula (III) or a form thereof in vitro, or in vivo, e.g., in a non-human animal or in a human. In a specific aspect, the human cell is from or in a human. In another specific aspect, the human cell is from or in a human with HD. In another specific aspect, the human cell is from or in a human with HD, caused by a CAG repeat in the Htt gene, resulting in a loss of HTT expression and/or function. In another aspect, the human cell is from a human with HD. In another aspect, the human cell is in a human with HD. In one aspect, the compound is a form of the compound of Formula (I), Formula (II), or Formula (III).

In certain aspects, treating or ameliorating HD with a compound of Formula (I), Formula (II), or Formula (III) or a form thereof (alone or in combination with an additional agent) has a therapeutic effect and/or beneficial effect. In a specific aspect, treating HD with a compound of Formula (I), Formula (II), or Formula (II) or a form thereof (alone or in combination with an additional agent) results in one, two or more of the following effects: (i) reduces or ameliorates the severity of HD; (ii) delays onset of HD; (iii) inhibits the progression of HD; (iv) reduces hospitalization of a subject; (v) reduces hospitalization length for a subject; (vi) increases the survival of a subject; (vii) improves the quality of life for a subject; (viii) reduces the number of symptoms associated with HD; (ix) reduces or ameliorates the severity of a symptom(s) associated with HD; (x) reduces the duration of a symptom associated with HD; (xi) prevents the recurrence of a symptom associated with HD; (xii) inhibits the development or onset of a symptom of HD; and/or (xiii) inhibits of the progression of a symptom associated with HD.

Metabolites

Another aspect included within the scope of the present description are the use of in vivo metabolic products of the compounds described herein. Such products may result, for example, from the oxidation, reduction, hydrolysis, amidation, esterification and the like of the administered compound, primarily due to enzymatic processes. Accordingly, the description includes the use of compounds produced by a process comprising contacting a compound described herein with a mammalian tissue or a mammal for a period of time sufficient to yield a metabolic product thereof.

Such products typically are identified by preparing a radio-labeled (e.g., $^{14}C$ or $^{3}H$) compound described herein, administering the radio-labeled compound in a detectable dose (e.g., greater than about 0.5 mg/kg) to a mammal such as a rat, mouse, guinea pig, dog, monkey or human, allowing sufficient time for metabolism to occur (typically about 30 seconds to about 30 hours), and identifying the metabolic conversion products from urine, bile, blood or other biological samples. The conversion products are easily isolated since they are "radiolabeled" by virtue of being isotopically-enriched (others are isolated by the use of antibodies capable of binding epitopes surviving in the metabolite). The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds described herein even if they possess no biological activity of their own.

Pharmaceutical Compositions

In accordance with the intended scope of the present description, aspects of the present description include compounds that have been identified and have been demonstrated to be useful in selectively preventing, treating or ameliorating HD and have been provided for use as one or more pharmaceutical compositions for preventing, treating or ameliorating HD.

An aspect of the present description includes a use for a compound of Formula (I), Formula (II), or Formula (III) or a form thereof in the preparation of a pharmaceutical composition for treating or ameliorating HD in a subject in need thereof comprising, administering to the subject an effective amount of the compound of Formula (I), Formula (II), or Formula (III) or a form thereof in admixture with one or more pharmaceutically acceptable excipients.

An aspect of the present description includes a use for a pharmaceutical composition of the compound of Formula (I), Formula (II), or Formula (III) or a form thereof in the preparation of a kit for treating or ameliorating HD in a subject in need thereof comprising, the pharmaceutical composition of the compound of Formula (I), Formula (II), or Formula (III) or a form thereof and instructions for administering the pharmaceutical composition.

As used herein, the term "composition" means a product comprising the specified ingredients in the specified amounts, as well as any product which results, directly or indirectly, from combination of the specified ingredients in the specified amounts.

The pharmaceutical composition may be formulated to achieve a physiologically compatible pH, ranging from about pH 3 to about pH 11. In certain aspects, the pharmaceutical composition is formulated to achieve a pH of from about pH 3 to about pH 7. In other aspects, the pharmaceutical composition is formulated to achieve a pH of from about pH 5 to about pH 8.

The term "pharmaceutically acceptable excipient" refers to an excipient for administration of a pharmaceutical agent, such as the compounds described herein. The term refers to any pharmaceutical excipient that may be administered without undue toxicity. Pharmaceutically acceptable excipients may be determined in part by the particular composition being administered, as well as by the particular mode of administration and/or dosage form. Nonlimiting examples of pharmaceutically acceptable excipients include carriers, solvents, stabilizers, adjuvants, diluents, etc. Accordingly, there exists a wide variety of suitable formulations of pharmaceutical compositions for the instant compounds described herein (see. e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive antibodies. Other exemplary excipients include antioxidants such as ascorbic acid; chelating agents such as EDTA; carbohydrates such as dextrin, hydroxyalkylcellulose, hydroxyalkylmethylcellulose (e.g., hydroxypropylmethylcellulose, also known as HPMC), stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions described herein may be formulated in any form suitable for the intended use described herein. Suitable formulations for oral administration include solids, liquid solutions, emulsions and suspensions, while suitable inhalable formulations for pulmonary administration include liquids and powders. Alternative formulations include syrups, creams, ointments, tablets, and lyophilized solids which can be reconstituted with a physiologically compatible solvent prior to administration.

When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents, and preserving agents, in order to provide a palatable preparation.

Pharmaceutically acceptable excipients suitable for use in conjunction with tablets include, for example, inert diluents, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid, or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate, or kaolin, or as soft gelatin capsules wherein the active ingredient is mixed with non-aqueous or oil medium, such as glycerin, propylene glycol, polyethylene glycol, peanut oil, liquid paraffin, or olive oil.

In other aspects, pharmaceutical compositions described herein may be formulated as suspensions comprising a compound of Formula (I), Formula (II), or Formula (III) or a form thereof in admixture with one or more pharmaceutically acceptable excipients suitable for the manufacture of a suspension. In yet other aspects, pharmaceutical compositions described herein may be formulated as dispersible powders and granules suitable for preparation of a suspension by the addition of one or more excipients.

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene-oxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin, or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions described herein may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions described herein may be in the form of a sterile injectable preparation, such as a sterile injectable aqueous emulsion or oleaginous suspension. Such emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propanediol. The sterile injectable preparation may also be prepared as a lyophilized powder. Among the acceptable vehicles and solvents that may be employed are water, Ringer's solution and isotonic sodium chloride solution. In addition, sterile fixed oils may be employed as a solvent or suspending medium. For this purpose any bland fixed oil may be employed including synthetic mono- or di-glycerides. In addition, fatty acids such as oleic acid may likewise be used in the preparation of injectables.

The compounds described herein may be substantially insoluble in water and sparingly soluble in most pharmaceutically acceptable protic solvents and vegetable oils, but generally soluble in medium-chain fatty acids (e.g., caprylic and capric acids) or triglycerides and in propylene glycol esters of medium-chain fatty acids. Thus, contemplated in the description are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In certain aspects, the compound described herein is formulated for oral administration in a lipid-based composition suitable for low solubility compounds. Lipid-based formulations can generally enhance the oral bioavailability of such compounds. As such, pharmaceutical compositions described herein may comprise a effective amount of a compound of Formula (I), Formula (II), or Formula (III) or a form thereof, together with at least one pharmaceutically acceptable excipient selected from medium chain fatty acids or propylene glycol esters thereof (e.g., propylene glycol esters of edible fatty acids such as caprylic and capric fatty acids) and pharmaceutically acceptable surfactants, such as polysorbate 20 or 80 (also referred to as Tween® 20 or Tween®, 80, respectively) or polyoxyl 40 hydrogenated castor oil.

In other aspects, the bioavailability of low solubility compounds may be enhanced using particle size optimization techniques including the preparation of nanoparticles or nanosuspensions using techniques known to those skilled in the art. The compound forms present in such preparations include amorphous, partially amorphous, partially crystalline or crystalline forms.

In alternative aspects, the pharmaceutical composition may further comprise one or more aqueous solubility enhancer(s), such as a cyclodextrin. Nonlimiting examples of cyclodextrin include hydroxypropyl, hydroxyethyl, glucosyl, maltosyl and maltotriosyl derivatives of α-, β-, and γ-cyclodextrin, and hydroxypropyl-β-cyclodextrin (HPBC). In certain aspects, the pharmaceutical composition further comprises HPBC in a range of from about 0.1% to about 20%, from about 1% to about 15%, or from about 2.5% to about 10%. The amount of solubility enhancer employed may depend on the amount of the compound in the composition.

Preparation of Compounds

General Synthetic Examples

As disclosed herein, general methods for preparing the compounds of Formula (I), Formula (II), or Formula (III) or a form thereof as described herein are available via standard, well-known synthetic methodology. Many of the starting materials are commercially available or, when not available, can be prepared using the routes described below using techniques known to those skilled in the art. The synthetic schemes provided herein comprise multiple reaction steps, each of which is intended to stand on its own and can be carried out with or without any preceding or succeeding step(s). In other words, each of the individual reaction steps of the synthetic schemes provided herein in isolation is contemplated.

Compounds of Formula (I), wherein $R_1$ is alkyl, cycloalkyl, heterocyclyl, aryl or heteroaryl; $R_2$ is monocyclic or bicyclic heterocyclyl or heteroaryl ring systems. W is O or NH or $NR_3$, where $R_3$ is alkyl, cycloalkyl, heterocyclyl, aryl or heteroaryl may be prepared as described in Scheme A below.

Scheme A

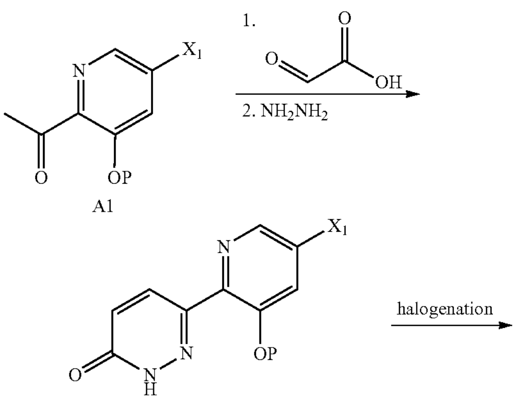

A1

A2

-continued

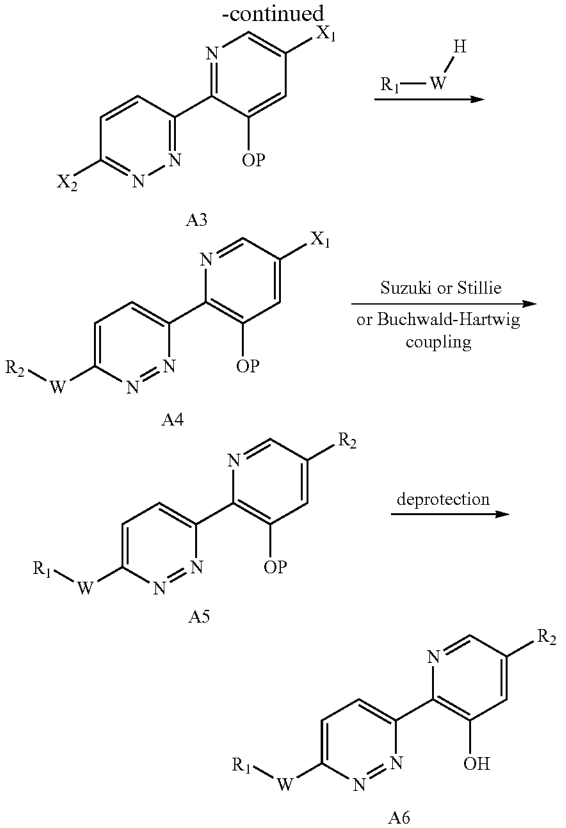

A3 A4 A5 A6

Compound A1 (where $X_1$ is bromine, chlorine and the like and P is a protecting group such as MOM and the like) is converted to Compound A2 by treatment with oxaldehydic acid hydrate in the presence of a suitable base (such as aq. $K_2CO_3$ and the like) in an appropriate solvent (such as MeOH and the like) followed by the treatment with hydrazine in an appropriate solvent (such as AcOH and the like). Compound A2 is converted to Compound A3 (where $X_2$ is bromine, chlorine and the like) by treatment with a dehydrative halogenating agent (such as $POCl_3$ and the like). Compound A3 is converted to Compound A4 by a nucleophilic substitution with a primary or secondary amine or an alcohol ($R_1WH$) in the presence of a suitable base (such as $Et_3N$ and the like) in a suitable solvent (such as DMF and the like). Alternatively, Compound A3 is converted to Compound A4 via cross coupling with a primary or a secondary amine in the presence of a suitable catalyst (such as RuPhos Pd G2 and the like) and base (such as sodium tert-butoxide and the like) in an appropriate solvent such as 1,4-dioxane and the like). Compound A4 is converted to Compound A5 by a Suzuki coupling with an aryl- or heteroaryl-boronic acid (or pinacol boronic ester) in the presence of a catalyst (such as $Pd(dppf)Cl_2$ and the like) and base (such as aqueous $K_2CO_3$ and the like) in a suitable solvent (such as 1,4-dioxane and the like). Alternatively, Compound A4 is converted to Compound A5 by a Stille coupling with an aryl- or heteroaryl-stannane in the presence of a catalyst (such as $Pd_2(dba)_3$ and the like), a ligand (such as X-Phos and the like) and a base (such as CsF and the like) in a suitable solvent (such as 1,4-dioxane and the like). Alternatively, Compound A4 is converted to Compound A5 by treatment with pinacolatodiboron and a base (such as KOAc and the like) in the presence of a catalyst (such as $Pd(dppf)Cl_2$ and the like) in an appropriate solvent (such as 1,4-dioxane and the like), followed by addition of an aryl- or heteroaryl-halide. Alternatively. Compound A4 is converted to Compound A5 by a Buchwald-Hartwig coupling with a heteroaryl or amine in the presence of a catalyst (such as $Pd_2(dba)_3$ and the like), a ligand (such as tBuX-Phos and the like) and a base (such as $K_3PO_4$ and the like) in a suitable solvent (such as 1,4-dioxane and the like). Compound A5 is converted to Compound A6 upon treatment with conditions appropriate to the removal of the protecting groups (such as HCl in dioxane for a MOM protecting group) in a suitable solvent (such as dioxane and the like).

Compounds of Formula (II), wherein $R_1$ is alkyl, cycloalkyl, heterocyclyl, aryl or heteroaryl; $R_2$ is monocyclic or bicyclic heterocyclyl or heteroaryl ring systems. W is O or NH or $NR_3$, where $R_3$ is alkyl, cycloalkyl, heterocyclyl, aryl or heteroaryl may be prepared as described in Scheme B below.

Scheme B

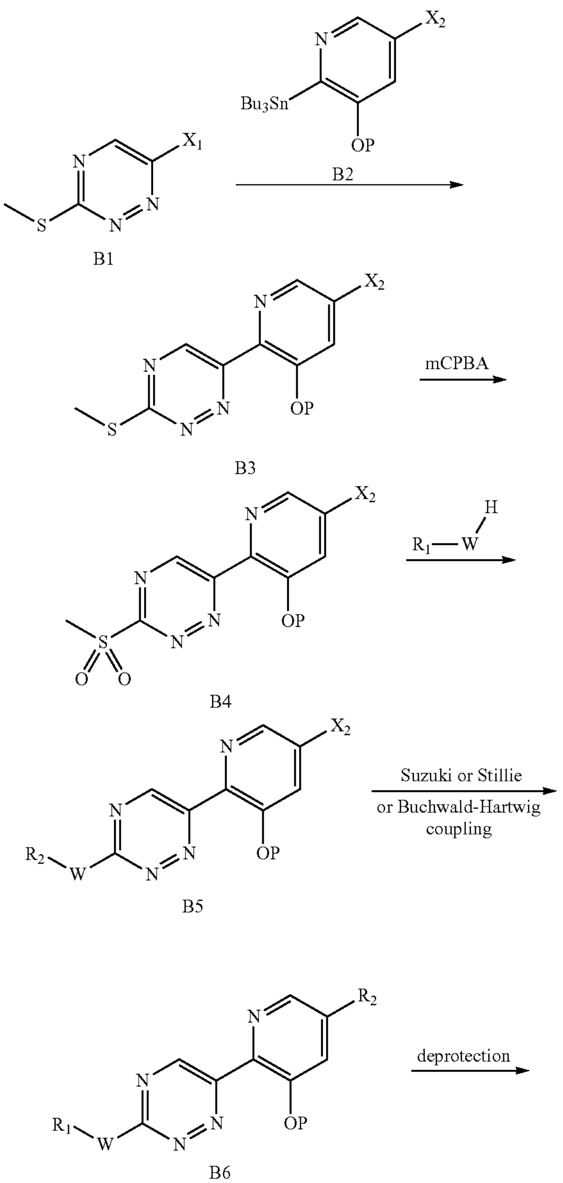

B1 B2 B3 B4 B5 B6

-continued

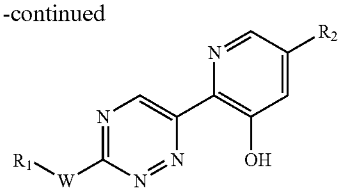

B7

Compound B1 (where $X_1$ is bromine, chlorine and the like) is converted to Compound B3 by a Stille coupling with an aryl-stanane B2 (where $X_2$ is bromine, chlorine and the like; and P is a protecting group such as MOM and the like) in the presence of a catalyst (such as $Pd(PPh_3)_2Cl_2$ and the like) and additive (such as CuI and the like) in a suitable solvent (such as 1,4-dioxane and the like). Compound B3 is converted to Compound B4 by treatment with an oxidizing agent (such as mCPBA or oxone and the like) in a suitable solvent (such as dichloromethane and the like). Compound B4 is converted to Compound B5 by a nucleophilic substitution with a primary or a secondary amine or an alcohol ($R_1WH$, where W is O or NH or $NR_3$, where $R_3$ is alkyl, cycloalkyl, heterocyclyl, aryl or heteroaryl) in the presence of a suitable base (such as $Et_3N$ and the like) in a suitable solvent (such as DMF and the like). Compound B5 is converted to Compound B6 by a Suzuki coupling with an aryl- or heteroaryl-boronic acid (or pinacol boronic ester) in the presence of a catalyst (such as $Pd(dppf)Cl_2$ and the like) and a base (such as aqueous $K_2CO_3$ and the like) in a suitable solvent (such as 1,4-dioxane and the like). Alternatively, Compound B5 is converted to Compound B6 by a Stille coupling with an aryl- or heteroaryl-stannane in the presence of a catalyst (such as $Pd_2(dba)_3$ and the like), a ligand (such as X-Phos and the like) and a base (such as CsF and the like) in a suitable solvent (such as 1,4-dioxane and the like). Alternatively, Compound B5 is converted to Compound B6 by treatment with pinacolatodiboron and a base (such as KOAc and the like) in the presence of a catalyst (such as $Pd(dppf)Cl_2$ and the like) in an appropriate solvent (such as 1,4-dioxane and the like), followed by addition of an aryl- or heteroaryl-halide. Alternatively, Compound B5 is converted to Compound B6 by a Buchwald-Hartwig coupling with a heteroaryl or amine in the presence of a catalyst (such as $Pd_2(dba)_3$ and the like), a ligand (such as tBuX-Phos and the like) and a base (such as $K_3PO_4$ and the like) in a suitable solvent (such as 1,4-dioxane and the like). Compound B6 is converted to Compound B7 upon treatment with conditions appropriate to the removal of the protecting groups (such as HCl in dioxane for a MOM protecting group) in a suitable solvent (such as dioxane and the like).

Compounds of Formula (III), wherein $R_1$ is alkyl, cycloalkyl, heterocyclyl, aryl or heteroaryl; $R_2$ is monocyclic or bicyclic heterocyclyl or heteroaryl ring systems. W is O or NH or $NR_3$, where $R_3$ is alkyl, cycloalkyl, heterocyclyl, aryl or heteroaryl may be prepared as described in Scheme C below.

Scheme C

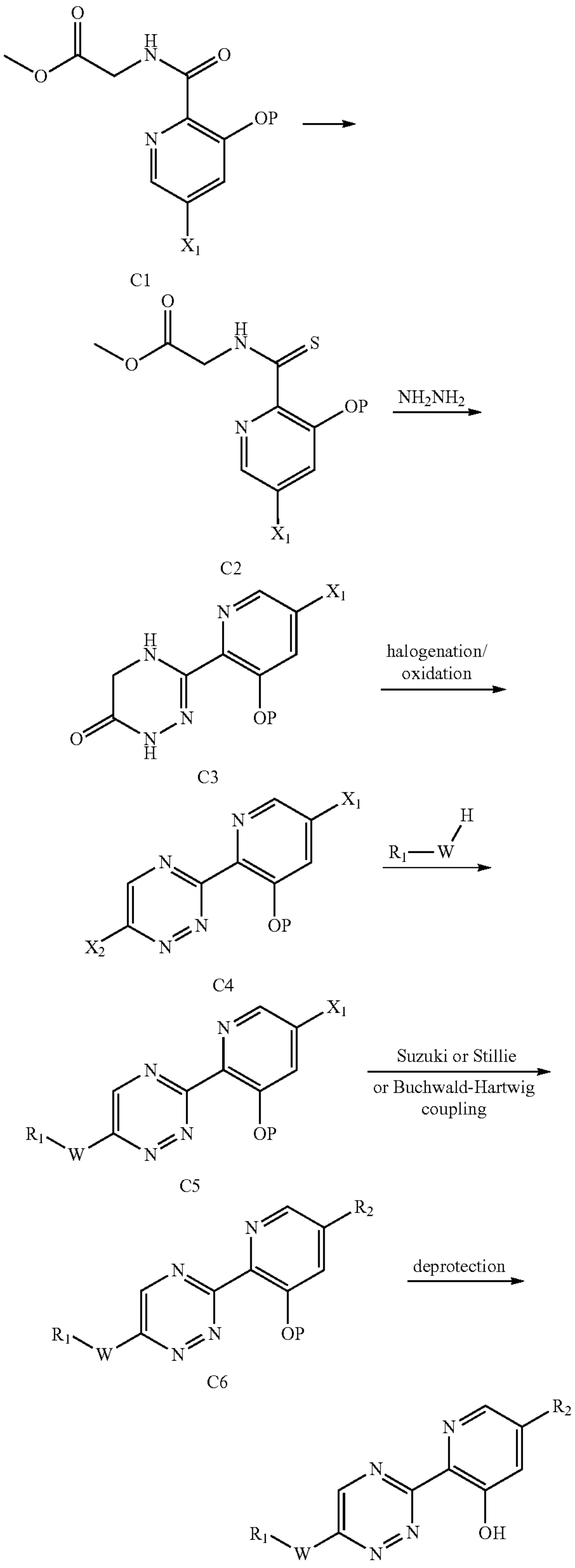

C1
C2
C3
C4
C5
C6
C7

Compound C1 (where $X_1$, is bromine, chlorine and the like, and P is a protecting group such as MOM and the like)

is converted to Compound C2 by a treatment with an appropriate thiation agent (such as Lawesson's reagent and the like) in an appropriate solvent (such as toluene and the like). Compound C2 is converted to Compound C3 by a condensation/cyclization sequence in presence of hydrazine in a suitable solvent (such as ethanol and the like). Compound C3 is converted to Compound C4 by treatment with a dehydrative halogenating agent (such as $POCl_3$ and the like) followed by treatment with an oxidizing agent (such as manganese dioxide and the like). Compound C4 is converted to Compound C5 by a nucleophilic substitution with a primary or a secondary amine or an alcohol ($R_1WH$, where W is O or NH or $NR_3$, where $R_3$ is alkyl, cycloalkyl, heterocyclyl, aryl or heteroaryl) in the presence of a suitable base (such as $Et_3N$ and the like) in a suitable solvent (such as DMF and the like). Alternatively, Compound C4 is converted to Compound C5 via cross coupling with a primary amine or a secondary amine or an alcohol in the presence of a suitable catalyst (such as RuPhos Pd G2 and the like) and base (such as sodium tert-butoxide and the like) in an appropriate solvent such as 1,4-dioxane and the like). Compound C5 is converted to Compound C6 by a Suzuki coupling with an aryl- or heteroaryl-boronic acid (or pinacol boronic ester) in the presence of a catalyst (such as Pd(dppf)$Cl_2$ and the like) and base (such as aqueous $K_2CO_3$ and the like) in a suitable solvent (such as 1,4-dioxane and the like). Alternatively. Compound C5 is converted to Compound C6 by a Stille coupling with an aryl- or heteroaryl-stannane in the presence of a catalyst (such as $Pd_2(dba)_3$ and the like), a ligand (such as X-Phos and the like) and a base (such as CsF and the like) in a suitable solvent (such as 1,4-dioxane and the like). Alternatively, Compound C5 is converted to Compound C6 by treatment with pinacolatodiboron and a base (such as KOAc and the like) in the presence of a catalyst (such as Pd(dppf)$Cl_2$ and the like) in an appropriate solvent (such as 1,4-dioxane and the like), followed by addition of an aryl- or heteroaryl-halide. Alternatively, Compound C5 is converted to Compound C6 by a Buchwald-Hartwig coupling with a heteroaryl or amine in the presence of a catalyst (such as $Pd_2(dba)_3$ and the like), a ligand (such as tBuX-Phos and the like) and a base (such as $K_3PO_4$ and the like) in a suitable solvent (such as 1,4-dioxane and the like). Compound C6 is converted to Compound C7 upon treatment with conditions appropriate to the removal of the protecting groups (such as HCl in dioxane for a MOM protecting group) in a suitable solvent (such as dioxane and the like).

SPECIFIC SYNTHETIC EXAMPLES

To describe in more detail and assist in understanding, the following non-limiting examples are offered to more fully illustrate the scope of compounds described herein and are not to be construed as specifically limiting the scope thereof. Such variations of the compounds described herein that may be now known or later developed, which would be within the purview of one skilled in the art to ascertain, are considered to fall within the scope of the compounds as described herein and hereinafter claimed. These examples illustrate the preparation of certain compounds. Those of skill in the art will understand that the techniques described in these examples represent techniques, as described by those of ordinary skill in the art, that function well in synthetic practice, and as such constitute preferred modes for the practice thereof. However, it should be appreciated that those of skill in the art should, in light of the present disclosure, appreciate that many changes can be made in the specific methods that are disclosed and still obtain a like or similar result without departing from the spirit and scope of the present description.

Other than in the following examples of the embodied compounds, unless indicated to the contrary, all numbers expressing quantities of ingredients, reaction conditions, experimental data, and so forth used in the specification and claims are to be understood as being modified by the term "about". Accordingly, all such numbers represent approximations that may vary depending upon the desired properties sought to be obtained by a reaction or as a result of variable experimental conditions. Therefore, within an expected range of experimental reproducibility, the term "about" in the context of the resulting data, refers to a range for data provided that may vary according to a standard deviation from the mean. As well, for experimental results provided, the resulting data may be rounded up or down to present data consistently, without loss of significant figures. At the very least, and not as an attempt to limit the application of the doctrine of equivalents to the scope of the claims, each numerical parameter should be construed in light of the number of significant digits and rounding techniques used by those of skill in the art.

While the numerical ranges and parameters setting forth the broad scope of the present description are approximations, the numerical values set forth in the examples set forth below are reported as precisely as possible. Any numerical value, however, inherently contains certain errors necessarily resulting from the standard deviation found in their respective testing measurements.

The starting materials used in the examples provided are commercially available or can be prepared according to methods known to one skilled in the art or can be prepared by the procedures disclosed herein.

Compound Examples

As used above, and throughout the present description, the following abbreviations, unless otherwise indicated, shall be understood to have the following meanings:

| Abbreviation | Meaning |
|---|---|
| Δ | heating (chemistry) or deletion (biology) |
| AcOH or HOAc | acetic acid |
| ACN | acetonitrile |
| aq. | aqueous |
| atm | atmosphere(s) |
| Boc | tert-butoxy-carbonyl |
| $Boc_2O$ | di-tert-butyl dicarbonate |
| BrettPhos Pd G3 | [(2-di-cyclohexylphosphino-3,6-dimethoxy-2',4',6'-triisopropyl-1,1'-biphenyl)-2-(2'-amino-1,1'-biphenyl)]palladium(II) methanesulfonate methanesulfonate |
| t-Bu | tert-butyl |
| t-BuOK or KOtBu | postassium tert-butoxide |
| BuOH or n-BuOH | n-butanol |
| ° C. | degrees Centigrade |
| Cbz | carboxybenzyl |
| Celite ® or Celite | diatomaceous earth |
| d/h/hr/hrs/min/s | day(d)/hour(h, hr or hrs)/minute(min)/second(s) |
| DBU | 1,8-diazabicyclo[5.4.0]undec-7-ene |
| DCM | dichloromethane |
| DMAP or 4-DMAP | 4-(dimethylamino)pyridine |
| DMF | dimethylformamide |
| DMSO | dimethylsulfoxide |
| EtOAc | ethyl acetate |
| EtOH | ethanol |
| $Et_2O$ | diethyl ether |
| equiv | equivalents |
| e.r. | enantiomeric ratio |

-continued

| Abbreviation | Meaning |
|---|---|
| LC/MS, LCMS or LC-MS | liquid chromatographic mass spectroscopy |
| LiHMDS | lithium bis(trimethylsilyl)amide |
| mCPBA | meta-chloroperoxybenzoic acid |
| $Me_4$tBuXPhos | 2-di-tert-butylphosphino-3,4,5,6-tetramethyl-2',4',6'-triisopropyl-1,1'-biphenyl |
| MeOH | methanol |
| $MeSO_3H$ | methanesulfonic acid |
| mL | mililiter |
| MOM | methoxymethyl |
| MS | mass spectroscopy |
| NFSI | N-fluorobenzenesulfonimide |
| NMP | N-methylpyrrolidone |
| NMR | nuclear magnetic resonance |
| Pd/C | palladium on carbon |
| $Pd_2(dba)_3$ | tris(dibenzylideneacetone)dipalladium(0) |
| Pd(dppf)$Cl_2$ or Pd(dppf)$Cl_2$—$CH_2Cl_2$ | [1,1'-bis(diphenylphosphino)ferrocene]dichloropalladium(II), complex with dichloromethane |
| $Pd(PPh_3)_2Cl_2$ | bis(triphenylphosphine)palladium(II) dichloride |
| PhMe | toluene |
| i-PrOAc | Isopropyl acetate |
| RT or Rt or rt | room temperature (approximately 25° C.) |
| L-Selectride ® | lithium tri-sec-butylborohydride |
| SFC | supercritical fluid chromatography |
| TBAF | tetrabutylammonium fluoride |
| TBS | tert-butyldimethylsilyl |
| TEA | triethylamine |
| Tf | trifluoromethane sulfonyl or triflate |
| TFA | trifluoroacetic acid |
| THF | tetrahydrofuran |
| THP | tetrahydropyranyl |
| TLC | thin layer chromatography |
| UPLC | Ulta performance liquid chromatography |
| XPhos Pd G3 | (2-dicyclohexylphosphino-2',4',6'-triisopropyl-1,1'-biphenyl)[2-(2'-amino-1,1'-biphenyl)]palladium(II) methanesulfonate |

Preparation of Starting Material

(3R,4S)-3-Fluoro-2,2,6,6-tetramethylpiperidin-4-ol and (3S,4R-3-fluoro-2,2,6,6-tetramethylpiperidin-4-ol Step 1: To a solution of 2,2,6,6-tetramethylpiperidin-4-one (8.0 g, 52.0 mmol) in 200 mL THF at −78° C. under $N_2$ atmosphere was added drop-wise LiHMDS in THF (1M, 67 mL, 67 mmol) over 40 min keeping temperature below −65° C. After addition, NFSI (20 g, 62.4 mmol) was added portion-wise to above solution over 30 min. The resulting mixture was warmed gradually to room temperature and stirred overnight. After completion, the reaction was quenched with water and the solvent was evaporated. The residue was dissolved in 200 mL DCM and extracted with 100 mL 1N HCl The aqueous layer was separated and basified with aq. $K_2CO_3$ to pH=10 and then extracted with DCM (200 mL×2). The organic phase was dried over $Na_2SO_4$ and concentrated to give crude product, which was purified by silica gel column chromatography eluting with a gradient 0-15% MeOH/DCM. The resulting product was further purified by trituration with petroleum ether to give 3-fluoro-2,2,6,6-tetramethylpiperidin-4-one (4.5 g, 50% yield) as a white solid. MS m/z 175.2 $[M+H]^+$.

Step 2: To a solution of 3-fluoro-2,2,6,6-tetramethylpiperidin-4-one (30.0 g, 170 mmol) in 400 mL THF at 0° C. was added L-Selectride (43.0 g, 226 mmol). The mixture was warmed up to room temperature and stirred overnight. The mixture was concentrated and purified by silica gel column chromatography eluting with a gradient 0-100% EtOAc/petroleum ether to give the crude product. To the solution of above product in 200 mL DCM was added 60 mL 4M HCl in 1,4-dioxane. The precipitate was filtered, dried and dissolved in aq. NaOH (6 g NaOH dissolved in 100 mL water). The mixture was extracted with 5% i-PrOH in DCM (200 mL×3). The organic layer was dried over $Na_2SO_4$ and concentrated to afford (rac)-cis-3-fluoro-2,2,6,6-tetramethylpiperidin-4-ol (16.5 g, 55% yield).

Step 3: To a solution of (rac)-cis-3-fluoro-2,2,6,6-tetramethylpiperidin-4-ol (8.0 g, 45.7 mmol) in 60 mL THF was added 60% NaH in oil (2.7 g, 68.5 mmol) at room temperature under $N_2$ atmosphere. The mixture was stirred for 2 h at 65° C., then cooled to room temperature, and BnBr (7.8 g, 45.7 mmol) was added into the mixture. The resulting mixture was stirred at 50° C. for 16 h. The mixture was

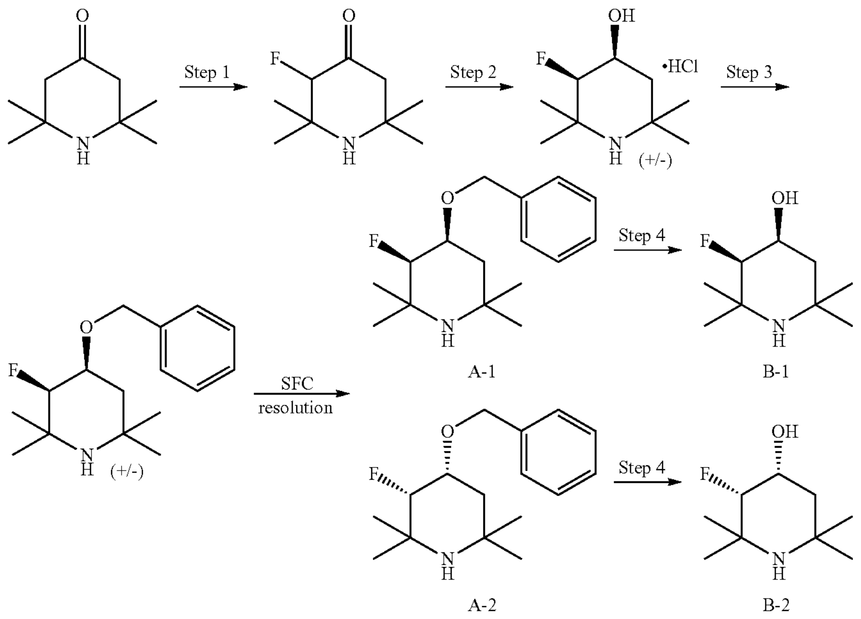

poured into water (100 mL) and extracted with EtOAc (250 mL). The organic phase was separated and washed with 1N HCl (100 mL). The aqueous layer was separated and basified with aq. $K_2CO_3$ to pH=10 and then extracted with EtOAc (200 mL). The organic phase was separated, dried over $Na_2SO_4$ and concentrated. The residue was purified by prep-HPLC to afford (rac)-cis-4-(benzyloxy)-3-fluoro-2,2,6,6-tetramethylpiperidine (9.6 g, 73%) as a light-yellow oil. 8 g racemate was separated by SFC to afford compound A-1 (3.5 g) and A-2 (3.6 g).

SFC Conditions:

1. Instrument: SFC-200 (Thar, Waters)
2. Column: OJ 20*250 mm, 10 μm (Daicel)
3. Column temperature: 35° C.
4. Mobile phase: $CO_2$/MeOH (0.2% methanol ammonia) =80/20
5. Flow rate: 130 g/min
6. Back pressure: 100 bar
7. Detection wavelength: 214 nm
8. Cycle time: 5 min
9. Sample solution: 8 g dissolved in 50 mL methanol Step 4: To a solution of A-1 (3.5 g, 8.7 mmol) in 50 mL MeOH was added Pd/C (0.7 g, 10 mass %) under nitrogen flow. The flask was vacuumed and backfilled with hydrogen for three times. The reaction mixture was stirred at 50° C. for 16 h. Then cooled to room temperature, catalyst was filtered, solvent was evaporated to give B-1 (2.2 g, 95%) as white solid.

$^1$H NMR (methanol-$d_4$) δ: 4.36 (d, J=2.0 Hz, 1H), 4.23 (d, J=1.8 Hz, 1H), 4.15 (ddd, J=12.1, 5.1, 1.8 Hz, 1H), 4.07 (ddd, J=12.0, 5.1, 2.0 Hz, 1H), 1.66 (dd, J=12.5, 5.0 Hz, 2H), 1.58 (t, J=12.5 Hz, 2H), 1.17-1.24 (m, 25H)

Using the same conditions, A-2 was converted to B-2 (2.0 g, 84%).

$^1$H NMR (methanol-$d_4$) δ: 4.65 (d, J=2.0 Hz, 1H), 4.53 (d, J=2.0 Hz, 1H), 4.36 (td, J=8.5, 1.9 Hz, 1H), 4.29 (td, J=8.5, 2.0 Hz, 1H), 1.93 (d, J=8.5 Hz, 1H), 1.49-1.57 (m, 6H).

Preparation of Starting Material

(3R,4S)-3-Fluoro-2,2,6,6-tetramethylpiperidin-4-ol and (3S,4R-3-fluoro-2,2,6,6-tetramethylpiperidin-4-ol

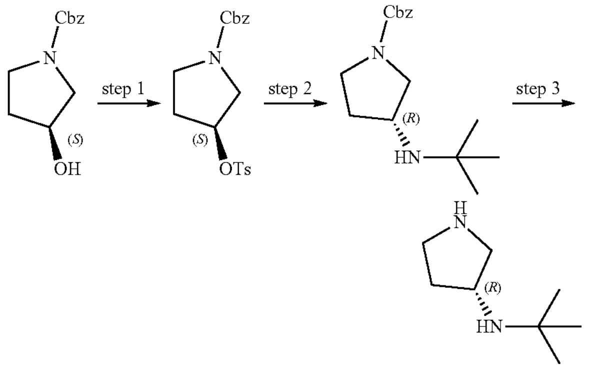

Step 1: To a mixture of benzyl (3S)-3-hydroxypyrrolidine-1-carboxylate (5 g, 22.6 mmol), DCM (40 mL) and TEA (5 mL, 35.9 mmol) was added 4-methylbenzenesulfonyl chloride (7 g, 36.716 mmol) in DCM (10 ml) at 0° C., followed by adding DMAP (30 mg, 0.24556 mmol). The resulting mixture was stirred at room temperature for 16 h. The mixture was partitioned between EtOAc and water, the organic phase was washed with brine, dried over $MgSO_4$, and then solvent was evaporated. The crude oil was purified by silica gel column chromatography, eluting with a gradient 0-100% EtOAc/hexanes to afford benzyl (3S)-3-(p-tolylsulfonyloxy)pyrrolidine-1-carboxylate as an oil, which was triturated with 10% ether in hexane to afford a white solid (7.2 g, 85% yield). MS m/z 376.4 [M+H]$^+$.

Step 2: To a sealed tube were added: benzyl (3S)-3-(p-tolylsulfonyloxy)pyrrolidine-1-carboxylate (6.8 g, 18 mmol), 2-methylpropan-2-amine (26 g, 355.5 mmol), and DMSO (20 mL). The mixture was heated at 70° C. for 48 h. The mixture was cooled to room temperature and partitioned between EtOAc and water. The organic phase was washed with brine, dried over $MgSO_4$, concentrated. The crude product was purified by silica gel column chromatography, eluting with a gradient 0-80% EtOAc/DCM, and then 5-10% MeOH in DCM to afford benzyl (3R)-3-(tert-butylamino) pyrrolidine-1-carboxylate as an oil (4.0 g, 90% yield). MS m/z 259.3 [M+H]$^+$.

Step 3: To a mixture of benzyl (3R)-3-(tert-butylamino) pyrrolidine-1-carboxylate (4.0 g, 14.47 mmol.), EtOAc (20 mL), EtOH (30 mL) was added Pd/C (800 mg, 20% w), then the mixture was vacuumed and backfilled with hydrogen for three times. The mixture was stirred at room temperature under $H_2$ (1 atm) for 14 h. The catalyst was filtered and the solvent was evaporated to afford (3R)—N-tert-butylpyrrolidin-3-amine (2.0 g, 97% yield) as a clear oil. Chiral HPLC analysis provided e.r. 99%.

Preparation of Starting Material

(5S,7R)-5-Methyl-4-azaspiro[2.5]octan-7-ol and (5S,7S)-5-methyl-4-azaspiro[2.5]octan-7-ol

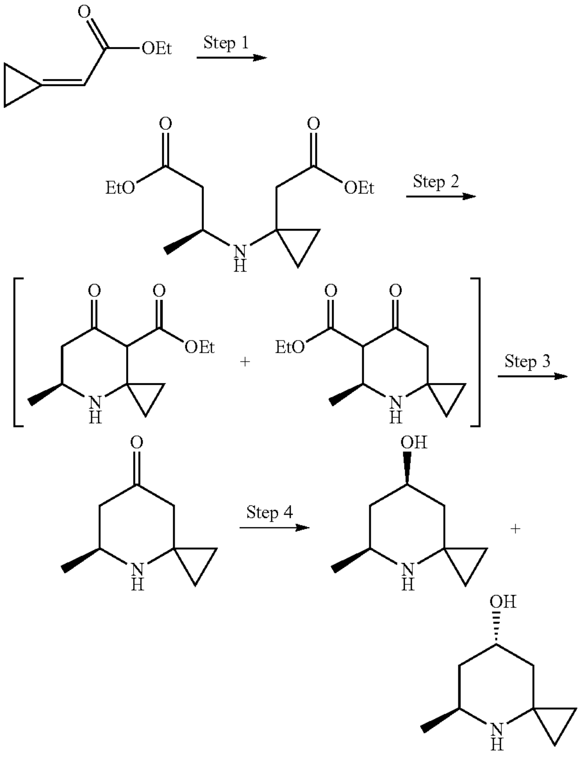

Step 1: To a sealed reaction vessel were added ethyl 2-cyclopropylideneacetate (~90% purity, 20.0 g, 143.0 mmol), [(1S)-3-ethoxy-1-methyl-3-oxo-propyl]ammonium chloride (24.0 g, 143.0 mmol), DIPEA (34 mL, 195.0 mmol), and chloroform (70 mL). The rection was heated at 75° C. for 16 h, then cooled down to rt, and washed with water (20 mL). The organic phase was separated, dried over anhydrous $Na_2SO_4$, concentrated, and purified by silica gel column chromatography eluting with a gradient 10-100% EtOAc/petroleum either to give ethyl (3S)-3-[[1-(2-ethoxy-2-oxo-ethyl)cyclopropyl]amino]butanoate (27.0 g, 73% yield) as a clear oil.

Step 2: To a solution of ethyl (3S)-3-[[1-(2-ethoxy-2-oxo-ethyl)cyclopropyl]amino]butanoate (27.0 g, 105.0 mmol) in THF (200.0 mL) at 0° C. was added tBuOK (1.0 M in THF, 157.0 mL). The reaction was stirred at 0° C. for 1 h and then the mixture was poured into ice-cold water (100 mL). The water phase was separated and extracted with DCM. The organic phases were combined, dried over anhydrous $Na_2SO_4$, and concentrated to give a crude mixture of ethyl (5S)-5-methyl-7-oxo-4-azaspiro[2.5]octane-6-carboxylate and ethyl (5S)-5-methyl-7-oxo-4-azaspiro[2.5]octane-8-carboxylate (20.2 g, 91%) that was used in the next step as is.

Step 3: To $H_2SO_4$ (60.0 g 50% w/w) was added the above mixture of ethyl (5S)-5-methyl-7-oxo-4-azaspiro[2.5]octane-6-carboxylate and ethyl (5S)-5-methyl-7-oxo-4-azaspiro[2.5]octane-8-carboxylate (20.2 g, 96.0 mmol). The mixture was heated to 120° C. and stirred at this temperature for 1 h. After completion, the mixture was poured onto water (200 mL) and washed with DCM. The water phase was basified with solid NaOH to pH to 11-12, and extracted with DCM (100 mL×5). The organic phases were combined, dried over anhydrous $Na_2SO_4$, and concentrated to give (5S)-5-methyl-4-azaspiro[2.5]octan-7-one (12.7 g, 95%). MS m/z 140.2 $[M+H]^+$.

Step 4: To a solution of (5S)-5-methyl-4-azaspiro[2.5]octan-7-one (5.5 g, 40 mmol) in MeOH (100 mL) was added $NaBH_4$ (4.5 g, 120.0 mmol) in portions. The mixture was stirred at room temperature for 1 h, monitored by TLC. Upon completion, the mixture was quenched with water (10 mL) and concentrated. The residue was purified by silica gel column chromatography eluting with a gradient 0-10% MeOH (2.5% $NH_4OH$)/DCM to give (5S,7R)-5-methyl-4-azaspiro[2.5]octan-7-ol (2.1 g, 38%) and (5S,7S)-5-methyl-4-azaspiro[2.5]octan-7-ol (1.1 g, 20%) both as a white solid.

(5S,7R)-5-methyl-4-azaspiro[2.5]octan-7-ol, $^1H$ NMR ($CDCl_3$) δ: 3.88-3.81 (m, 1H), 2.83-2.74 (m, 1H), 2.08-2.03 (m, 1H), 1.66 (t, J=10.9 Hz, 1H), 1.34-1.29 (m, 1H), 1.09 (d, J=6.4 Hz, 3H), 0.95 (q, J=11.3 Hz, 1H), 0.66-0.60 (m, 1H), 0.52-0.42 (m, 2H), 0.37-0.31 (m, 1H); 2Hs not observed (NH and OH).

(5S,7S)-5-methyl-4-azaspiro[2.5]octan-7-ol, $^1H$ NMR ($CDCl_3$) δ: 4.23-4.17 (m, 1H), 3.23-3.12 (m, 1H), 2.08-1.99 (m, 1H), 1.86-1.77 (m, 1H), 1.37-1.27 (m, 1H), 1.24-1.18 (m, 1H), 1.06 (d, J=2.5 Hz, 3H), 0.66-0.59 (m, 1H), 0.59-0.47 (m, 2H), 0.39-0.32 (m, 1H), 2Hs not observed (NH and OH).

Using the procedure described above, the following were prepared by substituting the appropriate starting material, suitable reagents, and reaction conditions.

| Starting Material | Data |
|---|---|
| 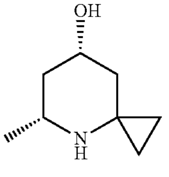 (5R,7S)-5-methyl-4-azaspiro[2.5]octan-7-ol | $^1H$ NMR (DMSO-$d_6$) δ: 4.53 (s, 1H), 3.62-3.48 (m, 1H), 2.60-2.51 (m, 1H), 1.85-1.76 (m, 1H), 1.50 (t, J = 11.4 Hz, 1H), 1.14-1.06 (m, 1H), 0.93 (d, J = 6.4 Hz, 3H), 0.81 (q, J = 11.4 Hz, 1H), 0.49-0.41 (m, 1H), 0.35-0.23 (m, 2H), 0.22-0.15 (m, 1H); 1H not observed (NH or OH). |
| 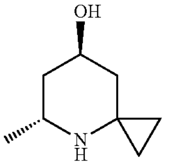 (5R,7R)-5-methyl-4-azaspiro[2.5]octan-7-ol | $^1H$ NMR (DMSO-$d_6$) δ: 4.22 (s, 1H), 4.02-3.92 (m, 1H), 3.10-2.99 (m, 1H), 1.74 (dd, J = 13.2, 2.7 Hz, 1H), 1.58-1.49 (m, 1H), 1.25-1.14 (m, 1H), 1.10-1.02 (m, 1H), 0.93 (d, J = 6.6 Hz, 3H), 0.31-0.24 (m, 1H), 0.42-0.32 (m, 2H), 0.20-0.12 (m, 1H); 1H not observed (NH or OH). |

Example 1: Preparation of Compound 20

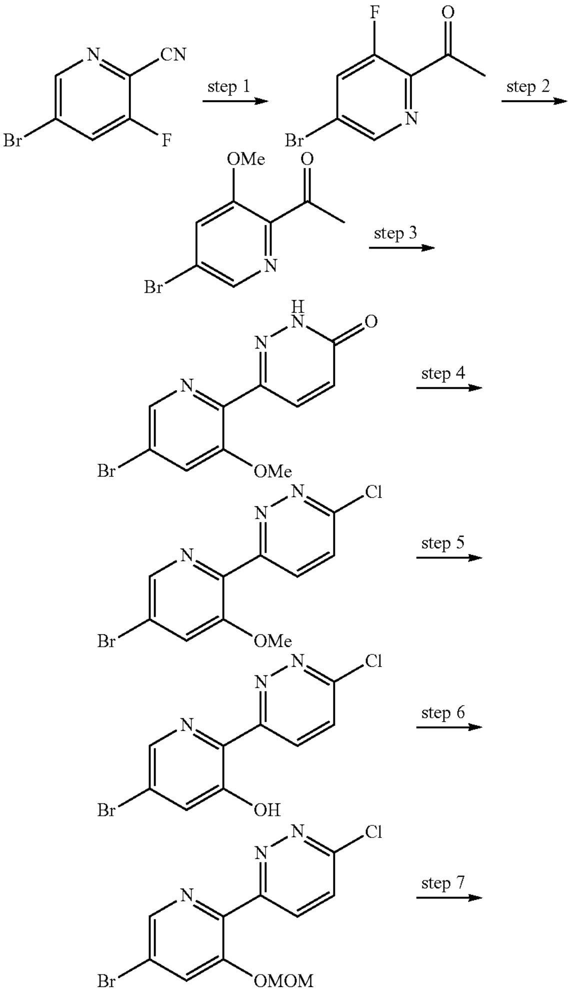

-continued

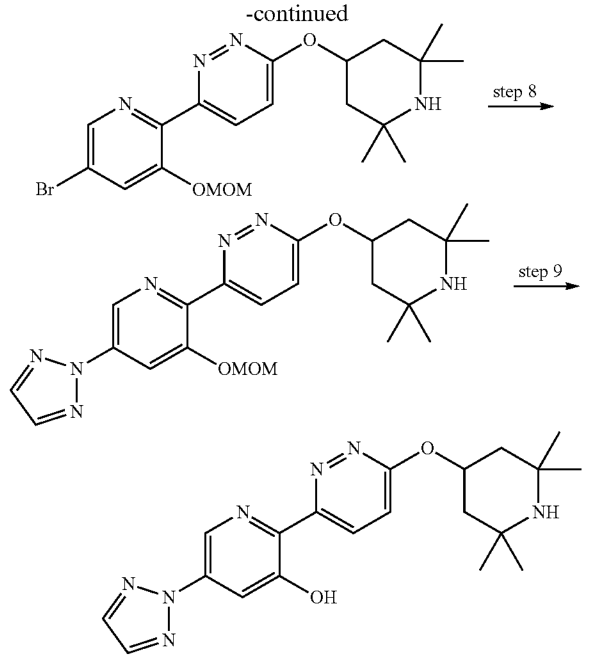

Step 1: To an oven-dried round bottom flask was added 5-bromo-3-fluoro-pyridine-2-carbonitrile (10.1 g, 50.0 mmol), which was cycled under nitrogen. THF (250 mL) was added and the stirred solution was cooled to 0'° C. MeMgCl (3.0 M, 16.75 mL) was added dropwise and the mixture stirred at 0° C. for 15 minutes. The cold reaction mixture was cannulated into a stirring solution of HCl (aqueous, 3 M, 500 mL) also at 0'° C. After addition, the mixture was warmed to room temperature and stirred for 16 hours. The solution was then reverse quenched by addition to a saturated aqueous sodium carbonate solution at 0'° C. The aqueous layer was extracted with ethyl acetate (2×500 mL). The organic layers were combined, dried over $Na_2SO_4$ and concentrated to afford 1-(5-bromo-3-fluoro-2-pyridyl) ethanone (10.1 g, 93%) as a solid. MS m/z 219.0 $[M+H]^+$.

Step 2: 1-(5-Bromo-3-fluoro-2-pyridyl)ethanone (10.1 g, 46.4 mmol) was suspended in methanol (12 mL) and cooled to 0° C. Sodium methoxide (30% mass in methanol, 16 mL) was added dropwise with stirring. After complete addition, the mixture was warmed to room temperature and stirred for 10 minutes. The reaction was partitioned between DCM and $H_2O$ and the layers separated. The aqueous layer was extracted once with DCM and the combined organic layers were dried over $Na_2SO_4$, filtered and concentrated. Purification by column chromatography on silica gel, eluting with 0-100% EtOAc in hexanes afforded 1-(5-bromo-3-methoxy-2-pyridyl)ethanone (6.2 g, 58%). MS m/z 230.0 $[M+H]^+$.

Step 3: 1-(5-Bromo-3-methoxy-2-pyridyl)ethanone (6.24 g, 25.6 mmol) was dissolved in methanol (50 mL). Oxaldehydic acid hydrate (2.45 g, 26.6 mmol) and $K_2CO_3$ (6.92 g, 50.1 mmol) were dissolved in $H_2O$ (50 mL) and the solution was cooled to 0° C. To the stirring aqueous solution was added the methanolic solution dropwise, using methanol (5 mL) to quantitatively transfer. The mixture was slowly warmed to room temperature and stirred for 12 hours. The reaction was then cooled to 0° C., and AcOH (10.5 mL) was added dropwise with stirring. The mixture was concentrated to afford an orange oil, which was transferred to a sealable tube. An ethanol/$H_2O$ mixture (3:1, 40 mL) was added, followed by hydrazine hydrate (2.3 mL, 30.4 mmol) and AcOH (0.75 mL). The reaction tube was sealed and heated to 100° C. under microwave radiation for 8 hours. $H_2O$ (100 mL) was added and the suspension stirred and filtered to afford a crude solid that was dried under vacuum to afford 3-(5-bromo-3-methoxy-2-pyridyl)-1H-pyridazin-6-one (6.3 g, 85%) as a dark brown solid.

MS m/z 282.0 $[M+H]^+$.

Step 4: To a round bottom flask was added $POCl_3$ (32 mL). 3-(5-bromo-3-methoxy-2-pyridyl)-1H-pyridazin-6-one (6.32 g, 22.4 mmol) was added portionwise as a solid with stirring. After full addition, a reflux condenser was fitted to the round bottom flask and the reaction was warmed to 100° C. for 20 minutes, then cooled to room temperature. The reaction mixture was diluted with DCM (200 mL), then poured into ice water. This bilayer was cooled to 0° C., then saturated aqueous $Na_2CO_3$ (100 mL) was added. The organic layer was collected and the aqueous layer was extracted with DCM (4×100 mL). The organic layers were combined, dried over $Na_2SO_4$, and concentrated. Purification by column chromatography on silica gel, eluting with 0-100% EtOAc in hexanes afforded 3-(5-bromo-3-methoxy-2-pyridyl)-6-chloro-pyridazine (3.6 g, 53%) as an off-white solid. MS m/z 300.0 $[M+H]^+$.

Step 5: To an oven-dried round bottom flask was added 3-(5-bromo-3-methoxy-2-pyridyl)-6-chloro-pyridazine (8.0 g, 27 mmol). The flask was cooled to −10° C., and $BBr_3$ (1.0 M in DCM, 60 mL) was added and the mixture stirred at −10° C. for 10 minutes. The mixture was then heated to 50° C. for 16 hours. The reaction was cooled to room temperature and slowly poured into ice-water. The pH was adjusted to 8 using saturated aqueous $NaHCO_3$, and the aqueous layer was extracted with EtOAc (2×150 mL). The organic layers were combined, dried over $Na_2SO_4$ and concentrated. The residue was purified by column chromatography on silica gel, eluting with 20% EtOAc in petroleum ether to afford 5-bromo-2-(6-chloropyridazin-3-yl)pyridin-3-ol (4.0 g, 52%). MS m/z 285.9 $[M+H]^+$.

Step 6: To an oven-dried round bottom flask at 0° C. was added NaH in mineral oil (60 mass %, 1.7 g, 43 mmol) and THF (50 mL). 5-Bromo-2-(6-chloropyridazin-3-yl)pyridin-3-ol (3.95 g, 13.8 mmol) was added and the mixture was stirred at 0° C. for 30 minutes. Chloro(methoxy)methane (2.62 mL, 34.5 mmol) was added and the reaction was stirred at 0° C. for 30 minutes. The reaction was quenched with $H_2O$ and the pH was adjusted to 8 by addition of saturated aqueous $NaHCO_3$. The aqueous layer was extracted with DCM (2×100 mL). The combined organic layers were dried over $Na_2SO_4$, filtered and concentrated. The residue was purified by column chromatography on silica gel, eluting with 20% EtOAc in petroleum ether to afford 3-[5-bromo-3-(methoxymethoxy)-2-pyridyl]-6-chloro-pyridazine (4.1 g, 90%). MS m/z 330.0 $[M+H]^+$.

Step 7: A mixture of 3-(5-bromo-3-(methoxymethoxy) pyridin-2-yl)-6-chloropyridazine (10.7 g, 32.4 mmol) and 2,2,6,6-tetramethylpiperidin-4-ol (6.1 g, 39 mmol, 1.2 equiv.) was dissolved in DMF (65 mL). The solution was cooled to 0° C., and NaOt-Bu (33 mL, 2M in THF) was added over the course of 5 minutes. The ice-bath was removed and the reaction was stirred for 30 minutes. The reaction mixture was partitioned between EtOAc (400 mL) and brine (200 mL). Water (100 mL) was added to dissolve the remaining insoluble solids and a clean bilayer was observed. The organic layers were collected and the aqueous layer extracted once more with EtOAc (200 mL). The organic layers were combined, dried over $Na_2SO_4$, concentrated and purified by column chromatography on silica gel, eluting with 5-20% MeOH in DCM to afford 3-(5-bromo- 3-(methoxymethoxy)pyridin-2-yl)-6-((2,2,6,6-tetramethylpiperidin-4-yl)oxy)pyridazine (9.2 g, 63%) as a white solid. MS m/z 451.1 $[M+H]^+$.

Step 8: $Pd_2dba_3$ (290 mg, 0.31 mmol) and $Me_4$tBuXPhos (390 mg, 0.78 mmol) were suspended in toluene (10 mL). The solution was sparged with argon, then heated to 115° C. for 5 minutes under argon atmosphere. In a separate flask, 3-(5-bromo-3-(methoxymethoxy)pyridin-2-yl)-6-((2,2,6,6-tetramethylpiperidin-4-yl)oxy)pyridazine (2.8 g, 6.2 mmol), 1,2,3-triazole (430 μL, 510 mg, 7.4 mmol) and $K_3PO_4$ (2.7 g, 12.4 mmol) were suspended in toluene and sparged with argon for 5 minutes. The catalyst solution prepared previously was cooled to room temperature and half (5 mL) was added. The resultant mixture was briefly sparged with argon, then heated to 115° C. for 15 minutes. The remaining catalyst solution was added, the mixture was briefly sparged with argon, then heated to 115° C. for 15 minutes. The reaction mixture was cooled to room temperature and filtered over Celite, washing with DCM. The organic phases were concentrated and the crude product was purified by column chromatography on silica gel, eluting with 5-20% MeOH in DCM to afford 3-(3-(methoxymethoxy)-5-(2H-1,2,3-triazol-2-yl)pyridin-2-yl)-6-((2,2,6,6-tetramethylpiperidin-4-yl)oxy)pyridazine (2.5 g, 92%) as a light yellow solid. MS m/z 440.2 $[M+H]^+$.

Step 9: 3-(3-(Methoxymethoxy)-5-(2H-1,2,3-triazol-2-yl)pyridin-2-yl)-6-((2,2,6,6-tetramethyl piperidin-4-yl)oxy)pyridazine (2.5 g, 5.7 mmol) was suspended in MeOH (25 mL) and HCl (30 mL, 4 M in dioxane) was added. The reaction was stirred at room temperature for 3 hours, then the volatiles were removed and the crude solid was dried under high vacuum. The crude solid was then suspended in 20% 1M $NH_3$/MeOH in DCM (20 mL). The mixture was purified by column chromatography on silica gel, eluting with 0-30% 1M $NH_3$/MeOH in DCM to afford 2-{6-[(2,2,6,6-tetramethylpiperidin-4-yl)oxy]pyridazin-3-yl}-5-(2H-1,2,3-triazol-2-yl)pyridin-3-ol (1.2 g, 53%) as a white solid. MS m/z 396.2 $[M+H]^+$. $^1H$ NMR (DMSO-$d_6$) δ: 8.96 (s, 1H), 8.66 (d, J=9.2 Hz, 1H), 8.27 (s, 2H), 7.97 (s, 1H), 7.54 (d, J=8.9 Hz, 1H), 5.70-5.74 (m, 1H), 2.07-2.15 (m, 2H), 1.22-1.35 (m, 8H), 1.11 (s, 6H); 2Hs not observed (OH and NH).

Using the procedure described for Example 1 above, additional compounds described herein may be prepared by substituting the appropriate starting material, suitable reagents, and reaction conditions, obtaining compounds such as those selected from:

| Cpd | Data |
|---|---|
| 11 | MS m/z 414.0 $[M + H]^+$; $^1H$ NMR (methanol-$d_4$) δ: 9.00 (d, J = 1.8 Hz, 1H), 8.77 (d, J = 9.4 Hz, 1H), 8.05 (s, 1H), 8.04 (s, 1H), 8.03 (s, 1H), 7.46 (d, J = 9.4 Hz, 1H), 5.93-6.08 (m, 1H), 4.88 (d, J = 52.7 Hz, 1H), 2.14 (m, 1H), 2.01 (t, J = 12.3 Hz, 1H), 1.49 (d, J = 3.7 Hz, 6H), 1.36 (s, 6H); 2Hs not observed (OH and NH) |
| 21 | MS m/z 394.4 $[M + H]^+$; $^1H$ NMR (methanol-$d_4$): δ: 8.91 (d, J = 2.0 Hz, 1H), 8.66 (d, J = 9.3 Hz, 1H), 8.05 (s, 3H), 7.37 (d, J = 9.8 Hz, 1H), 5.71-5.82 (m, 1H), 2.29-2.40 (m, 1H), 2.02-2.14 (m, 1H), 1.88-1.98 (m, 1H), 1.68-1.79 (m, 1H), 1.46 (s, 3H), 1.35 (s, 3H), 0.90-0.94 (m, 2H), 0.73-0.82 (m, 1H), 0.63-0.70 ppm (m, 1H). 2 Hs not observed. |
| 32 | MS m/z 394.4 $[M + H]^+$; $^1H$ NMR (methanol-$d_4$) δ: 9.00 (d, J = 1.8 Hz, 1H), 8.75 (br d, J = 9.5 Hz, 1H), 8.10-7.98 (m, 3H), 7.41 (br d, J = 9.5 Hz, 1H), 5.78-5.67 (m, 1H), 2.63-2.51 (m, 2H), 2.36-2.23 (m, 2H), 2.02-1.91 (m, 2H), 1.89-1.75 (m, 2H), 1.52 (s, 6H); 2H (OH and 2 NH) was no observed |
| 73 | MS m/z 392.4 $[M + H]^+$; $^1H$ NMR (methanol-$d_4$) δ: 8.96 (s, 1H), 8.72 (d, J = 9.5 Hz, 1H), 8.00 (s, 3H), 7.40 (d, J = 9.5 Hz, 1H), 5.72 (br s, 1H), 2.31-2.18 (m, 4H), 1.32-1.23 (m, 1H), 1.07-0.82 (m, 7H); 2Hs not observed (NH and OH). |

Example 2: Preparation of Compound 34

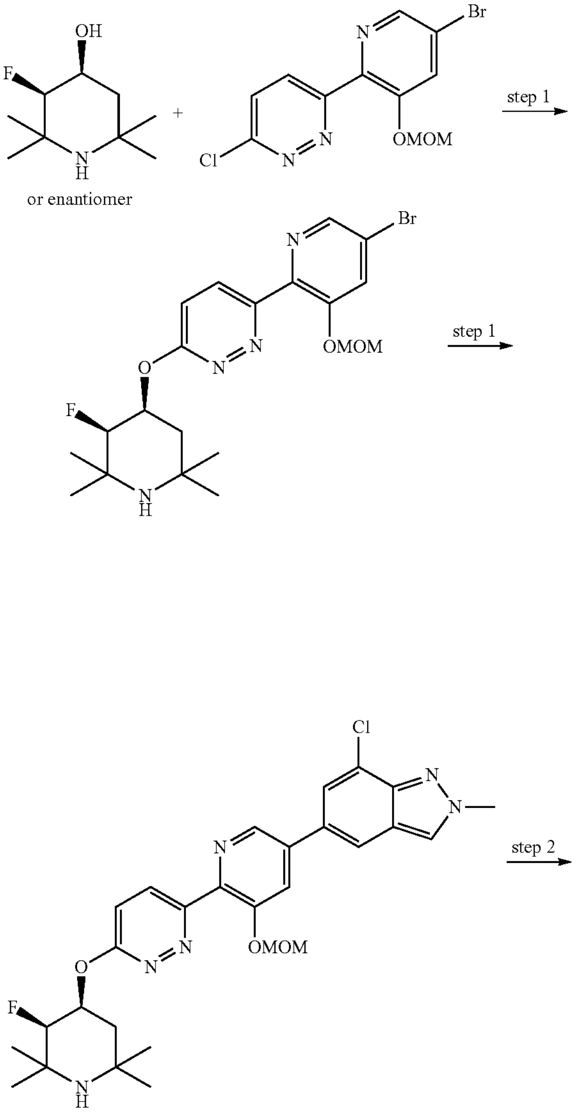

-continued

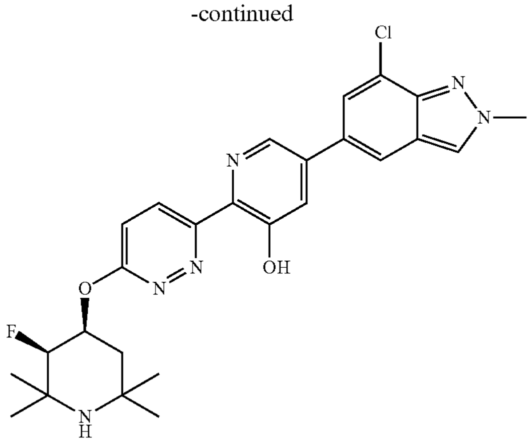

or enantiomer

Step 1: To a solution of 3-[5-bromo-3-(methoxymethoxy)-2-pyridyl]-6-chloro-pyridazine (450 mg, 1.36 mmol) and (3R,4S)-3-fluoro-2,2,6,6-tetramethyl-piperidin-4-ol (286 mg, 1.63 mmol) in tetrahydrofuran (5 mL) was added sodium tert-butoxide (2 mL, 4 mmol, 2 mol/L) in THF at 0° C. The ice bath was removed after addition, and the reaction stirred at room temperature for 1 h. The mixture was then partitioned between EtOAc and water. The aqueous layer was extracted with EtOAc and the organic layers were combined, washed with brine, dried over sodium sulfate, and concentrated. Purification by silica gel chromatography eluting with a gradient 0-10% MeOH/DCM afforded 3-[5-bromo-3-(methoxymethoxy)-2-pyridyl]-6-[[(3R,4S)-3-fluoro-2,2,6,6-tetramethyl-4-piperidyl]oxy]pyridazine (528 mg, 83% yield) as an off-white solid. MS m/z 469.2 $[M+H]^+$.

Step 2: C3-(5-Bromo-3-(methoxymethoxy)pyridin-2-yl)-6-(((3R,4S)-3-fluoro-2,2,6,6-tetramethylpiperidin-4-yl)oxy)pyridazine (50.9 mg, 0.11 mmol), 2-methyl-5-(4,4,5,5-tetramethyl-1,3,2-dioxaborolan-2-yl)indazole-7-carbonitrile (42.9 mg, 0.15 mmol), XPhos Pd G3 (11.3 mg, 0.013 mmol), 1,4-dioxane (0.7 mL), and aqueous potassium carbonate solution (1.0 M, 0.35 mL) were combined and heated to 100° C. for 1 h. The reaction was concentrated and the residue was chromatographed on silica gel, eluting with 0-30% MeOH in DCM to yield 5-(6-(6-(((3R,4S)-3-fluoro-2,2,6,6-tetramethylpiperidin-4-yl)oxy)pyridazin-3-yl)-5-(methoxymethoxy)pyridin-3-yl)-2-methyl-2H-indazole-7-carbonitrile (75.7 mg, 128% yield). MS m/z 546.3 $[M+H]^+$.

Step 3: 5-(6-(6-(((3R,4S)-3-Fluoro-2,2,6,6-tetramethylpiperidin-4-yl)oxy)pyridazin-3-yl)-5-(methoxymethoxy)pyridin-3-yl)-2-methyl-2H-indazole-7-carbonitrile (75.7 mg, 0.14 mmol) and trifluoroacetic acid (4 mL) were combined and stirred at 23° C. for 40 minutes. The reaction was concentrated and the residue was chromatographed on silica gel, eluting with 0-30% MeOH (2.5% v/v 30% aqueous ammonium hydroxide additive) in DCM to yield 5-[6-(6-{[(3R,4S)-3-fluoro-2,2,6,6-tetramethylpiperidin-4-yl]oxy}pyridazin-3-yl)-5-hydroxypyridin-3-yl]-2-methyl-2H-indazole-7-carbonitrile (26.0 mg, 49% yield). MS m/z 502.3 $[M+H]^+$; $^1H$ NMR (1:4 methanol-$d_4$: $CDCl_3$) δ: 8.79 (br s, 1H), 8.57 (br s, 1H), 8.50 (br s, 1H), 8.38 (br s, 1H), 8.15 (br s, 1H), 7.70 (br s, 1H), 7.45 (br s, 1H), 5.98-6.11 (m, 1H), 5.01-5.19 (m, 1H), 4.33 (br s, 3H), 2.16-2.41 (m, 2H), 1.68 (s, 6H), 1.58 (s, 3H), 1.56 (s, 3H); 2H not observed (1 OH, 1 NH).

Using the procedure described for Example 2 above, additional compounds described herein may be prepared by substituting the appropriate starting material, suitable reagents, and reaction conditions, obtaining compounds such as those selected from:

| Cpd | Data |
|---|---|
| 1 | MS m/z 395.5 $[M + H]^+$; $^1H$ NMR (methanol-$d_4$) δ: 8.75 (d, J = 9.5 Hz, 1H), 8.56 (d, J = 0.9 Hz, 1H), 8.19 (s, 2H), 7.70 (d, J = 1.8 Hz, 1H), 7.43 (d, J = 9.5 Hz, 1H), 5.82-5.91 (m, 1H), 2.52 (dd, J = 13.7, 4.0 Hz, 2H), 1.89 (dd, J = 13.4, 11.0 Hz, 2H), 1.66 (s, 6H), 1.58 (s, 6H); 3H not observed (1 OH, 2 NH). |
| 3 | MS m/z 412.5 $[M + H]^+$; $^1H$ NMR (methanol-$d_4$) δ: 9.72 (d, J = 9.2 Hz, 1H), 8.49 (br s, 1H), 8.17 (s, 1H), 7.98 (br s, 1H), 7.58 (s, 1H), 7.39 (d, J = 9.2 Hz, 1H), 5.81-5.93 (m, 1H), 2.52 (d, J = 12.2 Hz, 2H), 1.86 (t, J = 12.2 Hz, 2H), 1.66 (s, 6H), 1.56 (s, 6H); 2 Hs not observed (NH and OH). |
| 4 | MS m/z 409.5 $[M + H]^+$; $^1H$ NMR (DMSO-$d_6$) δ: 13.34 (s, 1H), 8.72 (d, J = 1.8 Hz, 1H), 8.64 (d, J = 9.4 Hz, 1H), 7.82 (d, J = 2.2 Hz, 1H), 7.78 (d, J = 1.8 Hz, 1H), 7.48 (d, J = 9.4 Hz, 1H), 6.93 (d, J = 2.2 Hz, 1H), 5.64-5.73 (m, 1H), 3.93 (s, 3H), 2.11 (dd, J = 11.8, 3.6 Hz, 2H), 1.27-1.34 (m, 2H), 1.25 (s, 6H), 1.12 (s, 6H); 1H not observed (OH or NH). |
| 6 | MS m/z 413.2 $[M + H]^+$; $^1H$ NMR (DMSO-$d_6$) δ: 13.22 (s, 1H), 13.17 (s, 1H), 8.64 (d, J = 9.1 Hz, 2H), 8.62 (s, 1H), 8.45 (s, 1H), 8.15 (s, 1H), 7.73 (s, 1H), 7.57 (d, J = 9.1 Hz, 1H), 5.76-5.94 (m, 1H), 4.71 (d, J = 52.6 Hz, 1H), 1.90 (m, 1H), 1.70 (t, J = 11.6 Hz, 1H), 1.26 (s, 6H), 1.13 (d, J = 7.6 Hz, 6H). |
| 7 | MS m/z 427.0 $[M + H]^+$; $^1H$ NMR (DMSO-$d_6$) δ: 13.25 (s, 1H), 8.73 (d, J = 1.8 Hz, 1H), 8.67 (d, J = 9.4 Hz, 1H), 7.83 (d, J = 2.2 Hz, 1H), 7.79 (d, J = 1.8 Hz, 1H), 7.58 (d, J = 9.4 Hz, 1H), 6.93 (d, J = 2.2 Hz, 1H), 5.78-5.94 (m, 1H), 4.71 (d, J = 52.0 Hz, 1H), 3.93 (s, 3H), 1.90 (m, 1H), 1.70 (m, 1H), 1.26 (s, 6H), 1.13 (d, J = 8.4 Hz, 6H); 1H not observed (OH or NH). |
| 22 | MS m/z 431.5 $[M + H]^+$; $^1H$ NMR (DMSO-$d_6$) δ: 13.20 (br s, 1H), 9.34 (d, J = 12.2 Hz, 1H), 8.60-8.80 (m, 2H), 8.36 (d, J = 12.5 Hz, 1H), 7.86 (s, 1H), 7.67 (br d, J = 9.2 Hz, 1H), 6.73 (br d, J = 5.2 Hz, 1H), 5.99 (dd, J = 28.8, 11.9 Hz, 1H), 5.18 (d, J = 49.1 Hz, 1H), 2.32 (dd, J = 12.8, 3.5 Hz, 1H), 2.05 (t, J = 12.8 Hz, 1H), 1.59 (br d, J = 7.3 Hz, 6H), 1.50 (br d, J = 9.5 Hz, 6H). |
| 26 | MS m/z 411.5 $[M + H]^+$; $^1H$ NMR (DMSO-$d_6$) δ: 13.24 (br s, 1H), 12.88 (s, 1H), 9.18 (d, J = 11.6 Hz, 1H), 8.67 (br d, J = 8.9 Hz, 1H), 8.53 (s, 1H), 8.43 (br s, 1H), 7.62 (s, 1H), 7.55 (br d, J = 9.5 Hz, 1H), 5.58-5.78 (m, 1H), 2.38 (d, J = 13.4 Hz, 2H), 2.11-2.20 (m, 1H), 2.05 (dd, J = 13.4, 2.5 Hz, 1H), 1.87 (t, J = 11.9 Hz, 1H), 1.48 (s, 3H), 1.43 (s, 3H), 0.93-1.11 (m, 3H), 0.74-0.89 (m, 1H) |

-continued

| Cpd | Data |
|---|---|
| 27 | MS m/z 393.5 $[M + H]^+$; $^1H$ NMR (methanol-$d_4$) δ: 8.87 (d, J = 9.5 Hz, 1H), 8.70 (s, 1H), 8.39 (s, 2H), 8.03 (s, 1H), 7.58 (d, J = 9.5 Hz, 1H), 5.82-5.86 (m, 1H), 2.50-2.53 (m, 1H), 2.28-2.33 (m, 1H), 2.18-2.21 (m, 1H), 2.03-2.07 (m, 1H), 1.57 (d, J = 6.0 Hz, 6H), 0.98-1.22 (m, 4H); 3Hs not observed (OH and NHs). |
| 31 | MS m/z 391.4 $[M + H]^+$; $^1H$ NMR (methanol-$d_4$) δ: 8.84 (d, J = 9.5 Hz, 1H) 8.65 (s, 1H) 8.31 (s, 2H) 7.94 (s, 1H) 7.55 (d, J = 9.5 Hz, 1H) 5.78 (dt, J = 7.4, 3.7 Hz, 1H) 2.31-2.38 (m, 2H) 2.25-2.30 (m, 2H) 1.10-1.16 (m, 4H) 0.93-1.02 (m, 4H); 3 Hs not observed (2 NHs and OH). |
| 33 | MS m/z 410.5 $[M + H]^+$; $^1H$ NMR (methanol-$d_4$) δ: 8.99-8.85 (m, 1H), 8.69 (br s, 1H), 8.40 (br s, 1H), 8.14 (br s, 1H), 8.04 (br s, 1H), 7.72-7.57 (m, 1H), 5.90-5.71 (m, 1H), 2.73-2.52 (m, 2H), 2.42-2.27 (m, 2H), 2.20-1.96 (m, 4H), 1.60 (br s, 6H); 2H (OH and NH) was not observed. |
| 35 | MS m/z 495.3 $[M + H]^+$; $^1H$ NMR (1:1 methanol-$d_4$: $CDCl_3$) δ: 8.77 (br s, 1H), 8.52 (br s, 1H), 8.26 (br s, 1H), 7.80 (br s, 1H), 7.63 (br s, 1H), 7.39 (br s, 1H), 7.31 (br s, 1H), 5.89-6.11 (m, 1H), 4.96-5.14 (m, 1H), 4.27 (br s, 3H), 2.30 (br s, 2H), 1.71 (br s, 6H), 1.60 (br s, 6H); 2H not observed (1 OH, 1 NH). |
| 36 | MS m/z 405.3 $[M + H]^+$; $^1H$ NMR (methanol-$d_4$) δ: 9.38-9.34 (m, 1H), 9.01-8.92 (m, 1H), 8.79-8.73 (m, 1H), 8.65 (br s, 1H), 8.05-7.93 (m, 1H), 7.74-7.67 (m, 2H), 5.81-5.71 (m, 1H), 2.65-2.60 (m, 2H), 2.35-2.27 (m, 2H), 2.10-1.96 (m, 4H), 1.60 (br s, 6H); 2H (OH and NH) wasn't observed. |
| 37 | MS m/z 454.4 $[M + H]^+$; $^1H$ NMR (1:1 methanol-$d_4$: $CDCl_3$) δ: 8.76 (d, J = 9.5 Hz, 1H), 8.49 (d, J = 1.8 Hz, 1H), 7.67 (d, J = 7.0 Hz, 1H), 7.63 (d, J = 2.1 Hz, 1H), 7.39 (d, J = 9.5 Hz, 1H), 6.87 (d, J = 1.8 Hz, 1H), 6.67 (dd, J = 7.0, 1.8 Hz, 1H), 5.91-6.04 (m, 1H), 4.84-5.02 (m, 1H), 3.64 (s, 3H), 2.06-2.25 (m, 2H), 1.59 (br d, J = 5.5 Hz, 6H), 1.46 (br s, 6H); 2H not observed (1 OH, 1 NH). |
| 39 | MS m/z 413.5 $[M + H]^+$; $^1H$ NMR (DMSO-$d_6$) δ: 13.24 (s, 1H), 13.18 (s, 1H), 8.62-8.65 (m, 2H), 8.46 (s, 1H), 8.16 (s, 1H), 7.74 (d, J = 1.5 Hz, 1H), 7.57 (d, J = 9.5 Hz, 1H), 5.81-5.90 (m, 1H), 4.71 (d, J = 52.0 Hz, 1H), 1.89-1.92 (m, 1H), 1.66-1.72 (m, 1H), 1.25 (d, J = 3.5 Hz, 6H), 1.12 (d, J = 10.5 Hz, 6H); 1H not observed (OH or NH). |
| 40 | MS m/z 431.5 $[M + H]^+$; $^1H$ NMR (methanol-$d_4$) δ: 8.87 (d, J = 9.5 Hz, 1H), 8.60 (s, 1H), 8.26 (s, 1H), 7.92 (s, 1H), 7.59 (d, J = 9.5 Hz, 1H), 6.06-6.14 (m, 1H), 5.17 (d, J = 49.0 Hz, 1H), 2.41-2.43 (m, 1H), 2.25-2.29 (m, 1H), 1.72 (d, J = 3.5 Hz, 6H), 1.62 (d, J = 10.5 Hz, 6H); 3Hs not observed (OH and NHs). |
| 43 | MS m/z 477.5 $[M + H]^+$; $^1H$ NMR (methanol-$d_4$) δ: 9.28 (s, 1H), 8.92 (d, J = 9.5 Hz, 1H), 8.72 (d, J = 2.0 Hz, 1H), 8.34-8.36 (m, 1H), 8.09 (s, 1H), 8.02 (d, J = 9.5 Hz, 1H), 7.95 (d, J = 2.0 Hz, 1H), 7.62 (d, J = 9.5 Hz, 1H), 6.06-6.15 (m, 1H), 5.18 (d, J = 49.5 Hz, 1H), 2.63 (s, 3H), 2.41-2.43 (m, 1H), 2.24-2.29 (m, 1H), 1.71 (d, J = 3.5 Hz, 6H), 1.61 (d, J = 10.5 Hz, 6H); 2Hs not observed (OH and NH). |
| 44 | MS m/z 491.6 $[M + H]^+$; $^1H$ NMR (methanol-$d_4$) δ: 9.07 (s, 1H), 8.86 (d, J = 9.0 Hz, 1H), 8.66 (d, J = 2.0 Hz, 1H), 8.17 (s, 1H), 8.05 (s, 1H), 7.85 (d, J = 2.0 Hz, 1H), 7.55 (d, J = 9.0 Hz, 1H), 6.06-6.15 (m, 1H), 5.18 (d, J = 49.5 Hz, 1H), 2.75 (s, 3H), 2.63 (s, 3H), 2.40-2.44 (m, 1H), 2.24-2.29 (m, 1H), 1.72 (d, J = 7.5 Hz, 6H), 1.61 (d, J = 15.0 Hz, 6H); 2Hs not observed (OH and NH). |
| 45 | MS m/z 505.6 $[M + H]^+$; $^1H$ NMR (methanol-$d_4$) δ: 9.09 (s, 1H), 8.88 (d, J = 9.0 Hz, 1H), 8.69 (d, J = 1.5 Hz, 1H), 8.16 (s, 1H), 8.06 (s, 1H), 7.89 (d, J = 2.0 Hz, 1H), 7.58 (d, J = 9.0 Hz, 1H), 6.07-6.14 (m, 1H), 5.18 (d, J = 49.0 Hz, 1H), 3.12 (q, J = 7.0 Hz, 2H), 2.64 (s, 3H), 2.41-2.44 (m, 1H), 2.24-2.29 (m, 1H), 1.72 (d, J = 7.0 Hz, 6H), 1.61 (d, J = 15.0 Hz, 6H), 1.50 (t, J = 7.5 Hz, 3H); 2Hs not observed (NH and OH). |
| 46 | MS m/z 545.5 $[M + H]^+$; $^1H$ NMR (methanol-$d_4$) δ: 9.51 (s, 1H), 8.89 (d, J = 9.5 Hz, 1H), 8.72-8.75 (m, 2H), 8.25 (s, 1H), 7.95 (d, J = 1.5 Hz, 1H), 7.58 (d, J = 9.5 Hz, 1H), 6.07-6.14 (m, 1H), 5.18 (d, J = 49.5 Hz, 1H), 2.68 (s, 3H), 2.41-2.44 (m, 1H), 2.24-2.29 (m, 1H), 1.72 (d, J = 7.0 Hz, 6H), 1.61 (d, J = 14.0 Hz, 6H); 2Hs not observed (OH and NH). |
| 51 | MS m/z 413.5 $[M + H]^+$; $^1H$ NMR (methanol-$d_4$) δ: 8.77 (d, J = 9.5 Hz, 1H), 8.55 (s, 1H), 8.17 (s, 2H), 7.63 (s, 1H), 7.47 (d, J = 9.5 Hz, 1H), 6.04-6.12 (m, 1H), 5.17 (d, J = 49.0 Hz, 1H), 2.39-2.43 (m, 1H), 2.01-2.09 (m, 1H), 1.71 (d, J = 7.5 Hz, 6H), 1.60 (d, J = 14.0 Hz, 6H); 3Hs not observed (2NHs and OH). |
| 52 | MS m/z 477.4 $[M + H]^+$; $^1H$ NMR (methanol-$d_4$) δ: 8.95-8.93 (m, 1H), 8.77 (s, 1H), 8.56 (br s, 1H), 8.17(s, 1H), 8.10 (br s, 1H), 7.765-7.63 (m, 1H), 7.53-7.49 (m, 1H), 6.00-5.89 (m, 1H), 4.31 (br s, 3H), 2.55-2.42 (m, 2H), 2.10-1.89 (m, 2H), 1.67 (br s, 6H), 1.62 (s, 6H); 2H (OH and NH) was not observed. |
| 54 | MS m/z 478.5 $[M + H]^+$; $^1H$ NMR (methanol-$d_4$) δ: 9.64 (d, J = 2.5 Hz, 1H), 9.40 (d, J = 2.0 Hz, 1H), 8.89 (d, J = 9.5 Hz, 1H), 8.72 (d, J = 2.0 Hz, 1H), 8.04 (s, 1H), 7.94 (d, J = 2.0 Hz, 1H), 7.58 (d, J = 9.0 Hz, 1H), 6.07-6.15 (m, 1H), 5.18 (d, J = 48.5 Hz, 1H), 2.66 (s, 3H), 2.41-2.44 (m, 1H), 2.24-2.29 (m, 1H), 1.72 (d, J = 7.0 Hz, 6H), 1.61 (d, J = 14.0 Hz, 6H); 2Hs not observed (OH and NH). |
| 55 | MS m/z 478.5 $[M + H]^+$; $^1H$ NMR (methanol-$d_4$) δ: 9.59 (s, 1H), 8.89 (d, J = 9.5 Hz, 1H), 8.73 (d, J = 2.0 Hz, 1H), 8.60-8.62 (m, 1H), 8.17 (d, J = 9.5 Hz, 1H), 7.94 (d, J = 2.0 Hz, 1H), 7.58 (d, J = 9.5 Hz, 1H), 6.07-6.15 (m, 1H), 5.18 (d, J = 48.5 Hz, 1H), 2.80 (s, 3H), 2.41-2.43 (m, 1H), 2.24-2.29 (m, 1H), 1.72 (d, J = 7.0 Hz, 6H), 1.61 (d, J = 14.5 Hz, 6H); 2Hs not observed (OH and NH). |

-continued

| Cpd | Data |
|---|---|
| 56 | MS m/z 492.6 [M + H]$^+$; $^1$H NMR (methanol-d$_4$) δ: 8.90 (d, J = 9.5 Hz, 1H), 8.71 (d, J = 1.5 Hz, 1H), 8.07 (d, J = 1.5 Hz, 1H), 7.88 (s, 1H), 7.60-7.62 (m, 2H), 6.00-6.18 (m, 1H), 5.18 (d, J = 49.0 Hz, 1H), 2.72 (s, 3H), 2.68 (s, 3H), 2.41-2.45 (m, 1H), 2.25-2.30 (m, 1H), 1.72 (d, J = 6.0 Hz, 6H), 1.62 (d, J = 16.0 Hz, 6H); 2Hs not observed (OH and NH). |
| 62 | MS m/z 485.3 [M + H]$^+$; $^1$H NMR (methanol-d$_4$) δ: 8.90 (br d, J = 9.3 Hz, 1H), 8.73 (s, 1H), 8.59 (s, 1H), 8.51 (s, 1H), 8.18 (s, 1H), 8.08 (s, 1H), 7.54-7.53 (m, 1H), 5.91-5.85 (m, 1H), 4.35 (s, 3H), 2.55-2.49 (m, 2H), 2.00-1.95 (m, 2H), 1.66 (s, 6H), 1.61 (s, 6H); 2H (OH and NH) was not observed. |
| 75 | MS m/z 410.4 [M + H]$^+$; $^1$H NMR (methanol-d$_4$) δ: 8.63 (d, J = 9.5 Hz, 1H), 8.42 (s, 1H), 8.11 (s, 1H), 7.93 (s, 1H), 7.52 (s, 1H), 7.29 (d, J = 9.5 Hz, 1H), 5.69 (br s, 1H), 2.30-2.25 (m, 1H), 2.00 (t, J = 10.5 Hz, 1H), 1.87-1.83 (m, 1H), 1.67-1.60 (m, 1H), 1.38 (s, 3H), 1.28 (s, 3H), 0.89-0.79 (m, 2H), 0.73-0.68 (m, 1H), 0.60-0.55 (m, 1); 2Hs not observed (NH and OH). |
| 82 | MS m/z 396.3 [M + H]$^+$; $^1$H NMR (methanol-d$_4$) δ: 8.56 (s, 1H), 8.18 (s, 1H), 7.94-8.04 (m, 2H), 7.88 (s, 1H), 7.21 (d, J = 9.2 Hz, 1H), 5.47-5.56 (m, 1H), 2.97-3.06 (m, 1H), 2.41 (br d, J = 12.5 Hz, 1H), 2.05 (br t, J = 11.7 Hz, 1H), 1.72 (br dd, J = 12.4, 4.1 Hz, 1H), 1.38 (q, J = 11.9 Hz, 1H), 1.11-1.23 (m, 3H), 0.70-0.77 (m, 1H), 0.53-0.69 (m, 3H); 2Hs not observed (NH and OH). |
| 83 | MS m/z 396.3 [M + H]$^+$; $^1$H NMR (methanol-d$_4$) δ: 8.56 (s, 1H), 8.18 (s, 1H), 7.94-8.04 (m, 2H), 7.88 (s, 1H), 7.21 (d, J = 9.2 Hz, 1H), 5.47-5.56 (m, 1H), 2.97-3.06 (m, 1H), 2.41 (br d, J = 12.5 Hz, 1H), 2.05 (br t, J = 11.7 Hz, 1H), 1.72 (br dd, J = 12.4, 4.1 Hz, 1H), 1.38 (q, J = 11.9 Hz, 1H), 1.11-1.23 (m, 3H), 0.70-0.77 (m, 1H), 0.53-0.69 (m, 3H); 2Hs not observed (NH and OH). |
| 84 | MS m/z 396.3 [M + H]$^+$; $^1$H NMR (methanol-d$_4$) δ: 8.86 (d, J = 9.5 Hz, 1H), 8.61 (s, 1H), 8.31 (s, 1H), 8.05 (s, 1H), 7.89 (s, 1H), 7.62 (d, J = 9.5 Hz, 1H), 5.81 (br s, 1H), 3.79-3.92 (m, 1H), 2.56 (br t, J = 17.2 Hz, 2H), 1.87-2.05 (m, 2H), 1.40 (br d, J = 6.4 Hz, 3H), 1.16-1.33 (m, 1H), 0.98-1.12 (m, 1H), 0.79-0.97 (m, 2H); 2Hs not observed (NH and OH). |
| 85 | MS m/z 396.3 [M + H]$^+$; $^1$H NMR (methanol-d$_4$) δ: 8.83 (d, J = 9.5 Hz, 1H), 8.54-8.67 (m, 1H), 8.28 (s, 1H), 8.03 (s, 1H), 7.78-7.89 (m, 1H), 7.58 (d, J = 9.5 Hz, 1H), 5.80 (br s, 1H), 3.78-3.92 (m, 1H), 3.34-3.54 (m, 1H), 2.56 (br t, J = 14.8 Hz, 2H), 1.87-2.05 (m, 2H), 1.40 (br d, J = 6.7 Hz, 3H), 1.13-1.32 (m, 1H), 0.97-1.09 (m, 1H), 0.77-0.97 (m, 1H); 2Hs not observed (NH and OH). |
| 114 | MS m/z 409.4 [M + H]$^+$; $^1$H NMR (methanol-d$_4$) δ: 8.69 (d, J = 8.5 Hz, 1H), 8.49 (d, J = 2.6 Hz, 1H), 8.10 (br s, 2H), 7.58 (d, J = 2.0 Hz, 1H), 7.33 (d, J = 9.2 Hz, 1H), 5.64-5.72 (m, 1H), 4.67-4.78 (m, 3H), 4.46 (d, J = 6.6 Hz, 1H), 2.90-2.98 (m, 1H), 2.12-2.21 (m, 1H), 1.88-1.96 (m, 1H), 1.59-1.68 (m, 1H), 1.29 (s, 3H), 1.21 (s, 3H), 3 Hs not observed (2 NHs and OH). |

Example 3: Preparation of Compound 38

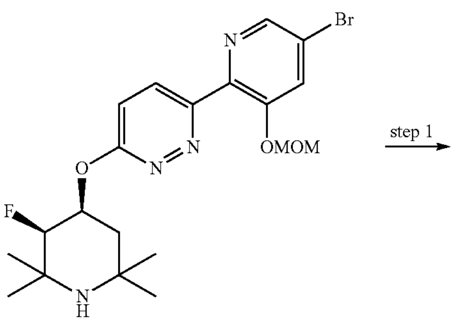

-continued

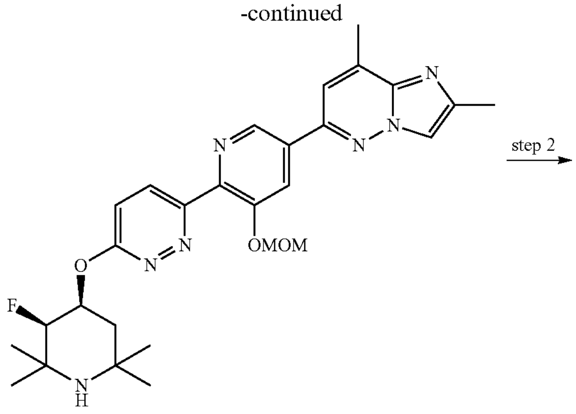

-continued

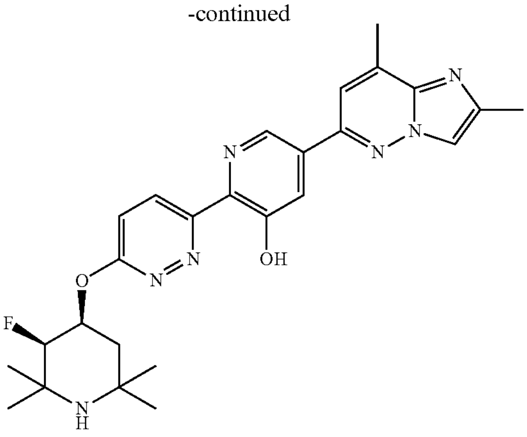

or enantiomer

Step 1: 3-[5-Bromo-3-(methoxymethoxy)-2-pyridyl]-6-[[(3R,4S)-3-fluoro-2,2,6,6-tetramethyl-4-piperidyl]oxy] pyridazine (46.8 mg, 0.099 mmol), bis(pinacolato)diboron (34.0 mg, 0.134 mmol), potassium acetate (dried at 250° C. under vacuum immediately prior to using, 30.9 mg, 0.315 mmol), XPhos Pd G3 (15.9 mg, 0.0178 mmol), and 1,4-dioxane (1.0 mL) were combined, degassed with argon, and stirred at 110° C. for 2 h, 6-Chloro-2,8-dimethyl-imidazo[1,2-b]pyridazine (25.0 mg, 0.138 mmol), X Phos Pd G3 (7.3 mg, 0.0082 mmol), and aqueous potassium carbonate (1.0 M, 0.35 mL) were added, the solution degassed with argon, and stirred at 80° C. for 1 h. The reaction was concentrated and the residue was chromatographed on silica gel, eluting with 0-30% MeOH in DCM to yield 6-(6-(6-(((3R,4S)-3-fluoro-2,2,6,6-tetramethylpiperidin-4-yl)oxy)pyridazin-3-yl)-5-(methoxymethoxy)pyridin-3-yl)-2,8-dimethylimidazo[1,2-b]pyridazine as a crude mixture that was carried directly into the next step. MS m/z 492.3 $[M+H]^+$.

Step 2: A crude mixture of 6-(6-(6-(((3R,4S)-3-fluoro-2,2,6,6-tetramethylpiperidin-4-yl)oxy)pyridazin-3-yl)-5-(methoxymethoxy)pyridin-3-yl)-2,8-dimethylimidazo[1,2-b]pyridazine was combined with trifluoroacetic acid (4 mL) and stirred at 23° C. for 1 h 30 min. The reaction was concentrated and the residue was chromatographed on silica gel, eluting with 0-10% MeOH (2.5% v/v 30% aqueous ammonium hydroxide additive) in DCM to yield 5-(2,8-dimethylimidazo[1,2-b]pyridazin-6-yl)-2-(6-{[(3R,4S)-3-fluoro-2,2,6,6-tetramethylpiperidin-4-yl]oxy}pyridazin-3-yl)pyridin-3-ol (2.8 mg, 5% yield over 2 steps). MS m/z 492.4 $[M+H]^+$; $^1$H NMR (1:1 methanol-$d_4$: chloroform-d) δ: 8.81 (d, J=1.8 Hz, 1H), 8.75 (d, J=9.2 Hz 1H), 7.96 (d, J=1.8 Hz, 1H), 7.85 (s, 1H), 7.44 (s, 1H), 7.36 (d, J=9.5 Hz, 7H), 5.88-6.01 (m, 1H), 4.73-4.90 (d, JH), 2.70 (s, 3H), 2.51 (s, 3H), 2.06-2.15 (m, 1H) 1.93-2.05 (m, 1H), 1.48 (br d, J=8.5 Hz, 6H), 1.36 (br s, 6H); 2H not observed (1 OH, 1 NH).

Using the procedure described for Example 3 above, additional compounds described herein may be prepared by substituting the appropriate starting material, suitable reagents, and reaction conditions, obtaining compounds such as those selected from:

| Cpd | Data |
|---|---|
| 10 | MS m/z 395.5 $[M + H]^+$; $^1$H NMR (DMSO-$d_6$) δ: 13.45 (s, 1H), 8.85 (d, J = 1.8 Hz, 1H), 8.71 (d, J = 9.4 Hz, 1H), 8.37 (d, J = 0.6 Hz, 1H), 7.90 (d, J = 1.8 Hz, 1H), 7.60 (d, J = 9.4 Hz, 1H), 7.52 (d, J = 0.6 Hz, 1H), 5.71-5.82 (m, 1H), 2.38 (dd, J = 13.3, 3.9 Hz, 2H), 1.74-1.86 (m, 2H), 1.53 (s, 6H), 1.49 (s, 6H); 1H not observed (OH or NH. |
| 12 | MS m/z 414.0 $[M + H]^+$; $^1$H NMR (methanol-$d_4$) δ: 8.89 (d, J = 1.8 Hz, 1H), 8.81 (d, J = 9.4 Hz, 1H), 8.12 (s, 1H), 7.97 (d, J = 1.8 Hz, 1H), 7.48 (d, J = 9.4 Hz, 1H), 7.42 (s, 1H), 5.99-6.08 (m, 1H), 4.99 (s, 1H), 4.87 (s, 1H), 2.14-2.21 (m, 1H), 2.05 (t, J = 12.6 Hz, 1H), 1.52 (d, J = 4.3 Hz, 6H), 1.40 (s, 6H); 1H not observed (OH or NH). |
| 28 | MS m/z 394.5 $[M + H]^+$; $^1$H NMR (methanol-$d_4$) δ: 8.82 (s, 1H), 8.73 (d, J = 9.3 Hz, 1H), 7.96 (s, 1H), 7.84 (s, 1H), 7.35 (s, 1H), 7.29-7.24 (m, 1H), 5.71-5.61 (m, 1H), 2.34-2.23 (m, 2H), 2.05-1.97 (m, 2H), 1.55 (m, 3H), 1.51 (s, 3H), 1.29-1.22 (m, 1H), 1.00-0.92 (m, 1H), 0.83-0.71 (m, 2H); 2H (OH and NH) wasn't observed. |
| 42 | MS m/z 455.4 $[M + H]^+$; $^1$H NMR (1:1 methanol-$d_4$: $CDCl_3$) δ: 8.73 (d, J = 1.8 Hz, 1H), 8.69 (d, J = 9.5 Hz, 1H), 8.38 (s, 1H), 7.90 (d, J = 1.8 Hz, 1H), 7.31 (d, J = 9.5 Hz, 1H), 6.93 (s, 1H), 5.81-5.94 (m, 1H), 4.65-4.82 (m, 1H), 3.25-3.30 (m, 3H), 1.97-2.05 (m, 1H), 1.86-1.95 (m, 1H), 1.39 (br d, J = 8.9 Hz, 6H), 1.27 (br d, J = 2.7 Hz, 6H); 2H not observed (1 OH, 1 NH). |
| 66 | MS m/z 464.3 $[M + H]^+$; $^1$H NMR (1:1 methanol-$d_4$: $CDCl_3$) δ: 9.15 (s, 1H), 9.08 (s, 1H), 8.88 (s, 1H), 8.79-8.83 (m, 1H), 8.08 (s, 1H), 8.03 (s, 1H), 7.86 (s, 1H), 7.43 (br d, J = 9.2 Hz, 1H), 5.96-6.08 (m, 1H), 5.00-5.15 (m, 1H), 2.33 (br d, J = 4.3 Hz, 1H), 2.24-2.31 (m, 1H), 1.71 (s, 3H), 1.69 (s, 3H), 1.61 (br s, 3H), 1.58 (s, 3H); 2H not observed (1 OH, 1 NH). |
| 67 | MS m/z 491.3 $[M + H]^+$; $^1$H NMR (1:1 methanol-$d_4$: $CDCl_3$) δ: 8.79 (d, J = 9.2 Hz, 1H), 8.68 (s, 1H), 8.57 (s, 1H), 8.27 (s, 1H), 8.01 (s, 1H), 7.80 (s, 1H), 7.42 (d, J = 9.2 Hz, 1H), 5.95-6.07 (m, 1H), 4.97-5.13 (m, 1H), 2.99 (s, 3H), 2.53 (s, 3H), 2.30 (br s, 2H), 1.71 (s, 3H), 1.69 (s, 3H), 1.61 (s, 3H), 1.58 (s, 3H); 2H not observed (1 OH, 1 NH). |
| 68 | MS m/z 503.3 $[M + H]^+$; $^1$H NMR (1:1 methanol-$d_4$: $CDCl_3$) δ: 8.87 (s, 1H), 8.81 (br d, J = 9.5 Hz, 1H), 8.17 (s, 1H), 8.10 (s, 1H), 8.02 (s, 1H), 7.42 (br d, J = 9.5 Hz, 1H), 5.96-6.08 (m, 1H), 4.98-5.13 (m, 1H), 2.59 (s, 3H), 2.31 (br s, 2H), 1.72 (s, 3H), 1.70 (s, 3H), 1.61 (s, 3H), 1.59 (s, 3H); 2H not observed (1 OH, 1 NH). |
| 72 | MS m/z 465.5 $[M + H]^+$; $^1$H NMR (methanol-$d_4$) δ: 9.37 (s, 1H), 9.15 (s, 1H), 8.96-8.98 (m, 1H), 8.85 (d, J = 8.9 Hz, 1H), 8.30-8.32 (m, 1H), 8.25 (s, 1H), 7.45-7.48 (m, 1H), 5.94-6.09 (m, 1H), 5.08 (d, J = 49.0 Hz, 1H), 2.22-2.26 (m, 1H), 2.06-2.10 (m, 1H), 1.23-1.56 (m, 12H); 2Hs not observed (OH and NH). |

-continued

| Cpd | Data |
|---|---|
| 74 | MS m/z 437.5 [M + H]$^+$; $^1$H NMR (methanol-$d_4$): δ: 8.93 (br s, 1H), 8.87 (s, 1H), 8.77 (d, J = 9.2 Hz, 1H), 8.08 (br s, 1H), 7.46 (s, 1H), 7.42 (br d, J = 9.5 Hz, 1H), 5.79-5.93 (m, 1H), 4.08 (s, 3H), 2.41 (d, J = 11.6 Hz, 2H), 1.75-1.87 (m, 2H), 1.61 (br s, 6H), 1.52 ppm (br s, 6H); 2Hs not observed. |
| 79 | MS m/z 410.4 [M + H]$^+$; $^1$H NMR (methanol-$d_4$) δ: 8.78 (s, 1H), 8.70 (d, J = 6.0 Hz, 1H), 7.95 (s, 1H), 7.88 (s, 1H), 7.72 (s, 1H), 7.33 (d, J = 11.0 Hz, 1H), 5.71 (br, s, 1H), 2.30-2.24 (m, 1H), 2.04-1.98 (m, 1H), 1.86-1.80 (m, 1H), 1.66-1.57 (m, 1H), 1.37 (s, 3H), 1.25 (s, 3H), 0.88-0.77 (m, 2H), 0.71-0.61 (m, 1H), 0.58-0.48 (m, 1); 2H not observed (1 OH, 1 NH). |

Example 4: Preparation of Compound 47

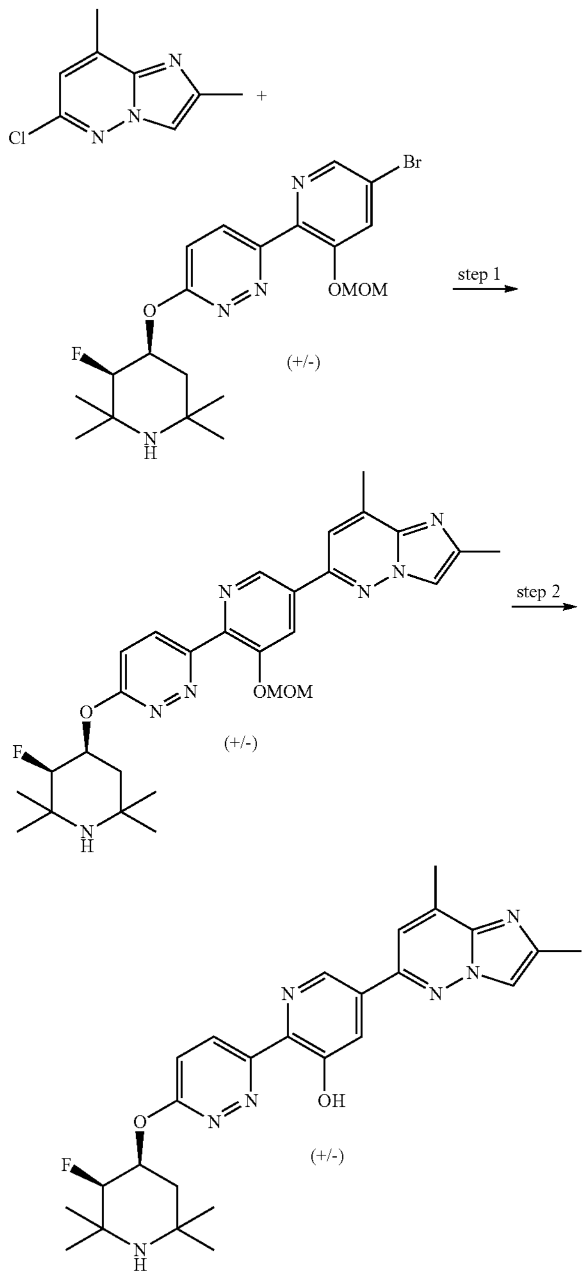

Step 1: Chloro-2,8-dimethyl-imidazo[1,2-b]pyridazine, PddppfCl$_2$ (18.8 mg, 0.023 mmol), bis(pinacolato)diboron (73.4 mg, 0.289 mmol), potassium acetate (dried at 250° C. under vacuum immediately prior to using, 76.1 mg, 0.775 mmol), and 1,4-dioxane (1.5 mL) were combined, argon degassed, and heated to 100° C. for 2 h 30 min. rac-3-[5-Bromo-3-(methoxymethoxy)-2-pyridyl]-6-[[(3R,4S)-3-fluoro-2,2,6,6-tetramethyl-4-piperidyl]oxy]pyridazine (47.1 mg, 0.100 mmol), Pd(dppf)Cl$_2$ (8.1 mg, 0.099 mmol), and aqueous potassium carbonate (1.0 M, 0.75 mL) were added and the reaction was heated to 80° C. for 1 h. The reaction was concentrated and the residue was chromatographed on silica gel, eluting with 0-30% MeOH in DCM to yield rac-6-(6-(6-(((3R,4S)-3-fluoro-2,2,6,6-tetramethylpiperidin-4-yl)oxy)pyridazin-3-yl)-5-(methoxymethoxy)pyridin-3-yl)-2,8-dimethylimidazo[1,2-b]pyridazine (56.8 mg, 99% yield). MS m/z 536.3 [M+H]$^+$.

Step 2: rac-6-(6-(6-(((3R,4S)-3-Fluoro-2,2,6,6-tetramethylpiperidin-4-yl)oxy)pyridazin-3-yl)-5-(methoxymethoxy)pyridin-3-yl)-2,8-dimethylimidazo[1,2-b]pyridazine (56.8 mg, 0.10 mmol) and trifluoroacetic acid (4 mL) were combined and stirred at 23° C. for 45 min. The reaction was concentrated and the residue chromatographed on silica gel, eluting with 0-30% MeOH (2.5% v/v 30% aqueous ammonium hydroxide additive) in DCM to yield rac-2-(6-{[(3R,4S)-3-fluoro-2,2,6,6-tetramethylpiperidin-4-yl]oxy}pyridazin-3-yl)-5-[2-methyl-8-(trifluoromethyl)imidazo[1,2-a]pyridin-6-yl]pyridin-3-ol (24.3 mg, 48% yield). MS m/z 492.4 [M+H]$^+$; $^1$H NMR (1:1 methanol-$d_4$: $CDCl_3$) δ: 8.78 (s, 1H), 8.70 (d, J=9.5 Hz, 1H), 7.92 (s, 1H), 7.83 (s, 1H), 7.43 (s, 1H), 7.34 (d, J=9.5 Hz, 1H), 5.85-6.00 (m, 1H), 4.83 (s, 1H), 2.68 (s, 3H), 2.50 (s, 3H), 2.01-2.11 (m, 1H), 1.90-2.00 (m, 1H), 1.44 (br d, J=9.2 Hz, 6H), 1.32 (br s, 6H); 2H not observed (1 OH, 1 NH).

Using the procedure described for Example 4 above, additional compounds described herein may be prepared by substituting the appropriate starting material, suitable reagents, and reaction conditions, obtaining compounds such as those selected from:

| Cpd | Data |
| --- | --- |
| 48 | MS m/z 478.3 $[M + H]^+$; $^1H$ NMR (1:3 methanol-$d_4$: $CDCl_3$) δ: 8.99 (s, 1H), 8.89 (br d, J = 9.2 Hz, 1H), 8.49-8.54 (m, 1H), 8.42-8.48 (m, 1H), 8.39 (s, 1H), 8.17 (s, 1H), 7.52 (d, J = 9.5 Hz, 1H), 5.99-6.11 (m, 1H), 5.04-5.17 (m, 1H), 2.70 (s, 3H), 2.34-2.40 (m, 1H), 2.29 (br d, J = 12.8 Hz, 1H), 1.72 (s, 3H), 1.71 (s, 3H), 1.62 (s, 3H), 1.59 (s, 3H); 2H not observed (1 OH, 1NH). |
| 49 | MS m/z 464.3 $[M + H]^+$; $^1H$ NMR (1:3 methanol-$d_4$: $CDCl_3$) δ: 8.83 (d, J = 1.5 Hz, 1H), 8.74 (d, J = 9.2 Hz, 1H), 8.10 (s, 1H), 8.08 (br d, J = 9.5 Hz, 1H), 7.98 (d, J = 1.8 Hz, 1H), 7.78 (s, 1H), 7.64 (br d, J = 9.5 Hz, 1H), 7.33 (d, J = 9.5 Hz, 1H), 5.86-5.99 (m, 1H), 4.69-4.88 (m, 1H), 2.02-2.10 (m, 1H), 1.99 (br d, J = 11.6 Hz, 1H), 1.41-1.55 (m, 6H), 1.35 (br s, 6H); 2H not observed (1 OH, 1 NH). |
| 50 | MS m/z 474.4 $[M + H]^+$; $^1H$ NMR (methanol-$d_4$) δ: 9.01-8.89 (m, 2H), 8.34-8.28 (m, 2H), 8.22 (s, 1H), 7.50(s, 1H), 5.87-5.77 (m, 1H), 2.86 (s, 3H), 2.70 (s, 3H) 2.49-2.40 (m, 2H), 2.00-1.85 (m, 2H), 1.67 (m, 6 H), 1.61 (s, 6H); 2H (OH and NH) was not observed. |
| 57 | MS m/z 508.3 $[M + H]^+$; $^1H$ NMR (1:1 methanol-$d_4$: $CDCl_3$) δ: 8.91 (br s, 1H), 8.83 (br d, J = 9.5 Hz, 1H), 8.05-8.10 (m, 2H), 7.46-7.51 (m, 1H), 7.41-7.46 (m, 1H), 5.95-6.07 (m, 1H), 4.96-5.12 (m, 1H), 4.31 (s, 3H), 2.59 (s, 3H), 2.31 (br s, 2H), 1.72 (s, 3H), 1.70 (s, 3H), 1.62 (br s, 3H), 1.59 (s, 3H); 2H not observed (1 OH, 1 NH). |
| 58 | MS m/z 495.3 $[M + H]^+$; $^1H$ NMR (1:1 methanol-$d_4$: $CDCl_3$) δ: 8.78 (d, J = 9.5 Hz, 1H), 8.53 (d, J = 1.5 Hz, 1H), 8.38 (d, J = 2.1 Hz, 1H), 7.67 (br d, J = 1.5 Hz, 1H), 7.40 (br d, J = 9.5 Hz, 1H), 7.22 (br dd, J = 7.8, 3.5 Hz, 1H), 7.09 (br dd, J = 10.8, 7.8 Hz, 1H), 5.93-6.06 (m, 1H), 4.92-5.07 (m, 1H), 4.29 (s, 3H), 2.14-2.32 (m, 2H), 1.60-1.77 (m, 6H), 1.52 (br s, 6H); 2H not observed (1 OH, 1 NH). |
| 59 | MS m/z 502.3 $[M + H]^+$; $^1H$ NMR (1:1 methanol-$d_4$: $CDCl_3$) δ: 9.19-9.30 (m, 1H), 8.82 (d, J = 9.2 Hz, 1H), 8.58 (s, 1H), 8.37-8.52 (m, 1H), 7.95-8.04 (m, 1H), 7.75 (br d, J = 1.8 Hz, 1H), 7.45 (d, J = 9.2 Hz, 1H), 5.97-6.09 (m, 1H), 5.01-5.15 (m, 1H), 2.58 (br d, J = 4.3 Hz, 3H), 2.33-2.39 (m, 1H), 2.23-2.32 (m, 1H), 1.71 (s, 3H), 1.70 (s, 3H), 1.61 (d, J = 1.8 Hz, 3H), 1.58 (s, 3H); 2Hs not observed (NH and OH). |
| 60 | MS m/z 506.3 $[M + H]^+$; $^1H$ NMR (1:1 methanol-$d_4$: $CDCl_3$) δ: 8.85 (d, J = 1.8 Hz, 1H), 8.80 (br d, J = 9.5 Hz, 1H), 7.98 (d, J = 1.5 Hz, 1H), 7.88 (s, 1H), 7.45 (s, 1H), 7.41 (br d, J = 9.5 Hz, 1H), 5.94-6.05 (m, 1H), 4.90-5.10 (m, 1H), 3.08-3.16 (m, 2H), 2.52 (s, 3H), 2.14-2.30 (m, 2H), 1.64 (br d, J = 3.7 Hz, 6H), 1.52 (br s, 6H), 1.44-1.49 (m, 3H); 2H not observed (1 OH, 1 NH). no |
| 65 | MS m/z 446.5 $[M + H]^+$; $^1H$ NMR (methanol-$d_4$) δ: 9.12-9.06 (m, 2H), 8.71-8.59 (m, 3H), 8.38-8.35 (m, 2H), 7.75 (br d, J = 9.3 Hz, 1H), 5.93-5.85 (m, 1H), 2.56-2.53 (m, 2H), 1.99-1.94 (m, 2H), 1.67 (br s, 6H), 1.61 (s, 6H); 2H (OH and NH) was not observed. |
| 81 | MS m/z 490.4 $[M + H]^+$; $^1H$ NMR (methanol-$d_4$): δ: 8.82 (s, 1H), 8.66 (d, J = 10.4 Hz, 1H), 7.97 (s, 1H), 7.62 (s, 2H), 7.23 (d, J = 11.0 Hz, 1H), 7.00 (s, 1H), 5.68-5.86 (m, 1H), 4.20 (s, 3H), 2.48 (s, 3H), 2.23 (d, J = 11.9 Hz, 2H), 1.46-1.55 (m, 2H), 1.43 (br s, 6H), 1.31 ppm (br s, 6H). 1 H not observed. |

Example 5: Preparation of Compound 41

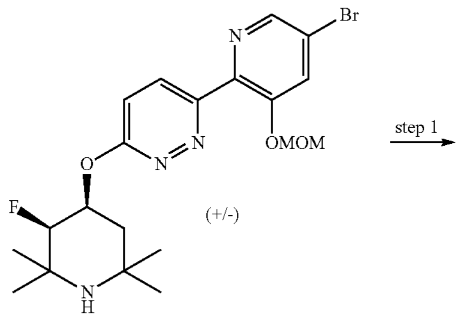

-continued

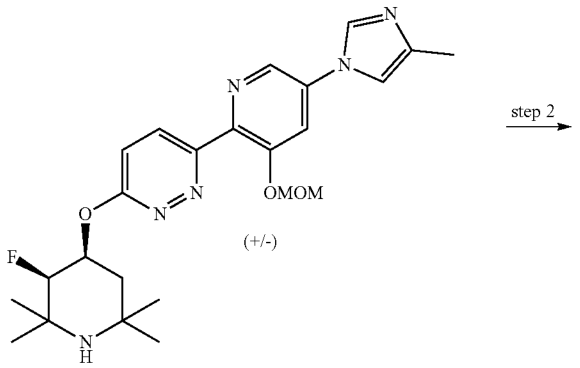

-continued

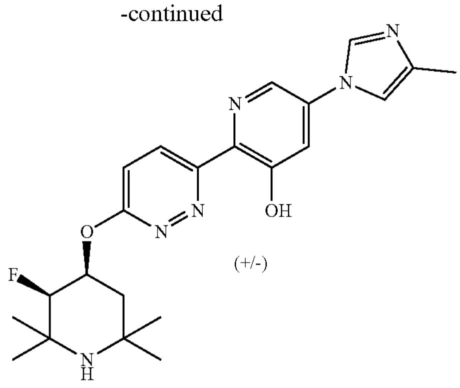

(+/-)

Step 1: 3-[5-Bromo-3-(methoxymethoxy)-2-pyridyl]-6-[[(3R,4S)-3-fluoro-2,2,6,6-tetramethyl-4-piperidyl]oxy]pyridazine (46.6 mg, 0.0993 mmol), 4-methyl-1H-imidazole (20.5 mg, 0.250 mmol), potassium carbonate (35.4 mg, 0.256 mmol), cuprous iodide (2.8 mg, 0.015 mmol), trans-N,N'-dimethylcyclohexane-1,2-diamine (4.0 μL, 0.025 mmol), and N,N-dimethylformamide (0.3 mL) were combined, argon degassed, and heated to 110° C. for 18 h. The reaction was concentrated and the residue was chromatographed on silica gel, eluting with 0-30% MeOH in DCM to yield rac-3-(((3R,4S)-3-fluoro-2,2,6,6-tetramethylpiperidin- 4-yl)oxy)-6-(3-(methoxymethoxy)-5-(4-methyl-1H-imidazol-1-yl)pyridin-2-yl)pyridazine (54.7 mg, 109% yield). MS m/z 493.3 $[M+Na]^+$.

Step 2: rac-3-(((3R,4S)-3-Fluoro-2,2,6,6-tetramethylpiperidin-4-yl)oxy)-6-(3-(methoxymethoxy)-5-(4-methyl-1H-imidazol-1-yl)pyridin-2-yl)pyridazine (54.7 mg, 0.108 mmol) and trifluoroacetic acid (4 mL) were combined and stirred at room temperature for 15 minutes. The reaction was concentrated and the residue was chromatographed on silica gel, eluting with 0-30% MeOH (2.5% v/v 30% aqueous ammonium hydroxide additive) in DCM to yield rac-2-(6-{[(3R,4S)-3-fluoro-2,2,6,6-tetramethylpiperidin-4-yl]oxy}pyridazin-3-yl)-5-(4-methyl-1H-imidazol-1-yl)pyridin-3-ol (15.6 mg, 34% yield). MS m/z 427.4 $[M+H]^+$; $^1H$ NMR (1:1 methanol-$d_4$: $CDCl_3$) δ: 8.59 (d, J=9.5 Hz, 1H), 8.32 (d, J=2.1 Hz, 1H), 7.94 (s, 1H), 7.41 (d, J=2.4 Hz, 1H), 7.27 (d, J=9.5 Hz, 1H), 7.17 (s, 1H), 5.77-5.91 (m, 1H), 4.63-4.76 (m, 1H), 2.20 (s, 3H), 1.92-2.00 (m, 1H), 1.81-1.91 (m, 1H), 1.30-1.40 (m, 6H), 1.19-1.26 (m, 6H); 2H not observed (1 OH, 2 NH).

Using the procedure described for Example 5 above, additional compounds described herein may be prepared by substituting the appropriate starting material, suitable reagents, and reaction conditions, obtaining compounds such as those selected from:

| Cpd | Data |
|---|---|
| 5 | MS m/z 394.5 $[M + H]^+$; $^1H$ NMR (DMSO-$d_6$) δ: 13.72 (s, 1H), 8.71 (d, J = 2.3 Hz, 1H), 8.62 (d, J = 9.4 Hz, 1H), 8.51 (s, 1H), 7.98 (s, 1H), 7.92 (d, J = 2.3 Hz, 1H), 7.51 (d, J = 9.4 Hz, 1H), 7.18 (s, 1H), 5.64-5.74 (m, 1H), 2.11 (dd, J = 11.8, 3.4 Hz, 2H), 1.27-1.34 (m, 2H), 1.25 (s, 6H), 1.12 (s, 6H); 1H not observed (NH or OH). |
| 9 | MS m/z 413.0 $[M + H]^+$; $^1H$ NMR (DMSO-$d_6$) δ: 13.58 (s, 1H), 8.72 (d, J = 2.3 Hz, 1H), 8.65 (d, J = 9.4 Hz, 1H), 8.52 (s, 1H), 8.18 (s, 1H), 7.98 (s, 1H), 7.92 (d, J = 2.3 Hz, 1H), 7.62 (d, J = 9.4 Hz, 1H), 7.18 (s, 1H), 5.80-5.94 (m, 1H), 4.74 (d, J = 52.7 Hz, 1H), 1.93 (dd, J = 12.0, 4.5 Hz, 1H), 1.72 (t, J = 12.3 Hz, 1H), 1.27 (d, J = 2.4 Hz, 6H), 1.09-1.20 (m, 6H). |
| 61 | MS m/z 396.5 $[M + H]^+$; $^1H$ NMR (methanol-$d_4$): δ: 9.20 (s, 1H), 8.30 (d, J = 8.7 Hz, 1H), 8.21 (s, 1H), 7.97 (d, J = 12.4 Hz, 1H), 7.50-7.53 (m, 1H), 7.44 (d, J = 8.5 Hz, 1H), 7.27 (d, J = 10.4 Hz, 1H), 5.72-5.84 (m, 1H), 2.22-2.30 (m, 2H), 1.42-1.50 (m, 2H), 1.40 (s, 6H), 1.28 ppm (s, 6H); 1 H not observed. |
| 63 | MS m/z 396.3 $[M + H]^+$; $^1H$ NMR (DMSO-$d_6$) δ: 9.03 (s, 1H), 8.92 (s, 1H), 8.67 (d, J = 9.3 Hz, 1H), 8.08 (s, 2H), 7.56 (d, J = 9.2 Hz, 1H), 5.76-5.68 (m, 1H), 2.26-2.14 (m, 2H), 1.53-1.41 (m, 2H), 1.34 (s, 6H), 1.24 (s, 6H); 2Hs not observed (NH and OH). |
| 71 | MS m/z 394.4 $[M + H]^+$; $^1H$ NMR (DMSO-$d_6$) δ 9.04 (s, 1H), 8.92 (d, J = 2.2 Hz, 1H), 8.69 (d, J = 9.3 Hz, 1H), 8.09 (d, J = 1.7 Hz, 2H), 7.60 (d, J = 9.3 Hz, 1H), 5.66-5.57 (m, 1H), 2.46-2.38 (m, 2H), 2.16-2.09 (m, 2H), 1.89-1.79 (m, 4H), 1.44 (s, 6H); 2Hs not observed (NH and OH). |

Example 6: Preparation of Compound 53

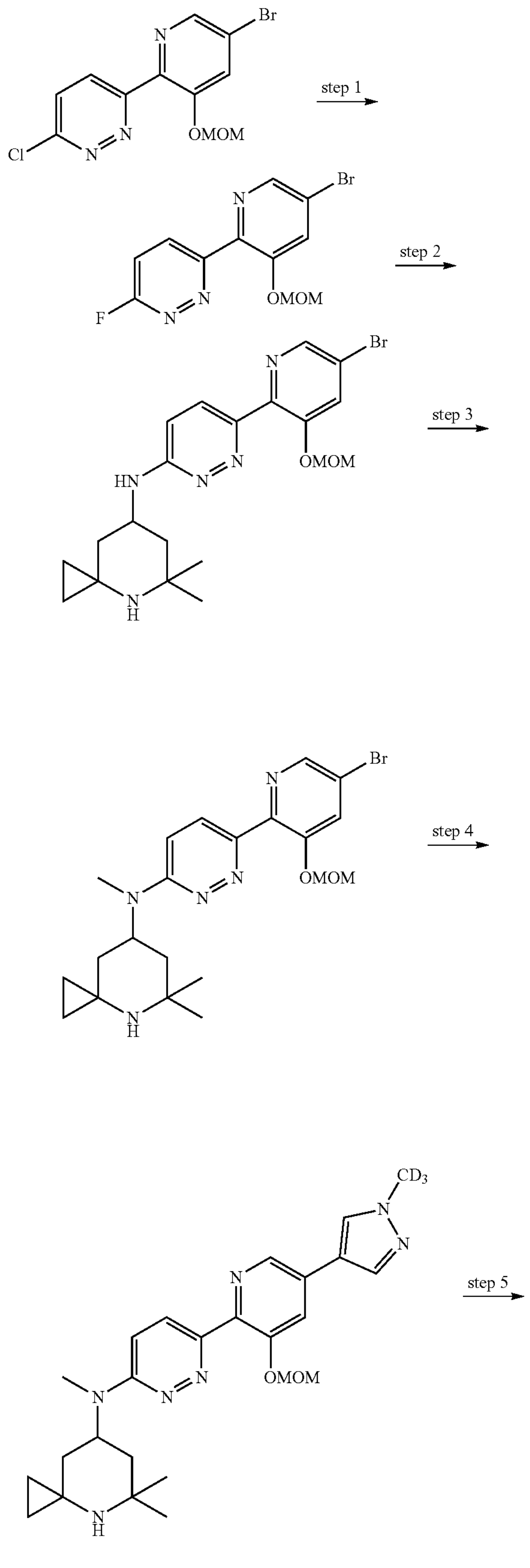

-continued

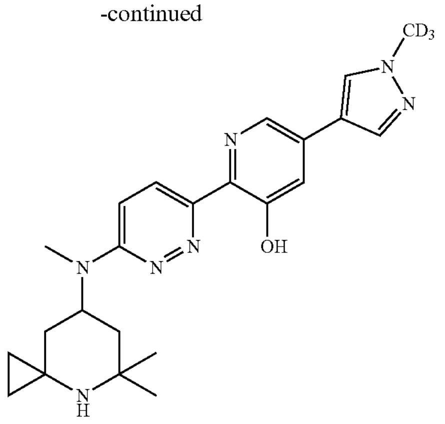

Step 1: To an oven dried 20 mL scintillation vial was added 3-[5-bromo-3-(methoxymethoxy)-2-pyridyl]-6-chloro-pyridazine (1.8 g, 5.4 mmol) followed by silver fluoride (1.5 g, 12 mmol). Acetonitrile (10 mL) was added and the vial was sealed under argon and heated to 100° C. for 1 h. The crude reaction mixture was cooled to room temperature and then filtered through Celite. After the filtrate was concentrated under reduced pressure, the crude residue was purified by silica gel chromatography eluting with a gradient 0-20% EtOAc/Hexanes to afford 3-[5-bromo-3-(methoxymethoxy)-2-pyridyl]-6-fluoro-pyridazine (400 mg, 23% yield) as a beige solid. MS m/z 314.0, 316.0 $[M+H]^+$; $^1H$ NMR ($CDCl_3$) δ: 8.49 (d, J=1.5 Hz, 1H), 8.12 (dd, J=8.8, 7.3 Hz, 1H), 7.86 (d, J=1.5 Hz, 1H), 7.32 (dd, J=9.2, 1.8 Hz, 1H), 5.27 (s, 2H), 3.50 (s, 3H).

Step 2: A mixture of 3-[5-bromo-3-(methoxymethoxy)-2-pyridyl]-6-fluoro-pyridazine (215 mg, 0.7 mmol), 5,5-dimethyl-4-azaspiro[2.5]octan-7-amine dihydrochloride (230 mg, 1.0 mmol), DMSO (1.5 mL), and triethylamine (0.6 mL, 4 mmol) was heated under Ar at 60° C. for 12 h. The reaction mixture was cooled to room temperature, diluted with water (20 mL), and extracted with EtOAc (3x25 mL). The combined organic phases were washed with saturated brine, dried over $MgSO_4$, and concentrated. The crude residue was purified by silica gel chromatography eluting with a gradient 0-10% MeOH/DCM to afford N-[6-[5-bromo-3-(methoxymethoxy)-2-pyridyl]pyridazin-3-yl]-5,5-dimethyl-4-azaspiro[2.5]octan-7-anine (186 mg, 61% yield) as alight brown solid. MS m/z 448.4, 450.4 $[M+H]^+$; $^1H$ NMR (methanol-$d_4$) δ: 8.39 (s, 1H), 7.92 (s, 1H), 7.68 (br d, J=9.2 Hz, 1H), 6.92 (br d, J=9.2 Hz, 1H), 5.29 (s, 2H), 4.55 (br t, J=11.3 Hz, 1H), 3.44 (s, 3H), 2.16 (br d, J=12.5 Hz, 1H), 1.89 (br t, J=12.1 Hz, 1H), 1.67 (br d, J=12.5 Hz, 1H), 1.40-1.47 (m, 3H), 1.37 (br d, J=6.1 Hz, 2H), 1.28 (s, 3H), 0.86-0.95 (m, 2H), 0.67-0.73 (m, 1H), 0.53-0.59 (m, 1H).

Step 3: To a solution of N-[6-[5-bromo-3-(methoxymethoxy)-2-pyridyl]pyridazin-3-yl]-5,5-dimethyl-4-azaspiro[2.5]octan-7-amine (186 mg, 0.4 mmol) in DMF (2 mL) was added cesium carbonate (180 mg, 0.56 mmol). After stirring for 10 min at room temperature, methyl iodide (40 μL, 0.56 mmol) was added and the reaction mixture was stirred at room temperature for 2 h. Then, the mixture was diluted with water (10 mL) and extracted with EtOAc (2×20 mL). The combined organic phases were washed with brine, dried over $MgSO_4$, filtered, and concentrated. The crude residue was purified by silica gel chromatography eluting with a gradient 0-5% MeOH/DCM to afford N-[6-[5-bromo-3-(methoxymethoxy)-2-pyridyl]pyridazin-3-yl]-N,5,5-trimethyl-4-azaspiro[2.5]octan-7-amine (164 mg, 86% Yield) as a beige solid. MS m/z 462.4, 464.4 $[M+H]^+$; $^1H$ NMR (methanol-$d_4$) δ: 8.38 (s, 1H), 7.92 (s, 1H), 7.67 (br d, J=9.5 Hz, 1H), 6.89 (br d, J=9.5 Hz, 1H), 5.29 (s, 2H), 4.52 (br t, J=11.3 Hz, 1H), 3.44 (s, 3H), 2.50 (br s, 3H), 2.00-2.06 (m, 1H), 1.70-1.80 (m, 2H), 1.44 (s, 3H), 1.14-1.30 (m, 5H), 0.88-0.97 (m, 2H), 0.60 (s, 1H), 0.37-0.42 (m, 1H).

Step 4: A mixture of 4-(4,4,5,5-tetramethyl-1,3,2-dioxaborolan-2-yl)-1-(trideuteriomethyl)pyrazole (55 mg, 0.3 mmol) and Pd(dppf)$Cl_2$*$CH_2Cl_2$ (10 mg, 0.01 mmol), N-[6-[5-bromo-3-(methoxymethoxy)-2-pyridyl]pyridazin-3-yl]-N,5,5-trimethyl-4-azaspiro[2.5]octan-7-amine (80 mg, 0.17 mmol), 1,4-dioxane (2 ML) and 2M potassium carbonate (0.3 mL, 0.6 mmol) was degassed by Ar and stirred at 80° C. for 3 h. The crude reaction mixture was cooled to room temperature and purified by silica gel chromatography eluting with a gradient 0-10% MeOH/DCM to afford N-[6-[3-(methoxymethoxy)-5-[1-(trideuteriomethyl)pyrazol-4-yl]-2-pyridyl]pyridazin-3-yl]-N,5,5-trimethyl-4-azaspiro[2.5]octan-7-amine (52 mg, 64% yield) as a yellow foam. MS m/z 467.5 $[M+H]^+$; $^1H$ NMR (methanol-$d_4$) δ: 8.49-8.53 (m, 1H), 8.16 (s, 1H), 7.96 (s, 1H), 7.85 (d, J=1.8 Hz, 1H), 7.68 (d, J=9.2 Hz, 1H), 6.92 (d, J=9.5 Hz, 1H), 5.33 (s, 2H), 4.51-4.60 (m, 1H), 3.44 (s, 3H), 2.60 (br s, 3H), 2.08 (br t, J=12.5 Hz, 1H), 1.73-1.89 (m, 2H), 1.50 (s, 3H), 1.32-1.43 (m, 1H), 1.25 (s, 3H), 0.88-1.10 (m, 2H), 0.68 (br s, 1H), 0.42-0.52 (m, 1H).

Step 5: A mixture of N-[6-[3-(methoxymethoxy)-5-[1-(trideuteriomethyl)pyrazol-4-yl]-2-pyridyl]pyridazin-3-yl]-N,5,5-trimethyl-4-azaspiro[2.5]octan-7-amine (52 mg, 0.1114 mmol) in HCl (4 M in dioxane) (1 mL, 4 mmol, 4 mol/L) was stirred at room temperature for 16 h. The crude reaction mixture was concentrated then triturated with diethyl ether. The solid formed was filtered, rinsed with diethyl ether, and dried under high vacuum to afford 2-[6-[(5,5-dimethyl-4-azaspiro[2.5]octan-7-yl)-methyl-amino]pyridazin-3-yl]-5-[1-(trideuteriomethyl)pyrazol-4-yl]pyridin-3-ol dihydrochloride (34 mg, 62% yield) as a yellow powder. MS m/z 423.5 $[M+H]^+$; $^1H$ NMR (methanol-$d_4$) δ: 8.73-8.81 (m, 1H), 8.63-8.72 (m, 1H), 8.30-8.42 (m, 1H), 8.07-8.16 (m, 1H), 7.90-8.00 (m, 1H), 7.63-7.81 (m, 1H), 4.60-4.75 (m, 1H), 3.08 (s, 3H), 2.40-2.51 (m, 1H), 2.11-2.30 (m, 2H), 1.80 (s, 3H), 1.69-1.76 (m, 1H), 1.53-1.60 (m, 2H), 1.49 (s, 3H), 1.04-1.11 (m, 1H), 0.82-0.98 (m, 1H).

Using the procedure described for Example 6 above, additional compounds described herein may be prepared by substituting the appropriate starting material, suitable reagents, and reaction conditions, obtaining compounds such as those selected from:

| Cpd | Data |
| --- | --- |
| 64 | MS m/z 488.4 $[M + H]^+$; $^1H$ NMR (methanol-$d_4$) δ: 8.81-8.90 (m, 1H), 8.72-8.78 (m, 1H), 8.45-8.55 (m, 1H), 8.02-8.09 (m, 1H), 7.93-8.02 (m, 1H), 7.68-7.81 (m, 1H), 7.42-7.53 (m, 1H), 4.60-4.79 (m, 1H), 4.30 (s, 3H), 3.10 (s, 3H), 2.40-2.51 (m, 1H), 2.08-2.33 (m, 2H), 1.82 (s, 3H), 1.71-1.79 (m, 1H), 1.55-1.65 (m, 2H), 1.52 (s, 3H), 1.09-1.17 (m, 1H), 0.90-0.98 (m, 1H); 2Hs not observed (NH and OH). |

Example 7: Preparation of Compound 76

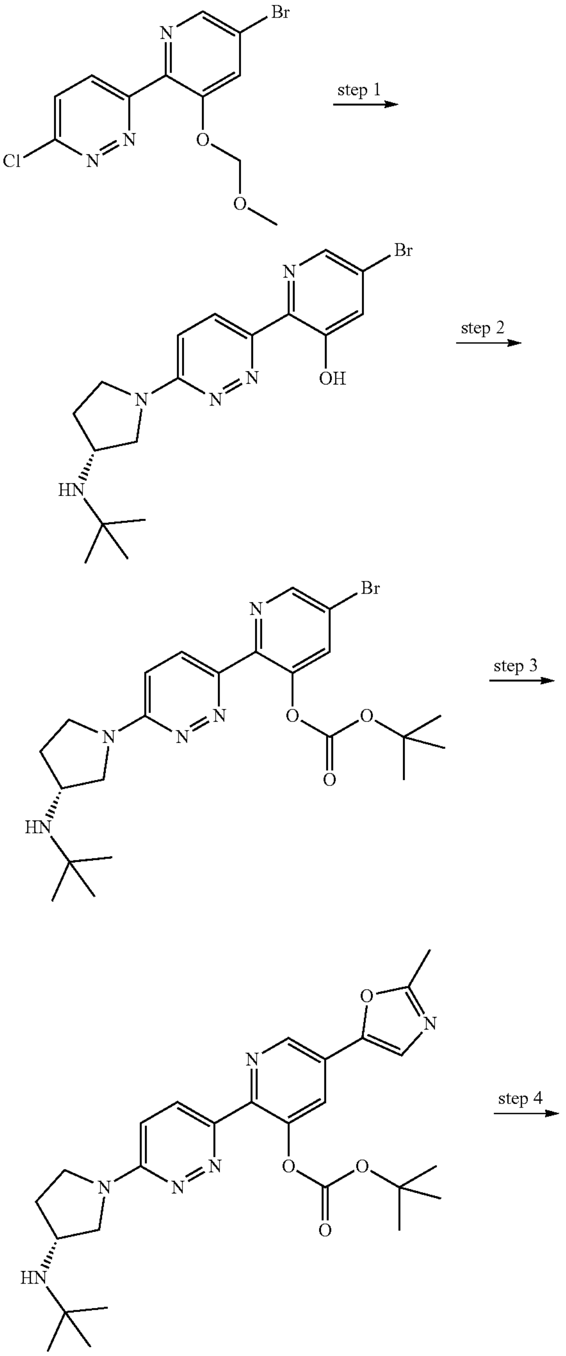

-continued

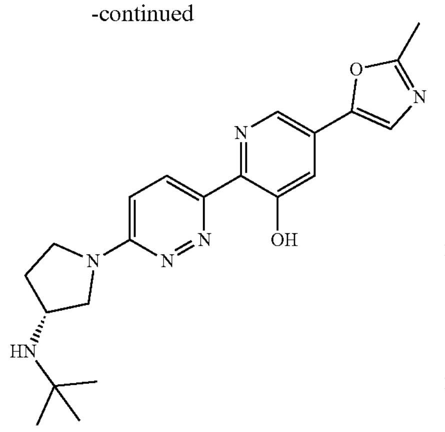

Step 1: A mixture of 3-[5-bromo-3-(methoxymethoxy)-2-pyridyl]-6-chloro-pyridazine (165 mg, 0.50 mmol) and (3R)—N-tert-butylpyrrolidin-3-amine (78.2 mg, 0.55 mmol) in DIPEA (0.26 mL, 3.0 eq.) and DMSO (1.0 mL) was stirred at 90° C. for 16 hr. After cooling, the reaction was diluted with saturated $NaHCO_3$ and extracted with $CH_2Cl_2$. The combined organic layers were washed with water followed by brine, then dried over $Na_2SO_4$, filtered, and concentrated. The crude material was purified by flash column chromatography on silica gel, eluting with 0-10% MeOH in $CH_2Cl_2$ to provide 5-bromo-2-[6-[(3R)-3-(tert-butylamino)pyrrolidin-1-yl]pyridazin-3-yl]pyridin-3-ol (136 mg, 69% yield). MS m/z 392.2, 394.2, $[M+H]^+$.

Step 2: A mixture of 5-bromo-2-[6-[(3R)-3-(tert-butylamino)pyrrolidin-1-yl]pyridazin-3-yl]pyridin-3-ol (136 mg, 0.34 mmol), 4-DMAP (4.3 mg, 0.035 mmol) and di-tert-butyl dicarbonate (85.8 mg, 0.38 mmol) in $CH_2Cl_2$ (1.2 mL) was stirred at room temperature for 2 h. then diluted with $CH_2Cl_2$ and saturated $NaHCO_3$. The combined organic layers were washed with brine, dried over $Na_2SO_4$, filtered and concentrated. The crude material was purified by silica gel column chromatography eluting with a gradient of 0-10% MeOH in $CH_2Cl_2$ to provide [5-bromo-2-[6-[(3R)-3-(tert-butylamino)pyrrolidin-1-yl]pyridazin-3-yl]-3-pyridyl] tert-butyl carbonate (93 mg, 54% yield). MS m/z 492.3/494.3, $[M+H]^+$.

Step 3: A mixture of [5-bromo-2-[6-[(3R)-3-(tert-butylamino)pyrrolidin-1-yl]pyridazin-3-yl]-3-pyridyl]tert-butyl carbonate (93 mg, 0.19 mmol), 2-methyl-5-(4,4,5,5-tetramethyl-1,3,2-dioxaborolan-2-yl)oxazole (59 mg, 0.28 mmol) and Pd(dppf)$Cl_2$ (15.6 mg, 0.1 eq.) in 2.0 M aq. $K_2CO_3$ (0.28 mL, 0.57 mmol) in dioxane (1.0 mL) was stirred at 90° C. for 3 h under an Ar atmosphere, then cooled and diluted with ethyl acetate. The mixture was washed with water and brine and the organic layer was dried over sodium sulfate and concentrated. The crude material was purified by silica gel column chromatography eluting with a gradient of 0-30% MeOH in DCM to provide tert-butyl [2-[6-[(3R)-3-(tert-butylamino)pyrrolidin-1-yl]pyridazin-3-yl]-5-(2-methyloxazol-5-yl)-3-pyridyl]carbonate (69 mg, 74% yield) as light brown oil. MS m/z 495.4, $[M+H]^+$.

Step 4: To a solution of tert-butyl [2-[6-[(3R)-3-(tert-butylamino)pyrrolidin-1-yl]pyridazin-3-yl]-5-(2-methyloxazol-5-yl)-3-pyridyl]carbonate (69 mg, 0.14 mmol) was suspended in MeOH (0.25 mL) was added HCl (4.0 M in dioxane, 1.0 mL). The reaction was stirred at room temperature for 3 h, then diluted with diethyl ether. The solids were filtered and washed with ether and the solids were dried under high vacuum to provide 2-{6-[(3R)-3-(tert-butylamino)pyrrolidin-1-yl]pyridazin-3-yl}-5-(2-methyl-1,3-oxazol-5-yl)pyridin-3-ol (55 mg, 85% yield) as dihydrochloride salts. MS m/z 395.4, $[M+H]^+$; $^1H$ NMR (methanol-$d_4$) δ: 8.96 (d, J=10.1 Hz, 1H), 8.73 (s, 1H), 7.90 (d, J=9.8 Hz, 1H), 7.81 (d, J=10.4 Hz, 2H), 4.33-4.43 (m, 1H), 4.26 (dd, J=11.6, 7.0 Hz, 1H), 3.88-4.05 (m, 2H), 3.82 (d, J=10.4 Hz, 1H), 2.69-2.78 (m, 1H), 2.65 (s, 3H), 2.44 (dd, J=12.5, 7.6 Hz, 1H), 1.53 (s, 9H); 2Hs not observed (OH and NH).

Using the procedure described for Example 7 above, additional compounds described herein may be prepared by substituting the appropriate starting material, suitable reagents, and reaction conditions, obtaining compounds such as those selected from:

| Cpd | Data |
|---|---|
| 17 | MS m/z 394.0 $[M + H]^+$; $^1H$ NMR (methanol-$d_4$) δ: 8.60 (s, 1H), 8.47 (d, J = 9.0 Hz, 1H), 7.69 (m, 2H), 7.20 (d, J = 9.0 Hz, 1H), 6.76 (s, 1H), 3.99 (s, 3H), 3.85-3.95 (m, 1H), 3.66-3.82 (m, 2H), 3.48-3.58 (m, 1H), 3.22-3.32 (m, 1H), 2.32-2.44 (m, 1H), 1.87-2.01 (m, 1H), 1.24 (s, 9H); 2Hs not observed (OH and NH). |
| 18 | MS m/z 380.2 $[M + H]^+$; $^1H$ NMR (methanol-$d_4$) δ: 8.53 (d, J = 9.6 Hz, 1H), 8.46 (s, 1H), 8.13 (s, 2H), 7.57 (s, 1H), 7.29 (d, J = 9.6 Hz, 1H), 4.18-4.28 (m, 1H), 4.08-4.16 (m, 1H) 3.80-3.90 (m, 1H), 3.60-3.72 (m, 2H), 2.58-2.70 (m, 1H), 2.20-2.34 (m, 1H), 1.48 (s, 9H); 3Hs not observed (OH and NHs). |
| 23 | MS m/z 397.5 $[M + H]^+$; $^1H$ NMR (methanol-$d_4$) δ: 8.45 (d, J = 9.46 Hz, 1H), 8.40 (s, 1H), 8.12 (s, 1H), 7.94 (s, 1H), 7.50 (s, 1H), 7.20 (d, J = 9.46 Hz, 1H), 3.80-3.95 (m, 1H), 3.73-3.79 (m, 2H), 3.42-3.60 (m, 1H), 2.41 (m, 1H), 1.95-2.03 (m, 1 H), 1.34 (m, 1H), 1.27 (s, 9H); 2Hs not observed (NH and OH). |
| 29 | MS m/z 397.5 $[M + H]^+$; $^1H$ NMR (methanol-$d_4$) δ: 8.51 (d, J = 9.8 Hz, 1H) 8.10 (s, 1H) 7.93 (s, 1H) 7.82 (d, J = 9.5 Hz, 1H) 7.70 (d, J = 8.2 Hz, 1H) 7.29 (br d, J = 7.9 Hz, 1H) 4.31-4.36 (m, 1H) 4.20 (m, J = 11.0, 7.0 Hz, 1H) 3.92-3.98 (m, 1H) 3.82-3.87 (m, 1H) 3.72-3.79 (m, 1H) 2.67-2.73 (m, 1H) 2.37-2.44 (m, 1H) 1.51 (s, 9H); 2 Hs not observed (NH and OH). |
| 88 | MS m/z 380.3 $[M + H]^+$; $^1H$ NMR (methanol-$d_4$) δ: 8.58 (d, J = 9.7 Hz, 1H), 8.50 (s, 1H), 8.14 (s, 2H), 7.75-7.63 (m, 1H), 7.60 (s, 1H), 3.94 (s, 4H), 1.55 (s, 12H); 3 Hs not observed (2NHs and OH). |
| 107 | MS m/z 414.5 $[M + H]^+$; $^1H$ NMR (DMSO-$d_6$) δ: 9.65 (s, 1H), 9.51 (s, 1H), 9.45 (s, 1H), 8.67 (s, 1H), 8.52 (d, J = 9.0 Hz, 1H), 8.37 (d, J = 9.0 Hz, 1H), 8.11 (s, 1H), 8.03 (d, J = 9.5 Hz, 1H), 7.88 (s, 1H), 7.37 (d, J = 10.0 Hz, 1H), 4.56 (d, J = 12.0 Hz, 1H), 3.66-3.92 (m, 6H), 2.89-2.95 (m, 1H), 2.68-2.75 (m, 1H), 2.30-2.39 (m, 1H), 2.55 (s, 3H). |

Example 8: Preparation of Compound 89

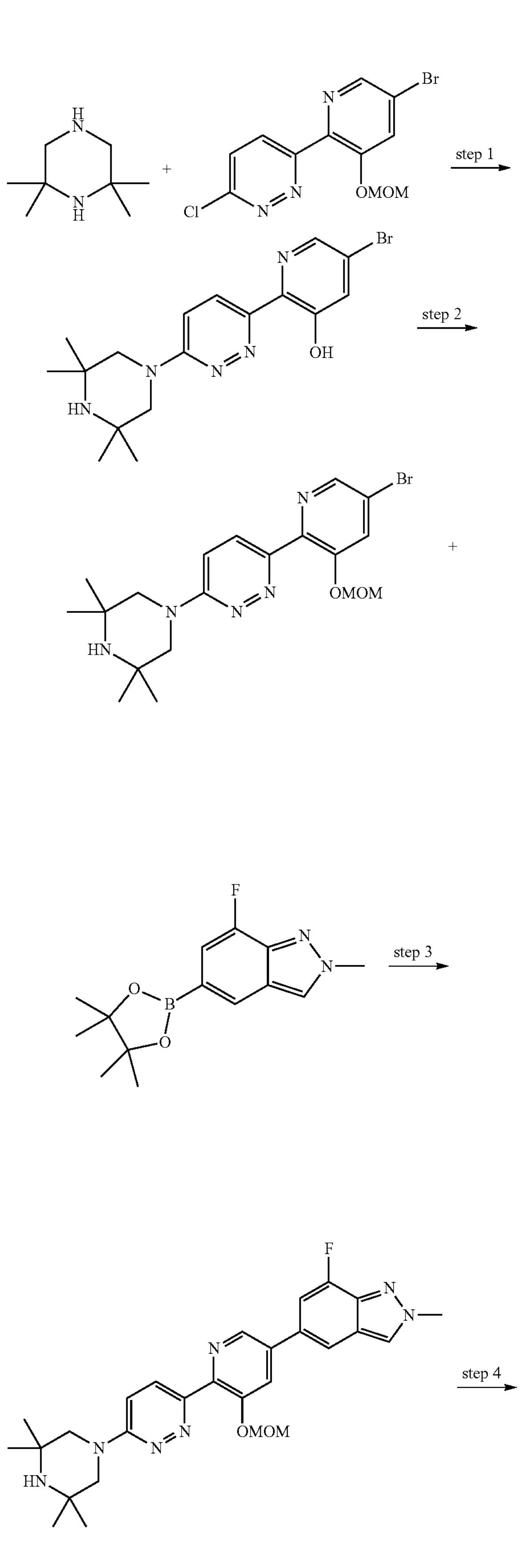

-continued

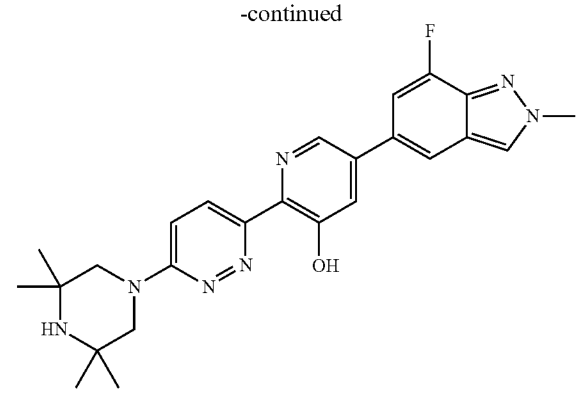

Step 1: 2,2,6,6-Tetramethylpiperazine (0.13 g, 0.91 mmol), 3-[5-bromo-3-(methoxymethoxy)-2-pyridyl]-6-chloro-pyridazine (0.15 g, 0.45 mmol) and N,N-dimethylformamide (3.0 mL, 38.8 mmol) were added into a screw-cap vial under nitrogen. Then 1,8-diazabicyclo[5,4,0]undec-7-ene (0.204 mL, 1.36 mmol) was added to the vial. The reaction mixture was stirred at 100° C. overnight. The solvent was removed and the residue was purified by silica gel column chromatography eluting with a gradient 0-20% MeOH in DCM to provide 5-bromo-2-[6-(3,3,5,5-tetramethylpiperazin-1-yl)pyridazin-3-yl]pyridin-3-ol (0.12 g, 67% yield). MS m/z 392.2 $[M+H]^+$.

Step 2: 5-Bromo-2-[6-(3,3,5,5-tetramethylpiperazin-1-yl)pyridazin-3-yl]pyridin-3-ol (0.1 g, 0.3 mmol) was dissolved in THF (5.0 mL) and chloromethyl methyl ether (0.03 mL, 0.4 mmol) was added followed by triethylamine (0.1 mL, 0.7 mmol). The reaction mixture was stirred at room temperature for 2 h. The solvent was removed and the crude material was used directly in the next step. MS m/z 436.3 $[M+H]^+$.

Step 3: 7-fluoro-2-methyl-5-(4,4,5,5-tetramethyl-1,3,2-dioxaborolan-2-yl)indazole (0.074 g, 0.27 mmol), potassium carbonate (0.074 g, 0.54 mmol), XPhos Pd G3 (0.031 g, 0.035 mmol), and water (2.0 mL, 111.020 mmol) was added to a screw-cap vial under nitrogen. Then 3-[5-bromo-3-(methoxymethoxy)-2-pyridyl]-6-(3,3,5,5-tetramethylpiperazin-1-yl)pyridazine (0.078 g, 0.18 mmol) in 1,4-dioxane (2.0 mL, 23.43 mmol) was added to the reaction mixture. The reaction mixture was stirred at 90° C. for 2 h. The solvent was removed and the residue was by purified by silica gel column chromatography eluting with a gradient 0-30% MeOH in DCM to give 7-fluoro-5-[5-(methoxymethoxy)-6-[6-(3,3,5,5-tetramethylpiperazin-1-yl)pyridazin-3-yl]-3-pyridyl]-2-methyl-indazole (0.06 g, 66% yield). MS m/z 506.4 $[M+H]^+$.

Step 4: 7-Fluoro-5-[5-(methoxymethoxy)-6-[6-(3,3,5,5-tetramethylpiperazin-1-yl)pyridazin-3-yl]-3-pyridyl]-2-methyl-indazole (0.06 g, 0.12 mmol) was dissolved in methanol (2.0 mL, 49.4 mmol) and HCl in dioxane (2.0 mL, 8.0 mmol, 4 mol/L) was added. The reaction mixture was stirred at room temperature for 2 h. The solvent was removed and the residue was purified by silica gel column chromatography eluting with a gradient 0-30% MeOH in DCM to provide 5-(7-fluoro-2-methyl-indazol-5-yl)-2-[6-(3,3,5,5-tetramethylpiperazin-1-yl)pyridazin-3-yl]pyridin-3-ol (0.03 g, 50% yield). MS m/z 462.4 $[M+H]^+$; $^1H$ NMR (DMSO-$d_6$) δ 8.63 (d, J=2.0 Hz, 1H), 8.59 (d, J=2.8 Hz, 1H), 8.50 (d, J=9.7 Hz, 1H), 8.04 (s, 1H), 7.81 (d, J=9.8 Hz, 1H), 7.76 (d, J=2.0 Hz, 1H), 7.55 (d, J=13.1 Hz, 1H), 4.24 (s, 3H), 3.94 (s, 4H), 1.49 (s, 12H).

Using the procedure described for Example 8 above, additional compounds described herein may be prepared by substituting the appropriate starting material, suitable reagents, and reaction conditions, obtaining compounds such as those selected from:

| Cpd | Data |
|---|---|
| 69 | MS m/z 434.4 $[M + H]^+$; $^1H$ NMR (methanol-$d_4$) δ: 8.95 (br d, J = 9.9 Hz, 1H), 8.72 (d, J = 2.0 Hz, 1H), 8.50 (br s, 1H), 8.07 (d, J = 9.8 Hz, 1H), 8.02 (s, 1H), 7.90 (m, 1H), 7.46-7.43 (m, 1H), 4.80 (d, J = 13.6 Hz, 2H), 4.31 (s, 3H), 3.64-3.55 (m, 2H), 3.23-3.18 (m, 2H), 1.50 (d, J = 6.4 Hz, 6H); 2H (OH and NH) was not observed. |
| 78 | MS m/z 441.4 $[M + H]^+$; $^1H$ NMR (methanol-$d_4$) δ: 8.96-8.94 (m, 1H), 8.75 (s, 1H), 8.63 (s, 1H), 8.52 (s, 1H), 8.21 (m, 1H), 8.14-8.12 (m, 1H), 7.93 (s, 1H), 4.81-4.78 (m, 2H), 4.35 (s, 3H), 3.67-3.59 (m, 2H), 3.28-3.25 (m, 2H), 1.51 (br d, J = 5.5 Hz, 6H); 2H (OH and NH) was not observed. |
| 86 | MS m/z 352.3 $[M + H]^+$; $^1H$ NMR (methanol-$d_4$) δ: 8.82 (br d, J = 9.9 Hz, 1H), 8.59 (s, 1H), 8.29 (s, 2H), 7.97 (d, J = 9.6 Hz, 1H), 7.75 (s, 1H), 4.67 (d, J = 14.0 Hz, 2H), 3.47 (br s, 2H), 3.11 (br t, J = 13.0 Hz, 2H), 1.38 (d, J = 6.4 Hz, 6H); 3Hs not observed (2NHs and OH). |
| 87 | MS m/z 446.4 $[M + H]^+$; $^1H$ NMR (methanol-$d_4$) δ: 8.94 (d, J = 9.9 Hz, 1H), 8.79 (s, 2H), 8.14 (d, J = 10.1 Hz, 1H), 8.04 (s, 1H), 7.90 (s, 1H), 7.34 (s, 1H), 4.80 (d, J = 13.6 Hz, 2H), 4.40 (s, 3H), 4.20 (s, 3H), 3.63 (br s, 2H), 3.31-3.26 (m, 2H), 1.52 (d, J = 6.4 Hz, 6H); 2Hs not observed (NH and OH). |
| 90 | MS m/z 366.3 $[M + H]^+$; $^1H$ NMR (methanol-$d_4$) δ: 8.96 (d, J = 9.9 Hz, 1H), 8.76 (d, J = 2.0 Hz, 1H), 8.67 (s, 2H), 8.20-8.18 (m, 1H), 7.98 (d, J = 2.0 Hz, 1H), 4.78 (d, J = 14.6 Hz, 2H), 3.67-3.59 (m, 2H), 3.59-3.49 (m, 2H), 3.04 (s, 3H), 1.61 (d, J = 6.3 Hz, 6H); 2H (OH and NH) was not observed. |
| 91 | MS m/z 448.4 $[M + H]^+$; $^1H$ NMR (methanol-$d_4$) δ: 8.95 (d, J = 9.8 Hz, 1H), 8.72 (s, 1H), 8.50 (d, J = 2.1 Hz, 1H), 8.06 (d, J = 9.8 Hz, 1H), 8.02 (s, 1H), 7.93 (s, 1H), 7.46-7.43 (m, 1H), 4.79 (d, J = 14.6 Hz, 2H), 4.31 (s, 3H), 3.58 (br s, 2H), 3.46-3.41 (m, 2H), 3.05 (s, 3H), 1.60 (d, J = 6.3 Hz, 6H); 1H (OH) was not observed. |
| 92 | MS m/z 416.3 $[M + H]^+$; $^1H$ NMR (methanol-$d_4$) δ: 9.26 (s, 1H), 8.94 (d, J = 9.8 Hz, 1H), 8.70 (s, 1H), 8.24 (d, J = 9.3 Hz, 1H), 8.15 (d, J = 9.9 Hz, 1H), 8.04 (s, 1H), 7.94 (d, J = 9.3 Hz, 1H), 7.89 (s, 1H), 4.68 (d, J = 14.0 Hz, 2H), 3.58-3.47 (m, 2H), 2.52 (s, 3H), 1.41 (d, J = 6.4 Hz, 6H); 4Hs not observed (NH, OH and 2 CHs overlap with methanol signal). |
| 93 | MS m/z 406.3 $[M + H]^+$; $^1H$ NMR (DMSO-$d_6$) δ: 8.64 (s, 1H), 8.58 (d, J = 2.0 Hz, 1H), 8.52 (d, J = 9.8 Hz, 1H), 8.04 (s, 1H), 7.76 (s, 1H), 7.73 (d, J = 9.8 Hz, 1H), 7.57-7.53 (m, 1H), 4.24 (s, 3H), 4.00-3.96 (m, 4H), 3.27-3.24 (m, 4H); 2H (OH and NH) was not observed. |
| 94 | MS m/z 403.3 $[M + H]^+$; $^1H$ NMR (methanol-$d_4$) δ: 9.60 (s, 1H), 9.19 (s, 1H), 8.95 (d, J = 9.9 Hz, 1H), 8.74 (s, 1H), 8.55 (d, J = 9.3 Hz, 1H), 8.19 (d, J = 9.2 Hz, 1H), 8.13 (d, J = 9.9 Hz, 1H), 7.90 (s, 1H), 4.68 (d, J = 14.2 Hz, 2H), 3.50 (br s, 2H), 3.20-3.13 (m, 2H), 1.40 (d, J = 6.4 Hz, 6H); 2H (OH and NH) was not observed. |
| 95 | MS m/z 432.4 $[M + H]^+$; $^1H$ NMR (methanol-$d_4$) δ: 8.94 (d, J = 9.9 Hz, 1H), 8.73 (s, 1H), 8.54 (s, 1H), 8.04-7.99 (m, 2H), 7.82-7.77 (m, 1H), 7.13 (s, 1H), 4.69 (br d, J = 14.3 Hz, 2H), 4.33 (s, 3H), 4.16 (s, 3H), 3.67-3.55 (m, 3H), 3.44-3.35 (m, 2H), 1.50 (d, J = 6.4 Hz, 3H); 2H (OH and NH) was not observed. |
| 96 | MS m/z 393.3 $[M + H]^+$; $^1H$ NMR (methanol-$d_4$) δ: 8.57-8.49 (m, 2H), 8.25 (d, J = 5.3 Hz, 1H), 7.69 (s, 1H), 7.57 (d, J = 9.8 Hz, 1H), 7.32 (d, J = 5.5 Hz, 1H), 7.15 (s, 1H), 4.49-4.45 (m, 2H), 3.99 (s, 3H), 3.11-3.00 (m, 2H), 2.73-2.68 (m, 2H), 1.26 (d, J = 6.4 Hz, 6H); 2H (OH and NH) was not observed. |
| 97 | MS m/z 420.4 $[M + H]^+$; $^1H$ NMR (methanol-$d_4$) δ: 8.49-8.46 (m, 2H), 8.38 (s, 1H), 7.84 (s, 1H), 7.59 (s, 1H), 7.53 (d, J = 9.8 Hz, 1H), 7.35 (d, J = 12.5 Hz, 1H), 4.41 (br d, J = 13.1 Hz, 2H), 4.27 (s, 3H), 3.30-3.25 (m, 1H), 3.20-3.14 (m, 1H), 3.13-3.00 (m, 2H), 2.90-2.84 (m, 1H), 1.28 (d, J = 6.4 Hz, 3H); 2H (OH and NH) was not observed. |
| 98 | MS m/z 432.4 $[M + H]^+$; $^1H$ NMR (methanol-$d_4$) δ: 8.77 (d, J = 9.6 Hz, 1H), 8.61 (s, 1H), 8.43 (s, 1H), 7.94 (s, 1H), 7.84 (s, 1H), 7.78 (s, 1H), 7.39 (d, J = 10.0 Hz, 1H), 4.29 (s, 3H), 4.23-4.15 (m, 2H), 4.04 (s, 2H), 3.59-3.51 (m, 2H), 1.25-1.10 (m, 4H); 2H (OH and NH) was not observed. |
| 99 | MS m/z 417.5 $[M + H]^+$; $^1H$ NMR (methanol-$d_4$) δ: 9.61 (s, 1H), 9.03 (d, J = 9.8 Hz, 1H), 8.82 (d, J = 2.0 Hz, 1H), 8.62 (d, J = 9.2 Hz, 1H), 8.24-8.17 (m, 2H), 7.99-7.97 (m, 1H), 4.79 (br d, J = 13.4 Hz, 2H), 3.65-3.56 (m, 2H), 3.31-3.23 (m, 2H), 2.81 (s, 3H), 1.51 (d, J = 6.6 Hz, 6H); 2H (OH and NH) was not observed. |
| 100 | MS m/z 446.4 $[M + H]^+$; $^1H$ NMR (DMSO-$d_6$) δ: 8.61 (s, 1H), 8.58 (s, 1H), 8.43 (d, J = 9.8 Hz, 1H), 8.03 (s, 1H), 7.73 (s, 1H), 7.65 (d, J = 10.0 Hz 1H), 7.56-7.53 (m, 1H), 4.24 (s, 3H), 3.69-3.66 (m, 4H), 2.69-2.66 (m, 4H), 1.71-1.67 (m, 1H), 0.47-0.39 (m, 4H); 1H (OH) was not observed. |
| 101 | MS m/z 420.4 $[M + H]^+$; $^1H$ NMR (methanol-$d_4$) δ: 8.96 (d, J = 9.9 Hz, 1H), 8.72 (s, 1H), 8.49 (s, 1H), 8.06-7.99 (m, 2H), 7.93 (s, 1H), 7.42 (d, J = 12.2 Hz, 1H), 4.77 (br d, J = 14.8 Hz, 2H), 4.31 (s, 3H), 3.74 (br d, J = 12.5 Hz, 2H), 3.71-3.60 (m, 2H), 3.39-3.35 (m, 2H), 3.03 (s, 3H); 1H not observed (OH). |
| 103 | MS m/z 420.3 $[M + H]^+$; $^1H$ NMR (methanol-$d_4$) δ: 8.64 (d, J = 9.8 Hz, 1H), 8.53 (s, 1H), 8.38 (s, 1H), 7.88 (s, 1H), 7.81 (s, 1H), 7.69-7.65 (m, 1H), 7.36 (d, J = 12.4 Hz, 1H), 4.66-4.61 (m, 2H), 4.29 (s, 3H), 3.57-3.46 (m, 3H), 3.31-3.16 (m, 2H), 1.47 (d, J = 6.4 Hz, 3H); 2H (OH and NH) was not observed. |

-continued

| Cpd | Data |
|---|---|
| 104 | MS m/z 420.3 $[M + H]^+$; $^1H$ NMR (DMSO-$d_6$) δ: 8.63 (s, 1H), 8.58 (s, 1H), 8.52-8.50 (m, 1H), 8.04 (s, 1H), 7.76-7.74 (br s, 2H), 7.55 (d, J = 13.1 Hz, 1H), 4.56-4.52 (m, 2H), 4.24 (s, 3H), 3.45-3.40 (m, 3H), 3.22-3.11 (m, 2H), 1.34 (d, J = 6.4 Hz, 3H); 2H (OH and NH) was not observed. |
| 105 | MS m/z 418.4 $[M + H]^+$; $^1H$ NMR (methanol-$d_4$) δ: 8.84 (d, J = 10.0 Hz, 1H), 8.66 (s, 1H), 8.45 (s, 1H), 7.97 (s, 1H), 7.83 (s, 1H), 7.64 (d, J = 8.5 Hz, 1H), 7.42 (d, J = 12.5 Hz, 1H), 5.25 (s, 1H), 4.69 (s, 1H), 4.29 (s, 3H), 3.93 (d, J = 13.5 Hz, 1H), 3.85 (d, J = 12.0 Hz, 1H), 3.52 (s, 2H), 2.40 (d, J = 12.0 Hz, 1H), 2.21 (d, J = 12.5 Hz, 1H); 2H not observed (1 OH, 1 NH). |
| 106 | MS m/z 434.4 $[M + H]^+$; $^1H$ NMR (methanol-$d_4$) δ: 8.54-8.52 (m, 1H), 8.49 (s, 1H), 8.35 (s, 1H), 7.84 (s, 1H), 7.61 (s, 1H), 7.53 (d, J = 9.9 Hz, 1H), 7.34 (d, J = 12.2 Hz, 1H), 4.28 (s, 3H), 3.97 (d, J = 10.7 Hz, 2H), 3.67-3.49 (m, 4H), 1.37-1.29 (m, 6H); 2H (OH and NH) was not observed. |
| 115 | MS m/z 417.4 $[M + H]^+$; $^1H$ NMR (methanol-$d_4$) δ: 9.43 (s, 1H), 9.18 (s, 1H), 8.65 (d, J = 9.5 Hz, 1H), 8.60 (d, J = 1.5 Hz, 1H), 7.88 (s, 1H), 7.82 (d, J = 2.0 Hz, 1H), 4.78 (dd, J = 14.5, 2.5 Hz, 1H), 3.57-3.50 (m, 2H), 3.46 (quin, J = 1.5 Hz, 1H), 3.18 (quin, J = 1.5 Hz, 1H), 3.07 (d, J = 11.5 Hz, 1H), 3.04 (d, J = 11.5 Hz, 1H), 2.59 (s, 3H), 1.46 (d, J = 6.5 Hz, 6H); 2H not observed (1 OH, 1 NH). |
| 116 | MS m/z 401.3 $[M + H]^+$; $^1H$ NMR (methanol-$d_4$) δ: 9.41 (d, J = 2.1 Hz, 1H), 9.20 (d, J = 2.1 Hz, 1H), 8.54 (d, J = 9.5 Hz, 1H), 8.51 (d, J = 1.8 Hz, 1H), 7.86 (s, 1H), 7.72 (d, J = 1.8 Hz, 1H), 7.28 (d, J = 9.5 Hz, 1H), 5.10 (br s, 1H), 4.55 (s, 1H), 3.81 (dd, J = 11.4, 2.3 Hz, 1H), 3.67 (br d, J = 11.3 Hz, 1H), 3.40 (s, 2H), 2.51 (s, 3H), 2.28 (br d, J = 11.0 Hz, 1H), 1.97-2.14 (m, 1H); 2Hs not observed (NH and OH). |
| 119 | MS m/z 352.3 $[M + H]^+$; $^1H$ NMR (methanol-$d_4$) δ: 8.95 (d, J = 9.9 Hz, 1H), 8.73 (d, J = 2.0 Hz, 1H), 8.50 (s, 2H), 8.10 (d, J = 9.9 Hz, 1H), 7.90 (d, J = 2.0 Hz, 1H), 4.74-4.64 (m, 2H), 3.68-3.59 (m, 2H), 3.47-3.35 (m, 3H), 1.90-1.82 (m, 2H), 1.19 (t, J = 7.6 Hz, 3H); 3H (OH and 2 NH) was not observed. |
| 120 | MS m/z 434.4 $[M + H]^+$; $^1H$ NMR (methanol-$d_4$) δ: 8.96 (d, J = 9.9 Hz, 1H), 8.71 (d, J = 2.0 Hz, 1H), 8.47 (d, J = 2.4 Hz, 1H), 8.04 (d, J = 9.9 Hz, 1H), 8.01-7.99 (m, 1H), 7.92 (d, J = 2.0 Hz, 1H), 7.44-7.38 (m, 1H), 4.75-4.65 (m, 2H), 4.31 (s, 3H), 3.68-3.57 (m, 2H), 3.44-3.35 (m, 3H), 1.86 (quin, J = 7.2 Hz, 2H), 1.19 (t, J = 7.6 Hz, 3H); 2H (OH and NH) was not observed. |
| 121 | MS m/z 366.2 $[M + H]^+$; $^1H$ NMR (DMSO-$d_6$) 5: 8.59 (s, 1H), 8.53-8.50 (m, 2H), 8.32 (s, 2H), 7.86-7.80 (m, 2H), 4.62 (br d, J = 13.6 Hz, 1H), 4.54-4.51 (m, 1H), 3.56-3.49 (m, 1H), 3.39-3.36 (m, 1H), 3.30-3.22 (m, 1H), 3.20-3.07 (m, 2H), 2.13-2.03 (m, 1H), 1.10-1.08 (m, 6H); 3H (OH and 2 NH) was not observed. |
| 122 | MS m/z 448.3 $[M + H]^+$; $^1H$ NMR (methanol-$d_4$) δ: 8.96 (d, J = 9.9 Hz, 1H), 8.73 (s, 1H), 8.51 (d, J = 2.4 Hz, 1H), 8.07 (d, J = 9.9 Hz, 1H), 8.03 (s, 1H), 7.94 (s, 1H), 7.46 (d, J = 12.2 Hz, 1H), 4.82 (br d, J = 14.0 Hz, 1H), 4.73-4.66 (m, 1H), 4.31 (s, 3H), 3.71-3.53 (m, 2H), 3.46-3.35 (m, 2H), 2.16-2.07 (m, 1H), 1.21 (d, J = 6.9 Hz, 6H); 3Hs not observed (OH, NH and one CH overlapped with solvent residual peak) |
| 123 | MS m/z 364.4 $[M + H]^+$; $^1H$ NMR (methanol-$d_4$) δ: 8.94 (d, J = 9.9 Hz, 1H), 8.74 (s, 1H), 8.59 (s, 2H), 8.15 (d, J = 10.1 Hz, 1H), 7.94 (s, 1H), 4.73 (br d, J = 13.4 Hz, 1H), 4.64 (d, J = 12.0 Hz, 1H), 3.79-3.63 (m, 4H), 2.87-2.83 (m, 1H), 1.19-1.13 (m, 1H), 0.88-0.81 (m, 2H), 0.71-0.63 (m, 2H); 3Hs (OH and 2 NH) not observed. |
| 124 | MS m/z 416.3 $[M + H]^+$; $^1H$ NMR (methanol-$d_4$) δ: 8.49-8.44 (m, 2H), 8.24 (s, 1H), 7.99 (s, 1H), 7.72 (d, J = 9.0 Hz, 1H), 7.63 (s, 1H), 7.60 (s, 1H), 7.48 (d, J = 9.8 Hz, 1H), 4.46-4.34 (m, 2H), 4.25 (s, 3H), 3.09-3.00 (m, 2H), 2.69 (dd, J = 11.4, 12.7 Hz, 2H), 1.25 (d, J = 6.4 Hz, 6H); 2H (OH and NH) was not observed. |
| 126 | MS m/z 416.5 $[M + H]^+$; $^1H$ NMR (methanol-$d_4$) δ: 8.95 (d, J = 9.8 Hz, 1H), 8.75 (d, J = 1.8 Hz, 1H), 8.24 (s, 1H), 8.18 (s, 1H), 8.06 (d, J = 10.1 Hz, 1H), 8.00 (s, 1H), 7.84-7.88 (m, 1H), 7.77-7.81 (m, 1H), 4.81 (br dd, J = 14.2, 2.0 Hz, 2H), 4.16 (s, 3H), 3.55-3.63 (m, 2H), 3.22 (dd, J = 14.3, 11.9 Hz, 2H), 1.50 (d, J = 6.4 Hz, 6H); 2H not observed (1 OH, 1 NH). |
| 129 | MS m/z 381.4 $[M + H]^+$; $^1H$ NMR (methanol-$d_4$): δ: 8.52 (d, J = 9.5 Hz, 1H), 8.42 (d, J = 3.1 Hz, 1H), 8.15 (s, 1H), 7.96 (s, 1H), 7.66 (d, J = 9.8 Hz, 1H), 7.54 (d, J = 1.7 Hz, 1H), 4.64 (d, J = 14.3 Hz, 1H), 4.49 (d, J = 14.3 Hz, 1H), 3.55-3.60 (m, 1H), 3.47-3.54 (m, 1H), 3.39-3.46 (m, 1H), 3.23-3.31 (m, 1H), 2.67-2.77 (m, 1H), 1.05-1.16 (m, 1H), 0.77-0.89 (m, 2H), 0.58-0.67 ppm (m, 2H); 2Hs not observed. |
| 131 | MS m/z 402.3 $[M + H]^+$; $^1H$ NMR (methanol-$d_4$) δ: 8.51-8.47 (m, 2H), 8.14 (s, 1H), 8.09 (s, 1H), 7.73 (d, J = 9.0 Hz, 1H), 7.69-7.66 (m, 1H), 7.62 (d, J = 2.0 Hz, 1H), 7.50 (d, J = 9.8 Hz, 1H), 4.42 (br d, J = 11.4 Hz, 2H), 3.11-3.01 (m, 2H), 2.70 (t, J = 12.1 Hz, 2H), 1.26 (d, J = 6.4 Hz, 6H); 3H (OH and 2 NH) was not observed. |
| 132 | MS m/z 352.2 $[M + H]^+$; $^1H$ NMR (methanol-$d_4$) δ: 8.96 (d, J = 9.9 Hz, 1H), 8.74 (s, 1H), 8.54 (s, 2H), 8.12 (d, J = 9.9 Hz, 1H), 7.91 (s, 1H), 4.74-4.65 (m, 2H), 3.69-3.59 (m, 2H), 3.47-3.36 (m, 3H), 1.86 (quin, J = 7.2 Hz, 2H), 1.19 (t, J = 7.6 Hz, 3H); 3H (OH and 2 NH) was not observed. |

Example 9: Preparation of Compound 8

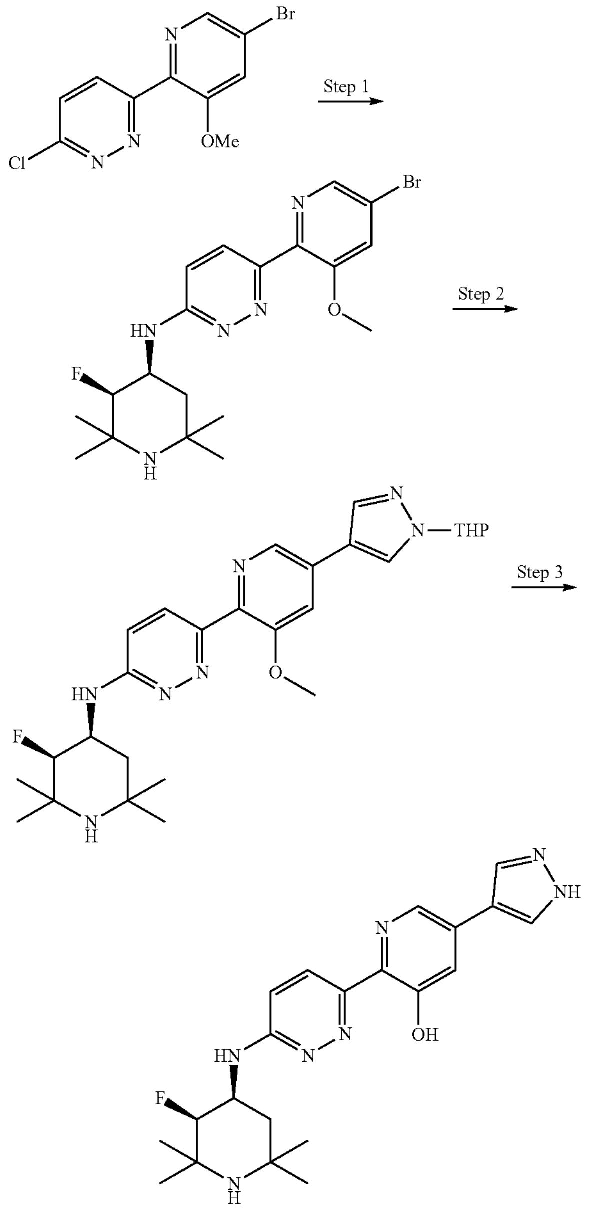

Step 1: A mixture of 3-(5-bromo-3-methoxy-2-pyridyl)-6-chloro-pyridazine (590 mg, 1.97 mmol), (t)-cis-3-fluoro-2,2,6,6-tetramethylpiperidin-4-amine (5.0 g, 28.7 mmol) and NaI (383 g, 2.56 mmol) was stirred under $N_2$ atmosphere at 80° C. overnight. After cooled to room temperature, the mixture was purified by silica gel column chromatography eluting with a gradient 0-10% MeOH in DCM to give 6-(5-bromo-3-methoxypyridin-2-yl)-N-(3-fluoro-2,2,6,6-tetramethylpiperidin-4-yl)pyridazin-3-amine (150 mg, 17% yield). MS m/z 438.0, 440.0 $[M+H]^+$.

Step 2: To a mixture of 6-(5-bromo-3-methoxypyridin-2-yl)-N-(3-fluoro-2,2,6,6-tetramethylpiperidin-4-yl) pyridazin-3-amine (150 mg, 0.34 mmol), 1-(tetrahydro-2H-pyran-2-yl)-4-(4,4,5,5-tetramethyl-1,3,2-dioxaborolan-2-yl)-1H-pyrazole (121 mg, 0.44 mmol) and $K_2CO_3$ (118 mg, 0.86 mmol) in DMF/$H_2O$ (4 mL/1 mL) was added Pd(dppf) $Cl_2$ (25 mg, 0.034 mmol). The reaction mixture was stirred under $N_2$ atmosphere at 95° C. for 8 h. The mixture was poured onto ice water and extracted with EtOAc. The combined organic layers were washed with water and brine, dried over $Na_2SO_4$, and concentrated. The residue was purified by silica gel column chromatography eluting with a gradient 0-20% MeOH in DCM to give (±)N-(3-fluoro-2,2,6,6-tetramethylpiperidin-4-yl)-6-(3-methoxy-5-(1-(tetrahydro-2H-pyran-2-yl)-1H-pyrazol-4-yl)pyridin-2-yl) pyridazin-3-amine (90 mg, 52% yield). MS m/z 510.3 $[M+H]^+$.

Step 3: To a solution of N-(3-fluoro-2,2,6,6-tetramethylpiperidin-4-yl)-6-(3-methoxy-5-(1-(tetrahydro-2H-pyran-2-yl)-1H-pyrazol-4-yl)pyridin-2-yl)pyridazin-3-amine (90 mg, 0.18 mmol) in DCM (1.0 mL) was added $BBr_3$ (1.0 M in DCM, 5 mL). The reaction mixture was stirred at 50° C. overnight. The mixture was cooled to room temperature and concentrated and the residue was mixed with ice water, neutralized with aq. $Na_2CO_3$, and extracted with DCM. The combined organic layers were dried over $Na_2SO_4$, concentrated, and purified by Prep-HPLC to give 2-(6-(((3S,4S)-3-fluoro-2,2,6,6-tetramethylpiperidin-4-yl)amino) pyridazin-3-yl)-5-(1H-pyrazol-4-yl)pyridin-3-ol (30 mg, 41% yield). MS m/z 412.9 $[M+H]^+$; $^1H$ NMR (DMSO-$d_6$) δ: 13.20 (s, 1H), 13.16 (s, 1H), 8.64 (d, J=9.4 Hz, 1H), 8.61 (d, J=1.8 Hz, 1H), 8.45 (s, 1H), 8.15 (s, 1H), 7.73 (d, J=1.8 Hz, 1H), 7.55 (d, J=9.4 Hz, 1H), 5.80-5.92 (m, 1H), 4.39 (dd, J=52.3, 9.3 Hz, 1H), 2.24-2.35 (m, 1H), 2.03 (br s, 1H), 1.54 (t, J=12.3 Hz, 1H), 1.31 (s, 3H), 1.24 (s, 3H), 1.16 (s, 3H), 1.09 (s, 3H); 1H not observed (OH or NH)

Using the procedure described for Example 9 above, additional compounds described herein may be prepared by substituting the appropriate starting material, suitable reagents, and reaction conditions, obtaining compounds such as those selected from:

| Cpd | Data |
|---|---|
| 2 | MS m/z 408.5 $[M + H]^+$; $^1H$ NMR (methanol-$d_4$) δ: 8.91 (br d, J = 9.2 Hz, 1H), 8.68 (s, 1H), 8.31 (s, 2H), 7.96 (br d, J = 8.9 Hz, 1H), 7.82 (s, 1H), 5.20 (br s, 1H), 3.21 (s, 3H), 2.09-2.18 (m, 2H), 2.00-2.04 (m, 2H), 1.68 (s, 6H), 1.60 (s, 6H); 3H not observed (1 OH, 2 NH). |
| 13 | MS m/z 422.6 $[M + H]^+$; $^1H$ NMR (DMSO-$d_6$) δ: 13.71 (s, 1H), 8.65 (d, J = 1.5 Hz, 1H), 8.42 (d, J = 9.8 Hz, 1H), 8.38 (s, 1H), 7.81 (d, J = 2.0 Hz, 1H), 7.70 (d, J = 1.5 Hz, 1H), 7.48 (d, J = 9.8 Hz, 1H), 6.88 (d, J = 2.0 Hz, 1H), 5.00-5.16 (m, 1H), 3.92 (s, 3H), 2.99 (s, 3H), 1.74 (t, J = 12.4 Hz, 2H), 1.63 (dd, J = 12.4, 3.0 Hz, 2H), 1.38 (s, 6H), 1.26 (s, 6H). |

-continued

| Cpd | Data |
|---|---|
| 16 | MS m/z 412.3 [M + H]$^+$; $^1$H NMR (methanol-d$_4$) δ: 8.45 (d, J = 1.8 Hz, 1H), 8.39 (d, J = 9.5 Hz, 1H), 8.12 (s, 2H), 7.56 (d, J = 1.8 Hz, 1H), 7.17 (d, J = 9.5 Hz, 1H), 4.79 (dd, J = 12.1, 3.8 Hz, 1H), 4.51 (d, J = 50.8 Hz, 1H), 1.64-1.81 (m, 2H), 1.33-1.43 (m, 6H), 1.25 (s, 6H); 4Hs not observed (OH and NHs). |
| 19 | MS m/z 429.7 [M + H]$^+$; $^1$H NMR (acetone-d$_6$) δ: 13.74 (br s, 1H), 8.37-8.50 (m, 2H), 8.16 (s, 1H), 7.96 (s, 1H), 7.49 (s, 1H), 7.28 (br d, J = 9.5 Hz, 1H), 6.55 (br d, J = 8.2 Hz, 1H), 4.83-5.03 (m, 1H), 4.53 (d, J = 51.6 Hz, 1H), 2.67-2.90 (m, 1H), 1.78 (br dd, J = 12.4, 3.2 Hz, 1H), 1.58 (br t, J = 12.5 Hz, 1H), 1.33 (br d, J = 7.6 Hz, 6H), 1.16 (br s, 6H). |

Example 10: Preparation of Compound 70

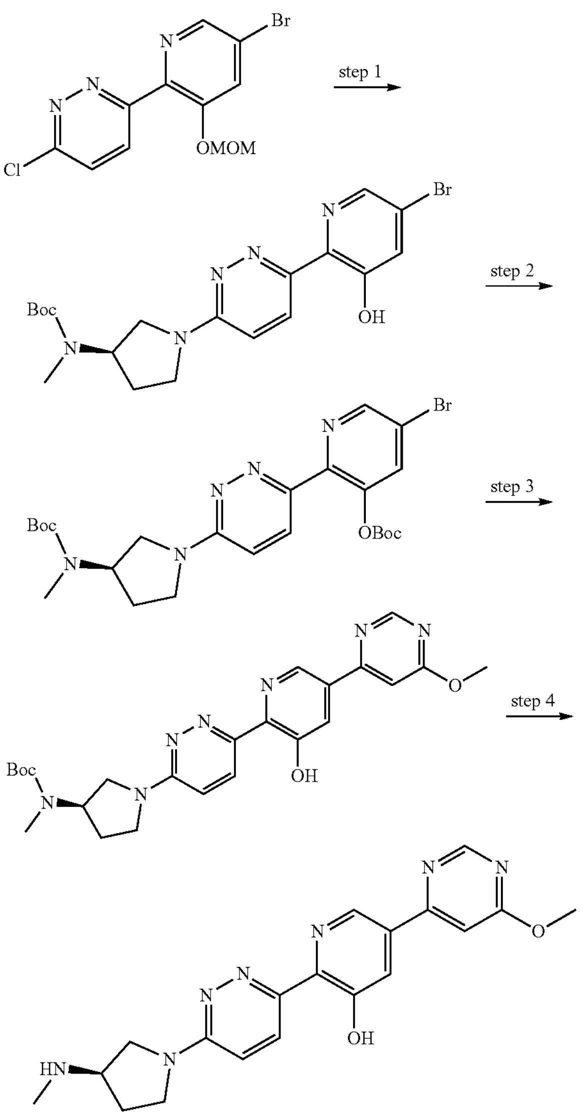

Step 1: 3-[5-Bromo-3-(methoxymethoxy)-2-pyridyl]-6-chloro-pyridazine (160 mg, 0.48 mmol), tert-butyl N-methyl-N-[(3R)-pyrrolidin-3-yl]carbamate (120 mg, 0.6 mmol), DMSO (1.2 mL), and DIPEA (0.32 mL, 1.8 mmol) were heated overnight at 100° C. The reaction mixture was partitioned between $H_2O$ and EtOAc. The organic layer was backwashed with $H_2O$, then brine. The organic layer was dried over $MgSO_4$ and concentrated under vacuum. The residue was purified by silica gel column chromatography eluting with a gradient 10-30% EtOAC in DCM to yield tert-butyl N-[(3R)-1-[6-(5-bromo-3-hydroxy-2-pyridyl)pyridazin-3-yl]pyrrolidin-3-yl]-N-methyl-carbamate (149 mg, 68% yield) as a white solid. $^1$H NMR (acetone-d$_6$) δ: 14.14 (s, 1H), 8.42 (d, J=9.5 Hz, 1H), 8.25 (s, 1H), 7.57 (s, 1H), 7.25 (d, J=9.5 Hz, 1H), 4.95 (m, 1H), 3.80-3.95 (m, 2H), 3.50-3.70 (m, 2H), 2.85 (s, 3H), 2.28 (m, 2H), 1.49 (s, 9H).

Step 2: tert-Butyl N-[(3R)-1-[6-(5-bromo-3-hydroxy-2-pyridyl)pyridazin-3-yl]pyrrolidin-3-yl]-N-methyl-carbamate (115 mg, 0.25 mmol), $Boc_2O$ (130 mg, 0.58 mmol), DCM (1.5 mL), and a crystal of DMAP were stirred at room temperature for 1 h, the reaction mixture was concentrated, purified by silica gel column chromatography eluting with a gradient 10-40% EtOAc in DCM to provide [5-bromo-2-[6-[(3R)-3-[tert-butoxycarbonyl(methyl)amino]pyrrolidin-1-yl]pyridazin-3-yl]-3-pyridyl]tert-butyl carbonate (142 mg, 100% yield) as a white solid. $^1$H NMR (acetone-d$_6$) δ: 8.68 (s, 1H), 8.10 (d, J=9.5 Hz, 1H), 8.00 (s, 1H), 6.98 (d, J=9.5 Hz, 1H), 4.90-5.00 (m, 1H), 3.80-3.95 (m, 2H), 3.50-3.70 (m, 2H), 2.88 (s, 3H), 2.28 (m, 2H), 1.55 (s, 9H), 1.48 (s, 9H).

Step 3: Potassium acetate (100 mg, 1.0 mmol) was dried under argon at 180° C. for 10 min then cooled to room temperature. [5-Bromo-2-[6-[(3R)-3-[tert-butoxycarbonyl(methyl)amino]pyrrolidin-1-yl]pyridazin-3-yl]-3-pyridyl] tert-butyl carbonate (60 mg, 0.11 mmol), bis(pinacolato)diboron (38 mg, 0.15 mmol), Pd(dppf)$Cl_2$-DCM complex (10 mg, 0.012 mmol), and 1,4-dioxane (1 mL) were added. This was heated overnight at 100° C. 4-Chloro-6-methoxy-pyrimidine (22 mg, 0.15 mmol), more Pd(dppf)$Cl_2$-DCM complex (10 mg, 0.012 mmol), and $K_2CO_3$ (2 M in $H_2O$, 0.5 mL, 1 mmol) were added. This was heated overnight at 90° C. The reaction mixture was then partitioned between DCM and water. The organic layer was dried over $MgSO_4$, concentrated and purification by silica gel column chromatography eluting with a gradient 10-20% acetone in DCM, followed by ether trituration to yield tert-butyl N-[(3R)-1-[6-[3-hydroxy-5-(6-methoxypyrimidin-4-yl)-2-pyridyl]pyridazin-3-yl]pyrrolidin-3-yl]-N-methyl-carbamate (17 mg, 32% yield) as an off-white solid. MS m/z 480.3 [M+H]$^+$.

Step 4: Tert-butyl N-[(3R)-1-[6-[3-hydroxy-5-(6-methoxypyrimidin-4-yl)-2-pyridyl]pyridazin-3-yl]pyrrolidin-3-yl]-N-methyl-carbamate (17 mg, 0.035 mmol), DCM (0.5 mL), and trifluoroacetic acid (0.5 mL, 7 mmol) were stirred at room temperature for 1 hour. The solvents were removed by a nitrogen stream. The mixture was then partitioned between aqueous $NaHCO_3$ and DCM. The organic layer was dried over $MgSO_4$ and concentrated to provide 5-(6-methoxypyrimidin-4-yl)-2-{6-[(3R)-3-(methylamino) pyrrolidin-1-yl]pyridazin-3-yl}pyridin-3-ol (14 mg, 100% yield) as an off-white solid. MS m/z 380.2 $[M+H]^+$; $^1H$ NMR (methanol-$d_4$) δ: 8.84 (m, 2H), 8.52 (d, J=10 Hz, 1H), 7.99 (s, 1H), 7.42 (s, 1H), 7.23 (d, J=10 Hz, 1H), 4.07 (s, 3H), 3.82 (m, 1H), 3.75 (m, 1H), 3.64 (m, 1H), 3.40-3.50 (m, 214), 2.48 (s, 3H), 2.34 (m, 1H), 2.03 (m, 1H).

Using the procedure described for Example 10 above, additional compounds described herein may be prepared by substituting the appropriate starting material, suitable reagents, and reaction conditions, obtaining compounds such as those selected from:

-continued

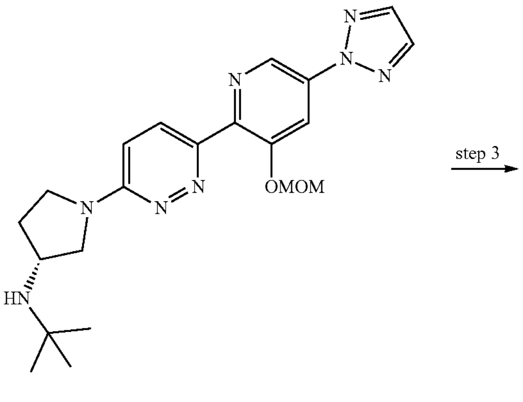

| Cpd | Data |
|---|---|
| 14 | MS m/z 409.3 $[M + H]^+$; $^1H$ NMR (methanol-$d_4$) δ: 8.84 (d, J = 1.8 Hz, 1H), 8.59 (d, J = 9.8 Hz, 1H), 8.10 (s, 1H), 7.91 (d, J = 1.8 Hz, 1H), 7.46 (d, J = 9.8 Hz, 1H), 7.41 (s, 1H), 5.45-5.56 (m, 1H), 3.10 (s, 3H), 1.96-2.05 (m, 4H), 1.69 (s, 6H), 1.55 (s, 6H); 2Hs not observed (OH and NH). |
| 25 | MS m/z 457.4 $[M + H]^+$; $^1H$ NMR (methanol-$d_4$) δ: 8.88 (s, 1H), 8.85 (s, 1H), 8.52 (br d, J = 9.2 Hz, 1H), 8.27 (br s, 2H), 8.02 (s, 1H), 7.43 (s, 1H), 7.23 (br d, J = 9.8 Hz, 1H), 4.97-5.12 (m, 1H), 4.91-4.97 (m, 1H), 1.97-2.16 (m, 2H), 1.68 (br d, J = 12.8 Hz, 6H), 1.57 (br d, J = 14.0 Hz, 6H), 2 NHs and 1 OH not observed, 2H from HCOOH observed. |
| 30 | MS m/z 422.5 $[M + H]^+$; $^1H$ NMR (methanol-$d_4$) δ: 8.87 (s, 1H), 8.84 (s, 1H), 8.56-8.58 (d, J = 9.46 Hz, 1H), 8.01 (d, J = 1.53 Hz, 1H), 7.43 (s, 1H), 7.27 (d, J = 9.77 Hz, 1H), 4.10-4.30 (m, 1H), 4.08 (s, 3H), 3.82-3.95 (m, 1H), 3.76-3.77 (m, 1H), 3.51-3.54 (m, 1H), 3.49-3.50 (m, 1H), 2.49-2.52 (m, 1H), 2.05-2.25 (m, 1H), 1.35 (s, 9H); 2Hs not observed (NH and OH). |
| 77 | MS m/z 353.3 $[M + H]^+$; $^1H$ NMR (methanol-$d_4$) δ 8.45-8.57 (m, 2H), 7.59 (s, 1H), 7.51 (s, 1H), 7.24 (d, J = 9.5, 1H), 3.84-380 (m, 1H), 3.76-3-71 (m, 1H), 3.68-3.63 (m, 1H), 3.40-3.50 (m, 2H), 2.71 (s, 3H), 2.58 (s, 3H), 2.36-2.30 (m, 1H), 2.08-2.02 (m, 1H); 2Hs not observed (NH and OH). |
| 80 | MS m/z 339.3 $[M + H]^+$; $^1H$ NMR (methanol-$d_4$) δ 8.79 (s, 1H), 8.51 (d, J = 9.5 Hz, 1H), 8.09 (s, 1H), 7.87 (s, 1H), 7.39 (s, 1H), 7.43 (d, J = 9.5 Hz, 1H), 3.85-3.81 (m, 1H), 3.76-3.72 (m, 1H), 3.68-3.60 (m, 1H), 3.40-3.50 (m, 2H), 2.48 (s, 3H), 2.38-2.33 (m, 1H), 2.06-2.04 (m, 1H); 2Hs not observed (NH and OH). |

Example 11: Preparation of Compound 24

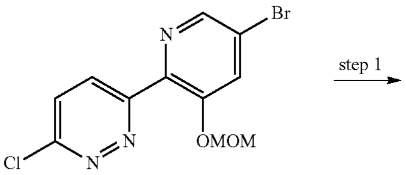

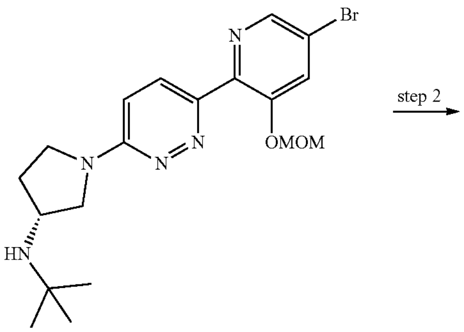

-continued

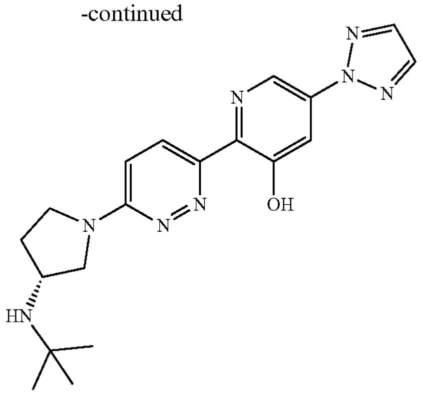

Step 1: To a suspension of (3R)—N-tert-butylpyrrolidin-3-amine dihydrochloride (200 mg, 0.92 mmol) in DMF (1.2 ml) was added DBU (560 mg, 3.68 mmol). The reaction mixture was stirred at 40° for 10 min until a clean solution formed. Then 3-[5-bromo-3-(methoxymethoxy)-2-pyridyl]-6-chloro-pyridazine (200 mg, 0.60 mmol) in THF (1.0 mL) was added. The mixture was stirred at 40° C. for 24 h. The mixture was partitioned between EtOAc and water. The organic layer was washed with brine, dried over $MgSO_4$, then concentrated. The crude product was purified by silica gel chromatography, eluting with a gradient 0-20% MeOH in DCM to afford (3R)-1-[6-[5-bromo-3-(methoxymethoxy)-2-pyridyl]pyridazin-3-yl]-N-tert-butyl-pyrrolidin-3-amine (190 mg, 73% yield). MS m/z 436.1, 438.1 $[M+H]^+$.

Step 2: A dried, screw-top, dram vial was charged with $Me_4$tBu-XPhos (22 mg, 0.045 mmol) and $Pd_2dba_3$ (26 mg, 0.029 mmol), followed by anhydrous toluene (1.0 mL) and 1,4-dioxane (0.2 mL). The vial was evacuated and back-filled with argon 3 times and then placed on a preheated aluminum block (110° C.) and gently stirred for 5 min. Separately, a second screw-top was fitted with a septum cap, swept with argon, and charged with (3R)-1-[6-[5-bromo-3-(methoxymethoxy)-2-pyridyl]pyridazin-3-yl]-N-tert-butyl-pyrrolidin-3-amine (190 mg, 0.44 mmol), 2H-triazole (45 mg, 0.65 mmol), and $K_3PO_4$ (220 mg, 1.0 mmol). The reaction mixture in the second vial was sparged with argon for 1 minute, after which the catalyst solution from the first vial was added via syringe to the second vial. The reaction vessel was placed on a pre-heated aluminum block (110° C.) and the reaction mixture was stirred for 3 h. The crude reaction mixture was cooled to room temperature, transferred to a separatory funnel, diluted with 1:1 sat. aq. $Na_2CO_3$/brine (1.5 mL and extracted with EtOAc. The combined extracts were dried over $MgSO_4$ and concentrated. The crude product was purified by silica gel column chromatography eluting with a gradient of 0-20% MeOH in DCM to afford (3R)—N-tert-butyl-1-[6-[3-(methoxymethoxy)-5-(triazol-2-yl)-2-pyridyl]pyridazin-3-yl]pyrrolidin-3-amine (130 mg, 70% yield). MS m/z 425.5 $[M+H]^+$.

Step 3: A mixture of (3R)—N-tert-butyl-1-[6-[3-(methoxymethoxy)-5-(triazol-2-yl)-2-pyridyl]pyridazin-3-yl]pyrrolidin-3-amine (130 mg, 0.31 mmol) and HCl in dioxane (4N, 1.0 ml) was stirred at 35° C. for 2 h, the crude mixture was concentrated and purified by reversed phase column chromatography, eluting with a gradient of 0-100% $CH_3CN$/water (0.1% TFA) to afford the desired product. The combined solid was treated with 1.5M HCl in MeOH (5 mL) and the solvent was evaporated to afford 2-{6-[(3R)-3-(tert-butylamino)pyrrolidin-1-yl]pyridazin-3-yl}-5-(2H-1,2,3-triazol-2-yl)pyridin-3-ol (95 mg, 68% yield) as a yellow solid. MS m/z 381.5 $[M+H]^+$, $^1H$ NMR (methanol-$d_4$) δ: ppm 1.51 (s, 9H), 2.30-2.37 (m, 1H), 2.65-2.72 (m, 1H), 3.75-3.77 (m, 2H), 3.86-3.94 (m, 1H), 4.17-4.21 (m, 1H), 4.25-4.39 (m, 1H), 7.40-7.42 (d, J=9.77 Hz, 1H), 8.01-8.04 (m, 3H), 8.63-8.65 (d, J=9.46 Hz, 1H), 8.97 (s, 1H).

Using the procedure described for Example 11 above, additional compounds described herein may be prepared by substituting the appropriate starting material, suitable reagents, and reaction conditions, obtaining compounds such as those selected from:

| Cpd | Data |
|---|---|
| 128 | MS m/z 365.3 $[M + H]^+$; $^1H$ NMR (methanol-$d_4$) δ: 8.88 (d, J = 2.1 Hz, 1H), 8.43 (d, J = 11.0 Hz, 1H), 8.02 (s, 2H), 7.98 (d, J = 2.0 Hz, 1H), 7.53 (d, J = 9.5 Hz, 1H), 4.42 (d, J = 12.8 Hz, 1H), 4.34 (br d, J = 13.3 Hz, 1H), 3.11-3.21 (m, 1H), 2.94 (t, J = 11.4 Hz, 1H), 2.87-2.90 (m, 1H), 2.81-2.92 (m, 1H), 1.98 (dd, J = 11.0, 7.3 Hz, 1H), 0.82-0.94 (m, 1H), 0.56-0.66 (m, 2H), 0.32-0.45 ppm (m, 2H); 2Hs not observed. |

Example 12: Preparation of Compound 15

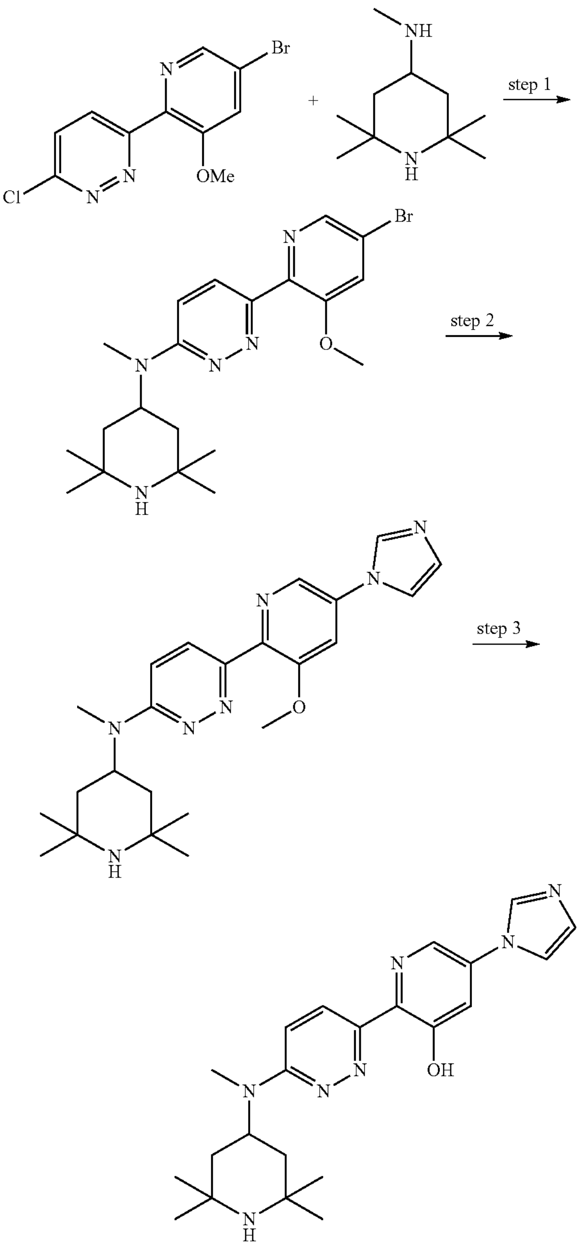

Step 1; To a solution of of 3-(5-bromo-3-methoxy-2-pyridyl)-6-chloro-pyridazine (1.6 g, 5.33 mmol) in DMF (10 mL) were added N,2,2,6,6-pentamethylpiperidin-4-amine (8 g, 47.1 mmol) and NaI (1.3 g, 8.6 mmol). The reaction mixture was stirred under $N_2$ atmosphere at 70° C. for 16 h, then cooled to room temperature, concentrated under stream of $N_2$. The residue was purified by silica gel column chromatography eluting with a gradient 0-20% MeOH in DCM to give 6-(5-bromo-3-methoxypyridin-2-yl)-N-methyl-N-(2,2,6,6-tetramethylpiperidin-4-yl)pyridazin-3-amine (0.9 g, 39% yield). MS m/z 434.2, 436.2 $[M+H]^+$.

Step 2 In a sealed tube, a mixture of 3-(5-bromo-3-methoxy-2-pyridyl)-6-[(3-fluoro-2,2,6,6-tetramethyl-4-piperidyl)oxy]pyridazine (300 mg, 0.69 mmol), imidazole (103 mg, 1.52 mmol), iron (111) acetylacetonate (73 mg, 0.21 mmol), CuI (13 mg, 0.07 mmol), and $CS_2CO_3$ (563 mg, 1.73 mmol) in 10 mL DMF was stirred at 100° C. for 24 h. After cooling to room temperature, the mixture was filtered, and the filtrate was mixed with ice water and extracted with EtOAc. The combined organic layers were dried over $Na_2SO_4$, concentrated, and purified by silica gel column chromatography eluting with a gradient 0-30% MeOH in DCM to provide 3-(5-(1H-imidazol-1-yl)-3-methoxypyridin-2-yl)-6-((3-fluoro-2,2,6,6-tetramethylpiperidin-4-yl)oxy)pyridazine (90 mg, 31% yield). MS m/z 422.3 $[M+H]^+$.

Step 3: To a solution of 6-(5-(1H-imidazol-1-yl)-3-methoxypyridin-2-yl)-N-methyl-N-(2,2,6,6-tetramethylpiperidin-4-yl)pyridazin-3-amine (90 mg, 0.21 mmol) in DCM (1.0 mL) was added $BBr_3$ (1.0 M in DCM, 5 mL) and the reaction was stirred at 50° C. overnight. The mixture was cooled to room temperature and concentrated, and the residue was mixed with ice water, neutralized with aq. $Na_2CO_3$, and extracted with DCM. The combined organic layers were dried over $Na_2SO_4$, concentrated, and purified by Prep-HPLC to give 5-(1H-imidazol-1-yl)-2-{6-[methyl(2,2,6,6-tetramethylpiperidin-4-yl)amino]pyridazin-3-yl}pyridin-3-ol (17 mg, 20% yield). MS m/z 408.0 $[M+H]^+$; $^1H$ NMR (methanol-$d_4$) δ: 8.51 (d, J=9.8 Hz, 1H), 8.49 (d, J=2.2 Hz, 1H), 8.32 (s, 1H), 7.73 (s, 1H), 7.64 (d, J=2.2 Hz, 1H), 7.42 (d, J=9.8 Hz, 1H), 7.23 (s, 1H), 5.19-5.35 (m, 1H), 3.07 (s, 3H), 1.64-1.84 (m, 4H), 1.49 (s, 6H), 1.34 (s, 6H); 2Hs not observed (OH and NH).

Example 13: Preparation of Compound 130

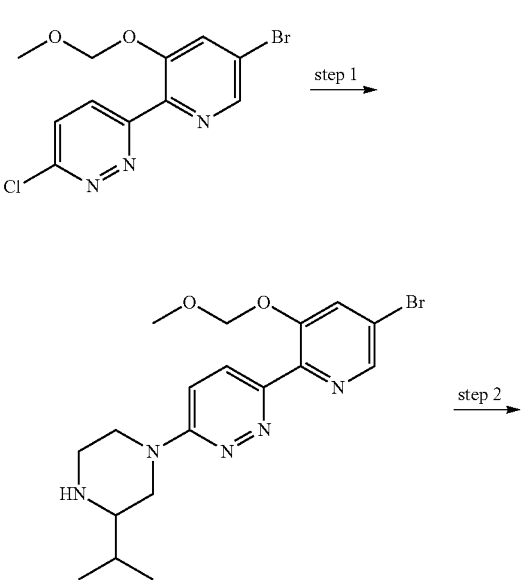

-continued

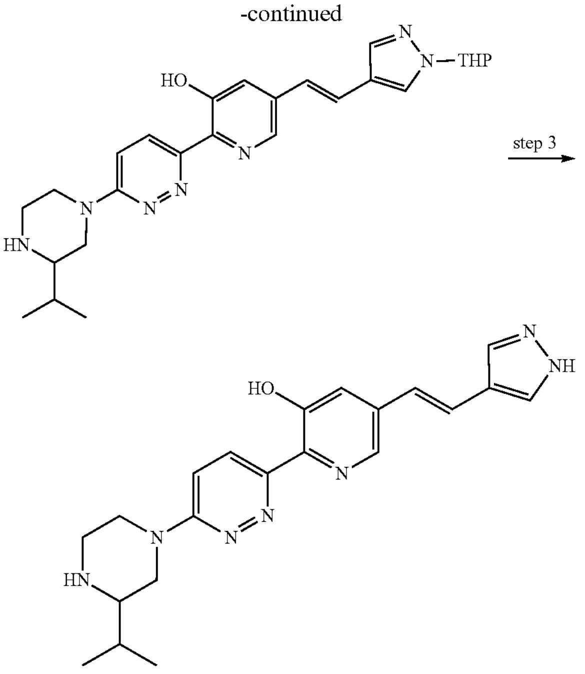

Step 1: A mixture of 3-[5-bromo-3-(methoxymethoxy)-2-pyridyl]-6-chloro-pyridazine (2.0 g, 6.05 mmol), 2-isopropylpiperazine (956.0 mg, 7.08 mmol), ACN (10 mL) and DBU (2.0 g, 12.9 mmol) was stirred at 60° C. for 16 h. After cooling, the mixture was partitioned between EtOAc and water. The organic phase was washed with brine, dried over $MgSO_4$, concentrated. The crude product was purified by silica gel column chromatography eluting with a gradient 0-10% MeOH in DCM to afford 3-[5-bromo-3-(methoxymethoxy)-2-pyridyl]-6-(3-isopropylpiperazin-1-yl)pyridazine (1.51 g, 58.9% yield). MS m/z 422.1, 424.1 $[M+H]^+$.

Step 2: A mixture of 3-[5-bromo-3-(methoxymethoxy)-2-pyridyl]-6-(3-isopropylpiperazin-1-yl)pyridazine (80.0 mg, 0.2 mmol), 1-methyl-4-vinyl-pyrazole (150 mg, 0.36 mmol), $Pd_2dba_3$ (25 mg, 0.02 mmol), tri-tert-butylphosphonium tetrafluoroborate (25.0 mg, 0.082 mmol) was sparged with argon, then DIEA (100 mg, 0.74 mmol) and toluene (2.0 ml) were added. The mixture was stirred under argon atmosphere at 110° C. for 2 h. After cooling, the mixture was partitioned between EtOAc and water. The aqueous phase was extracted with EtOAc (2 times). The combined organic phase was washed with brine, dried over $MgSO_4$, then concentrated. The crude product was purified by silica gel column chromatography eluting with a gradient 0-10% MeOH in DCM to afford 2-[6-(3-isopropylpiperazin-1-yl)pyridazin-3-yl]-5-[(E)-2-(1-tetrahydropyran-2-ylpyrazol-4-yl)vinyl]pyridin-3-ol (15 mg, 9% yield) as a clear oil. MS m/z 476.5 $[M+H]^+$.

Step 3: A mixture of 2-[6-(3-isopropylpiperazin-1-yl)pyridazin-3-yl]-5-[(E)-2-(1-tetrahydropyran-2-ylpyrazol-4-yl)vinyl]pyridin-3-ol (15 mg, 0.03 mmol) and HCl (0.5 ml, 1.4N in MeOH) was stirred at rt for 1 h to afford solid, which was collected by filtration, followed by washing with ether to afford 2-{6-[3-(propan-2-yl)piperazin-1-yl]pyridazin-3-yl}-5-[(E)-2-(1H-pyrazol-4-yl)ethenyl]pyridin-3-ol; dihydrochloride (5 mg, 34.1% yield). MS m/z 392.4 $[M+H]^+$; $^1H$ NMR (DMSO-4): δ ppm 1.07-1.09 (d, 6H), 1.55-1.56 (m, 1H), 1.98-2.04 (m, 1H), 3.52-3.57 (m, 1H), 3.75-3.78 (m, 2H), 3.93-3.98 (m, 1H), 6.79-7.06 (d, 1H), 7.20-7.42 (d, 1H), 7.56 (s, 1H), 7.77-7.79 (d, 1H), 7.92 (s, 2H), 8.35 (s, 1H), 8.48-8.49 (d, 1H), 8.84 (s, 1H), 9.10 (s, 1H).

Using the procedure described for Example 13 above, additional compounds described herein may be prepared by substituting the appropriate starting material, suitable reagents, and reaction conditions, obtaining compounds such as those selected from:

| Cpd | Data |
|---|---|
| 118 | MS m/z 392.3 $[M + H]^+$; $^1H$ NMR (DMSO-$d_6$) δ: 1.37-1.38 (d, 6H), 3.16-3.21 (m, 2H), 3.35 (m, 2H), 3.87 (s, 3H), 4.61 (m, 2H), 6.96-7.0 (d, J = 15.87 Hz, 1H), 7.32-7.35 (d, J = 15.87 Hz, 1H), 7.75-7.81 (m, 3H), 7.97 (s, 1H), 8.39 (s, 1H), 8.51-8.53 (d, J = 9.77 Hz, 1H), 8.65 (br, s, 1 H), 9.94 (br, s, 1H). |

Example 14: Preparation of Compound 108

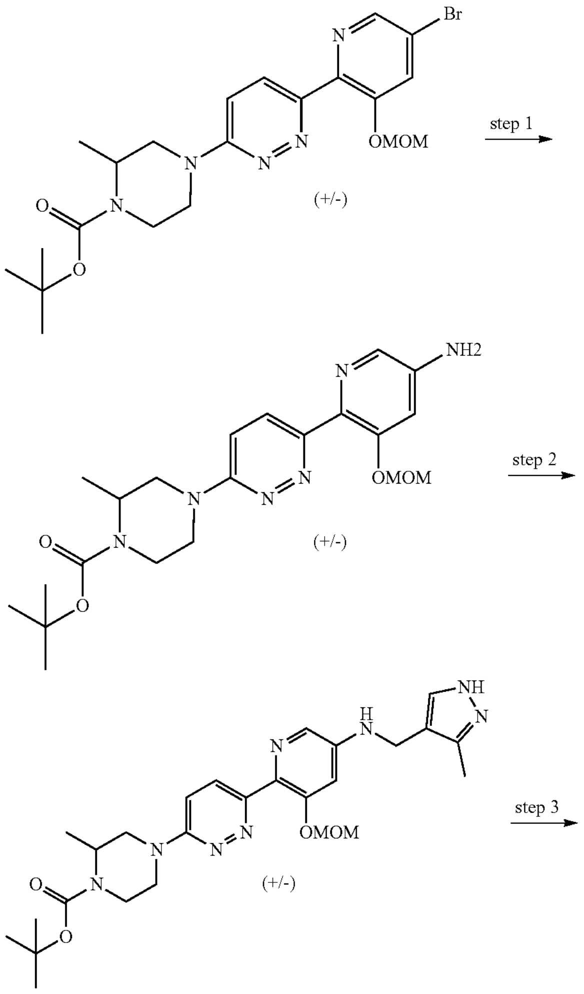

-continued

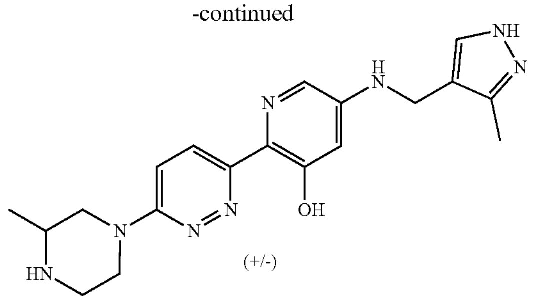

Step 1:tert-Butyl 4-[6-[5-bromo-3-(methoxymethoxy)-2-pyridyl]pyridazin-3-yl]-2-methyl-piperazine-1-carboxylate (3.015 g, 6.098 mmol), sodium tert-butoxide (1.78 g, 18.5 mmol), $Pd_2dba_3$ (157 mg, 0.171 mmol), rac-2,2'-bis(diphenylphosphino)-1,1'-binaphthyl (283 mg, 0.454 mmol), toluene (60 mL), and benzophenone imine (1.22 mL, 7.29 mmol) were combined, degassed with argon, and heated to 80° C. for 5 h. Hydroxylamine hydrochloride (1.58 g, 22.7 mmol), potassium acetate (2.98 g, 30.4 mmol), and methanol (150 mL) were added and the reaction was stirred at 23° C. for 16 h. The reaction was concentrated and the residue was suspended in DCM/MeOH and filtered. The filtrate was concentrated and the residue was purified by silica gel column chromatography eluting with a gradient of 0-10% MeOH in DCM (MeOH with 2.5% v/v 30% aqueous ammonium hydroxide additive) to yield tert-butyl 4-(6-(5-amino-3-(methoxymethoxy)pyridin-2-yl)pyridazin-3-yl)-2-methylpiperazine-1-carboxylate (1.97 g, 75% yield). MS m/z 431.5 $[M+H]^+$.

Step 2: tert-Butyl 4-(6-(5-amino-3-(methoxymethoxy)pyridin-2-yl)pyridazin-3-yl)-2-methylpiperazine-1-carboxylate (76.2 mg, 0.177 mmol), 3-methyl-1H-pyrazole-4-carbaldehyde (21.6 mg, 0.196 mmol), DCM (1.5 mL), and acetic acid (11 μL) were combined and stirred at room temperature for 30 min. Sodium triacetoxyborohydride (90 mg, 0.42 mmol) was added and the reaction stirred at room temperature for 19 h. The reaction was filtered through a small amount of Celite, rinsing with DCM/MeOH. The filtrate was concentrated and the residue was purified by silica gel column chromatography eluting with a gradient 0-15% MeOH in DCM (MeOH with 2.5% v/v 30% aqueous ammonium hydroxide additive) to yield tert-butyl 4-(6-(3-(methoxymethoxy)-5-(((3-methyl-1H-pyrazol-4-yl)methyl)amino)pyridin-2-yl)pyridazin-3-yl)-2-methylpiperazine-1-carboxylate, which was carried directly into the next step.

Step 3: rac-tert-Butyl 4-(6-(3-(methoxymethoxy)-5-(((3-methyl-1H-pyrazol-4-yl)methyl)amino)pyridin-2-yl)pyridazin-3-yl)-2-methylpiperazine-1-carboxylate, DCM (1.0 mL), methanol (0.5 mL), and hydrochloric acid (2.0 M in $Et_2O$, 1 mL) were combined and stirred at 50° C. for 1 h. The reaction was concentrated to yield 2-[6-(3-methylpiperazin-1-yl)pyridazin-3-yl]-5-{[(3-methyl-1H-pyrazol-4-yl)

methyl]amino}pyridin-3-ol dihydrochloride (55.5 mg, 69% over 2 steps). MS m/z 381.5 $[M+H]^+$; $^1H$ NMR (methanol-$d_4$) δ: 8.83 (d, J=10.1 Hz, 1H), 8.28 (s, 1H), 8.02 (d, J=10.1 Hz, 1H), 7.93 (s, 1H), 6.81 (s, 1H), 4.59 (br d, J=14.6 Hz, 2H), 4.44 (s, 2H), 3.59 (br t, J=12.7 Hz, 3H), 3.37 (s, 2H), 2.55 (s, 3H), 1.47 (br d, J=6.4 Hz, 3H); 4H not observed (3 NHs and OH).

Using the procedure described for Example 14 above, additional compounds described herein may be prepared by substituting the appropriate starting material, suitable reagents, and reaction conditions, obtaining compounds such as those selected from:

-continued

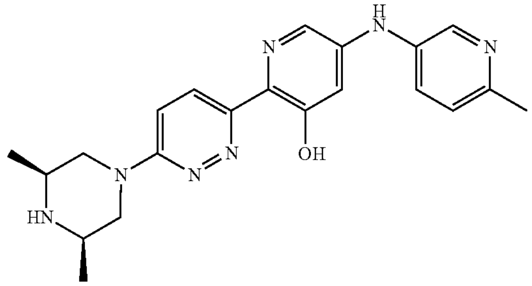

| Cpd | Data |
|---|---|
| 109 | MS m/z 378.3 $[M + H]^+$; $^1H$ NMR (methanol-$d_4$) δ: 8.83-8.91 (m, 2H), 8.63-8.70 (m, 1H), 8.16 (br d, J = 8.2 Hz, 1H), 8.02-8.09 (m, 2H), 8.01 (d, J = 1.8 Hz, 1H), 6.69 (br s, 1H), 4.99 (s, 2H), 4.59 (br d, J = 13.7 Hz, 2H), 3.44-3.63 (m, 4H), 3.26-3.31 (m, 1H), 1.46 (br d, J = 6.7 Hz, 3H); 3H not observed (2 NHs and OH). |
| 110 | MS m/z 378.3 $[M + H]^+$; $^1H$ NMR (methanol-$d_4$) δ: 8.96 (s, 1H), 8.82-8.91 (m, 2H), 8.72 (br d, J = 7.6 Hz, 1H), 8.13-8.18 (m, 1H), 8.01 (br d, J = 10.1 Hz, 1H), 7.96 (d, J = 0.9 Hz, 1H), 6.69 (br s, 1H), 4.79 (s, 2H), 4.58 (br d, J = 14.6 Hz, 2H), 3.45-3.64 (m, 4H), 3.25-3.31 (m, 1H), 1.46 (br d, J = 6.4 Hz, 3H); 3H not observed (1 OH, 2 NH). |
| 111 | MS m/z 378.3 $[M + H]^+$; $^1H$ NMR (methanol-$d_4$) δ: 8.83-8.95 (m, 3H), 8.15 (br d, J = 6.1 Hz, 2H), 8.03 (d, J = 10.1 Hz, 1H), 7.97 (s, 1H), 6.62 (br s, 1H), 4.90 (br s, 2H), 4.58 (br d, J = 14.3 Hz, 2H), 3.45-3.65 (m, 4H), 3.26-3.32 (m, 1H), 1.46 (d, J = 6.4 Hz, 3H); 3H not observed (1 OH, 2 NH). |
| 112 | MS m/z 428.4 $[M + H]^+$; $^1H$ NMR (methanol-$d_4$) δ: 9.36 (s, 1H), 9.25 (s, 1H), 8.84 (d, J = 10.1 Hz, 1H), 8.39 (d, J = 8.5 Hz, 1H), 8.31 (d, J = 8.9 Hz, 1H), 8.19-8.26 (m, 1H), 7.98-8.08 (m, 3H), 6.79 (s, 1H), 4.93 (s, 2H), 4.58 (br d, J = 14.0 Hz, 2H), 3.44-3.64 (m, 4H), 3.25-3.31 (m, 1H), 1.46 (d, J = 6.7 Hz, 3H); 3H not observed (1 OH, 2 NH). |
| 113 | MS m/z 428.4 $[M + H]^+$; $^1H$ NMR (methanol-$d_4$) δ: 9.31 (br d, J = 8.2 Hz, 1H), 9.28 (br d, J = 4.3 Hz, 1H), 8.85 (br d, J = 9.8 Hz, 1H), 8.38 (br d, J = 7.9 Hz, 1H), 8.18-8.28 (m, 2H), 7.96-8.04 (m, 3H), 6.81 (br s, 1H), 5.13 (s, 2H), 4.54-4.63 (m, 2H), 3.44-3.63 (m, 4H), 3.24-3.30 (m, 1H), 1.47 (br d, J = 6.4 Hz, 3H); 3H not observed (1 OH, 2 NH). |

Example 15: Preparation of Compound 125

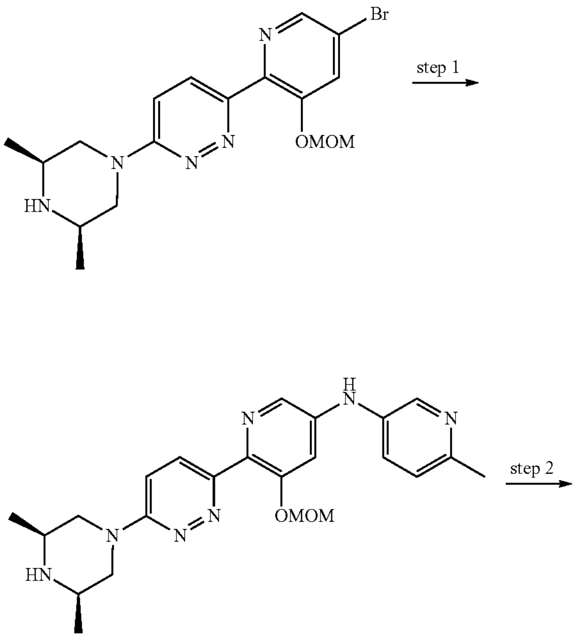

Step 1: 3-[5-Bromo-3-(methoxymethoxy)-2-pyridyl]-6-[(3R,5S)-3,5-dimethylpiperazin-1-yl]pyridazine (60.0 mg, 0.147 mmol), 4,5-bis(diphenylphosphino)-9,9-dimethylxanthene (25.5 mg, 0.0441 mmol), $Pd_2dba_3$ (13.5 mg, 0.0147 mmol), 6-methylpyridin-3-amine (31.2 mg, 0.294 mmol), cesium carbonate (170 mg, 0.522 mmol), and 1,4-dioxane (1.0 mL) were combined, degassed with argon, and heated to 100° C. for 16 h. The reaction was concentrated and the residue was purified by silica gel column chromatography eluting with a gradient 0-30% MeOH in DCM (MeOH with 2.5% v/v 30% aqueous ammonium hydroxide additive) to yield crude 6-(6-((3S,5R)-3,5-dimethylpiperazin-1-yl)pyridazin-3-yl)-5-(methoxymethoxy)-N-(6-methylpyridin-3-yl)pyridin-3-amine which was carried directly into the next step. MS m/z 436.5 $[M+H]^+$.

Step 2: 6-(6-((3S,5R)-3,5-dimethylpiperazin-1-yl)pyridazin-3-yl)-5-(methoxymethoxy)-N-(6-methylpyridin-3-yl)pyridin-3-amine from Step 1 and trifluoroacetic acid (4 mL) was combined and stirred at room temperature for 1 h 30 min. The reaction was concentrated and the residue was dissolved in a mixture of hydrochloric acid (2.0 M in $Et_2O$, 4 mL) and methanol (2 mL), then concentrated to yield 2-{6-[(3R,5S)-3,5-dimethylpiperazin-1-yl]pyridazin-3-yl}-5-[(6-methylpyridin-3-yl)amino]pyridin-3-ol dihydrochloride (25.1 mg, 37% yield over 2 steps). MS m/z 392.5 $[M+H]^+$; $^1H$ NMR (methanol-$d_4$) δ: 8.98 (d, J=10.1 Hz, 1H), 8.56 (d, J=2.7 Hz 1H), 8.35 (dd, J=8.9, 2.4 Hz, 1H) 8.30 (d, J=1.8 Hz, H), 8.16 (d, J=10.1 Hz, 1H), 7.89 (d, J=8.9 Hz, 1H), 7.35 (d, J=1.8 Hz, 1H), 4.73 (br dd, J=14.0, 1.8 Hz, 2H), 3.58 (ddd, J=10.8, 6.7, 3.5 Hz, 2H), 3.19 (dd, J=14.3, 11.9 Hz 2H), 2.77 (s, 3H), 1.49 (d, J=6.7 Hz, 6H); 3H not observed (2 NHs and OH).

Using the procedure described for Example 15 above, additional compounds described herein may be prepared by substituting the appropriate starting material, suitable reagents, and reaction conditions, obtaining compounds such as those selected from:

| Cpd | Data |
|---|---|
| 117 | MS m/z 364.3 [M + H]$^+$; $^1$H NMR (methanol-d$_4$) δ: 8.99 (d, J = 9.8 Hz, 1H), 8.70-8.73 (m, 1H), 8.42-8.47 (m, 2H), 8.36 (d, J = 2.1 Hz, 1H), 8.15 (d, J = 10.1 Hz, 1H), 8.02-8.06 (m, 1H), 7.41 (d, J = 2.1 Hz, 1H), 4.64 (br dd, J = 14.5, 2.9 Hz, 2H), 3.52-3.65 (m, 3H), 3.34-3.40 (m, 2H), 1.48 (d, J = 6.7 Hz, 3H); 3H not observed (1 OH, 2 NH). |
| 127 | MS m/z 406.5 [M + H]$^+$; $^1$H NMR (methanol-d$_4$) δ: 8.96 (d, J = 9.8 Hz, 1H), 8.54 (d, J = 2.7 Hz, 1H), 8.34 (dd, J = 8.9, 2.7 Hz, 1H), 8.29 (d, J = 2.1 Hz, 1H), 8.12 (br d, J = 10.1 Hz, 1H), 7.88 (d, J = 8.9 Hz, 1H), 7.33 (d, J = 2.1 Hz, 1H), 4.75 (br d, J = 13.4 Hz, 1H), 4.64 (br d, J = 15.3 Hz, 1H), 3.46-3.65 (m, 3H), 3.27-3.42 (m, 2H), 2.76 (s, 3H), 2.09 (dt, J = 13.5, 6.8 Hz, 1H), 1.20 (d, J = 6.7 Hz, 6H); 3H not observed (1 OH, 2 NH). |
| 133 | MS m/z 407.5 [M + H]$^+$; $^1$H NMR (methanol-d$_4$) δ: 8.94 (br d, J = 9.8 Hz, 1H), 8.59 (s, 1H), 8.48 (d, J = 1.8 Hz, 1H), 8.36 (s, 1H), 8.27 (s, 1H), 8.07 (br d, J = 10.1 Hz, 1H), 4.76 (br d, J = 13.7 Hz, 1H), 4.64 (br d, J = 14.3 Hz, 1H), 3.60 (br d, J = 12.8 Hz, 1H), 3.38-3.58 (m, 2H), 3.25-3.32 (m, 2H), 2.54 (s, 3H), 2.08 (td, J = 13.5, 6.6 Hz, 1H), 1.20 (d, J = 7.0 Hz, 6H); 3H not observed (1 OH, 2 NH). |
| 134 | MS m/z 407.5 [M + H]$^+$; $^1$H NMR (methanol-d$_4$) δ: 8.92 (br d, J = 10.1 Hz, 1H), 8.78 (s, 2H), 8.19 (br d, J = 2.1 Hz, 1H), 8.07 (br d, J = 10.1 Hz, 1H), 7.20 (br d, J = 2.1 Hz, 1H), 4.74 (br d, J = 12.5 Hz, 1H), 4.62 (br d, J = 13.7 Hz, 1H), 3.60 (br d, J = 12.5 Hz, 1H), 3.48-3.56 (m, 1H), 3.38-3.47 (m, 1H), 3.24-3.32 (m, 2H), 2.72-2.78 (m, 3H), 2.07 (td, J = 13.0, 6.9 Hz, 1H), 1.19 (d, J = 6.7 Hz, 6H); 3H not observed (1 OH, 2 NH). |

Example 16: Preparation of Compound 102

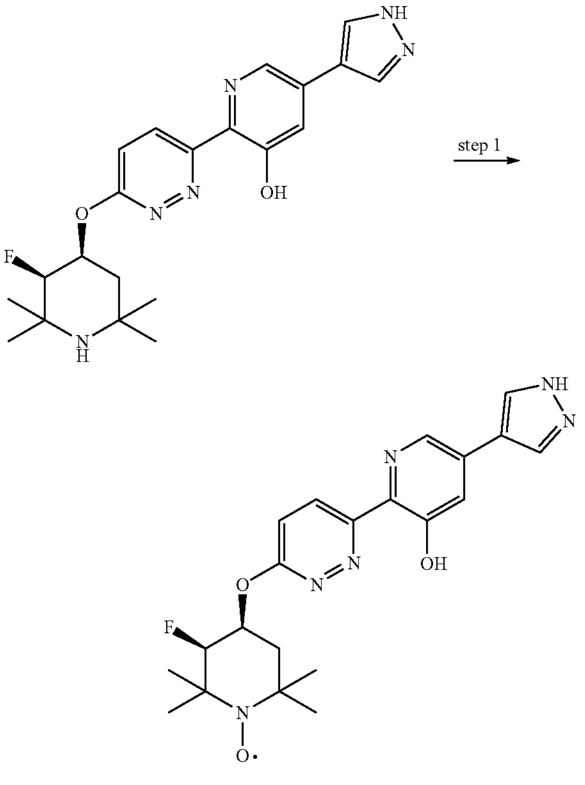

Step 1: To a suspension of 2-[6-[[(3R,4S)-3-fluoro-2,2,6,6-tetramethyl-4-piperidyl]oxy]pyridazin-3-yl]-5-(1H-pyrazol-4-yl)pyridin-3-ol (Compound 51, 50 mg, 0.12) in dichloromethane (1.0 mL) was added 3-chloroperoxybenzoic acid (56 mg, 0.24 mmol, 75 mass %). The mixture was stirred at room temperature for 12 h. The reaction mixture was concentrated, and the product purified by silica gel column chromatography eluting with a gradient 0-30% MeOH in DCM to afford [(3R,4S)-3-fluoro-4-({6-[3-hydroxy-5-(1H-pyrazol-4-yl)pyridin-2-yl]pyridazin-3-yl}oxy)-2,2,6,6-tetramethylpiperidin-1-yl]oxidanyl (20.0 mg, 39% yield) as a white solid. MS m/Z 428.4 [M+H]$^+$.

Example 17: Preparation of Compound 141

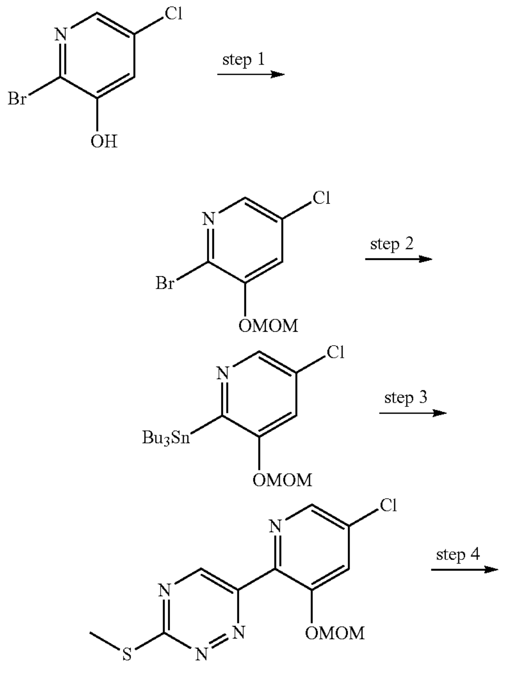

-continued

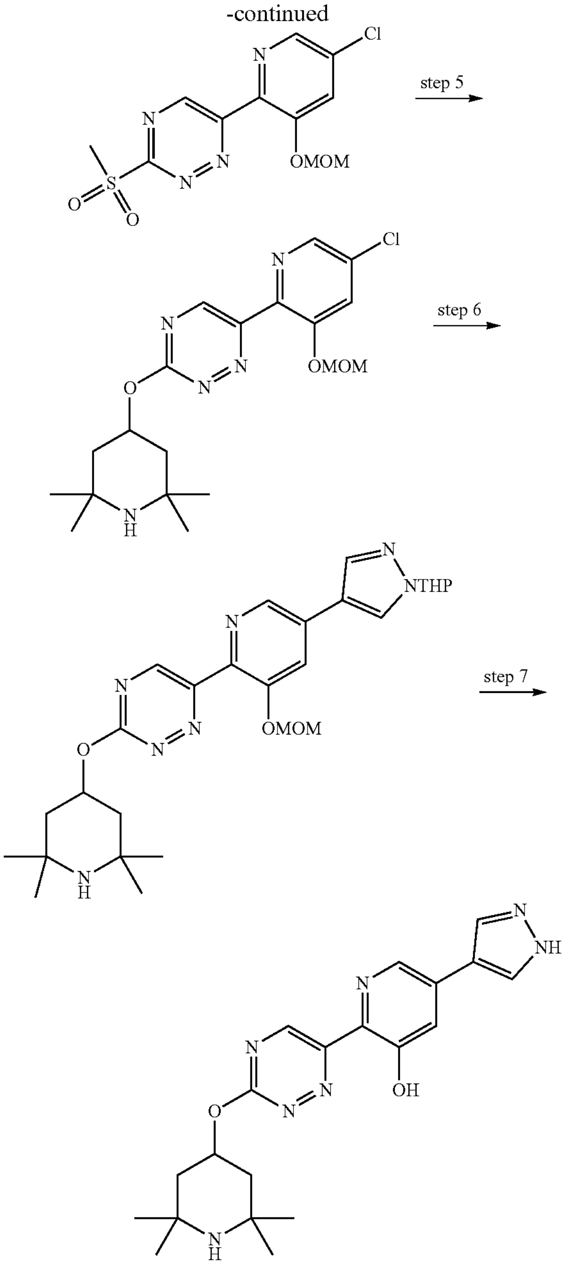

Step 1. A solution of 2-bromo-5-chloropyridin-3-ol (5.0 g, 24.0 mmol, 1.) in DMF (100 mL) was cooled to 0° C. Sodium hydride (1.15 g, 28.8 mmol) was slowly added and the mixture was allowed to stir at 0° C. for 30 minutes. Then, MOM-Cl (2.4 mL, 37.0 mmol) was slowly added using a syringe. The mixture was allowed to warm to room temperature and then was stirred for 2 h. The mixture was diluted with EtOAc and $NH_4Cl$. The organic layer was washed with water, brine, dried over $MgSO_4$, and concentrated. The crude oil was purified by silica gel chromatography using a gradient from 0-40% EtOAc/hexanes to afford 2-bromo-5-chloro-3-(methoxymethoxy)pyridine (4.2 g, 69;% yield) as a white solid. MS m/z 252.2 $[M+H]^+$.

Step 2: 2-Bromo-5-chloro-3-(methoxymethoxy)pyridine (4.2 g, 17.0 mmol) was dissolved in toluene (100 mL) and cooled to −30° C. under argon. nBuLi (12.0 mL, 19.0 mmol) was slowly added and the solution was allowed to stir at −30° C. for 30 min. Tributyltin chloride (5.9 mL, 22.0 mmol) was added slowly to the reaction mixture and the solution was allowed to warm to room temperature and stir for 2 h. A small pad of silica gel was deactivated with 10% $NEt_3$/hexanes and the stannane was passed over this silica gel using hexanes. Concentration afforded 5-chloro-3-(methoxymethoxy)-2-(tributylstannyl)pyridine (7.7 g, 94% yield) as a yellow oil. MS m/z 486.4 $[M+Na]^+$.

Step 3: A microwave vial charged with 6-bromo-3-(methylthio)-1,2,4-triazine (2.0 g, 9.7 mmol), 5-chloro-3-(methoxymethoxy)-2-(tributylstannyl)pyridine (5.8 g, 13.0 mmol), copper iodide (0.37 g, 1.9 mmol), $Pd(PPh_3)_2Cl_2$ (0.68 g, 1.0 mmol) was purged with argon and dioxane (15 mL) was added. The vial was heated in a microwave at 120° C. for 1 h. The black solution was filtered and concentrated under vacuum. The crude oil was purified by silica gel chromatography using a gradient from 70-100% EtOAc/hexanes to afford 6-(5-chloro-3-(methoxymethoxy)pyridin-2-yl)-3-(methylthio)-1,2,4-triazine (1.8 g, 62% yield) as a yellow oil which crystallized upon standing. MS mi 299.3 $[M+H]^+$.

Step 4: To a solution of 6-(5-chloro-3-(methoxymethoxy)pyridin-2-yl)-3-(methylthio)-1,2,4-triazine (0.6 g, 2.0 mmol, 1.0 equiv.) in $CH_2Cl_2$ (10 mL) was slowly added dry m-CPBA (0.76 g, 4.4 mmol, 2.2 equiv.) and the reaction was stirred for 4 h at room temperature. The crude mixture was directly purified by silica gel chromatography using a gradient from 0-100% EtOAc/hexanes to afford 6-(5-chloro-3-(methoxymethoxy)pyridin-2-yl)-3-(methylsulfonyl)-1,2,4-triazine (0.35 g, 53% yield) as a yellow solid. MS m/z 331.2 $[M+H]^+$.

Step 5: 2,2,6,6-Tetramethylpiperidin-4-ol (0.17 g, 1.06 mmol) was dissolved in THF (3.0 mL) and cooled to 0° C. under Ar. LiOtBu (0.85 mL, 0.85 mmol, 1.0 M in THF) was added to the reaction mixture dropwise and allowed to stir 20 min at 0° C. To a separate vial was added 6-(5-chloro-3-(methoxymethoxy)pyridin-2-yl)-3-(methylsulfonyl)-1,2,4-triazine (0.14 g, 0.42 mmol, 1.0 equiv.) and dissolved in THF (3.0 mL) and cooled to 0° C. The solution of alkoxide (the first vial) was added dropwise to the vial containing sulfone (the second vial) and the reaction was stirred 45 min at 0° C. The solution was diluted with EtOAc and washed with water, dried over $MgSO_4$, filtered and concentrated. The crude mixture was purified by silica gel chromatography using a gradient from 0-30% $MeOH/CH_2Cl_2$ to afford 6-(5-chloro-3-(methoxymethoxy)pyridin-2-yl)-3-((2,2,6,6-tetramethylpiperidin-4-yl)oxy)-1,2,4-triazine (0.12 g, 70% yield) as a yellow solid. MS m/z 408.5 $[M+H]^+$.

Step 6: A vial was charged with 6-(5-chloro-3-(methoxymethoxy)pyridin-2-yl)-3-((2,2,6,6-tetramethylpiperidin-4-yl)oxy)-1,2,4-triazine (0.07 g, 0.17 mmol), 1-(tetrahydro-2H-pyran-2-yl)-4-(4,4,5,5-tetramethyl-1,3,2-dioxaborolan-2-yl)-1H-pyrazole (0.08 g, 0.29 mmol, 1.5 equiv.), XPhos Pd G3 (0.02 g, 0.08 mmol), $K_2CO_3$ (0.07 g, 0.58 mmol), dioxane (5 mL), water (1 mL) and purged with argon. The mixture was stirred for 1 h at 100° C. Once cooled and concentrated, the mixture was purified by silica gel column chromatography eluting with a gradient from 0-25% $MeOH/CH_2Cl_2$ to afford 6-(3-(methoxymethoxy)-5-(1-(tetrahydro-2H-pyran-2-yl)-1H-pyrazol-4-yl)pyridin-2-yl)-3-((2,2,6,6-tetramethylpiperidin-4-yl)oxy)-1,2,4-triazine (0.08 g, 89% yield) as an orange oil. MS m/z 524.6 $[M+H]^+$.

Step 7: To a solution of 6-(3-(methoxymethoxy)-5-(1-(tetrahydro-2H-pyran-2-yl)-1H-pyrazol-4-yl)pyridin-2-yl)-3-((2,2,6,6-tetramethylpiperidin-4-yl)oxy)-1,2,4-triazine (0.08 g, 0.15 mmol) in MeOH (1 mL) was added 4.0M HCl/dioxane (0.5 mL) dropwise and the reaction was allowed to stir 1 h at room temperature. The mixture was concentrated and purified by silica gel column chromatography eluting with a gradient from 0-30% MeOH/$CH_2Cl_2$ to afford 5-(1H-pyrazol-4-yl)-2-{3-[(2,2,6,6-tetramethylpiperidin-4-yl)oxy]-1,2,4-triazin-6-yl}pyridin-3-ol (0.05 g, 0.13 mmol, 84% yield) as the HCl salt as a yellow solid. MS m/z 396.5 $[M+H]^+$; $^1H$ NMR (methanol-$d_4$) δ: 9.69 (s, 1H), 8.60 (s, 1H), 8.18 (s, 2H), 7.70 (s, 1H), 5.78 (br, s, 1H), 2.52 (d, J=14.5 Hz, 2H), 1.94 (t, J=12.0 Hz, 2H), 1.64 (s, 6H), 1.56 (s, 6H); 3Hs not observed (2 NHs and OH).

Example 18: Preparation of Compound 145

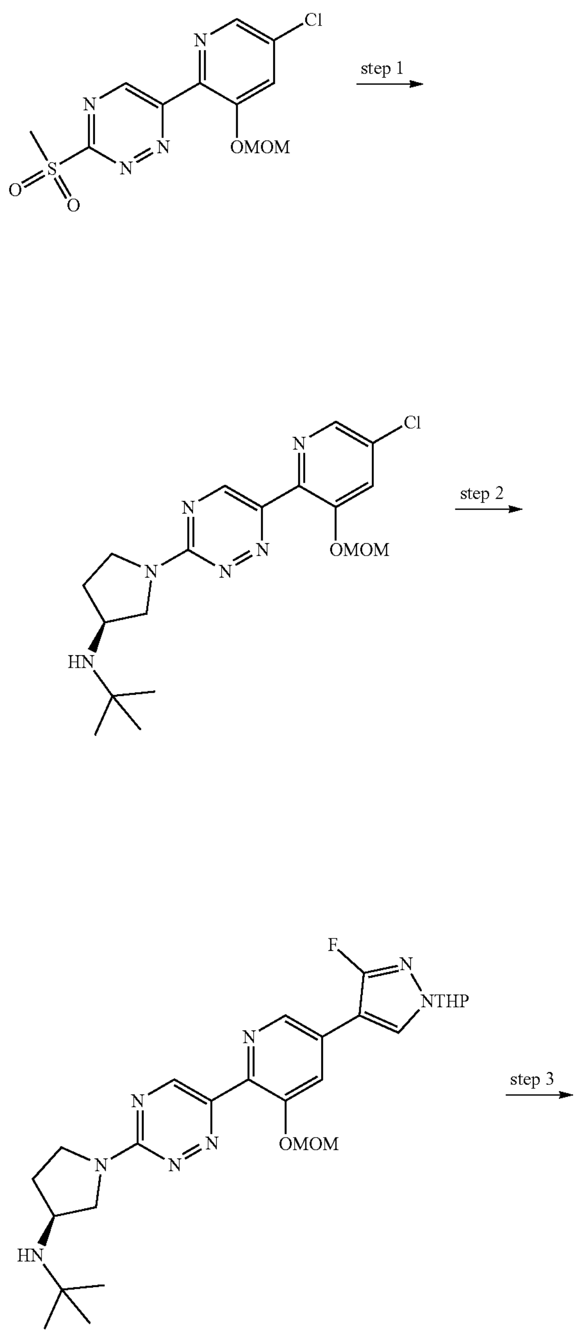

-continued

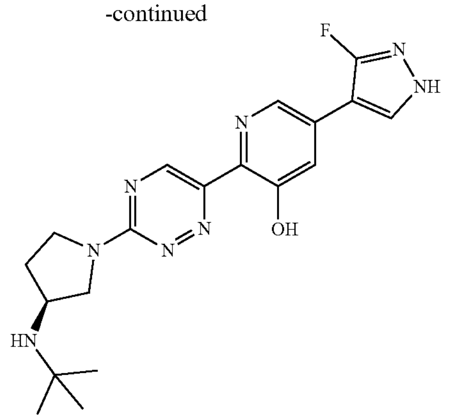

Step 1: 6-(5-Chloro-3-(methoxymethoxy)pyridin-2-yl)-3-(methylsulfonyl)-1,2,4-triazine (0.16 g, 0.48 mmol) and (S)—N-(tert-butyl)pyrrolidin-3-amine (0.09 g, 0.60 mmol) were dissolved in DMF (4 mL) and $NEt_3$ (0.7 mL, 4.8 mmol) was added. The mixture was stirred for 2 h at room temperature. The solvent was removed and the crude mixture was purified by silica gel column chromatography eluting with a gradient from 0-20% MeOH/$CH_2Cl_2$ to afford (S)—N-(tert-butyl)-1-(6-(5-chloro-3-(methoxymethoxy)pyridin-2-yl)-1,2,4-triazin-3-yl)pyrrolidin-3-amine (0.04 g, 52% yield) as a yellow oil. MS m/z 393.4 $[M+H]^+$.

Step 2: To a vial containing (S)—N-(tert-butyl)-1-(6-(5-chloro-3-(methoxymethoxy)pyridin-2-yl)-1,2,4-triazin-3-yl)pyrrolidin-3-amine (0.05 g, 0.13 mmol), 3-fluoro-1-(tetrahydro-2H-pyran-2-yl)-4-(4,4,5,5-tetramethyl-1,3,2-dioxaborolan-2-yl)-1H-pyrrole (0.06 g, 0.20 mmol), XPhos Pd G3 (0.01 g, 0.03 mmol) and $K_2CO_3$ (0.05 g, 0.38 mmol, 3.0 equiv.) was added dioxane (5 mL), water (I mL) and the vial was purged with argon. The mixture stirred for 1 h at 100° C. Once cooled and concentrated, the mixture was purified by silica gel column chromatography eluting with a gradient from 0-25% MeOH/$CH_2Cl_2$ to afford (3S)—N-(tert-butyl)-1-(6-(5-(3-fluoro-1-(tetrahydro-2H-pyran-2-yl)-1H-pyrazol-4-yl)-3-(methoxymethoxy)pyridin-2-yl)-1,2,4-triazin-3-yl)pyrrolidin-3-amine (0.04 g, 52% yield) as an orange oil. MS m/z 527.6 $[M+H]^+$.

Step 3: To a vial containing (3S)—N-(tert-butyl)-1-(6-(5-(3-fluoro-1-(tetrahydro-2H-pyran-2-yl)-1H-pyrazol-4-yl)-3-(methoxymethoxy)pyridin-2-yl)-1,2,4-triazin-3-yl)pyrrolidin-3-amine (0.04 g, 0.07 mmol,) in MeOH (1 mL) was added 4.0M HCl/dioxane (0.5 mL) dropwise and the solution was stirred for 1 h at room temperature. The solution was concentrated and purified by silica gel column chromatography eluting with a gradient from 0-30% MeOH/$CH_2Cl_2$ to afford 2-{3-[(3S)-3-(tert-butylamino)pyrrolidin-1-yl]-1,2,4-triazin-6-yl}-5-(3-fluoro-1H-pyrazol-4-yl)pyridin-3-ol (0.01 g, 47% yield) as a yellow solid. MS m/z 399.5 $[M+H]^+$; $^1H$ NMR (methanol-$d_4$) δ: 9.41 (s, 1H), 8.46 (s, 1H), 8.12 (s, 1H), 7.56 (s, 1H), 4.11 (t, J=9.5 Hz, 1H), 3.94 (t, J=11.0 Hz, 1H), 3.90-3.83 (m, 1H), 3.73-3.63 (m, 1H), 3.51-3.41 (m, 1H), 2.50-2.41 (m, 1H), 2.10-2.00 (m, 1H), 1.31 (s, 9H); 3H not observed (1 OH, 2 NH).

Using the procedure described for Example 18 above, additional compounds described herein may be prepared by substituting the appropriate starting material, suitable reagents, and reaction conditions, obtaining compounds such as those selected from:

| Cpd | Data |
|---|---|
| 135 | MS m/z 409.4 [M + H]$^+$; $^1$H NMR (methanol-$d_4$) δ: 9.43 (s, 1H), 8.55 (s, 1H), 8.15 (s, 2H), 7.66 (s, 1H), 5.50-5.36 (m, 1H), 3.26 (s, 3H), 2.02 (d, J = 8.0 Hz, 4H), 1.65 (s, 6H), 1.54 (s, 6H); 3Hs not observed (2NHs and OH). |
| 136 | MS m/z 381.4 [M + H]$^+$; $^1$H NMR (DMSO-$d_6$) δ: 9.39 (s, 2H), 9.18-9.31 (m, 1H), 9.06-9.18 (m, 1H), 8.59 (s, 1H), 8.29 (br s, 2H), 7.73 (s, 1H), 4.13-4.25 (m, 2H), 4.04-4.13 (m, 1H), 3.78-3.96 (m, 2H), 3.55-3.77 (m, 1H), 2.26-2.47 (m, 1H), 1.40 (s, 9H) |
| 137 | MS m/z 398.5 [M + H]$^+$; $^1$H NMR (DMSO-$d_6$) δ: 9.39-9.47 (m, 1H), 9.36 (s, 1H), 9.29-9.34 (m, 1H), 8.55 (s, 1H), 8.38 (s, 1H), 8.07 (s, 1H), 7.74 (br s, 1H), 4.01-4.23 (m, 2H), 3.79-4.01 (m, 2H), 3.56-3.74 (m, 1H), 2.25-2.47 (m, 2H), 1.40 (s, 9H). |
| 139 | MS m/z 413.5 [M + H]$^+$; $^1$H NMR (DMSO-$d_6$) δ: 9.31 (s, 1H), 8.62 (s, 1H), 8.32 (s, 2H), 7.88 (s, 1H), 4.70-4.90 (m, 2H), 1.99-2.07 (m, 1H), 1.90-1.96 (m, 1H), 1.53-1.60 (m, 6H), 1.48 (s, 6H); 4Hs not observed (3 NHs and OH). |
| 140 | MS m/z 430.7 [M + H]$^+$; $^1$H NMR (methanol-$d_4$) δ: 9.43 (s, 1H), 8.48 (s, 1H), 8.17 (s, 1H), 7.95 (s, 1H), 7.51 (s, 1H), 4.70-4.85 (m, 1H), 4.40-4.60 (m, 1H), 1.76-1.80 (m, 2H), 1.38 (s, 6H), 1.27 (s, 6H); 3Hs not observed (2 NHs and OH). |
| 142 | MS m/z 426.4 [M + H]$^+$; $^1$H NMR (DMSO-$d_6$) δ: 9.31 (s, 1H), 8.81 (d, J = 11.9 Hz, 1H), 8.56 (s, 1H), 8.41 (s, 1H), 8.09 (s, 1H), 7.79-7.96 (m, 2H), 5.18-5.40 (m, 1H), 3.17 (s, 3H), 1.98 (t, J = 12.8 Hz, 2H), 1.83-1.92 (m, 2H), 1.51 (s, 6H), 1.44 (s, 6H). |
| 143 | MS m/z 427.5 [M + H]$^+$; $^1$H NMR (DMSO-$d_6$) δ: 13.15 (br s, 1H), 9.34 (s, 1H), 8.64 (s, 1H), 7.80 (s, 1H), 7.36-7.56 (m, 1H), 6.69 (d, J = 5.8 Hz, 1H), 5.07-5.35 (m, 1H), 3.12 (s, 3H), 1.55-1.70 (m, 4H), 1.32 (s, 6H), 1.21 (s, 6H); 1 H not observed (NH). |
| 146 | MS m/z 475.5 [M + H]$^+$; $^1$H NMR (DMSO-$d_6$) δ: 9.36 (s, 1H), 8.64 (s, 1H), 8.38 (s, 1H), 7.75 (s, 1H), 7.68 (s, 1H), 6.97 (s, 1H) 4.17 (s, 3H), 4.02 (s, 3H), 3.96-3.87 (m, 1H), 3.83-3.71 (m, 1H), 3.63-3.50 (m, 1H), 2.57 (t, J = 6.5 Hz, 1H), 2.30-2.20 (m, 1H), 1.96-1.83 (m, 1H), 1.14 (s, 9H), 0.85 (t, J = 6.5 Hz, 1H); 3H not observed (1 OH, 2 NH). |
| 147 | MS m/z 470.4 [M + H]$^+$; $^1$H NMR (methanol-$d_4$) δ: 9.54 (s, 1H), 9.46 (br s, 1H), 8.83 (d, J = 12.2 Hz, 1H), 8.68 (d, J = 24.1 Hz, 1H), 8.16 (s, 1H), 7.88 (d, J = 9.2 Hz, 1H), 4.29-4.44 (m, 1H), 4.14-4.28 (m, 1H), 3.91-4.13 (m, 2H), 3.74-3.90 (m, 1H), 2.67-2.80 (m, 1H), 2.64 (s, 3H), 2.26-2.53 (m, 1H), 1.53 (s, 9H); 2Hs not observed (NH and OH). |
| 148 | MS m/z 473.5 [M + H]$^+$; $^1$H NMR (methanol-$d_4$) δ: 9.54 (s, 1H), 9.06 (d, J = 8.9 Hz, 1H), 8.67 (d, J = 28.1 Hz, 1H), 8.14 (s, 1H), 8.05 (s, 1H), 7.85 (br d, J = 10.4 Hz, 1H), 4.28-4.42 (m, 1H), 4.12-4.26 (m, 1H), 4.02-4.09 (m, 1H), 3.92-3.99 (m, 1H), 3.75-3.89 (m, 1H), 3.12 (q, J = 7.5 Hz, 2H), 2.67-2.76 (m, 1H), 2.63 (s, 3H), 2.29-2.52 (m, 1H), 1.53 (s, 9H), 1.49 (t, J = 7.5 Hz, 3H); 2Hs not observed (NH and OH). |
| 149 | MS m/z 433.4 [M + H]$^+$; $^1$H NMR (DMSO-$d_6$) δ: 11.71-12.29 (m, 1H), 9.28-9.39 (m, 1H), 8.66 (d, J = 1.8 Hz, 1H), 8.39 (s, 1H), 7.77 (d, J = 1.8 Hz, 1H), 7.69 (s, 1H), 6.99 (s, 1H), 4.18 (s, 3H), 4.03 (s, 3H), 3.84-3.94 (m, 2H), 3.18 (d, J = 5.1 Hz, 2H), 2.46 (br t, J = 5.1 Hz, 2H), 2.26 (s, 3H), 1.24 (s, 2H). |
| 150 | MS m/z 433.4 [M + H]$^+$; $^1$H NMR (DMSO-$d_6$) δ: 11.71-12.29 (m, 1H), 9.28-9.39 (m, 1H), 8.66 (d, J = 1.8 Hz, 1H), 8.39 (s, 1H), 7.77 (d, J = 1.8 Hz, 1H), 7.69 (s, 1H), 6.99 (s, 1H), 4.18 (s, 3H), 4.03 (s, 3H), 3.84-3.94 (m, 2H), 3.18 (d, J = 5.1 Hz, 2H), 2.46 (br t, J = 5.1 Hz, 2H), 2.26 (s, 3H), 1.24 (s, 2H). |
| 151 | MS m/z 421.4 [M + H]$^+$; $^1$H NMR (DMSO-$d_6$) δ: 9.41 (s, 1H), 8.98 (s, 1H), 8.66 (s, 1H), 7.85 (s, 1H), 7.83 (s, 1H), 7.67 (d, J = 12.0 Hz, 1H), 3.72-3.50 (m, 4H), 3.16 (s, 3H), 2.78 (s, 4H), 2.39 (s, 3H); 3H not observed (1 OH, 2 NH). |
| 152 | MS m/z 339.2 [M + H]$^+$; $^1$H NMR (DMSO-$d_6$) δ: 13.21 (s, 1H), 12.00 (s, 1H), 9.31 (s, 1H), 8.57 (s, 1H), 8.41 (s, 1H), 8.10 (s, 1H), 7.67 (s, 1H), 3.88 (s, 4H), 2.45 (s, 4H), 2.24 (s, 3H). |
| 153 | MS m/z 417.4 [M + H]$^+$; $^1$H NMR (DMSO-$d_6$) δ: 12.04 (s, 1H), 11.57 (s, 1H), 9.42 (s, 1H), 9.20 (s, 1H), 8.69 (s, 1H), 8.02 (s, 1H), 7.87 (s, 1H), 4.80 (s, 2H), 3.65-3.53 (m, 4H), 3.22-3.17 (m, 2H), 2.80 (s, 3H), 2.64 (s, 6H). |
| 155 | MS m/z 449.5 [M + H]$^+$; $^1$H NMR (DMSO-$d_6$) δ: 12.08 (s, br, 1H), 9.35 (s, 1H), 8.66 (s, 1H), 8.59 (s, 1H), 8.04 (s, 1H), 7.78 (s, 1H), 7.56 (d, J = 14.0 Hz, 1H), 4.71-4.52 (m, 2H), 3.07 (t, J = 11.5 Hz, 2H), 2.82 (t, J = 11.5 Hz, 2H), 2.71 (t, J = 12.0 Hz, 2H), 1.70-1.64 (m, 1H), 0.98 (d, J = 7.0 Hz, 6H); 3H not observed (1 OH, 2 NH). |
| 157 | MS m/z 431.4 [M + H]$^+$; $^1$H NMR (DMSO-$d_6$) δ: 12.03 (s, 1H), 9.46 (s, 1H), 9.26 (s, 1H), 9.18 (br s, 1H), 8.91 (s, 1H), 8.79 (s, 1H), 8.00 (s, 1H), 4.80-4.61 (m, 2H), 4.61 (s, 3H), 3.50 (t, J = 13.0 Hz, 3H), 3.12 (t, J = 11.5 Hz, 1H), 2.71 (t, J = 9.5 Hz, 1H), 1.06 (s, br, 1H), 0.73-0.64 (m, 2H), 0.55 (s, br, 1H), 0.46 (s, 1H); 3H not observed (1 OH, 2 NH). |
| 158 | MS m/z 447.4 [M + H]$^+$; $^1$H NMR (DMSO-$d_6$) δ: 11.98 (br s, 1H), 9.32 (s, 1H), 8.61 (d, J = 2.0 Hz, 1H), 8.54 (d, J = 2.0 Hz, 1H), 8.00 (d, J = 1.0 Hz, 1H), 7.73 (d, J = 2.0 Hz, 1H), 7.51 (dd, J = 13.0, 1.0 Hz, 1H), 4.65 (d, J = 13.0 Hz, 1H), 4.56 (d, J = 13.0 Hz, 1H), 4.19 (s, 3H), 3.20-3.05 (m, 4H), 2.75 (t, J = 11.5 Hz, 1H), 2.13 (br s, 1H), 0.89-0.81 (m, 1H), 0.53-0.44 (m, 2H), 0.35-0.32 (m, 1H), 0.29-0.26 (m, 1H). |

Example 19: Preparation of Compound 156

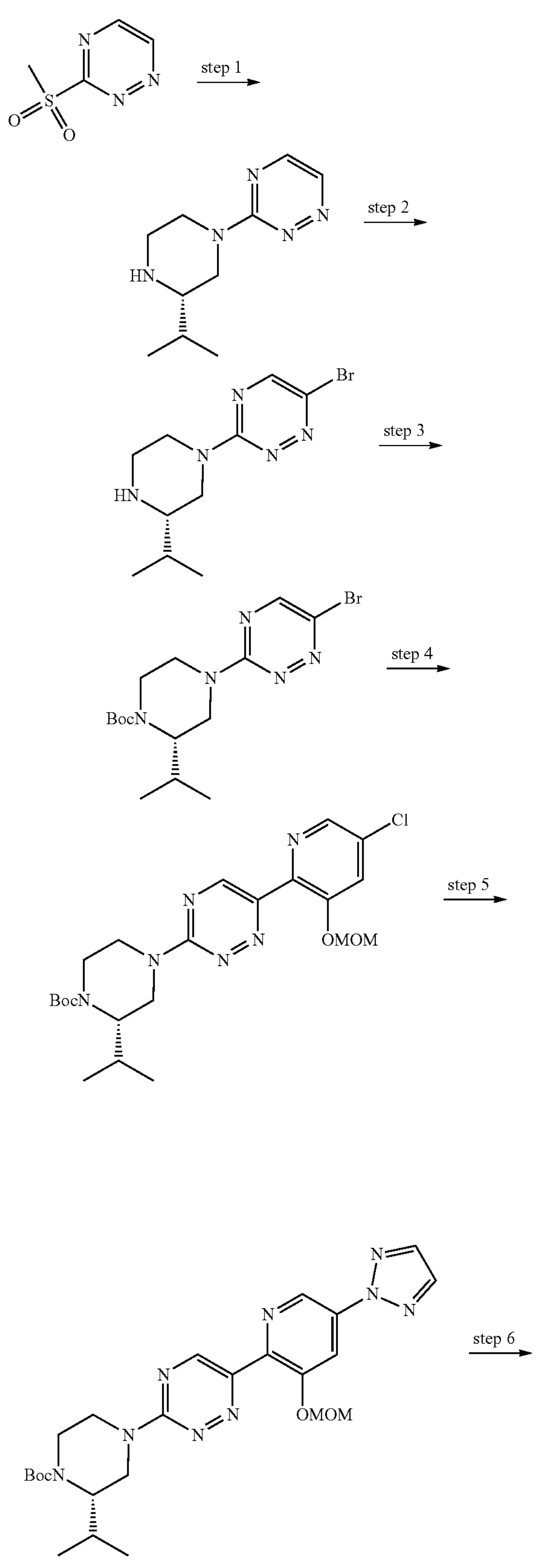

-continued

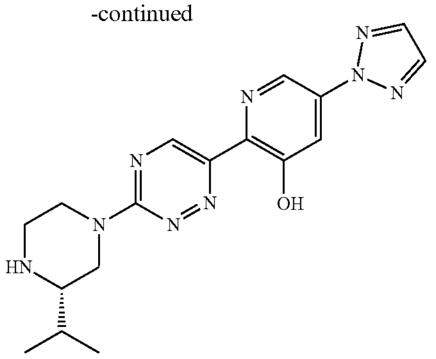

Step 1: To a flask containing 3-(methylsulfonyl)-1,2,4-triazine (3.0 g, 18.8 mmol) and the bis-TFA salt of (S)-2-isopropylpiperazine (7.33 g, 22.6 mmol) in DMF (200 mL) was added $NEt_3$ (26 mL, 187.0 mmol) and the reaction was stirred for 12 h at room temperature. The solvent was removed and the crude mixture was purified by silica gel column chromatography eluting with a gradient 0-30% $MeOH/CH_2Cl_2$ to afford (S)-3-(3-isopropylpiperazin-1-yl)-1,2,4-triazine (1.8 g, 46% yield) as a brown solid. MS m/z 208.3 $[M+H]^+$.

Step 2: To a solution of (S)-3-(3-isopropylpiperazin-1-yl)-1,2,4-triazine (1.8 g, 8.7 mmol) in a mixture of methanol (25 mL) and water (100 mL) was added bromine (0.7 mL, 13.0 mmol) dropwise and the reaction was stirred for 12 h at room temperature. The mixture was partitioned between EtOAc and water and washed with $NaHCO_3$, water and brine, dried over $MgSO_4$, filtered and concentrated. The crude oil was purified by silica gel column chromatography eluting with a gradient from 0-25% $MeOH/CH_2Cl_2$ to afford (S)-6-bromo-3-(3-isopropylpiperazin-1-yl)-1,2,4-triazine (1.7 g, 68% yield) as a dark brown solid. MS m/z 286.2, 288.2 $[M+H]^+$.

Step 3: To a flask containing (S)-6-bromo-3-(3-isopropylpiperazin-1-yl)-1,2,4-triazine (1.7 g, 6.0 mmol), $Boc_2O$ (1.7 g, 7.8 mmol) and $NEt_3$ (2.5 mL, 18.0 mmol) in $CH_2Cl_2$ (100 mL) was added DMAP (0.2 g, 1.2 mmol) and the reaction mixture was stirred for 12 h at room temperature. The mixture was washed with water, dried over $MgSO_4$, filtered and concentrated. The crude product was purified by silica gel column chromatography eluting with a gradient from 0-100% EtOAc/hexanes to afford tert-butyl (S)-4-(6-bromo-1,2,4-triazin-3-yl)-2-isopropylpiperazine-1-carboxylate (2.1 g, 90% yield) as a yellow solid. MS m/z 386.3, 388.3 $[M+H]^+$.

Step 4: To a microwave vial containing tert-butyl (S)-4-(6-bromo-1,2,4-triazin-3-yl)-2-isopropylpiperazine-1-carboxylate (1.3 g, 3.4 mmol), 5-chloro-3-(methoxymethoxy)-2-(tributylstannyl)pyridine (1.9 g, 4.1 mmol), copper iodide (0.1 g, 0.7 mmol), $Pd(PPh_3)_2Cl_2$ (0.24 g, 0.3 mmol) was added dioxane (20 mL) and purged with argon. The vial was heated in the microwave at 120° C. for 1 h. The crude mixture was filtered, concentrated and purified by silica gel column chromatography eluting with a gradient of 0-100% EtOAc/hexanes to afford tert-butyl (S)-4-(6-(5-chloro-3-(methoxymethoxy)pyridin-2-yl)-1,2,4-triazin-3-yl)-2-isopropylpiperazine-1-carboxylate (0.8 g, 51% yield) as a yellow solid. MS m/z 479.3 $[M+H]^+$.

Step 5: To a microwave vial containing $Pd_2(dba)_3$ (0.01 g, 0.01 mmol), 4-MetBuXPhos (0.01 g, 0.01 mmol) was added toluene (3.0 mL). The vial was purged with argon and heated in the microwave at 120° C. for 10 min to generate the active catalyst. In a separate vial were mixed tert-butyl (S)-4-(6-(5-chloro-3-(methoxymethoxy)pyridin-2-yl)-1,2,4-triazin-3-yl)-2-isopropylpiperazine-1-carboxylate (0.06 g, 0.1 mmol), triazole (0.06 g, 0.2 mmol), $K_3PO_4$ (0.3 g, 1.4 mmol) and toluene (3 mL) and purged with argon. The catalyst solution was added to this vial by syringe and then heated in the microwave at 120° C. for 1 h. The solvent was removed and the crude mixture was purified by silica gel column chromatography eluting with a gradient of 0-100% EtOAc/hexanes to afford tert-butyl (S)-2-isopropyl-4-(6-(3-(methoxymethoxy)-5-(2H-1,2,3-triazol-2-yl)pyridin-2-yl)-1,2,4-triazin-3-yl)piperazine-1-carboxylate (0.04 g, 72% yield) as a yellow oil. MS m/z 512.4 $[M+H]^+$.

Step 6: To a solution of tert-butyl (S)-2-isopropyl-4-(6-(3-(methoxymethoxy)-5-(2H-1,2,3-triazol-2-yl)pyridin-2-yl)-1,2,4-triazin-3-yl)piperazine-1-carboxylate (0.04 g, 0.08 mmol) in MeOH (1 mL) was added 4.0M HCl/dioxane (0.5 mL) dropwise and the reaction was stirred for 1 h at room temperature. The mixture was concentrated and purified by silica gel column chromatography eluting with a gradient from 0-30% MeOH/$CH_2Cl_2$ to afford 2-{3-[(3S)-3-(propan-2-yl)piperazin-1-yl]-1,2,4-triazin-6-yl}-5-(2H-1,2,3-triazol-2-yl)pyridin-3-ol (0.02 g, 73% yield) as a yellow solid.

MS m/z 368.3 $[M+H]^+$; $^1H$ NMR (DMSO-$d_6$) δ: 9.28 (s, 1H), 8.91 (d, J=2.0 Hz, 1H), 8.26 (s, 2H), 7.94 (d, J=2.0 Hz, 1H), 4.68-4.58 (m, 2H), 3.07 (t, J=11.0 Hz, 2H), 2.83 (t, J=11.5 Hz, 1H), 2.71 (t, J=10.0 Hz, 2H), 2.40 (s, br, 1H), 1.71-1.64 (m, 1H), 0.98 (d, J=6.5 Hz, 6H); 3Hs not observed (2 NHs and OH).

Using the procedure described for Example 19 above, additional compounds described herein may be prepared by substituting the appropriate starting material, suitable reagents, and reaction conditions, obtaining compounds such as those selected from:

-continued

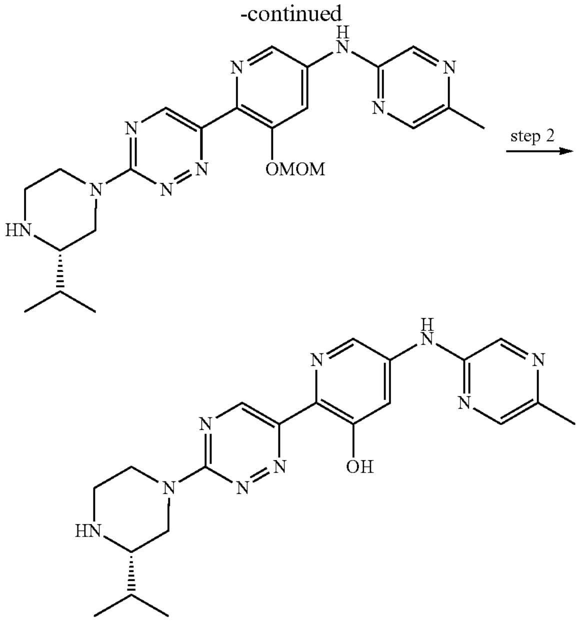

Step 1: A microwave vial was charged with (S)-6-(5-chloro-3-(methoxymethoxy)pyridin-2-yl)-34(3-isopropylpiperazin-1-yl)-1,2,4-triazine (0.03 g, 0.08 mmol), 5-methylpyrazin-2-amine (0.01 g, 0.13 mmol), $K_2CO_3$ (0.04 g, 0.25 mmol) and BrettPhos Pd G3 (0.01 g, 0.01 mmol). tBuOH (2.0 mL) was added then and the vial was purged with argon. The reaction was heated in the microwave at 110° C. for 1 h. The solvent was removed and the crude mixture was purified by silica gel column chromatography eluting with a

| Cpd | Data |
| --- | --- |
| 138 | MS m/z 382.4 $[M + H]^+$; $^1H$ NMR (DMSO-$d_6$) δ: 12.29 (br s, 1H), 9.36 (s, 1H), 8.94 (s, 1H), 8.64-8.80 (m, 1H), 8.26 (s, 1H), 7.97 (s, 1H), 6.46-6.61 (m, 1H), 4.07-4.27 (m, 3H), 3.67-3.91 (m, 3H), 2.20-2.31 (m, 1H), 1.38 (s, 9H). |
| 144 | MS m/z 410.4 $[M + H]^+$; $^1H$ NMR (DMSO-$d_6$) δ: 9.31 (s, 1H), 8.78-9.01 (m, 1H), 8.33 (s, 1H), 8.03 (d, J = 11.6 Hz, 1H), 7.96 (s, 1H), 7.59-7.82 (m, 2H), 5.15-5.33 (m, 1H), 3.17 (s, 3H), 2.01 (t, J = 13.2 Hz, 2H), 1.86 (d, J = 13.2 Hz, 2H), 1.52 (s, 6H), 1.45 (s, 6H). |
| 159 | MS m/z 366.4 $[M + H]^+$; $^1H$ NMR (DMSO-$d_6$) δ: 12.15 (s, 1H), 9.35 (s, 1H), 9.09 (br s, 1H), 8.95 (d, J = 2.5 Hz, 1H), 8.27 (s, 1H), 7.98 (d, J = 2.0 Hz, 1H), 4.78 (d, J = 14.0 Hz, 1H), 4.72 (d, J = 14.0 Hz, 1H), 3.53-3.47 (m, 4H), 3.16-3.09 (m, 1H), 2.76-2.67 (m, 1H), 1.08-1.00 (m, 1H), 0.72-0.63 (m, 2H), 0.59-0.52 (m, 1H), 0.48-0.42 (m, 1H). |

Example 20: Preparation of Compound 154

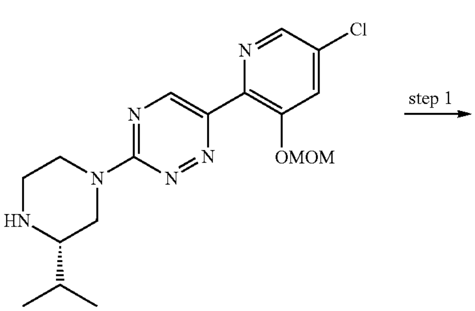

gradient 0-30% MeOH/$CH_2Cl_2$ to afford (S)—N-(6-(3-(3-isopropylpiperazin-1-yl)-1,2,4-triazin-6-yl)-5-(methoxymethoxy)pyridin-3-yl)-5-methylpyrazin-2-amine (0.02 g, 60% yield) as a dark red oil. MS m/z 452.5 $[M+H]^+$.

Step 2: To a solution of (S)—N-(6-(3-(3-isopropylpiperazin-1-yl)-1,2,4-triazin-6-yl)-5-(methoxymethoxy)pyridin-3-yl)-5-methylpyrazin-2-amine (0.02 g, 0.05 mmol) in MeOH (1.0 mL) was added 4.0M HCl/dioxane (0.5 mL) dropwise and the mixture was stirred for 1 h at room temperature. The mixture was concentrated and purified by silica gel column chromatography eluting with a gradient from 0-30% MeOH/$CH_2Cl_2$ to afford 5-[(5-methylpyrazin- 2-yl)amino]-2-{3-[(35)-3-(propan-2-yl)piperazin-1-yl]-1,2,4-triazin-6-yl}pyridin-3-ol (0.02 g, 83% yield) as an orange solid.

MS m/z 408.4 $[M+H]^+$; $^1H$ NMR (methanol-$d_4$) d: 9.33 (s, 1H), 8.37 (s, 1H), 8.16 (s, 1H), 8.14 (s, 1H), 8.07 (s, 1H), 4.92 (d, J=14.5 Hz, 1H), 4.81 (d, J=12.5 Hz, 1H), 3.27 (t, J=14.0 Hz, 2H), 3.02 (t, J=13.0 Hz, 2H), 2.76 (t, J=7.5 Hz, 1H), 2.45 (s, 3H), 1.90-1.83 (m, 1H), 1.11 (d, J=7.5 Hz, 6H); 3H not observed (2 NHs and OH).

Using the procedure described for Example 20 above, additional compounds described herein may be prepared by substituting the appropriate starting material, suitable reagents, and reaction conditions, obtaining compounds such as those selected from:

-continued

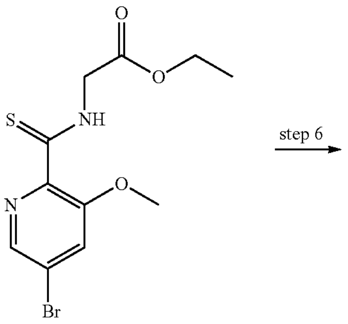

| Cpd | Data |
| --- | --- |
| 160 | MS m/z 406.3 $[M + H]^+$; $^1H$ NMR (DMSO-$d_6$) δ: 12.02 (s, 1H), 9.87 (s, 1H), 9.25 (s, 1H), 8.38 (d, J = 2.5 Hz, 1H), 8.23 (d, J = 2.0 Hz, 1H), 8.14 (s, 1H), 8.03 (d, J = 2.0 Hz, 1H), 4.61 (d, J = 11.5 Hz, 1H), 4.52 (d, J = 11.5 Hz, 1H), 3.07 (t, J = 11.0 Hz, 2H), 2.95-2.90 (m, 1H), 2.72-2.65 (m, 1H), 2.39 (s, 3H), 2.36 (br s, 1H), 2.02-1.94 (m, 1H), 1.07 (br s, 1H), 0.85-0.76 (m, 1H), 0.49-0.42 (m, 2H), 0.32-0.23 (m, 1H). |

Example 21: Preparation of Compound 161

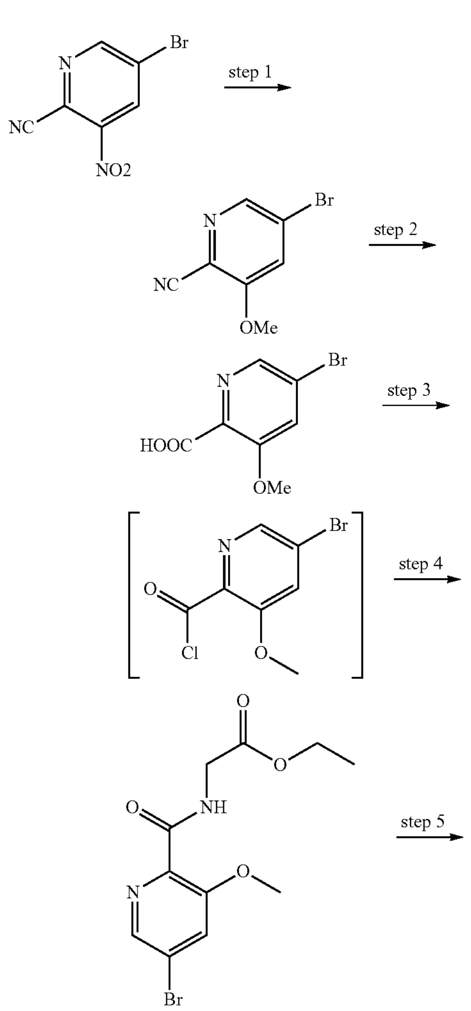

-continued

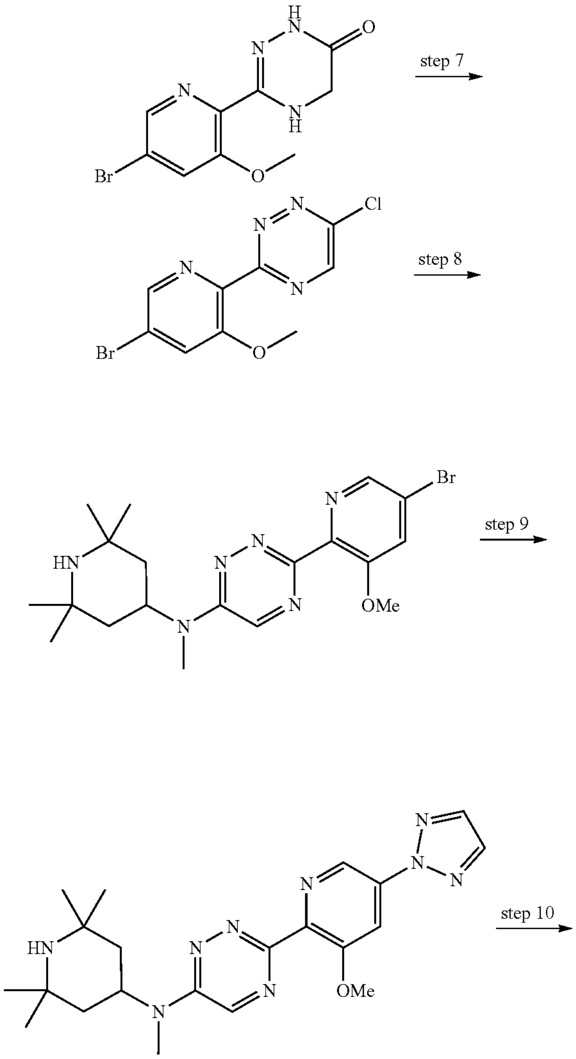

-continued

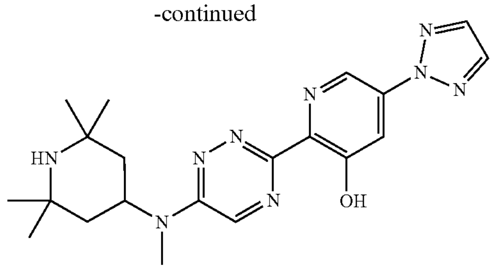

Step 1; To a solution of 5-bromo-3-nitro-pyridine-2-carbonitrile (45 g, 197.37 mmol) in MeOH (400 mL) was added NaOMe (0.5 mol/L) in MeOH (375 mL, 200 mmol, 0.5 mol/L) slowly. The mixture was stirred at 75° C. under nitrogen for 8 hours. The solvent was removed to give a crude 5-bromo-3-methoxypicolinonitrile, which was purified by silica gel chromatography eluting with a gradient 0-20% EtOAc/petroleum ether to give 5-bromo-3-methoxypicolinonitrile (25.0 g, 60% yield). MS m/z 210.9, 212.9 $[M+H]^+$.

Step 2: A solution of 5-bromo-3-methoxy-pyridine-2-carbonitrile (25.0 g, 117.35 mmol) in THF (200.0 mL) was mixed with a solution of NaOH (20 g, 500.039 mmol) in water (100 mL). The mixture was stirred at 70° C. for 12 hours. The mixture was neutralized with 4N HCl, then extracted with EtOAc. The organic phase was dried over $MgSO_4$ and concentrated to give 5-bromo-3-methoxypicolinic acid (23.5 g, 87% yield) which was used in the next step without further purification. MS m/z 231.7, 233.9 $[M+H]^+$.

Step 3 and Step 4: To a solution of 5-bromo-3-methoxy-pyridine-2-carboxylic acid (30 g, 129.29 mmol) in DCM (600.0 mL) was slowly added thionyl chloride (47 g, 395.06 mmol). The mixture was stirred at 50° C. for 3 h, then cooled to 0° C., and glycine ethyl ester hydrochloride (28 g, 200.6 mmol) and $Et_3N$ (40 g, 395.3 mmol) were added to the mixture. The reaction was stirred at room temperature for 16 h, then concentrated and purified by silica gel chromatography eluting with a gradient of 0-20% EtOAc/petroleum ether to afford ethyl (5-bromo-3-methoxypicolinoyl)glycinate (27.5 g, 67% yield). MS m/z 315.0, 317.0 $[M+H]^+$.

Step 5: To a solution of ethyl 2-[(5-bromo-3-methoxy-pyridine-2-carbonyl)amino]acetate (25 g, 78.830 mmol) in THF (3W) mL) was added Lawesson's reagent (27.0 g, 64.7506 mmol). The mixture was stirred at 66° C. for 16 h until UPLC showed completion of the reaction. The mixture was concentrated and purified by silica gel chromatography eluting with a gradient of 0-20% EtOAc/petroleum ether to afford ethyl (5-bromo-3-methoxypyridine-2-carbonothioyl) glycinate (17.5 g, 67% yield). MS m/z 331.0, 333.3 $[M+H]^+$.

Step 6: To a solution of ethyl 2-[(5-bromo-3-methoxy-pyridine-2-carbothioyl)amino]acetate (30.0 g, 90.04 mmol) in EtOH (300 mL), was added hydrazine (30.0 mL, 898.0 mmol). The mixture was stirred at 90° C. for 5 h. The solvent was removed and the crude mixture was purified by silica gel chromatography eluting with a gradient 50-100% EtOAc/petroleum ether to give 3-(5-bromo-3-methoxypyridin-2-yl)-4,5-dihydro-1,2,4-triazin-6(1H)-one (16.7 g, 65% yield). MS m/z 285.0, 287.0 $[M+H]^+$.

Step 7: 3-(5-Bromo-3-methoxypyridin-2-yl)-4,5-dihydro-1,2,4-triazin-6(1H)-one (10.0 g, 35.08 mmol) and $POCl_3$ (100 mL) were heated at 70° C. for 2.5 h. $POCl_3$ was subsequently removed using a rotavap, and the crude product was dissolved in EtOAc (200 mL), and the mixture was washed with aqueous $NaHCO_3$. The organic phase was separated, dried over $MgSO_4$, and the solvent was removed under vacuum. The remainder was redissolved in dioxane (200 mL) and $MnO_2$ (60 g, 690.16 mmol) was added to the mixture. The reaction was stirred at 90° C. for 16 h. After cooling to room temperature, the mixture was filtered through Celite and the filtrate was concentrated and purified by silica gel chromatography eluting with a gradient of 50-100% EtOAc/petroleum ether to give 3-(5-bromo-3-methoxypyridin-2-yl)-6-chloro-1,2,4-triazine (2.5 g 24% yield) as a yellow solid. MS m/z 300.9, 302.9 $[M+H]^+$; $^1H$ NMR (DMSO-$d_6$) δ: 3.88 (s, 3H), 8.06 (d, J=2.0 Hz, 1H), 8.47 (d, J=1.6 Hz, 1H), 9.19 (s, 1H).

Step 8: To a 50-mL round bottom flask, 3-(5-bromo-3-methoxypyridin-2-yl)-6-chloro-1,2,4-triazine (1.0 g, 3.3 mmol), N,2,2,6,6-pentamethylpiperidin-4-amine (678 mg, 4.0 mmol), diisopropylethylamine (1.5 mL, 8.6 mmol), and N,N-dimethylacetamide (17 mL) were added. The reaction was placed under a nitrogen atmosphere and stirred for 21 hours at 110° C. The reaction mixture was transferred to a separatory funnel and partitioned between 100 mL i-PrOAc and 100 mL $H_2O$. The aqueous layer was extracted 3 times with 100 mL i-PrOAc, after which the combined organic layers were diluted with an additional 100 mL i-PrOAc, washed 3 times with 400 mL $H_2O$, washed once with 400 mL brine, and dried with $Na_2SO_4$. The crude material was purified by C18 chromatography (10-100% ACN in $H_2O$) to obtain 3-(5-bromo-3-methoxypyridin-2-yl)-N-methyl-N-(2,2,6,6-tetramethylpiperidin-4-yl)-1,2,4-triazin-6-amine as a light orange solid (603.0 mg, 43% yield). MS mi 285.0, 287.0 $[M+H]^+$.

Step 9: To a 50-mL round bottom flask, $Pd_2dba_3$ (II mg, 0.012 mmol), 2-di-tert-butylphosphino-3,4,5,6-tetramethyl-2',4',6'-triisopropyl-1,1'-biphenyl (16 mg, 0.033 mmol), and degassed toluene (2.0 mL) were added. The reaction vessel was evacuated and back-filled with argon 3 times and then heated, under an argon atmosphere, for 2 minutes at 120° C., during which time the solution turned from purple to brown. The heat source was removed, and 1,2,3-triazole (16.0 μL, 0.28 mmol), tribasic potassium phosphate (98 mg, 0.46 mmol), and 3-(5-bromo-3-methoxypyridin-2-yl)-N-methyl-N-(2,2,6,6-tetramethylpiperidin-4-yl)-1,2,4-triazin-6-amine (100 mg, 0.23 mmol) were added. The reaction vessel was evacuated and back-filled with argon 3 times and allowed to stir, under an argon atmosphere, for 2 hours at 120° C. The crude reaction mixture was dry-loaded directly onto Celite and purified by C18 chromatography (10-100% ACN in $H_2O$) to obtain 3-(3-methoxy-5-(2H-1,2,3-triazol-2-yl)pyridin-2-yl)-N-methyl-N-(2,2,6,6-tetramethylpiperidin-4-yl)-1,2,4-triazin-6-amine as a yellow oil (78.0 mg, 80% yield). MS m/z 424.5 $[M+H]^+$.

Step 10: To a 50-mL round bottom flask, 3-(3-methoxy-5-(2H-1,2,3-triazol-2-yl)pyridin-2-yl)-N-methyl-N-(2,2,6,6-tetramethylpiperidin-4-yl)-1,2,4-triazin-6-amine (77.0 mg, 0.18 mmol) and dichloromethane (7.5 mL) were added. After cooling in an ice bath, under a nitrogen atmosphere, a 1M solution of boron tribromide in dichloromethane (2.0 mL) was slowly added via syringe. The reaction was warmed to ambient temperature and stirred for 17 hours. The reaction mixture was diluted with additional dichloromethane and cooled in an ice bath, then several chunks of ice, followed by 20 mL saturated aqueous $NaHCO_3$, were added. The layers were separated, the aqueous layer was extracted 2 times with 20 mL dichloromethane, and the combined organic layers were dried over $Na_2SO_4$. The crude material was purified by C18 chromatography (10-100% ACN in $H_2O$), and lyophilized to obtain 2-{6-[methyl(2,2,6,6-tetramethylpiperidin-4-yl)amino]-1,2,4-triazin-3-yl}-5-(2H-1, 2,3-triazol-2-yl)pyridin-3-ol as a yellow solid (30.0 mg, 40% yield). MS m/z 410.5 $[M+H]^+$; $^1H$ NMR (DMSO-$d_6$) δ: 8.90-8.97 (m, 1H), 8.79 (s, 1H), 8.26 (s, 2H), 7.91-7.95 (m, 1H), 4.93-5.08 (br m, 1H), 3.07 (s, 3H), 1.54-1.62 (m, 2H), 1.38-1.54 (m, 2H), 1.26 (s, 6H), 1.11 (s, 6H).

Using the procedure described for Example 21 above, additional compounds described herein may be prepared by substituting the appropriate starting material, suitable reagents, and reaction conditions, obtaining compounds such as those selected from:

| Cpd | Data |
|---|---|
| 163 | MS m/z 396.5 $[M + H]^+$; $^1H$ NMR (DMSO-$d_6$) δ: 8.88-8.91 (m, 1H), 8.42 (s, 1H), 8.24 (s, 2H), 7.88-7.92 (m, 1H), 7.84 (br d, J = 7.48 Hz, 1H), 4.34 (dtd, J = 11.69, 7.89, 7.89, 3.81 Hz, 1H), 1.91 (dd, J = 12.13, 3.43 Hz, 2 H), 1.22 (s, 6H), 1.05-1.12 (m, 2H), 1.07 (s, 6H); 2Hs missing (NHs or OH). |

Example 22: Preparation of Compound 162

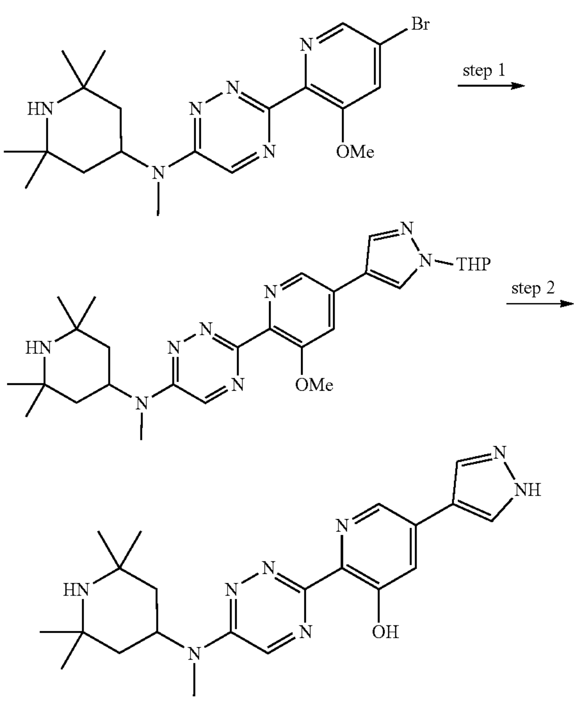

Step 1: To a 50-mL round bottom flask were added: 3-(5-bromo-3-methoxypyridin-2-yl)-N-methyl-N-(2,2,6,6-tetramethylpiperidin-4-yl)-1,2,4-triazin-6-amine (199.1 mg, 0.46 mmol), 1-tetrahydropyran-2-yl-4-(4,4,5,5-tetramethyl-1,3,2-dioxaborolan-2-yl)pyrazole (156 mg, 0.55 mmol), potassium carbonate (190.0 mg, 1.37 mmol), and Pd(dppf)$Cl_2$ (34.0 mg, 0.046 mmol). The reaction vessel was evacuated and back-filled with argon 3 times, then degassed dioxane (6.0 mL) and water (1.5 mL) were added and the reaction mixture was stirred for 20 h at 90° C. The crude reaction mixture was dry-loaded directly onto Celite and purified by C18 chromatography (10-100% ACN in $H_2O$) to obtain 3-(3-methoxy-5-(1-(tetrahydro-2H-pyran-2-yl)-1H-pyrazol-4-yl)pyridin-2-yl)-N-methyl-N-(2,2,6,6-tetramethylpiperidin-4-yl)-1,2,4-triazin-6-amine as a yellow oil (196 mg, 85% yield). MS m/z 507.5 $[M+H]^+$.

Step 2: To a 50-mL round bottom flask, 3-(3-methoxy-5-(1-(tetrahydro-2H-pyran-2-yl)-1H-pyrazol-4-yl)pyridin-2-yl)-N-methyl-N-(2,2,6,6-tetramethylpiperidin-4-yl)-1,2,4-triazin-6-amine (196 mg, 0.39 mmol) and dichloromethane (10.0 mL) were added. After cooling in an ice bath, under a nitrogen atmosphere, a 1M solution of boron tribromide in dichloromethane (2.0 mL) was slowly added via syringe. The reaction was stirred for 18 h at room temperature. After cooling in an ice bath, 10 mL of $H_2O$ was added. The mixture was warmed to ambient temperature and stirred vigorously, open to air, for several hours, after which 40 mL of saturated aqueous $NaHCO_3$ was added. The mixture was concentrated, slurried in dichloromethane, dry-loaded directly onto Celite, and purified by C18 chromatography (10-100% ACN in $H_2O$), and lyophilized to obtain 2-{6-[methyl(2,2,6,6-tetramethylpiperidin-4-yl)amino]-1,2,4-triazin-3-yl}-5-(1H-pyrazol-4-yl)pyridin-3-ol 1 as a yellow solid (59 mg, 37% yield). MS m/z 409.5 $[M+H]^+$; $^1H$ NMR (DMSO-$d_6$) δ: 13.12 (br s, 1H), 12.62 (br s, 1H), 8.76 (s, 1H), 8.57 (s, 1H), 8.17-8.37 (br m, 1H), 7.66 (s, 1H), 4.90-5.06 (br s, 1H), 3.05 (s, 3H), 1.52-1.62 (m, 2H), 1.42-1.50 (m, 2H), 1.25 (s, 6H), 1.09 (s, 6H).

Using the procedure described for Example 22 above, additional compounds described herein may be prepared by substituting the appropriate starting material, suitable reagents, and reaction conditions, obtaining compounds such as those selected from:

| Cpd | Data |
|---|---|
| 164 | MS m/z 435.4 $[M + H]^+$; $^1H$ NMR (methanol-$d_4$) δ: 8.82 (s, 1H), 8.54 (s, 1H), 8.39 (s, 1H), 7.91 (s, 1H), 7.71 (s, 1H), 7.40 (d, J = 12.5 Hz, 1H), 4.53 (br d, J = 13.4 Hz, 2H), 4.28 (s, 3H), 2.93-3.18 (m, 2H), 2.74 (t, J = 12.1 Hz, 2H), 1.26 (d, J = 6.7 Hz, 6H); 2Hs missing (NH and OH). |

BIOLOGICAL EXAMPLES

The following in vitro biological examples demonstrate the usefulness of the compounds of the present description for treating Huntington's disease.

To describe in more detail and assist in understanding the present description, the following non-limiting biological examples are offered to more fully illustrate the scope of the description and are not to be construed as specifically limiting the scope thereof. Such variations of the present description that may be now known or later developed, which would be within the purview of one skilled in the art to ascertain, are considered to fall within the scope of the present description and as hereinafter claimed.

Compounds of Formula (I), Formula (II), or Formula (III) were tested using the Meso Scale Discovery (MSD) Assay provided in International Application No. PCT/US2016/066042, filed on Dec. 11, 2016 and claiming priority to U.S. Provisional Application U.S. 62/265,652 filed on Dec. 10, 2015, the entire contents of which are incorporated herein by reference.

The Endogenous Huntingtin Protein assay used in Example 1 was developed using the ELISA-based MSD electrochemiluminescence assay platform.

Example 1: Endogenous Huntingtin Protein Assay

Meso Scale Discovery (MSD) 96-well or 384-well plates were coated overnight at 4° C. with MW1 (expanded polyglutamine) or MAB2166 monoclonal antibody (for capture) at a concentration of 1 μg/mL in PBS (30 μL per well). Plates were then washed three times with 300 μL wash buffer (0.05% Tween-20 in PBS) and blocked (100 μL blocking buffer; 5% BSA in PBS) for 4-5 hours at room temperature with rotational shaking and then washed three times with wash buffer.

Samples (25 μL) were transferred to the antibody-coated MSD plate and incubated overnight at 4° C. After removal of the lysates, the plate was washed three times with wash buffer, and 25 μL of #5656S (Cell signaling; rabbit monoclonal) secondary antibody (diluted to 0.25 μg/mL in 0.05% Tween-20 in blocking buffer) was added to each well and incubated with shaking for 1 Hour at room temperature. Following incubation with the secondary antibody, the wells were rinsed with wash buffer after which 25 μL of goat anti-rabbit SULFO TAG secondary detection antibody (required aspect of the MSD system) (diluted to 0.25 μg/mL in 0.05% Tween-20 in blocking buffer) was added to each well and incubated with shaking for 1 hour at room temperature. After rinsing three times with wash buffer, 150 μL of read buffer T with surfactant (MSD) were added to each empty well, and the plate was imaged on a SI 6000 imager (MSD) according to manufacturers' instructions provided for 96- or 384-well plates. The resulting $IC_{50}$ values (μM) for compounds tested are shown in Table 1.

As shown in Table 1, test compounds described herein had the following values, an $IC_{50}$ value between >3 μM and ≤9 μM is indicated by a single star (*), an $IC_{50}$ value between >1 μM and ≤3 μM is indicated by two stars "", an $IC_{50}$ value between >0.5 μM and ≤1 μM is indicated by three stars "", an $IC_{50}$ value between >0.1 μM and ≤0.5 μM is indicated by four stars "**", and an $IC_{50}$ value of ≤0.1 μM is indicated by five stars "***".

TABLE 1

| $IC_{50}$ Values (μM) for Compounds 1-164 | |
|---|---|
| Cpd | $IC_{50}$ |
| 1 | ***** |
| 2 | ***** |
| 3 | ***** |
| 4 | ***** |
| 5 | ***** |
| 6 | ***** |

TABLE 1-continued

| $IC_{50}$ Values (μM) for Compounds 1-164 | |
|---|---|
| Cpd | $IC_{50}$ |
| 7 | **** |
| 8 | ***** |
| 9 | **** |
| 10 | ***** |
| 11 | ***** |
| 12 | ***** |
| 13 | ***** |
| 14 | ***** |
| 15 | ***** |
| 16 | ***** |
| 17 | *** |
| 18 | ***** |
| 19 | ***** |
| 20 | ***** |
| 21 | ***** |
| 22 | **** |
| 23 | ***** |
| 24 | ***** |
| 25 | ***** |
| 26 | ***** |
| 27 | ***** |
| 28 | ***** |
| 29 | ***** |
| 30 | ***** |
| 31 | **** |
| 32 | ***** |
| 33 | ***** |
| 34 | ***** |
| 35 | ***** |
| 36 | *** |
| 37 | **** |
| 38 | ***** |
| 39 | ***** |
| 40 | ***** |
| 41 | **** |
| 42 | *** |
| 43 | ***** |
| 44 | ***** |
| 45 | ***** |
| 46 | **** |
| 47 | ***** |
| 48 | ***** |
| 49 | ***** |
| 50 | ***** |
| 51 | ***** |
| 52 | ***** |
| 53 | ***** |
| 54 | ***** |
| 55 | ***** |
| 56 | ***** |
| 57 | ***** |
| 58 | *** |
| 59 | ***** |
| 60 | ***** |
| 61 | ***** |
| 62 | ***** |
| 63 | **** |
| 64 | ***** |
| 65 | ***** |
| 66 | **** |
| 67 | ***** |
| 68 | ***** |
| 69 | ***** |
| 70 | ***** |
| 71 | **** |
| 72 | **** |
| 73 | **** |
| 74 | ***** |
| 75 | ***** |
| 76 | ***** |
| 77 | ***** |
| 78 | ***** |
| 79 | ***** |
| 80 | **** |
| 81 | ***** |
| 82 | ***** |

TABLE 1-continued

| IC$_{50}$ Values (μM) for Compounds 1-164 | |
|---|---|
| Cpd | IC$_{50}$ |
| 83 | **** |
| 84 | *** |
| 85 | *** |
| 86 | **** |
| 87 | ***** |
| 88 | **** |
| 89 | ***** |
| 90 | **** |
| 91 | ***** |
| 92 | ***** |
| 93 | ***** |
| 94 | *** |
| 95 | ***** |
| 96 | **** |
| 97 | ***** |
| 98 | ***** |
| 99 | **** |
| 100 | **** |
| 101 | ***** |
| 102 | *** |
| 103 | ***** |
| 104 | ***** |
| 105 | ***** |
| 106 | ***** |
| 107 | ***** |
| 108 | *** |
| 109 | *** |
| 110 | *** |
| 111 | *** |
| 112 | *** |
| 113 | *** |
| 114 | ***** |
| 115 | **** |
| 116 | *** |
| 117 | *** |
| 118 | ***** |
| 119 | ***** |
| 120 | ***** |
| 121 | ***** |
| 122 | ***** |
| 123 | ***** |
| 124 | ***** |
| 125 | **** |
| 126 | **** |
| 127 | ***** |
| 128 | ***** |
| 129 | ***** |
| 130 | *** |
| 131 | *** |
| 132 | ***** |
| 133 | ***** |
| 134 | *** |
| 135 | ***** |
| 136 | ***** |
| 137 | ***** |
| 138 | ***** |
| 139 | ***** |
| 140 | ***** |
| 141 | *** |
| 142 | ***** |
| 143 | **** |
| 144 | ***** |
| 145 | ***** |
| 146 | ***** |
| 147 | **** |
| 148 | **** |
| 149 | ***** |
| 150 | ***** |
| 151 | ***** |
| 152 | *** |
| 153 | ***** |
| 154 | ***** |
| 155 | ***** |
| 156 | **** |
| 157 | ***** |
| 158 | ***** |
| 159 | **** |
| 160 | ***** |
| 161 | ***** |
| 162 | ***** |
| 163 | ***** |
| 164 | **** |

Without regard to whether a document cited herein was specifically and individually indicated as being incorporated by reference, all documents referred to herein are incorporated by reference into the present application for any and all purposes to the same extent as if each individual reference was fully set forth herein.

Having now fully described the subject matter of the claims, it will be understood by those having ordinary skill in the art that the same can be performed within a wide range of equivalents without affecting the scope of the subject matter or particular aspects described herein. It is intended that the appended claims be interpreted to include all such equivalents.

What is claimed is:

1. A compound comprising, a compound of Formula (I) or Formula (III):

(I)

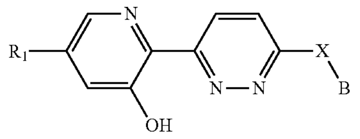

(III)

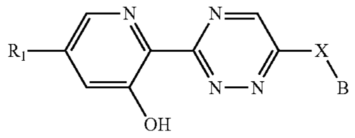

or a form thereof, wherein:

X is selected from the group consisting of O, NR$_x$, and a bond;

R$_x$ is selected from the group consisting of hydrogen and C$_{1-4}$alkyl;

B is heterocyclyl, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, optionally substituted where allowed by available valences with 1, 2, 3, 4, or 5 R$_b$ substituents;

R$_b$ is independently selected from the group consisting of halogen, C$_{1-4}$alkyl, amino, C$_{1-4}$alkyl-amino, (C$_{1-4}$alkyl)$_2$-amino, and C$_{3-6}$cycloalkyl;

R$_1$ is selected from the group consisting of heteroaryl, heterocyclyl, phenyl, heteroaryl-C$_{1-4}$alkyl, heteroaryl-C$_{2-4}$alkenyl, heteroaryl-amino, and heteroaryl-C$_{1-4}$alkyl-amino, wherein heteroaryl is a 3-7 membered monocyclic or 6-10 membered bicyclic ring system having 1, 2, 3, or 4 heteroatom ring members independently selected from N, O, or S, wherein heterocyclyl is a saturated or partially unsaturated 3-7 membered monocyclic, 6-10 membered bicyclic or 13-16 membered polycyclic ring system having 1, 2, or 3 heteroatom ring members independently selected from N, O, or S, and wherein each instance of phenyl, heteroaryl or heterocyclyl is optionally substituted where allowed by available valences with 1 or 2 $R_{1a}$ substituents; and $R_{1a}$ is independently selected from the group consisting of halogen, hydroxyl, cyano, $C_{1-4}$alkyl, deutero-$C_{1-4}$alkyl, halo-$C_{1-4}$alkyl, amino, $C_{1-4}$alkyl-amino, $(C_{1-4}alkyl)_2$-amino, $C_{1-4}$alkoxy, deutero-$C_{1-4}$alkoxy, and halo-$C_{1-4}$alkoxy;

wherein a form of the compound is selected from the group consisting of a salt, hydrate, solvate, racemate, enantiomer, diastereomer, tautomer, and mixtures thereof.

2. The compound of claim 1, wherein the compound is a compound of Formula (I):

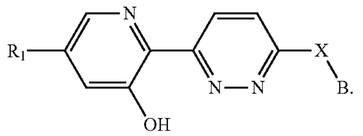

(I)

3. The compound of claim 1, wherein X is selected from the group consisting of O and a bond.

4. The compound of claim 1, wherein B is heterocyclyl selected from the group consisting of pyrrolidinyl, piperidinyl, piperidin-1-olate-yl, piperazinyl, 4-azaspiro[2.5]octanyl, 8-azabicyclo[3.2.1]octanyl, 2,5-diazabicyclo[2.2.1]heptanyl, 1,6-diazaspiro[3.4]octanyl, 2-oxa-5,8-diazaspiro[3.5]nonanyl, and 4-azadispiro[$2.1.2^5.3^3$]decanyl, optionally substituted where allowed by available valences with 1, 2, 3, 4, or 5 $R_b$ substituents.

5. The compound of claim 1, wherein $R_1$ is heteroaryl selected from the group consisting of 1H-pyrazolyl, 1H-imidazolyl, 1,3-thiazolyl, oxazolyl, 1H-1,2,3-triazolyl, 2H-1,2,3-triazolyl, 1H-1,2,4-triazolyl, pyridinyl, pyridin-2(1H)-on-yl, pyrimidin-4(3H)-on-yl, pyridazinyl, 1H-indazolyl, 2H-indazolyl, 1,3-benzoxazolyl, pyrrolo[1,2-a]pyrazinyl, imidazo[1,2-a]pyridinyl, imidazo[1,2-a]pyrazinyl, imidazo[1,2-a]pyrimidinyl, imidazo[1,2-b]pyridazinyl, 2H-[1,2,3]triazolo[4,5-b]pyridinyl, [1,2,4]triazolo[1,5-a]pyridinyl, and [1,2,4]triazolo[1,5-a]pyrazinyl.

6. The compound of claim 5, wherein $R_1$ is heteroaryl selected from the group consisting of 1H-pyrazolyl and 2H-indazolyl.

7. The compound of claim 1, wherein $R_{1a}$ is selected from the group consisting of halogen, cyano, $C_{1-4}$alkyl, deutero-$C_{1-4}$alkyl, halo-$C_{1-4}$alkyl, $C_{1-4}$alkoxy, and deutero-$C_{1-4}$alkoxy.

8. The compound of claim 7, wherein $R_{1a}$ is selected from the group consisting of halogen, $C_{1-4}$alkyl, and $C_{1-4}$alkoxy.

9. A compound selected from the group consisting of:

5-(1H-pyrazol-4-yl)-2-{6-[(2,2,6,6-tetramethylpiperidin-4-yl)oxy]pyridazin-3-yl}pyridin-3-ol;

2-{6-[methyl(2,2,6,6-tetramethylpiperidin-4-yl)amino]pyridazin-3-yl}-5-(1H-pyrazol-4-yl)pyridin-3-ol;

5-[1-($^2H_3$)methyl-1H-pyrazol-4-yl]-2-{6-[(2,2,6,6-tetramethylpiperidin-4-yl)oxy]pyridazin-3-yl}pyridin-3-ol;

5-(1-methyl-1H-pyrazol-3-yl)-2-{6-[(2,2,6,6-tetramethylpiperidin-4-yl)oxy]pyridazin-3-yl}pyridin-3-ol;

5-(1H-imidazol-1-yl)-2-{6-[(2,2,6,6-tetramethylpiperidin-4-yl)oxy]pyridazin-3-yl}pyridin-3-ol;

2-(6-{[(3R,4S)-3-fluoro-2,2,6,6-tetramethylpiperidin-4-yl]oxy}pyridazin-3-yl)-5-(1H-pyrazol-4-yl)pyridin-3-ol;

2-(6-{[(3S,4R)-3-fluoro-2,2,6,6-tetramethylpiperidin-4-yl]oxy}pyridazin-3-yl)-5-(1H-pyrazol-4-yl)pyridin-3-ol;

2-(6-{[(3R,4S)-3-fluoro-2,2,6,6-tetramethylpiperidin-4-yl]oxy}pyridazin-3-yl)-5-(1-methyl-1H-pyrazol-3-yl)pyridin-3-ol;

2-(6-{[(3S,4R)-3-fluoro-2,2,6,6-tetramethylpiperidin-4-yl]oxy}pyridazin-3-yl)-5-(1-methyl-1H-pyrazol-3-yl)pyridin-3-ol;

2-(6-{[(3R,4S)-3-fluoro-2,2,6,6-tetramethylpiperidin-4-yl]amino}pyridazin-3-yl)-5-(1H-pyrazol-4-yl)pyridin-3-ol;

2-(6-{[(3R,4S)-3-fluoro-2,2,6,6-tetramethylpiperidin-4-yl]oxy}pyridazin-3-yl)-5-(1H-imidazol-1-yl)pyridin-3-ol;

2-(6-{[(3S,4R)-3-fluoro-2,2,6,6-tetramethylpiperidin-4-yl]oxy}pyridazin-3-yl)-5-(1H-imidazol-1-yl)pyridin-3-ol;

5-(1,3-oxazol-2-yl)-2-{6-[(2,2,6,6-tetramethylpiperidin-4-yl}oxy]pyridazin-3-yl)pyridin-3-ol;

2-(6-{[(3R,4S)-3-fluoro-2,2,6,6-tetramethylpiperidin-4-yl]oxy}pyridazin-3-yl)-5-(2H-1,2,3-triazol-2-yl)pyridin-3-ol;

2-(6-{[(3S,4R)-3-fluoro-2,2,6,6-tetramethylpiperidin-4-yl]oxy}pyridazin-3-yl)-5-(2H-1,2,3-triazol-2-yl)pyridin-3-ol;

2-(6-{[(3R,4S)-3-fluoro-2,2,6,6-tetramethylpiperidin-4-yl]oxy}pyridazin-3-yl)-5-(1,3-oxazol-2-yl)pyridin-3-ol;

2-(6-{[(3S,4R)-3-fluoro-2,2,6,6-tetramethylpiperidin-4-yl]oxy}pyridazin-3-yl)-5-(1,3-oxazol-2-yl)pyridin-3-ol;

5-(1-methyl-1H-pyrazol-3-yl)-2-{6-[methyl(2,2,6,6-tetramethylpiperidin-4-yl)amino]pyridazin-3-yl}pyridin-3-ol;

2-{6-[methyl(2,2,6,6-tetramethylpiperidin-4-yl)amino]pyridazin-3-yl}-5-(1,3-oxazol-2-yl)pyridin-3-ol;

5-(1H-imidazol-1-yl)-2-{6-[methyl(2,2,6,6-tetramethylpiperidin-4-yl)amino]pyridazin-3-yl}pyridin-3-ol;

2-(6-{[(3S,4S)-3-fluoro-2,2,6,6-tetramethylpiperidin-4-yl]amino}pyridazin-3-yl)-5-(1H-pyrazol-3-yl)pyridin-3-ol;

2-(6-{[(3R,4R)-3-fluoro-2,2,6,6-tetramethylpiperidin-4-yl]amino}pyridazin-3-yl)-5-(1H-pyrazol-3-yl)pyridin-3-ol;

2-{6-[(3R)-(tert-butylamino)pyrrolidin-1-yl]pyridazin-3-yl}-5-(1-methyl-1H-pyrazol-3-yl)pyridin-3-ol;

2-{6-[(3S)-(tert-butylamino)pyrrolidin-1-yl]pyridazin-3-yl}-5-(1-methyl-1H-pyrazol-3-yl)pyridin-3-ol;

2-{6-[(3R)-(tert-butylamino)pyrrolidin-1-yl]pyridazin-3-yl}-5-(1H-pyrazol-4-yl)pyridin-3-ol;

2-{6-[(3S)-(tert-butylamino)pyrrolidin-1-yl]pyridazin-3-yl}-5-(1H-pyrazol-4-yl)pyridin-3-ol;

2-(6-{[(3R,4R)-3-fluoro-2,2,6,6-tetramethylpiperidin-4-yl]amino}pyridazin-3-yl)-5-[1-($^2H_3$)methyl-1H-pyrazol-4-yl]pyridin-3-ol;

2-(6-{[(3S,4S)-3-fluoro-2,2,6,6-tetramethylpiperidin-4-yl]amino}pyridazin-3-yl)-5-[1-($^2H_3$)methyl-1H-pyrazol-4-yl]pyridin-3-ol;

2-{6-[(2,2,6,6-tetramethylpiperidin-4-yl)oxy]pyridazin-3-yl}-5-(2H-1,2,3-triazol-2-yl)pyridin-3-ol;

2-{6-[(5,5-dimethyl-4-azaspiro[2.5]octan-7-yl)oxy]pyridazin-3-yl}-5-(2H-1,2,3-triazol-2-yl)pyridin-3-ol;

5-(5-fluoro-1H-pyrazol-4-yl)-2-(6-{[(3R,4S)-3-fluoro-2,2,6,6-tetramethylpiperidin-4-yl]oxy}pyridazin-3-yl)pyridin-3-ol;

5-(5-fluoro-1H-pyrazol-4-yl)-2-(6-{[(3S,4R)-3-fluoro-2,2,6,6-tetramethylpiperidin-4-yl]oxy}pyridazin-3-yl)pyridin-3-ol;

2-{6-[(3R)-3-(tert-butylamino)pyrrolidin-1-yl]pyridazin-3-yl}-5-[1-($^2H_3$)methyl-1H-pyrazol-4-yl]pyridin-3-ol;

2-{6-[(3R)-3-(tert-butylamino)pyrrolidin-1-yl]pyridazin-3-yl}-5-(2H-1,2,3-triazol-2-yl)pyridin-3-ol;

2-(6-{[(3R,4R)-3-fluoro-2,2,6,6-tetramethylpiperidin-4-yl]amino}pyridazin-3-yl)-5-{6-[($^2H_3$)methyloxy]pyrimidin-4-yl}pyridin-3-ol;

2-{6-[(5,5-dimethyl-4-azaspiro[2.5]octan-7-yl)oxy]pyridazin-3-yl}-5-(5-fluoro-1H-pyrazol-4-yl)pyridin-3-ol;

2-{6-[(5,5-dimethyl-4-azaspiro[2.5]octan-7-yl)oxy]pyridazin-3-yl}-5-(1H-pyrazol-4-yl)pyridin-3-ol;

2-{6-[(5,5-dimethyl-4-azaspiro[2.5]octan-7-yl)oxy]pyridazin-3-yl}-5-(1,3-oxazol-2-yl)pyridin-3-ol;

2-{6-[3-(tert-butylamino)pyrrolidin-1-yl]pyridazin-3-yl}-5-[1-($^2H_3$)methyl-1H-pyrazol-4-yl]pyridin-3-ol;

2-{6-[(3R)-3-(tert-butylamino)pyrrolidin-1-yl]pyridazin-3-yl}-5-(6-methoxypyrimidin-4-yl)pyridin-3-ol;

2-{6-[(4-azadispiro[2.1.2$^5$.3$^3$]decan-9-yl)oxy]pyridazin-3-yl}-5-(1H-pyrazol-4-yl)pyridin-3-ol;

2-(6-{[(1R,3s,5S)-1,5-dimethyl-8-azabicyclo[3.2.1]octan-3-yl]oxy}pyridazin-3-yl)-5-(2H-1,2,3-triazol-2-yl)pyridin-3-ol;

2-(6-{[(1S,3r,5R)-1,5-dimethyl-8-azabicyclo[3.2.1]octan-3-yl]oxy}pyridazin-3-yl)-5-(2H-1,2,3-triazol-2-yl)pyridin-3-ol;

2-(6-{[(1R,3s,5S)-1,5-dimethyl-8-azabicyclo[3.2.1]octan-3-yl]oxy}pyridazin-3-yl)-5-[1-($^2H_3$)methyl-1H-pyrazol-4-yl]pyridin-3-ol;

2-(6-{[(1S,3r,5R)-1,5-dimethyl-8-azabicyclo[3.2.1]octan-3-yl]oxy}pyridazin-3-yl)-5-[1-($^2H_3$)methyl-1H-pyrazol-4-yl]pyridin-3-ol;

5-[6-(6-{[(3R,4S)-3-fluoro-2,2,6,6-tetramethylpiperidin-4-yl]oxy}pyridazin-3-yl)-5-hydroxypyridin-3-yl]-2-methyl-2H-indazole-7-carbonitrile;

5-[6-(6-{[(3S,4R)-3-fluoro-2,2,6,6-tetramethylpiperidin-4-yl]oxy}pyridazin-3-yl)-5-hydroxypyridin-3-yl]-2-methyl-2H-indazole-7-carbonitrile;

5-(7-fluoro-2-methyl-2H-indazol-5-yl)-2-(6-{[(3R,4S)-3-fluoro-2,2,6,6-tetramethylpiperidin-4-yl]oxy}pyridazin-3-yl)pyridin-3-ol;

5-(7-fluoro-2-methyl-2H-indazol-5-yl)-2-(6-{[(3S,4R)-3-fluoro-2,2,6,6-tetramethylpiperidin-4-yl]oxy}pyridazin-3-yl)pyridin-3-ol;

2-(6-{[(1R,3s,5S)-1,5-dimethyl-8-azabicyclo[3.2.1]octan-3-yl]oxy}pyridazin-3-yl)-5-(pyrimidin-5-yl)pyridin-3-ol;

2-(6-{[(1S,3r,5R)-1,5-dimethyl-8-azabicyclo[3.2.1]octan-3-yl]oxy}pyridazin-3-yl)-5-(pyrimidin-5-yl)pyridin-3-ol;

6-(6-{[(3R,4S)-3-fluoro-2,2,6,6-tetramethylpiperidin-4-yl]oxy}pyridazin-3-yl)-5-hydroxy-1'-methyl[3,4'-bipyridin]-2'(1'H)-one;

6-(6-{[(3S,4R)-3-fluoro-2,2,6,6-tetramethylpiperidin-4-yl]oxy}pyridazin-3-yl)-5-hydroxy-1'-methyl[3,4'-bipyridin]-2'(1'H)-one;

5-(2,8-dimethylimidazo[1,2-b]pyridazin-6-yl)-2-(6-{[(3R,4S)-3-fluoro-2,2,6,6-tetramethylpiperidin-4-yl]oxy}pyridazin-3-yl)pyridin-3-ol;

5-(2,8-dimethylimidazo[1,2-b]pyridazin-6-yl)-2-(6-{[(3S,4R)-3-fluoro-2,2,6,6-tetramethylpiperidin-4-yl]oxy}pyridazin-3-yl)pyridin-3-ol;

2-(6-{[(3R,4R)-3-fluoro-2,2,6,6-tetramethylpiperidin-4-yl]oxy}pyridazin-3-yl)-5-(1H-pyrazol-4-yl)pyridin-3-ol;

2-(6-{[(3S,4S)-3-fluoro-2,2,6,6-tetramethylpiperidin-4-yl]oxy}pyridazin-3-yl)-5-(1H-pyrazol-4-yl)pyridin-3-ol;

2-(6-{[(3R,4S)-3-fluoro-2,2,6,6-tetramethylpiperidin-4-yl]oxy}pyridazin-3-yl)-5-(4-methyl-1H-imidazol-1-yl)pyridin-3-ol;

2-(6-{[(3S,4R)-3-fluoro-2,2,6,6-tetramethylpiperidin-4-yl]oxy}pyridazin-3-yl)-5-(4-methyl-1H-imidazol-1-yl)pyridin-3-ol;

6-[6-(6-{[(3R,4S)-3-fluoro-2,2,6,6-tetramethylpiperidin-4-yl]oxy}pyridazin-3-yl)-5-hydroxypyridin-3-yl]-3-methylpyrimidin-4(3H)-one;

6-[6-(6-{[(3S,4R)-3-fluoro-2,2,6,6-tetramethylpiperidin-4-yl]oxy}pyridazin-3-yl)-5-hydroxypyridin-3-yl]-3-methylpyrimidin-4(3H)-one;

2-(6-{[(3R,4S)-3-fluoro-2,2,6,6-tetramethylpiperidin-4-yl]oxy}pyridazin-3-yl)-5-(2-methylimidazo[1,2-a]pyridin-6-yl)pyridin-3-ol;

2-(6-{[(3S,4R)-3-fluoro-2,2,6,6-tetramethylpiperidin-4-yl]oxy}pyridazin-3-yl)-5-(2-methylimidazo[1,2-a]pyridin-6-yl)pyridin-3-ol;

5-(2,8-dimethylimidazo[1,2-a]pyridin-6-yl)-2-(6-{[(3R,4S)-3-fluoro-2,2,6,6-tetramethylpiperidin-4-yl]oxy}pyridazin-3-yl)pyridin-3-ol;

5-(2,8-dimethylimidazo[1,2-a]pyridin-6-yl)-2-(6-{[(3S,4R)-3-fluoro-2,2,6,6-tetramethylpiperidin-4-yl]oxy}pyridazin-3-yl)pyridin-3-ol;

5-(8-ethyl-2-methylimidazo[1,2-a]pyridin-6-yl)-2-(6-{[(3R,4S)-3-fluoro-2,2,6,6-tetramethylpiperidin-4-yl]oxy}pyridazin-3-yl)pyridin-3-ol;

5-(8-ethyl-2-methylimidazo[1,2-a]pyridin-6-yl)-2-(6-{[(3S,4R)-3-fluoro-2,2,6,6-tetramethylpiperidin-4-yl]oxy}pyridazin-3-yl)pyridin-3-ol;

2-(6-{[(3R,4S)-3-fluoro-2,2,6,6-tetramethylpiperidin-4-yl]oxy}pyridazin-3-yl)-5-[2-methyl-8-(trifluoromethyl)imidazo[1,2-a]pyridin-6-yl]pyridin-3-ol;

2-(6-{[(3S,4R)-3-fluoro-2,2,6,6-tetramethylpiperidin-4-yl]oxy}pyridazin-3-yl)-5-[2-methyl-8-(trifluoromethyl)imidazo[1,2-a]pyridin-6-yl]pyridin-3-ol;

5-(2,8-dimethylimidazo[1,2-b]pyridazin-6-yl)-2-(6-{[(3R,4R)-3-fluoro-2,2,6,6-tetramethylpiperidin-4-yl]oxy}pyridazin-3-yl)pyridin-3-ol;

5-(2,8-dimethylimidazo[1,2-b]pyridazin-6-yl)-2-(6-{[(3S,4S)-3-fluoro-2,2,6,6-tetramethylpiperidin-4-yl]oxy}pyridazin-3-yl)pyridin-3-ol;

2-(6-{[(3R,4S)-3-fluoro-2,2,6,6-tetramethylpiperidin-4-yl]oxy}pyridazin-3-yl)-5-(2-methylimidazo[1,2-b]pyridazin-6-yl)pyridin-3-ol;

2-(6-{[(3S,4R)-3-fluoro-2,2,6,6-tetramethylpiperidin-4-yl]oxy}pyridazin-3-yl)-5-(2-methylimidazo[1,2-b]pyridazin-6-yl)pyridin-3-ol;

2-(6-{[(3R,4S)-3-fluoro-2,2,6,6-tetramethylpiperidin-4-yl]oxy}pyridazin-3-yl)-5-(imidazo[1,2-b]pyridazin-6-yl)pyridin-3-ol;

2-(6-{[(3S,4R)-3-fluoro-2,2,6,6-tetramethylpiperidin-4-yl]oxy}pyridazin-3-yl)-5-(imidazo[1,2-b]pyridazin-6-yl)pyridin-3-ol;

5-(2,8-dimethylimidazo[1,2-b]pyridazin-6-yl)-2-{6-[(2,2,6,6-tetramethylpiperidin-4-yl)oxy]pyridazin-3-yl}pyridin-3-ol;

2-(6-{[(3R,4R)-3-fluoro-2,2,6,6-tetramethylpiperidin-4-yl]oxy}pyridazin-3-yl)-5-(1H-pyrazol-4-yl)pyridin-3-ol;

2-(6-{[(3S,4S)-3-fluoro-2,2,6,6-tetramethylpiperidin-4-yl]oxy}pyridazin-3-yl)-5-(1H-pyrazol-4-yl)pyridin-3-ol;

5-(7-fluoro-2-methyl-2H-indazol-5-yl)-2-{6-[(2,2,6,6-tetramethylpiperidin-4-yl)oxy]pyridazin-3-yl}pyridin-3-ol;

2-{6-[(5,5-dimethyl-4-azaspiro[2.5]octan-7-yl)(methyl)amino]pyridazin-3-yl}-5-[1-($^2H_3$)methyl-1H-pyrazol-4-yl]pyridin-3-ol;

2-(6-{[(3R,4S)-3-fluoro-2,2,6,6-tetramethylpiperidin-4-yl]oxy}pyridazin-3-yl)-5-(2-methylimidazo[1,2-a]pyrimidin-6-yl)pyridin-3-ol;

2-(6-{[(3S,4R)-3-fluoro-2,2,6,6-tetramethylpiperidin-4-yl]oxy}pyridazin-3-yl)-5-(2-methylimidazo[1,2-a]pyrimidin-6-yl)pyridin-3-ol;

2-(6-{[(3R,4S)-3-fluoro-2,2,6,6-tetramethylpiperidin-4-yl]oxy}pyridazin-3-yl)-5-(2-methyl[1,2,4]triazolo[1,5-a]pyridin-6-yl)pyridin-3-ol;

2-(6-{[(3S,4R)-3-fluoro-2,2,6,6-tetramethylpiperidin-4-yl]oxy}pyridazin-3-yl)-5-(2-methyl[1,2,4]triazolo[1,5-a]pyridin-6-yl)pyridin-3-ol;

5-(2,4-dimethyl-1,3-benzoxazol-6-yl)-2-(6-{[(3R,4S)-3-fluoro-2,2,6,6-tetramethylpiperidin-4-yl]oxy}pyridazin-3-yl)pyridin-3-ol;

5-(2,4-dimethyl-1,3-benzoxazol-6-yl)-2-(6-{[(3S,4R)-3-fluoro-2,2,6,6-tetramethylpiperidin-4-yl]oxy}pyridazin-3-yl)pyridin-3-ol;

2-(6-{[(3R,4S)-3-fluoro-2,2,6,6-tetramethylpiperidin-4-yl]oxy}pyridazin-3-yl)-5-(8-methoxy-2-methylimidazo[1,2-b]pyridazin-6-yl)pyridin-3-ol;

2-(6-{[(3S,4R)-3-fluoro-2,2,6,6-tetramethylpiperidin-4-yl]oxy}pyridazin-3-yl)-5-(8-methoxy-2-methylimidazo[1,2-b]pyridazin-6-yl)pyridin-3-ol;

5-(7-fluoro-2-methyl-2H-indazol-4-yl)-2-(6-{[(3R,4S)-3-fluoro-2,2,6,6-tetramethylpiperidin-4-yl]oxy}pyridazin-3-yl)pyridin-3-ol;

5-(7-fluoro-2-methyl-2H-indazol-4-yl)-2-(6-{[(3S,4R)-3-fluoro-2,2,6,6-tetramethylpiperidin-4-yl]oxy}pyridazin-3-yl)pyridin-3-ol;

6-[6-(6-{[(3R,4S)-3-fluoro-2,2,6,6-tetramethylpiperidin-4-yl]oxy}pyridazin-3-yl)-5-hydroxypyridin-3-yl]-2-methylimidazo[1,2-a]pyridine-8-carbonitrile;

6-[6-(6-{[(3S,4R)-3-fluoro-2,2,6,6-tetramethylpiperidin-4-yl]oxy}pyridazin-3-yl)-5-hydroxypyridin-3-yl]-2-methylimidazo[1,2-a]pyridine-8-carbonitrile;

5-(8-ethyl-2-methylimidazo[1,2-b]pyridazin-6-yl)-2-(6-{[(3R,4S)-3-fluoro-2,2,6,6-tetramethylpiperidin-4-yl]oxy}pyridazin-3-yl)pyridin-3-ol;

5-(8-ethyl-2-methylimidazo[1,2-b]pyridazin-6-yl)-2-(6-{[(3S,4R)-3-fluoro-2,2,6,6-tetramethylpiperidin-4-yl]oxy}pyridazin-3-yl)pyridin-3-ol;

2-{6-[(2,2,6,6-tetramethylpiperidin-4-yl)oxy]pyridazin-3-yl}-5-(1H-1,2,4-triazol-1-yl)pyridin-3-ol;

5-[6-(6-{[2,2,6,6-tetramethylpiperidin-4-yl]oxy}pyridazin-3-yl)-5-hydroxypyridin-3-yl]-2-methyl-2H-indazole-7-carbonitrile;

2-{6-[(2,2,6,6-tetramethylpiperidin-4-yl)oxy]pyridazin-3-yl}-5-(1H-1,2,3-triazol-1-yl)pyridin-3-ol;

2-{6-[(5,5-dimethyl-4-azaspiro[2.5]octan-7-yl)(methyl)amino]pyridazin-3-yl}-5-(7-fluoro-2-methyl-2H-indazol-5-yl)pyridin-3-ol;

5-(imidazo[1,2-b]pyridazin-6-yl)-2-{6-[(2,2,6,6-tetramethylpiperidin-4-yl)oxy]pyridazin-3-yl}pyridin-3-ol;

2-(6-{[(3R,4S)-3-fluoro-2,2,6,6-tetramethylpiperidin-4-yl]oxy}pyridazin-3-yl)-5-(imidazo[1,2-a]pyrazin-6-yl)pyridin-3-ol;

2-(6-{[(3S,4R)-3-fluoro-2,2,6,6-tetramethylpiperidin-4-yl]oxy}pyridazin-3-yl)-5-(imidazo[1,2-a]pyrazin-6-yl)pyridin-3-ol;

5-(1,3-dimethylpyrrolo[1,2-a]pyrazin-7-yl)-2-(6-{[(3R,4S)-3-fluoro-2,2,6,6-tetramethylpiperidin-4-yl]oxy}pyridazin-3-yl)pyridin-3-ol;

5-(1,3-dimethylpyrrolo[1,2-a]pyrazin-7-yl)-2-(6-{[(3S,4R)-3-fluoro-2,2,6,6-tetramethylpiperidin-4-yl]oxy}pyridazin-3-yl)pyridin-3-ol;

6-[6-(6-{[(3R,4S)-3-fluoro-2,2,6,6-tetramethylpiperidin-4-yl]oxy}pyridazin-3-yl)-5-hydroxypyridin-3-yl]-2-methylimidazo[1,2-b]pyridazine-8-carbonitrile;

6-[6-(6-{[(3S,4R)-3-fluoro-2,2,6,6-tetramethylpiperidin-4-yl]oxy}pyridazin-3-yl)-5-hydroxypyridin-3-yl]-2-methylimidazo[1,2-b]pyridazine-8-carbonitrile;

2-{6-[(3R,5S)-3,5-dimethylpiperazin-1-yl]pyridazin-3-yl}-5-(7-fluoro-2-methyl-2H-indazol-5-yl)pyridin-3-ol;

2-{6-[(3S,5R)-3,5-dimethylpiperazin-1-yl]pyridazin-3-yl}-5-(7-fluoro-2-methyl-2H-indazol-5-yl)pyridin-3-ol;

5-(6-methoxypyrimidin-4-yl)-2-{6-[(3R)-3-(methylamino)pyrrolidin-1-yl]pyridazin-3-yl}pyridin-3-ol;

2-(6-{[(1R,3s,5S)-1,5-dimethyl-8-azabicyclo[3.2.1]octan-3-yl]oxy}pyridazin-3-yl)-5-(1H-1,2,3-triazol-1-yl)pyridin-3-ol;

2-(6-{[(1S,3r,5S)-1,5-dimethyl-8-azabicyclo[3.2.1]octan-3-yl]oxy}pyridazin-3-yl)-5-(1H-1,2,3-triazol-1-yl)pyridin-3-ol;

2-(6-{[(3R,4S)-3-fluoro-2,2,6,6-tetramethylpiperidin-4-yl]oxy}pyridazin-3-yl)-5-([1,2,4]triazolo[1,5-a]pyrazin-2-yl)pyridin-3-ol;

2-(6-{[(3S,4R)-3-fluoro-2,2,6,6-tetramethylpiperidin-4-yl]oxy}pyridazin-3-yl)-5-([1,2,4]triazolo[1,5-a]pyrazin-2-yl)pyridin-3-ol;

2-{6-[(4-azadispiro[2.1.2$^5$.3$^3$]decan-9-yl)oxy]pyridazin-3-yl}-5-(2H-1,2,3-triazol-2-yl)pyridin-3-ol;

5-(6-methoxypyrimidin-4-yl)-2-{6-[(2,2,6,6-tetramethylpiperidin-4-yl)oxy]pyridazin-3-yl}pyridin-3-ol;

2-{6-[(5,5-dimethyl-4-azaspiro[2.5]octan-7-yl)oxy]pyridazin-3-yl}-5-[1-($^2H_3$)methyl-1H-pyrazol-4-yl]pyridin-3-ol;

2-{6-[(3R)-3-(tert-butylamino)pyrrolidin-1-yl]pyridazin-3-yl}-5-(2-methyl-1,3-oxazol-5-yl)pyridin-3-ol;

2-{6-[(3R)-3-(methylamino)pyrrolidin-1-yl]pyridazin-3-yl}-5-(2-methyl-1,3-oxazol-5-yl)pyridin-3-ol;

5-(6-{6-[(3R,5S)-3,5-dimethylpiperazin-1-yl]pyridazin-3-yl}-5-hydroxypyridin-3-yl)-2-methyl-2H-indazole-7-carbonitrile;

5-(6-{6-[(3S,5R)-3,5-dimethylpiperazin-1-yl]pyridazin-3-yl}-5-hydroxypyridin-3-yl)-2-methyl-2H-indazole-7-carbonitrile;

2-{6-[(5,5-dimethyl-4-azaspiro[2.5]octan-7-yl)oxy]pyridazin-3-yl}-5-(1,3-thiazol-2-yl)pyridin-3-ol;

2-{6-[(3R)-3-(methylamino)pyrrolidin-1-yl]pyridazin-3-yl}-5-(1,3-oxazol-2-yl)pyridin-3-ol;

5-(8-methoxy-2-methylimidazo[1,2-b]pyridazin-6-yl)-2-{6-[(2,2,6,6-tetramethylpiperidin-4-yl)oxy]pyridazin-3-yl}pyridin-3-ol;

2-(6-{[(5R,7S)-5-methyl-4-azaspiro[2.5]octan-7-yl]oxy}pyridazin-3-yl)-5-[1-($^2H_3$)methyl-1H-pyrazol-4-yl]pyridin-3-ol;

2-(6-{[(5S,7R)-5-methyl-4-azaspiro[2.5]octan-7-yl]oxy}pyridazin-3-yl)-5-[1-($^2H_3$)methyl-1H-pyrazol-4-yl]pyridin-3-ol;
2-(6-{[(5S,7S)-5-methyl-4-azaspiro[2.5]octan-7-yl]oxy}pyridazin-3-yl)-5-[1-($^2H_3$)methyl-1H-pyrazol-4-yl]pyridin-3-ol;
2-(6-{[(5R,7R)-5-methyl-4-azaspiro[2.5]octan-7-yl]oxy}pyridazin-3-yl)-5-[1-($^2H_3$)methyl-1H-pyrazol-4-yl]pyridin-3-ol;
2-{6-[(3R,5S)-3,5-dimethylpiperazin-1-yl]pyridazin-3-yl}-5-(1H-pyrazol-4-yl)pyridin-3-ol;
2-{6-[(3S,5R)-3,5-dimethylpiperazin-1-yl]pyridazin-3-yl}-5-(1H-pyrazol-4-yl)pyridin-3-ol;
2-{6-[(3R,5S)-3,5-dimethylpiperazin-1-yl]pyridazin-3-yl}-5-(7-methoxy-2-methyl-2H-indazol-5-yl)pyridin-3-ol;
2-{6-[(3S,5R)-3,5-dimethylpiperazin-1-yl]pyridazin-3-yl}-5-(7-methoxy-2-methyl-2H-indazol-5-yl)pyridin-3-ol;
5-(1H-pyrazol-4-yl)-2-[6-(3,3,5,5-tetramethylpiperazin-1-yl)pyridazin-3-yl]pyridin-3-ol;
5-(7-fluoro-2-methyl-2H-indazol-5-yl)-2-[6-(3,3,5,5-tetramethylpiperazin-1-yl)pyridazin-3-yl]pyridin-3-ol;
5-(1H-pyrazol-4-yl)-2-{6-[(3R,5S)-3,4,5-trimethylpiperazin-1-yl]pyridazin-3-yl}pyridin-3-ol;
5-(1H-pyrazol-4-yl)-2-{6-[(3S,5R)-3,4,5-trimethylpiperazin-1-yl]pyridazin-3-yl}pyridin-3-ol;
5-(7-fluoro-2-methyl-2H-indazol-5-yl)-2-{6-[(3R,5S)-3,4,5-trimethylpiperazin-1-yl]pyridazin-3-yl}pyridin-3-ol;
5-(7-fluoro-2-methyl-2H-indazol-5-yl)-2-{6-[(3S,5R)-3,4,5-trimethylpiperazin-1-yl]pyridazin-3-yl}pyridin-3-ol;
2-{6-[(3R,5S)-3,5-dimethylpiperazin-1-yl]pyridazin-3-yl}-5-(2-methylimidazo[1,2-a]pyridin-6-yl)pyridin-3-ol;
2-{6-[(3S,5R)-3,5-dimethylpiperazin-1-yl]pyridazin-3-yl}-5-(2-methylimidazo[1,2-a]pyridin-6-yl)pyridin-3-ol;
5-(7-fluoro-2-methyl-2H-indazol-5-yl)-2-[6-(piperazin-1-yl)pyridazin-3-yl]pyridin-3-ol;
2-{6-[(3R,5S)-3,5-dimethylpiperazin-1-yl]pyridazin-3-yl}-5-([1,2,4]triazolo[1,5-a]pyridin-6-yl)pyridin-3-ol;
2-{6-[(3S,5R)-3,5-dimethylpiperazin-1-yl]pyridazin-3-yl}-5-([1,2,4]triazolo[1,5-a]pyridin-6-yl)pyridin-3-ol;
5-(7-methoxy-2-methyl-2H-indazol-5-yl)-2-[6-(3-methylpiperazin-1-yl)pyridazin-3-yl]pyridin-3-ol;
6-{6-[(3R,5S)-3,5-dimethylpiperazin-1-yl]pyridazin-3-yl}-2'-methoxy[3,4'-bipyridin]-5-ol;
6-{6-[(3S,5R)-3,5-dimethylpiperazin-1-yl]pyridazin-3-yl}-2'-methoxy[3,4'-bipyridin]-5-ol;
5-(7-fluoro-2-methyl-2H-indazol-5-yl)-2-[6-(3-methylpiperazin-1-yl)pyridazin-3-yl]pyridin-3-ol;
2-[6-(4,7-diazaspiro[2.5]octan-7-yl)pyridazin-3-yl]-5-(7-fluoro-2-methyl-2H-indazol-5-yl)pyridin-3-ol;
2-{6-[(3R,5S)-3,5-dimethylpiperazin-1-yl]pyridazin-3-yl}-5-(2-methyl[1,2,4]triazolo[1,5-a]pyridin-6-yl)pyridin-3-ol;
2-{6-[(3S,5R)-3,5-dimethylpiperazin-1-yl]pyridazin-3-yl}-5-(2-methyl[1,2,4]triazolo[1,5-a]pyridin-6-yl)pyridin-3-ol;
2-[6-(4-cyclopropylpiperazin-1-yl)pyridazin-3-yl]-5-(7-fluoro-2-methyl-2H-indazol-5-yl)pyridin-3-ol;
5-(7-fluoro-2-methyl-2H-indazol-5-yl)-2-[6-(4-methylpiperazin-1-yl)pyridazin-3-yl]pyridin-3-ol;
[(3R,4S)-3-fluoro-4-({6-[3-hydroxy-5-(1H-pyrazol-4-yl)pyridin-2-yl]pyridazin-3-yl}oxy)-2,2,6,6-tetramethylpiperidin-1-yl]oxidanyl;
5-(7-fluoro-2-methyl-2H-indazol-5-yl)-2-{6-[(3S)-3-methylpiperazin-1-yl]pyridazin-3-yl}pyridin-3-ol;
5-(7-fluoro-2-methyl-2H-indazol-5-yl)-2-{6-[(3R)-3-methylpiperazin-1-yl]pyridazin-3-yl}pyridin-3-ol;
2-[6-(2,5-diazabicyclo[2.2.1]heptan-2-yl)pyridazin-3-yl]-5-(7-fluoro-2-methyl-2H-indazol-5-yl)pyridin-3-ol;
2-{6-[(3R,5R)-3,5-dimethylpiperazin-1-yl]pyridazin-3-yl}-5-(7-fluoro-2-methyl-2H-indazol-5-yl)pyridin-3-ol;
2-{6-[(3S,5S)-3,5-dimethylpiperazin-1-yl]pyridazin-3-yl}-5-(7-fluoro-2-methyl-2H-indazol-5-yl)pyridin-3-ol;
2-[6-(1,6-diazaspiro[3.4]octan-6-yl)pyridazin-3-yl]-5-(2-methylimidazo[1,2-a]pyridin-6-yl)pyridin-3-ol;
2-[6-(3-methylpiperazin-1-yl)pyridazin-3-yl]-5-{[(3-methyl-1H-pyrazol-4-yl)methyl]amino}pyridin-3-ol;
2-[6-(3-methylpiperazin-1-yl)pyridazin-3-yl]-5-{[(pyridin-2-yl)methyl]amino}pyridin-3-ol;
2-[6-(3-methylpiperazin-1-yl)pyridazin-3-yl]-5-{[(pyridin-3-yl)methyl]amino}pyridin-3-ol;
2-[6-(3-methylpiperazin-1-yl)pyridazin-3-yl]-5-{[(pyridin-4-yl)methyl]amino}pyridin-3-ol;
2-[6-(3-methylpiperazin-1-yl)pyridazin-3-yl]-5-{[(quinolin-3-yl)methyl]amino}pyridin-3-ol;
2-[6-(3-methylpiperazin-1-yl)pyridazin-3-yl]-5-{[(quinolin-8-yl)methyl]amino}pyridin-3-ol;
2-{6-[(6,6-dimethyl-2-oxa-5-azaspiro[3.5]nonan-8-yl)oxy]pyridazin-3-yl}-5-(1H-pyrazol-4-yl)pyridin-3-ol;
2-{6-[(3R,5S)-3,5-dimethylpiperazin-1-yl]pyridazin-3-yl}-5-(2-methylimidazo[1,2-a]pyrimidin-6-yl)pyridin-3-ol;
2-{6-[(3S,5R)-3,5-dimethylpiperazin-1-yl]pyridazin-3-yl}-5-(2-methylimidazo[1,2-a]pyrimidin-6-yl)pyridin-3-ol;
2-[6-(2,5-diazabicyclo[2.2.1]heptan-2-yl)pyridazin-3-yl]-5-(2-methylimidazo[1,2-a]pyrimidin-6-yl)pyridin-3-ol;
2-[6-(3-methylpiperazin-1-yl)pyridazin-3-yl]-5-[(pyridin-3-yl)amino]pyridin-3-ol;
2-{6-[(3R,5S)-3,5-dimethylpiperazin-1-yl]pyridazin-3-yl}-5-[(E)-2-(1-methyl-1H-pyrazol-4-yl)ethenyl]pyridin-3-ol;
2-{6-[(3S,5R)-3,5-dimethylpiperazin-1-yl]pyridazin-3-yl}-5-[(E)-2-(1-methyl-1H-pyrazol-4-yl)ethenyl]pyridin-3-ol;
2-[6-(3-ethylpiperazin-1-yl)pyridazin-3-yl]-5-(1H-pyrazol-4-yl)pyridin-3-ol;
2-[6-(3-ethylpiperazin-1-yl)pyridazin-3-yl]-5-(7-fluoro-2-methyl-2H-indazol-5-yl)pyridin-3-ol;
2-{6-[(3S)-3-(propan-2-yl)piperazin-1-yl]pyridazin-3-yl}-5-(1H-pyrazol-4-yl)pyridin-3-ol;
2-{6-[(3R)-3-(propan-2-yl)piperazin-1-yl]pyridazin-3-yl}-5-(1H-pyrazol-4-yl)pyridin-3-ol;
5-(7-fluoro-2-methyl-2H-indazol-5-yl)-2-{6-[(3S)-3-(propan-2-yl)piperazin-1-yl]pyridazin-3-yl}pyridin-3-ol;
2-[6-(3-cyclopropylpiperazin-1-yl)pyridazin-3-yl]-5-(1H-pyrazol-4-yl)pyridin-3-ol;
2-{6-[(3R,5S)-3,5-dimethylpiperazin-1-yl]pyridazin-3-yl}-5-(2-methyl-2H-indazol-5-yl)pyridin-3-ol;
2-{6-[(3S,5R)-3,5-dimethylpiperazin-1-yl]pyridazin-3-yl}-5-(2-methyl-2H-indazol-5-yl)pyridin-3-ol;
2-{6-[(3R,5S)-3,5-dimethylpiperazin-1-yl]pyridazin-3-yl}-5-[(6-methylpyridin-3-yl)amino]pyridin-3-ol;

2-{6-[(3R,5S)-3,5-dimethylpiperazin-1-yl]pyridazin-3-yl}-5-(1-methyl-1H-indazol-5-yl)pyridin-3-ol;

2-{6-[(3S,5R)-3,5-dimethylpiperazin-1-yl]pyridazin-3-yl}-5-(1-methyl-1H-indazol-5-yl)pyridin-3-ol;

5-[(6-methylpyridin-3-yl)amino]-2-{6-[(3R)-3-(propan-2-yl)piperazin-1-yl]pyridazin-3-yl}pyridin-3-ol;

5-[(6-methylpyridin-3-yl)amino]-2-{6-[(3S)-3-(propan-2-yl)piperazin-1-yl]pyridazin-3-yl}pyridin-3-ol;

2-{6-[(3S)-3-cyclopropylpiperazin-1-yl]pyridazin-3-yl}-5-(2H-1,2,3-triazol-2-yl)pyridin-3-ol;

2-{6-[(3S)-3-cyclopropylpiperazin-1-yl]pyridazin-3-yl}-5-[1-($^2H_3$)methyl-1H-pyrazol-4-yl]pyridin-3-ol;

2-{6-[3-(propan-2-yl)piperazin-1-yl]pyridazin-3-yl}-5-[(E)-2-(1H-pyrazol-4-yl)ethenyl]pyridin-3-ol;

2-{6-[(3R,5S)-3,5-dimethylpiperazin-1-yl]pyridazin-3-yl}-5-(2H-indazol-5-yl)pyridin-3-ol;

2-{6-[(3S,5R)-3,5-dimethylpiperazin-1-yl]pyridazin-3-yl}-5-(2H-indazol-5-yl)pyridin-3-ol;

2-{6-[(3S)-3-ethylpiperazin-1-yl]pyridazin-3-yl}-5-(1H-pyrazol-4-yl)pyridin-3-ol;

5-[(5-methylpyrazin-2-yl)amino]-2-{6-[(3R)-3-(propan-2-yl)piperazin-1-yl]pyridazin-3-yl}pyridin-3-ol;

5-[(5-methylpyrazin-2-yl)amino]-2-{6-[(3S)-3-(propan-2-yl)piperazin-1-yl]pyridazin-3-yl}pyridin-3-ol;

5-[(2-methylpyrimidin-5-yl)amino]-2-{6-[(3R)-3-(propan-2-yl)piperazin-1-yl]pyridazin-3-yl}pyridin-3-ol;

5-[(2-methylpyrimidin-5-yl)amino]-2-{6-[(3S)-3-(propan-2-yl)piperazin-1-yl]pyridazin-3-yl}pyridin-3-ol;

2-{6-[methyl(2,2,6,6-tetramethylpiperidin-4-yl)amino]-1,2,4-triazin-3-yl}-5-(2H-1,2,3-triazol-2-yl)pyridin-3-ol;

2-{6-[methyl(2,2,6,6-tetramethylpiperidin-4-yl)amino]-1,2,4-triazin-3-yl}-5-(1H-pyrazol-4-yl)pyridin-3-ol;

2-{6-[(2,2,6,6-tetramethylpiperidin-4-yl)amino]-1,2,4-triazin-3-yl}-5-(2H-1,2,3-triazol-2-yl)pyridin-3-ol;

2-{6-[(3R,5S)-3,5-dimethylpiperazin-1-yl]-1,2,4-triazin-3-yl}-5-(7-fluoro-2-methyl-2H-indazol-5-yl)pyridin-3-ol; and 2-{6-[(3S,5R)-3,5-dimethylpiperazin-1-yl]-1,2,4-triazin-3-yl}-5-(7-fluoro-2-methyl-2H-indazol-5-yl)pyridin-3-ol;

or a salt, hydrate, solvate, racemate, enantiomer, diastereomer, tautomer, or mixtures thereof.

10. A method for treating or ameliorating Huntington's disease (HD) in a subject in need thereof comprising, administering to the subject an effective amount of the compound or the form thereof of claim 1.

11. The method of claim 10, wherein the effective amount of the compound or the form thereof is in a range of from about 0.001 mg/kg/day to about 500 mg/kg/day.

12. A method for treating or ameliorating Huntington's disease (HD) in a subject in need thereof comprising, administering to the subject an effective amount of the compound or the form thereof of claim 1 in admixture with one or more pharmaceutically acceptable excipients.

13. The method of claim 12, wherein the effective amount of the compound or the form thereof is in a range of from about 0.001 mg/kg/day to about 500 mg/kg/day.

14. A pharmaceutical composition comprising the compound or the form thereof of claim 1 in admixture with one or more pharmaceutically acceptable excipients.

15. A pharmaceutical composition comprising the compound or the form thereof of claim 9 or a salt, hydrate, solvate, racemate, enantiomer, diastereomer, tautomer, or mixtures thereof in admixture with one or more pharmaceutically acceptable excipients.

16. A method for treating or ameliorating Huntington's disease (HD) in a subject in need thereof comprising, administering to the subject an effective amount of the compound of claim 9 or a salt, hydrate, solvate, racemate, enantiomer, diastereomer, tautomer, or mixtures thereof.

* * * * *